US012655430B2

(12) United States Patent
Fishilevich et al.

(10) Patent No.: US 12,655,430 B2
(45) Date of Patent: Jun. 16, 2026

(54) HUMAN CHROMOSOME 9 OPEN READING FRAME 72 (C9ORF72) iRNA AGENT COMPOSITIONS AND METHODS OF USE THEREOF

(71) Applicants: Alnylam Pharmaceuticals, Inc., Cambridge, MA (US); Regeneron Pharmaceuticals, Inc., Tarrytown, NY (US)

(72) Inventors: Elane Fishilevich, Rochester, MA (US); Stuart Milstein, Arlington, MA (US); Kirk Brown, Swampscott, MA (US); Tracy Zimmermann, Winchester, MA (US); James D. McIninch, Burlington, MA (US); David Frendewey, Tarrytown, NY (US); Eric Chiao, Tarrytown, NY (US); Aarti Sharma-Kanning, Tarrytown, NY (US); Anthony Gagliardi, Tarrytown, NY (US); Gustavo Droguett, Tarrytown, NY (US); Brittany Savage, Tarrytown, NY (US); Brian Zambrowicz, Tarrytown, NY (US)

(73) Assignees: Alnylam Pharmaceuticals, Inc., Cambridge, MA (US); Regeneron Pharmaceuticals, Inc., Tarrytown, NY (US)

( * ) Notice: Subject to any disclaimer, the term of this patent is extended or adjusted under 35 U.S.C. 154(b) by 917 days.

(21) Appl. No.: 17/836,020

(22) Filed: Jun. 9, 2022

(65) Prior Publication Data

US 2023/0114649 A1 Apr. 13, 2023

Related U.S. Application Data

(63) Continuation of application No. PCT/US2020/064159, filed on Dec. 10, 2020.

(60) Provisional application No. 62/947,605, filed on Dec. 13, 2019, provisional application No. 62/947,768, filed on Dec. 13, 2019.

(51) Int. Cl.
*C12N 15/113* (2010.01)
*A61P 25/28* (2006.01)

(52) U.S. Cl.
CPC ............ *C12N 15/113* (2013.01); *A61P 25/28* (2018.01); *C12N 2310/14* (2013.01); *C12N 2310/315* (2013.01); *C12N 2310/3515* (2013.01)

(58) Field of Classification Search
CPC .............. C12N 15/113; C12N 2310/14; C12N 2310/315; C12N 2310/351; A61K 31/713
USPC ..................... 435/6.1, 91.1, 91.31, 455, 458; 514/44 A; 536/23.1, 24.5
See application file for complete search history.

(56) References Cited

U.S. PATENT DOCUMENTS

| | | | | |
|---|---|---|---|---|
| 9,605,263 | B2 | 3/2017 | Rigo | |
| 9,963,699 | B2 | 5/2018 | Bennett et al. | |
| 10,138,482 | B2 | 11/2018 | Rigo | |
| 10,221,414 | B2 | 3/2019 | Freier et al. | |
| 10,307,678 | B2 | 6/2019 | Eda | |
| 10,443,052 | B2 | 10/2019 | Freier | |
| 10,793,855 | B2 | 10/2020 | Rigo | |
| 10,815,483 | B2 | 10/2020 | Rigo | |
| 11,142,545 | B2 | 10/2021 | Shi et al. | |
| 11,162,096 | B2 | 11/2021 | Bennett et al. | |
| 11,192,128 | B2 | 12/2021 | Posselius et al. | |
| 11,260,073 | B2 | 3/2022 | Prakash et al. | |
| 11,339,393 | B2 * | 5/2022 | Freier | G01N 33/6896 |
| 2017/0233735 | A1 | 8/2017 | Corey et al. | |
| 2018/0094267 | A1 | 4/2018 | Heslin et al. | |
| 2018/0119142 | A1 | 5/2018 | Rigo | |
| 2020/0385737 | A1 | 12/2020 | Khvorova et al. | |
| 2021/0169916 | A1 | 6/2021 | Bennett et al. | |
| 2024/0240182 | A1 | 7/2024 | Dang et al. | |

FOREIGN PATENT DOCUMENTS

| | | | |
|---|---|---|---|
| WO | WO-2013/075035 | A1 | 5/2013 |
| WO | WO-2014/062686 | A1 | 4/2014 |
| WO | WO-2015/054676 | A2 | 4/2015 |
| WO | WO-2016/168592 | A2 | 10/2016 |
| WO | WO-2019/051025 | A2 | 3/2019 |
| WO | WO-2019/217459 | A1 | 11/2019 |
| WO | WO-2020/205605 | A2 | 10/2020 |
| WO | WO-2021/119226 | A1 | 6/2021 |
| WO | WO-2022/256290 | A2 | 12/2022 |

OTHER PUBLICATIONS

U.S. Appl. No. 18/525,924, filed Dec. 1, 2023, US 20240240182, Published.
PCT/US2022/031519, May 31, 2022, WO 2022/256290, Completed.
Lagier-Tourenne et al., "Targeted degradation of sense and antisense C9orf72 RNA foci as therapy for ALS and frontotemporal degeneration," Proc. Natl. Acad. Sci. U.S.A. 110(47):E4530-E4539, (2013).
Martier et al., "Targeting RNA-Mediated Toxicity in C9orf72 ALS and/or FTD by RNAi-Based Gene Therapy", Molecular Therapy: Nucleic Acids vol. 16 Jun. 2019.
Mis et al., "Development of Therapeutics for C9ORF72 ALS/FTD-Related Disorders", Mol Neurobiol 54, 4466-4476 (2017).
Amick et al., "C9orf72 binds SMCR8, localizes to lysosomes, and regulates mTORC1 signaling", Mol Biol Cell. Oct. 15, 2016;27(20):3040-3051.

(Continued)

*Primary Examiner* — Jane J Zara
(74) *Attorney, Agent, or Firm* — McCarter & English, LLP; Maria Laccotripe Zacharakis; Deborah L. Nagle

(57) ABSTRACT

The disclosure relates to double stranded ribonucleic acid (dsRNAi) agents and compositions targeting a human chromosome 9 open reading frame 72 (C9orf72) gene, as well as methods of inhibiting expression of a C9orf72 gene and methods of treating subjects having a C9orf72-associated disease or disorder, e.g., C9orf72 amyotrophic lateral sclerosis/frontotemporal dementia or Huntington-Like Syndrome Due To C9orf72 Expansions, using such dsRNAi agents and compositions.

25 Claims, 36 Drawing Sheets

Specification includes a Sequence Listing.

(56) References Cited

OTHER PUBLICATIONS

Hu et al. "Engineering Duplex RNAs for Challenging Targets: Recognition of GGGGCC/CCCCGG Repeats at the ALS/FTD C9orf72 Locus", Chem Biol. Nov. 19, 2015;22(11):1505-1511.
Farg et al., "C9ORF72, implicated in amytrophic lateral sclerosis and frontotemporal dementia, regulates endosomal trafficking", Hum Mol Genet. Oct. 15, 2017;26(20):4093-4094.
Foster et al., "Advanced siRNA Designs Further Improve In Vivo Performance of GalNAc-siRNA Conjugates", Mol Ther. Mar. 7, 2018;26(3):708-717.
Ui-Tei et al., "Functional dissection of siRNA sequence by systematic DNA substitution: modified siRNA with a DNA seed arm is a powerful tool for mammalian gene silencing with significantly reduced off-target effect", Nucleic Acids Res. Apr. 2008;36(7):2136-51.
Chernikov et al., "Current Development of siRNA Bioconjugates: From Research to the Clinic", Front Pharmacol. Apr. 26, 2019:10:444.
Hu et al., "Therapeutic siRNA: state of the art", Signal Transduction and Targeted Therapy (2020) 5:101.
Nair et al., "Impact of enhanced metabolic stability on pharmacokinetics and pharmacodynamics of GalNAc-siRNA conjugates", Nucleic Acids Res.Nov. 2, 2017;45(19):10969-10977.
Shukla et al., "Exploring Chemical Modifications for siRNA Therapeutics: A Structural and Functional Outlook", ChemMedChem. Mar. 1, 2010;5(3):328-49.
International Search Report and Written Opinion from PCT/US2020/064159, mailed May 11, 2021.
Gendron et al, Poly(GP) proteins are a useful pharmacodynamic marker for C90RF72-associated amyotrophic lateral sclerosis, Sci Transl Med Mar. 29, 2017; 9(383):pp. 1-27.

* cited by examiner

Transcripts Containing Intron Sequence Near 1A

HUMAN CHROMOSOME 9 OPEN READING FRAME 72 (C9ORF72) iRNA AGENT COMPOSITIONS AND METHODS OF USE THEREOF

RELATED APPLICATIONS

This application is a 35 § U.S.C. 111(a) continuation application which claims the benefit of priority to PCT/US2020/064159, filed on Dec. 10, 2020, which claims the benefit of priority to U.S. Provisional Application No. 62/947,605, filed on Dec. 13, 2019, and U.S. Provisional Application No. 62/947,768, filed on Dec. 13, 2019. The entire contents of each of the foregoing applications are incorporated herein by reference.

SEQUENCE LISTING

The instant application contains a Sequence Listing which has been submitted electronically in ASCII format and is hereby incorporated by reference in its entirety. Said ASCII copy, created on May 10, 2022, is named 121301_10202_SL.txt and is 473,202 bytes in size.

BACKGROUND OF THE INVENTION

Human chromosome 9 open reading frame 72 (C9orf72) is a protein encoded by the c9orf72 gene. C9orf72 is found in many regions of the brain, such as the cerebral cortex, in the cytoplasm of neurons as well as in presynaptic terminals.

Differential use of transcription alternative start and termination sites generates three RNA transcripts from C9orf72 DNA. These encode two protein isoforms consisting of a long isoform (isoform A) of approximately 54 kDa derived from variants 2 (NM_018325.4) and 3 (NM_001256054.2), and a short isoform (isoform B) of approximately 24 kDa derived from variant 1 (NM_145005.6) (see, e.g., FIG. 1 of Barker, et al. (2017) *Frontiers Cell Neurosci* 11:1-15).

The two alternatively used first exons of the C9orf72 gene are exons 1a and 1b (see, e.g., FIG. 1 of Barker, et al., supra). A large GGGGCC ($G_4C_2$) (SEQ ID NO: 1) hexanucleotide repeat expansion (from about 2-22 copies to 700-1600 copies) in the first intron of the C9orf72 gene between exons 1a and 1b has been shown to interfere with the function of the C9orf72 protein and to be pathogenic resulting in several neurodegenerative diseases with distinct clinical features but common pathological features and genetic causes (Ling, et al. (2013) *Neuron* 79:416-438). In particular, the presence of a hexanucleotide repeat expansion in the C9orf72 gene is the most common genetic cause of familial and sporadic Amyotrophic lateral sclerosis (ALS), a devastating degenerative disease of motor neurons in the brain and spinal cord. Indeed, C9orf72 mutation hexanucleotide repeat expansions are present in approximately 40% of familial ALS and 8-10% of sporadic ALS subjects. Hexanucleotide repeat expansion in the C9orf72 gene is also the most common familial cause of Frontotemporal Dementia (FTD), the second most common form of presenile dementia after Alzheimer's disease which is characterized by behavioral and language deficits and manifests pathologically by neuronal atrophy in the frontal and anterior temporal lobes in the brain. Huntington-Like Syndrome Due To C9orf72 Expansions, characterized by movement disorders, including dystonia, chorea, myoclonus, tremor and rigidity, cognitive and memory impairment, early psychiatric disturbances and behavioral problems, is also associated with hexanucleotide repeat expansion in the C9orf72 gene.

Although the functions of the C9orf72 protein are still being investigated, C9orf72 has been shown to interact with and activate Rab proteins that are involved in regulating the cytoskeleton, autophagy and endocytic transport. In addition, numerous cellular pathways have been demonstrated to be misregulated in neurodegenerative diseases associated with C9orf72 hexanucleotide repeat expansion. For example, altered RNA processing has consistently appeared at the forefront of research into C9orf72 disease. This includes bidirectional transcription of the repeat sequence, accumulation of repeat RNA into nuclear foci sequestering specific RNA-binding proteins (RBPs) and translation of RNA repeats into dipeptide repeat proteins (DPRs) by repeat-associated non-AUG (RAN)-initiated translation. Additionally, disruptions in release of the C9orf72 RNA from RNA polymerase II, translation in the cytoplasm and degradation have been shown to be disrupted by C9orf72 hexanucleotide repeat expansion. Furthermore, several alterations have been identified in the processing of the C9orf72 RNA itself, in terms of its transcription, splicing and localization (see, e.g., Barker, et al., supra).

Irrespective of the mechanism, several groups have identified the presence of sense and antisense C9orf72-containing foci as well as the presence of aberrant dipeptide-repeat (DPR) proteins (poly(GA), poly(GR), poly(GP), poly(PA), and poly(PR)) produced from all reading frames of either sense or antisense repeat-containing C9orf72 RNAs through repeat-associated non-AUG-dependent (RAN) translation in several cell types in the nervous systems of subjects having a C9orf72-associated disease (Lagier-Tourenne, et al. (2013) *Proc Natl Acad Sci USA* doi/10.1073/pnas.1318835110; Jiang, et al. (2016) *Neuron* 90:535-550). Furthermore, in mice with one allele of C9orf72 inactivated no disease was provoked but, in mice with both C9orf72 alleles inactivated, splenomegaly, enlarged lymph nodes, and mild social interaction deficits, but no motor dysfunction was observed. In addition, in mice expressing human C9orf72 RNAs with up to 450 GGGGCC repeats (SEQ ID NO: 135) it was shown that hexanucleotide expansions caused age-, repeat-length-, and expression-level-dependent accumulation of sense and antisense RNA-containing foci and dipeptide-repeat proteins synthesized by AUG-independent translation, accompanied by loss of hippocampal neurons, increased anxiety, and impaired cognitive function (Jiang, et al. (2016) Neuron 90:535-550).

There is currently no cure for subjects having a C9orf72-associated disease, e.g., C9orf72 amyotrophic lateral sclerosis, C9orf72 frontotemporal dementia or Huntington's disease, e.g., Huntington-Like Syndrome Due To C9orf72 Expansions, and treatments are only aimed at alleviating the symptoms and improving the patient's quality of life as the disease progresses.

Accordingly, there is a need in the art for agents that can selectively and efficiently inhibit the expression of the C9orf72 gene for, e.g., the treatment of subjects having a C9orf72-associated disorder.

BRIEF SUMMARY OF THE INVENTION

The present disclosure provides RNAi compositions, which effect the RNA-induced silencing complex (RISC)-mediated cleavage of RNA transcripts of a C9orf72 gene, such as a C9orf72 gene having an expanded GGGGCC ($G_4C_2$) repeat (SEQ ID NO: 1). The C9orf72 gene may be within a cell, e.g., a cell within a subject, such as a human.

The use of these iRNAs enables the targeted degradation of mRNAs of the corresponding gene (C9orf72 gene) in mammals.

The iRNAs of the invention have been designed to target a C9orf72 gene, e.g., a C9orf72 gene having an expanded GGGGCC hexanucleotide repeat (SEQ ID NO: 1) in an intron of the gene, and having a combination of nucleotide modifications. The agents may target a mature C9orf72 mRNA (an mRNA having introns spliced out) or a C9orf72 RNA containing a hexanucleotide-repeat (an RNA containing C9orf72 intron 1A). The iRNAs of the invention may decrease the levels of C9orf72 mature mRNA less than they decrase the levels of C9orf72 RNA containing a hexanucleotide repeat. For example, the iRNAs of the invention may decrease the levels of the C9orf72 mature mRNA by no more than about 50%, and reduce the level of sense- and antisense-containing foci and aberrant dipeptide-repeat (DPR) proteins (poly(GA), poly(GR), poly(GP), poly(PA), and poly(PR)), and/or decrease the levels of C9orf72 RNA containing a hexanucleotide-repeat by more than about 50%, and reduce the level of sense- and antisense-containing foci and aberrant dipeptide-repeat (DPR) proteins (poly(GA), poly(GR), poly(GP), poly(PA), and poly(PR)). Without intending to be limited by theory, it is believed that a combination or sub-combination of the foregoing properties and the specific target sites, or the specific modifications in these iRNAs confer to the iRNAs of the invention improved efficacy, stability, potency, durability, and safety.

In one aspect, the present invention provides double stranded ribonucleic acid (dsRNA) agents for knocking down a C9orf72 target RNA in a cell.

In one embodiment, the dsRNA agents target a region of a C9orf72 target RNA containing a hexanucleotide repeat.

In one aspect, the present invention provides a double stranded ribonucleic acid (dsRNA) agent for inhibiting expression of C9orf72, such as a C9orf72 RNA containing a hexanucleotide-repeat, wherein the dsRNA agent comprises a sense strand and an antisense strand forming a double stranded region, wherein the antisense strand comprises at least 15 contiguous nucleotides differing by no more than 3 nucleotides from the nucleotide sequence of SEQ ID NO: 125, and wherein the sense strand, the antisense strand, or both the sense strand and the antisense strand is conjugated to one or more lipophilic moieties.

In another aspect, the present invention provides a double stranded ribonucleic acid (dsRNA) agent for inhibiting expression of C9orf72, such as a C9orf72 RNA containing a hexanucleotide-repeat, wherein the dsRNA agent comprises a sense strand and an antisense strand forming a double stranded region, wherein the sense strand comprises at least 15 contiguous nucleotides differing by no more than three nucleotides from nucleotides 200-290 of SEQ ID NO: 133, and the antisense strand comprises at least 15 contiguous nucleotides from the corresponding nucleotide sequence of SEQ ID NO: 134, and wherein the sense strand, the antisense strand, or both the sense strand and the antisense strand is conjugated to one or more lipophilic moieties.

In one aspect, the present invention provides a double stranded ribonucleic acid (dsRNA) agent for inhibiting expression of C9orf72, such as a C9orf72 RNA containing a hexanucleotide-repeat, wherein the dsRNA agent comprises a sense strand and an antisense strand forming a double stranded region, wherein the sense strand comprises at least 15 contiguous nucleotides differing by no more than 3 nucleotides from any one of the antisense nucleotide sequences in any one of Tables 10A, 10B, 12-15, 19, 20, or 21.

In one embodiment, the nucleotide sequence of the sense and antisense strand comprise any one of the sense and antisense strand nucleotide sequences in any one of Tables 12 or 13. In one embodiment, the nucleotide sequence of the antisense strand comprises any one of the antisense strand nucleotide sequences in any one of Tables 12 or 13.

In one embodiment, the sense strand comprises at least 15 contiguous nucleotides differing by no more than three nucleotides from any one of the nucleotide sequence of nucleotides 230-270, 233-262, 800-840, 800-830, 802-828, 1240-1290, 1240-1280, 1247-1288, 1590-1645, 1590-1620, and 1594-1642 of SEQ ID NO:121, and the antisense strand comprises at least 15 contiguous nucleotides from the corresponding nucleotide sequence of SEQ ID NO:125.

In one embodiment, the sense strand comprises at least 15 contiguous nucleotides differing by no more than three nucleotides from any one of the nucleotide sequence of nucleotides 1594-1616, 802-824, 239-261, 1308-1330, 233-255, 1595-1617, 240-262, 1532-1554, 237-259, 3268-3290, 806-828, 1620-1642, 526-548, 1169-1191, 1266-1288, 1247-1269, 586-608, 1257-1279, and 400-422 of SEQ ID NO:121, and the antisense strand comprises at least 15 contiguous nucleotides from the corresponding nucleotide sequence of SEQ ID NO:125.

In one embodiment, the antisense strand comprises at least 15 contiguous nucleotides differing by no more than three nucleotides from any one of the antisense strand nucleotide sequences of a duplex selected from the group consisting of AD-348904.1, AD-348136.1, AD-347612.1, AD-348639.1, AD-347606.1, AD-348905.1, AD-347613.1, AD-348842.1, AD-347610.1, AD-350329.1, AD-348140.1, AD-348930.1, AD-347863.1, AD-348500.1, AD-348597.1, AD-348578.1, AD-347923.1, AD-348588.1, and AD-347773.1.

In one embodiment, the nucleotide sequence of the sense and antisense strand comprise any one of the sense and antisense strand nucleotide sequences in any one of Tables 14, 15, 19, 20, or 21.

In one aspect, the present invention provides a double stranded ribonucleic acid (dsRNA) agent for selectively inhibiting expression of C9orf72 comprising a hexanucleotide repeat comprising multiple contiguous copies of SEQ ID NO: 1, wherein the dsRNA agent comprises a sense strand and an antisense strand forming a double stranded region, wherein the antisense strand comprises at least contiguous nucleotides differing by no more than 3 nucleotides from any one of the antisense nucleotide sequences in any one of Tables 14, 15, and 21.

In one embodiment, the antisense strand comprises at least 15 contiguous nucleotides differing by no more than three nucleotides from any one of the antisense strand nucleotide sequences of a duplex selected from the group consisting of AD-463863.1, AD-463862.1, AD-463869.1, AD-463873.1, AD-463872.1, and AD-463860.1.

In one embodiment, the antisense strand comprises at least 15, 16, 17, 18, 19, or 20 contiguous nucleotides differing by no more than three nucleotides from any one of the antisense strand nucleotide sequences of a duplex selected from the group consisting of AD-463863.1, AD-463862.1, AD-463869.1, AD-463873.1, AD-463872.1, and AD-463860.1. In some embodiments, the the sense and antisense strand are each independently 19, 20, 21, 23, 23 24, or 25 nucleotides in length.

In one embodiment, the antisense strand comprises at least 15, 16, 17, 18, 19, or 20 contiguous nucleotides differing by no more than two nucleotides from any one of the antisense strand nucleotide sequences of a duplex selected from the group consisting of AD-463863.1, AD-463862.1, AD-463869.1, AD-463873.1, AD-463872.1, and AD-463860.1. In some embodiments, the sense and antisense strand are each independently 19, 20, 21, 23, 23 24, or 25 nucleotides in length.

In one embodiment, the antisense strand comprises at least 15, 16, 17, 18, 19, or 20 contiguous nucleotides differing by no more than one nucleotide from any one of the antisense strand nucleotide sequences of a duplex selected from the group consisting of AD-463863.1, AD-463862.1, AD-463869.1, AD-463873.1, AD-463872.1, and AD-463860.1. In some embodiments, the sense and antisense strand are each independently 19, 20, 21, 23, 23 24, or 25 nucleotides in length.

In one embodiment, the antisense strand comprises at least 15, 16, 17, 18, 19, or 20 contiguous nucleotides from any one of the antisense strand nucleotide sequences of a duplex selected from the group consisting of AD-463863.1, AD-463862.1, AD-463869.1, AD-463873.1, AD-463872.1, and AD-463860.1. In some embodiments, the sense and antisense strand are each independently 19, 20, 21, 23, 23 24, or 25 nucleotides in length.

In one embodiment, the C9orf72 target RNA comprises a hexanucleotide repeat comprising multiple contiguous copies of SEQ ID NO: 1, the dsRNA agent comprises a sense strand and an antisense strand, the antisense strand comprises a region of complementarity to the C9orf72 target RNA, and the region of complementarity comprises at least 15 contiguous nucleotides differing by no more than 3 nucleotides from the reverse complement of a nucleotide sequence between the start of exon 1A and the start of exon 2 of the C9orf72 target RNA.

In one embodiment, the C9orf72 target RNA comprises a hexanucleotide repeat comprising multiple contiguous copies of SEQ ID NO: 1, the dsRNA agent comprises a sense strand and an antisense strand, and the antisense strand comprises a sequence of 15-25 contiguous nucleotides having at least 80% complementarity to a sequence of 15-25 contiguous nucleotides present in a sequence between the start of exon 1A and the start of exon 2 of the C9orf72 target RNA.

In one embodiment, the region of complementarity comprises the reverse complement of at least 15 contiguous nucleotides differing by no more than 3 nucleotides from a nucleotide sequence between exon 1A and exon 1B of the C9orf72 target RNA.

In one embodiment, the region of complementarity comprises the reverse complement of at least 15 contiguous nucleotides differing by no more than 3 nucleotides from a nucleotide sequence between exon 1A and the hexanucleotide repeat of the C9orf72 target RNA.

In one embodiment, the sense strand comprises at least 15 contiguous nucleotides differing by no more than 3 nucleotides from the nucleotide sequence of SEQ ID NO: 115, and the antisense strand comprises at least 15 contiguous nucleotides differing by no more than 3 nucleotides from the nucleotide sequence of SEQ ID NO: 116.

In one embodiment, the sense strand comprises at least 15 contiguous nucleotides differing by no more than 3 nucleotides from the nucleotide sequence of SEQ ID NO: 117, and the antisense strand comprises at least 15 contiguous nucleotides differing by no more than 3 nucleotides from the nucleotide sequence of SEQ ID NO: 118.

In one embodiment, the antisense strand comprises at least 15 contiguous nucleotides differing by no more than 3 nucleotides from any one of the antisense strand sequences in SEQ ID NOS: 3, 5, 7, 9, 11, and 13, and/or wherein the sense strand comprises at least 15 contiguous nucleotides differing by no more than 3 nucleotides from any one of the sense strand sequences in SEQ ID NOS: 2, 4, 6, 8, 10, and 12.

In one embodiment, the nucleotide sequence between the start of exon 1A and the start of exon 2 of the C9orf72 target RNA is not present in a mature C9orf72 messenger RNA.

In one embodiment, the sense strand, the antisense strand, or both the sense strand and the antisense strand is conjugated to one or more lipophilic moieties.

In one embodiment, the lipophilic moiety is conjugated to one or more internal positions in the double stranded region of the dsRNA agent.

In one embodiment, the lipophilic moiety is conjugated via a linker or carrier.

In one embodiment, the lipophilicity of the lipophilic moiety, measured by log Kow, exceeds 0.

In one embodiment, the hydrophobicity of the double-stranded RNAi agent, measured by the unbound fraction in a plasma protein binding assay of the double-stranded RNAi agent, exceeds 0.2.

In one embodiment, the plasma protein binding assay is an electrophoretic mobility shift assay using human serum albumin protein.

In some embodiments, the dsRNA agent comprises at least one modified nucleotide.

In one embodiment, no more than five of the sense strand nucleotides and no more than five of the nucleotides of the antisense strand are unmodified nucleotides In one embodiment, all of the nucleotides of the sense strand and all of the nucleotides of the antisense strand are modified nucleotides.

In one embodiment, at least one of the modified nucleotides is selected from the group a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxly-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a 5'-phosphorothioate group, a nucleotide comprising a 5'-methylphosphonate group, a nucleotide comprising a 5' phosphate or 5' phosphate mimic, a nucleotide comprising vinyl phosphonate, a nucleotide comprising adenosine-glycol nucleic acid (GNA), a nucleotide comprising thymidine-glycol nucleic acid (GNA) S-Isomer, a nucleotide comprising 2-hydroxymethyl-tetrahydrofurane-5-phosphate, a nucleotide comprising 2'-deoxythymidine-3'phosphate, a nucleotide comprising 2'-deoxyguanosine-3'-phosphate, and a terminal nucleotide linked to a cholesteryl derivative and a dodecanoic acid bisdecylamide group; and combinations thereof.

In one embodiment, the modified nucleotide is selected from the group consisting of a 2'-deoxy-2'-fluoro modified nucleotide, a 2'-deoxy-modified nucleotide, 3'-terminal deoxy-thymine nucleotides (dT), a locked nucleotide, an abasic nucleotide, a 2'-amino-modified nucleotide, a 2'-alkyl-modified nucleotide, a morpholino nucleotide, a phosphoramidate, and a non-natural base comprising nucleotide.

In one embodiment, the modified nucleotide comprises a short sequence of 3'-terminal deoxy-thymine nucleotides (dT).

In one embodiment, the modifications on the nucleotides are 2'-O-methyl, GNA and 2'fluoro modifications.

In one embodiment, substantially all of the nucleotides of the sense strand comprise a modification selected from the group consisting of a 2'-O-methyl modification and a 2'-fluoro modification. In some embodiments, all of the nucleotides of the sense strand comprise a modification selected from the group consisting of a 2'-O-methyl modification and a 2'-fluoro modification.

In one embodiment, substantially all of the nucleotides of the antisense strand comprise a modification selected from the group consisting of a 2'-O-methyl modification and a 2'-fluoro modification. In some embodiments, all of the nucleotides of the antisense strand comprise a modification selected from the group consisting of a 2'-O-methyl modification and a 2'-fluoro modification.

In one embodiment, substantially all of the nucleotides of the sense strand comprise a modification selected from the group consisting of a 2'-O-methyl modification, a 2'-fluoro modification, and a glycol nucleic acid (GNA) modification. In some embodiments, all of the nucleotides of the sense strand comprise a modification selected from the group consisting of a 2'-O-methyl modification, a 2'-fluoro modification, and a glycol nucleic acid (GNA) modification.

In one embodiment, substantially all of the nucleotides of the antisense strand comprise a modification selected from the group consisting of a 2'-O-methyl modification, a 2'-fluoro modification, and a glycol nucleic acid (GNA) modification. In some embodiments, all of the nucleotides of the antisense strand comprise a modification selected from the group consisting of a 2'-O-methyl modification, a 2'-fluoro modification, and a glycol nucleic acid (GNA) modification.

In some embodiments, the dsRNA agent further comprises at least one phosphorothioate internucleotide linkage.

In one embodiment, the dsRNA agent comprises 6-8 phosphorothioate internucleotide linkages.

In one embodiment, the sense strand comprises at least one phosphorothioate or methylphosphonate internucleotide linkage and the antisense strand comprises at least one phosphorothioate or methylphosphonate internucleotide linkage.

In one embodiment, the sense strand comprises at least two phosphorothioate or methylphosphonate internucleotide linkages.

In one embodiment, the antisense strand comprises at least two, at least three, or at least four phosphorothioate or methylphosphonate internucleotide linkages.

In one embodiment, the at least one phosphorothioate or methylphosphonate internucleotide linkage is at the 5'-terminus of one strand, at the 3'-terminus of one strand, or is at both the 5'-terminus and the 3'-terminus of one strand.

In one embodiment, the at least one phosphorothioate or methylphosphonate internucleotide linkage is at the 5'-terminus of the sense strand. In some embodiments, the sense strand comprises two phosphorothioate internucleotide linkages at the 5'-terminus.

In one embodiment, the at least one phosphorothioate or methylphosphonate internucleotide linkage is at both the 5' terminus and the 3' terminus of the antisense strand. In some embodiments, the antisense strand comprises two phosphorothioate internucleotide linkages at the 5'-terminus and two phosphorothioate internucleotide linkages at the 3'-terminus.

In one embodiment, all of the nucleotides of the sense strand comprise a modification selected from the group consisting of a 2'-O-methyl modification and a 2'-fluoro modification, all of the nucleotides of the antisense strand comprise a modification selected from the group consisting of a 2'-O-methyl modification and a 2'-fluoro modification, the sense strand comprises two phosphorothioate internucleotide linkages at the 5'-terminus, and the antisense strand comprises two phosphorothioate internucleotide linkages at the 5'-terminus and two phosphorothioate internucleotide linkages at the 3'-terminus.

In one embodiment, (I) the sense strand comprises: (a) 2'-O-methyl modifications at multiple nucleotides; (b) 2'-fluoro modifications at multiple nucleotides; and (c) multiple phosphorothioate internucleotide linkages; and (II) the antisense strand comprises: (a) 2'-O-methyl modifications at multiple nucleotides; (c) 2'-fluoro modifications at multiple nucleotides; and (d) phosphorothioate internucleotide linkages between multiple nucleotides. Optionally, the dsRNA agent comprises an overhang at the 3'-end of the antisense strand and a blunt end at the 5' end of the antisense strand.

In one embodiment, (I) the sense strand comprises: (a) a length of 21 nucleotides; (b) 2'-O-methyl modifications at nucleotide positions 1-6, 8, and 12-21 counting from the 5' end; (c) 2'-fluoro modifications at nucleotide positions 7 and 9-11 counting from the 5' end; and (d) phosphorothioate internucleotide linkages between nucleotide positions 1 and 2 and between nucleotide positions 2 and 3 counting from the 5' end; and (II) the antisense strand comprises: (a) a length of 23 nucleotides; (b) 2'-O-methyl modifications at positions 1, 3-5, 7, 10-13, 15, and 17-23 counting from the 5' end; (c) 2'-fluoro modifications at positions 2, 6, 8, 9, 14, and 16 counting from the 5' end; and (d) phosphorothioate internucleotide linkages between nucleotide positions 1 and 2, between nucleotide positions 2 and 3, between nucleotide positions 21 and 22, and between nucleotide positions 22 and 23 (counting from the 5' end), wherein the dsRNA agent comprises a two-nucleotide overhang at the 3'-end of the antisense strand and a blunt end at the 5' end of the antisense strand.

In one embodiment, the antisense strand comprises any one of the antisense strand sequences in SEQ ID NOS: 3, 5, 7, 9, 11, and 13, and/or wherein the sense strand comprises any one of the sense strand sequences in SEQ ID NOS: 2, 4, 6, 8, 10, and 12.

In one embodiment, the sense strand is no more than 30 nucleotides in length. In another embodiment, the antisense strand is no more than 30 nucleotides in length. In one embodiment, the sense strand and the antisense strand are each independently no more than 30 nucleotides in length.

In one embodiment, at least one strand comprises a 3'-overhang of at least 1 nucleotide. In another embodiment, at least one strand comprises a 3'-overhang of at least 2 nucleotides. In one embodiment, the antisense strand comprises the 3'-overhang.

The double stranded region may be 15-30 nucleotide pairs in length; 17-23 nucleotide pairs in length; 17-25 nucleotide pairs in length; 23-27 nucleotide pairs in length; 19-21 nucleotide pairs in length; 21-23 nucleotide pairs in length, or 21 nucleotide pairs in length.

The sense strand and the antisense strand may each be independently 19-30 nucleotides; 19-25 nucleotides; 19-23 nucleotides; or 21-23 nucleotides in length, or 21 nucleotides in length.

In one embodiment, the region of complementarity is at least 17 nucleotides in length. In other embodiments, the region of complementarity is 19-30 nucleotides in length; 19-25 nucleotides in length; or 21-23 nucleotides in length.

In one embodiment, the region of complementarity is at least 17 nucleotides in length. In other embodiments, the region of complementarity is 19-30 nucleotides in length; 19-25 nucleotides in length; or 21-23 nucleotides in length.

In one embodiment, the region of complementarity is at least 85% complementary to the sequence between the start of exon 1A and the start of exon 2 of the C9orf72 gene. In some embodiments, the antisense strand comprises a sequence of 15-25 contiguous nucleotides having at least 85% complementarity to a sequence of 15-25 contiguous nucleotides present in the sequence between the start of exon 1A and the start of exon 2 of the C9orf72 target RNA. In other embodiments, the region of complementarity is at least 90% complementary to the sequence between the start of exon 1A and the start of exon 2 of the C9orf72 target RNA. In one embodiment, the region of complementarity is at least 95% complementary to the sequence between the start of exon 1A and the start of exon 2 of the C9orf72 target RNA. In some embodiments, the region of complementarity is 100% complementary to the sequence between the start of exon 1A and the start of exon 2 of the C9orf72 target RNA. In some embodiments, the region of complementarity is 100% complementary to the sequence between the end of exon 1A and the start of the hexanucleotide repeat region of the C9orf72 target RNA.

In one embodiment, the region of complementarity is at least 85% complementary to the sequence between the end of exon 1A and the start of hexanucleotide repeat in intron 1A of the C9orf72 gene. In some embodiments, the antisense strand comprises a sequence of 15-25 contiguous nucleotides having at least 85% complementarity to a sequence of 15-25 contiguous nucleotides present in the sequence between the end of exon 1A and the start of hexanucleotide repeat in intron 1A of the C9orf72 target RNA. In other embodiments, the region of complementarity is at least 90% complementary to the sequence between the end of exon 1A and the start of hexanucleotide repeat in intron 1A of the C9orf72 target RNA. In one embodiment, the region of complementarity is at least 95% complementary to the sequence between the end of exon 1A and the start of hexanucleotide repeat in intron 1A of the C9orf72 target RNA. In some embodiments, the region of complementarity is 100% complementary to the sequence between the end of exon 1A and the start of hexanucleotide repeat in intron 1A of the C9orf72 target RNA.

In one embodiment, one or more lipophilic moieties are conjugated to one or more internal positions on at least one strand, such as via a linker or carrier.

In one embodiment, the internal positions include all positions except the terminal two positions from each end of the at least one strand.

In another embodiment, the internal positions include all positions except the terminal three positions from each end of the at least one strand.

In one embodiment, the internal positions exclude a cleavage site region of the sense strand.

In one embodiment, the internal positions include all positions except positions 9-12, counting from the 5'-end of the sense strand.

In another embodiment, the internal positions include all positions except positions 11-13, counting from the 3'-end of the sense strand.

In one embodiment, the internal positions exclude a cleavage site region of the antisense strand.

In one embodiment, the internal positions include all positions except positions 12-14, counting from the 5'-end of the antisense strand.

In one embodiment, the internal positions include all positions except positions 11-13 on the sense strand, counting from the 3'-end, and positions 12-14 on the antisense strand, counting from the 5'-end.

In one embodiment, the one or more lipophilic moieties are conjugated to one or more of the internal positions selected from the group consisting of positions 4-8 and 13-18 on the sense strand, and positions 6-10 and 15-18 on the antisense strand, counting from the 5'end of each strand.

In another embodiment, the one or more lipophilic moieties are conjugated to one or more of the internal positions selected from the group consisting of positions 5, 6, 7, 15, and 17 on the sense strand, and positions 15 and 17 on the antisense strand, counting from the 5'-end of each strand.

In one embodiment, the internal positions in the double stranded region exclude a cleavage site region of the sense strand.

In one embodiment, the sense strand is 21 nucleotides in length, the antisense strand is 23 nucleotides in length, and the lipophilic moiety is conjugated to position 21, position 20, position 15, position 1, position 7, position 6, or position 2 of the sense strand or position 16 of the antisense strand.

In one embodiment, the lipophilic moiety is conjugated to position 21, position 20, position 15, position 1, or position 7 of the sense strand.

In another embodiment, the lipophilic moiety is conjugated to position 21, position 20, or position 15 of the sense strand.

In yet another embodiment, the lipophilic moiety is conjugated to position 20 or position 15 of the sense strand.

In one embodiment, the lipophilic moiety is conjugated to position 16 of the antisense strand.

In one embodiment, the lipophilic moiety is an aliphatic, alicyclic, or polyalicyclic compound.

In one embodiment, the lipophilic moiety is selected from the group consisting of lipid, cholesterol, retinoic acid, cholic acid, adamantane acetic acid, 1-pyrene butyric acid, dihydrotestosterone, 1,3-bis-O(hexadecyl)glycerol, geranyloxyhexyanol, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine.

In one embodiment, the lipophilic moiety contains a saturated or unsaturated C4-C30 hydrocarbon chain, and an optional functional group selected from the group consisting of hydroxyl, amine, carboxylic acid, sulfonate, phosphate, thiol, azide, and alkyne.

In one embodiment, the lipophilic moiety contains a saturated or unsaturated C6-C18 hydrocarbon chain.

In one embodiment, the lipophilic moiety contains a saturated or unsaturated C16 hydrocarbon chain.

In one embodiment, the saturated or unsaturated C16 hydrocarbon chain is conjugated to position 6, counting from the 5'-end of the strand.

In one embodiment, the lipophilic moiety is conjugated via a carrier that replaces one or more nucleotide(s) in the internal position(s) or the double stranded region.

In one embodiment, the carrier is a cyclic group selected from the group consisting of pyrrolidinyl, pyrazolinyl, pyrazolidinyl, imidazolinyl, imidazolidinyl, piperidinyl, piperazinyl, [1,3]dioxolanyl, oxazolidinyl, isoxazolidinyl, morpholinyl, thiazolidinyl, isothiazolidinyl, quinoxalinyl, pyridazinonyl, tetrahydrofuranyl, and decalinyl; or is an acyclic moiety based on a serinol backbone or a diethanolamine backbone.

In one embodiment, the lipophilic moiety is conjugated to the double-stranded iRNA agent via a linker containing an ether, thioether, urea, carbonate, amine, amide, maleimide-thioether, disulfide, phosphodiester, sulfonamide linkage, a product of a click reaction, or carbamate.

In one embodiment, the lipophilic moiety is conjugated to a nucleobase, sugar moiety, or internucleosidic linkage.

In one embodiment, the lipophilic moiety or targeting ligand is conjugated via a bio-clevable linker selected from the group consisting of DNA, RNA, disulfide, amide, funtionalized monosaccharides or oligosaccharides of galactosamine, glucosamine, glucose, galactose, mannose, and combinations thereof.

In one embodiment, the 3' end of the sense strand is protected via an end cap which is a cyclic group having an amine, said cyclic group being selected from the group consisting of pyrrolidinyl, pyrazolinyl, pyrazolidinyl, imidazolinyl, imidazolidinyl, piperidinyl, piperazinyl, [1,3]dioxolanyl, oxazolidinyl, isoxazolidinyl, morpholinyl, thiazolidinyl, isothiazolidinyl, quinoxalinyl, pyridazinonyl, tetrahydrofuranyl, and decalinyl.

In one embodiment, the dsRNA agent further comprises a targeting ligand that targets a liver tissue.

In one embodiment, the targeting ligand is a GalNAc conjugate.

In one embodiment, the dsRNA agent further comprises a terminal, chiral modification occurring at the first internucleotide linkage at the 3' end of the antisense strand, having the linkage phosphorus atom in Sp configuration, a terminal, chiral modification occurring at the first internucleotide linkage at the 5' end of the antisense strand, having the linkage phosphorus atom in Rp configuration, and a terminal, chiral modification occurring at the first internucleotide linkage at the 5' end of the sense strand, having the linkage phosphorus atom in either Rp configuration or Sp configuration.

In another embodiment, the dsRNA agent further comprises a terminal, chiral modification occurring at the first and second internucleotide linkages at the 3' end of the antisense strand, having the linkage phosphorus atom in Sp configuration, a terminal, chiral modification occurring at the first internucleotide linkage at the 5' end of the antisense strand, having the linkage phosphorus atom in Rp configuration, and a terminal, chiral modification occurring at the first internucleotide linkage at the 5' end of the sense strand, having the linkage phosphorus atom in either Rp or Sp configuration.

In yet another embodiment, the dsRNA agent further comprises a terminal, chiral modification occurring at the first, second and third internucleotide linkages at the 3' end of the antisense strand, having the linkage phosphorus atom in Sp configuration, a terminal, chiral modification occurring at the first internucleotide linkage at the 5' end of the antisense strand, having the linkage phosphorus atom in Rp configuration, and a terminal, chiral modification occurring at the first internucleotide linkage at the 5' end of the sense strand, having the linkage phosphorus atom in either Rp or Sp configuration.

In another embodiment, the dsRNA agent further comprises a terminal, chiral modification occurring at the first, and second internucleotide linkages at the 3' end of the antisense strand, having the linkage phosphorus atom in Sp configuration, a terminal, chiral modification occurring at the third internucleotide linkages at the 3' end of the antisense strand, having the linkage phosphorus atom in Rp configuration, a terminal, chiral modification occurring at the first internucleotide linkage at the 5' end of the antisense strand, having the linkage phosphorus atom in Rp configuration, and a terminal, chiral modification occurring at the first internucleotide linkage at the 5' end of the sense strand, having the linkage phosphorus atom in either Rp or Sp configuration.

In another embodiment, the dsRNA agent further comprises a terminal, chiral modification occurring at the first, and second internucleotide linkages at the 3' end of the antisense strand, having the linkage phosphorus atom in Sp configuration, a terminal, chiral modification occurring at the first, and second internucleotide linkages at the 5' end of the antisense strand, having the linkage phosphorus atom in Rp configuration, and a terminal, chiral modification occurring at the first internucleotide linkage at the 5' end of the sense strand, having the linkage phosphorus atom in either Rp or Sp configuration.

In one embodiment, the dsRNA agent further comprises a phosphate or phosphate mimic at the 5'-end of the antisense strand.

In one embodiment, the phosphate mimic is a 5'-vinyl phosphonate (VP).

In one embodiment, the base pair at the 1 position of the 5'-end of the antisense strand of the duplex is an AU base pair.

In one embodiment, the sense strand has a total of 21 nucleotides and the antisense strand has a total of 23 nucleotides.

In one embodiment, the dsRNA agent inhibits expression of the C9orf72 target RNA comprising the hexanucleotide repeat by at least 10%, at least 20%, at least 30%, at least 40%, at least 50%, or at least 60% within 24-48 hours after administration to a cell expressing the C9orf72 target RNA comprising the hexanucleotide repeat.

In one embodiment, the dsRNA agent selectively inhibits expression of the C9orf72 target RNA comprising the hexanucleotide repeat relative to expression of a mature C9orf72 messenger RNA.

In one embodiment, the dsRNA agent inhibits expression of the mature C9orf72 messenger RNA by less than 50%, less than 40%, less than 30%, less than 20%, or less than 10% within 24-48 hours after administration to a cell expressing the mature C9orf72 messenger RNA.

In one embodiment, the dsRNA agent reduces dipeptide repeat protein synthesis within 24-48 hours after administration to a cell expressing the C9orf72 target RNA comprising the hexanucleotide repeat. In some embodiments, the dsRNA agent reduces dipeptide repeat protein synthesis by at least 10%, at least 20%, at least 30%, at least 40%, at least 50%, at least 60%, at least 70%, or at least 80% within 24-48 hours after administration to the cell.

The present invention also provides cells and pharmaceutical compositions for inhibiting expression of a gene encoding C9orf72 comprising the dsRNA agents of the invention, such.

In one embodiment, the dsRNA agent is in an unbuffered solution, such as saline or water.

In another embodiment, the dsRNA agent is in a buffer solution, such as a buffer solution comprising acetate, citrate, prolamine, carbonate, or phosphate or any combination thereof; or phosphate buffered saline (PBS).

In one aspect, the present invention provides a method of inhibiting expression of a C9orf72, such as a C9orf72 RNA containing a hexanucleotide-repeat, such as a C9orf72 gene comprising multiple contiguous copies of a hexanucleotide repeat, in a cell, e.g., a neuron, such as a motor neuron, the method comprising contacting the cell with a dsRNA agent of the invention, or a pharmaceutical composition of the invention, thereby inhibiting expression of the C9orf72 gene in the cell.

In another aspect, the present invention provides methods of reducing dipeptide repeat protein synthesis or dipeptide repeat protein aggregates in a cell. The methods include introducing into the cell a dsRNA agent of the invention, thereby reducing dipeptide repeat protein synthesis or dipeptide repeat protein aggregates in the cell.

In another aspect, the present invention provides methods of reducing nuclear and/or cytoplasmic sense and/or antisense C9orf72 RNA foci in a cell. The methods include introducing into the cell a dsRNA agent of the invention, thereby reducing nuclear and/or cytoplasmic sense and/or antisense C9orf72 RNA foci in the cell.

In one embodiment, cell is within a subject.

In one embodiment, the subject is a human.

In one embodiment, the subject has or is at risk of developing a C9orf72-associated disorder, such as a C9orf72-hexanucleotide-repeat-expansion-associated disease, condition, or disorder.

In one embodiment, the C9orf72-associated disorder is selected from the group consisting of C9orf72 amyotrophic lateral sclerosis/frontotemporal dementia or Huntington-Like Syndrome Due To C9orf72 Expansions.

In one embodiment, contacting the cell with the dsRNA agent inhibits the expression of C9orf72 by no more than 50%.

In one embodiment, the dsRNA agent inhibits expression of a C9orf72 target mRNA comprising the hexanucleotide repeat by at least 10%, at least 20%, at least 30%, at least 40%, at least 50%, or at least 60% within 24-48 hours after administration to a cell expressing the C9orf72 target RNA comprising the hexanucleotide repeat.

In some embodiments, the dsRNA agent selectively inhibits expression of a C9orf72 target RNA comprising the hexanucleotide repeat relative to expression of a mature C9orf72 messenger RNA. In other embodiments, the dsRNA agent inhibits expression of a mature C9orf72 messenger RNA by less than 50%, less than 40%, less than 30%, less than 20%, or less than 10% within 24-48 hours after administration to a cell expressing the mature C9orf72 messenger RNA.

In some embodiments, the dsRNA agent reduces dipeptide repeat protein synthesis or dipeptide repeat protein aggregates in the cell.

In some embodiments, the dsRNA agent reduces nuclear and/or cytoplasmic sense and/or antisense C9orf72 RNA foci in the cell.

In one embodiment, inhibiting expression of C9orf72 decreases C9orf72 protein level in serum of the subject by no more than 50%.

In some embodiments, the dsRNA agent reduces dipeptide repeat protein synthesis or dipeptide repeat protein aggregates by at least 10%, at least 20%, at least 30%, at least 40%, at least 50%, at least 60%, at least 70%, or at least 80% within 24-48 hours after administration to the cell.

In one aspect, the present invention provides method of treating a subject having a disorder that would benefit from knocking down a target C9orf72 RNA, such as a C9orf72-hexanucleotide-repeat-expansion-associated disease, condition, or disorder, comprising administering to the subject a therapeutically effective amount of a dsRNA agent of the invention, or a pharmaceutical composition of the invention, thereby treating the subject having the disorder that would benefit from reduction in C9orf72 expression.

In another aspect, the present invention provides a method of preventing at least one symptom in a subject having a disorder that would benefit from reduction in C9orf72 expression, such as a C9orf72-hexanucleotide-repeat-expansion-associated disease, condition, or disorder, comprising administering to the subject a prophylactically effective amount of a dsRNA agent of the invention, or a pharmaceutical composition of the invention, thereby preventing at least one symptom in the subject having the disorder that would benefit from reduction in C9orf72 expression.

In one embodiment, the disorder is a C9orf72-associated disorder.

In one embodiment, the C9orf723-associated disorder is selected from the group consisting of C9orf72 amyotrophic lateral sclerosis/frontotemporal dementia or Huntington-Like Syndrome Due To C9orf72 Expansions.

In one embodiment, the subject is human.

In one embodiment, the administration of the agent to the subject causes a decrease in C9orf72 protein accumulation.

In some embodiments, the method reduces dipeptide repeat protein synthesis or reduces dipeptide repeat protein aggregates in the subject. In some embodiments, the method decreases expression of a C9orf72 target RNA comprising a hexanucleotide repeat comprising multiple contiguous copies of SEQ ID NO: 1 in the subject.

In one embodiment, the dsRNA agent is administered to the subject at a dose of about 0.01 mg/kg to about 50 mg/kg.

In one embodiment, the dsRNA agent is administered to the subject subcutaneously.

In another embodiment, the dsRNA agent is administered to the subject intrathecally.

In one embodiment, the methods of the invention further comprise determining the level of C9orf72 in a sample(s) from the subject.

In one embodiment, the level of C9orf72 in the subject sample(s) is a C9orf72 protein level in a blood, serum, or cerebrospinal fluid sample(s).

In one embodiment, the methods of the invention further comprise administering to the subject an additional therapeutic agent.

In one aspect, the present invention provides a kit comprising a dsRNA agent of the invention, or a pharmaceutical composition of the invention.

In another aspect, the present invention provides a vial comprising a dsRNA agent of the invention, or a pharmaceutical composition of the invention.

In yet another aspect, the present invention provides a syringe comprising a dsRNA agent of the invention, or a pharmaceutical composition of the invention.

BRIEF DESCRIPTION OF THE FIGURES

FIG. 8 shows results from capillary electrophoresis. Signal intensity is on the Y axis, and PCR product size is on the X axis. The readout is the number of peaks.

FIGS. 12A-12D disclose "G4C2 3X" as SEQ ID NO: 140.

FIGS. 12E-12H discloses "G4C2 3X" as SEQ ID NO: 140.

FIG. 13 (bottom) shows quantification of the western slot blots in the top portion of the figure. FIG. 13 discloses "G4C2" as SEQ ID NO: 1.

FIG. 18B discloses "(G4C2)n" as SEQ ID NO: 1.

DETAILED DESCRIPTION OF THE INVENTION

Figure 1:
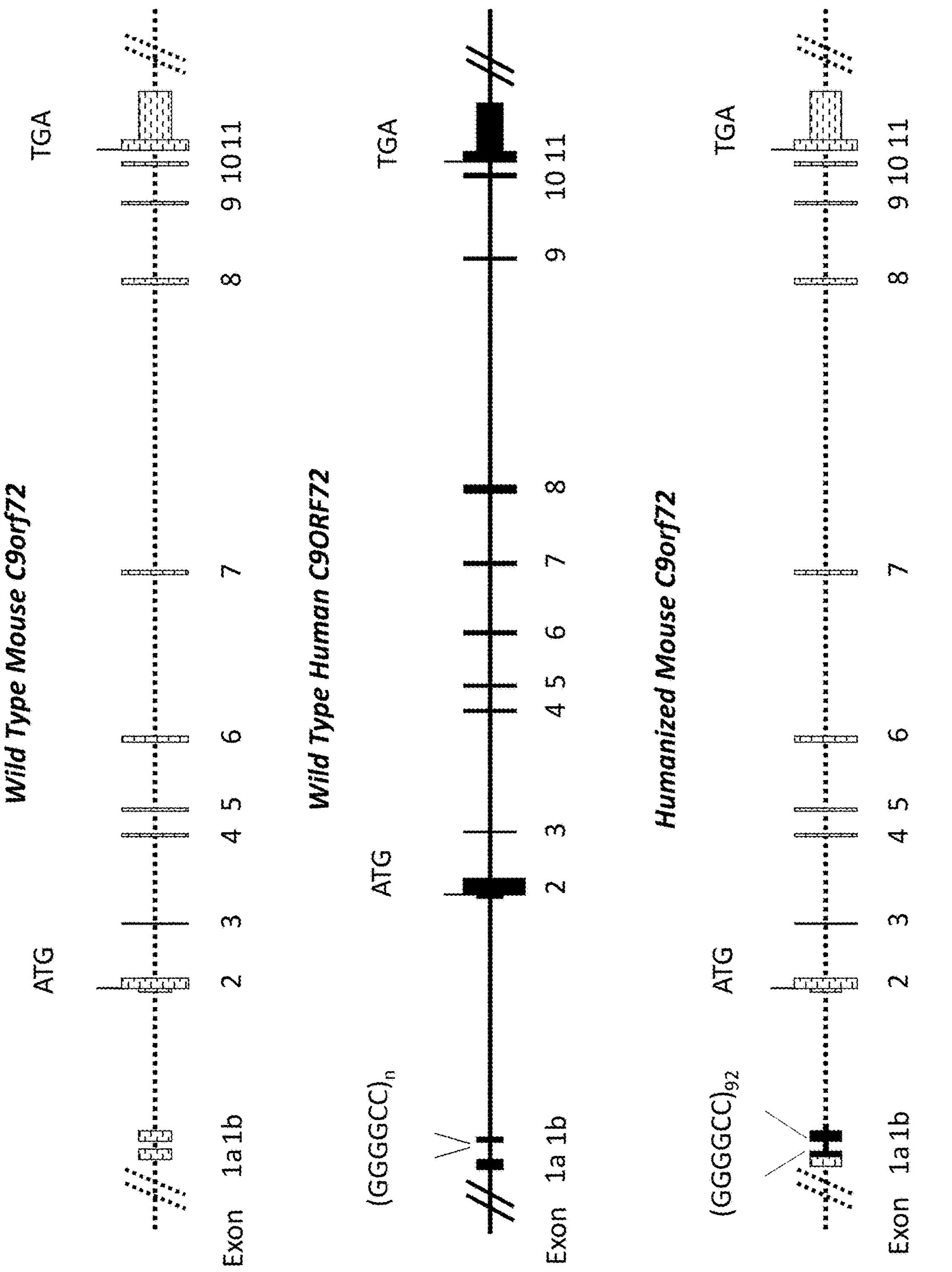
FIG. 1 (not to scale) are schematics of the wild type mouse C9orf72 locus, the wild type human C9orf72 locus, and a humanized mouse C9orf72 locus comprising 92 repeats of the hexanucleotide sequence set forth in SEQ ID NO: 1 (GGGGCC) ("(GGGGCC)92" disclosed as SEQ ID NO: 141) (MAID8029a). Mouse sequences are indicated by dashed lines and boxes with dashes, and human sequences are indicated by solid black. The exons are represented by the boxes. The position of the hexanucleotide repeat sequence is shown.

The present disclosure provides RNAi compositions, which effect the RNA-induced silencing complex (RISC)-mediated cleavage of RNA transcripts of a C9orf72 gene, such as a C9orf72 gene having an expanded GGGGCC ($G_4C_2$) repeat (SEQ ID NO: 1). The C9orf72 gene may be within a cell, e.g., a cell within a subject, such as a human. The use of these iRNAs enables the targeted degradation of mRNAs of the corresponding gene (C9orf72 gene) in mammals.

The iRNAs of the invention have been designed to target a C9orf72 target RNA, e.g., a C9orf72 target RNA having an expanded GGGGCC hexanucleotide repeat (SEQ ID NO: 1) in an intron of the gene, and having a combination of nucleotide modifications. The agents may target a mature C9orf72 mRNA (an mRNA having the introns spliced out) or a C9orf7 mRNA precursor (an mRNA containing introns). The iRNAs of the invention may inhibit the expression of the C9orf7gene (e.g., mature mRNA) by no more than about 50%, and reduce the level of sense- and antisense-containing foci and aberrant dipeptide-repeat (DPR) proteins (poly(GA), poly(GR), poly(GP), poly(PA), and poly(PR)), and/or inhibit the expression of the C9orf7gene (e.g., precursor mRNA) by more than about 50%, and reduce the level of sense- and antisense-containing foci and aberrant dipeptide-repeat (DPR) proteins (poly(GA), poly (GR), poly(GP), poly(PA), and poly(PR)). Without intending to be limited by theory, it is believed that a combination or sub-combination of the foregoing properties and the specific target sites, or the specific modifications in these iRNAs confer to the iRNAs of the invention improved efficacy, stability, potency, durability, and safety.

Accordingly, the present disclosure also provides methods of using the RNAi compositions of the disclosure for inhibiting the expression of a C9orf72 gene or for treating a subject having a disorder that would benefit from inhibiting or reducing the expression of a C9orf72 gene, e.g., a C9orf72-associated disease, for example, a disease associated with an expanded GGGGCC hexanucleotide repeat (SEQ ID NO: 1) in an intron of the C9orf72 gene, such as C9orf72 amyotrophic lateral sclerosis/frontotemporal dementia, or Huntington's disease, e.g., Huntington-Like Syndrome Due To C9orf72 Expansions.

The RNAi agents of the disclosure include an RNA strand (the antisense strand) having a region which is about 30 nucleotides or less in length, e.g., 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 nucleotides in length, which region is substantially complementary to at least part of an target RNA transcript of a C9orf72 gene, e.g., a C9orf72 intron. In certain embodiments, the RNAi agents of the disclosure include an RNA strand (the antisense strand) having a region which is about 21-23 nucleotides in length, which region is substantially complementary to at least part of an target RNA transcript of a C9orf72 gene, e.g., a C9orf72 intron.

In certain embodiments, the RNAi agents of the disclosure include an RNA strand (the antisense strand) which can include longer lengths, for example up to 66 nucleotides, e.g., 36-66, 26-36, 25-36, 31-60, 22-43, 27-53 nucleotides in length with a region of at least 19 contiguous nucleotides that is substantially complementary to at least a part of an mRNA transcript of a C9orf72 gene. These RNAi agents with the longer length antisense strands preferably include a second RNA strand (the sense strand) of 20-60 nucleotides in length wherein the sense and antisense strands form a duplex of 18-30 contiguous nucleotides.

The use of these RNAi agents enables the targeted degradation of target RNAs of a C9orf72 gene in mammals. Thus, methods and compositions including these RNAi agents are useful for treating a subject who would benefit by knockdown of a target C9orf72 RNA, a reduction in normal C9orf72 protein and/or or a reduction reduction of the pathogenic dipeptide repeat proteins that are generated from the pathogenic hexnucleotide repeat expansion, such as a subject having a C9orf72-associated disease, such as C9orf72 amyotrophic lateral sclerosis/frontotemporal dementia or Huntington's disease, e.g., Huntington-Like Syndrome Due To C9orf72 Expansions.

The following detailed description discloses how to make and use compositions containing RNAi agents to inhibit the expression of a C9orf72 gene, as well as compositions and methods for treating subjects having diseases and disorders that would benefit from inhibition or reduction of the expression of the genes.

I. Definitions

In order that the present disclosure may be more readily understood, certain terms are first defined. In addition, it should be noted that whenever a value or range of values of a parameter are recited, it is intended that values and ranges intermediate to the recited values are also intended to be part of this disclosure.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to". The term "or" is used herein to mean, and is used interchangeably with, the term "and/or," unless context clearly indicates otherwise.

The term "about" is used herein to mean within the typical ranges of tolerances in the art. For example, "about" can be understood as about 2 standard deviations from the mean. In certain embodiments, about means±10%. In certain embodiments, about means±5%. When about is present before a series of numbers or a range, it is understood that "about" can modify each of the numbers in the series or range.

The term "at least" prior to a number or series of numbers is understood to include the number adjacent to the term "at least", and all subsequent numbers or integers that could logically be included, as clear from context. For example, the number of nucleotides in a nucleic acid molecule must be an integer. For example, "at least 18 nucleotides of a 21 nucleotide nucleic acid molecule" means that 18, 19, 20, or 21 nucleotides have the indicated property. When at least is present before a series of numbers or a range, it is understood that "at least" can modify each of the numbers in the series or range.

As used herein, "no more than" or "less than" is understood as the value adjacent to the phrase and logical lower values or integers, as logical from context, to zero. For example, a duplex with an overhang of "no more than 2 nucleotides" has a 2, 1, or 0 nucleotide overhang. When "no more than" is present before a series of numbers or a range, it is understood that "no more than" can modify each of the numbers in the series or range.

As used herein, methods of detection can include determination that the amount of analyte present is below the level of detection of the method.

In the event of a conflict between an indicated target site and the nucleotide sequence for a sense or antisense strand, the indicated sequence takes precedence.

In the event of a conflict between a chemical structure and a chemical name, the chemical structure takes precedence.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which the event or circumstance does not.

The term "C9orf72" gene, also known as "C9orf72-SMCR8 Complex Subunit," Guanine Nucleotide Exchange C9orf72," "Chromosome 9 Open Reading Frame 72, "Protein C9orf72," "DENNL72," "FTDALS1," "ALSFTD", and "FTDALS," refers to the gene encoding the well-known protein involved in the regulation of endosomal trafficking, C9orf72. The C9orf72 protein has been shown to interact with Rab proteins that are involved in autophagy and endocytic transport. Expansion of a GGGGCC repeat (SEQ ID NO: 1) from about 2 to about 22 copies to about 700 to about 1600 copies in the intronic sequence between alternate 5' exons in transcripts from this gene is associated with C9orf72 amyotrophic lateral sclerosis/frontotemporal dementia and Huntington's disease, e.g., Huntington-Like Syndrome Due To C9orf72 Expansions. Alternative splicing results in multiple transcript variants encoding different isoforms.

Exemplary nucleotide and amino acid sequences of C9orf72 can be found, for example, at GenBank Accession No. NM_001256054.2 (*Homo sapiens* C9orf72, SEQ ID NO:121, reverse complement SEQ ID NO:125; GenBank Accession No.: XM_005581570.2 (*Macaca fascicularis* C9orf72, SEQ ID NO:122, reverse complement SEQ ID NO:126); GenBank Accession No. NM_001081343.2 (*Mus musculus* C9orf72, SEQ ID NO:123, reverse complement SEQ ID NO:127); and GenBank Accession No.: NM_001007702.1 (*Rattus norvegicus* C9orf72, SEQ ID NO:124, reverse complement SEQ ID NO:128).

Additional nucleotide and amino acid sequences of human C9orf72 can be found, for example, at GenBank Accession No. NM_145005.6, transcript variant 1 (SEQ ID NO:129, reverse complement SEQ ID NO:130); and NM_018325.5, transcript variant 2 (SEQ ID NO:131, reverse complement SEQ ID NO:132).

The nucleotide sequence of the genomic region of human chromosome 9 harboring the C9orf72 gene may be found in, for example, the Genome Reference Consortium Human Build 38 (also referred to as Human Genome build 38 or GRCh38) available at GenBank. The nucleotide sequence of the genomic region of human chromosome 9 harboring the C9orf72 gene may also be found at, for example, GenBank Accession No. NC_000009.12 (SEQ ID NO:133, reverse complement SEQ ID NO:134), corresponding to nucleotides 27546545 to 27573866 of human chromosome 9. The nucleotide sequence of the human c9orf72 gene may be found in, for example, GenBank Accession No. NG_031977.1

Further examples of C9orf72 sequences can be found in publicly available databases, for example, GenBank, OMIM, and UniProt.

Additional information on C9orf72 can be found, for example, at www.ncbi.nlm.nih.gov/gene/203228. The term C9orf72 as used herein also refers to variations of the C9orf72 gene including variants provided in the clinical variant database, for example, at www.ncbi.nlm.nih.gov/clinvar/?term=NM_001256054.2.

The entire contents of each of the foregoing GenBank Accession numbers and the Gene database numbers are incorporated herein by reference as of the date of filing this application.

As used herein, "target sequence" refers to a contiguous portion of the nucleotide sequence of an mRNA molecule formed during the transcription of a C9orf72 gene, including mRNA that is a product of RNA processing of a primary transcription product. In one embodiment, the target portion of the sequence will be at least long enough to serve as a substrate for RNAi-directed cleavage at or near that portion of the nucleotide sequence of an mRNA molecule formed during the transcription of a C9orf72 gene.

A C9orf72 mRNA (target C9orf72 RNA) is an RNA transcribed from a C9orf72 gene. A C9orf72 mRNA includes C9orf72 mature mRNA, a C9orf72 precursor mRNA, or any portions thereof (e.g., spliced out intronic regions or alternatively spliced RNAs). C9orf72 mature mRNA is C9orf72 mRNA in which the introns have been removed (spliced out) and from which C9orf72 protein is translated. C9orf72 precursor mRNA is C9orf72 mRNA in which at least 1 intron, particularly the first intron (intron 1), has not been removed.

A C9orf72 protein includes any protein expressed from a C9orf72 mRNA. A C9orf72 protein includes the protein expressed from C9orf72 mature mRNA, as well as dipeptide repeat proteins (e.g., poly(glycine-alanine), poly(glycine-proline), poly(glycine-arginine), poly(alanine-proline), and poly(proline-arginine)) resulting from repeat-associated non-AUG (AUG) translation from C9orf72 RNAs containing hexanucleotide repeats.

A C9orf72 target RNA may include a hexanucleotide repeat comprising multiple contiguous copies of SEQ ID NO: 1. The C9orf72 target RNA can be, for example, one with a pathogenic hexanucleotide repeat expansion (having, for example, at least about 30, at least about 35, at least about 40, at least about 50, at least about 60, at least about 70, at least about 80, at least about 100, at least about 200, at least about 300, at least about 400, or at least about 500 copies of the hexanucleotide repeat).

The target sequence may be about 15-30 nucleotides in length. For example, the target sequence can be from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 nucleotides in length. In certain embodiments, the target sequence is 19-23 nucleotides in length, optionally 21-23 nucleotides in length. Ranges and lengths intermediate to the above recited ranges and lengths are also contemplated to be part of the disclosure.

As used herein, the term "strand comprising a sequence" refers to an oligonucleotide comprising a chain of nucleotides that is described by the sequence referred to using the standard nucleotide nomenclature.

"G," "C," "A," "T", and "U" each generally stand for a nucleotide that contains guanine, cytosine, adenine, thymidine, and uracil as a base, respectively in the context of a modified or unmodified nucleotide. However, it will be understood that the term "ribonucleotide" or "nucleotide" can also refer to a modified nucleotide, as further detailed below, or a surrogate replacement moiety (see, e.g., Table 11). The skilled person is well aware that guanine, cytosine, adenine, thymidine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the disclosure by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the disclosure.

The terms "iRNA", "RNAi agent," "iRNA agent," "RNA interference agent" as used interchangeably herein, refer to an agent that contains RNA as that term is defined herein, and which mediates the targeted cleavage of an RNA transcript via an RNA-induced silencing complex (RISC) pathway. RNA interference (RNAi) is a process that directs the sequence-specific degradation of mRNA. RNAi modulates, e.g., inhibits, the expression of C9orf72, a C9orf72-related transcript, or a C9orf72-related peptide in a cell, e.g., a cell within a subject, such as a mammalian subject.

In one embodiment, an RNAi agent of the disclosure includes a single stranded RNAi that interacts with a target RNA sequence, e.g., a C9orf72 target mRNA sequence, to direct the cleavage of the target RNA. Without wishing to be bound by theory it is believed that long double stranded RNA introduced into cells is broken down into double-stranded short interfering RNAs (siRNAs) comprising a sense strand and an antisense strand by a Type III endonuclease known as Dicer (Sharp et al. (2001) *Genes Dev.* 15:485). Dicer, a ribonuclease-III-like enzyme, processes these dsRNA into 19-23 base pair short interfering RNAs with characteristic two base 3' overhangs (Bernstein, et al., (2001) *Nature* 409:363). These siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the disclosure relates to a single stranded RNA (ssRNA) (the antisense strand of a siRNA duplex) generated within a cell and which promotes the formation of a RISC complex to effect silencing of the target gene, i.e., a C9orf72 gene. Accordingly, the term "siRNA" is also used herein to refer to an RNAi as described above.

In another embodiment, the RNAi agent may be a single-stranded RNA that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded RNAs are described in U.S. Pat. No. 8,101,348 and in Lima et al., (2012) *Cell* 150:883-894, the entire contents of each of which are hereby incorporated herein by reference. Any of the antisense nucleotide sequences described herein may be used as a single-stranded siRNA as described herein or as chemically modified by the methods described in Lima et al., (2012) *Cell* 150:883-894.

In another embodiment, a "RNAi agent" for use in the compositions and methods of the disclosure is a double stranded RNA and is referred to herein as a "double stranded RNAi agent," "double stranded RNA (dsRNA) molecule," "dsRNA agent," or "dsRNA". The term "dsRNA" refers to a complex of ribonucleic acid molecules, having a duplex structure comprising two anti-parallel and substantially complementary nucleic acid strands, referred to as having "sense" and "antisense" orientations with respect to a target RNA, i.e., a C9orf72 gene. In some embodiments of the disclosure, a double stranded RNA (dsRNA) triggers the degradation of a target RNA, e.g., an mRNA, through a post-transcriptional gene-silencing mechanism referred to herein as RNA interference or RNAi.

The dsRNA agents described herein can differ from (i.e., do not include) antisense oligonucleotides (ASOs) or gapmer antisense oligonucleotides (ASOs).

In general, a dsRNA molecule can include ribonucleotides, but as described in detail herein, each or both strands can also include one or more non-ribonucleotides, e.g., a deoxyribonucleotide, a modified nucleotide. In addition, as used in this specification, an "RNAi agent" may include ribonucleotides with chemical modifications; an RNAi agent may include substantial modifications at multiple nucleotides. As used herein, the term "modified nucleotide" refers to a nucleotide having, independently, a modified sugar moiety, a modified internucleotide linkage, or a modified nucleobase.

Thus, the term modified nucleotide encompasses substitutions, additions or removal of, e.g., a functional group or atom, to internucleoside linkages, sugar moieties, or nucleobases. The modifications suitable for use in the agents of the disclosure include all types of modifications disclosed herein or known in the art. Any such modifications, as used in a siRNA type molecule, are encompassed by "RNAi agent" for the purposes of this specification and claims.

In certain embodiments of the instant disclosure, inclusion of a deoxy-nucleotide if present within an RNAi agent can be considered to constitute a modified nucleotide.

The duplex region may be of any length that permits specific degradation of a desired target RNA through a RISC pathway, and may range from about 15-36 base pairs in length, for example, about 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 base pairs in length. In certain embodiments, the duplex region is 19-21 base pairs in length, e.g., 21 base pairs in length. Ranges and lengths intermediate to the above recited ranges and lengths are also contemplated to be part of the disclosure.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at at least 4, at least 5, at least 6, at least 7, at least 8, at least 9, at least 10, at least 20, at least 23 or more unpaired nucleotides or nucleotides not directed to the target site of the dsRNA. In some embodiments, the hairpin loop can be 10 or fewer nucleotides. In some embodiments, the hairpin loop can be 8 or fewer unpaired nucleotides. In some embodiments, the hairpin loop can be 4-10 unpaired nucleotides. In some embodiments, the hairpin loop can be 4-8 nucleotides.

Where the two substantially complementary strands of a dsRNA are comprised by separate RNA molecules, those molecules need not, but can be covalently connected. In certain embodiments where the two strands are connected covalently by means other than an uninterrupted chain of nucleotides between the 3'-end of one strand and the 5'-end of the respective other strand forming the duplex structure, the connecting structure is referred to as a "linker" (though it is noted that certain other structures defined elsewhere herein can also be referred to as a "linker"). The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs. In one embodiment of the RNAi agent, at least one strand comprises a 3' overhang of at least 1 nucleotide. In another embodiment, at least one strand comprises a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide.

In one embodiment, an RNAi agent of the disclosure is a dsRNA, each strand of which independently comprises 19-23 nucleotides, that interacts with a target RNA sequence, e.g., a C9orf72 target mRNA sequence, to direct the cleavage of the target RNA.

In some embodiments, an iRNA of the invention is a dsRNA of 24-30 nucleotides that interacts with a target RNA sequence, e.g., a C9orf72 target mRNA sequence, to direct the cleavage of the target RNA.

As used herein, the term "nucleotide overhang" refers to at least one unpaired nucleotide that protrudes from the duplex structure of an RNAi agent, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively, the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

In one embodiment, the antisense strand of a dsRNA has a 1-10 nucleotide, e.g., a 1, 2, 3, 4, 5, 6, 7, 8, 9, or 10 nucleotide, overhang at the 3'-end or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end or the 5'-end. In another embodiment, one or more of the nucleotides in the overhang is replaced with a nucleoside thiophosphate.

In certain embodiments, the antisense strand of a dsRNA has a 1-10 nucleotide, e.g., 0-3, 1-3, 2-4, 2-5, 4-10, 5-10, e.g., a 1, 2, 3, 4, 5, 6, 7, 8, 9, or 10 nucleotide, overhang at the 3'-end or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end or the 5'-end. In another embodiment, one or more of the nucleotides in the overhang is replaced with a nucleoside thiophosphate.

In certain embodiments, the overhang on the sense strand or the antisense strand, can include extended lengths longer than 10 nucleotides, e.g., 1-30 nucleotides, 2-30 nucleotides, 10-30 nucleotides, or 10-15 nucleotides in length. In certain embodiments, an extended overhang is on the sense strand of the duplex. In certain embodiments, an extended overhang is present on the 3'end of the sense strand of the duplex. In certain embodiments, an extended overhang is present on the 5'end of the sense strand of the duplex. In certain embodiments, an extended overhang is on the antisense strand of the duplex. In certain embodiments, an extended overhang is present on the 3'end of the antisense strand of the duplex. In certain embodiments, an extended overhang is present on the 5'end of the antisense strand of the duplex. In certain embodiments, one or more of the nucleotides in the overhang is replaced with a nucleoside thiophosphate. In certain embodiments, the overhang includes a self-complementary portion such that the overhang is capable of forming a hairpin structure that is stable under physiological conditions.

In certain embodiments, at least one end of at least one strand is extended beyond a duplex targeting region, including structures where one of the strands includes a thermodynamically-stabilizing tetraloop structure (see, e.g., U.S. Pat. Nos. 8,513,207 and 8,927,705, as well as WO2010033225, the entire contents of each of which are incorporated by reference herein). Such structures may include single-stranded extensions (on one or both sides of the molecule) as well as double-stranded extensions.

In certain embodiments, the 3' end of the sense strand and the 5' end of the antisense strand are joined by a polynucleotide sequence comprising ribonucleotides, deoxyribonucleotides or both, optionally wherein the polynucleotide sequence comprises a tetraloop sequence. In certain embodiments, the sense strand is 25-35 nucleotides in length.

A tetraloop may contain ribonucleotides, deoxyribonucleotides, modified nucleotides, and combinations thereof. Typically, a tetraloop has 4 to 5 nucleotides. In some embodiments, the loop comprises a sequence set forth as GAAA. In some embodiments, at least one of the nucleotide of the loop (GAAA) comprises a nucleotide modification. In some embodiments, the modified nucleotide comprises a 2'-modification. In some embodiments, the 2 '-modification is a modification selected from the group consisting of 2'-aminoethyl, 2'-fluoro, 2'-O-methyl, 2'-O-methoxyethyl, 2'-aminodiethoxymethanol, 2'-adem, and 2'-deoxy-2'-fhioro-d-arabinonucleic acid. In some embodiments, all of the nucleotides of the loop are modified. In some embodiments, the G in the GAAA sequence comprises a 2'-OH. In some embodiments, each of the nucleotides in the GAAA sequence comprises a 2'-O-methyl modification. In some embodiments, each of the A in the GAAA sequence comprises a 2'-OH and the G in the GAAA sequence comprises a 2'-O-methyl modification. In preferred embodiments, In some embodiments, each of the A in the GAAA sequence comprises a 2'-O-methoxyethyl (MOE) modification and the G in the GAAA sequence comprises a 2'-O-methyl modification; or each of the A in the GAAA sequence comprises a 2'-adem modification and the G in the GAAA sequence comprises a 2'-O-methyl modification. See, e.g., PCT Publication No. WO 2020/206350, the entire contents of which are incorporated herein by reference.

An exemplary 2' adem modified nucleotide is shown below:

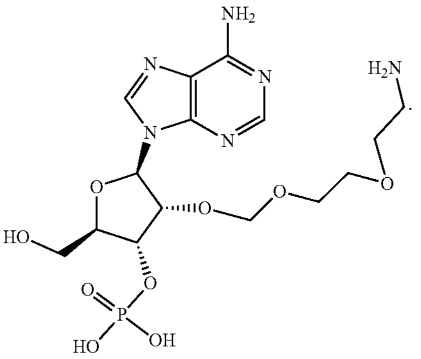 [SMILES: NCCOCCOCO[C@@H]1[C@H](OP(=O)(O)O)[C@@H](CO)O[C@H]1n1cnc2c(N)ncnc21]

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double stranded over its entire length.

The term "antisense strand" or "guide strand" refers to the strand of an RNAi agent, e.g., a dsRNA, which includes a region that is substantially complementary to a target sequence, e.g., a C9orf72 mRNA.

As used herein, the term "region of complementarity" refers to the region on the antisense strand that is substantially complementary to a sequence, for example a target sequence, e.g., a C9orf72 nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- or 3'-terminus of the RNAi agent. In some embodiments, a double stranded RNA agent of the invention includes a nucleotide mismatch in the antisense strand. In some embodiments, the antisense strand of the double stranded RNA agent of the invention includes no more than 4 mismatches with the target mRNA, e.g., the antisense strand includes 4, 3, 2, 1, or 0 mismatches with the target mRNA. In some embodiments, the antisense strand double stranded RNA agent of the invention includes no more than 4 mismatches with the sense strand, e.g., the antisense strand includes 4, 3, 2, 1, or 0 mismatches with the sense strand. In some embodiments, a double stranded RNA agent of the invention includes a nucleotide mismatch in the sense strand. In some embodiments, the sense strand of the double stranded RNA agent of the invention includes no more than 4 mismatches with the antisense strand, e.g., the sense strand includes 4, 3, 2, 1, or 0 mismatches with the antisense strand. In some embodiments, the nucleotide mismatch is, for example, within 5, 4, 3 nucleotides from the 3'-end of the iRNA. In another embodiment, the nucleotide mismatch is, for example, in the 3'-terminal nucleotide of the iRNA agent. In some embodiments, the mismatch(s) is not in the seed region.

Thus, an RNAi agent as described herein can contain one or more mismatches to the target sequence. In one embodiment, an RNAi agent as described herein contains no more than 3 mismatches (i.e., 3, 2, 1, or 0 mismatches). In one embodiment, an RNAi agent as described herein contains no more than 2 mismatches. In one embodiment, an RNAi agent as described herein contains no more than 1 mismatch. In one embodiment, an RNAi agent as described herein contains 0 mismatches. In certain embodiments, if the antisense strand of the RNAi agent contains mismatches to the target sequence, the mismatch can optionally be restricted to be within the last 5 nucleotides from either the 5'- or 3'-end of the region of complementarity. For example, in such embodiments, for a 23 nucleotide RNAi agent, the strand which is complementary to a region of a C9orf72 gene, generally does not contain any mismatch within the central 13 nucleotides. The methods described herein or methods known in the art can be used to determine whether an RNAi agent containing a mismatch to a target sequence is effective in inhibiting the expression of a C9orf72 gene. Consideration of the efficacy of RNAi agents with mismatches in inhibiting expression of a C9orf72 gene is important, especially if the particular region of complementarity in a C9orf72 gene is known to have polymorphic sequence variation within the population.

As used herein, "substantially all of the nucleotides are modified" are largely but not wholly modified and can include not more than 5, 4, 3, 2, or 1 unmodified nucleotides.

The term "sense strand" or "passenger strand" as used herein, refers to the strand of an RNAi agent that includes a region that is substantially complementary to a region of the antisense strand as that term is defined herein.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an RNAi agent, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an RNAi agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding C9orf72). For example, a polynucleotide is complementary to at least a part of a C9orf72 mRNA if the sequence is substantially complementary to a non-interrupted portion of an mRNA encoding C9orf72.

Accordingly, in some embodiments, the antisense polynucleotides disclosed herein are fully complementary to the target C9orf72 sequence. In other embodiments, the antisense polynucleotides disclosed herein are substantially complementary to the target C9orf72 sequence and comprise a contiguous nucleotide sequence which is at least 80% complementary over its entire length to the equivalent region of the nucleotide sequence of any one of SEQ ID NOs:121-124 and 133 SEQ D NOs: 121-124 and 133, such as about 85%, about 90%, about 91%, about 92%, about 93%, about 94%, about 95%, about 96%, about 97%, about 98%, or about 99% complementary.

In some embodiments, the antisense polynucleotides disclosed herein are substantially complementary to a fragment of a target C9orf72 sequence and comprise a contiguous nucleotide sequence which is at least 80% complementary over its entire length to a fragment of SEQ ID NO:121 selected from the group of nucleotides 1594-1616, 802-824, 239-261, 1308-1330, 233-255, 1595-1617, 240-262, 1532-1554, 237-259, 3268-3290, 806-828, 1620-1642, 526-548, 1169-1191, 1266-1288, 1247-1269, 586-608, 1257-1279, and 400-422 of SEQ ID NO:121, such as about 85%, about 90%, about 91%, about 92%, about 93%, about 94%, about 95%, about 96%, about 97%, about 98%, or about 99% complementary.

In some embodiments, the antisense polynucleotides disclosed herein are substantially complementary to a fragment of a target C9orf72 sequence and comprise a contiguous nucleotide sequence which is at least 80% complementary over its entire length to a fragment of SEQ ID NO:133, such as nucleotides 200-290, e.g., nucleotides 200-290, 200-280, 200-270, 200-260, 200-250, 200-240, 200-230, 200-225, 210-290, 210-280, 210-270, 210-260, 210-250, 210-240, 210-235, 220-290, 220-280, 220-270, 220-260, 220-250, 220-245, 225-250, 225-245, 230-290, 230-280, 230-270, 230-260, 230-255, 235-260, 240-265, 240-290, 240-280, 240-270, 240-265, 250-290, 250-280, 250-275, 260-290, 260-285) of SEQ ID NO:133, such as about 85%, about 90%, about 91%, about 92%, about 93%, about 94%, about 95%, about 96%, about 97%, about 98%, or about 99% complementary. Ranges intermediate to the above recited ranges are also contemplated to be part of the disclosure.

In other embodiments, the antisense polynucleotides disclosed herein are substantially complementary to the target C9orf72 sequence and comprise a contiguous nucleotide sequence which is at least about 80% complementary over its entire length to any one of the sense strand nucleotide sequences in any one of any one of Tables 10A, 10B, 12-15, 19 or 20, or a fragment of any one of the sense strand nucleotide sequences in any one of Tables 10A, 10B, 12-15, 19 or 20, such as about 85%, about 90%, about 91%, about 92%, about 93%, about 94%, about 95%, about 96%, about 97%, about 98%, about 99%, or 100% complementary.

In one embodiment, an RNAi agent of the disclosure includes a sense strand that is substantially complementary to an antisense polynucleotide which, in turn, is the same as a target C9orf72 sequence, and wherein the sense strand polynucleotide comprises a contiguous nucleotide sequence which is at least about 80% complementary over its entire length to the equivalent region of the nucleotide sequence of SEQ ID NOs: 125-128 and 134, such as about 85%, about 90%, about 91%, about 92%, about 93%, about 94%, about 95%, about 96%, about 97%, about 98%, about 99%, or 100% complementary.

In some embodiments, an iRNA of the invention includes a sense strand that is substantially complementary to an antisense polynucleotide which, in turn, is complementary to a target C9orf72 sequence, and wherein the sense strand polynucleotide comprises a contiguous nucleotide sequence which is at least about 80% complementary over its entire length to any one of the antisense strand nucleotide sequences in any one of any one of Tables 10A, 10B, 12-15, 19 or 20, or a fragment of any one of the antisense strand nucleotide sequences in any one of Tables 10A, 10B, 12-25, 19 or 20, such as about 85%, about 90%, about 91%, about 92%, about 93%, about 94%, about 95%, about 96%, about 97%, about 98%, about 99%, or 100% complementary.

In certain embodiments, the sense and antisense strands are selected from any one of duplexes AD-348904.1, AD-348136.1, AD-347612.1, AD-348639.1, AD-347606.1, AD-348905.1, AD-347613.1, AD-348842.1, AD-347610.1, AD-350329.1, AD-348140.1, AD-348930.1, AD-347863.1, AD-348500.1, AD-348597.1, AD-348578.1, AD-347923.1, AD-348588.1, AD-347773.1, and AD-348136.1.

In certain embodiments, the sense and antisense strands are selected from any one of duplexes AD-463863.1, AD-463862.1, AD-463869.1, AD-463873.1, AD-463872.1, and AD-463860.1.

In one embodiment, at least partial suppression of the expression of a C9orf72 gene, is assessed by a reduction of the amount of C9orf72 mRNA, e.g., sense mRNA, antisense mRNA, total C9orf72 mRNA, sense C9orf72 repeat-containing mRNA, and/or antisense C9orf72 repeat-containing mRNA, which can be isolated from or detected in a first cell or group of cells in which a C9orf72 gene is transcribed and which has or have been treated such that the expression of a C9orf72 gene is inhibited, as compared to a second cell or group of cells substantially identical to the first cell or group of cells but which has or have not been so treated (control cells). The degree of inhibition may be expressed in terms of:

$$\frac{(mRNA \text{ in control cells}) - (mRNA \text{ in treated cells})}{(mRNA \text{ in control cells})} \cdot 100\%$$

The phrase "contacting a cell with an RNAi agent," such as a dsRNA, as used herein, includes contacting a cell by any possible means. Contacting a cell with an RNAi agent includes contacting a cell in vitro with the RNAi agent or contacting a cell in vivo with the RNAi agent. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, e.g., the central nervous system (CNS), optionally via intrathecal, intravitreal or other injection, or to the bloodstream or the subcutaneous space, such that the agent will subsequently reach the tissue where the cell to be contacted is located. For example, the RNAi agent may contain or be coupled to a ligand, e.g., a lipophilic moiety or moieties as described below and further detailed, e.g., in PCT/US2019/031170, which is incorporated herein by reference, that directs or otherwise stabilizes the RNAi agent at a site of interest, e.g., the CNS. Combinations of in vitro and in vivo methods of contacting are also possible. For example, a cell may also be contacted in vitro with an RNAi agent and subsequently transplanted into a subject.

In one embodiment, contacting a cell with an RNAi agent includes "introducing" or "delivering the RNAi agent into the cell" by facilitating or effecting uptake or absorption into the cell.

Absorption or uptake of an RNAi agent can occur through unaided diffusive or active cellular processes, or by auxiliary agents or devices. Introducing an RNAi agent into a cell may be in vitro or in vivo. For example, for in vivo introduction, an RNAi agent can be injected into a tissue site or administered systemically. In vitro introduction into a cell includes methods known in the art such as electroporation and lipofection. Further approaches are described herein below or are known in the art.

The term "lipophile" or "lipophilic moiety" broadly refers to any compound or chemical moiety having an affinity for lipids. One way to characterize the lipophilicity of the lipophilic moiety is by the octanol-water partition coefficient, log $K_{ow}$, where $K_{ow}$ is the ratio of a chemical's concentration in the octanol-phase to its concentration in the aqueous phase of a two-phase system at equilibrium. The octanol-water partition coefficient is a laboratory-measured property of a substance. However, it may also be predicted by using coefficients attributed to the structural components of a chemical which are calculated using first-principle or empirical methods (see, for example, Tetko et al., *J. Chem. Inf. Comput. Sci.* 41:1407-21 (2001), which is incorporated herein by reference in its entirety). It provides a thermodynamic measure of the tendency of the substance to prefer a non-aqueous or oily milieu rather than water (i.e. its hydrophilic/lipophilic balance). In principle, a chemical substance is lipophilic in character when its log $K_{ow}$ exceeds 0. Typically, the lipophilic moiety possesses a log $K_{ow}$ exceeding 1, exceeding 1.5, exceeding 2, exceeding 3, exceeding 4, exceeding 5, or exceeding 10. For instance, the log $K_{ow}$ of 6-amino hexanol, for instance, is predicted to be approximately 0.7. Using the same method, the log $K_{ow}$ of cholesteryl N-(hexan-6-ol) carbamate is predicted to be 10.7.

The lipophilicity of a molecule can change with respect to the functional group it carries. For instance, adding a hydroxyl group or amine group to the end of a lipophilic moiety can increase or decrease the partition coefficient (e.g., log $K_{ow}$) value of the lipophilic moiety.

Alternatively, the hydrophobicity of the double-stranded RNAi agent, conjugated to one or more lipophilic moieties, can be measured by its protein binding characteristics. For instance, in certain embodiments, the unbound fraction in the plasma protein binding assay of the double-stranded RNAi agent could be determined to positively correlate to the relative hydrophobicity of the double-stranded RNAi agent, which could then positively correlate to the silencing activity of the double-stranded RNAi agent.

In one embodiment, the plasma protein binding assay determined is an electrophoretic mobility shift assay (EMSA) using human serum albumin protein. An exemplary protocol of this binding assay is illustrated in detail in, e.g., PCT/US2019/031170. The hydrophobicity of the double-stranded RNAi agent, measured by fraction of unbound siRNA in the binding assay, exceeds 0.15, exceeds 0.2, exceeds 0.25, exceeds 0.3, exceeds 0.35, exceeds 0.4, exceeds 0.45, or exceeds 0.5 for an enhanced in vivo delivery of siRNA.

Accordingly, conjugating the lipophilic moieties to the internal position(s) of the double-stranded RNAi agent provides optimal hydrophobicity for the enhanced in vivo delivery of siRNA.

The term "lipid nanoparticle" or "LNP" is a vesicle comprising a lipid layer encapsulating a pharmaceutically active molecule, such as a nucleic acid molecule, e.g., a rNAi agent or a plasmid from which an RNAi agent is transcribed. LNPs are described in, for example, U.S. Pat.

Nos. 6,858,225, 6,815,432, 8,158,601, and 8,058,069, the entire contents of which are hereby incorporated herein by reference.

As used herein, a "subject" is an animal, such as a mammal, including a primate (such as a human, a non-human primate, e.g., a monkey, and a chimpanzee), or a non-primate (such as a a rat, or a mouse). In a preferred embodiment, the subject is a human, such as a human being treated or assessed for a disease, disorder, or condition that would benefit from reduction in C9orf72 expression; a human at risk for a disease, disorder, or condition that would benefit from reduction in levels of target C9orf72 RNA; a human having a disease, disorder, or condition that would benefit from reduction in C9orf72 expression; or human being treated for a disease, disorder, or condition that would benefit from reduction in C9orf72 expression as described herein. In some embodiments, the subject is a female human In other embodiments, the subject is a male human. In one embodiment, the subject is an adult subject. In one embodiment, the subject is a pediatric subject. In another embodiment, the subject is a juvenile subject, i.e., a subject below 20 years of age.

As used herein, the terms "treating" or "treatment" refer to a beneficial or desired result including, but not limited to, alleviation or amelioration of one or more signs or symptoms associated with C9orf72 gene expression or C9orf72 protein production, e.g., C9orf72-associated diseases, such as C9orf72-associated disease. "Treatment" can also mean prolonging survival as compared to expected survival in the absence of treatment.

The term "lower" in the context of the level of C9orf72 in a subject or a disease marker or symptom refers to a statistically significant decrease in such level. The decrease can be, for example, at least 10%, 15%, 20%, 25%, 30%, %, 40%, 45%, 50%, 55%, 60%, 65%, 70%, 75%, 80%, 85%, 90%, 95%, or more. In certain embodiments, a decrease is at least 20%. In certain embodiments, the decrease is at least 50% in a disease marker, e.g., the level of sense- or anti-sense-containing foci and/or the level of aberrant dipeptide repeat protein, e.g., a decrease of 50%, 55%, 60%, 65%, 70%, 75%, 80%, 85%, 90%, 95%, or more. In some embodiments, a decrease is no more than 50% in a disease marker, e.g., C9orf72 protein and/or gene expression level, e.g., no more than 50%, 45%, 40%, 35%, 30%, 25%, 20%, 15%, 10%, or 5%. "Lower" in the context of the level of C9orf72 in a subject is preferably down to a level accepted as within the range of normal for an individual without such disorder. In certain embodiments, "lower" is the decrease in the difference between the level of a marker or symptom for a subject suffering from a disease and a level accepted within the range of normal for an individual, e.g., the level of decrease in bodyweight between an obese individual and an individual having a weight accepted within the range of normal.

As used herein, "prevention" or "preventing," when used in reference to a disease, disorder, or condition thereof, that would benefit from a reduction in expression of a C9orf72 gene or production of a C9orf72 protein, refers to a reduction in the likelihood that a subject will develop a symptom associated with such a disease, disorder, or condition, e.g., a symptom of a C9orf72-associated disease. The failure to develop a disease, disorder, or condition, or the reduction in the development of a symptom associated with such a disease, disorder, or condition (e.g., by at least about 10% on a clinically accepted scale for that disease or disorder), or the exhibition of delayed symptoms delayed (e.g., by days, weeks, months or years) is considered effective prevention.

As used herein, the term "C9orf72-associated disease" or "C9orf72-associated disorder" includes any disease or disorder that would benefit from reduction in the expression and/or activity of C9orf72. Exemplary C9orf72-associated diseases include those diseases in which subjects carry a hexanucleotide repeat (GGGGCC (SEQ ID NO: 1)) expansion in the intron between exons 1a and 1b in the C9orf72 gene, e.g., amyotrophic lateral sclerosis (ALS) or frontotemporal dementia (FTD) and Huntington-Like Syndrome Due To C9orf72 Expansions.

Normal G4C2 repeats (SEQ ID NO: 1) are ~25 units or less, and high penetrance disease alleles are typically greater than ~60 repeat units, ranging up to more than 4,000 units; rarely, repeats between 47 and 60 segregate with disease in families A repeat-primed PCR assay is typically used to detect smaller expansions (<80), but accurately sizing larger repeats requires other techniques (e.g. Southern blot hybridization) that provides an estimate of length.

Subjects having a GGGGCC (or G4C2) hexanucleotide (SEQ ID NO: 1) expansion in an intron of the C9orf72 gene can present as amyotrophic lateral sclerosis (ALS) or frontotemporal dementia (FTD) even in the same family and, therefore, the neurodegeneration associated with this expansion is referred to herein as "C9orf72 Amyotrophic lateral sclerosis/frontotemporal dementia" or C9orf72 ALS/FTD." It is an autosomal dominant disease and is the most common form of familial ALS, accounting for about a third of ALS families and 5-10% of sporadic cases in an ALS clinic. It is also a common cause of FTD, explaining about one fourth of familial FTD. Age of symptom onset ranges from 30 to 70 years of age with a mean onset in the late 50s. C9orf72-mediated ALS most often resembles typical ALS, can be bulbar or limb onset, can progress rapidly (though not always) and can be associated with later cognitive symptoms. Thus, C9orf72-mediated ALS is evaluated and treated just as in any ALS patient. The pattern of C9orf72-mediated FTD most commonly is behavioral variant FTD, with the full range of behavioral and cognitive symptoms including disinhibition, apathy and executive dysfunction. Less commonly, C9orf72-mediated FTD presents semantic variant primary progressive aphasia (PPA) or nonfluent variant PPA, and, very rarely, can resemble corticobasal syndrome, progressive supranuclear palsy or an HD-like syndrome. Occasionally parkinsonian features are seen in C9orf72-mediated ALS or FTD.

Subjects may exhibit frontotemporal lobar degeneration (FTLD) characterized by progressive changes in behavior, executive dysfunction, and/or language impairment. Of the three FTLD clinical syndromes, behavioral variant FTD (bvFTD) is most often, but not exclusively, present. It is characterized by progressive behavioral impairment and a decline in executive function with predominant frontal lobe atrophy on brain MRI. Motor neuron disease, including upper or lower motor neuron dysfunction (or both) that may or may not fulfill criteria for the full ALS phenotype may also be present. Some degree of parkinsonism, which is present in many individuals with C9orf72-associated bvFTD, is typically of the akinetic-rigid type without tremor, and is levodopa unresponsive.

Huntington's disease-like syndromes (HD-like syndromes, or HDL syndromes) are a family of inherited neurodegenerative diseases that closely resemble Huntington's disease (HD) in that they typically produce a combination of chorea, cognitive decline or dementia and behavioural or psychiatric problems.

Subjects having Huntington disease-like syndrome due to C9orf72 expansions are characterized as having movement disorders, including dystonia, chorea, myoclonus, tremor and rigidity. Associated features are also cognitive and memory impairment, early psychiatric disturbances and behavioral problems. The mean age at onset is about 43 years (range 8-60). Early psychiatric and behavioral problems (including depression, apathy, obsessive behaviour, and psychosis) are common. Cognitive symptoms present as executive dysfunction. Movement disorders are prominent: Parkinsonian features and pyramidal features may also be present. "Therapeutically effective amount," as used herein, is intended to include the amount of an RNAi agent that, when administered to a subject having a C9orf72-associated disease, is sufficient to effect treatment of the disease (e.g., by diminishing, ameliorating, or maintaining the existing disease or one or more symptoms of disease). The "therapeutically effective amount" may vary depending on the RNAi agent, how the agent is administered, the disease and its severity and the history, age, weight, family history, genetic makeup, the types of preceding or concomitant treatments, if any, and other individual characteristics of the subject to be treated.

"Prophylactically effective amount," as used herein, is intended to include the amount of an RNAi agent that, when administered to a subject having a C9orf72-associated disorder, is sufficient to prevent or ameliorate the disease or one or more symptoms of the disease. Ameliorating the disease includes slowing the course of the disease or reducing the severity of later-developing disease. The "prophylactically effective amount" may vary depending on the RNAi agent, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylactically effective amount" also includes an amount of an RNAi agent that produces some desired local or systemic effect at a reasonable benefit/risk ratio applicable to any treatment. An RNAi agent employed in the methods of the present disclosure may be administered in a sufficient amount to produce a reasonable benefit/risk ratio applicable to such treatment.

The phrase "pharmaceutically acceptable" is employed herein to refer to those compounds, materials, compositions, or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates or polyanhydrides; (22) bulking agents, such as polypeptides and amino acids (23) serum component, such as serum albumin, HDL and LDL; and (22) other non-toxic compatible substances employed in pharmaceutical formulations.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs or localized regions. For example, samples may be derived from particular organs, parts of organs, or fluids or cells within those organs. In certain embodiments, samples may be derived from the brain (e.g., whole brain or certain segments of brain, e.g., striatum, or certain types of cells in the brain, such as, e.g., neurons and glial cells (astrocytes, oligodendrocytes, microglial cells)). In some embodiments, a "sample derived from a subject" refers to blood drawn from the subject or plasma or serum derived therefrom. In further embodiments, a "sample derived from a subject" refers to brain tissue (or subcomponents thereof) or retinal tissue (or subcomponents thereof) derived from the subject.

II. RNAi Agents of the Disclosure

As described elsewhere herein, mutations in C9orf72 have been linked to familial frontotemporal dementia (FTD) and amyotrophic lateral sclerosis (ALS). The mutations are the result of expansion of G4C2 (SEQ ID NO: 1) hexanucleotide repeats located within the intron between exon 1A and exon 1B of the C9orf72 gene. The hexanucleotide repeats may be translated through a non-AUG-initiated mechanism. Accumulation of the repeat expansion-containing RNA (target RNA) or translation of the repeat sequences may cause or contribute to FTD and/or ALS or disease symptoms associated with FTD and/or ALS.

Accordingly, the present invention provides dsRNA RNAi agents that selectively and efficiently decrease expression of C9orf72-related expression products, RNA and/or translated polypeptides, associated with the hexanucleotide repeat expansions. In some embodiment, the dsRNA agents target (e.g., selectively target) the hexanucleotide-repeat-containing RNA (target RNA) and knock down the target RNA and polypeptides expressed from the hexanucleotide-repeat-containing RNA. The dsRNA agents may be used in methods for therapeutic treatment and/or prevention of signs or symptoms associated with FTD and/or ALS, including, but not limited to, repeat-length-dependent formation of RNA foci, sequestration of specific RNA-binding proteins, and accumulation and aggregation of dipeptide repeat proteins (e.g., poly(glycine-alanine), poly(glycine-proline), poly(glycine-arginine), poly(alanine-proline), and poly(proline-arginine)) resulting from repeat-associated non-AUG (AUG) translation in neurons. The dsRNA agents may be used in methods for therapeutic treatment and/or prevention of signs or symptoms associated with FTD and/or ALS, including, but not limited to, signs and symptoms of motor neuron disease and signs and symptoms of dementia. Signs and symptoms of motor neuron disease can include, for example, tripping, dropping things, abnormal fatigue of the arms and/or legs, slurred speech, muscle cramps and twitches, uncontrollable periods of laughing or crying, and trouble breathing. Signs and symptoms of dementia can include, for example, behavioral changes, personality changes, speech and language problems, and movement-related problems. Such methods comprise administration of one or more dsRNA agents as described herein to a subject (e.g., a human or animal subject).

The dsRNA agents described herein may stop or reduce the accumulation of repeat-containing C9orf72 RNA (e.g., assayed as RNA foci) and thereby prevent the synthesis of dipeptide repeat proteins by RAN translation.

In some embodiments, the dsRNA agents of the invention target mature C9orf72 mRNAs (i.e., mRNAs in which introns have been spliced out). In other embodiments, the dsRNA agents of the invention target C9orf72 RNAs containing an intron, such as intron 1A (i.e., mRNAs in which introns have not been spliced out, RNA regions spliced out of a precursor mRNA, or alternatively spliced RNAs).

In some embodiments, the dsRNA agents of the invention target C9orf72 transcripts that initiate at non-coding exon 1A upstream of the repeat. C9orf72 repeat expansions are dominant mutations that occur essentially always as heterozygous mutations. Thus, in some embodiments, the dsRNA agents described herein target transcripts that initiate at exon 1A and primarily affect only the pathogenic allele; the normal allele initiates transcription almost exclusively at exon 1B downstream of the repeat. The normal (non-pathogenic) transcripts are, thus, be spared, so the dsRNA agents do not wipe out all C9orf72 protein production.

In one embodiment, the RNAi agent includes double stranded ribonucleic acid (dsRNA) molecules for inhibiting the expression of a C9orf72 gene in a cell, such as a cell within a subject, e.g., a mammal, such as a human having a C9orf72-associated disease, e.g., C9orf72-associated disease. The dsRNA includes an antisense strand having a region of complementarity which is complementary to at least a part of an mRNA formed in the expression of a C9orf72 gene. The region of complementarity is about 15-30 nucleotides or less in length. Upon contact with a cell expressing the C9orf72 gene, the RNAi agent inhibits the expression of the C9orf72 gene (e.g., a human gene, a primate gene, a non-primate gene) by at least 50% as assayed by, for example, a PCR or branched DNA (bDNA)-based method, or by a protein-based method, such as by immunofluorescence analysis, using, for example, western blotting or flowcytometric techniques. In a preferred embodiment, the level of knockdown is assayed in human neuroblastoma BE(2)C cells using a Dual-Luciferase assay method provided in Example 1 below.

In some embodiments, the dsRNA agents agents described herein are designed to stop or reduce the accumulation of repeat-containing C9orf72 RNA (e.g., assayed as RNA foci) and thereby prevent the synthesis of dipeptide repeat proteins by RAN translation. To achieve this, in certain embodiments, the dsRNA agents target C9orf72 mRNA protein coding sequences (see, e.g., Tables 12 and 13). In other embodiments, the dsRNA agents target C9orf72 transcripts that initiate at non-coding exon 1A upstream of the repeat. Transcripts that initiate downstream of the repeat will not contain the pathogenic RNA. C9orf72 repeat expansions are dominant mutations that occur essentially always as heterozygous mutations. Thus, when the dsRNA agents described herein target transcripts that initiate at exon 1A they therefore primarily affect only the pathogenic allele; the normal allele initiates transcription almost exclusively at exon 1B downstream of the repeat and, thus, the normal (non-pathogenic) transcripts are spared.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of a C9orf72 gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is 15 to 30 base pairs in length, e.g., 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 base pairs in length. In certain preferred embodiments, the duplex structure is 18 to 25 base pairs in length, e.g., 18-25, 18-24, 18-23, 18-22, 18-21, 18-20, 19-25, 19-24, 19-23, 19-22, 19-21, 19-20, 20-25, 20-24,20-23, 20-22, 20-21, 21-25, 21-24, 21-23, 21-22, 22-25, 22-24, 22-23, 23-25, 23-24 or 24-25 base pairs in length, for example, 19-21 basepairs in length. Ranges and lengths intermediate to the above recited ranges and lengths are also contemplated to be part of the disclosure.

Similarly, the region of complementarity to the target sequence is 15 to 30 nucleotides in length, e.g., 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 nucleotides in length, for example 19-23 nucleotides in length or 21-23 nucleotides in length. Ranges and lengths intermediate to the above recited ranges and lengths are also contemplated to be part of the disclosure.

In some embodiments, the duplex structure is 19 to 30 base pairs in length. Similarly, the region of complementarity to the target sequence is 19 to 30 nucleotides in length.

In some embodiments, the dsRNA is 15 to 23 nucleotides in length, 19 to 23 nucleotides in length, or 25 to 30 nucleotides in length. In general, the dsRNA is long enough to serve as a substrate for the Dicer enzyme. For example, it is well known in the art that dsRNAs longer than about 21-23 nucleotides can serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 15 to 36 base pairs, e.g., 15-36, 15-35, 15-34, 15-33, 15-32, 15-31, 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 base pairs, for example, 19-21 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an RNAi agent useful to target C9orf72 expression is not generated in the target cell by cleavage of a larger dsRNA.

A dsRNA as described herein can further include one or more single-stranded nucleotide overhangs e.g., 1, 2, 3, or 4 nucleotides. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

A dsRNA can be synthesized by standard methods known in the art. Double stranded RNAi compounds of the invention may be prepared using a two-step procedure. First, the individual strands of the double stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Similarly, single-stranded oligonucleotides of the invention can be prepared using solution-phase or solid-phase organic synthesis or both.

In certain embodiments, the dsRNA agents of the invention target a C9orf72 target RNA comprising a hexanucleotide repeat comprising multiple contiguous copies of SEQ ID NO: 1, for example, a C9orf72 target RNA with a pathogenic hexanucleotide repeat expansion (having, for example, at least about 30, at least about 35, at least about 40, at least about 50, at least about 60, at least about 70, at least about 80, at least about 100, at least about 200, at least about 300, at least about 400, or at least about 500 copies of the hexanucleotide repeat).

The dsRNA agents described herein can target any region of a hexanucleotide-repeat containing C9orf72 RNA (a C9orf72 target RNA). In certain embodiments, the dsRNA agents described herein can target a nucleotide sequence between the start of exon 1A and the start of exon 2 (i.e., including exon 1A but not including exon 2) of a C9orf72 RNA (i.e., corresponding to the region from the start of exon 1A to the start of exon 2 in the corresponding C9orf72 gene). In certain embodiments, the dsRNA agents described herein can target a nucleotide sequence between the start of exon 1A and the end of exon 1B (i.e., including exon 1A and exon 1B) of a C9orf72 RNA. In certain embodiments, the dsRNA agents described herein can target a nucleotide sequence between the start of exon 1A and the start of exon 1B (i.e., including exon 1A but not exon 1B) of a C9orf72 RNA. In certain embodiments, the dsRNA agents described herein can target a nucleotide sequence between the start of exon 1A and the end of the hexanucleotide repeat sequence (i.e., including exon 1A and the hexanucleotide repeat sequence) of a C9orf72 RNA. In certain embodiments, the dsRNA agents described herein can target a nucleotide sequence between the start of exon 1A and the start of the hexanucleotide repeat sequence (i.e., including exon 1A but not the hexanucleotide repeat sequence) of a C9orf72 RNA. In certain embodiments, the dsRNA agents described herein can target a nucleotide sequence between the start of exon 1A and the end of exon 1A of a C9orf72 RNA.

In certain embodiments, the dsRNA agents described herein can target a nucleotide sequence between the end of exon 1A and the start of exon 2 (i.e., not including exon 1A and not including exon 2) of a C9orf72 RNA. In certain embodiments, the dsRNA agents described herein can target a nucleotide sequence between the end of exon 1A and the end of exon 1B (i.e., not including exon 1A but including exon 1B) of a C9orf72 RNA. In certain embodiments, the dsRNA agents described herein can target a nucleotide sequence between the end of exon 1A and the start of exon 1B (i.e., not including exon 1A and not including exon 1B) of a C9orf72 RNA. In certain embodiments, the dsRNA agents described herein can target a nucleotide sequence between the end of exon 1A and the end of the hexanucleotide repeat sequence (i.e., not including exon 1A but including the hexanucleotide repeat sequence) of a C9orf72 RNA. In certain embodiments, the dsRNA agents described herein can target a nucleotide sequence between the end of exon 1A and the start of the hexanucleotide repeat sequence (i.e., not including exon 1A and not including the hexanucleotide repeat sequence) of a C9orf72 RNA.

In certain embodiments, the dsRNA agents described herein can target a nucleotide sequence between the start of the hexanucleotide repeat sequence and the start of exon 2 (i.e., including the hexanucleotide repeat sequence but not including exon 2) of a C9orf72 RNA. In certain embodiments, the dsRNA agents described herein can target a nucleotide sequence between the start of the hexanucleotide repeat sequence and the end of exon 1B (i.e., including the hexanucleotide repeat sequence and exon 1B) of a C9orf72 RNA. In certain embodiments, the dsRNA agents described herein can target a nucleotide sequence between the start of the hexanucleotide repeat sequence and the start of exon 1B (i.e., including the hexanucleotide repeat sequence but not exon 1B) of a C9orf72 RNA. In certain embodiments, the dsRNA agents described herein can target a nucleotide sequence between the start of the hexanucleotide repeat sequence and the end of the hexanucleotide repeat sequence of a C9orf72 RNA.

In certain embodiments, the dsRNA agents described herein can target a nucleotide sequence between the end of the hexanucleotide repeat sequence and the start of exon 2 (i.e., not including the hexanucleotide repeat sequence and not including exon 2) of a C9orf72 RNA. In certain embodiments, the dsRNA agents described herein can target a nucleotide sequence between the end of the hexanucleotide repeat sequence and the end of exon 1B (i.e., not including the hexanucleotide repeat sequence but including exon 1B) of a C9orf72 RNA. In certain embodiments, the dsRNA agents described herein can target a nucleotide sequence between the end of the hexanucleotide repeat sequence and the start of exon 1B (i.e., not including the hexanucleotide repeat sequence and not including exon 1B) of a C9orf72 RNA.

In certain embodiments, the dsRNA agents described herein can target a nucleotide sequence between the end of the start of exon 1B and the start of exon 2 (i.e., including exon 1B and not including exon 2) of a C9orf72 RNA.

In certain embodiments, the dsRNA agents described herein can target a nucleotide sequence between the end of the start of exon 1B and the end of exon 1B of a C9orf72 RNA.

In certain embodiments, the dsRNA agents described herein can target a nucleotide sequence between the end of the end of exon 1B and the start of exon 2 (i.e., not including exon 1B and not including exon 2) of a C9orf72 RNA.

Some dsRNA agents target an intronic region of a C9orf72 RNA. For example, the dsRNA agents described herein can target the intron between exon 1A and exon 1B of the C9orf72 gene (i.e., the intron between the end of exon 1A and the start of exon 1B of the C9orf72 target RNA). The region targeted by the dsRNA agent can be upstream (5') or downstream (3') of the hexanucleotide repeats in the intronic sequence between exon 1A and the hexanucleotide repeat sequence of C9orf72 target RNA. In a specific example, the dsRNA agents target a region upstream (5') of the hexanucleotide repeats in the C9orf72 target RNA. For example, the dsRNA agents can target the intronic sequence between the end of exon 1A and the start of the hexanucleotide repeat sequence.

In one embodiment, the dsRNA agents target a region in the C9orf72 target RNA corresponding to the region of the human C9orf72 gene between human genome assembly GRCh38/hg38 coordinates chr9:27,567,165-27,573,866 (corresponding to the region from the start of exon1A to the start of exon 2 (i.e., end of the intron before exon 2); an exemplary RNA sequence with three GGGGCC repeats transcribed from this region is set forth in SEQ ID NO: 111, with the reverse complement set forth in SEQ ID NO: 112). In another specific example, the dsRNA agents target a region in the C9orf72 target RNA corresponding to the region of the human C9orf72 gene between human genome assembly GRCh38/hg38 coordinates chr9:27,573,494-27,573,708 (corresponding to the region of the intron sequence between exon 1A and exon 1B (i.e., between the end of exon 1A and the start of exon 1B); an exemplary RNA sequence with three GGGGCC repeats transcribed from this region is set forth in SEQ ID NO: 113, with the reverse complement set forth in SEQ ID NO: 114). In another specific example, the dsRNA agents target a region in the C9orf72 target RNA corresponding to the region of the human C9orf72 gene between human genome assembly GRCh38/hg38 coordinates chr9:27,573,547-27,573,708 (corresponding to the region of the intron sequence between exon 1A and the start of the hexanucleotide repeat sequence (i.e., between the end of exon 1A and the start of the hexanucleotide repeat sequence); an exemplary RNA sequence transcribed from this region is set forth in SEQ ID NO: 115, with the reverse complement set forth in SEQ ID NO: 116). In another specific example, the dsRNA agents target a region in the C9orf72 target RNA corresponding to the region of the human C9orf72 gene between human genome assembly GRCh38/hg38 coordinates chr9:27,573,605-27,573,640 (corresponding to a fragment from the region of the intron sequence between exon 1A and the start of the hexanucleotide repeat sequence; an exemplary RNA sequence transcribed from this region is set forth in SEQ ID NO: 117, with the reverse complement set forth in SEQ ID NO: 118).

In certain embodiments, the dsRNA agents of the invention target the dsRNA agents target nucleotides 200-290 of SEQ ID NO: 133.

In certain embodiments, the dsRNA agents target nucleotides from any one of the nucleotide sequence of nucleotides 230-270, 233-262, 800-840, 800-830, 802-828, 1240-1290, 1240-1280, 1247-1288, 1590-1645, 1590-1620, and 1594-1642 of SEQ ID NO:121.

In certain embodiments, the dsRNA agents target nucleotides from any one of the nucleotide sequence of nucleotides 1594-1616, 802-824, 239-261, 1308-1330, 233-255, 1595-1617, 240-262, 1532-1554, 237-259, 3268-3290, 806-828, 1620-1642, 526-548, 1169-1191, 1266-1288, 1247-1269, 586-608, 1257-1279, and 400-422 of SEQ ID NO:121.

In one aspect, a dsRNA of the disclosure includes at least two nucleotide sequences, a sense sequence and an antisense sequence. The sense strand sequence for C9orf72 may be selected from the group of sequences provided in any one of Tables 10A, 10B, 12-15, 19 or 20, and the corresponding nucleotide sequence of the antisense strand of the sense strand may be selected from the group of sequences of any one of Tables 10A, 10B, 12-15, 19 or 20. In this aspect, one of the two sequences is complementary to the other of the two sequences, with one of the sequences being substantially complementary to a sequence of an mRNA generated in the expression of a C9orf72 gene. As such, in this aspect, a dsRNA will include two oligonucleotides, where one oligonucleotide is described as the sense strand (passenger strand) in any one of Tables 10A, 10B, 12-15, 19 or 20, and the second oligonucleotide is described as the corresponding antisense strand (guide strand) of the sense strand in any one of Tables 10A, 10B, 12-15, 19 or 20.

In one embodiment, the substantially complementary sequences of the dsRNA are contained on separate oligonucleotides. In another embodiment, the substantially complementary sequences of the dsRNA are contained on a single oligonucleotide.

It will be understood that, although the sequences in Tables 10A, 10B, 12-15, 19 or 20 are described as modified or conjugated sequences, the RNA of the RNAi agent of the disclosure e.g., a dsRNA of the disclosure, may comprise any one of the sequences set forth in any one of Tables 10A, 10B, 12-15, 19 or 20 that is un-modified, un-conjugated, or modified or conjugated differently than described therein. For example, although the sense strands of the agents of the invention shown in Tables 13 and 15 are conjugated to a GalNAc ligand, these agents may be conjugated to a moiety that directs delivery to the CNS, e.g., a C16 ligand, as described herein. A lipophilic ligand can be included in any of the positions provided in the instant application.

The skilled person is well aware that dsRNAs having a duplex structure of about 20 to 23 base pairs, e.g., 21, base pairs have been hailed as particularly effective in inducing RNA interference (Elbashir et al., (2001) *EMBO J.,* 20:6877-6888). However, others have found that shorter or longer RNA duplex structures can also be effective (Chu and Rana (2007) RNA 14:1714-1719; Kim et al. (2005) *Nat Biotech* 23:222-226). In the embodiments described above, by virtue of the nature of the oligonucleotide sequences provided herein, dsRNAs described herein can include at least one strand of a length of minimally 21 nucleotides. It can be reasonably expected that shorter duplexes minus only a few nucleotides on one or both ends can be similarly effective as compared to the dsRNAs described above. Hence, dsRNAs having a sequence of at least 15, 16, 17, 18, 19, 20, or more contiguous nucleotides derived from one of the sequences provided herein, and differing in their ability to inhibit the expression of a C9orf72 gene by not more than 10, 15, 20, 25, or 30% inhibition from a dsRNA comprising the full sequence using the in vitro assay with, e.g., Be(2)c cells and a 10 nM concentration of the RNA agent and the PCR assay as provided in the examples herein, are contemplated to be within the scope of the present disclosure.

In addition, the RNAs described herein identify a site(s) in a C9orf72 transcript that is susceptible to RISC-mediated cleavage. As such, the present disclosure further features RNAi agents that target within this site(s). As used herein, an RNAi agent is said to target within a particular site of an RNA transcript if the RNAi agent promotes cleavage of the transcript anywhere within that particular site. Such an RNAi agent will generally include at least about 15 contiguous nucleotides, preferably at least 19 nucleotides, from one of the sequences provided herein coupled to additional nucleotide sequences taken from the region contiguous to the selected sequence in a C9orf72 gene.

The dsRNA agents disclosed herein inhibit expression of the C9orf72 target RNA comprising the hexanucleotide repeat. Inhibiting expression includes any level of inhibition (e.g., partial inhibition of expression). For example, the dsRNA agents may inhibit expression of the C9orf72 target RNA comprising the hexanucleotide repeat by at least about 10%, at least about 20%, at least about 30%, at least about 40%, at least about 50%, at least about 60%, at least about 70%, at least about 80%, or at least about 90% (or to a point where the C9orf72 target RNA is undetectable). For example, these levels of inhibition can be within 24-48 hours after administration to a cell expressing the C9orf72 target RNA comprising the hexanucleotide repeat. The decrease can be, for example, relative to the cell before treatment with dsRNA agent or relative to a control cell that was not treated with the dsRNA agent.

The dsRNA agents disclosed herein may also, for example, selectively inhibit expression of the C9orf72 target RNA comprising the intronic hexanucleotide repeat relative to expression of a mature C9orf72 messenger RNA. A mature C9orf72 messenger RNA in this context is a C9orf72 RNA transcript that has been spliced and processed. A mature C9orf72 messenger RNA consists exclusively of exons and has all introns removed. A dsRNA agent may selectively inhibit expression of the C9orf72 target RNA comprising the intronic hexanucleotide repeat relative to expression of a mature C9orf72 messenger RNA if the relative decrease in expression of the C9orf72 target RNA is greater than the relative decrease in expression of a mature C9orf72 messenger RNA after administration of the dsRNA agent to a cell expressing the C9orf72 target RNA. For example, dsRNA agents may inhibit expression of the mature C9orf72 messenger RNA by less than about 50%, less than about 40%, less than about 30%, less than about 20%, less than about 10%, or less than about 5% (or, for example, does not have any statistically significant or functionally significant effect on expression). For example, these levels of inhibition can be within 24-48 hours after administration to a cell expressing the mature C9orf72 messenger RNA.

The dsRNA agents disclosed herein can also, for example, reduce dipeptide repeat protein synthesis or dipeptide repeat protein levels in a cell (e.g., within 24-48 hours after administration to the cell). For example, the dsRNA agent may reduce dipeptide repeat protein synthesis or dipeptide repeat protein levels by at least about 10%, at least about 20%, at least about 30%, at least about 40%, at least about 50%, at least about 60%, at least about 70%, at least about 80%, or at least about 90%. The decrease can be, for example, relative to the cell before treatment with dsRNA agent or relative to a control cell that was not treated with the dsRNA agent.

III. Modified RNAi Agents of the Disclosure

In one embodiment, the RNA of the RNAi agent of the disclosure e.g., a dsRNA, is un-modified, and does not comprise, e.g., chemical modifications or conjugations known in the art and described herein. In preferred embodiments, the RNA of an RNAi agent of the disclosure, e.g., a dsRNA, is chemically modified to enhance stability or other beneficial characteristics. In certain embodiments of the disclosure, substantially all of the nucleotides of an RNAi agent of the disclosure are modified. In other embodiments of the disclosure, all of the nucleotides of an RNAi agent of the disclosure are modified. RNAi agents of the disclosure in which "substantially all of the nucleotides are modified" are largely but not wholly modified and can include not more than 5, 4, 3, 2, or unmodified nucleotides. In still other embodiments of the disclosure, RNAi agents of the disclosure can include not more than 5, 4, 3, 2 or 1 modified nucleotides.

The nucleic acids featured in the disclosure can be synthesized or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; or backbone modifications, including modification or replacement of the phosphodiester linkages. Specific examples of RNAi agents useful in the embodiments described herein include, but are not limited to, RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified RNAi agent will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included. In some embodiments of the invention, the dsRNA agents of the invention are in a free acid form. In other embodiments of the invention, the dsRNA agents of the invention are in a salt form. In one embodiment, the dsRNA agents of the invention are in a sodium salt form. In certain embodiments, when the dsRNA agents of the invention are in the sodium salt form, sodium ions are present in the agent as counterions for substantially all of the phosphodiester and/or phosphorothiotate groups present in the agent. Agents in which substantially all of the phosphodiester and/or phosphorothioate linkages have a sodium counterion include not more than 5, 4, 3, 2, or 1 phosphodiester and/or phosphorothioate linkages without a sodium counterion. In some embodiments, when the dsRNA agents of the invention are in the sodium salt form, sodium ions are present in the agent as counterions for all of the phosphodiester and/or phosphorothiotate groups present in the agent.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in RNAi agents, in which both the sugar and the internucleoside linkage, i.e., the backbone, of the nucleotide units are replaced with novel groups. The base units are maintained for hybridization with an appropriate nucleic acid target compound. One such oligomeric compound, a RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the RNAi agents of the disclosure are described in, for example, in Nielsen et al., Science, 1991, 254, 1497-1500.

Some embodiments featured in the disclosure include RNAs with phosphorothioate backbones and oligonucleosides with heteroatom backbones, and in particular $—CH_2—NH—CH_2—$, $—CH_2—N(CH_3)—O—CH_2$-[known as a methylene (methylimino) or MMI backbone], $—CH_2—O—N(CH_3)—CH_2—$, $—CH_2—N(CH_3)—N(CH_3)—CH_2—$ and $—N(CH_3)—CH_2—CH_2$-[wherein the native phosphodiester backbone is represented as $—O—P—O—CH_2—$] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The RNAi agents, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an RNAi agent, or a group for improving the pharmacodynamic properties of an RNAi agent, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$. Further exemplary modifications include: 5'-Me-2'-F nucleotides, 5'-Me-2'-OMe nucleotides, 5'-Me-2'-deoxynucleotides, (both R and S isomers in these three families); 2'-alkoxyalkyl; and 2'-NMA (N-methylacetamide).

Other modifications include 2'-methoxy (2'-$OCH_3$), 2'-aminopropoxy (2'-$OCH_2CH_2CH_2NH_2$), 2'-O-hexadecyl, and 2'-fluoro (2'-F). Similar modifications can also be made at other positions on the RNA of an RNAi agent, particularly the 3' position of the sugar on the 3' terminal nucleotide or in 2'-5' linked dsRNAs and the 5' position of 5' terminal nucleotide. RNAi agents can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An RNAi agent of the disclosure can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., (1991) *Angewandte Chemie, International Edition,* 30:613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the disclosure. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

An RNAi agent of the disclosure can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193).

An RNAi agent of the disclosure can also be modified to include one or more bicyclic sugar moities. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the disclosure may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-CH2-O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193). Examples of bicyclic nucleosides for use in the polynucleotides of the disclosure include without limitation nucleosides comprising a bridge between the 4' and the 2' ribosyl ring atoms. In certain embodiments, the antisense polynucleotide agents of the disclosure include one or more bicyclic nucleosides comprising a 4' to 2' bridge. Examples of such 4' to 2' bridged bicyclic nucleosides, include but are not limited to 4'-(CH2)-O-2' (LNA); 4'-(CH2)-S-2'; 4'-$(CH2)_2$—O-2' (ENA); 4'-CH(CH3)-O-2' (also referred to as "constrained ethyl" or "cEt") and 4'-CH(CH2OCH3)-O-2' (and analogs thereof; see, e.g., U.S. Pat. No. 7,399,845); 4'-C(CH3)(CH3)-O-2' (and analogs thereof; see e.g., U.S. Pat. No. 8,278,283); 4'-CH2-N(OCH3)-2' (and analogs thereof; see e.g., U.S. Pat. No. 8,278,425); 4'-CH2-0-N(CH3)-2' (see, e.g., U.S. Patent Publication No. 2004/0171570); 4'-CH2-N(R)—O-2', wherein R is H, C1-C12 alkyl, or a protecting group (see, e.g., U.S. Pat. No. 7,427,672); 4'-CH2-C(H)(CH3)-2' (see, e.g., Chattopadhyaya et al., J. Org. Chem., 2009, 74, 118-134); and 4'-CH2-C(=CH2)-2' (and analogs thereof; see, e.g., U.S. Pat. No. 8,278,426). The entire contents of each of the foregoing are hereby incorporated herein by reference.

Additional representative US Patents and US Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example a-L-ribofuranose and I3-D-ribofuranose (see WO 99/14226).

An RNAi agent of the disclosure can also be modified to include one or more constrained ethyl nucleotides. As used herein, a "constrained ethyl nucleotide" or "cEt" is a locked nucleic acid comprising a bicyclic sugar moiety comprising a 4'-CH(CH3)-O-2' bridge. In one embodiment, a constrained ethyl nucleotide is in the S conformation referred to herein as "S-cEt."

An RNAi agent of the disclosure may also include one or more "conformationally restricted nucleotides" ("CRN"). CRN are nucleotide analogs with a linker connecting the C2' and C4' carbons of ribose or the C3 and —C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US 2013/0190383; and WO 2013/036868, the entire contents of each of which are hereby incorporated herein by reference.

In some embodiments, an RNAi agent of the disclosure comprises one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'-C4' have been removed (i.e. the covalent carbon-oxygen-carbon bond between the C1' and C4' carbons). In another example, the C2'-C3' bond (i.e. the covalent carbon-carbon bond between the C2' and C3' carbons) of the sugar has been removed (see *Nuc. Acids Symp. Series,* 52, 133-134 (2008) and Fluiter et al., *Mol. Biosyst.,* 2009, 10, 1039 hereby incorporated by reference).

Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in WO 2011/005861.

Other modifications of an RNAi agent of the disclosure include a 5' phosphate or 5' phosphate mimic, e.g., a 5'-terminal phosphate or phosphate mimic on the antisense strand of an RNAi agent. Suitable phosphate mimics are disclosed in, for example US 2012/0157511, the entire contents of which are incorporated herein by reference.

A. Modified RNAi Agents Comprising Motifs of the Disclosure

In certain aspects of the disclosure, the double-stranded RNAi agents of the disclosure include agents with chemical modifications as disclosed, for example, in WO 2013/075035, the entire contents of which are incorporated herein by reference. As shown herein and in WO 2013/075035, a superior result may be obtained by introducing one or more motifs of three identical modifications on three consecutive nucleotides into a sense strand or antisense strand of an RNAi agent, particularly at or near the cleavage site. In some embodiments, the sense strand and antisense strand of the RNAi agent may otherwise be completely modified. The introduction of these motifs interrupts the modification pattern, if present, of the sense or antisense strand. The RNAi agent may be optionally conjugated with a lipophilic ligand, e.g., a C16 ligand, for instance on the sense strand. The RNAi agent may be optionally modified with a (S)-glycol nucleic acid (GNA) modification, for instance on one or more residues of the antisense strand. The resulting RNAi agents present superior gene silencing activity.

Accordingly, the disclosure provides double stranded RNAi agents capable of inhibiting the expression of a target gene (i.e., a C9orf72 gene) in vivo. The RNAi agent comprises a sense strand and an antisense strand. Each strand of the RNAi agent may be 15-30 nucleotides in length. For example, each strand may be 16-30 nucleotides in length, 17-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length. In certain embodiments, each strand is 19-23 nucleotides in length.

The sense strand and antisense strand typically form a duplex double stranded RNA ("dsRNA"), also referred to herein as an "RNAi agent." The duplex region of an RNAi agent may be 15-30 nucleotide pairs in length. For example, the duplex region can be 16-30 nucleotide pairs in length, 17-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotides in length. In preferred embodiments, the duplex region is 19-21 nucleotide pairs in length.

In one embodiment, the RNAi agent may contain one or more overhang regions or capping groups at the 3'-end, 5'-end, or both ends of one or both strands. The overhang can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. In preferred embodiments, the nucleotide overhang region is 2 nucleotides in length. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In one embodiment, the nucleotides in the overhang region of the RNAi agent can each independently be a modified or unmodified nucleotide including, but no limited to 2'-sugar modified, such as, 2-F, 2'-O-methyl, thymidine (T), and any combinations thereof.

For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand or both strands of the RNAi agent may be phosphorylated. In some embodiments, the overhang region(s) contains two nucleotides having a phosphorothioate between the two nucleotides, where the two nucleotides can be the same or different. In one embodiment, the overhang is present at the 3'-end of the sense strand, antisense strand, or both strands. In one embodiment, this 3'-overhang is present in the antisense strand. In one embodiment, this 3'-overhang is present in the sense strand.

The RNAi agent may contain only a single overhang, which can strengthen the interference activity of the RNAi, without affecting its overall stability. For example, the single-stranded overhang may be located at the 3'-terminal end of the sense strand or, alternatively, at the 3'-terminal end of the antisense strand. The RNAi may also have a blunt end, located at the 5'-end of the antisense strand (or the 3'-end of the sense strand) or vice versa. Generally, the antisense strand of the RNAi has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

In one embodiment, the RNAi agent is a double ended bluntmer of 19 nucleotides in length, wherein the sense strand contains at least one motif of three 2'-F modifications on three consecutive nucleotides at positions 7, 8, 9 from the 5'end. The antisense strand contains at least one motif of three 2'-O-methyl modifications on three consecutive nucleotides at positions 11, 12, 13 from the 5'end.

In another embodiment, the RNAi agent is a double ended bluntmer of 20 nucleotides in length, wherein the sense strand contains at least one motif of three 2'-F modifications on three consecutive nucleotides at positions 8, 9, 10 from the 5'end. The antisense strand contains at least one motif of three 2'-O-methyl modifications on three consecutive nucleotides at positions 11, 12, 13 from the 5'end.

In yet another embodiment, the RNAi agent is a double ended bluntmer of 21 nucleotides in length, wherein the sense strand contains at least one motif of three 2'-F modifications on three consecutive nucleotides at positions 9, 10, 11 from the 5'end. The antisense strand contains at least one motif of three 2'-O-methyl modifications on three consecutive nucleotides at positions 11, 12, 13 from the 5'end.

In one embodiment, the RNAi agent comprises a 21 nucleotide sense strand and a 23 nucleotide antisense strand, wherein the sense strand contains at least one motif of three 2'-F modifications on three consecutive nucleotides at positions 9, 10, 11 from the 5'end; the antisense strand contains at least one motif of three 2'-O-methyl modifications on three consecutive nucleotides at positions 11, 12, 13 from the 5' end, wherein one end of the RNAi agent is blunt, while the other end comprises a 2 nucleotide overhang. Preferably, the 2 nucleotide overhang is at the 3'-end of the antisense strand. When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In one embodiment, every nucleotide in the sense strand and the antisense strand of the RNAi agent, including the nucleotides that are part of the motifs are modified nucleotides. In one embodiment each residue is independently modified with a 2'-O-methyl or 3'-fluoro, e.g., in an alternating motif. Optionally, the RNAi agent further comprises a ligand (e.g., a lipophilic ligand, optionally a C16 ligand).

In one embodiment, the RNAi agent comprises a sense and an antisense strand, wherein the sense strand is 25-30 nucleotide residues in length, wherein starting from the 5' terminal nucleotide (position 1) positions 1 to 23 of the first strand comprise at least 8 ribonucleotides; the antisense strand is 36-66 nucleotide residues in length and, starting from the 3' terminal nucleotide, comprises at least 8 ribonucleotides in the positions paired with positions 1-23 of sense strand to form a duplex; wherein at least the 3 ‘ terminal nucleotide of antisense strand is unpaired with sense strand, and up to 6 consecutive 3’ terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when the double stranded nucleic acid is introduced into a mammalian cell; and wherein the sense strand contains at least one motif of three 2'-F modifications on three consecutive nucleotides, where at least one of the motifs occurs at or near the cleavage site. The antisense strand contains at least one motif of three 2'-O-methyl modifications on three consecutive nucleotides at or near the cleavage site.

In one embodiment, the RNAi agent comprises sense and antisense strands, wherein the RNAi agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein the 3' end of the first strand and the 5' end of the second strand form a blunt end and the second strand is 1-4 nucleotides longer at its 3' end than the first strand, wherein the duplex region region which is at least 25 nucleotides in length, and the second strand is sufficiently complemenatary to a target mRNA along at least 19 nucleotide of the second strand length to reduce target gene expression when the RNAi agent is introduced into a mammalian cell, and wherein dicer cleavage of the RNAi agent preferentially results in an siRNA comprising the 3' end of the second strand, thereby reducing expression of the target gene in the mammal. Optionally, the RNAi agent further comprises a ligand.

In one embodiment, the sense strand of the RNAi agent contains at least one motif of three identical modifications on three consecutive nucleotides, where one of the motifs occurs at the cleavage site in the sense strand.

In one embodiment, the antisense strand of the RNAi agent can also contain at least one motif of three identical modifications on three consecutive nucleotides, where one of the motifs occurs at or near the cleavage site in the antisense strand.

For an RNAi agent having a duplex region of 17-23 nucleotide in length, the cleavage site of the antisense strand is typically around the 10, 11 and 12 positions from the 5'-end. Thus the motifs of three identical modifications may occur at the 9, 10, 11 positions; 10, 11, 12 positions; 11, 12, 13 positions; 12, 13, 14 positions; or 13, 14, 15 positions of the antisense strand, the count starting from the $1^{st}$ nucleotide from the 5'-end of the antisense strand, or, the count starting from the $1^{st}$ paired nucleotide within the duplex region from the 5'-end of the antisense strand. The cleavage site in the antisense strand may also change according to the length of the duplex region of the RNAi from the 5'-end.

The sense strand of the RNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In one embodiment, the sense strand of the RNAi agent may contain more than one motif of three identical modifications on three consecutive nucleotides. The first motif may occur at or near the cleavage site of the strand and the other motifs may be a wing modification. The term "wing modification" herein refers to a motif occurring at another portion of the strand that is separated from the motif at or near the cleavage site of the same strand. The wing modification is either adajacent to the first motif or is separated by at least one or more nucleotides. When the motifs are immediately adjacent to each other then the chemistry of the motifs are distinct from each other and when the motifs are separated by one or more nucleotide than the chemistries can be the same or different. Two or more wing modifications may be present. For instance, when two wing modifications are present, each wing modification may occur at one end relative to the first motif which is at or near cleavage site or on either side of the lead motif.

Like the sense strand, the antisense strand of the RNAi agent may contain more than one motif of three identical modifications on three consecutive nucleotides, with at least one of the motifs occurring at or near the cleavage site of the strand. This antisense strand may also contain one or more wing modifications in an alignment similar to the wing modifications that may be present on the sense strand.

In one embodiment, the wing modification on the sense strand or antisense strand of the RNAi agent typically does not include the first one or two terminal nucleotides at the 3'-end, 5'-end or both ends of the strand.

In another embodiment, the wing modification on the sense strand or antisense strand of the RNAi agent typically does not include the first one or two paired nucleotides within the duplex region at the 3'-end, 5'-end or both ends of the strand.

When the sense strand and the antisense strand of the RNAi agent each contain at least one wing modification, the wing modifications may fall on the same end of the duplex region, and have an overlap of one, two or three nucleotides.

When the sense strand and the antisense strand of the RNAi agent each contain at least two wing modifications, the sense strand and the antisense strand can be so aligned that two modifications each from one strand fall on one end of the duplex region, having an overlap of one, two or three nucleotides; two modifications each from one strand fall on the other end of the duplex region, having an overlap of one, two or three nucleotides; two modifications one strand fall on each side of the lead motif, having an overlap of one, two, or three nucleotides in the duplex region.

In one embodiment, the RNAi agent comprises mismatch (es) with the target, within the duplex, or combinations thereof. The mistmatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In one embodiment, the RNAi agent comprises at least one of the first 1, 2, 3, 4, or 5 base pairs within the duplex regions from the 5'-end of the antisense strand independently selected from the group of: A:U, G:U, I:C, and mismatched pairs, e.g., non-canonical or other than canonical pairings or pairings which include a universal base, to promote the dissociation of the antisense strand at the 5'-end of the duplex.

In one embodiment, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

In another embodiment, the nucleotide at the 3'-end of the sense strand is deoxy-thymine (dT). In another embodiment, the nucleotide at the 3'-end of the antisense strand is deoxy-thymine (dT). In one embodiment, there is a short sequence of deoxy-thymine nucleotides, for example, two dT nucleotides on the 3'-end of the sense or antisense strand.

In one embodiment, the sense strand sequence may be represented by formula (I):

$$5' n_p\text{-}N_a\text{-}(X\ X\ X)_i\text{—}N_b\text{-}Y\ Y\ Y\text{-}N_b\text{-}(Z\ Z\ Z)_j\text{-}N_a\text{-}n_q 3' \quad \text{(I)}$$

wherein:

i and j are each independently 0 or 1;

p and q are each independently 0-6;

each $N_a$ independently represents an oligonucleotide sequence comprising 0-25 modified nucleotides, each sequence comprising at least two differently modified nucleotides;

each $N_b$ independently represents an oligonucleotide sequence comprising 0-10 modified nucleotides;

each $n_p$ and $n_q$ independently represent an overhang nucleotide;

wherein $N_b$ and Y do not have the same modification; and

XXX, YYY and ZZZ each independently represent one motif of three identical modifications on three consecutive nucleotides. Preferably YYY is all 2'-F modified nucleotides.

In one embodiment, the $N_a$ or $N_b$ comprise modifications of alternating pattern.

In one embodiment, the YYY motif occurs at or near the cleavage site of the sense strand. For example, when the RNAi agent has a duplex region of 17-23 nucleotides in length, the YYY motif can occur at or the vicinity of the cleavage site (e.g.: can occur at positions 6, 7, 8, 7, 8, 9, 8, 9, 10, 9, 10, 11, 10, 11,12 or 11, 12, 13) of—the sense strand, the count starting from the $1^{st}$ nucleotide, from the 5'-end; or optionally, the count starting at the $1^{st}$ paired nucleotide within the duplex region, from the 5'-end.

In one embodiment, i is 1 and j is 0, or i is 0 and j is 1, or both i and j are 1. The sense strand can therefore be represented by the following formulas:

$$5' n_p\text{-}N_a\text{-}YYY\text{-}N_b\text{-}ZZZ\text{-}N_a\text{-}n_q 3' \quad \text{(Ib);}$$

$$5' n_p\text{-}N_a\text{-}XXX\text{-}N_b\text{-}YYY\text{-}N_a\text{-}n_q 3' \quad \text{(Ic); or}$$

$$5' n_p\text{-}N_a\text{-}XXX\text{-}N_b\text{-}YYY\text{-}N_b\text{-}ZZZ\text{-}N_a\text{-}n_q 3' \quad \text{(Id).}$$

When the sense strand is represented by formula (Ib), $N_b$ represents an oligonucleotide sequence comprising 0-10, 0-7, 0-5, 0-4, 0-2 or 0 modified nucleotides.

Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-10, 0-7, 0-5, 0-4, 0-2 or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2 or 0 modified nucleotides. Preferably, $N_b$ is 0, 1, 2, 3, 4, 5 or 6. Each $N_a$ can independently represent an oligonucleotide sequence comprising 2-20, 2-15, or 2-10 modified nucleotides.

Each of X, Y and Z may be the same or different from each other.

In other embodiments, i is 0 and j is 0, and the sense strand may be represented by the formula:

$$5'n_p\text{-}N_a\text{-YYY-}N_a\text{-}n_q3' \quad \text{(Ia).}$$

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

$$5'n_{q'}\text{-}N_a'\text{-}(Z'Z'Z')_k\text{—}N_b'\text{-}Y'Y'Y'\text{-}N_b'\text{-}(X'X'X')_l\text{-}N'_a\text{-}n_p'3' \quad \text{(II)}$$

wherein:

k and l are each independently 0 or 1;

p' and q' are each independently 0-6;

each $N_a'$ independently represents an oligonucleotide sequence comprising 0-25 modified nucleotides, each sequence comprising at least two differently modified nucleotides;

each $N_b'$ independently represents an oligonucleotide sequence comprising 0-10 modified nucleotides;

each $n_p'$ and $n_q'$ independently represent an overhang nucleotide;

wherein $N_b'$ and Y' do not have the same modification;

and X'X'X', Y'Y'Y' and Z'Z'Z' each independently represent one motif of three identical modifications on three consecutive nucleotides.

In one embodiment, the $N_a'$ or $N_b'$ comprise modifications of alternating pattern.

The Y'Y'Y' motif occurs at or near the cleavage site of the antisense strand. For example, when the RNAi agent has a duplex region of 17-23nucleotide in length, the Y'Y'Y' motif can occur at positions 9, 10, 11; 10, 11, 12; 11, 12, 13; 12, 13, 14; or 13, 14, 15 of the antisense strand, with the count starting from the 1st nucleotide, from the 5'-end; or optionally, the count starting at the 1st paired nucleotide within the duplex region, from the 5'-end. Preferably, the Y'Y'Y' motif occurs at positions 11, 12, 13.

In one embodiment, Y'Y'Y' motif is all 2'-OMe modified nucleotides.

In one embodiment, k is 1 and l is 0, or k is 0 and l is 1, or both k and l are 1.

The antisense strand can therefore be represented by the following formulas:

$$5'n_{q'}\text{-}N_a'\text{-}Z'Z'Z'\text{-}N_b'\text{-}Y'Y'Y'\text{-}N_a'\text{-}n_{p'}3' \quad \text{(IIb);}$$

$$5'n_q'\text{-}N_a'\text{-}Y'Y'Y'\text{-}N_b'\text{-}X'X'X'\text{-}n_{p'}3' \quad \text{(IIc); or}$$

$$5'n_{q'}\text{-}N_a'\text{-}Z'Z'Z'\text{-}N_b'\text{-}Y'Y'Y'\text{-}N_b'\text{-}X'X'X'\text{-}N_a'\text{-}n_{p'}3' \quad \text{(IId).}$$

When the antisense strand is represented by formula (IIb), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IIc), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IId), each Nb' independently represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides. Preferably, $N_b$ is 0, 1, 2, 3, 4, 5 or 6.

In other embodiments, k is 0 and 1 is 0 and the antisense strand may be represented by the formula:

$$5'n_{p'}\text{-}N_{a'}\text{-}Y'Y'Y'\text{-}N_{a'}\text{-}n_{q'}3' \quad \text{(Ia).}$$

When the antisense strand is represented as formula (IIa), each $N_a'$ independently represents an oligonucleotide sequence comprising 2-20, 2-15, or 2-10 modified nucleotides.

Each of X', Y' and Z' may be the same or different from each other.

Each nucleotide of the sense strand and antisense strand may be independently modified with LNA, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y' and Z', in particular, may represent a 2'-O-methyl modification or a 2'-fluoro modification.

In one embodiment, the sense strand of the RNAi agent may contain YYY motif occurring at 9, 10 and 11 positions of the strand when the duplex region is 21 nt, the count starting from the 1st nucleotide from the 5'-end, or optionally, the count starting at the 1st paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In one embodiment the antisense strand may contain Y'Y'Y' motif occurring at positions 11, 12, 13 of the strand, the count starting from the 1st nucleotide from the 5'-end, or optionally, the count starting at the 1st paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with a antisense strand being represented by any one of formulas (IIa), (IIb), (IIc), and (IId), respectively.

Accordingly, the RNAi agents for use in the methods of the disclosure may comprise a sense strand and an antisense strand, each strand having 14 to 30 nucleotides, the RNAi duplex represented by formula (III):

$$\text{sense:}5'n_p\text{-}N_a\text{-}(X\ X\ X)_i\text{-}N_b\text{-}Y\ Y\ Y\text{-}Nb\text{-}(Z\ Z\ Z)_j\text{-}N_a\text{-}n_q3'$$

$$\text{antisense:}3'n_p'\text{-}N_a'\text{-}(X'X'X')_k\text{-}N_b'\text{-}Y'Y'Y'\text{-}N_b'\text{-}(Z'Z'Z')_l\text{—}N_a'\text{-}n_q'5' \quad \text{(III)}$$

wherein:

j, k, and l are each independently 0 or 1;

p, p', q, and q' are each independently 0-6;

each $N_a$ and $N_a'$ independently represents an oligonucleotide sequence comprising 0-25 modified nucleotides, each sequence comprising at least two differently modified nucleotides;

each $N_b$ and Nb' independently represents an oligonucleotide sequence comprising 0-10 modified nucleotides; wherein each $n_p'$, $n_p$, $n_q'$, and $n_q$, each of which may or may not be present, independently represents an overhang nucleotide; and XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and l is 0; or k is 1 and l is 0; k is 0 and l is 1; or both k and l are 0; or both k and l are 1.

Exemplary combinations of the sense strand and antisense strand forming an RNAi duplex include the formulas below:

5'$n_p$-$N_a$-Y Y Y-$N_a$-$n_q$3'

3'$n_p'$-$N_a'$-Y'Y'Y'-$N_a$$n_q'$5' (IIIa)

5'$n_p$-$N_a$-Y Y Y-$N_b$-Z Z Z-$N_a$-$n_q$3'

3'$n_p'$-$N_a'$-Y'Y'Y'-$N_b'$-Z'Z'Z'-$N_a$$n_q'$5' (Mb)

5'$n_p$-$N_a$-X X X-$N_b$-Y Y Y-$N_a$-$n_q$3'

3'$n_p'$-$N_a'$-X'X'X'-$N_b'$-Y'Y'Y'-$N_a'$-$n_q'$5' (IIIc)

5'$n_p$-$N_a$-X X X-$N_b$-Y Y Y-$N_b$-Z Z Z-$N_a$-$n_q$3'

3'$n_p'$-$N_a'$-X'X'X'-$N_b'$-Y'Y'Y'-$N_b'$-Z'Z'Z'—$N_a$-$n_q'$5' (IIId)

When the RNAi agent is represented by formula (IIIa), each $N_a$ independently represents an oligonucleotide sequence comprising 2-20, 2-15, or 2-10 modified nucleotides.

When the RNAi agent is represented by formula (IIIb), each $N_b$ independently represents an oligonucleotide sequence comprising 1-10, 1-7, 1-5 or 1-4 modified nucleotides. Each $N_a$ independently represents an oligonucleotide sequence comprising 2-20, 2-15, or 2-10 modified nucleotides.

When the RNAi agent is represented as formula (IIIc), each Nb, Nb' independently represents an oligonucleotide sequence comprising 0-10, 0-7, 0-10, 0-7, 0-5, 0-4, 0-2 or 0 modified nucleotides. Each $N_a$ independently represents an oligonucleotide sequence comprising 2-20, 2-15, or 2-10 modified nucleotides.

When the RNAi agent is represented as formula (IIId), each Nb, Nb' independently represents an oligonucleotide sequence comprising 0-10, 0-7, 0-10, 0-7, 0-5, 0-4, 0-2 or 0 modified nucleotides. Each $N_a$, $N_a'$ independently represents an oligonucleotide sequence comprising 2-20, 2-15, or 2-10 modified nucleotides. Each of $N_a$, $N_a'$, $N_b$ and Nb' independently comprises modifications of alternating pattern.

In one embodiment, when the RNAi agent is represented by formula (IIId), the $N_a$ modifications are 2'-O-methyl or 2'-fluoro modifications. In another embodiment, when the RNAi agent is represented by formula (IIId), the $N_a$ modifications are 2'-O-methyl or 2'-fluoro modifications and $n_p'$>0 and at least one $n_p'$ is linked to a neighboring nucleotide a via phosphorothioate linkage. In yet another embodiment, when the RNAi agent is represented by formula (IIId), the $N_a$ modifications are 2'-O-methyl or 2'-fluoro modifications, $n_p'$>0 and at least one $n_p'$ is linked to a neighboring nucleotide via phosphorothioate linkage, and the sense strand is conjugated to one or more C16 (or related) moieties attached through a bivalent or trivalent branched linker (described below). In another embodiment, when the RNAi agent is represented by formula (IIId), the $N_a$ modifications are 2'-O-methyl or 2'-fluoro modifications, $n_p'$>0 and at least one $n_p'$ is linked to a neighboring nucleotide via phosphorothioate linkage, the sense strand comprises at least one phosphorothioate linkage, and the sense strand is conjugated to one or more lipophilic, e.g., C16 (or related) moieties, optionally attached through a bivalent or trivalent branched linker.

In one embodiment, when the RNAi agent is represented by formula (IIIa), the $N_a$ modifications are 2'-O-methyl or 2'-fluoro modifications, $n_p'$>0 and at least one $n_p'$ is linked to a neighboring nucleotide via phosphorothioate linkage, the sense strand comprises at least one phosphorothioate linkage, and the sense strand is conjugated to one or more lipophilic, e.g., C16 (or related) moieties attached through a bivalent or trivalent branched linker.

In one embodiment, the RNAi agent is a multimer containing at least two duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, the RNAi agent is a multimer containing three, four, five, six or more duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two RNAi agents represented by formula (III), (IIIa), (IIIb), (IIIc), and (IIId) are linked to each other at the 5' end, and one or both of the 3' ends and are optionally conjugated to a ligand. Each of the agents can target the same gene or two different genes; or each of the agents can target same gene at two different target sites.

Various publications describe multimeric RNAi agents that can be used in the methods of the disclosure. Such publications include WO2007/091269, WO2010/141511, WO2007/117686, WO2009/014887, and WO2011/031520; and U.S. Pat. No. 7,858,769, the entire contents of each of which are hereby incorporated herein by reference.

In certain embodiments, the compositions and methods of the disclosure include a vinyl phosphonate (VP) modification of an RNAi agent as described herein. In exemplary embodiments, a vinyl phosphonate of the disclosure has the following structure:

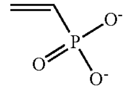

A vinyl phosphonate of the instant disclosure may be attached to either the antisense or the sense strand of a dsRNA of the disclosure. In certain preferred embodiments, a vinyl phosphonate of the instant disclosure is attached to the antisense strand of a dsRNA, optionally at the 5' end of the antisense strand of the dsRNA.

Vinyl phosphate modifications are also contemplated for the compositions and methods of the instant disclosure. An exemplary vinyl phosphate structure is:

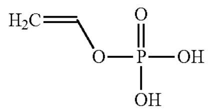

i. Thermally Destabilizing Modifications

In certain embodiments, a dsRNA molecule can be optimized for RNA interference by incorporating thermally destabilizing modifications in the seed region of the antisense strand (i.e., at positions 2-9 of the 5'-end of the antisense strand) to reduce or inhibit off-target gene silencing. It has been discovered that dsRNAs with an antisense strand comprising at least one thermally destabilizing modification of the duplex within the first 9 nucleotide positions, counting from the 5' end, of the antisense strand have reduced off-target gene silencing activity. Accordingly, in some embodiments, the antisense strand comprises at least one (e.g., one, two, three, four, five or more) thermally destabilizing modification of the duplex within the first 9 nucleotide positions of the 5' region of the antisense strand. In some embodiments, one or more thermally destabilizing modification(s) of the duplex is/are located in positions 2-9, or preferably positions 4-8, from the 5'-end of the antisense strand. In some further embodiments, the thermally destabilizing modification(s) of the duplex is/are located at position 6, 7 or 8 from the 5'-end of the antisense strand. In still some further embodiments, the thermally destabilizing modification of the duplex is located at position 7 from the 5'-end of the antisense strand. The term "thermally destabilizing modification(s)" includes modification(s) that would result with a dsRNA with a lower overall melting temperature (Tm) (preferably a Tm with one, two, three or four degrees lower than the Tm of the dsRNA without having such modification(s). In some embodiments, the thermally destabilizing modification of the duplex is located at position 2, 3, 4, 5 or 9 from the 5'-end of the antisense strand.

The thermally destabilizing modifications can include, but are not limited to, abasic modification; mismatch with the opposing nucleotide in the opposing strand; and sugar modification such as 2'-deoxy modification or acyclic nucleotide, e.g., unlocked nucleic acids (UNA) or glycol nucleic acid (GNA).

Exemplified abasic modifications include, but are not limited to the following:

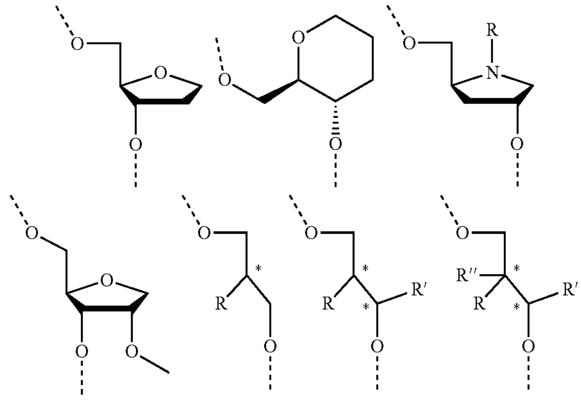

Wherein R=H, Me, Et or OMe; R'=H, Me, Et or OMe; R"=H, Me, Et or OMe

Mod2

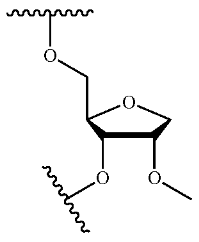

(2'-OMe Abasic Spacer)

Mod3

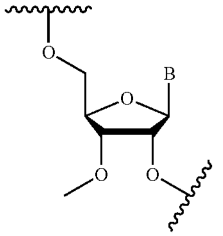

(3'-OMe)

Mod4

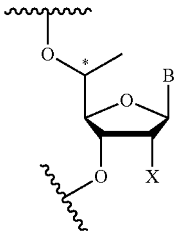

(5'-Me)

X = OMe, F

Mod5

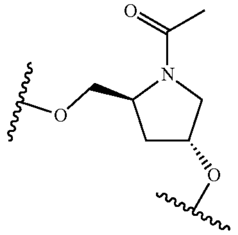

(Hyp-spacer)

wherein B is a modified or unmodified nucleobase.

Exemplified sugar modifications include, but are not limited to the following:

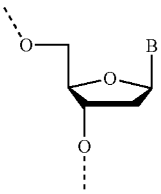

2'-deoxy

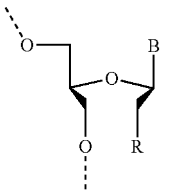

unlocked nucleic acid
R = H, OH, O-alkyl

-continued

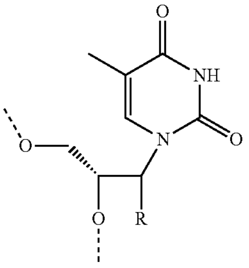

glycol nucleic acid R = H, OH, O-alkyl

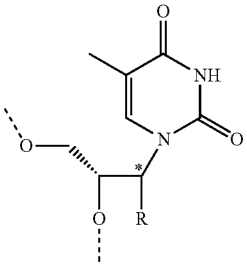

glycol nucleic acid R = H, OH, O-alkyl

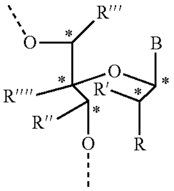

unlocked nucleic acid
R = H, OH, $CH_3$, $CH_2CH_3$, O-alkyl, $NH_2$, NHMe, $NMe_2$
R' = H, OH, $CH_3$, $CH_2CH_3$, O-alkyl, $NH_2$, NHMe, $NMe_2$
R'' = H, OH, $CH_3$, $CH_2CH_3$, O-alkyl, $NH_2$, NHMe, $NMe_2$
R''' = H, OH, $CH_3$, $CH_2CH_3$, O-alkyl, $NH_2$, NHMe, $NMe_2$
R'''' = H, OH, $CH_3$, $CH_2CH_3$, O-alkyl, $NH_2$, NHMe, $NMe_2$

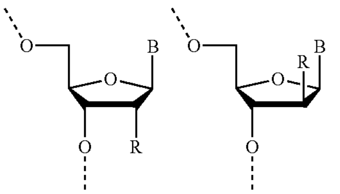

R = H, methyl, ethyl wherein B is a modified or unmodified nucleobase.

In some embodiments the thermally destabilizing modification of the duplex is selected from the group consisting of:

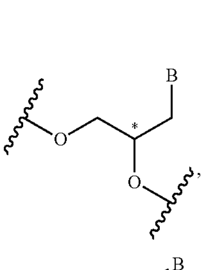

,

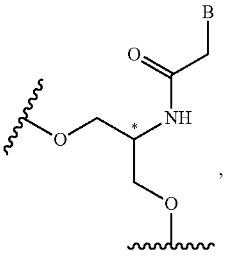

,

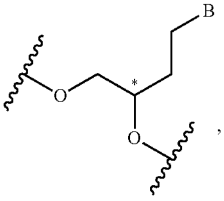

,

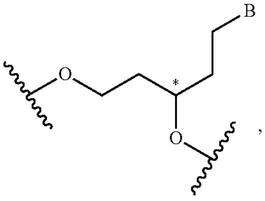

,

-continued

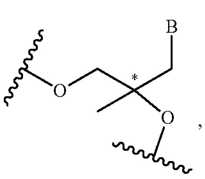

, and

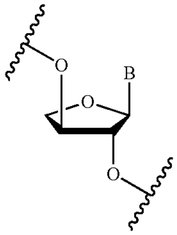

wherein B is a modified or unmodified nucleobase and the asterisk on each structure represents either R, S or racemic.

The term "acyclic nucleotide" refers to any nucleotide having an acyclic ribose sugar, for example, where any of bonds between the ribose carbons (e.g., C1'-C2', C2'-C3', C3'-C4', C4'-O4', or C1'-O4') is absent or at least one of ribose carbons or oxygen (e.g., C C2', C3', C4' or O4') are independently or in combination absent from the nucleotide. In some embodiments, acyclic nucleotide

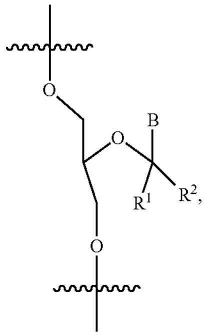

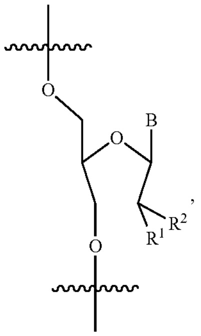

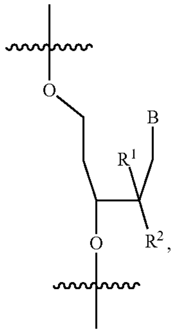

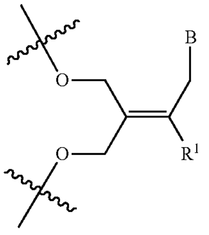

or

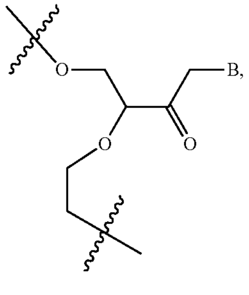

is wherein B is a modified or unmodified nucleobase, $R^1$ and $R^2$ independently are H, halogen, $OR_3$, or alkyl; and $R_3$ is H, alkyl, cycloalkyl, aryl, aralkyl, heteroaryl or sugar). The term "UNA" refers to unlocked acyclic nucleic acid, wherein any of the bonds of the sugar has been removed, forming an unlocked "sugar" residue. In one example, UNA also encompasses monomers with bonds between C1'-C4' being removed (i.e. the covalent carbon-oxygen-carbon bond between the C1' and C4' carbons). In another example, the C2'-C3' bond (i.e. the covalent carbon-carbon bond between the C2' and C3' carbons) of the sugar is removed (see Mikhailov et. al., Tetrahedron Letters, 26 (17): 2059 (1985); and Fluiter et al., Mol. Biosyst., 10: 1039 (2009), which are hereby incorporated by reference in their entirety). The acyclic derivative provides greater backbone flexibility without affecting the Watson-Crick pairings. The acyclic nucleotide can be linked via 2'-5' or 3'-5' linkage.

The term 'GNA' refers to glycol nucleic acid which is a polymer similar to DNA or RNA but differing in the composition of its "backbone" in that is composed of repeating glycerol units linked by phosphodiester bonds:

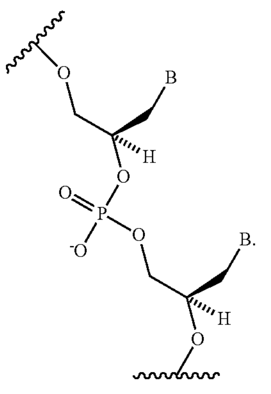

(R)-GNA

The thermally destabilizing modification of the duplex can be mismatches (i.e., noncomplementary base pairs) between the thermally destabilizing nucleotide and the opposing nucleotide in the opposite strand within the dsRNA duplex. Exemplary mismatch base pairs include G:G, G:A, G:U, G:T, A:A, A:C, C:C, C:U, C:T, U:U, T:T, U:T, or a combination thereof. Other mismatch base pairings known in the art are also amenable to the present invention. A mismatch can occur between nucleotides that are either naturally occurring nucleotides or modified nucleotides, i.e., the mismatch base pairing can occur between the nucleobases from respective nucleotides independent of the modifications on the ribose sugars of the nucleotides. In certain embodiments, the dsRNA molecule contains at least one nucleobase in the mismatch pairing that is a 2'-deoxy nucleobase; e.g., the 2'-deoxy nucleobase is in the sense strand.

In some embodiments, the thermally destabilizing modification of the duplex in the seed region of the antisense strand includes nucleotides with impaired W-C H-bonding to complementary base on the target mRNA, such as:

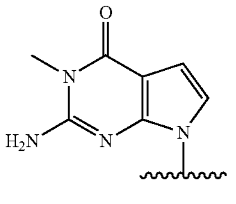

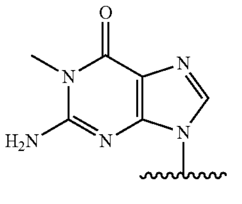

-continued

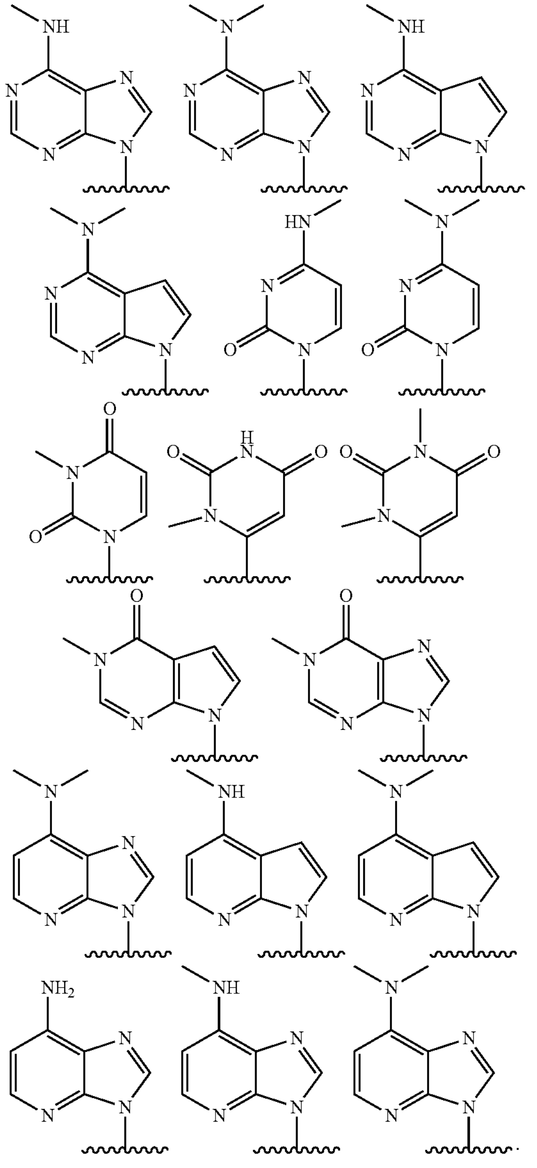

More examples of abasic nucleotide, acyclic nucleotide modifications (including UNA and GNA), and mismatch modifications have been described in detail in WO 2011/133876, which is herein incorporated by reference in its entirety.

The thermally destabilizing modifications may also include universal base with reduced or abolished capability to form hydrogen bonds with the opposing bases, and phosphate modifications.

In some embodiments, the thermally destabilizing modification of the duplex includes nucleotides with non-canonical bases such as, but not limited to, nucleobase modifications with impaired or completely abolished capability to form hydrogen bonds with bases in the opposite strand. These nucleobase modifications have been evaluated for destabilization of the central region of the dsRNA duplex as described in WO 2010/0011895, which is herein incorporated by reference in its entirety. Exemplary nucleobase modifications are:

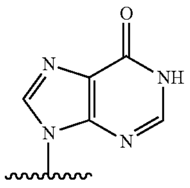

inosine

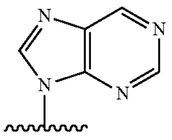

nebularine

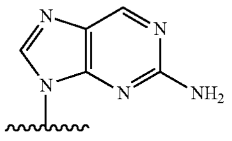

2-aminopurine

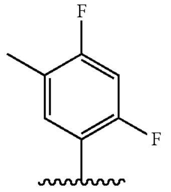

2,4-difluorotoluene

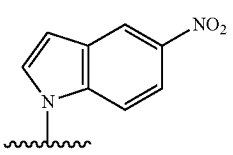

5-nitroindole

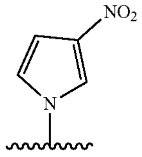

3-nitropyrrole

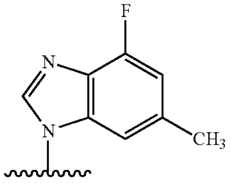

4-Flouro-6-methylbenzimidazole

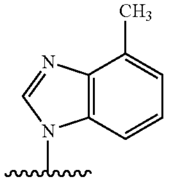

4-Methylbenzimidazole

In some embodiments, the thermally destabilizing modification of the duplex in the seed region of the antisense strand includes one or more a-nucleotide complementary to the base on the target mRNA, such as:

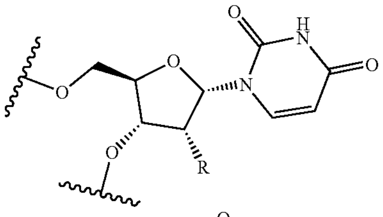

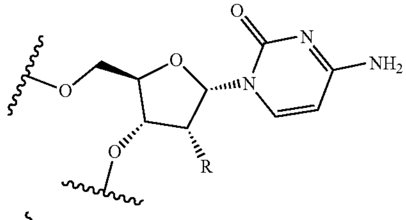

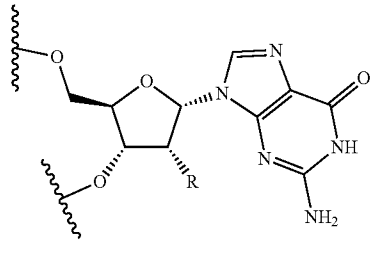

-continued

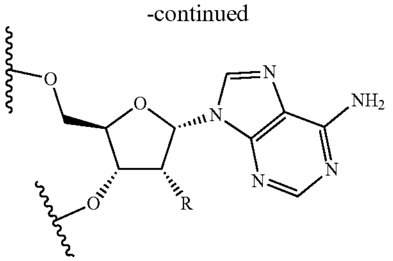

wherein R is H, OH, $OCH_3$, F, $NH_2$, NHMe, $NMe_2$ or O-alkyl.

Exemplary phosphate modifications known to decrease the thermal stability of dsRNA duplexes compared to natural phosphodiester linkages are:

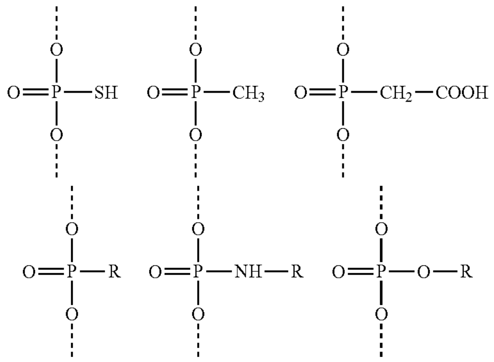

R=alkyl

The alkyl for the R group can be a $C_1$-$C_6$alkyl. Specific alkyls for the R group include, but are not limited to methyl, ethyl, propyl, isopropyl, butyl, pentyl and hexyl.

As the skilled artisan will recognize, in view of the functional role of nucleobases is defining specificity of an RNAi agent of the disclosure, while nucleobase modifications can be performed in the various manners as described herein, e.g., to introduce destabilizing modifications into an RNAi agent of the disclosure, e.g., for purpose of enhancing on-target effect relative to off-target effect, the range of modifications available and, in general, present upon RNAi agents of the disclosure tends to be much greater for non-nucleobase modifications, e.g., modifications to sugar groups or phosphate backbones of polyribonucleotides. Such modifications are described in greater detail in other sections of the instant disclosure and are expressly contemplated for RNAi agents of the disclosure, either possessing native nucleobases or modified nucleobases as described above or elsewhere herein.

In addition to the antisense strand comprising a thermally destabilizing modification, the dsRNA can also comprise one or more stabilizing modifications. For example, the dsRNA can comprise at least two (e.g., two, three, four, five, six, seven, eight, nine, ten or more) stabilizing modifications. Without limitations, the stabilizing modifications all can be present in one strand. In some embodiments, both the sense and the antisense strands comprise at least two stabilizing modifications. The stabilizing modification can occur on any nucleotide of the sense strand or antisense strand. For instance, the stabilizing modification can occur on every nucleotide on the sense strand or antisense strand; each stabilizing modification can occur in an alternating pattern on the sense strand or antisense strand; or the sense strand or antisense strand comprises both stabilizing modification in an alternating pattern. The alternating pattern of the stabilizing modifications on the sense strand may be the same or different from the antisense strand, and the alternating pattern of the stabilizing modifications on the sense strand can have a shift relative to the alternating pattern of the stabilizing modifications on the antisense strand.

In some embodiments, the antisense strand comprises at least two (e.g., two, three, four, five, six, seven, eight, nine, ten or more) stabilizing modifications. Without limitations, a stabilizing modification in the antisense strand can be present at any positions. In some embodiments, the antisense comprises stabilizing modifications at positions 2, 6, 8, 9, 14, and 16 from the 5'-end. In some other embodiments, the antisense comprises stabilizing modifications at positions 2, 6, 14, and 16 from the 5'-end. In still some other embodiments, the antisense comprises stabilizing modifications at positions 2, 14, and 16 from the 5'-end.

In some embodiments, the antisense strand comprises at least one stabilizing modification adjacent to the destabilizing modification. For example, the stabilizing modification can be the nucleotide at the 5'-end or the 3'-end of the destabilizing modification, i.e., at position −1 or +1 from the position of the destabilizing modification. In some embodiments, the antisense strand comprises a stabilizing modification at each of the 5'-end and the 3'-end of the destabilizing modification, i.e., positions −1 and +1 from the position of the destabilizing modification.

In some embodiments, the antisense strand comprises at least two stabilizing modifications at the 3'-end of the destabilizing modification, i.e., at positions +1 and +2 from the position of the destabilizing modification.

In some embodiments, the sense strand comprises at least two (e.g., two, three, four, five, six, seven, eight, nine, ten or more) stabilizing modifications. Without limitations, a stabilizing modification in the sense strand can be present at any positions. In some embodiments, the sense strand comprises stabilizing modifications at positions 7, 10, and 11 from the 5'-end. In some other embodiments, the sense strand comprises stabilizing modifications at positions 7, 9, 10, and 11 from the 5'-end. In some embodiments, the sense strand comprises stabilizing modifications at positions opposite or complimentary to positions 11, 12, and 15 of the antisense strand, counting from the 5'-end of the antisense strand. In some other embodiments, the sense strand comprises stabilizing modifications at positions opposite or complimentary to positions 11, 12, 13, and 15 of the antisense strand, counting from the 5'-end of the antisense strand. In some embodiments, the sense strand comprises a block of two, three, or four stabilizing modifications.

In some embodiments, the sense strand does not comprise a stabilizing modification in position opposite or complimentary to the thermally destabilizing modification of the duplex in the antisense strand.

Exemplary thermally stabilizing modifications include, but are not limited to, 2'-fluoro modifications. Other thermally stabilizing modifications include, but are not limited to, LNA.

In some embodiments, the dsRNA of the disclosure comprises at least four (e.g., four, five, six, seven, eight, nine, ten, or more) 2'-fluoro nucleotides. Without limitations, the 2'-fluoro nucleotides all can be present in one strand. In some embodiments, both the sense and the antisense strands comprise at least two 2'-fluoro nucleotides. The 2'-fluoro modification can occur on any nucleotide of the sense strand or antisense strand. For instance, the 2'-fluoro modification can occur on every nucleotide on the sense strand or antisense strand; each 2'-fluoro modification can occur in an alternating pattern on the sense strand or antisense strand; or the sense strand or antisense strand comprises both 2'-fluoro modifications in an alternating pattern. The alternating pattern of the 2'-fluoro modifications on the sense strand may be the same or different from the antisense strand, and the alternating pattern of the 2'-fluoro modifications on the sense strand can have a shift relative to the alternating pattern of the 2'-fluoro modifications on the antisense strand.

In some embodiments, the antisense strand comprises at least two (e.g., two, three, four, five, six, seven, eight, nine, ten, or more) 2'-fluoro nucleotides. Without limitations, a 2'-fluoro modification in the antisense strand can be present at any positions. In some embodiments, the antisense comprises 2'-fluoro nucleotides at positions 2, 6, 8, 9, 14, and 16 from the 5'-end. In some other embodiments, the antisense comprises 2'-fluoro nucleotides at positions 2, 6, 14, and 16 from the 5'-end. In still some other embodiments, the antisense comprises 2'-fluoro nucleotides at positions 2, 14, and 16 from the 5'-end.

In some embodiments, the antisense strand comprises at least one 2'-fluoro nucleotide adjacent to the destabilizing modification. For example, the 2'-fluoro nucleotide can be the nucleotide at the 5'-end or the 3'-end of the destabilizing modification, i.e., at position −1 or +1 from the position of the destabilizing modification. In some embodiments, the antisense strand comprises a 2'-fluoro nucleotide at each of the 5'-end and the 3'-end of the destabilizing modification, i.e., positions −1 and +1 from the position of the destabilizing modification.

In some embodiments, the antisense strand comprises at least two 2'-fluoro nucleotides at the 3'-end of the destabilizing modification, i.e., at positions +1 and +2 from the position of the destabilizing modification.

In some embodiments, the sense strand comprises at least two (e.g., two, three, four, five, six, seven, eight, nine, ten or more) 2'-fluoro nucleotides. Without limitations, a 2'-fluoro modification in the sense strand can be present at any positions. In some embodiments, the antisense comprises 2'-fluoro nucleotides at positions 7, 10, and 11 from the 5'-end. In some other embodiments, the sense strand comprises 2'-fluoro nucleotides at positions 7, 9, 10, and 11 from the 5'-end. In some embodiments, the sense strand comprises 2'-fluoro nucleotides at positions opposite or complimentary to positions 11, 12, and 15 of the antisense strand, counting from the 5'-end of the antisense strand. In some other embodiments, the sense strand comprises 2'-fluoro nucleotides at positions opposite or complimentary to positions 11, 12, 13, and 15 of the antisense strand, counting from the 5'-end of the antisense strand. In some embodiments, the sense strand comprises a block of two, three or four 2'-fluoro nucleotides.

In some embodiments, the sense strand does not comprise a 2'-fluoro nucleotide in position opposite or complimentary to the thermally destabilizing modification of the duplex in the antisense strand.

In some embodiments, the dsRNA molecule of the disclosure comprises a 21 nucleotides (nt) sense strand and a 23 nucleotides (nt) antisense, wherein the antisense strand contains at least one thermally destabilizing nucleotide, where the at least one thermally destabilizing nucleotide occurs in the seed region of the antisense strand (i.e., at position 2-9 of the 5'-end of the antisense strand), wherein one end of the dsRNA is blunt, while the other end is comprises a 2 nt overhang, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the dsRNA comprises a blunt end at 5'-end of the antisense strand. Preferably, the 2 nt overhang is at the 3'-end of the antisense.

In some embodiments, the dsRNA molecule of the disclosure comprising a sense and antisense strands, wherein: the sense strand is 25-30 nucleotide residues in length, wherein starting from the 5' terminal nucleotide (position 1), positions 1 to 23 of said sense strand comprise at least 8 ribonucleotides; antisense strand is 36-66 nucleotide residues in length and, starting from the 3' terminal nucleotide, at least 8 ribonucleotides in the positions paired with positions 1-23 of sense strand to form a duplex; wherein at least the 3 ‘ terminal nucleotide of antisense strand is unpaired with sense strand, and up to 6 consecutive 3’ terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the antisense strand contains at least one thermally destabilizing nucleotide, where at least one thermally destabilizing nucleotide is in the seed region of the antisense strand (i.e. at position 2-9 of the 5'-end of the antisense strand). For example, the thermally destabilizing nucleotide occurs between positions opposite or complimentary to positions 14-17 of the 5'-end of the sense strand, and wherein the dsRNA optionally further has at least one (e.g., one, two, three, four, five, six or all seven) of the following characteristics: (i) the antisense comprises 2, 3, 4, 5, or 6 2'-fluoro modifications; (ii) the antisense comprises 1, 2, 3, 4, or 5 phosphorothioate internucleotide linkages; (iii) the sense strand is conjugated with a ligand; (iv) the sense strand comprises 2, 3, 4, or 5 2'-fluoro modifications; (v) the sense strand comprises 1, 2, 3, 4, or 5 phosphorothioate internucleotide linkages; and (vi) the dsRNA comprises at least four 2'-fluoro modifications; and (vii) the dsRNA comprises a duplex region of 12-30 nucleotide pairs in length.

In some embodiments, the dsRNA molecule of the disclosure comprises a sense and antisense strands, wherein said dsRNA molecule comprises a sense strand having a length which is at least 25 and at most 29 nucleotides and an antisense strand having a length which is at most 30 nucleotides with the sense strand comprises a modified nucleotide that is susceptible to enzymatic degradation at position 11 from the 5'end, wherein the 3' end of said sense strand and the 5' end of said antisense strand form a blunt end and said antisense strand is 1~4 nucleotides longer at its 3' end than the sense strand, wherein the duplex region which is at least 25 nucleotides in length, and said antisense strand is sufficiently complementary to a target mRNA along at least 19 nt of said antisense strand length to reduce target gene expression when said dsRNA molecule is introduced into a mammalian cell, and wherein dicer cleavage of said dsRNA preferentially results in an siRNA comprising said 3' end of said antisense strand, thereby reducing expression of the target gene in the mammal, wherein the antisense strand contains at least one thermally destabilizing nucleotide, where the at least one thermally destabilizing nucleotide is in the seed region of the antisense strand (i.e. at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5, or 6 2'-fluoro modifications; (ii) the antisense comprises 1, 2, 3, 4, or 5 phosphorothioate internucleotide linkages; (iii) the sense strand is conjugated with a ligand; (iv) the sense strand comprises 2, 3, 4, or 5 2'-fluoro modifications; (v) the sense strand comprises 1, 2, 3, 4, or 5 phosphorothioate internucleotide linkages; and (vi) the dsRNA comprises at least four 2'-fluoro modifications; and (vii) the dsRNA has a duplex region of 12-29 nucleotide pairs in length.

In some embodiments, every nucleotide in the sense strand and antisense strand of the dsRNA molecule may be modified. Each nucleotide may be modified with the same or different modification which can include one or more alteration of one or both of the non-linking phosphate oxygens or of one or more of the linking phosphate oxygens; alteration of a constituent of the ribose sugar, e.g., of the 2' hydroxyl on the ribose sugar; wholesale replacement of the phosphate moiety with “dephospho” linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases, the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of an RNA. E.g., a phosphorothioate modification at a non-linking 0 position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In some embodiments, each residue of the sense strand and antisense strand is independently modified with LNA, HNA, CeNA, 2'-methoxyethyl, 2'-O-methyl, 2'-O-allyl, 2'-C-allyl, 2'-deoxy, or 2'-fluoro. The strands can contain more than one modification. In some embodiments, each residue of the sense strand and antisense strand is independently modified with 2'-O-methyl or 2'-fluoro. It is to be understood that these modifications are in addition to the at least one thermally destabilizing modification of the duplex present in the antisense strand.

At least two different modifications are typically present on the sense strand and antisense strand. Those two modifications may be the 2'-deoxy, 2'-O-methyl or 2'-fluoro modifications, acyclic nucleotides or others. In some embodiments, the sense strand and antisense strand each comprises two differently modified nucleotides selected from 2'-O-methyl or 2'-deoxy. In some embodiments, each residue of the sense strand and antisense strand is independently modified with 2'-O-methyl nucleotide, 2'-deoxy nucleotide, 2'-deoxy-2'-fluoro nucleotide, 2'-O-N-methylacetamido (2'-O-NMA) nucleotide, a 2'-O-dimethylaminoethoxyethyl (2'-O-DMAEOE) nucleotide, 2'-O-aminopropyl (2'-O-AP) nucleotide, or 2'-ara-F nucleotide. Again, it is to be understood that these modifications are in addition to the at least one thermally destabilizing modification of the duplex present in the antisense strand.

In some embodiments, the dsRNA molecule of the disclosure comprises modifications of an alternating pattern, particular in the B1, B2, B3, B1', B2', B3', B4' regions. The term "alternating motif" or "alternative pattern" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AABBAABBAABB . . . ," "AABAABAABAAB . . . ," "AAABAAABAAAB . . . ," "AAABBBAAABBB . . . ," or "ABCABCABCABC . . . ," etc. The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB . . . ", "ACACAC . . . " "BDBDBD . . . " or "CDCDCD . . . ," etc.

In some embodiments, the dsRNA molecule of the disclosure comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 3'-5' of the strand within the duplex region. As another example, the alternating motif in the sense strand may start with "AABBAABB" from 5'-3' of the strand and the alternating motif in the antisense strand may start with "BBAABBAA" from 3'-5' of the strand within the duplex region, so that there is a complete or partial shift of the modification patterns between the sense strand and the antisense strand.

The dsRNA molecule of the disclosure may further comprise at least one phosphorothioate or methylphosphonate internucleotide linkage. The phosphorothioate or methylphosphonate internucleotide linkage modification may occur on any nucleotide of the sense strand or antisense strand or both in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand comprises both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In some embodiments, the dsRNA molecule comprises the phosphorothioate or methylphosphonate internucleotide linkage modification in the overhang region. For example, the overhang region comprises two nucleotides having a phosphorothioate or methylphosphonate internucleotide linkage between the two nucleotides. Internucleotide linkage modifications also may be made to link the overhang nucleotides with the terminal paired nucleotides within duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. Preferably, these terminal three nucleotides may be at the 3'-end of the antisense strand.

In some embodiments, the sense strand of the dsRNA molecule comprises 1-10 blocks of two to ten phosphorothioate or methylphosphonate internucleotide linkages separated by 1, 2, 3, 4, 5, 6, 7, 8, 9, 10, 11, 12, 13, 14, 15, or 16 phosphate internucleotide linkages, wherein one of the phosphorothioate or methylphosphonate internucleotide linkages is placed at any position in the oligonucleotide sequence and the said sense strand is paired with an antisense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of two phosphorothioate or methylphosphonate internucleotide linkages separated by 1, 2, 3, 4, 5, 6, 7, 8, 9, 10, 11, 12, 13, 14, 15, 16, 17, or 18 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of three phosphorothioate or methylphosphonate internucleotide linkages separated by 1, 2, 3, 4, 5, 6, 7, 8, 9, 10, 11, 12, 13, 14, 15, or 16 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of four phosphorothioate or methylphosphonate internucleotide linkages separated by 1, 2, 3, 4, 5, 6, 7, 8, 9, 10, 11, 12, 13, or 14 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of five phosphorothioate or methylphosphonate internucleotide linkages separated by 1, 2, 3, 4, 5, 6, 7, 8, 9, 10, 11, or 12 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of six phosphorothioate or methylphosphonate internucleotide linkages separated by 1, 2, 3, 4, 5, 6, 7, 8, 9, or 10 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of seven phosphorothioate or methylphosphonate internucleotide linkages separated by 1, 2, 3, 4, 5, 6, 7, or 8 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of eight phosphorothioate or methylphosphonate internucleotide linkages separated by 1, 2, 3, 4, 5, or 6 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of nine phosphorothioate or methylphosphonate internucleotide linkages separated by 1, 2, 3, or 4 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the dsRNA molecule of the disclosure further comprises one or more phosphorothioate or methylphosphonate internucleotide linkage modification within 1-10 of the termini position(s) of the sense or antisense strand. For example, at least 2, 3, 4, 5, 6, 7, 8, 9, or 10 nucleotides may be linked through phosphorothioate or methylphosphonate internucleotide linkage at one end or both ends of the sense or antisense strand.

In some embodiments, the dsRNA molecule of the disclosure further comprises one or more phosphorothioate or methylphosphonate internucleotide linkage modification within 1-10 of the internal region of the duplex of each of the sense or antisense strand. For example, at least 2, 3, 4, 5, 6, 7, 8, 9, or 10 nucleotides may be linked through phosphorothioate methylphosphonate internucleotide linkage at position 8-16 of the duplex region counting from the 5'-end of the sense strand; the dsRNA molecule can optionally further comprise one or more phosphorothioate or methylphosphonate internucleotide linkage modification within 1-10 of the termini position(s).

In some embodiments, the dsRNA molecule of the disclosure further comprises one to five phosphorothioate or methylphosphonate internucleotide linkage modification(s) within position 1-5 and one to five phosphorothioate or methylphosphonate internucleotide linkage modification(s) within position 18-23 of the sense strand (counting from the 5'-end), and one to five phosphorothioate or methylphosphonate internucleotide linkage modification at positions 1 and 2 and one to five within positions 18-23 of the antisense strand (counting from the 5'-end).

In some embodiments, the dsRNA molecule of the disclosure further comprises one phosphorothioate internucleotide linkage modification within position 1-5 and one phosphorothioate or methylphosphonate internucleotide linkage modification within position 18-23 of the sense strand (counting from the 5'-end), and one phosphorothioate internucleotide linkage modification at positions 1 and 2 and two phosphorothioate or methylphosphonate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and one phosphorothioate internucleotide linkage modification within positions 18-23 of the antisense strand (counting from the 5'-end).

In some embodiments, the dsRNA molecule of the disclosure further comprises one phosphorothioate internucleotide linkage modification within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA molecule of the disclosure further comprises one phosphorothioate internucleotide linkage modification within position 1-5 and one within position 18-23 of the sense strand (counting from the 5'-end), and two phosphorothioate internucleotide linkage modification at positions 1 and 2 and one phosphorothioate internucleotide linkage modification within positions 18-23 of the antisense strand (counting from the 5'-end).

In some embodiments, the dsRNA molecule of the disclosure further comprises one phosphorothioate internucleotide linkage modification within position 1-5 (counting from the 5'-end) of the sense strand, and two phosphorothioate internucleotide linkage modifications at positions 1 and 2 and one phosphorothioate internucleotide linkage modification within positions 18-23 of the antisense strand (counting from the 5'-end).

In some embodiments, the dsRNA molecule of the disclosure further comprises two phosphorothioate internucleotide linkage modifications within position 1-5 (counting from the 5'-end) of the sense strand, and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and one within position 18-23 of the sense strand (counting from the 5'-end), and two phosphorothioate internucleotide linkage modifications at positions 1 and 2 and one phosphorothioate internucleotide linkage modification within positions 18-23 of the antisense strand (counting from the 5'-end).

In some embodiments, the dsRNA molecule of the disclosure further comprises two phosphorothioate internucleotide linkage modifications within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications at position 1 and 2, and two phosphorothioate internucleotide linkage modifications at position 20 and 21 of the sense strand (counting from the 5'-end), and one phosphorothioate internucleotide linkage modification at positions 1 and one at position 21 of the antisense strand (counting from the 5'-end).

In some embodiments, the dsRNA molecule of the disclosure further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 20 and 21 the antisense strand (counting from the 5'-end).

In some embodiments, the dsRNA molecule of the disclosure further comprises two phosphorothioate internucleotide linkage modifications at position 1 and 2, and two phosphorothioate internucleotide linkage modifications at position 21 and 22 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA molecule of the disclosure further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 21 and 22 the antisense strand (counting from the 5'-end).

In some embodiments, the dsRNA molecule of the disclosure further comprises two phosphorothioate internucleotide linkage modifications at position 1 and 2, and two phosphorothioate internucleotide linkage modifications at position 22 and 23 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA molecule of the disclosure further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 23 and 23 the antisense strand (counting from the 5'-end).

In some embodiments, compound of the disclosure comprises a pattern of backbone chiral centers. In some embodiments, a common pattern of backbone chiral centers comprises at least 5 internucleotidic linkages in the Sp configuration. In some embodiments, a common pattern of backbone chiral centers comprises at least 6 internucleotidic linkages in the Sp configuration. In some embodiments, a common pattern of backbone chiral centers comprises at least 7 internucleotidic linkages in the Sp configuration. In some embodiments, a common pattern of backbone chiral centers comprises at least 8 internucleotidic linkages in the Sp configuration. In some embodiments, a common pattern of backbone chiral centers comprises at least 9 internucleotidic linkages in the Sp configuration. In some embodiments, a common pattern of backbone chiral centers comprises at least 10 internucleotidic linkages in the Sp configuration. In some embodiments, a common pattern of backbone chiral centers comprises at least 11 internucleotidic linkages in the Sp configuration. In some embodiments, a common pattern of backbone chiral centers comprises at least 12 internucleotidic linkages in the Sp configuration. In some embodiments, a common pattern of backbone chiral centers comprises at least 13 internucleotidic linkages in the Sp configuration. In some embodiments, a common pattern of backbone chiral centers comprises at least 14 internucleotidic linkages in the Sp configuration. In some embodiments, a common pattern of backbone chiral centers comprises at least 15 internucleotidic linkages in the Sp configuration. In some embodiments, a common pattern of backbone chiral centers comprises at least 16 internucleotidic linkages in the Sp configuration. In some embodiments, a common pattern of backbone chiral centers comprises at least 17 internucleotidic linkages in the Sp configuration. In some embodiments, a common pattern of backbone chiral centers comprises at least 18 internucleotidic linkages in the Sp configuration. In some embodiments, a common pattern of backbone chiral centers comprises at least 19 internucleotidic linkages in the Sp configuration. In some embodiments, a common pattern of backbone chiral centers comprises no more than 8 internucleotidic linkages in the Rp configuration. In some embodiments, a common pattern of backbone chiral centers comprises no more than 7 internucleotidic linkages in the Rp configuration. In some embodiments, a common pattern of backbone chiral centers comprises no more than 6 internucleotidic linkages in the Rp configuration. In some embodiments, a common pattern of backbone chiral centers comprises no more than 5 internucleotidic linkages in the Rp configuration. In some embodiments, a common pattern of backbone chiral centers comprises no more than 4 internucleotidic linkages in the Rp configuration. In some embodiments, a common pattern of backbone chiral centers comprises no more than 3 internucleotidic linkages in the Rp configuration. In some embodiments, a common pattern of backbone chiral centers comprises no more than 2 internucleotidic linkages in the Rp configuration. In some embodiments, a common pattern of backbone chiral centers comprises no more than 1 internucleotidic linkages in the Rp configuration. In some embodiments, a common pattern of backbone chiral centers comprises no more than 8 internucleotidic linkages which are not chiral (as a non-limiting example, a phosphodiester). In some embodiments, a common pattern of backbone chiral centers comprises no more than 7 internucleotidic linkages which are not chiral. In some embodiments, a common pattern of backbone chiral centers comprises no more than 6 internucleotidic linkages which are not chiral. In some embodiments, a common pattern of backbone chiral centers comprises no more than 5 internucleotidic linkages which are not chiral. In some embodiments, a common pattern of backbone chiral centers comprises no more than 4 internucleotidic linkages which are not chiral. In some embodiments, a common pattern of backbone chiral centers comprises no more than 3 internucleotidic linkages which are not chiral. In some embodiments, a common pattern of backbone chiral centers comprises no more than 2 internucleotidic linkages which are not chiral. In some embodiments, a common pattern of backbone chiral centers comprises no more than 1 internucleotidic linkages which are not chiral. In some embodiments, a common pattern of backbone chiral centers comprises at least 10 internucleotidic linkages in the Sp configuration, and no more than 8 internucleotidic linkages which are not chiral. In some embodiments, a common pattern of backbone chiral centers comprises at least 11 internucleotidic linkages in the Sp configuration, and no more than 7 internucleotidic linkages which are not chiral. In some embodiments, a common pattern of backbone chiral centers comprises at least 12 internucleotidic linkages in the Sp configuration, and no more than 6 internucleotidic linkages which are not chiral. In some embodiments, a common pattern of backbone chiral centers comprises at least 13 internucleotidic linkages in the Sp configuration, and no more than 6 internucleotidic linkages which are not chiral. In some embodiments, a common pattern of backbone chiral centers comprises at least 14 internucleotidic linkages in the Sp configuration, and no more than 5 internucleotidic linkages which are not chiral. In some embodiments, a common pattern of backbone chiral centers comprises at least 15 internucleotidic linkages in the Sp configuration, and no more than 4 internucleotidic linkages which are not chiral. In some embodiments, the internucleotidic linkages in the Sp configuration are optionally contiguous or not contiguous. In some embodiments, the internucleotidic linkages in the Rp configuration are optionally contiguous or not contiguous. In some embodiments, the internucleotidic linkages which are not chiral are optionally contiguous or not contiguous.

In some embodiments, compound of the disclosure comprises a block is a stereochemistry block. In some embodiments, a block is an Rp block in that each internucleotidic linkage of the block is Rp. In some embodiments, a 5'-block is an Rp block. In some embodiments, a 3'-block is an Rp block. In some embodiments, a block is an Sp block in that each internucleotidic linkage of the block is Sp. In some embodiments, a 5'-block is an Sp block. In some embodiments, a 3'-block is an Sp block. In some embodiments, provided oligonucleotides comprise both Rp and Sp blocks. In some embodiments, provided oligonucleotides comprise one or more Rp but no Sp blocks. In some embodiments, provided oligonucleotides comprise one or more Sp but no Rp blocks. In some embodiments, provided oligonucleotides comprise one or more PO blocks wherein each internucleotidic linkage in a natural phosphate linkage.

In some embodiments, compound of the disclosure comprises a 5'-block is an Sp block wherein each sugar moiety comprises a 2'-F modification. In some embodiments, a 5'-block is an Sp block wherein each of internucleotidic linkage is a modified internucleotidic linkage and each sugar moiety comprises a 2'-F modification. In some embodiments, a 5'-block is an Sp block wherein each of internucleotidic linkage is a phosphorothioate linkage and each sugar moiety comprises a 2'-F modification. In some embodiments, a 5'-block comprises 4 or more nucleoside units. In some embodiments, a 5'-block comprises 5 or more nucleoside units. In some embodiments, a 5'-block comprises 6 or more nucleoside units. In some embodiments, a 5'-block comprises 7 or more nucleoside units. In some embodiments, a 3'-block is an Sp block wherein each sugar moiety comprises a 2'-F modification. In some embodiments, a 3'-block is an Sp block wherein each of internucleotidic linkage is a modified internucleotidic linkage and each sugar moiety comprises a 2'-F modification. In some embodiments, a 3'-block is an Sp block wherein each of internucleotidic linkage is a phosphorothioate linkage and each sugar moiety comprises a 2'-F modification. In some embodiments, a 3'-block comprises 4 or more nucleoside units. In some embodiments, a 3'-block comprises 5 or more nucleoside units. In some embodiments, a 3'-block comprises 6 or more nucleoside units. In some embodiments, a 3'-block comprises 7 or more nucleoside units.

In some embodiments, compound of the disclosure comprises a type of nucleoside in a region or an oligonucleotide is followed by a specific type of internucleotidic linkage, e.g., natural phosphate linkage, modified internucleotidic linkage, Rp chiral internucleotidic linkage, Sp chiral internucleotidic linkage, etc. In some embodiments, A is followed by Sp. In some embodiments, A is followed by Rp. In some embodiments, A is followed by natural phosphate linkage (PO). In some embodiments, U is followed by Sp. In some embodiments, U is followed by Rp. In some embodiments, U is followed by natural phosphate linkage (PO). In some embodiments, C is followed by Sp. In some embodiments, C is followed by Rp. In some embodiments, C is followed by natural phosphate linkage (PO). In some embodiments, G is followed by Sp. In some embodiments, G is followed by Rp. In some embodiments, G is followed by natural phosphate linkage (PO). In some embodiments, C and U are followed by Sp. In some embodiments, C and U are followed by Rp. In some embodiments, C and U are followed by natural phosphate linkage (PO). In some embodiments, A and G are followed by Sp. In some embodiments, A and G are followed by Rp.

In some embodiments, the antisense strand comprises phosphorothioate internucleotide linkages between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand.

In some embodiments, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 12-40 nucleotide pairs in length; (vii) the dsRNA comprises a duplex region of 12-40 nucleotide pairs in length; and (viii) the dsRNA has a blunt end at 5'-end of the antisense strand.

In some embodiments, the sense strand comprises phosphorothioate internucleotide linkages between nucleotide positions 1 and 2, and between nucleotide positions 2 and 3, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand.

In some embodiments, the sense strand comprises phosphorothioate internucleotide linkages between nucleotide positions 1 and 2, and between nucleotide positions 2 and 3, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 3, 4 or 5 phosphorothioate internucleotide linkages; (v) the dsRNA comprises at least four 2'-fluoro modifications; (vi) the dsRNA comprises a duplex region of 12-40 nucleotide pairs in length; and (vii) the dsRNA has a blunt end at 5'-end of the antisense strand.

In some embodiments, the dsRNA molecule of the disclosure comprises mismatch(es) with the target, within the duplex, or combinations thereof. The mismatch can occur in the overhang region or the duplex region. The base pair can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In some embodiments, the dsRNA molecule of the disclosure comprises at least one of the first 1, 2, 3, 4, or 5 base pairs within the duplex regions from the 5'-end of the antisense strand can be chosen independently from the group of: A:U, G:U, I:C, and mismatched pairs, e.g., non-canonical or other than canonical pairings or pairings which include a universal base, to promote the dissociation of the antisense strand at the 5'-end of the duplex.

In some embodiments, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

It was found that introducing 4'-modified or 5'-modified nucleotide to the 3'-end of a phosphodiester (PO), phosphorothioate (PS), or phosphorodithioate (PS2) linkage of a dinucleotide at any position of single stranded or double stranded oligonucleotide can exert steric effect to the internucleotide linkage and, hence, protecting or stabilizing it against nucleases.

In some embodiments, 5'-modified nucleoside is introduced at the 3'-end of a dinucleotide at any position of single stranded or double stranded siRNA. For instance, a 5'-alkylated nucleoside may be introduced at the 3'-end of a dinucleotide at any position of single stranded or double stranded siRNA. The alkyl group at the 5' position of the ribose sugar can be racemic or chirally pure R or S isomer. An exemplary 5'-alkylated nucleoside is 5'-methyl nucleoside. The 5'-methyl can be either racemic or chirally pure R or S isomer.

In some embodiments, 4'-modified nucleoside is introduced at the 3'-end of a dinucleotide at any position of single stranded or double stranded siRNA. For instance, a 4'-alkylated nucleoside may be introduced at the 3'-end of a dinucleotide at any position of single stranded or double stranded siRNA. The alkyl group at the 4' position of the ribose sugar can be racemic or chirally pure R or S isomer. An exemplary 4'-alkylated nucleoside is 4'-methyl nucleoside. The 4'-methyl can be either racemic or chirally pure R or S isomer. Alternatively, a 4'-O-alkylated nucleoside may be introduced at the 3'-end of a dinucleotide at any position of single stranded or double stranded siRNA. The 4'-O-alkyl of the ribose sugar can be racemic or chirally pure R or S isomer. An exemplary 4'-O-alkylated nucleoside is 4'-O-methyl nucleoside. The 4'-O-methyl can be either racemic or chirally pure R or S isomer.

In some embodiments, 5'-alkylated nucleoside is introduced at any position on the sense strand or antisense strand of a dsRNA, and such modification maintains or improves potency of the dsRNA. The 5'-alkyl can be either racemic or chirally pure R or S isomer. An exemplary 5'-alkylated nucleoside is 5'-methyl nucleoside. The 5'-methyl can be either racemic or chirally pure R or S isomer.

In some embodiments, 4'-alkylated nucleoside is introduced at any position on the sense strand or antisense strand of a dsRNA, and such modification maintains or improves potency of the dsRNA. The 4'-alkyl can be either racemic or chirally pure R or S isomer. An exemplary 4'-alkylated nucleoside is 4'-methyl nucleoside. The 4'-methyl can be either racemic or chirally pure R or S isomer.

In some embodiments, 4'-O-alkylated nucleoside is introduced at any position on the sense strand or antisense strand of a dsRNA, and such modification maintains or improves potency of the dsRNA. The 5'-alkyl can be either racemic or chirally pure R or S isomer. An exemplary 4'-O-alkylated nucleoside is 4'-O-methyl nucleoside. The 4'-O-methyl can be either racemic or chirally pure R or S isomer.

In some embodiments, the dsRNA molecule of the disclosure can comprise 2'-5' linkages (with 2'-H, 2'-OH and 2'-OMe and with P═O or P═S). For example, the 2'-5' linkages modifications can be used to promote nuclease resistance or to inhibit binding of the sense to the antisense strand, or can be used at the 5' end of the sense strand to avoid sense strand activation by RISC.

In another embodiment, the dsRNA molecule of the disclosure can comprise L sugars (e.g., L ribose, L-arabinose with 2'-H, 2'-OH and 2'-OMe). For example, these L sugars modifications can be used to promote nuclease resistance or to inhibit binding of the sense to the antisense strand, or can be used at the 5' end of the sense strand to avoid sense strand activation by RISC.

Various publications describe multimeric siRNA which can all be used with the dsRNA of the disclosure. Such publications include WO2007/091269, U.S. Pat. No. 7,858, 769, WO2010/141511, WO2007/117686, WO2009/014887, and WO2011/031520 which are hereby incorporated by their entirely.

As described in more detail below, the RNAi agent that contains conjugations of one or more carbohydrate moieties to an RNAi agent can optimize one or more properties of the RNAi agent. In many cases, the carbohydrate moiety will be attached to a modified subunit of the RNAi agent. For example, the ribose sugar of one or more ribonucleotide subunits of a dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The RNAi agents may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and and decalin; preferably, the acyclic group is selected from serinol backbone or diethanolamine backbone.

In certain specific embodiments, the RNAi agent for use in the methods of the disclosure is an agent selected from the group of agents listed in any one of Tables 10A, 10B, 12-15, 19 or 20. These agents may further comprise a ligand.

IV. iRNAs Conjugated to Ligands

Another modification of the RNA of an iRNA of the invention involves chemically linking to the iRNA one or more ligands, moieties or conjugates that enhance the activity, cellular distribution or cellular uptake of the iRNA, e.g., into a cell. Such moieties include but are not limited to lipid moieties such as a cholesterol moiety (Letsinger et al., *Proc. Natl. Acid. Sci. USA,* 1989, 86: 6553-6556), cholic acid (Manoharan et al., *Biorg. Med. Chem. Let.,* 1994, 4:1053-1060), a thioether, e.g., beryl-S-tritylthiol (Manoharan et al., *Ann. N.Y. Acad. Sci.,* 1992, 660:306-309; Manoharan et al., *Biorg. Med. Chem. Let.,* 1993, 3:2765-2770), a thiocholesterol (Oberhauser et al., *Nucl. Acids Res.,* 1992, 20:533-538), an aliphatic chain, e.g., dodecandiol or undecyl residues (Saison-Behmoaras et al., *EMBO J,* 1991, 10:1111-1118; Kabanov et al., *FEBS Lett.,* 1990, 259:327-330; Svinarchuk et al., *Biochimie,* 1993, 75:49-54), a phospholipid, e.g., di-hexadecyl-rac-glycerol or triethyl-ammonium 1,2-di-O-hexadecyl-rac-glycero-3-phosphonate (Manoharan et al., *Tetrahedron Lett.,* 1995, 36:3651-3654; Shea et al., *Nucl. Acids Res.,* 1990, 18:3777-3783), a polyamine or a polyethylene glycol chain (Manoharan et al., *Nucleosides & Nucleotides,* 1995, 14:969-973), or adamantane acetic acid (Manoharan et al., *Tetrahedron Lett.,* 1995, 36:3651-3654), a palmityl moiety (Mishra et al., *Biochim. Biophys. Acta,* 1995, 1264:229-237), or an octadecylamine or hexylamino-carbonyloxycholesterol moiety (Crooke et al., *J. Pharmacol. Exp. Ther.,* 1996, 277:923-937).

In certain embodiments, a ligand alters the distribution, targeting or lifetime of an iRNA agent into which it is incorporated. In some embodiments, a ligand provides an enhanced affinity for a selected target, e.g., molecule, cell or cell type, compartment, e.g., a cellular or organ compartment, tissue, organ or region of the body, as, e.g., compared to a species absent such a ligand. Typical ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an $\alpha$ helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. In certain embodiments, the ligand is a multivalent galactose, e.g., an N-acetyl-galactosamine.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid,O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated iRNAs of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems® (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In certain embodiments, the ligand or conjugate is a lipid or lipid-based molecule. Such a lipid or lipid-based molecule can typically bind a serum protein, such as human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, or (c) can be used to adjust binding to a serum protein, e.g., HSA.

A lipid-based ligand can be used to modulate, e.g., control (e.g., inhibit) the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In certain embodiments, the lipid-based ligand binds HSA. For example, the ligand can bind HSA with a sufficient affinity such that distribution of the conjugate to a non-kidney tissue is enhanced. However, the affinity is typically not so strong that the HSA-ligand binding cannot be reversed.

In certain embodiments, the lipid-based ligand binds HSA weakly or not at all, such that distribution of the conjugate to the kidney is enhanced. Other moieties that target to kidney cells can also be used in place of or in addition to the lipid-based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

B. Cell Permeation Agents

In another aspect, the ligand is a cell-permeation agent, such as a helical cell-permeation agent. In certain embodiments, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is typically an a-helical agent and can have a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp, or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 136). An RFGF analogue (e.g., amino acid sequence AALLPVLLAAP (SEQ ID NO: 137)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 138)) and the *Drosophila* Antennapedia protein (RQIKIWFQNRRMKWKK (SEQ ID NO: 139)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Typically, the peptide or peptidomimetic tethered to a dsRNA agent via an incorporated monomer unit is a cell targeting peptide such as an arginine-glycine-aspartic acid (RGD)-peptide, or RGD mimic A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics In addition to RGD, one can use other moieties that target the integrin ligand. Preferred conjugates of this ligand target PECAM-1 or VEGF.

An RGD peptide moiety can be used to target a particular cell type, e.g., a tumor cell, such as an endothelial tumor cell or a breast cancer tumor cell (Zitzmann et al., *Cancer Res.,* 62:5139-43, 2002). An RGD peptide can facilitate targeting of an dsRNA agent to tumors of a variety of other tissues, including the lung, kidney, spleen, or liver (Aoki et al., *Cancer Gene Therapy* 8:783-787, 2001). Typically, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_V\beta_3$ (Haubner et al., *Jour. Nucl. Med.,* 42:326-336, 2001).

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., *Nucl. Acids Res.* 31:2717-2724, 2003).

C. Carbohydrate Conjugates

In some embodiments of the compositions and methods of the invention, an iRNA further comprises a carbohydrate. The carbohydrate conjugated iRNA are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and tri-saccharides include sugars having two or three monosaccharide units (e.g., C5, C6, C7, or C8).

In certain embodiments, a carbohydrate conjugate comprises a monosaccharide.

In certain embodiments, the monosaccharide is an N-acetylgalactosamine (GalNAc). GalNAc conjugates, which comprise one or more N-acetylgalactosamine (GalNAc) derivatives, are described, for example, in U.S. Pat. No. 8,106,022, the entire content of which is hereby incorporated herein by reference. In some embodiments, the GalNAc conjugate serves as a ligand that targets the iRNA to particular cells. In some embodiments, the GalNAc conjugate targets the iRNA to liver cells, e.g., by serving as a ligand for the asialoglycoprotein receptor of liver cells (e.g., hepatocytes).

In some embodiments, the carbohydrate conjugate comprises one or more GalNAc derivatives. The GalNAc derivatives may be attached via a linker, e.g., a bivalent or trivalent branched linker. In some embodiments the GalNAc conjugate is conjugated to the 3' end of the sense strand. In some embodiments, the GalNAc conjugate is conjugated to the iRNA agent (e.g., to the 3' end of the sense strand) via a linker, e.g., a linker as described herein. In some embodiments the GalNAc conjugate is conjugated to the 5' end of the sense strand. In some embodiments, the GalNAc conjugate is conjugated to the iRNA agent (e.g., to the 5' end of the sense strand) via a linker, e.g., a linker as described herein.

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker. In other embodiments of the invention, the GalNAc or GalNAc derivative is attached to an iRNA agent of the invention via a tetravalent linker.

In certain embodiments, the double stranded RNAi agents of the invention comprise one GalNAc or GalNAc derivative attached to the iRNA agent. In certain embodiments, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of monovalent linkers.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker. The hairpin loop may also be formed by an extended overhang in one strand of the duplex.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker. The hairpin loop may also be formed by an extended overhang in one strand of the duplex.

In some embodiments. the GalNAc conjugate is
Formula II
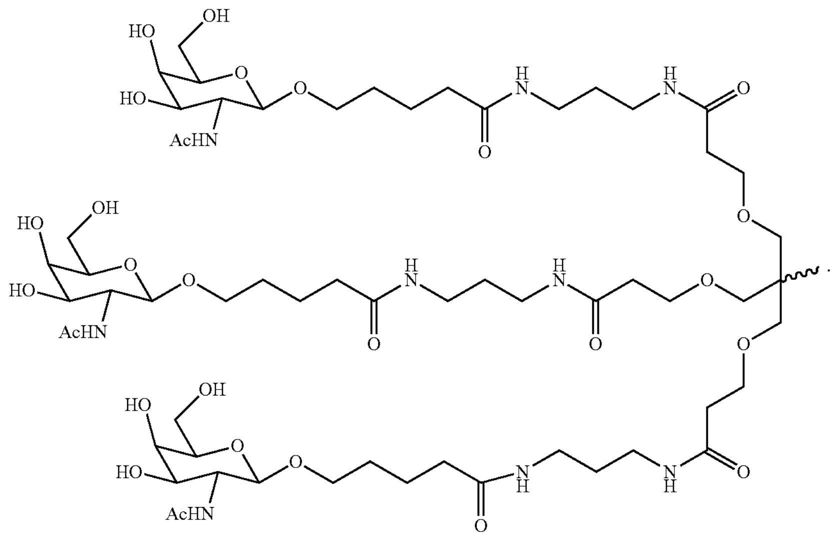
In some embodiments, the RNAi agent is attached to the carbohydrate conjugate via a linker as shown in the following schematic, wherein X is O or S
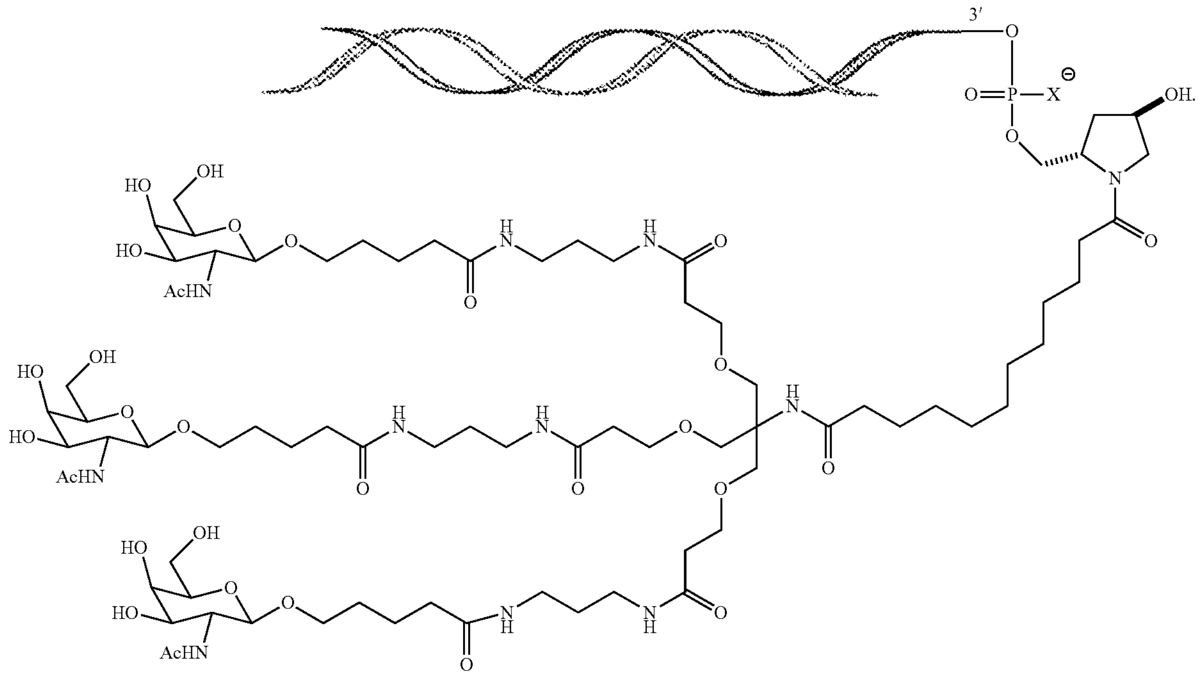

In some embodiments, the RNAi agent is conjugated to L96 as defined in Table 11 and shown below:
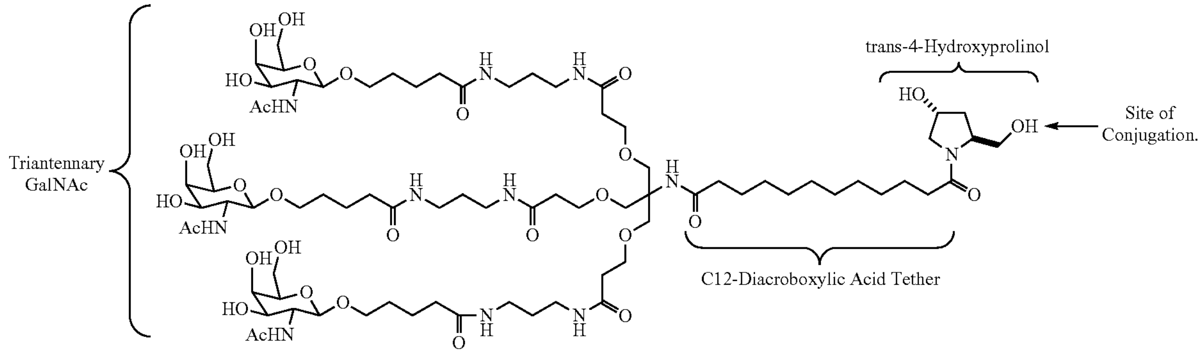
In certain embodiments, a carbohydrate conjugate for use in the compositions and methods of the invention is selected from the group consisting of:
Formula II
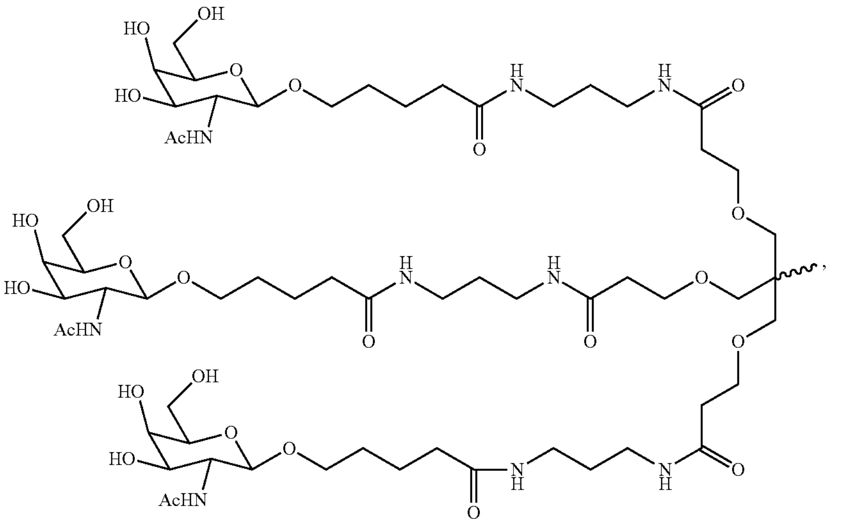
Formula III
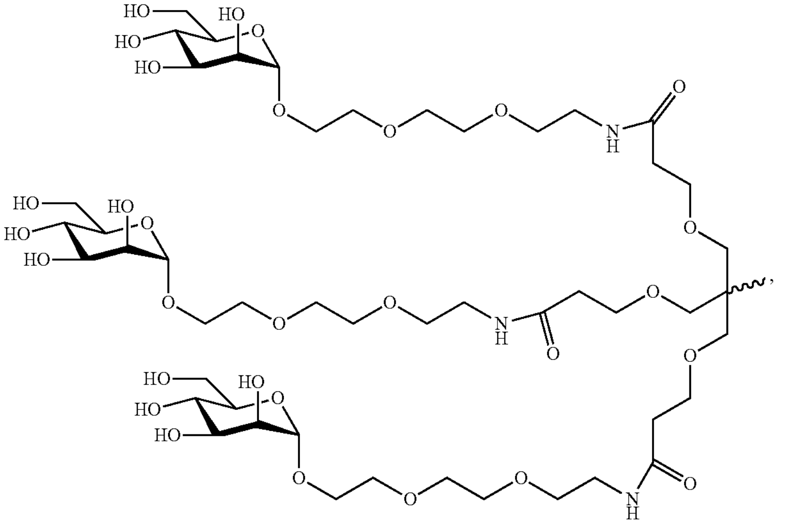

-continued
Formula IV
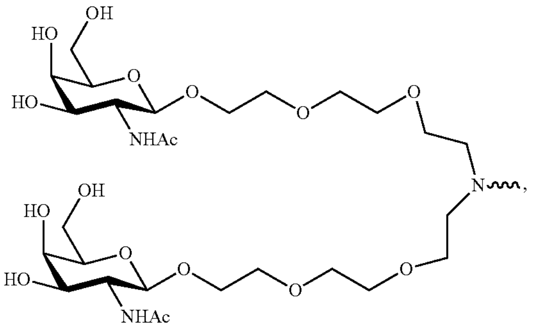
Formula V
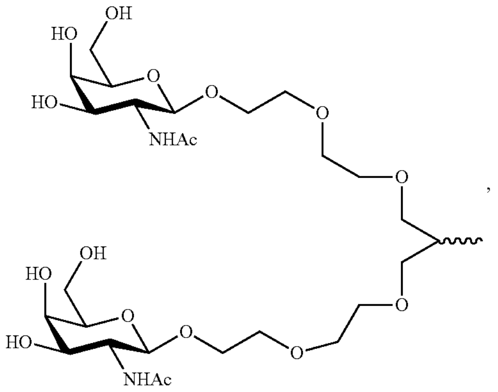
Formula VI
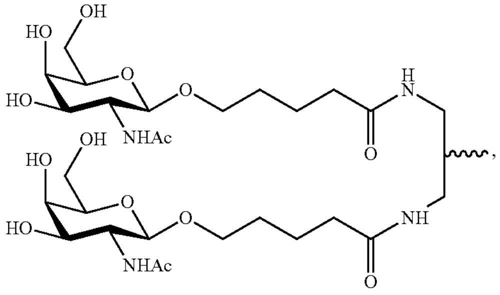
Formula VII
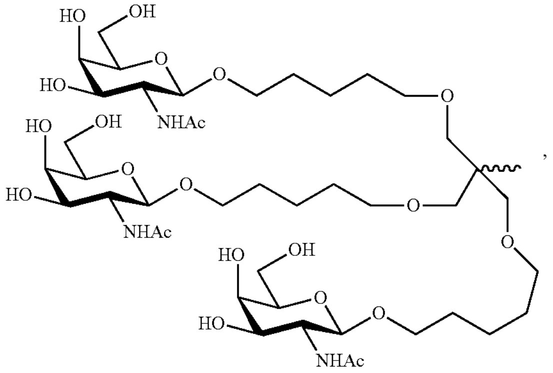
Formula VIII
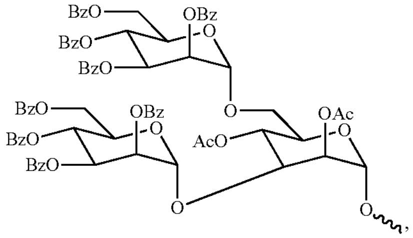
Formula IX
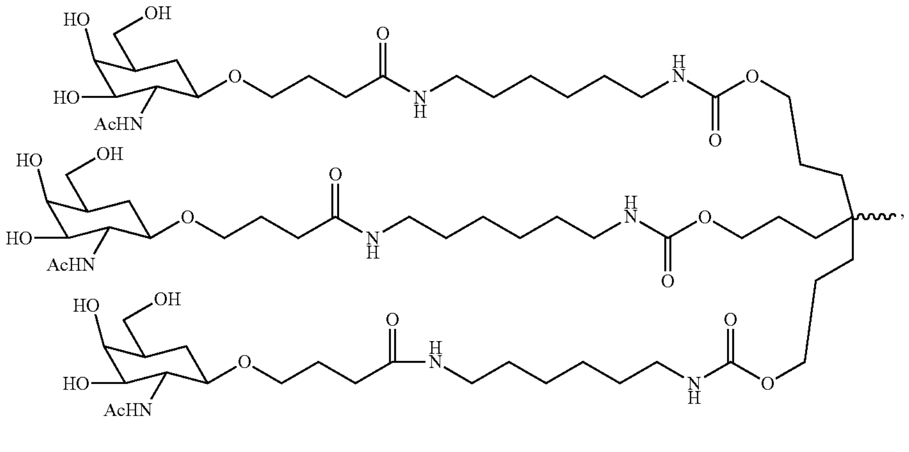

-continued
Formula X
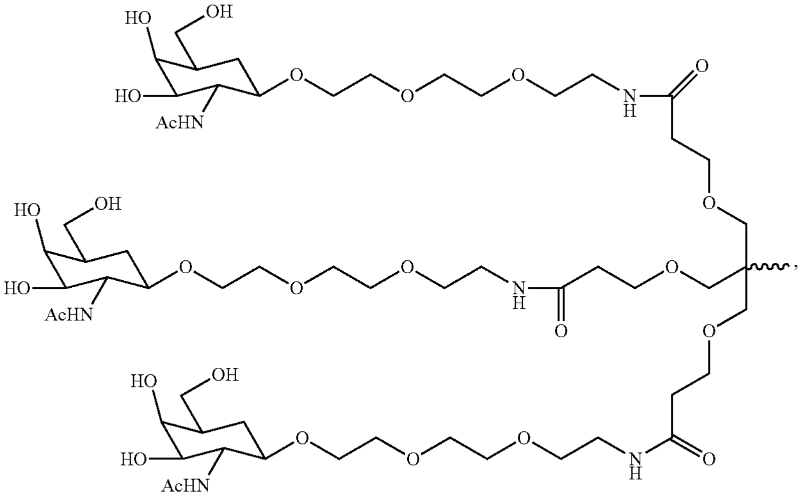
Formula XI
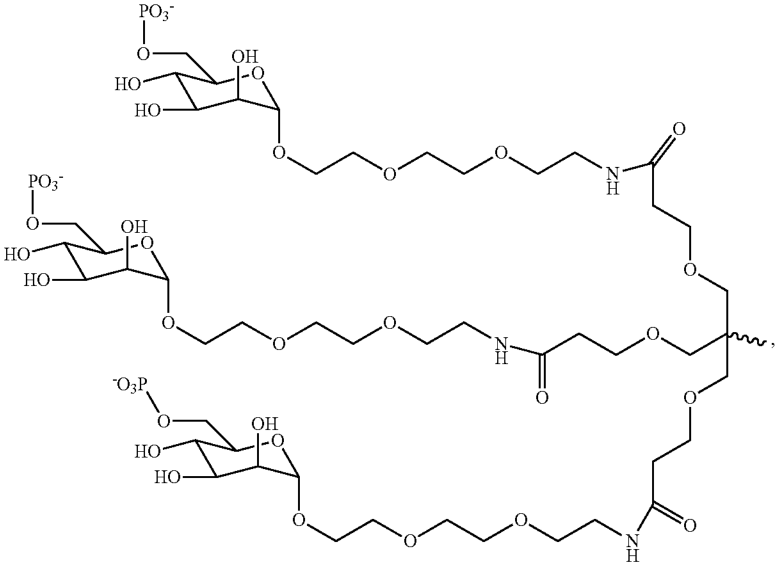
Formula XII
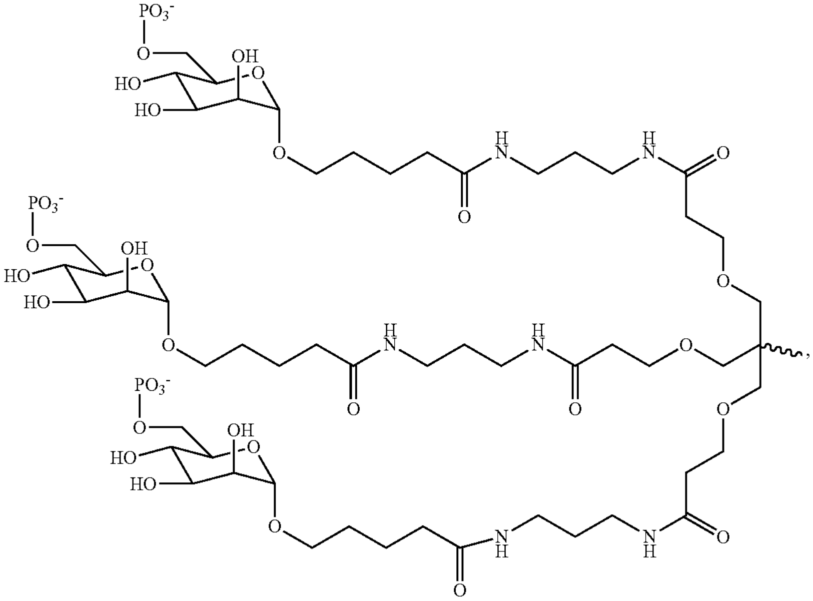

-continued
Formula XIII
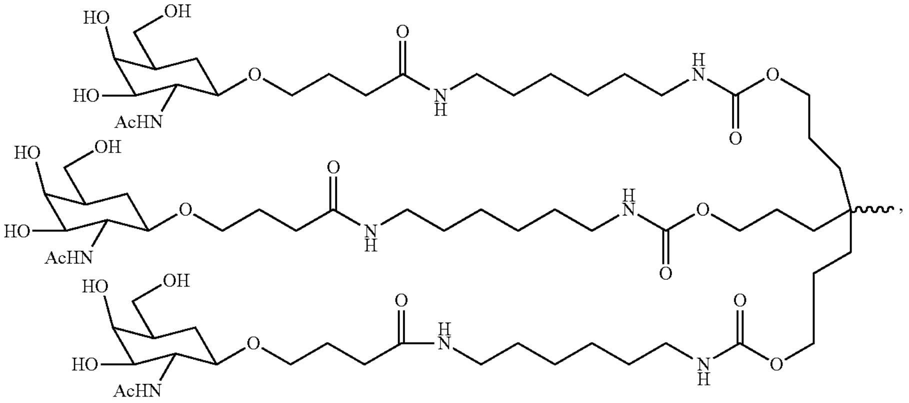
Formula XIV
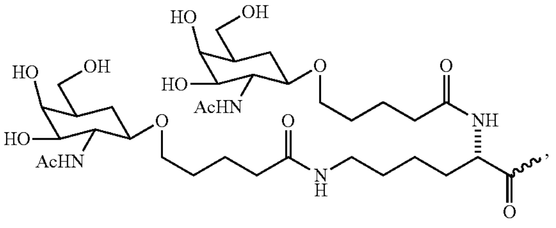
Formula XV
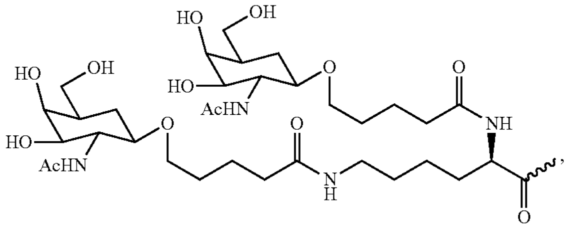
Formula XVI
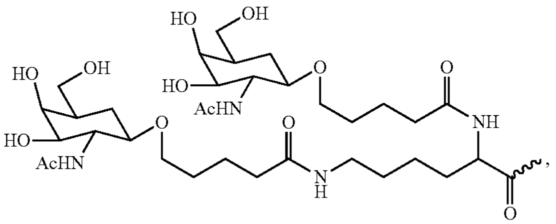
Formula XVII
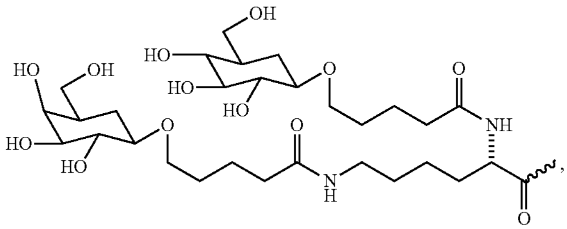
Formula XVIII
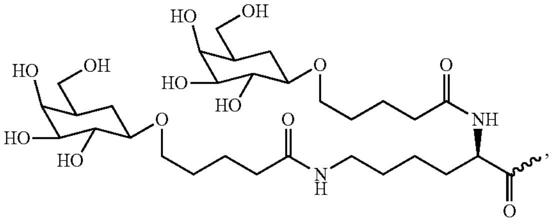
Formula XIX
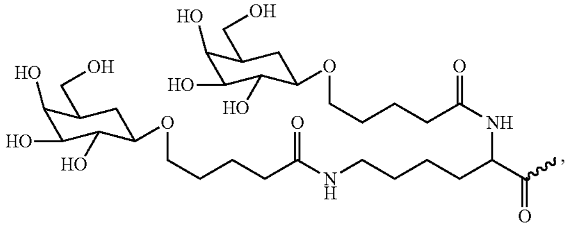
Formula XX
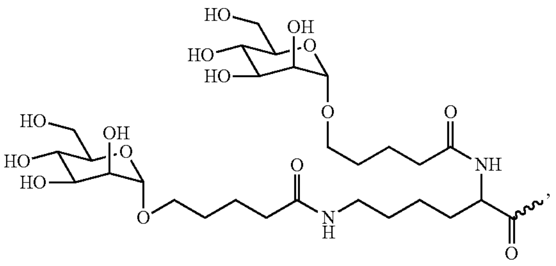
Formula XXI
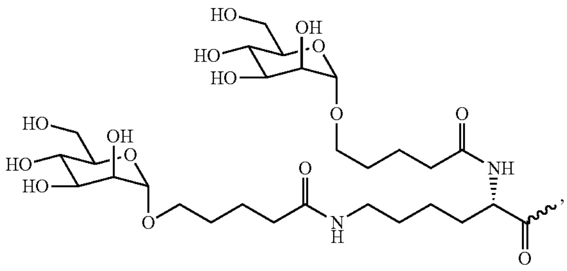

-continued
XXII
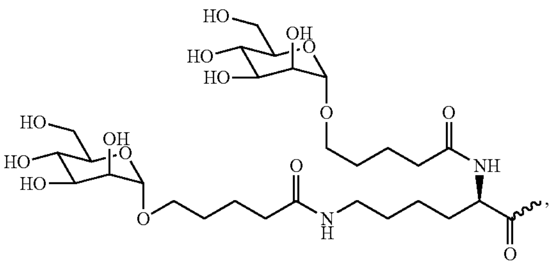
XXIII
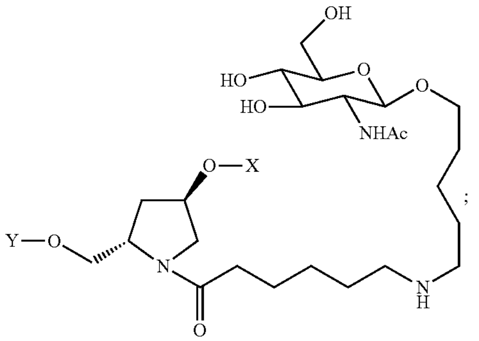
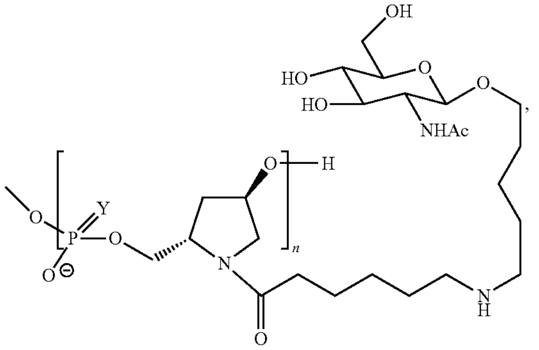
wherein Y is O or S and n is 3-6 (Formula XXIV);
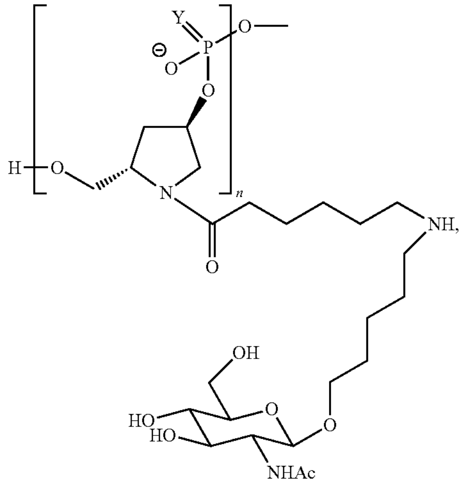
wherein Y is O or S and n is 3-6 (Formula XXV);
Formula XXVI
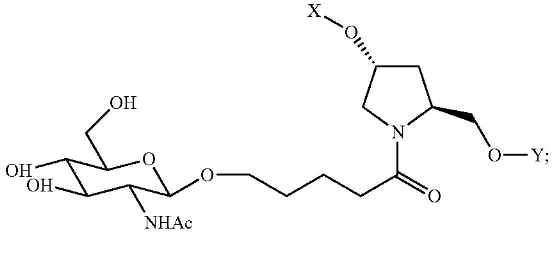

-continued
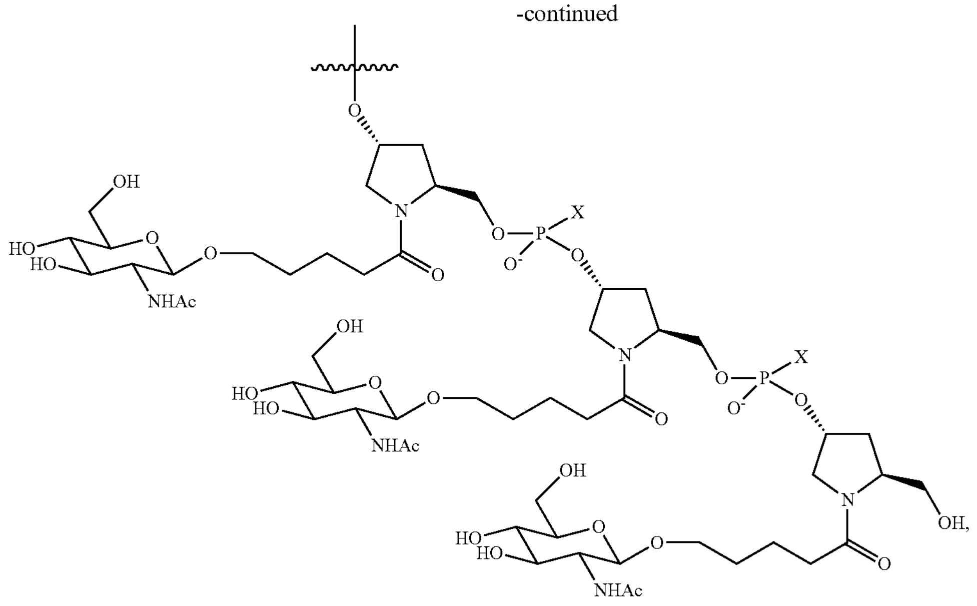
wherein X is O or S (Formula XXVII);
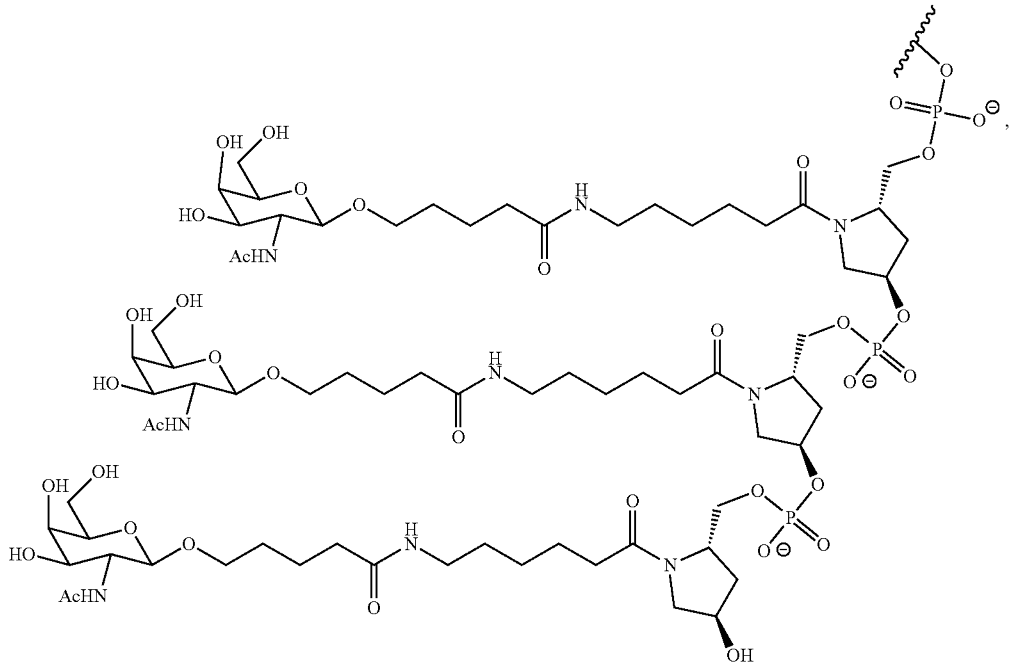

Formula XXVII
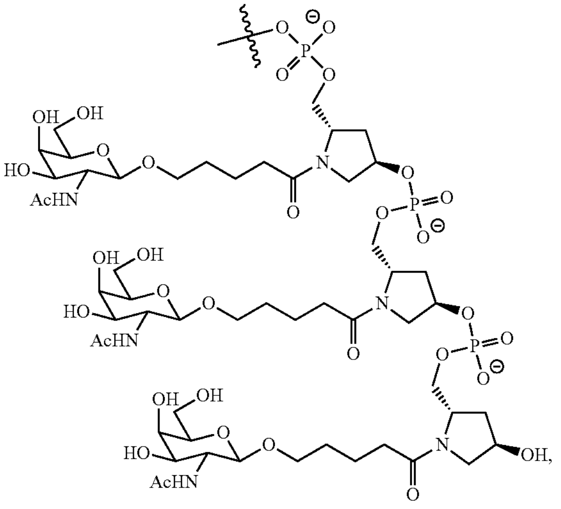
Formula XXIX
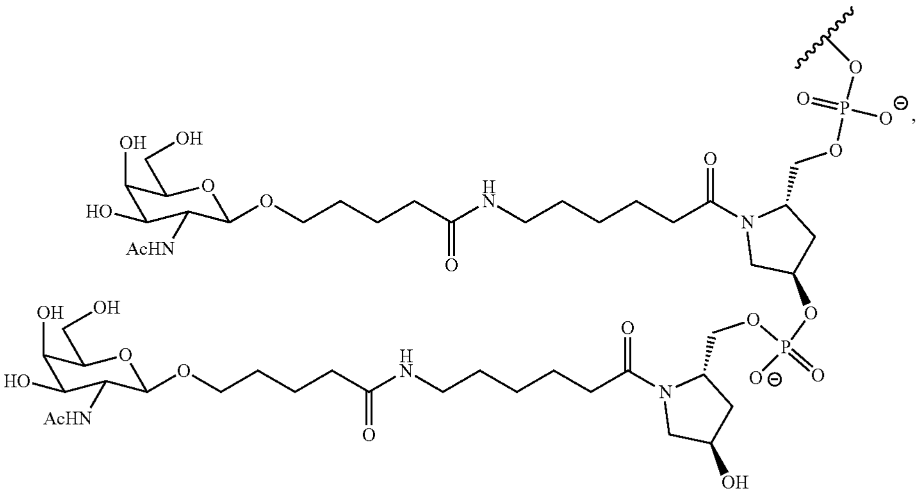
Formula XXX
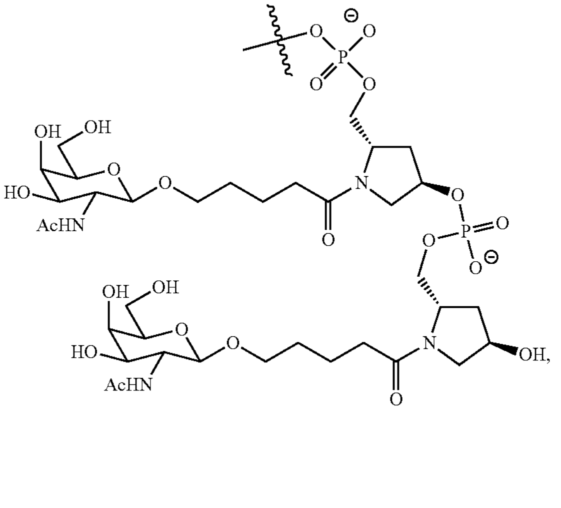

-continued
Formula XXXI
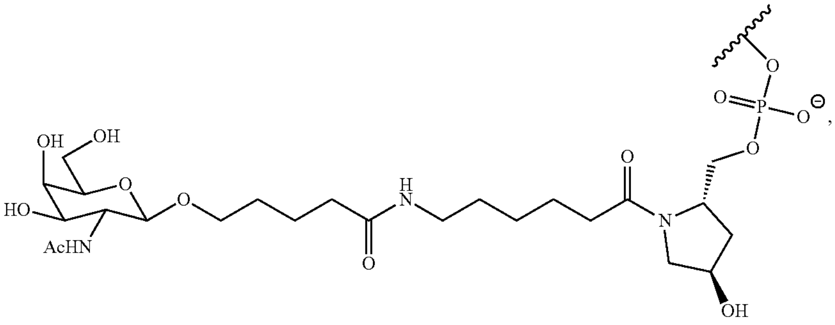
, and
Formula XXXII
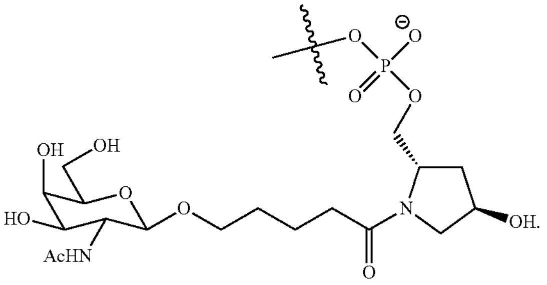
Formula XXXIII
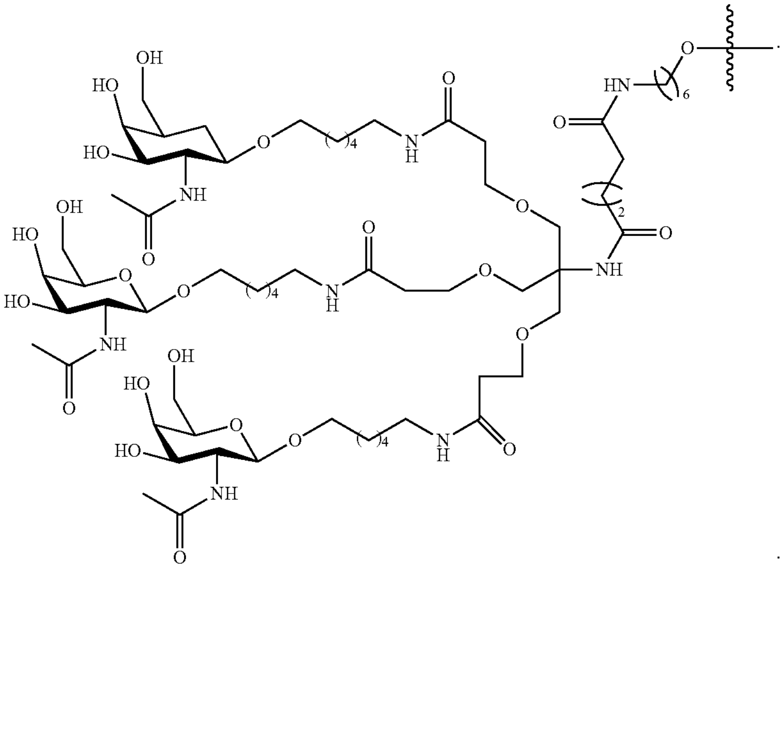

Formula XXXIV.

In certain embodiments, a carbohydrate conjugate for use in the compositions and methods of the invention is a monosaccharide. In certain embodiments, the monosaccharide is an N-acetylgalactosamine, such as Formula II

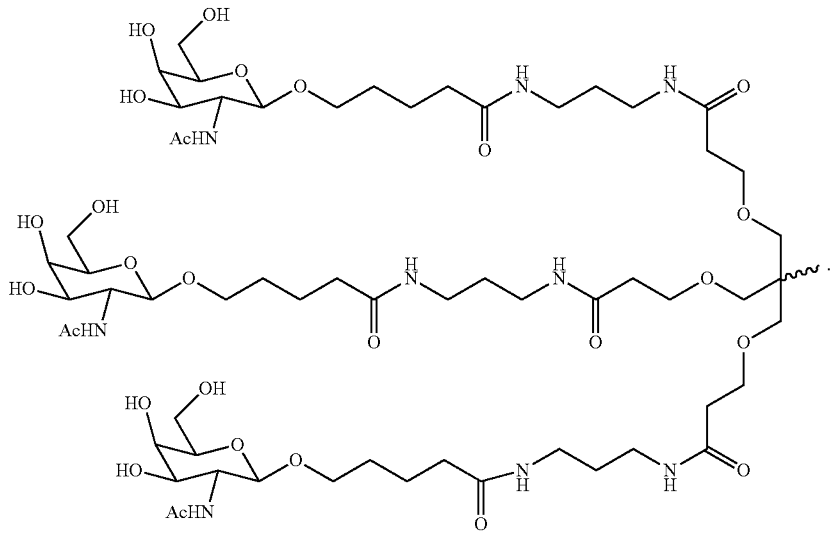

Another representative carbohydrate conjugate for use in the embodiments described herein includes, but is not limited to, (Formula XXXVI)

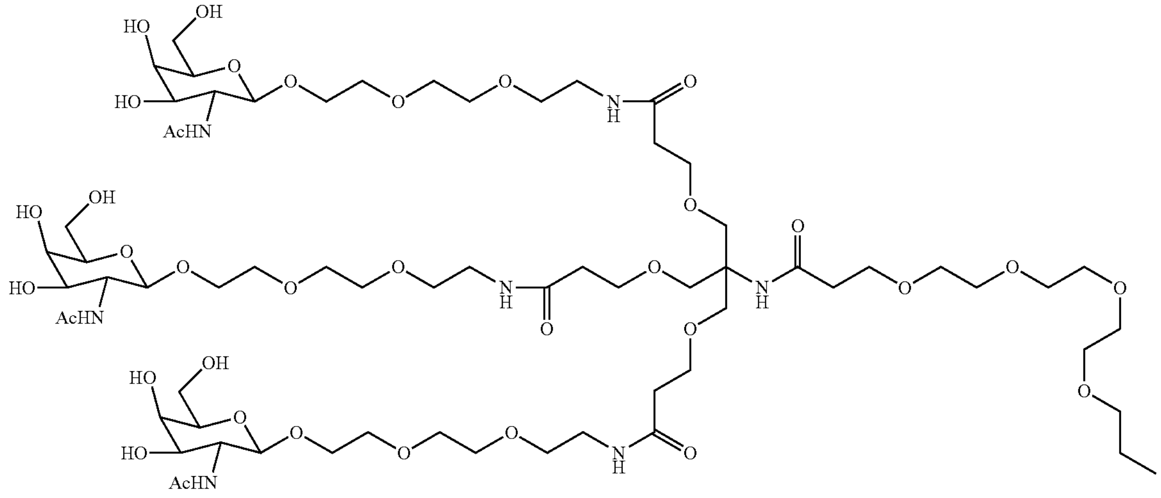

-continued

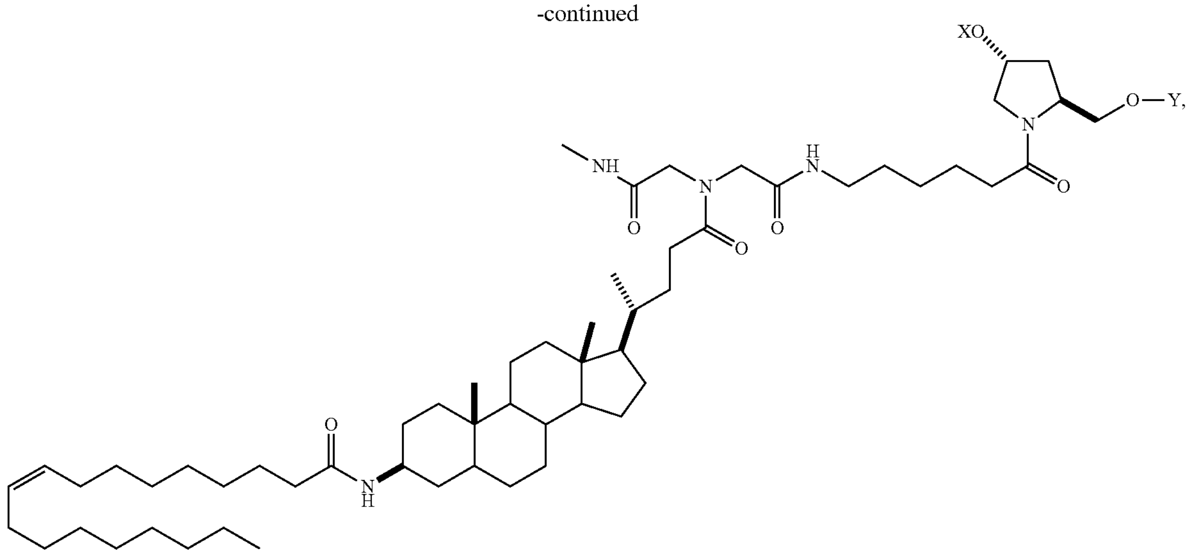

when one of X or Y is an oligonucleotide, the other is a hydrogen.

In some embodiments, a suitable ligand is a ligand disclosed in WO 2019/055633, the entire contents of which are incorporated herein by reference. In one embodiment the ligand comprises the structure below:

(NAG37)s

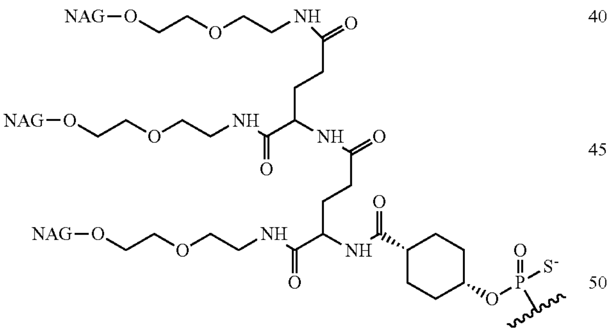

In certain embodiments, the RNAi agents of the disclosure may include GalNAc ligands, even if such GalNAc ligands are currently projected to be of limited value for the preferred intrathecal/CNS delivery route(s) of the instant disclosure.

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker.

In one embodiment, the double stranded RNAi agents of the invention comprise one or more GalNAc or GalNAc derivative attached to the iRNA agent. The GalNAc may be attached to any nucleotide via a linker on the sense strand or antisense strand. The GalNac may be attached to the 5'-end of the sense strand, the 3' end of the sense strand, the 5'-end of the antisense strand, or the 3'-end of the antisense strand. In one embodiment, the GalNAc is attached to the 3' end of the sense strand, e.g., via a trivalent linker.

In other embodiments, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of linkers, e.g., monovalent linkers.

In some embodiments, for example, when the two strands of an iRNA agent of the invention is part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker.

In some embodiments, the carbohydrate conjugate further comprises one or more additional ligands as described above, such as, but not limited to, a PK modulator or a cell permeation peptide.

Additional carbohydrate conjugates and linkers suitable for use in the present invention include those described in WO 2014/179620 and WO 2014/179627, the entire contents of each of which are incorporated herein by reference.

D. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In certain embodiments, the linker is between about 1-24 atoms, 2-24, 3-24, 4-24, 5-24, 6-24, 6-18, 7-18, 8-18 atoms, 7-17, 8-17, 6-16, 7-16, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

i. Redox Cleavable Linking Groups

In certain embodiments, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In certain embodiments, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O-P(O)(ORk)-O—, —O—P(S)(ORk)-O—, —O—P(S)(SRk)-O—, —S-P(O)(ORk)-O—, —O-P(O)(ORk)-S—, —S-P(O)(ORk)-S—, —O—P(S)(ORk)-S—, —S—P(S)(ORk)-O—, —O-P(O)(Rk)-O—, —O—P(S)(Rk)-O—, —S-P(O)(Rk)-O—, —S—P(S)(Rk)-O—, —S-P(O)(Rk)-S—, —O—P(S)(Rk)-S—. Preferred embodiments are —O—P(O)(OH)-O—, —O—P(S)(OH)-O—, —O-P(S)(SH)-O—, —S—P(O)(OH)-O—, —O—P(O)(OH)-S—, —S—P(O)(OH)-S—, —O—P(S)(OH)-S—, —S—P(S)(OH)-O—, —O—P(O)(H)-O—, —O—P(S)(H)-O—, —S—P(O)(H)-O, —S—P(S)(H)-O—, —S—P(O)(H)-S—, —O—P(S)(H)-S—. A preferred embodiment is —O—P(O)(OH)-O—. These candidates can be evaluated using methods analogous to those described above.

iii. Acid Cleavable Linking Groups

In certain embodiments, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C═NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Cleavable Linking Groups

In certain embodiments, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

v. Peptide-Based Cleavable Linking Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In some embodiments, an iRNA of the invention is conjugated to a carbohydrate through a linker. Non-limiting examples of iRNA carbohydrate conjugates with linkers of the compositions and methods of the invention include, but are not limited to, (Formula XXXVII)

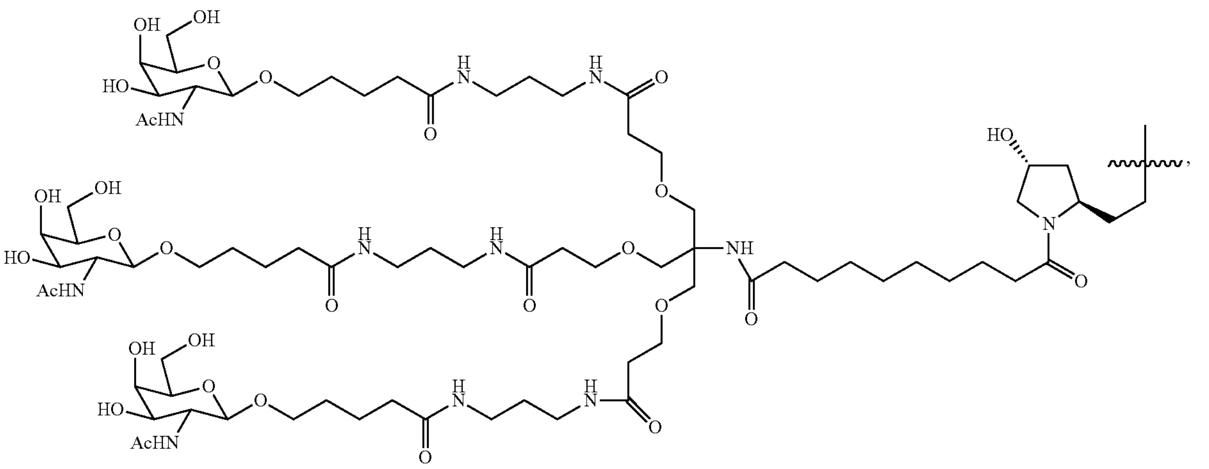

-continued
(Formula XXXVIII)
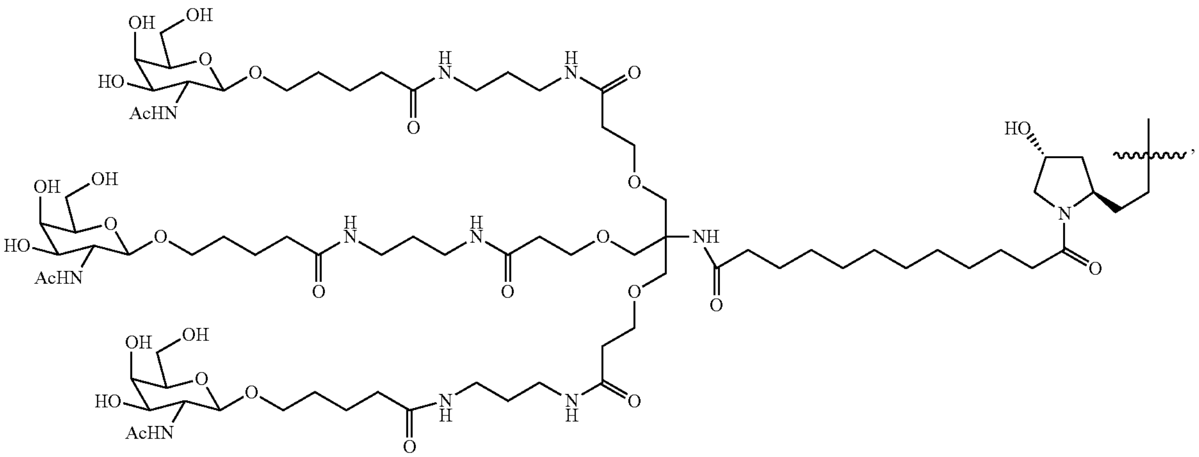
(Formula XXXIX)
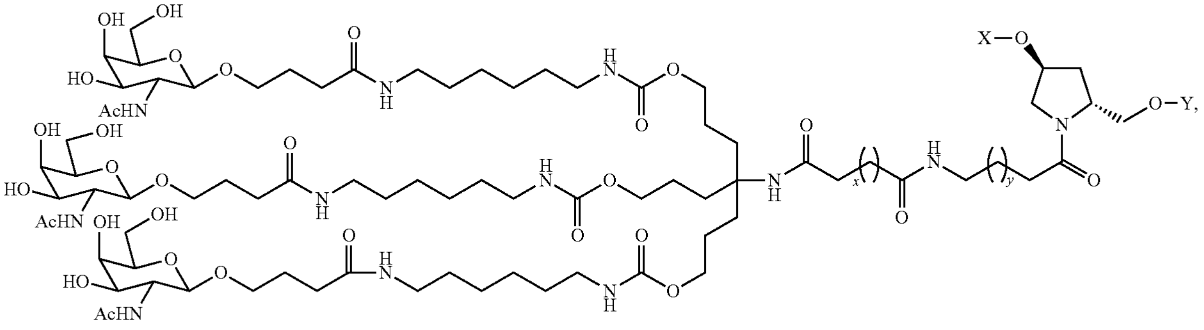
x = 1-30
y = 1-15
(Formula XL)
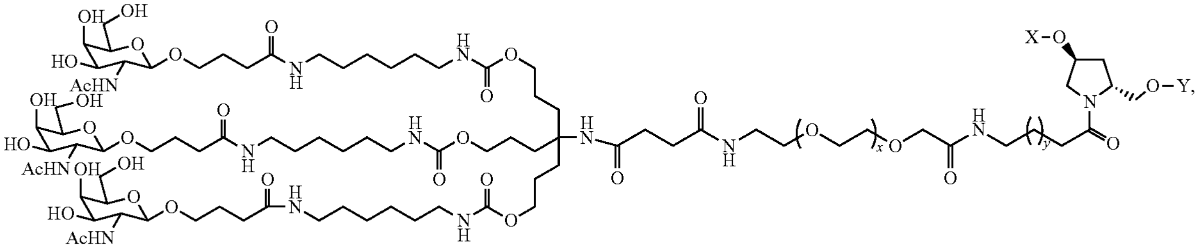
x = 1-30
y = 1-15
(Formula XLI)
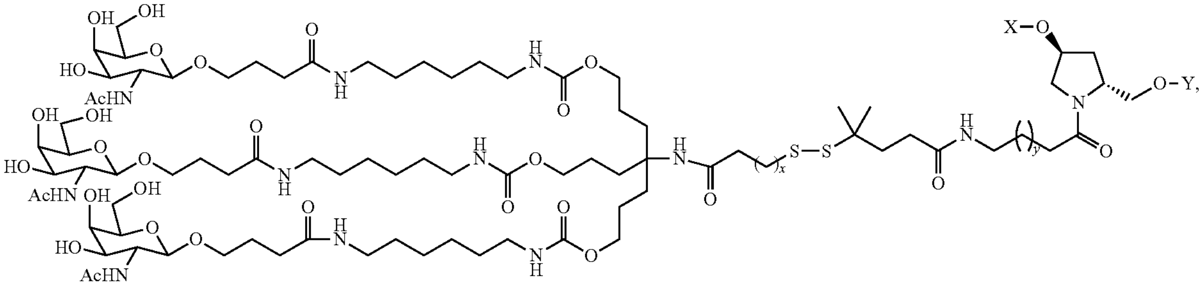
x = 0-30
y = 1-15

-continued (Formula XLII)

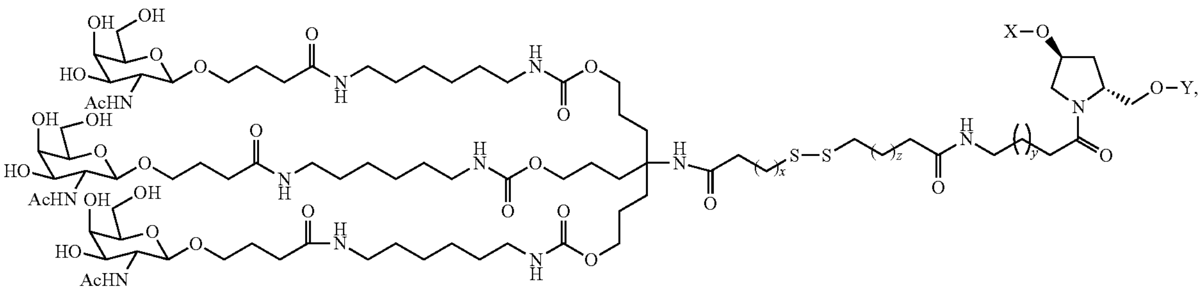

x = 0-30
y = 1-15
z = 1-20

(Formula XLIII)

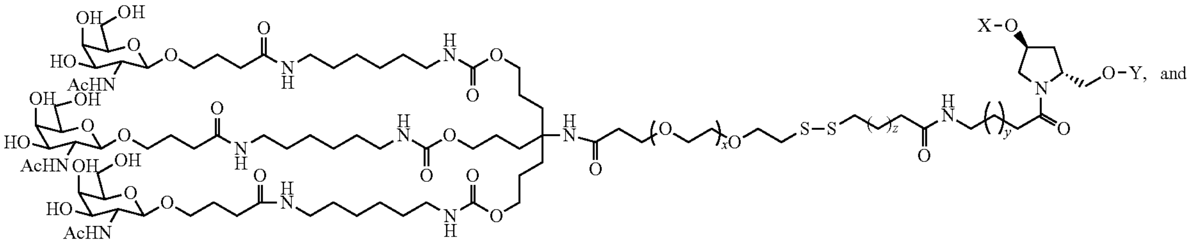

x = 1-30
y = 1-15
z = 1-20

(Formula XLIV)

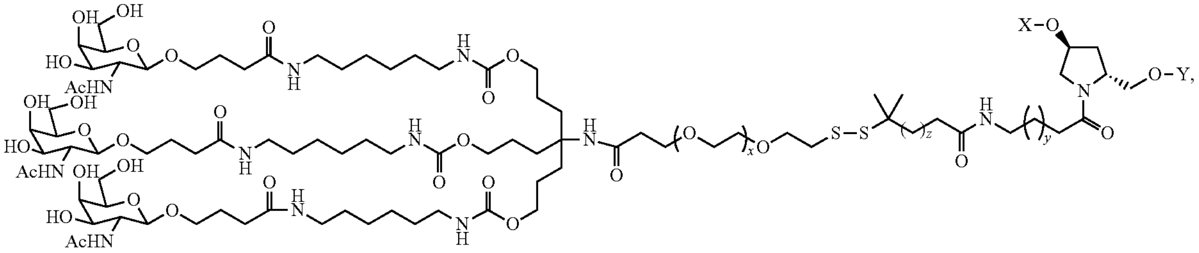

x = 1-30
y = 1-15
z = 1-20 when one of X or Y is an oligonucleotide, the other is a hydrogen.

In certain embodiments of the compositions and methods of the invention, a ligand is one or more "GalNAc" (N-acetylgalactosamine) derivatives attached through a bivalent or trivalent branched linker.

In certain embodiments, a dsRNA of the invention is conjugated to a bivalent or trivalent branched linker selected from the group of structures shown in any of formula (XLV)— (XLVI):

Formula XXXXV

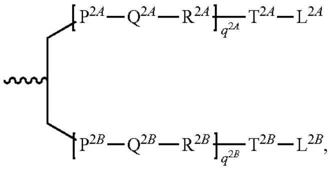

(IV)

-continued

Formula XLVI

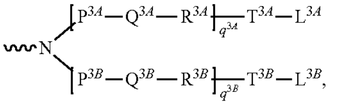

V)

Formula XLVII

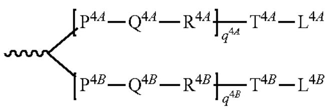

Formula XLVIII

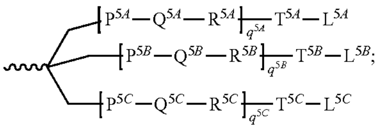

wherein:

$q^{2A}$, $q^{2B}$, $q^{3A}$, $q^{3B}$, $q^{4A}$, $q^{4B}$, $q^{5A}$, $q^{5B}$ and $q^{5C}$ represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')=C(R"), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, $—C(O)—CH(R^a)—NH—$, CO, CH=N-O,

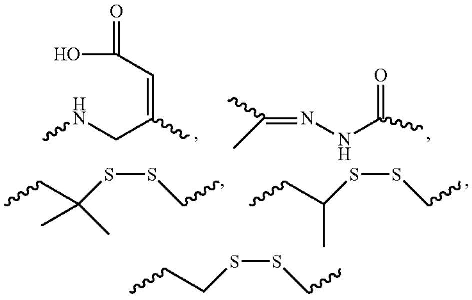

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XLIX):

Formula XLIX

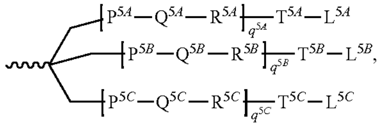

Form wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

Representative U.S. Patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,688,941; 6,294,664; 6,320,017; 6,576,752; 6,783,931; 6,900,297; 7,037,646; and 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNA agents, that contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., *Biochem. Biophys. Res. Comm.,* 2007, 365(1):54-61; Letsinger et al., *Proc. Natl. Acad. Sci. USA,* 1989, 86:6553), cholic acid (Manoharan et al., *Bioorg. Med. Chem. Lett.,* 1994, 4:1053), a thioether, e.g., hexyl-S-tritylthiol (Manoharan et al., *Ann. N.Y. Acad. Sci.,* 1992, 660:306; Manoharan et al., *Bioorg. Med. Chem. Let.,* 1993, 3:2765), a thiocholesterol (Oberhauser et al., *Nucl. Acids Res.,* 1992, 20:533), an aliphatic chain, e.g., dodecandiol or undecyl residues (Saison-Behmoaras et al., *EMBO J.,* 1991, 10:111; Kabanov et al., *FEBS Lett.,* 1990, 259:327; Svinarchuk et al., *Biochimie,* 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36:3651; Shea et al., *Nucl. Acids Res.,* 1990, 18:3777), a polyamine or a polyethylene glycol chain (Manoharan et al., *Nucleosides & Nucleotides,* 1995, 14:969), or adamantane acetic acid (Manoharan et al., *Tetrahedron Lett.,* 1995, 36:3651), a palmityl moiety (Mishra et al., *Biochim. Biophys. Acta,* 1995, 1264:229), or an octadecylamine or hexylamino-carbonyl-oxycholesterol moiety (Crooke et al., *J. Pharmacol. Exp. Ther.,* 1996, 277:923). Representative United States patents that teach the preparation of such RNA conjugates have been listed above. Typical conjugation protocols involve the synthesis of RNAs bearing an aminolinker at one or more positions of the sequence.

The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

V. Delivery of an RNAi Agent of the Disclosure

The delivery of an RNAi agent of the disclosure to a cell e.g., a cell within a subject, such as a human subject (e.g., a subject in need thereof, such as a subject having a C9orf72-associated disorder, e.g., C9orf72-associated disease, can be achieved in a number of different ways. For example, delivery may be performed by contacting a cell with an RNAi agent of the disclosure either in vitro or in vivo. In vivo delivery may also be performed directly by administering a composition comprising an RNAi agent, e.g., a dsRNA, to a subject. Alternatively, in vivo delivery may be performed indirectly by administering one or more vectors that encode and direct the expression of the RNAi agent. These alternatives are discussed further below.

In general, any method of delivering a nucleic acid molecule (in vitro or in vivo) can be adapted for use with an RNAi agent of the disclosure (see e.g., Akhtar S. and Julian R L., (1992) *Trends Cell. Biol.* 2(5):139-144 and WO94/02595, which are incorporated herein by reference in their entireties). For in vivo delivery, factors to consider in order to deliver an RNAi agent include, for example, biological stability of the delivered agent, prevention of non-specific effects, and accumulation of the delivered agent in the target tissue. The non-specific effects of an RNAi agent can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the RNAi agent to be administered. Several studies have shown successful knockdown of gene products when an RNAi agent is administered locally. For example, intraocular delivery of a VEGF dsRNA by intravitreal injection in cynomolgus monkeys (Tolentino, M J. et al., (2004) *Retina* 24:132-138) and subretinal injections in mice (Reich, S J. et al. (2003) *Mol. Vis.* 9:210-216) were both shown to prevent neovascularization in an experimental model of age-related macular degeneration. In addition, direct intratumoral injection of a dsRNA in mice reduces tumor volume (Pille, J. et al. (2005) *Mol. Ther.* 11:267-274) and can prolong survival of tumor-bearing mice (Kim, W J. et al., (2006) *Mol. Ther.* 14:343-350; Li, S. et al., (2007) *Mol. Ther.* 15:515-523). RNA interference has also shown success with local delivery to the CNS by direct injection (Dorn, G. et al., (2004) *Nucleic Acids* 32:e49; Tan, P H. et al. (2005) *Gene Ther.* 12:59-66; Makimura, H. et al. (2002) *BMC Neurosci.* 3:18; Shishkina, G T., et al. (2004) *Neuroscience* 129:521-528; Thakker, E R., et al. (2004) *Proc. Natl. Acad. Sci. U.S.A.* 101:17270-17275; Akaneya, Y., et al. (2005) *J. Neurophysiol.* 93:594-602) and to the lungs by intranasal administration (Howard, K A. et al., (2006) *Mol. Ther.* 14:476-484; Zhang, X. et al., (2004) *J. Biol. Chem.* 279:10677-10684; Bitko, V. et al., (2005) *Nat. Med.* 11:50-55). For administering an RNAi agent systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the RNAi agent to the target tissue and avoid undesirable off-target effects (e.g., without wishing to be bound by theory, use of GNAs as described herein has been identified to destabilize the seed region of a dsRNA, resulting in enhanced preference of such dsRNAs for on-target effectiveness, relative to off-target effects, as such off-target effects are significantly weakened by such seed region destabilization). RNAi agents can be modified by chemical conjugation to lipophilic groups such as cholesterol to enhance cellular uptake and prevent degradation. For example, an RNAi agent directed against ApoB conjugated to a lipophilic cholesterol moiety was injected systemically into mice and resulted in knockdown of apoB mRNA in both the liver and jejunum (Soutschek, J. et al., (2004) *Nature* 432:173-178). Conjugation of an RNAi agent to an aptamer has been shown to inhibit tumor growth and mediate tumor regression in a mouse model of prostate cancer (McNamara, J O. et al., (2006) *Nat. Biotechnol.* 24:1005-1015). In an alternative embodiment, the RNAi agent can be delivered using drug delivery systems such as a nanoparticle, a dendrimer, a polymer, liposomes, or a cationic delivery system. Positively charged cationic delivery systems facilitate binding of molecule RNAi agent (negatively charged) and also enhance interactions at the negatively charged cell membrane to permit efficient uptake of an RNAi agent by the cell. Cationic lipids, dendrimers, or polymers can either be bound to an RNAi agent, or induced to form a vesicle or micelle (see e.g., Kim S H. et al., (2008) *Journal of Controlled Release* 129(2):107-116) that encases an RNAi agent. The formation of vesicles or micelles further prevents degradation of the RNAi agent when administered systemically. Methods for making and administering cationic-RNAi agent complexes are well within the abilities of one skilled in the art (see e.g., Sorensen, D R., et al. (2003) *J. Mol. Biol* 327:761-766; Verma, U N. et al., (2003) *Clin. Cancer Res.* 9:1291-1300; Arnold, A S et al. (2007) *J. Hypertens.* 25:197-205, which are incorporated herein by reference in their entirety). Some non-limiting examples of drug delivery systems useful for systemic delivery of RNAi agents include DOTAP (Sorensen, D R., et al (2003), supra; Verma, U N. et al., (2003), supra), Oligofectamine, "solid nucleic acid lipid particles" (Zimmermann, T S. et al., (2006) *Nature* 441:111-114), cardiolipin (Chien, P Y. et al., (2005) *Cancer Gene Ther.* 12:321-328; Pal, A. et al., (2005) *Int J. Oncol.* 26:1087-1091), polyethyleneimine (Bonnet M E. et al., (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A. et al., (2007) *Biochem. Soc. Trans.* 35:61-67; Yoo, H. et al., (1999) *Pharm. Res.* 16:1799-1804). In some embodiments, an RNAi agent forms a complex with cyclodextrin for systemic administration. Methods for administration and pharmaceutical compositions of RNAi agents and cyclodextrins can be found in U.S. Pat. No. 7,427,605, which is herein incorporated by reference in its entirety.

Certain aspects of the instant disclosure relate to a method of reducing the expression of a C9orf72 target gene in a cell, comprising contacting said cell with the double-stranded RNAi agent of the disclosure. In one embodiment, the cell is an extraheptic cell, optionally a CNS cell.

Another aspect of the disclosure relates to a method of reducing the expression of a C9orf72 target gene in a subject, comprising administering to the subject the double-stranded RNAi agent of the disclosure.

Another aspect of the disclosure relates to a method of treating a subject having a CNS disorder, comprising administering to the subject a therapeutically effective amount of the double-stranded C9orf72-targeting RNAi agent of the disclosure, thereby treating the subject. Exemplary CNS disorders that can be treated by the method of the disclosure include C9orf72-associated disease.

In one embodiment, the double-stranded RNAi agent is administered intrathecally. By intrathecal administration of the double-stranded RNAi agent, the method can reduce the expression of a C9orf72 target gene in a brain (e.g., striatum) or spine tissue, for instance, cortex, cerebellum, cervical spine, lumbar spine, and thoracic spine.

For ease of exposition the formulations, compositions and methods in this section are discussed largely with regard to modified siRNA compounds. It may be understood, however, that these formulations, compositions and methods can be practiced with other siRNA compounds, e.g., unmodified siRNA compounds, and such practice is within the disclosure. A composition that includes an RNAi agent can be delivered to a subject by a variety of routes. Exemplary routes include: intrathecal, intravenous, topical, rectal, anal, vaginal, nasal, pulmonary, and ocular.

The RNAi agents of the disclosure can be incorporated into pharmaceutical compositions suitable for administration. Such compositions typically include one or more species of RNAi agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present disclosure may be administered in a number of ways depending upon whether local or systemic treatment is desired and upon the area to be treated. Administration may be topical (including ophthalmic, vaginal, rectal, intranasal, transdermal), oral, or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the RNAi agent in aerosol form. The vascular endothelial cells could be targeted by coating a balloon catheter with the RNAi agent and mechanically introducing the RNA.

Formulations for topical administration may include transdermal patches, ointments, lotions, creams, gels, drops, suppositories, sprays, liquids, and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water, syrups, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening or flavoring agents can be added.

Compositions for intrathecal or intraventricular administration may include sterile aqueous solutions which may also contain buffers, diluents, and other suitable additives.

Formulations for parenteral administration may include sterile aqueous solutions which may also contain buffers, diluents, and other suitable additives. Intraventricular injection may be facilitated by an intraventricular catheter, for example, attached to a reservoir. For intravenous use, the total concentration of solutes may be controlled to render the preparation isotonic.

In one embodiment, the administration of the siRNA compound, e.g., a double-stranded siRNA compound, or ssiRNA compound, composition is parenteral, e.g., intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral, or ocular. Administration can be provided by the subject or by another person, e.g., a health care provider. The medication can be provided in measured doses or in a dispenser which delivers a metered dose. Selected modes of delivery are discussed in more detail below.

A. Intrathecal Administration.

In one embodiment, the double-stranded RNAi agent is delivered by intrathecal injection (i.e., injection into the spinal fluid which bathes the brain and spinal cord tissue). Intrathecal injection of RNAi agents into the spinal fluid can be performed as a bolus injection or via minipumps which can be implanted beneath the skin, providing a regular and constant delivery of siRNA into the spinal fluid. The circulation of the spinal fluid from the choroid plexus, where it is produced, down around the spinal chord and dorsal root ganglia and subsequently up past the cerebellum and over the cortex to the arachnoid granulations, where the fluid can exit the CNS, that, depending upon size, stability, and solubility of the compounds injected, molecules delivered intrathecally could hit targets throughout the entire CNS.

In some embodiments, the intrathecal administration is via a pump. The pump may be a surgically implanted osmotic pump. In one embodiment, the osmotic pump is implanted into the subarachnoid space of the spinal canal to facilitate intrathecal administration.

In some embodiments, the intrathecal administration is via an intrathecal delivery system for a pharmaceutical including a reservoir containing a volume of the pharmaceutical agent, and a pump configured to deliver a portion of the pharmaceutical agent contained in the reservoir. More details about this intrathecal delivery system may be found in WO 2015/116658, which is incorporated by reference in its entirety.

The amount of intrathecally injected RNAi agents may vary from one target gene to another target gene and the appropriate amount that has to be applied may have to be determined individually for each target gene. Typically, this amount ranges from 10 μg to 2 mg, preferably 50 μg to 1500 μg, more preferably 100 μg to 1000 μg.

B. Vector Encoded RNAi Agents of the Disclosure

RNAi agents targeting the C9orf72 gene can be expressed from transcription units inserted into DNA or RNA vectors (see, e.g., Couture, A, et al., *TIG*. (1996), 12:5-10; WO 00/22113, WO 00/22114, and U.S. Pat. No. 6,054,299). Expression is preferably sustained (months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., (1995) *Proc. Natl. Acad. Sci. USA* 92:1292).

The individual strand or strands of an RNAi agent can be transcribed from a promoter on an expression vector. Where two separate strands are to be expressed to generate, for example, a dsRNA, two separate expression vectors can be co-introduced (e.g., by transfection or infection) into a target cell. Alternatively, each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

RNAi agent expression vectors are generally DNA plasmids or viral vectors. Expression vectors compatible with eukaryotic cells, preferably those compatible with vertebrate cells, can be used to produce recombinant constructs for the expression of an RNAi agent as described herein. Delivery of RNAi agent expressing vectors can be systemic, such as by intravenous or intramuscular administration, by administration to target cells ex-planted from the patient followed by reintroduction into the patient, or by any other means that allows for introduction into a desired target cell.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an RNAi agent will generally require regulatory elements, e.g., promoters, enhancers, etc., to ensure the expression of the RNAi agent in target cells. Other aspects to consider for vectors and constructs are known in the art.

VI. Pharmaceutical Compositions of the Invention

The present disclosure also includes pharmaceutical compositions and formulations which include the RNAi agents of the disclosure. In one embodiment, provided herein are pharmaceutical compositions containing an RNAi agent, as described herein, and a pharmaceutically acceptable carrier. The pharmaceutical compositions containing the RNAi agent are useful for treating a disease or disorder associated with the expression or activity of C9orf72, e.g., C9orf72-associated disease.

In some embodiments, the pharmaceutical compositions of the invention are sterile. In another embodiment, the pharmaceutical compositions of the invention are pyrogen free.

Such pharmaceutical compositions are formulated based on the mode of delivery. One example is compositions that are formulated for systemic administration via parenteral delivery, e.g., by intravenous (IV), intramuscular (IM), or for subcutaneous (subQ) delivery. Another example is compositions that are formulated for direct delivery into the CNS, e.g., by intrathecal or intravitreal routes of injection, optionally by infusion into the brain (e.g., striatum), such as by continuous pump infusion.

The pharmaceutical compositions of the disclosure may be administered in dosages sufficient to inhibit expression of a C9orf72 gene. In general, a suitable dose of an RNAi agent of the disclosure will be in the range of about 0.001 to about 200 0 milligrams per kilogram body weight of the recipient per day, generally in the range of about 1 to 50 mg per kilogram body weight per day.

A repeat-dose regimen may include administration of a therapeutic amount of an RNAi agent on a regular basis, such as monthly to once every six months. In certain embodiments, the RNAi agent is administered about once per quarter (i.e., about once every three months) to about twice per year.

After an initial treatment regimen (e.g., loading dose), the treatments can be administered on a less frequent basis.

In other embodiments, a single dose of the pharmaceutical compositions can be long lasting, such that subsequent doses are administered at not more than 1, 2, 3, or 4 or more month intervals. In some embodiments of the disclosure, a single dose of the pharmaceutical compositions of the disclosure is administered once per month. In other embodiments of the disclosure, a single dose of the pharmaceutical compositions of the disclosure is administered once per quarter to twice per year.

The skilled artisan will appreciate that certain factors can influence the dosage and timing required to effectively treat a subject, including but not limited to the severity of the disease or disorder, previous treatments, the general health or age of the subject, and other diseases present. Moreover, treatment of a subject with a therapeutically effective amount of a composition can include a single treatment or a series of treatments.

Advances in mouse genetics have generated a number of mouse models for the study of various human diseases, such as ALS and FTD that would benefit from reduction in the expression of C9orf72. Such models can be used for in vivo testing of RNAi agents, as well as for determining a therapeutically effective dose. Suitable rodent models are known in the art and include, for example, those described in, for example, Cepeda, et al. (*ASN Neuro* (2010) 2(2):e00033) and Pouladi, et al. (*Nat Reviews* (2013) 14:708).

The pharmaceutical compositions of the present disclosure can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The RNAi agents can be delivered in a manner to target a particular tissue, such as the CNS (e.g., neuronal, glial or vascular tissue of the brain).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the RNAi agents featured in the disclosure are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). RNAi agents featured in the disclosure can be encapsulated within liposomes or can form complexes thereto, in particular to cationic liposomes. Alternatively, RNAi agents can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference.

A. RNAi Agent Formulations Comprising Membranous Molecular Assemblies

An RNAi agent for use in the compositions and methods of the disclosure can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the RNAi agent composition. The lipophilic material isolates the aqueous interior from an aqueous exterior, which typically does not include the RNAi agent composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the RNAi agent are delivered into the cell where the RNAi agent can specifically bind to a target RNA and can mediate RNAi. In some cases the liposomes are also specifically targeted, e.g., to direct the RNAi agent to particular cell types.

A liposome containing an RNAi agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The RNAi agent preparation is then added to the micelles that include the lipid component. The cationic groups on the lipid interact with the RNAi agent and condense around the RNAi agent to form a liposome. After condensation, the detergent is removed, e.g., by dialysis, to yield a liposomal preparation of RNAi agent.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Methods for producing stable polynucleotide delivery vehicles, which incorporate a polynucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., (1987) *Proc. Natl. Acad. Sci. USA* 8:7413-7417; U.S. Pat. Nos. 4,897,355; 5,171,678; Bangham et al., (1965) *M. Mol. Biol.* 23:238; Olson et al., (1979) *Biochim. Biophys. Acta* 557:9; Szoka et al., (1978) *Proc. Natl. Acad. Sci.* 75: 4194; Mayhew et al., (1984) *Biochim. Biophys. Acta* 775:169; Kim et al., (1983) *Biochim. Biophys. Acta* 728:339; and Fukunaga et al., (1984) *Endocrinol.* 115:757. Commonly used techniques for preparing lipid aggregates of appropriate size for use as delivery vehicles include sonication and freeze-thaw plus extrusion (see, e.g., Mayer et al., (1986) *Biochim. Biophys. Acta* 858:161. Microfluidization can be used when consistently small (50 to 200 nm) and relatively uniform aggregates are desired (Mayhew et al., (1984) *Biochim. Biophys. Acta* 775:169. These methods are readily adapted to packaging RNAi agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al. (1987) *Biochem. Biophys. Res. Commun.*, 147:980-985).

Liposomes, which are pH-sensitive or negatively charged, entrap nucleic acids rather than complex with them. Since both the nucleic acid and the lipid are similarly charged, repulsion rather than complex formation occurs. Nevertheless, some nucleic acid is entrapped within the aqueous interior of these liposomes. pH sensitive liposomes have been used to deliver nucleic acids encoding the thymidine kinase gene to cell monolayers in culture. Expression of the exogenous gene was detected in the target cells (Zhou et al. (1992) *Journal of Controlled Release*, 19:269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid or phosphatidylcholine or cholesterol.

Examples of other methods to introduce liposomes into cells in vitro and in vivo include U.S. Pat. Nos. 5,283,185; 5,171,678; WO 94/00569; WO 93/24640; WO 91/16024; Felgner, (1994) *J. Biol. Chem.* 269:2550; Nabel, (1993) *Proc. Natl. Acad. Sci.* 90:11307; Nabel, (1992) *Human Gene Ther.* 3:649; Gershon, (1993) *Biochem.* 32:7143; and Strauss, (1992) *EMBO J.* 11:417.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al., (1994) *S.T.P. Pharma. Sci.,* 4(6):466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., (1987) *FEBS Letters,* 223:42; Wu et al., (1993) *Cancer Research,* 53:3765).

Various liposomes comprising one or more glycolipids are known in the art. Papahadjopoulos et al. (*Ann. N.Y. Acad. Sci*., (1987), 507:64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A*., (1988), 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver RNAi agents to macrophages.

Further advantages of liposomes include: liposomes obtained from natural phospholipids are biocompatible and biodegradable; liposomes can incorporate a wide range of water and lipid soluble drugs; liposomes can protect encapsulated RNAi agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of RNAi agent (see, e.g., Felgner, P. L. et al., (1987) *Proc. Natl. Acad. Sci. USA* 8:7413-7417, and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Indiana) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wisconsin) and dipalmitoylphosphatidylethanolamine 5-carboxyspermylamide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., (1991) *Biochim. Biophys. Res. Commun.* 179:280). Lipopolylysine, made by conjugating polylysine to DOPE, has been reported to be effective for transfection in the presence of serum (Zhou, X. et al., (1991) *Biochim. Biophys. Acta* 1065:8). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, California) and Lipofectamine (DOSPA) (Life Technology, Inc., Gaithersburg, Maryland). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer RNAi agent into the skin. In some implementations, liposomes are used for delivering RNAi agent to epidermal cells and also to enhance the penetration of RNAi agent into dermal tissues, e.g., into skin. For example, the liposomes can be applied topically. Topical delivery of drugs formulated as liposomes to the skin has been documented (see, e.g., Weiner et al., (1992) *Journal of Drug Targeting*, vol. 2, 405-410 and du Plessis et al., (1992) *Antiviral Research,* 18:259-265; Mannino, R. J. and Fould-Fogerite, S., (1998) *Biotechniques* 6:682-690; Itani, T. et al., (1987) *Gene* 56:267-276; Nicolau, C. et al. (1987) *Meth. Enzymol.* 149: 157-176; Straubinger, R. M. and Papahadjopoulos, D. (1983) *Meth. Enzymol.* 101:512-527; Wang, C. Y. and Huang, L., (1987) *Proc. Natl. Acad. Sci. USA* 84:7851-7855).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with RNAi agent are useful for treating a dermatological disorder.

Liposomes that include RNAi agents can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include RNAi agent can be delivered, for example, subcutaneously by infection in order to deliver RNAi agent to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present disclosure are described in U.S. provisional application Ser. No. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application number PCT/US2007/080331, filed Oct. 3, 2007, also describes formulations that are amenable to the present disclosure.

Transfersomes, yet another type of liposomes, are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as those described herein, particularlay in emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general, their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

The RNAi agent for use in the methods of the disclosure can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol or m-cresol may be added to the mixed micellar composition to stabilize the formulation and protect against bacterial growth. Alternatively, phenol or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

B. Lipid Particles

RNAi agents, e.g., dsRNAs of in the disclosure may be fully encapsulated in a lipid formulation, e.g., a LNP, or other nucleic acid-lipid particle.

As used herein, the term "LNP" refers to a stable nucleic acid-lipid particle. LNPs typically contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in WO 00/03683. The particles of the present disclosure typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present disclosure are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; United States Patent publication No. 2010/0324120 and WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the disclosure.

Certain specific LNP formulations for delivery of RNAi agents have been described in the art, including, e.g., "LNP01" formulations as described in, e.g., WO 2008/042973, which is hereby incorporated by reference.

Additional exemplary lipid-dsRNA formulations are identified in the Table 2 below.

TABLE 2

| | Ionizable/Cationic Lipid | cationic lipid/non-cationic lipid/cholesterol/PEG-lipid conjugate Lipid:siRNA ratio |
|---|---|---|
| SNALP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA ~ 7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA ~ 7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~ 6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~ 11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~ 6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~ 11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1- | Tech G1/DSPC/Cholesterol/PEG-DMG 50/10/38.5/1.5 |

TABLE 2-continued

| | Ionizable/Cationic Lipid | cationic lipid/non-cationic lipid/cholesterol/PEG-lipid conjugate Lipid:siRNA ratio |
|---|---|---|
| | yl)ethylazanediyl)didodecan-2-ol (Tech G1) | Lipid:siRNA 10:1 |
| LNP13 | XTC | XTC/DSPC/Chol/PEG-DMG<br>50/10/38.5/1.5<br>Lipid:siRNA: 33:1 |
| LNP14 | MC3 | MC3/DSPC/Chol/PEG-DMG<br>40/15/40/5<br>Lipid:siRNA: 11:1 |
| LNP15 | MC3 | MC3/DSPC/Chol/PEG-DSG/GalNAc-PEG-DSG<br>50/10/35/4.5/0.5<br>Lipid:siRNA: 11:1 |
| LNP16 | MC3 | MC3/DSPC/Chol/PEG-DMG<br>50/10/38.5/1.5<br>Lipid:siRNA: 7:1 |
| LNP17 | MC3 | MC3/DSPC/Chol/PEG-DSG<br>50/10/38.5/1.5<br>Lipid:siRNA: 10:1 |
| LNP18 | MC3 | MC3/DSPC/Chol/PEG-DMG<br>50/10/38.5/1.5<br>Lipid:siRNA: 12:1 |
| LNP19 | MC3 | MC3/DSPC/Chol/PEG-DMG<br>50/10/35/5<br>Lipid:siRNA: 8:1 |
| LNP20 | MC3 | MC3/DSPC/Chol/PEG-DPG<br>50/10/38.5/1.5<br>Lipid:siRNA: 10:1 |
| LNP21 | C12-200 | C12-200/DSPC/Chol/PEG-DSG<br>50/10/38.5/1.5<br>Lipid:siRNA: 7:1 |
| LNP22 | XTC | XTC/DSPC/Chol/PEG-DSG<br>50/10/38.5/1.5<br>Lipid:siRNA: 10:1 |

DSPC: distearoylphosphatidylcholine

DPPC: dipalmitoylphosphatidylcholine

PEG-DMG: PEG-didimyristoyl glycerol (C14-PEG, or PEG-C14) (PEG with avg mol wt of 2000)

PEG-DSG: PEG-distyryl glycerol (C18-PEG, or PEG-C18) (PEG with avg mol wt of 2000)

PEG-cDMA: PEG-carbamoyl-1,2-dimyristyloxypropylamine (PEG with avg mol wt of 2000)

SNALP (1,2-Dilinolenyloxy-N,N-dimethylaminopropane (DLinDMA)) comprising formulations are described in WO 2009/127060, which is hereby incorporated by reference.

XTC comprising formulations are described in WO 2010/088537, the entire contents of which are hereby incorporated herein by reference.

MC3 comprising formulations are described, e.g., in United States Patent Publication No. 2010/0324120, the entire contents of which are hereby incorporated by reference.

ALNY-100 comprising formulations are described in WO 2010/054406, the entire contents of which are hereby incorporated herein by reference.

C12-200 comprising formulations are described in WO 2010/129709, the entire contents of which are hereby incorporated herein by reference.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the disclosure are administered in conjunction with one or more penetration enhancer surfactants and chelators. Suitable surfactants include fatty acids or esters or salts thereof, bile acids or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the disclosure can be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, U.S. 2003/0027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the brain when treating APP-associated diseases or disorders.

The pharmaceutical formulations of the present disclosure, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present disclosure can be formulated into any of many possible dosage forms such as, but not limited to, tablets, capsules, gel capsules, liquid syrups, soft gels, suppositories, and enemas. The compositions of the present disclosure can also be formulated as suspensions in aqueous, non-aqueous or mixed media. Aqueous suspensions can further contain substances which increase the viscosity of the suspension including, for example, sodium carboxymethylcellulose, sorbitol or dextran. The suspension can also contain stabilizers.

C. Additional Formulations i. Emulsions

The compositions of the present disclosure can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise, a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present disclosure, the compositions of RNAi agents and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Rosoff, in Pharmaceutical Dosage Forms, Lieberman, Rieger and Banker (Eds.), 1988, Marcel Dekker, Inc., New York, N.Y., volume 1, p. 245). Typically, microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used, and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (M0310), hexaglycerol monooleate (PO310), hexaglycerol pentaoleate (PO500), decaglycerol monocaprate (MCA750), decaglycerol monooleate (M0750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions can form spontaneously when their components are brought together at ambient temperature. This can be particularly advantageous when formulating thermolabile drugs, peptides or RNAi agents. Microemulsions have also been effective in the transdermal delivery of active components in both cosmetic and pharmaceutical applications. It is expected that the microemulsion compositions and formulations of the present disclosure will facilitate the increased systemic absorption of RNAi agents and nucleic acids from the gastrointestinal tract, as well as improve the local cellular uptake of RNAi agents and nucleic acids.

Microemulsions of the present disclosure can also contain additional components and additives such as sorbitan monostearate (Grill 3), Labrasol, and penetration enhancers to improve the properties of the formulation and to enhance the absorption of the RNAi agents and nucleic acids of the present disclosure. Penetration enhancers used in the microemulsions of the present disclosure can be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

iii. Microparticles

An RNAi agent of the disclosure may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present disclosure employs various penetration enhancers to effect the efficient delivery of nucleic acids, particularly RNAi agents, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, NY, 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of RNAi agents through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, MA, 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, NY, 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, NY, 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating agents, as used in connection with the present disclosure, can be defined as compounds that remove metallic ions from solution by forming complexes therewith, with the result that absorption of RNAi agents through the mucosa is enhanced. With regards to their use as penetration enhancers in the present disclosure, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, MA, 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rd., 1990, 14, 43-51).

As used herein, non-chelating non-surfactant penetration enhancing compounds can be defined as compounds that demonstrate insignificant activity as chelating agents or as surfactants but that nonetheless enhance absorption of RNAi agents through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of RNAi agents at the cellular level can also be added to the pharmaceutical and other compositions of the present disclosure. For example, cationic lipids, such as lipofectin (Junichi et al, U.S. Pat. No. 5,705,188), cationic glycerol derivatives, and polycationic molecules, such as polylysine (WO 97/30731), are also known to enhance the cellular uptake of dsRNAs.

Other agents can be utilized to enhance the penetration of the administered nucleic acids, including glycols such as ethylene glycol and propylene glycol, pyrrols such as 2-pyrrol, azones, and terpenes such as limonene and menthone.

vi. Excipients

In contrast to a carrier compound, a “pharmaceutical carrier” or “excipient” is a pharmaceutically acceptable solvent, suspending agent or any other pharmacologically inert vehicle for delivering one or more nucleic acids to an animal The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present disclosure. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present disclosure can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings or aromatic substances and the like which do not deleteriously interact with the nucleic acid(s) of the formulation.

Aqueous suspensions can contain substances which increase the viscosity of the suspension including, for example, sodium carboxymethylcellulose, sorbitol or dextran. The suspension can also contain stabilizers.

In some embodiments, pharmaceutical compositions featured in the disclosure include (a) one or more RNAi agents and (b) one or more agents which function by a non-RNAi mechanism and which are useful in treating a C9orf72-associated disorder. Examples of such agents include, but are not limited to, monoamine inhibitors, reserpine, anticonvulsants, antipsychotic agents, and antidepressants.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$ Compounds that exhibit high therapeutic indices are preferred.

The data obtained from cell culture assays and animal studies can be used in formulating a range of dosage for use in humans. The dosage of compositions featured herein in the disclosure lies generally within a range of circulating concentrations that include the $ED_{50}$ with little or no toxicity. The dosage can vary within this range depending upon the dosage form employed and the route of administration utilized. For any compound used in the methods featured in the disclosure, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the RNAi agents featured in the disclosure can be administered in combination with other known agents effective in treatment of pathological processes mediated by nucleotide repeat expression. In any event, the administering physician can adjust the amount and timing of RNAi agent administration on the basis of results observed using standard measures of efficacy known in the art or described herein.

VII. Kits

In certain aspects, the instant disclosure provides kits that include a suitable container containing a pharmaceutical formulation of a siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof).

Such kits include one or more dsRNA agent(s) and instructions for use, e.g., instructions for administering a prophylactically or therapeutically effective amount of a dsRNA agent(s). The dsRNA agent may be in a vial or a pre-filled syringe. The kits may optionally further comprise means for administering the dsRNA agent (e.g., an injection device, such as a pre-filled syringe), or means for measuring the inhibition of C3 (e.g., means for measuring the inhibition of C9orf72 mRNA, C9orf72 protein, and/or C9orf72 activity). Such means for measuring the inhibition of C9orf72 may comprise a means for obtaining a sample from a subject, such as, e.g., a CSF and/or plasma sample. The kits of the invention may optionally further comprise means for determining the therapeutically effective or prophylactically effective amount.

In certain embodiments the individual components of the pharmaceutical formulation may be provided in one container. Alternatively, it may be desirable to provide the components of the pharmaceutical formulation separately in two or more containers, e.g., one container for a siRNA compound preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

VII. Methods for Inhibiting C9orf72 Expression

The present disclosure also provides methods of inhibiting expression of a C9orf72 gene in a cell. The methods include contacting a cell with an RNAi agent, e.g., double stranded RNAi agent, in an amount effective to inhibit expression of C9orf72 in the cell, thereby inhibiting expression of C9orf72 in the cell. In certain embodiments of the disclosure, C9orf72 is inhibited preferentially in CNS (e.g., brain) cells.

Contacting of a cell with an RNAi agent, e.g., a double stranded RNAi agent, may be done in vitro or in vivo. Contacting a cell in vivo with the RNAi agent includes contacting a cell or group of cells within a subject, e.g., a human subject, with the RNAi agent. Combinations of in vitro and in vivo methods of contacting a cell are also possible.

Contacting a cell may be direct or indirect, as discussed above. Furthermore, contacting a cell may be accomplished via a targeting ligand, including any ligand described herein or known in the art. In some embodiments, the targeting ligand is a carbohydrate moiety, e.g., a GalNAc ligand, or any other ligand that directs the RNAi agent to a site of interest.

The term "inhibiting," as used herein, is used interchangeably with "reducing," "silencing," "downregulating," "suppressing" and other similar terms, and includes any level of inhibition. In certain embodiments, a level of inhibition, e.g., for an RNAi agent of the instant disclosure, can be assessed in cell culture conditions, e.g., wherein cells in cell culture are transfected via Lipofectamine™-mediated transfection at a concentration in the vicinity of a cell of 10 nM or less, 1 nM or less, etc. Knockdown of a given RNAi agent can be determined via comparison of pre-treated levels in cell culture versus post-treated levels in cell culture, optionally also comparing against cells treated in parallel with a scrambled or other form of control RNAi agent. Knockdown in cell culture of, e.g., about 50%, can thereby be identified as indicative of "inhibiting" or "reducing", "downregulating" or "suppressing", etc. having occurred. It is expressly contemplated that assessment of targeted mRNA or encoded protein levels (and therefore an extent of "inhibiting", etc. caused by an RNAi agent of the disclosure) can also be assessed in in vivo systems for the RNAi agents of the instant disclosure, under properly controlled conditions as described in the art.

The phrase "inhibiting expression of a C9orf72 gene" or "inhibiting expression of C9orf72," as used herein, includes inhibition of expression of any C9orf72 gene (such as, e.g., a mouse C9orf72 gene, a rat C9orf72 gene, a monkey C9orf72 gene, or a human C9orf72 gene) as well as variants or mutants of a C9orf72 gene that encode a C9orf72 protein, e.g., a C9orf72 gene having an expanded hexanucleotide repeat in an intron of the gene. Thus, the C9orf72 gene may be a wild-type C9orf72 gene, a mutant C9orf72 gene, or a transgenic C9orf72 gene in the context of a genetically manipulated cell, group of cells, or organism.

"Inhibiting expression of a C9orf72 gene" includes any level of inhibition of a C9orf72 gene, e.g., at least partial suppression of the expression of a C9orf72 gene, such as an inhibition by at least 20%. In certain embodiments, inhibition is by at least 30%, at least 40%, or preferably, by at least 50%. In other embodiments, inhibition is no more than 50%, e.g., no more than 50%, 45%, 40%, 35%, 30%, 25%, 20%, 15%, 10%, or 5%.

The expression of a C9orf72 gene may be assessed based on the level of any variable associated with C9orf72 gene expression, e.g., C9orf72 mRNA level (e.g., sense mRNA, antisense mRNA, total C9orf72 mRNA, sense C9orf72 repeat-containing mRNA, and/or antisense C9orf72 repeat-containing mRNA) or C9orf72 protein level (e.g., total C9orf72 protein, wild-type C9orf72 protein, or expanded repeat-containing protein), or, for example, the level of sense- or antisense-containing foci and/or the level of aberrant dipeptide repeat protein.

Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

For example, in some embodiments of the methods of the disclosure, expression of a C9orf72 gene (e.g., as assessed by sense- or antisense-containing foci and/or aberrant dipeptide repeat protein level) is inhibited by at least 20%, 30%, 40%, 50%, 60%, 70%, 80%, 85%, 90%, or 95%, or to below the level of detection of the assay. In other embodiments of the methods of the disclosure, expression of a C9orf72 gene (e.g., as assessed by mRNA or protein expression level) is inhibited by no more than 50%, 45%, 40%, 35%, 30%, 25%, 20%, 15%, 10%, or 5%. In certain embodiments, the methods include a clinically relevant inhibition of expression of C9orf72, e.g. as demonstrated by a clinically relevant outcome after treatment of a subject with an agent to reduce the expression of C9orf72.

Inhibition of the expression of a C9orf72 gene may be manifested by a reduction of the amount of mRNA expressed by a first cell or group of cells (such cells may be present, for example, in a sample derived from a subject) in which a C9orf72 gene is transcribed and which has or have been treated (e.g., by contacting the cell or cells with an RNAi agent of the disclosure, or by administering an RNAi agent of the disclosure to a subject in which the cells are or were present) such that the expression of a C9orf72 gene is inhibited, as compared to a second cell or group of cells substantially identical to the first cell or group of cells but which has not or have not been so treated (control cell(s) not treated with an RNAi agent or not treated with an RNAi agent targeted to the gene of interest). The degree of inhibition may be expressed in terms of:

$$\frac{(mRNA \text{ in control cells}) - (mRNA \text{ in treated cells})}{(mRNA \text{ in control cells})} \cdot 100\%$$

In other embodiments, inhibition of the expression of a C9orf72 gene may be assessed in terms of a reduction of a parameter that is functionally linked to a C9orf72 gene expression, e.g., C9orf72 protein expression, sense- or antisense-containing foci and/or the level of aberrant dipeptide repeat protein. C9orf72 gene silencing may be determined in any cell expressing C9orf72, either endogenous or heterologous from an expression construct, and by any assay known in the art.

Inhibition of the expression of a C9orf72 protein may be manifested by a reduction in the level of the C9orf72 protein (or functional parameter, e.g., as described herein) that is expressed by a cell or group of cells (e.g., the level of protein expressed in a sample derived from a subject). As explained above, for the assessment of mRNA suppression, the inhibition of protein expression levels in a treated cell or group of cells may similarly be expressed as a percentage of the level of protein in a control cell or group of cells.

A control cell or group of cells that may be used to assess the inhibition of the expression of a C9orf72 gene includes a cell or group of cells that has not yet been contacted with an RNAi agent of the disclosure. For example, the control cell or group of cells may be derived from an individual subject (e.g., a human or animal subject) prior to treatment of the subject with an RNAi agent.

The level of C9orf72 mRNA that is expressed by a cell or group of cells may be determined using any method known in the art for assessing mRNA expression. In one embodiment, the level of expression of C9orf72 in a sample is determined by detecting a transcribed polynucleotide, or portion thereof, e.g., mRNA of the C9orf72 gene. RNA may be extracted from cells using RNA extraction techniques including, for example, using acid phenol/guanidine isothiocyanate extraction (RNAzol B; Biogenesis), RNeasy™ RNA preparation kits (Qiagen®) or PAXgene (PreAnalytix, Switzerland). Typical assay formats utilizing ribonucleic acid hybridization include nuclear run-on assays, RT-PCR, RNase protection assays, northern blotting, in situ hybridization, and microarray analysis. Strand specific C9orf72 mRNAs may be detected using the quantitative RT-PCR and.or droplet digital PCR methods described in, for example, Jiang, et al. supra, Lagier-Tourenne, et al., supra and Jiang, et al., supra. Circulating C9orf72 mRNA may be detected using methods the described in WO2012/177906, the entire contents of which are hereby incorporated herein by reference.

In some embodiments, the level of expression of C9orf72 is determined using a nucleic acid probe. The term "probe", as used herein, refers to any molecule that is capable of selectively binding to a specific C9orf72 nucleic acid or protein, or fragment thereof. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses and probe arrays. One method for the determination of mRNA levels involves contacting the isolated mRNA with a nucleic acid molecule (probe) that can hybridize to C9orf72 mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix® gene chip array. A skilled artisan can readily adapt known mRNA detection methods for use in determining the level of C9orf72 mRNA.

An alternative method for determining the level of expression of C9orf72 in a sample involves the process of nucleic acid amplification or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the disclosure, the level of expression of C9orf72 is determined by quantitative fluorogenic RT-PCR (i.e., the TaqMan' System), by a Dual-Glo® Luciferase assay, or by other art-recognized method for measurement of C9orf72 expression or mRNA level.

The expression level of C9orf72 mRNA may be monitored using a membrane blot (such as used in hybridization analysis such as northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of C9orf72 expression level may also comprise using nucleic acid probes in solution.

In some embodiments, the level of mRNA expression is assessed using branched DNA (bDNA) assays or real time PCR (qPCR). The use of this PCR method is described and exemplified in the Examples presented herein. Such methods can also be used for the detection of C9orf72 nucleic acids.

The level of C9orf72 protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like. Such assays can also be used for the detection of proteins indicative of the presence or replication of C9orf72 proteins.

The level of sense- or antisense-containing foci and the level of aberrant dipeptide repeat protein may be assessed using methods well-known to one of ordinary skill in the art, including, for example, fluorescent in situ hybridization (FISH), immunohistochemistry and immunoassay (see, e.g., Jiang, et al. supra),In some embodiments, the efficacy of the methods of the disclosure in the treatment of a C9orf72-associated disease is assessed by a decrease in C9orf72 mRNA level (e.g, by assessment of a CSF sample and/or plasma sample for C9orf72 level, by brain biopsy, or otherwise).

In some embodiments of the methods of the disclosure, the RNAi agent is administered to a subject such that the RNAi agent is delivered to a specific site within the subject. The inhibition of expression of C9orf72 may be assessed using measurements of the level or change in the level of C9orf72 mRNA (e.g., sense mRNA, antisense mRNA, total C9orf72 mRNA, sense C9orf72 repeat-containing mRNA, and/or antisense C9orf72 repeat-containing mRNA), C9orf72 protein (e.g., total C9orf72 protein, wild-type C9orf72 protein, or expanded repeat-containing protein), sense-containing foci, antisense-containing foci, aberrant dipeptide repeat protein in a sample derived from a specific site within the subject, e.g., CNS cells. In certain embodiments, the methods include a clinically relevant inhibition of expression of C9orf72, e.g. as demonstrated by a clinically relevant outcome after treatment of a subject with an agent to reduce the expression of C9orf72, such as, for example, stabilization or inhibition of caudate atrophy (e.g., as assessed by volumetric MRI (vMRI)), a stabilization or reduction in neurofilament light chain (Nfl) levels in a CSF sample from a subject, a reduction in mutant C9orf72 mRNA or a cleaved mutant C9orf72 protein, e.g., one or both of full-length mutant C9orf72 mRNA or protein and a cleaved mutant C9orf72 mRNA or protein, and a stabilization or improvement in Unified C9orf72-associated disease Rating Scale (UHDRS) score.

As used herein, the terms detecting or determining a level of an analyte are understood to mean performing the steps to determine if a material, e.g., protein, RNA, is present. As used herein, methods of detecting or determining include detection or determination of an analyte level that is below the level of detection for the method used.

IX. Methods of Treating or Preventing C9orf72-Associated Diseases

As described herein, reducing C9orf72 repeat-containing RNAs may be achieved through the natural process of RNA interference, in which dsRNAs direct cleavage of the target RNAs by the RNA-induced silencing complex followed by degradation of the RNA cleavage fragments by cellular nucleases. RNA interference is, however, a predominantly cytoplasmic process that would not be expected to act on RNAs retained in the nucleus. Intron-containing RNAs are usually short-lived, either as mRNA precursors, which are rapidly spliced into mature mRNAs, or as spliced-out introns, which are rapidly degraded in the nucleus. It is reasonable, therefore, to expect that intron-containing RNAs would not be available for targeting by RNA interference.

However, as demonstrated herein, siRNAs that targeted intron sequences adjacent to the GGGGCC repeat (SEQ ID NO: 1) expansion promoted reduced accumulation of intron-containing C9orf72 RNAs while having little to no effect on the C9orf72 mature mRNA. The intron-targeting siRNAs also reduced production of dipeptide repeat proteins. Surprisingly, we have shown that the disclosed siRNAs targeting this region are effective at reducing the level intron-containing C9orf72 RNAs. The results show that a significant fraction of the intron-containing C9orf72 RNAs responsible for dipeptide repeat protein synthesis resides in the cytoplasm. In contrast, siRNAs that targeted the C9orf72 mRNA protein coding sequence produced a strong knock down of the mRNA but had no effect on the intron-containing transcripts and did not appreciably reduce dipeptide repeat protein synthesis. The divergence in results between the intron-targeting and mRNA-targeting siRNAs suggests that the two classes of targeted sequences are present on separate RNAs that are not covalently linked.

The methods disclosed herein provide for the therapeutic reduction in the synthesis of dipeptide repeat proteins, a principle pathogenic component of C9orf72 repeat expansion disease, while sparing the C9orf72 mRNA, thereby avoiding possible adverse effects of reduction of C9orf72 protein, as could occur with therapeutic strategies, such as the use of antisense oligonucleotides, that target the primary C9orf72 transcript in the nucleus.

Some of the methods disclosed herein are for inhibiting expression of a C9orf72 target RNA comprising a hexanucleotide repeat comprising multiple contiguous copies of SEQ ID NO: 1 in a cell. The C9orf72 target RNA can be, for example, one with a pathogenic hexanucleotide repeat expansion (having, for example, at least about 30, at least about 35, at least about 40, at least about 50, at least about 60, at least about 70, at least about 80, at least about 100, at least about 200, at least about 300, at least about 400, or at least about 500 copies of the hexanucleotide repeat). Such methods can comprise introducing into the cell any of the dsRNA agents disclosed herein, thereby inhibiting expression of the C9orf72 target RNA in the cell.

Thus, the present disclosure also provides methods of using an RNAi agent of the disclosure or a composition containing an RNAi agent of the disclosure to reduce or inhibit C9orf72 expression in a cell. The methods include contacting the cell with a dsRNA of the disclosure and maintaining the cell for a time sufficient to obtain degradation of the mRNA transcript of a C9orf72 gene, thereby inhibiting expression of the C9orf72 gene in the cell.

In addition, the present disclosure also provides methods of using an RNAi agent of the disclosure or a composition containing an RNAi agent of the disclosure to reduce the level and/or inhibit formation of sense- and antisense-containing foci in a cell. The methods include contacting the cell with a dsRNA of the disclosure, thereby reducing the level of the C9orf72 sense- and antisense-containing foci in the cell.

The present disclosure also provides methods of using an RNAi agent of the disclosure or a composition containing an RNAi agent of the disclosure to reduce the level and/or inhibit formation of aberrant dipeptide repeat protein in a cell. The methods include contacting the cell with a dsRNA of the disclosure, thereby reducing the level of the aberrant dipeptide repeat protein in the cell. Such methods can further comprise assessing expression of the C9orf72 target RNA in the cell and/or assessing expression of a mature C9orf72 mRNA in the cell. The assessing can be done, for example, by reverse-transcription quantitative polymerase chain reactions to detect the C9orf72 target RNA. However, any other suitable method may be used.

In the methods of the disclosure the cell may be contacted in vitro or in vivo, i.e., the cell may be within a subject.

A cell suitable for treatment using the methods of the disclosure may be any cell that expresses a C9orf72 gene or a cell that expresses a C9orf72 gene having an expand end GGGGCC repeat (SEQ ID NO: 1). A cell suitable for use in the methods of the disclosure may be a mammalian cell, e.g., a primate cell (such as a human cell or a non-human primate cell, e.g., a monkey cell or a chimpanzee cell), a non-primate cell (such as a a rat cell, or a mouse cell). In one embodiment, the cell is a human cell, e.g., a human CNS cell. In some embodiments, the cell is a non-human animal one-cell stage embryos, non-human animal embryonic stem cells, embryonic stem-cell derived motor neurons, brain cells, cortical cells, neuronal cells, muscle cells, heart cells, or germ cells.

In some embodiments, the cell can comprise a C9orf72 locus comprising a pathogenic hexanucleotide repeat expansion. A pathogenic hexanucleotide repeat expansion is an expansion consisting of a number of repeats of GGGGCC (SEQ ID NO: 1) in an intervening sequence separating two putative first, non-coding exons (exons 1A and 1B) in the gene C9orf72 that is associated with one or both of the following pathological readouts: (1) sense and antisense repeat-containing RNA can be visualized as distinct foci in neurons and other cells; and (2) dipeptide repeat proteins-poly(glycine-alanine), poly(glycine-proline), poly(glycine-arginine), poly(alanine-proline), and poly(proline-arginine)—synthesized by repeat-associated non-AUG-dependent translation from the sense and antisense repeat-containing RNA can be detected in cells. The number of repeats can be a higher number of repeats than is normally seen in a locus from someone that does not have C9orf72 ALS or C9orf72 FTD. Alternatively, a pathogenic hexanucleotide repeat expansion can be an expansion (i.e., number of repeats) in a C9orf72 locus from a subject having C9orf72 ALS or C9orf72 FTD. A pathogenic hexanucleotide repeat expansion has a plurality of repeats of GGGGCC (SEQ ID NO: 1). For example, a pathogenic hexanucleotide repeat expansion can have, for example, at least about 30, at least about 35, at least about 40, at least about 50, at least about 60, at least about 70, at least about 80, at least about 100, at least about 200, at least about 300, at least about 400, or at least about 500 copies of the hexanucleotide repeat.

The cell can be a cell (e.g. a neuron or a motor neuron) from a subject having, or at risk for developing, a C9orf72-hexanucleotide-repeat-expansion associated disease including, for example, C9orf72 ALS or C9orf72 FTD.

The cells in the methods disclosed herein can be any type of cell comprising a C9orf72 locus. The C9orf72 locus can comprise a hexanucleotide repeat expansion sequence or a pathogenic hexanucleotide repeat expansion sequence as described elsewhere herein. The hexanucleotide repeat expansion sequence may comprise more than 100 repeats of the hexanucleotide sequence set forth as SEQ ID NO: 1.

A C9orf72 hexanucleotide repeat expansion sequence is generally a nucleotide sequence comprising at least two instances (i.e., two repeats) of the hexanucleotide sequence GGGGCC set forth as SEQ ID NO: 1. In some hexanucleotide repeat expansion sequences, the repeats are contiguous (adjacent to each other without intervening sequence). The repeat expansion sequence can be located, for example, between the first non-coding endogenous exon and exon 2 of the endogenous C9orf72 locus.

The hexanucleotide repeat expansion sequence can have any number of repeats. For example, the repeat expansion sequence can comprise more than about 95 repeats, more than about 96 repeats, more than about 97 repeats, more than about 98 repeats, more than about 99 repeats, more than about 100 repeats, more than about 101 repeats, more than about 102 repeats, more than about 103 repeats, more than about 104 repeats, more than about 105 repeats, more than about 150 repeats, more than about 200 repeats, more than about 250 repeats, more than about 295 repeats, more than about 296 repeats, more than about 297 repeats, more than about 298 repeats, more than about 299 repeats, more than about 300 repeats, more than about 301 repeats, more than about 302 repeats, more than about 303 repeats, more than about 304 repeats, more than about 305 repeats, more than about 350 repeats, more than about 400 repeats, more than about 450 repeats, more than about 500 repeats, more than about 550 repeats, more than about 595 repeats, more than about 596 repeats, more than about 597 repeats, more than about 598 repeats, more than about 599 repeats, more than about 600 repeats, more than about 601 repeats, more than about 602 repeats, more than about 603 repeats, more than about 604 repeats, or more than about 605 repeats. Alternatively, the repeat expansion sequence can comprise at least about 95 repeats, at least about 96 repeats, at least about 97 repeats, at least about 98 repeats, at least about 99 repeats, at least about 100 repeats, at least about 101 repeats, at least about 102 repeats, at least about 103 repeats, at least about 104 repeats, at least about 105 repeats, at least about 150 repeats, at least about 200 repeats, at least about 250 repeats, at least about 295 repeats, at least about 296 repeats, at least about 297 repeats, at least about 298 repeats, at least about 299 repeats, at least about 300 repeats, at least about 301 repeats, at least about 302 repeats, at least about 303 repeats, at least about 304 repeats, at least about 305 repeats, at least about 350 repeats, at least about 400 repeats, at least about 450 repeats, at least about 500 repeats, at least about 550 repeats, at least about 595 repeats, at least about 596 repeats, at least about 597 repeats, at least about 598 repeats, at least about 599 repeats, at least about 600 repeats, at least about 601 repeats, at least about 602 repeats, at least about 603 repeats, at least about 604 repeats, or at least about 605 repeats. In a specific example, the hexanucleotide repeat expansion sequence comprises more than about 100 repeats, more than about 300 repeats, more than about 600 repeats, at least about 100 repeats, at least about 300 repeats, or at least about 600 repeats.

In cells that are non-human cells, the repeat expansion sequence can be a heterologous repeat expansion sequence. Alternatively, the repeat expansion sequence can be an endogenous repeat expansion sequence. The term heterologous when used in the context of a nucleic acid indicates that the nucleic acid comprises at least two segments that do not naturally occur together in the same molecule. For example, the term heterologous, when used with reference to segments of a nucleic acid, indicates that the nucleic acid comprises two or more sub-sequences that are not found in the same relationship to each other (e.g., joined together) in nature. As one example, a heterologous region of a nucleic acid is a segment of nucleic acid within or attached to another nucleic acid molecule that is not found in association with the other molecule in nature. For example, a heterologous region of a nucleic acid could include a C9orf72 sequence flanked by repeat expansion sequence not found in association with the C9orf72 sequence in nature. Alternatively, a heterologous region of nucleic acid could include a human nucleic acid sequence flanked by endogenous non-human nucleic acid sequence.

In some examples, the modified endogenous non-human C9orf72 locus can also comprise additional orthologous C9orf72 sequence. As one example, the non-human C9orf72 locus can comprise a human C9orf72 nucleotide sequence. For example, the non-human animal C9orf72 locus can comprise a replacement of 5' untranslated and/or non-coding endogenous non-human sequences of the endogenous C9orf72 locus with the hexanucleotide repeat expansion sequence and flanking orthologous human C9orf72 sequence (i.e., heterologous (e.g., human) sequences that flank the repeats of the hexanucleotide sequence set forth as SEQ ID NO: 1). The heterologous repeat expansion sequence and/or the flanking sequence can be naturally occurring genomic sequence (e.g., naturally occurring human genomic sequence). As a specific example, the untranslated and/or non-coding sequence spanning between (and optionally encompassing at least a portion of) endogenous exon 1 (e.g., exon 1A and/or 1B) and the ATG start codon of the endogenous non-human C9orf72 locus, or a portion thereof, can be replaced with the heterologous hexanucleotide repeat expansion sequence, and optionally together with flanking orthologous human C9orf72 sequence. For example, the sequence inserted into an endogenous C9orf72 locus can comprise from 5' to 3': a first heterologous hexanucleotide flanking sequence, a plurality of repeats of the hexanucleotide set forth in SEQ ID NO: 1, and a second heterologous hexanucleotide flanking sequence.

In one embodiment, a heterologous human C9orf72 sequence spanning (and optionally encompassing) all or portions of exon 1A and/or exon 1B of a human C9orf72 gene is inserted into the endogenous C9orf72 locus. For example, the first heterologous hexanucleotide flanking sequence can comprise the sequence set forth as SEQ ID NO: 46, or a portion thereof, and/or the second heterologous hexanucleotide flanking sequence can comprise the sequence set forth as SEQ ID NO: 47, or a portion thereof. Accordingly, in some examples, the endogenous C9orf72 locus into which the heterologous hexanucleotide repeat expansion sequence is inserted can comprise a human sequence comprising the sequence set forth in SEQ ID NO: 46 and/or SEQ ID NO: 47.

In another embodiment example, the endogenous C9orf72 locus comprises the replacement of a part of a non-coding sequence of a mouse C9orf72 locus with a heterologous human hexanucleotide repeat expansion sequence placed in operable linkage with a mouse C9orf72 promoter and/or human regulatory elements (e.g., those that may be found in exons 1A and/or 1B of the human C9orf72 gene). See US 2018/0094267 and WO 2018/064600, each of which is herein incorporated by reference in its entirety for all purposes. For purposes of insertion into an endogenous non-human C9orf72 locus, a heterologous hexanucleotide repeat expansion sequence can comprise a plurality of (i.e., at least two instances (repeats) of) the hexanucleotide sequence set forth as SEQ ID NO: 1 and may be identical to, or substantially identical to a genomic nucleic acid sequence spanning (and optionally including) non coding exons 1A and 1B of a human chromosome 9 open reading frame 72 (C9orf72), or a portion thereof.

The cells can be in vitro, ex vivo, or in vivo. For example, the cells can be in vivo within an animal. The cells or animals can be male or female. The cells or animals can be heterozygous or homozygous for the hexanucleotide repeat expansion sequence inserted at the endogenous C9orf72 locus. A diploid organism has two alleles at each genetic locus. Each pair of alleles represents the genotype of a specific genetic locus. Genotypes are described as homozygous if there are two identical alleles at a particular locus and as heterozygous if the two alleles differ. The non-human animals can comprise the heterologous hexanucleotide repeat expansion sequence inserted at the endogenous C9orf72 locus in their germline genome.

C9orf72 expression (e.g., as assessed by sense mRNA, antisense mRNA, total C9orf72 mRNA, sense C9orf72 repeat-containing mRNA, antisense C9orf72 repeat-containing mRNA level, total C9orf72 protein, and/or C9orf72 repeat-containing protein) is inhibited in the cell by about 20, 25, 30, 35, 40, 45, or 50%. In preferred embodiments, C9orf72 expression is inhibited by no more than 50%, e.g., no more than 50%, 45%, 40%, 35%, 30%, 25%, 20%, 15%, 10%, or 5%.

The decrease in expression in the C9orf72 target RNA can be by any amount. Inhibition, as assessed by sense- or antisense-containing foci and/or aberrant dipeptide repeat protein level) is inhibited in the cell by at least 20%, 30%, 40%, preferably at least 50%, 60%, 70%, 80%, 85%, 90%, or 95%, or to below the level of detection of the assay.

In some embodiments, the dsRNA agent may inhibit expression of the C9orf72 target RNA, such as a C9orf72 target RNA comprising a hexanucleotide repeat, by at least about 10%, at least about 20%, at least about 30%, at least about 40%, at least about 50%, at least about 60%, at least about 70%, at least about 80%, or at least about 90% (or to a point where the C9orf72 target RNA is undetectable). For example, these levels of inhibition can be within about 1 day, within about 2 days, within about 3 days, within about 4 days, within about 5 days, within about 6 days, within about a week, or within about 24 to about 48 hours after administration to a cell expressing the C9orf72 target RNA comprising the hexanucleotide repeat. The decrease can be, for example, relative to the cell before treatment with dsRNA agent or relative to a control cell that was not treated with the dsRNA agent.

In some of the methods, the dsRNA agents of the invention selectively inhibit expression of the C9orf72 target RNA, such as a C9orf72 target RNA comprising a hexanucleotide repeat, relative to expression of a mature C9orf72 messenger RNA. A mature C9orf72 messenger RNA in this context is a C9orf72 RNA transcript that has been spliced and processed. A mature C9orf72 messenger RNA consists exclusively of exons and has all introns removed. A dsRNA agent selectively inhibits expression of the C9orf72 target RNA comprising the intronic hexanucleotide repeat relative to expression of a mature C9orf72 messenger RNA if the relative decrease in expression of the C9orf72 target RNA is greater than the relative decrease in expression of a mature C9orf72 messenger RNA after administration of the dsRNA agent to a cell expressing the C9orf72 target RNA. For example, in certain embodiments, dsRNA agents of the invention inhibit expression of the mature C9orf72 messenger RNA by less than about 50%, less than about 40%, less than about 30%, less than about 20%, less than about 10%, or less than about 5% (or, for example, does not have any statistically significant or functionally significant effect on expression). For example, these levels of inhibition can be within about 1 day, within about 2 days, within about 3 days, within about 4 days, within about 5 days, within about 6 days, within about a week, or within about 24 to about 48 hours after administration to a cell expressing the C9orf72 target RNA comprising the hexanucleotide repeat. The decrease can be, for example, relative to the cell before treatment with the dsRNA agent or relative to a control cell that was not treated with the dsRNA agent.

Some of the methods disclosed herein are for reducing dipeptide repeat protein synthesis or dipeptide repeat protein aggregates in a cell. Such methods can comprise introducing into the cell any of the dsTNA agents disclosed herein, thereby reducing dipeptide repeat protein synthesis or dipeptide repeat protein aggregates in the cell.

Such methods can further comprise assessing the presence of dipeptide repeat protein aggregates (e.g., poly(glycine-alanine), poly(glycine-proline), poly(glycine-arginine), poly (alanine-proline), and poly(proline-arginine)) in the cell. In a specific example, the dipeptide repeat protein can be poly(glycine-alanine) and/or poly(glycine-proline). The assessing can be done, for example, by immunohistochemistry or western blot analysis to detect the dipeptide repeat protein aggregates. However, any other suitable method may be used.

The decrease in dipeptide repeat protein synthesis or dipeptide repeat protein aggregates can be by any amount. For example, the dsRNAagent can reduce dipeptide repeat protein synthesis or dipeptide repeat protein aggregates by at least about 10%, at least about 20%, at least about 30%, at least about 40%, at least about 50%, at least about 60%, at least about 70%, at least about 80%, or at least about 90% (or to a point where the dipeptide repeat protein aggregates are undetectable). For example, these levels of inhibition can be within about 1 day, within about 2 days, within about 3 days, within about 4 days, within about 5 days, within about 6 days, within about a week, or within about 24 to about 48 hours after administration to a cell expressing the C9orf72 target RNA comprising the hexanucleotide repeat. The decrease can be, for example, relative to the cell before treatment with dsRNA agent or relative to a control cell that was not treated with the dsRNAagent.

Such methods can further comprise assessing the presence of nuclear and/or cytoplasmic sense and/or antisense C9orf72 RNA foci in the cell.

The decrease in the presence of nuclear and/or cytoplasmic sense and/or antisense C9orf72 RNA foci can be by any amount. For example, the dsRNA agent can reduce the presence of nuclear and/or cytoplasmic sense and/or antisense C9orf72 RNA foci by at least about 10%, at least about 20%, at least about 30%, at least about 40%, at least about 50%, at least about 60%, at least about 70%, at least about 80%, or at least about 90% (or to a point where the nuclear and/or cytoplasmic sense and/or antisense C9orf72 RNA foci are undetectable). For example, these levels of inhibition can be within about 1 day, within about 2 days, within about 3 days, within about 4 days, within about 5 days, within about 6 days, within about a week, or within about 24 to about 48 hours after administration to a cell expressing the C9orf72 target RNA comprising the hexanucleotide repeat. The decrease can be, for example, relative to the cell before treatment with dsRNA agent or relative to a control cell that was not treated with the dsRNAagent.

The in vivo methods of the disclosure may include administering to a subject a composition containing an RNAi agent, where the RNAi agent includes a nucleotide sequence that is complementary to at least a part of an RNA transcript of the C9orf72 gene of the mammal to be treated. When the organism to be treated is a mammal such as a human, the composition can be administered by any means known in the art including, but not limited to oral, intraperitoneal, or parenteral routes, including intracranial (e.g., intraventricular, intraparenchymal, and intrathecal), intravenous, intramuscular, intravitreal, subcutaneous, transdermal, airway (aerosol), nasal, rectal, and topical (including buccal and sublingual) administration. In certain embodiments, the compositions are administered by intravenous infusion or injection. In certain embodiments, the compositions are administered by subcutaneous injection. In certain embodiments, the compositions are administered by intrathecal injection.

In some embodiments, the administration is via a depot injection. A depot injection may release the RNAi agent in a consistent way over a prolonged time period. Thus, a depot injection may reduce the frequency of dosing needed to obtain a desired effect, e.g., a desired inhibition of C9orf72, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intracranial, intravenous, subcutaneous, arterial, or epidural infusions. In preferred embodiments, the infusion pump is a subcutaneous infusion pump. In other embodiments, the pump is a surgically implanted pump that delivers the RNAi agent to the CNS.

The mode of administration may be chosen based upon whether local or systemic treatment is desired and based upon the area to be treated. The route and site of administration may be chosen to enhance targeting.

In one aspect, the present disclosure also provides methods for inhibiting the expression of a C9orf72 gene in a mammal The methods include administering to the mammal a composition comprising a dsRNA that targets a C9orf72 gene in a cell of the mammal, thereby inhibiting expression of the C9orf72 gene in the cell. Reduction in gene expression can be assessed by any methods known it the art and by methods, e.g. qRT-PCR, described herein. Reduction in protein production can be assessed by any methods known it the art and by methods, e.g. ELISA, described herein. In one embodiment, a CNS biopsy sample or a cerebrospinal fluid (CSF) sample serves as the tissue material for monitoring the reduction in C9orf72 gene or protein expression (or of a proxy therefore).

The present disclosure further provides methods of treatment of a subject in need thereof. The treatment methods of the disclosure include administering an RNAi agent of the disclosure to a subject, e.g., a subject that would benefit from inhibition of C9orf72 expression, such as a subject having a GGGGCC (SEQ ID NO: 1) expanded nucleotide repeat in an intron of the C9orf72 gene, in a therapeutically effective amount of an RNAi agent targeting a C9orf72 gene or a pharmaceutical composition comprising an RNAi agent targeting aC9orf72 gene.

In addition, the present disclosure provides methods of preventing, treating or inhibiting the progression of a C9orf72-associated disease or disorder (e.g., a C9orf72-associated disorder), in a subject. The methods include administering to the subject a therapeutically effective amount of any of the RNAi agent, e.g., dsRNA agents, or the pharmaceutical composition provided herein, thereby preventing, treating or inhibiting the progression of a C9orf72-associated disease or disorder in the subject.

In some embodiment, the methods are for treating a subject suffering from a C9orf72-hexanucleotide-repeat-expansion-associated disease, condition, or disorder. Such methods can also be for preventing or ameliorating at least one symptom in a subject having a disease, disorder, or condition that would benefit from reduction in expression of a C9orf72 target RNA comprising a hexanucleotide repeat comprising multiple contiguous copies of SEQ ID NO: 1 (e.g., a subject having or at risk of developing a C9orf72-hexanucleotide-repeat-expansion-associated disease, condition, or disorder). The C9orf72 target RNA can be, for example, one with a pathogenic hexanucleotide repeat expansion (having, for example, at least about 30, at least about 35, at least about 40, at least about 50, at least about 60, at least about 70, at least about 80, at least about 100, at least about 200, at least about 300, at least about 400, or at least about 500 copies of the hexanucleotide repeat). A C9orf72-hexanucleotide-repeat-expansion-associated disease, condition, or disorder is one in which caused by or associated with an expansion of a hexanucleotide repeat (GGGGCC; SEQ ID NO: 1) in the 5' non-coding part of the C9orf72 gene. Examples include amyotrophic lateral sclerosis (ALS) and frontotemporal dementia (FTD). Signs or symptoms associated with FTD and/or ALS, include, but are not limited to, repeat-length-dependent formation of RNA foci, sequestration of specific RNA-binding proteins, and accumulation and aggregation of dipeptide repeat proteins (e.g., poly(glycine-alanine), poly(glycine-proline), poly (glycine-arginine), poly(alanine-proline), and poly(proline-arginine)) resulting from repeat-associated non-AUG (AUG) translation in neurons. The dsRNA agents of the invention may be used in methods for therapeutic treatment and/or prevention of signs or symptoms associated with FTD and/or ALS, including, but not limited to, signs and symptoms of motor neuron disease and signs and symptoms of dementia. Signs and symptoms of motor neuron disease can include, for example, tripping, dropping things, abnormal fatigue of the arms and/or legs, slurred speech, muscle cramps and twitches, uncontrollable periods of laughing or crying, and trouble breathing. Signs and symptoms of dementia can include, for example, behavioral changes, personality changes, speech and language problems, and movement-related problems.

An RNAi agent of the disclosure may be administered as a "free RNAi agent." A free RNAi agent is administered in the absence of a pharmaceutical composition. The naked RNAi agent may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the RNAi agent can be adjusted such that it is suitable for administering to a subject.

Alternatively, an RNAi agent of the disclosure may be administered as a pharmaceutical composition, such as a dsRNA liposomal formulation.

Subjects that would benefit from a reduction or inhibition of C9orf72 gene expression are those having a C9orf72-associated disease, e.g., C9orf72-associated disease. Exemplary C9orf72-associated diseases include, but are not limited to, ALS, FTD, C9ALS/FTD and Huntington-Like Syndrome Due To C9orf72 Expansions, e.g., subjects having an expanded GGGGCC hexanucleotide repeat (SEQ ID NO: 1) in an intron of the C9orf72 gene.

The disclosure further provides methods for the use of an RNAi agent or a pharmaceutical composition thereof, e.g., for treating a subject that would benefit from reduction or inhibition of C9orf72 expression, e.g., a subject having a C9orf72-associated disorder, in combination with other pharmaceuticals or other therapeutic methods, e.g., with known pharmaceuticals or known therapeutic methods, such as, for example, those which are currently employed for treating these disorders. For example, in certain embodiments, an RNAi agent targeting C9orf72 is administered in combination with, e.g., an agent useful in treating a C9orf72-associated disorder as described elsewhere herein or as otherwise known in the art. For example, additional agents suitable for treating a subject that would benefit from reducton in C9orf72 expression, e.g., a subject having a C9orf72-associated disorder, may include agents currently used to treat symptoms of C9orf72-associated diseases. The RNAi agent and additional therapeutic agents may be administered at the same time or in the same combination, e.g., intrathecally, or the additional therapeutic agent can be administered as part of a separate composition or at separate times or by another method known in the art or described herein.

Exemplary additional therapeutics include, for example, a monoamine inhibitor, e.g., tetrabenazine (Xenazine), deutetrabenazine (Austedo), and reserpine, an anticonvulsant, e.g., valproic acid (Depakote, Depakene, Depacon), and clonazepam (Klonopin), an antipsychotic agent, e.g., risperidone (Risperdal), and haloperidol (Haldol), and an antidepressant, e.g., paroxetine (Paxil).

In one embodiment, the method includes administering a composition featured herein such that expression of the target C9orf72 gene is decreased, for at least one month. In preferred embodiments, expression is decreased for at least 2 months, 3 months, or 6 months.

Preferably, the RNAi agents useful for the methods and compositions featured herein specifically target RNAs (primary or processed) of the target C9orf72 gene. Compositions and methods for inhibiting the expression of these genes using RNAi agents can be prepared and performed as described herein.

Administration of the dsRNA according to the methods of the disclosure may result in a reduction of the severity, signs, symptoms, or markers of such diseases or disorders in a patient with a C9orf72-associated disorder. By "reduction" in this context is meant a statistically significant or clinically significant decrease in such level. The reduction can be, for example, at least 5%, 10%, 15%, 20%, 25%, 30%, 35%, 40%, 45%, 50%, 55%, 60%, 65%, 70%, 75%, 80%, 85%, 90%, 95%, or about 100%.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of a C9orf72-associated disorder may be assessed, for example, by periodic monitoring of a subject's. Comparisons of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of an RNAi agent targeting C9orf72 or pharmaceutical composition thereof, "effective against" a C9orf72-associated disorder indicates that administration in a clinically appropriate manner results in a beneficial effect for at least a statistically significant fraction of patients, such as an improvement of symptoms, a cure, a reduction in disease, extension of life, improvement in quality of life, or other effect generally recognized as positive by medical doctors familiar with treating C9orf72-associated disorders and the related causes.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given RNAi agent drug or formulation of that drug can also be judged using an experimental animal model for the given disease as known in the art. When using an experimental animal model, efficacy of treatment is evidenced when a statistically significant reduction in a marker or symptom is observed.

Alternatively, the efficacy can be measured by a reduction in the severity of disease as determined by one skilled in the art of diagnosis based on a clinically accepted disease severity grading scale. Any positive change resulting in e.g., lessening of severity of disease measured using the appropriate scale, represents adequate treatment using an RNAi agent or RNAi agent formulation as described herein.

Subjects can be administered a therapeutic amount of dsRNA, such as about 0.01 mg/kg to about 200 mg/kg.

The RNAi agent can be administered intrathecally, via intravitreal injection, or by intravenous infusion over a period of time, on a regular basis. In certain embodiments, after an initial treatment regimen, the treatments can be administered on a less frequent basis. Administration of the RNAi agent can reduce C9orf72 levels, e.g., in a cell, tissue, blood, CSF sample or other compartment of the patient. In one embodiment, administration of the RNAi agent can reduce C9orf72 levels, e.g., in a cell, tissue, blood, CSF sample or other compartment of the patient by no more than 50%.

Before administration of a full dose of the RNAi agent, patients can be administered a smaller dose, such as a 5% infusion reaction, and monitored for adverse effects, such as an allergic reaction. In another example, the patient can be monitored for unwanted immunostimulatory effects, such as increased cytokine (e.g., TNF-alpha or INF-alpha) levels.

Alternatively, the RNAi agent can be administered subcutaneously, i.e., by subcutaneous injection. One or more injections may be used to deliver the desired, e.g., monthly dose of RNAi agent to a subject. The injections may be repeated over a period of time. The administration may be repeated on a regular basis. In certain embodiments, after an initial treatment regimen, the treatments can be administered on a less frequent basis. A repeat-dose regimine may include administration of a therapeutic amount of RNAi agent on a regular basis, such as monthly or extending to once a quarter, twice per year, once per year. In certain embodiments, the RNAi agent is administered about once per month to about once per quarter (i.e., about once every three months).

Unless otherwise defined, all technical and scientific terms used herein have the same meaning as commonly understood by one of ordinary skill in the art to which this invention belongs. Although methods and materials similar or equivalent to those described herein can be used in the practice or testing of the RNAi agents and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

A Sequence Listing is filed herewith and forms part of the specification as filed.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. If one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus. Table 3 below, provides a brief description of certain of the sequences disclosed herein.

TABLE 3

Description of Certain Sequences.

Figure 2:
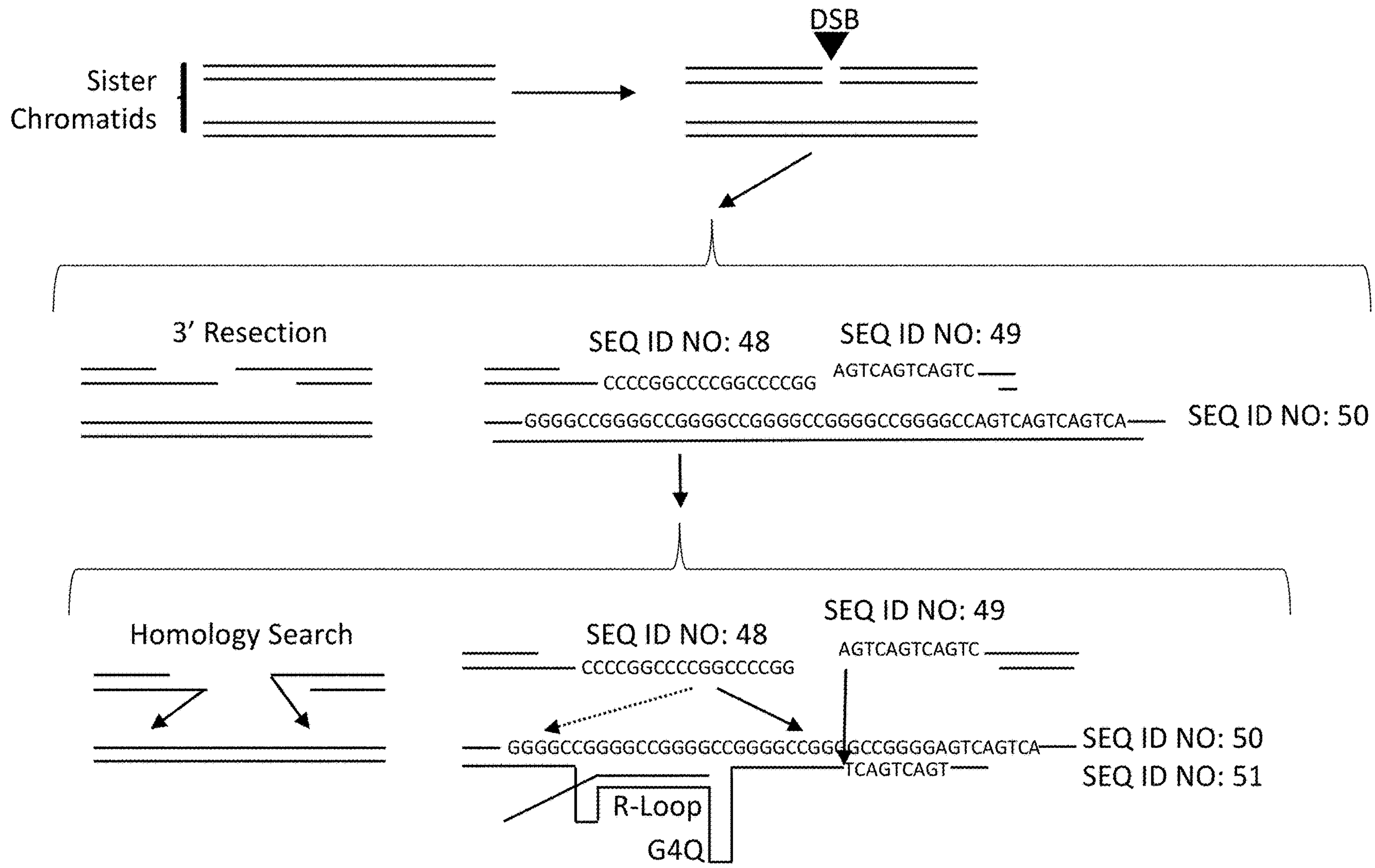
FIG. 2 (not to scale) is a schematic of the concept of using nuclease agents to introduce a double-strand break near a repeat sequence in order to use the recombination machinery to expand the repeat sequence at a target genomic locus (such as the hexanucleotide sequence set forth in SEQ ID NO: 1 at the C9orf72 locus).
Figure 3:
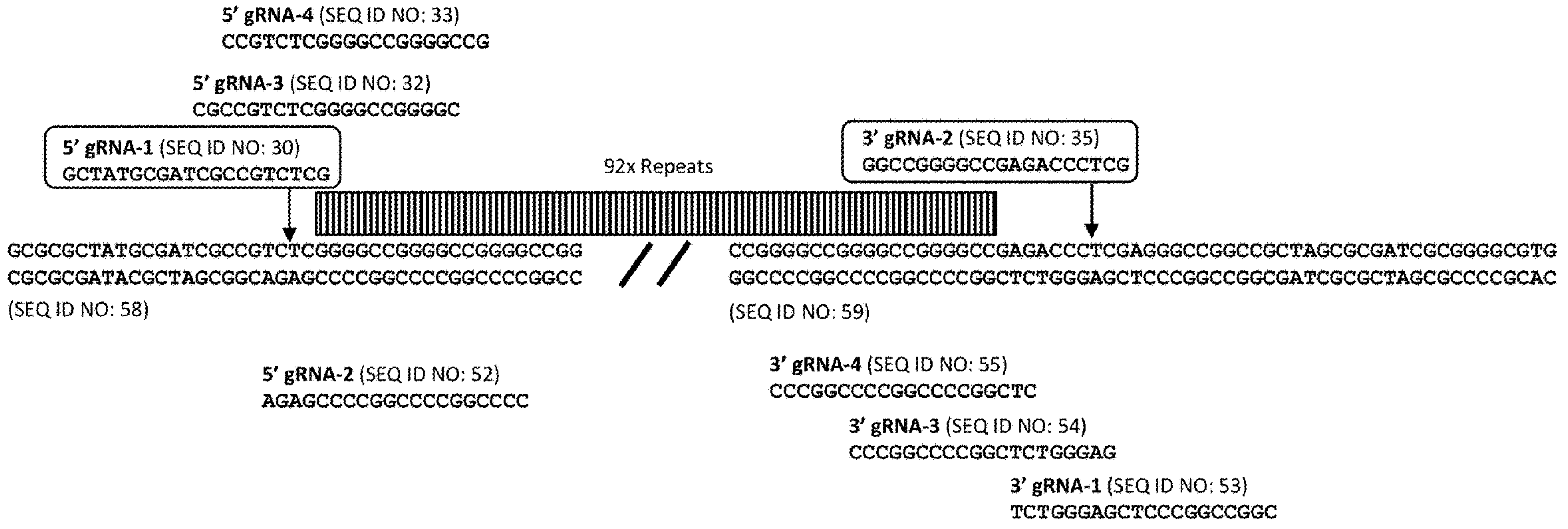
FIG. 3 (not to scale) is a schematic with the locations of eight guide RNA target sequences located near the ends of the hexanucleotide repeat expansion sequence in C9orf72 humanized, 92×-repeat-containing ES cells (MAID8029a).
Figure 6A:
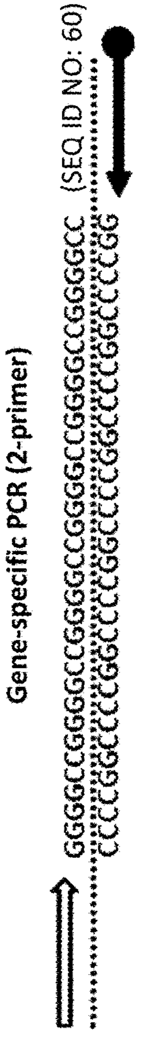
FIG. 6A (not to scale) is a schematic of the conventional two-primer PCR used to assess the number of instances of the hexanucleotide sequence set forth in SEQ ID NO: 1 in the endogenous C9orf72 ES cell clones.
Figure 6B:
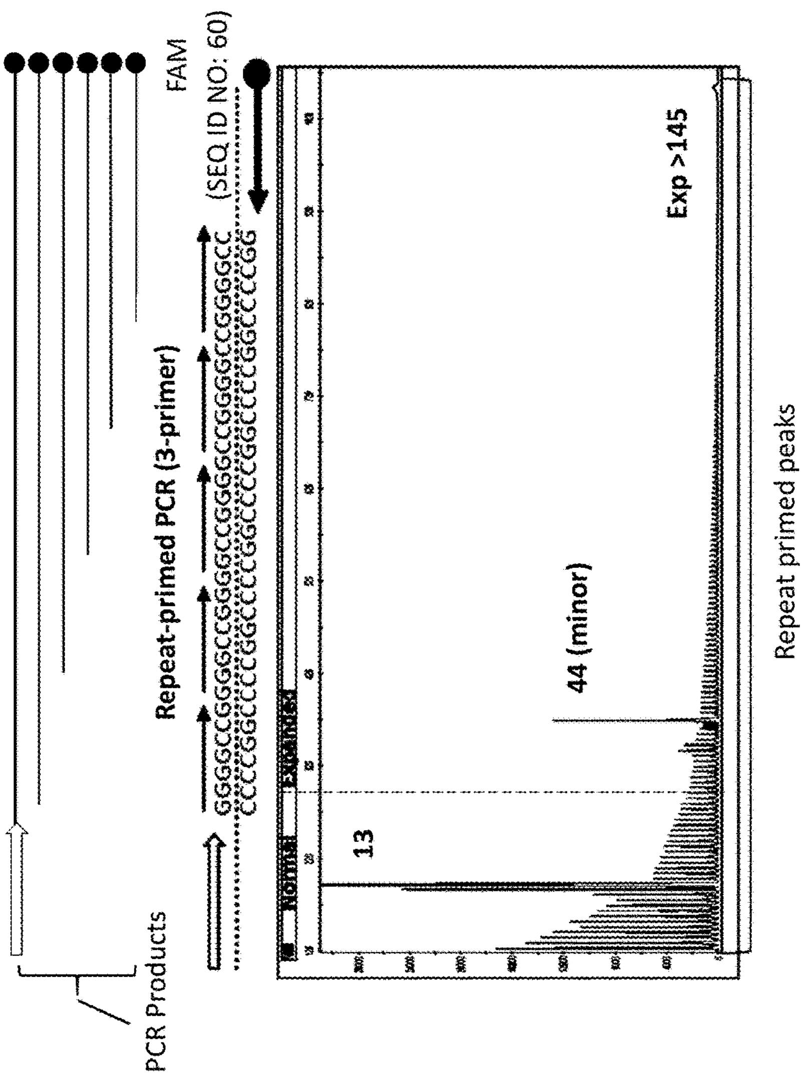
FIG. 6B (not to scale) is a schematic of the prime PCR that uses three primers to assess the number of instances of the hexanucleotide sequence set forth in SEQ ID NO: 1 in the endogenous C9orf72 ES cell clones.

| SEQ ID NO | Type | Description |
|---|---|---|
| 1 | DNA | GGGGCC C9orf72 Hexanucleotide Repeat |
| 2-25 | RNA | C9orf72 siRNA Sense and Antisense Strands |
| 26 | DNA | *Homo sapiens* C9orf72 mRNA (NM_018325.4) |
| 27 | Protein | *Homo sapiens* C9orf72 Amino Acid (NP_060795.1) |
| 28 | DNA | *Homo sapiens* C9orf72 mRNA (NM_001256054.2) |
| 29 | Protein | *Homo sapiens* C9orf72 Amino Acid (NP_001242983.1) |
| 30 | DNA | 5' gRNA-1 Target Sequence |
| 31 | DNA | 5' gRNA-2 Target Sequence |
| 32 | DNA | 5' gRNA-3 Target Sequence |
| 33 | DNA | 5' gRNA-4 Target Sequence |
| 34 | DNA | 3' gRNA-1 Target Sequence |
| 35 | DNA | 3' gRNA-2 Target Sequence |
| 36 | DNA | 3' gRNA-3 Target Sequence |
| 37 | DNA | 3' gRNA-4 Target Sequence |
| 38 | DNA | Locked Nucleic Acid (LNA) Sense RNA Probe |
| 39 | DNA | Locked Nucleic Acid (LNA) Antisense RNA Probe |
| 40 | DNA | *Mus musculus* C9orf72 mRNA (NM_001081343.1) |
| 41 | Protein | *Mus musculus* C9orf72 Amino Acid (NP_001074812.1) |
| 42 | DNA | *Rattus norvegicus* C9orf72 mRNA (NM_001007702.1) |
| 43 | Protein | *Rattus norvegicus* C9orf72 Amino Acid (NP_001007703.1) |
| 44 | DNA | DNA Sense Probe |
| 45 | DNA | DNA Antisense Probe |
| 46 | DNA | Human 5' Flanking Sequence |
| 47 | DNA | Human 3' Flanking Sequence |
| 48 | DNA | Sequence 1 from FIG. 2 |
| 49 | DNA | Sequence 2 from FIG. 2 |
| 50 | DNA | Sequence 3 from FIG. 2 |
| 51 | DNA | Sequence 4 from FIG. 2 |
| 52 | DNA | gRNA_5side_repeat_2 from FIG. 3 |
| 53 | DNA | gRNA_3side_repeat_1 from FIG. 3 |
| 54 | DNA | gRNA_3side_repeat_3 from FIG. 3 |
| 55 | DNA | gRNA_3side_repeat_4 from FIG. 3 |
| 56 | RNA | 5' gRNA-1 crRNA |
| 57 | RNA | 5' gRNA-2 crRNA |
| 58 | DNA | 5' Target Locus from FIG. 3 |
| 59 | DNA | 3' Target Locus from FIG. 3 |
| 60 | DNA | Sequence from FIGS. 6A and 6B |
| 61 | DNA | Analysis A - Forward Primer |

TABLE 3-continued

| Description of Certain Sequences. | | |
|---|---|---|
| SEQ ID NO | Type | Description |
| 62 | DNA | Analysis A - Reverse Primer |
| 63 | DNA | Analysis A - Probe |
| 64 | DNA | Analysis B - Forward Primer |
| 65 | DNA | Analysis B - Reverse Primer |
| 66 | DNA | Analysis B - Probe |
| 67 | DNA | Analysis D - Forward Primer |
| 68 | DNA | Analysis D - Reverse Primer |
| 69 | DNA | Analysis D - Probe |
| 70 | DNA | Analysis G - Forward Primer |
| 71 | DNA | Analysis G - Reverse Primer |
| 72 | DNA | Analysis G - Probe |
| 73 | DNA | Analysis H - Forward Primer |
| 74 | DNA | Analysis H - Reverse Primer |
| 75 | DNA | Analysis H - Probe |
| 76 | RNA | 5' gRNA-3 crRNA |
| 77 | RNA | 5' gRNA-4 crRNA |
| 78 | RNA | 3' gRNA-1 crRNA |
| 79 | RNA | 3' gRNA-2 crRNA |
| 80 | RNA | 3' gRNA-3 crRNA |
| 81 | RNA | 3' gRNA-4 crRNA |
| 82 | RNA | TracrRNA v2 |
| 83 | RNA | GGGGU G-Rich RNA Repeat |
| 84 | RNA | 5'-gRNA-1 Guide Sequence |
| 85 | RNA | 5'-gRNA-2 Guide Sequence |
| 86 | RNA | 5'-gRNA-3 Guide Sequence |
| 87 | RNA | 5'-gRNA-4 Guide Sequence |
| 88 | RNA | 3'-gRNA-1 Guide Sequence |
| 89 | RNA | 3'-gRNA-2 Guide Sequence |
| 90 | RNA | 3'-gRNA-3 Guide Sequence |
| 91 | RNA | 3'-gRNA-4 Guide Sequence |
| 92 | DNA | 2-Primer Fwd |
| 93 | DNA | 2-Primer Rev |
| 94 | DNA | *Homo sapiens* C9orf72 mRNA (NM_145005.6) |
| 95 | DNA | Analysis C - Forward Primer |
| 96 | DNA | Analysis C - Reverse Primer |
| 97 | DNA | Analysis C - Probe |
| 98 | DNA | Analysis E - Forward Primer |

TABLE 3-continued

Description of Certain Sequences.

| SEQ ID NO | Type | Description |
|---|---|---|
| 99 | DNA | Analysis E - Reverse Primer |
| 100 | DNA | Analysis E - Probe |
| 101 | DNA | Analysis F - Forward Primer |
| 102 | DNA | Analysis F - Reverse Primer |
| 103 | DNA | Analysis F - Probe |
| 104 | DNA | Analysis I - Forward Primer |
| 105 | DNA | Analysis I - Reverse Primer |
| 106 | DNA | Analysis I - Probe |
| 107 | DNA | Analysis J - Forward Primer |
| 108 | DNA | Analysis J - Reverse Primer |
| 109 | DNA | Analysis J - Probe |
| 110 | Protein | *Homo sapiens* C9orf72 Amino Acid (NP_659442.2) |
| 111 | RNA | Start of Exon1A to Start of Exon2 |
| 112 | RNA | Reverse Complement - Start of Exon1A to Start of Exon2 (RNA) |
| 113 | RNA | Intron Sequence Between Exon1A to Exon 1B Including 3 Full GGGGCC Repeats (RNA) |
| 114 | RNA | Reverse Complement - Intron Sequence Between Exon1A to Exon 1B Including 3 Full GGGGCC Repeats (RNA) |
| 115 | RNA | Intron Sequence Between Exon 1A and First Hexanucleotide Repeat (RNA) |
| 116 | RNA | Reverse Complement - Intron Sequence Between Exon 1A and First Hexanucleotide Repeat (RNA) |
| 117 | RNA | Fragment Between Exon 1A and Repeat (RNA) |
| 118 | RNA | Reverse Complement - Fragment Between Exon 1A and Repeat (RNA) |

EXAMPLES

Example 1. Hexanucleotide Repeat Expansion at the C9orf72 Gene Locus

I. Overview

Amyotrophic lateral sclerosis (ALS) and frontotemporal dementia (FTD) are devastating neurodegenerative diseases that cause motor neuron disease in the case of ALS and dementia in the case of FTD. Both are invariably fatal. ALS and FTD can present as either a spontaneous or familial (i.e., genetic) disease. The most common genetic cause of ALS and FTD is an expansion of a hexanucleotide repeat (GGGGCC; SEQ ID NO: 1) in the 5' non-coding part of the C9orf72 gene, which encodes a protein whose function is not fully understood. Unaffected people usually have between a few and a few dozen hexanucleotide repeats in their C9orf72 genes, while those that develop ALS and FTD inherit a repeat expansion of hundreds to thousands of copies of the hexanucleotide repeat from only one of their parents. Genetic observations suggest that C9orf72 ALS and FTD are dominant genetic diseases and result from a gain of pathological function.

It is not known how the C9orf72 hexanucleotide repeat expansion causes motor neuron disease and dementia, but two universal postmortem pathological findings in C9orf72 ALS and FTLD patients are associated with the repeat expansion: (1) sense and antisense repeat-containing RNA can be visualized as distinct foci in neurons and other cells by fluorescent in situ hybridization; and (2) dipeptide repeat proteins—poly(glycine-alanine), poly(glycine-proline), poly(glycine-arginine), poly(alanine-proline), and poly(proline-arginine)—synthesized by repeat-associated non-AUG-dependent translation from the sense and antisense repeat-containing RNAs—can be detected in cells by immunohistochemistry. One disease hypothesis proposes that the repeat-containing RNAs, visualized as foci, disrupt cellular RNA metabolism by sequestering RNA binding proteins. A second disease hypothesis posits that the dipeptide repeat proteins exert wide-spread toxic effects on RNA metabolism, proteostasis, and nucleocytoplasmic transport. Both pathogenic mechanisms could contribute to disease. If C9orf72 repeat-containing RNA transcripts, either on their own or as templates for translation of dipeptide repeat proteins, promote pathogenesis in ALS and FTLD, then a general therapeutic strategy would be to destroy GGGGCC repeat-containing RNA ("GGGGCC" disclosed as SEQ ID NO: 1) or abolish its ability to be translated into dipeptide repeat protein.

The C9orf72 gene produces transcripts from two transcription initiation sites. The upstream site initiates transcription with alternative non-coding exon 1A, while the downstream site initiates transcription with alternative exon 1B. Both exons 1A and 1B can be spliced to exon 2, which contains the start of the protein-coding sequence. The pathogenic hexanucleotide repeat expansion is located between exons 1A and 1B. Therefore, transcription initiated from exon 1A can produce repeat-containing RNAs, while initiation from exon 1B cannot.

To model C9orf72 repeat expansion disease in mice, as described below, an allelic series was constructed in mouse embryonic stem (ES) cells in which a fragment from the human C9orf72 gene, including part of exon 1A, the intron sequence between 1A and 1B, all of exon 1B and part of the downstream intron, was placed precisely at its homologous position in one allele of the mouse C9orf72 gene. See, e.g., US 2018/0094267 and WO 2018/064600, each of which is herein incorporated by reference in its entirety for all purposes. A series of hexanucleotide repeat expansions were placed at the position found in the human gene that ranged from the normal three repeats up to the pathological 600 repeats.

Mouse ES cell clones carrying the different repeat expansions were differentiated into motor neurons in culture to study the effects of the expansions on a cell type relevant to ALS. In examining the transcripts produced from the genetically modified humanized C9orf72 alleles it was found that there was a switch from exon 1B spliced transcripts, which predominate in the three repeat normal control, to increased appearance of exon 1A spliced transcripts in the alleles with longer repeat expansions. It was also observed the accumulation of unspliced intron-containing transcripts whose abundance was directly correlated with the length of the hexanucleotide repeat expansion, suggesting a selfish feed-forward loop in which the longer the repeat expansion, the more repeat-containing transcripts are produced from the C9orf72 gene. Targeting the repeat-containing intronic transcripts for destruction or inactivation as templates for dipeptide repeat protein synthesis while sparing synthesis of the normal C9orf72 mRNA and protein would be expected to be a safe and effective therapeutic strategy for C9orf72 repeat expansion disease.

One possible approach to reducing C9orf72 repeat-containing RNAs is through the natural process of RNA interference, in which siRNAs direct cleavage of the target RNAs by the RNA-induced silencing complex followed by degradation of the RNA cleavage fragments by cellular nucleases. RNA interference is, however, a predominantly cytoplasmic process that would not be expected to act on RNAs retained in the nucleus. Intron-containing RNAs are usually short-lived, either as mRNA precursors, which are rapidly spliced into mature mRNAs, or as spliced-out introns, which are rapidly degraded in the nucleus. It is reasonable, therefore, to expect that intron-containing RNAs would not be available for targeting by RNA interference.

However, it has been demonstrated that siRNAs that targeted intron sequences adjacent to the GGGGCC repeat (SEQ ID NO: 1) expansion promoted reduced accumulation of intron-containing C9orf72 RNAs while having little to no effect on the C9orf72 mature mRNA. The intron-targeting siRNAs also reduced production of dipeptide repeat proteins. These unexpected experimental results indicate that the intron-containing RNAs that accumulate in cells with a C9orf72 hexanucleotide repeat expansion are susceptible to RNA interference. The results show that a significant fraction of the intron-containing C9orf72 RNAs responsible for dipeptide repeat protein synthesis resides in the cytoplasm. In contrast, siRNAs that targeted the C9orf72 mRNA protein coding sequence produced a strong knock down of the mRNA but had no effect on the intron-containing transcripts and did not appreciably reduce dipeptide repeat protein synthesis. The divergence in results between the intron-targeting and mRNA-targeting siRNAs suggests that the two classes of targeted sequences are present on separate RNAs that are not covalently linked.

The methods and compositions disclosed herein provide for the therapeutic reduction in the synthesis of dipeptide repeat proteins, a principle pathogenic component of C9orf72 repeat expansion disease, while sparing the C9orf72 mRNA, thereby avoiding possible adverse effects of reduction of C9orf72 protein, as could occur with therapeutic strategies, such as the use of antisense oligonucleotides, that target the primary C9orf72 transcript in the nucleus.

II. C9orf72, Hexanucleotide Repeat Expansion Sequences, and Associated Diseases

Amyotrophic lateral sclerosis (ALS), also referred to as Lou Gehrig's disease, is the most frequent adult-onset paralytic disorder, characterized by the loss of upper and/or lower motor neurons. ALS occurs in as many as 20,000 individuals across the United States with about 5,000 new cases occurring each year. Frontotemporal dementia (FTD; also referred to as Pick's disease, frontotemporal lobar degeneration, or FTLD) is a group of disorders caused by progressive cell degeneration in the frontal or temporal lobes of the brain. FTD is reported to account for 10%-15% of all dementia cases. A hexanucleotide repeat expansion sequence between (and optionally spanning) exons 1A and 1B, two non-coding exons, of the human C9orf72 gene have been linked to both ALS and FTD. It is estimated that the GGGGCC (SEQ ID NO: 1) hexanucleotide repeat expansion accounts for about 50% of familial and many non-familial ALS cases. Because C9orf72 repeat expansions are dominant mutations that occur essentially always as heterozygous mutations. It is present in about 25% of familial FTD cases and about 8% of sporadic FTD cases.

Many pathological aspects related to the hexanucleotide repeat expansion sequence in C9orf72 have been reported such as, for example, repeat-length-dependent formation of RNA foci, sequestration of specific RNA-binding proteins, and accumulation and aggregation of dipeptide repeat proteins (e.g., poly(glycine-alanine), poly(glycine-proline), poly(glycine-arginine), poly(alanine-proline), and poly(proline-arginine)) resulting from repeat-associated non-AUG (AUG) translation in their neurons.

Although C9orf72 has been reported to regulate endosomal trafficking, much of the cellular function of C9orf72 remains unknown. Indeed, C9orf72 is a gene that encodes an uncharacterized protein with unknown function.

Mouse C9orf72 transcript variants have been reported. See, e.g., Koppers et al. (2015) *Ann. Neurol.* 78:426-438 and Atkinson et al. (2015) *Acta Neuropathologica Communications* 3:59, each of which is herein incorporated by reference in its entirety for all purposes. The genomic information for the three reported mouse C9orf72 transcript variants is also available at the Ensembl web site under designations of ENSMUST00000108127 (V1), ENSMUST00000108126 (V2), and ENSMUST00000084724 (V3). Exemplary non-human (e.g., rodent) C9orf72 mRNA and amino acid sequences are set forth in SEQ ID NOS: 40-43, 123, and 124. The mRNA and amino acid sequences of mouse C9orf72 can be found at GenBank accession numbers NM_001081343 and NP_001074812, respectively, and are hereby incorporated by reference in their entirety for all purposes. The sequences of NM_001081343.1 and NP_001074812.1 are set forth in SEQ ID NOS: 40 (and SEQ ID NO:123) and 41, respectively. The mRNA and amino acid sequences of rat C9orf72 can be found at GenBank accession numbers NM_001007702 and NP_001007703, respectively, and are hereby incorporated by reference in their entirety for all purposes. The sequences of NM_001007702.1 and NP_001007703.1 are set forth in SEQ ID NOS: 42 (and SEQ ID NO:124) and 43, respectively.

Human C9orf72 transcript variants are also known. One human C9orf72 transcript variant lacks multiple exons in the central and 3' coding regions, and its 3' terminal exon extends beyond a splice site that is used in variant 3 (see below), which results in a novel 3' untranslated region (UTR) as compared to variant 3. This variant encodes a significantly shorter polypeptide and its C-terminal amino acid is distinct as compared to that which is encoded by two other variants. The mRNA and amino acid sequences of this variant can be found at GenBank accession numbers NM_145005.6 and NP_659442.2, respectively, and are hereby incorporated by reference in their entirety for all purposes. The sequences of NM_145005.6 and NP_659442.2 are set forth in SEQ ID NO: 94 and SEQ ID NO: 110, respectively. A second human C9orf72 transcript variant (2) differs in the 5' untranslated region (UTR) compared to variant 3. The mRNA and amino acid sequences of this variant can be found at GenBank accession numbers NM_018325.4 and NP_060795.1, respectively, and are hereby incorporated by reference in their entirety for all purposes. The sequences of NM_018325.4 and NP_060795.1 are set forth in SEQ ID NO: 26 and SEQ ID NO: 27, respectively. A third human C9orf72 transcript variant (3) contains the longest sequence among three reported variants and encodes the longer isoform. The mRNA and amino acid sequences of this variant can be found at GenBank accession numbers NM_001256054.2 and NP_001242983.1, respectively, and are hereby incorporated by reference in their entirety for all purposes. The sequences of NM_001256054.2 and NP_001242983.1 are set forth in SEQ ID NO: 28 (and SEQ ID NO:121) and SEQ ID NO: 29, respectively. Variants 2 and 3 encode the same protein.

III. Generation of ES Cell Clones Comprising a Hexanucleotide Repeat Expansion at the C9orf72 Gene Locus As discussed above, amyotrophic lateral sclerosis (ALS) is a progressive neurodegenerative disorder that causes motor neuron death, leading to paralysis. Five thousand people in the US are diagnosed with ALS each year. Ten percent of the disease is transmitted in families, and among this category the most common cause is GGGGCC (SEQ ID NO: 1) hexanucleotide repeat expansion at the C9orf72 gene locus. Healthy individuals typically have less than 30 repeats, and affected patients often have more than 1000 copies of the repeat. The precise mechanism of how this long stretch of repeat causes disease has not yet been elucidated because of the lack of useful animal models. The high GC content in hexanucleotide repeat sequence makes it difficult to synthesize DNA fragments with the repeat as well as maintain the repeat in microorganisms. Therefore, preparing materials such as targeting vectors to generate transgenic animals is very challenging. This is one of the major reasons why few useful animal models for C9orf72 repeat expansion type of ALS are available to date, and there is a strong need for better animal models in the field.

To bypass these difficult intermediate steps for targeting vector construction, an approach to expand a relatively shorter hexanucleotide repeat that is already inserted in the right location in the genome was taken, rather than de novo targeting vector production and ES cell targeting. As a starting material for the repeat expansion, a heterozygous ES cell clone in which a part of the mouse C9orf72 gene locus was replaced with a human counterpart containing 92× repeats of the GGGGCC (SEQ ID NO: 1; "92× repeats of the GGGGCC" disclosed as SEQ ID NO: 141)) hexanucleotide was used. See FIG. 1. This allele was previously developed. See US 2018/0094267 and WO 2018/064600, each of which is herein incorporated by reference in its entirety for all purposes.

When a DNA double-strand break (DSB) occurs in a mammalian cell chromosome, the cells recognize the DSB and repair the damage through either homologous recombination (HR) or a non-homologous recombination pathway such as non-homology end joining (NHEJ) or single-strand annealing (SSA). In HR, the damaged chromatid utilizes the non-damaged chromatid as a template for its repair. In this pathway, once a DSB occurs, the edges of the DSB are modified through many processes including 3' strand resection. The exposed 5' single strands are coated by multiple molecules of Rad51, and then the Rad51 filament begins to search for a homology sequence in the genome. The Rad51 filament is able to insert itself into double-stranded DNA where the exposed 5' single strand has homology. The invaded 5' strand initiates restoration using the very sequence where the Rad51 filament enters. The accuracy with which Rad51 filaments find a homology sequence is the key to preserving the correct DNA sequence. The approach for expanding the repeat was based on the hypothesis that by introducing a DSB near the hexanucleotide repeat so that the exposed 5' strand contains only repetitive sequence, the Rad51 filament could enter into a wrong location, and it could mislead the homology search by the Rad51 filament leading to expansion or contraction of the repeat. See FIG. 2.

Specifically, the approach used herein was expanding an existing GGGGCC (SEQ ID NO: 1) hexanucleotide repeat at the C9orf72 intron 1 in humanized mouse embryonic stem cells by introducing a DSB near the end of the hexanucleotide repeat using a CRISPR/Cas9 nuclease. Several guide RNAs (gRNAs) were designed near the hexanucleotide repeat as close as possible to expose repetitive sequence at the 5' single strand after resection. See FIG. 3 and Table 4.

TABLE 4

C9orf72 gRNA Target Sequences.

| Guide RNA | Target Sequence (Upstream of NGG PAM) | SEQ ID NO |
|---|---|---|
| 5' gRNA-1 | GCTATGCGATCGCCGTCTCG | 30 |
| 5' gRNA-2 | CCCCGGCCCCGGCCCCGAGA | 31 |
| 5' gRNA-3 | CGCCGTCTCGGGGCCGGGGC | 32 |
| 5' gRNA-4 | CCGTCTCGGGGCCGGGGCCG | 33 |
| 3' gRNA-1 | CGGCCGGCCCTCGAGGGTCT | 34 |
| 3' gRNA-2 | GGCCGGGGCCGAGACCCTCG | 35 |

TABLE 4-continued

C9orf72 gRNA Target Sequences.

| | | |
|---|---|---|
| 3' gRNA-3 | GAGGGTCTCGGCCCCGGCCC | 36 |
| 3' gRNA-4 | CTCGGCCCCGGCCCCGGCCC | 37 |

| Guide RNA | Guide Sequence | SEQ ID NO |
|---|---|---|
| 5' gRNA-1 | GCUAUGCGAUCGCCGUCUCG | 84 |
| 5' gRNA-2 | CCCCGGCCCCGGCCCCGAGA | 85 |
| 5' gRNA-3 | CGCCGUCUCGGGGCCGGGGC | 86 |
| 5' gRNA-4 | CCGUCUCGGGGCCGGGGCCG | 87 |
| 3' gRNA-1 | CGGCCGGCCCUCGAGGGUCU | 88 |
| 3' gRNA-2 | GGCCGGGGCCGAGACCCUCG | 89 |
| 3' gRNA-3 | GAGGGUCUCGGCCCCGGCCC | 90 |
| 3' gRNA-4 | CUCGGCCCCGGCCCCGGCCC | 91 |

| Guide RNA | crRNA Sequence | SEQ ID NO |
|---|---|---|
| 5' gRNA-1 | GCUAUGCGAUCGCCGUCUCGGUUUUAGAGCUAUGCU GUUUUG | 56 |
| 5' gRNA-2 | CCCCGGCCCCGGCCCCGAGAGUUUUAGAGCUAUGCU GUUUUG | 57 |
| 5' gRNA-3 | CGCCGUCUCGGGGCCGGGGCGUUUUAGAGCUAUGCU GUUUUG | 76 |
| 5' gRNA-4 | CCGUCUCGGGGCCGGGGCCGGUUUUAGAGCUAUGCU GUUUUG | 77 |
| 3' gRNA-1 | CGGCCGGCCCUCGAGGGUCUGUUUUAGAGCUAUGCU GUUUUG | 78 |
| 3' gRNA-2 | GGCCGGGGCCGAGACCCUCGGUUUUAGAGCUAUGCU GUUUUG | 79 |
| 3' gRNA-3 | GAGGGUCUCGGCCCCGGCCCGUUUUAGAGCUAUGCU GUUUUG | 80 |
| 3' gRNA-4 | CUCGGCCCCGGCCCCGGCCCGUUUUAGAGCUAUGCU GUUUUG | 81 |

| Guide RNA | TracrRNA Sequence | SEQ ID NO |
|---|---|---|
| All | GUUGGAACCAUUCAAAACAGCAUAGCAAGUUAAAA UAAGGCUAGUCCGUUAUCAACUUGAAAAAGUGGCA CCGAGUCGGUGCUUUUUUU | 82 |

Figure 4:
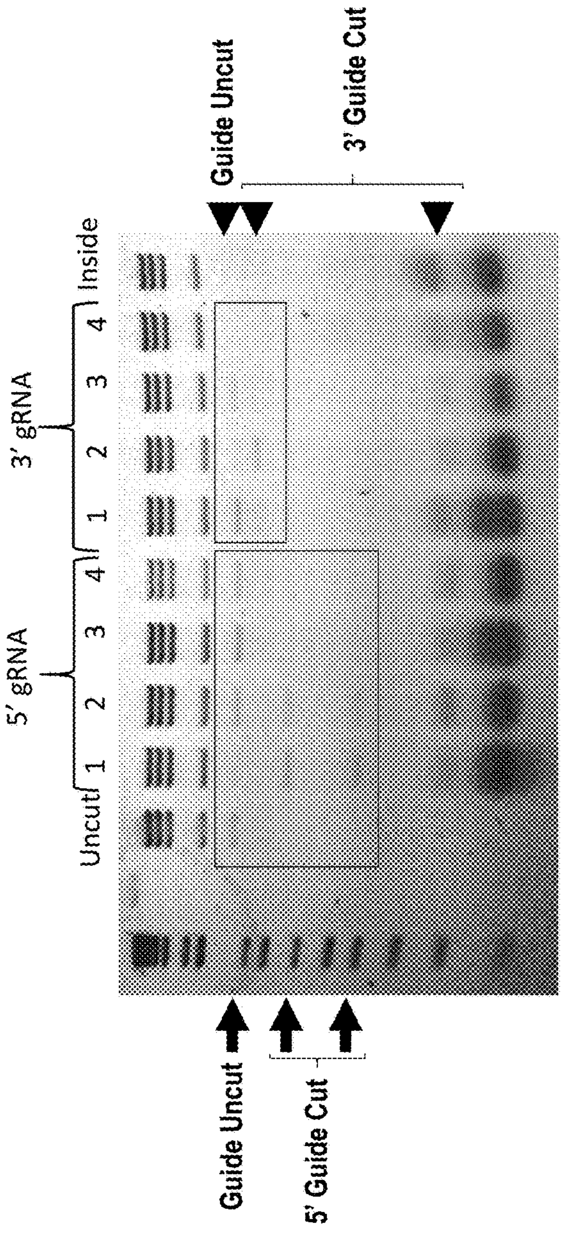
FIG. 4 depicts the cleavage efficiency of the eight guide RNAs assessed in a cell-free system using a plasmid (8028 Stvec) that contains the same sequence as the humanized, 92×-repeat-containing allele (MAID8029a).

The goal was to obtain gRNAs that cleave as close as possible to the repeat and with high cleavage efficiency. DNA cleavage efficiency was tested in vitro using a plasmid (8028 Stvec) that contains the same sequence as the humanized, 92×-repeat-containing allele. The gRNAs with the highest cleavage efficiencies were chosen from both the 5' side and the 3' side of the repeat. These were 5' gRNA-1 and 3' gRNA-2. See FIG. 4.

Figure 5:
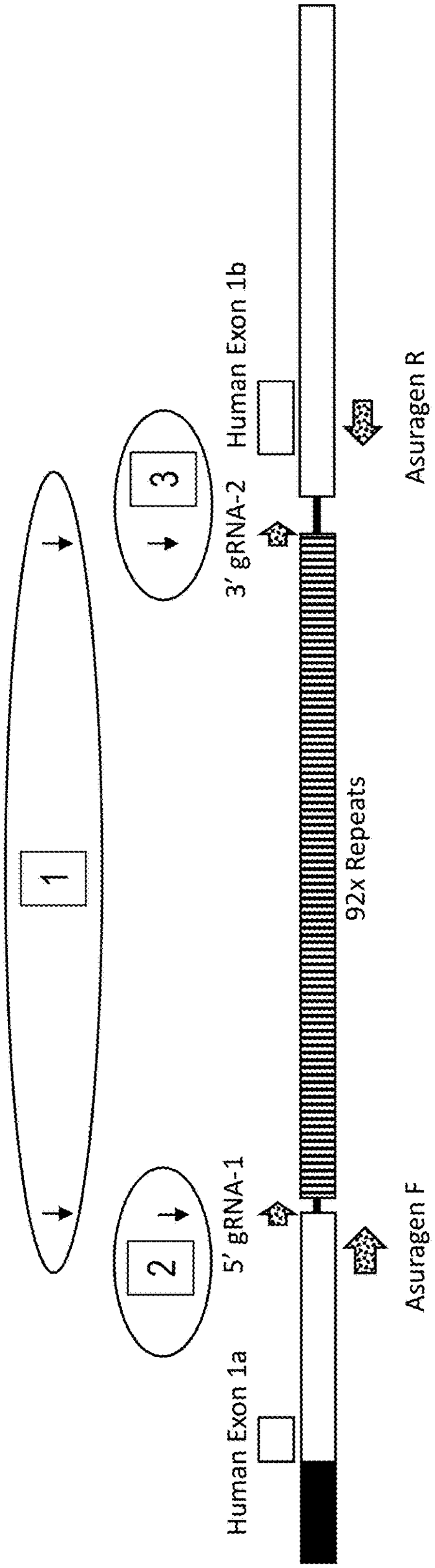
FIG. 5 (not to scale) is a schematic of the scheme for expanding the 92× repeat by introducing a double-strand break near the 5' end (box 2), near the 3' end (box 3), or near both the 5' and 3' ends (box 1) of the 92× repeat expansion sequence. Black boxes indicate endogenous mouse sequence; white boxes indicate humanized regions.

To modify DNA in the ES cells, SpCas9 (*Streptococcus pyogenes* Cas9; Thermo Fisher) and gRNA were introduced into the C9orf72 humanized, 92×-repeat-containing ES cells (MAID8029a) as an RNA and protein complex (RNP) by electroporation. ES cell colonies were picked, the colonies were grown in a 96-well culture plate, and genomic DNA was purified for analysis. Three experiments were done: (1) introducing a single DSB at the 5' side of the repeat; (2) introducing a single DSB at the 3' side of the repeat; and (3) introducing DSBs at both the 5' and 3' sides of the repeat. See FIG. 5. The analysis was done using conventional two-primer PCR (FIG. 6A) and prime PCR that used three primers using an AmplideX PCR/CE C9orf72 kit (FIG. 6B). For prime PCR, genomic DNA from ES cells was used as the template. Three primers were used: a primer located 5' outside of the repeat, a primer located 3' outside of the repeat, and a third primer that anneals to the repetitive sequence inside the repeat as shown in FIG. 6B. This PCR reaction produces many different sizes of PCR product as shown in FIG. 6B. Because the third primer can prime the polymerase reaction in any given unit of the repeat, the number of PCR products obtained is basically the number of repeats the clone has. These PCR products were run with capillary electrophoresis, which detects fluorescent signals (one of the primers is fluorescently labeled).

The AmplideX PCR/CE C9orf72 Kit (Asuragen) was used according to the manufacturer's instructions to confirm the number of instances of the hexanucleotide sequence set forth as SEQ ID NO: 1 in the endogenous C9orf72 ES cell clones. Purified mESC genomic total DNA from a 3× repeat clone, a 92× repeat clone, and a 30× repeat clone was used as controls. PCR using the primers in Table 5 and a repeat-specific primer from the AmplideX PCR/CE C9orf72 Kit was performed on an ABI 9700 thermal cycler (Thermo Fisher). Amplicons were sized by capillary electrophoresis on an ABI 3500xL GeneScan using POP-7 polymer (Thermo Fisher) and NuSieve agarose gels (Lonza). 2-log DNA ladder (New England BioLabs) molecular weight marker was loaded on agarose gels for comparison, and bands were visualized with SYBR Gold Nucleic Acid Stain (Thermo Fisher).

TABLE 5

Primers for PCR.

| Primer Name | Sequence | SEQ ID NO: |
|---|---|---|
| 2-Primer Fwd | TGCGCCTCCGCCGCCGCGGGCGCAGGCACCGCAAC CGCA | 92 |
| 2-Primer Rev | CGCAGCCTGTAGCAAGCTCTGGAACTCAGGAGTCG | 93 |

Figure 7B:
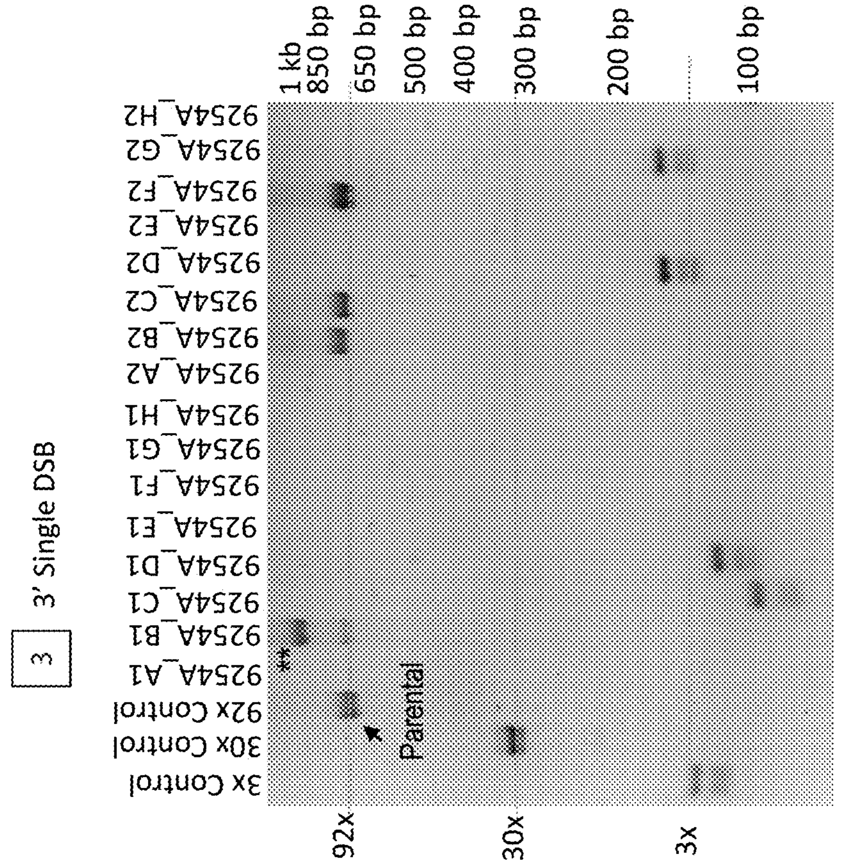
FIG. 7B shows the results of conventional PCR of the C9orf72 locus to assess the size of the repeat area following cleavage near of the 3' end of the 92× repeat expansion sequence. Expanded repeats are marked by asterisks.
Figure 7A:
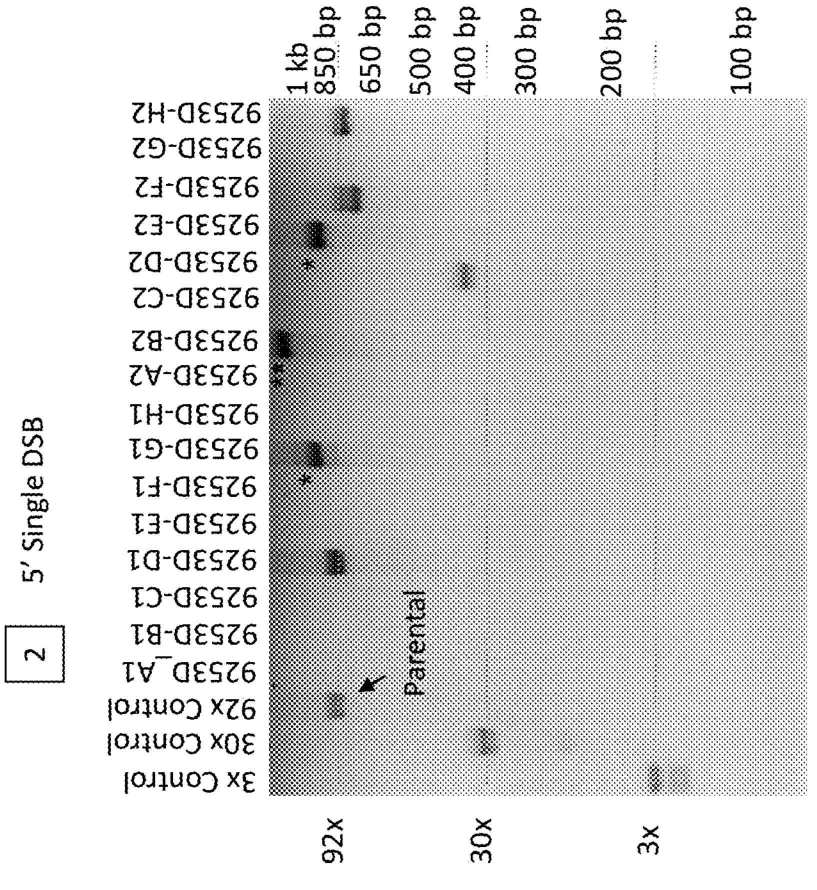
FIG. 7A shows the results of conventional PCR of the C9orf72 locus to assess the size of the repeat area following cleavage near of the 5' end of the 92× repeat expansion sequence. Expanded repeats are marked by asterisks.
Figure 8:
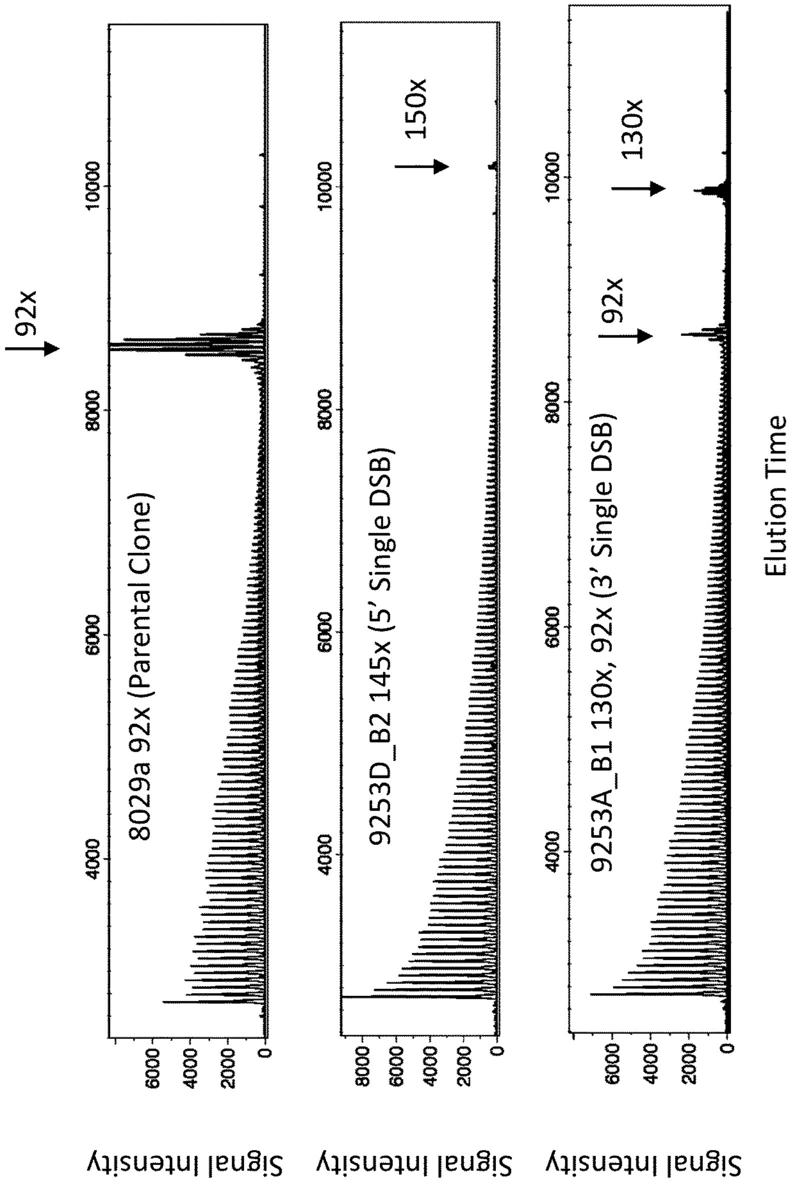
FIG. 8 shows the results of prime PCR to confirm the number of repeats in one of the clones from FIG. 7A and one of the clones from FIG. 7B. The parental 8029a (92× repeat) clone was used as a control.
Figure 9:
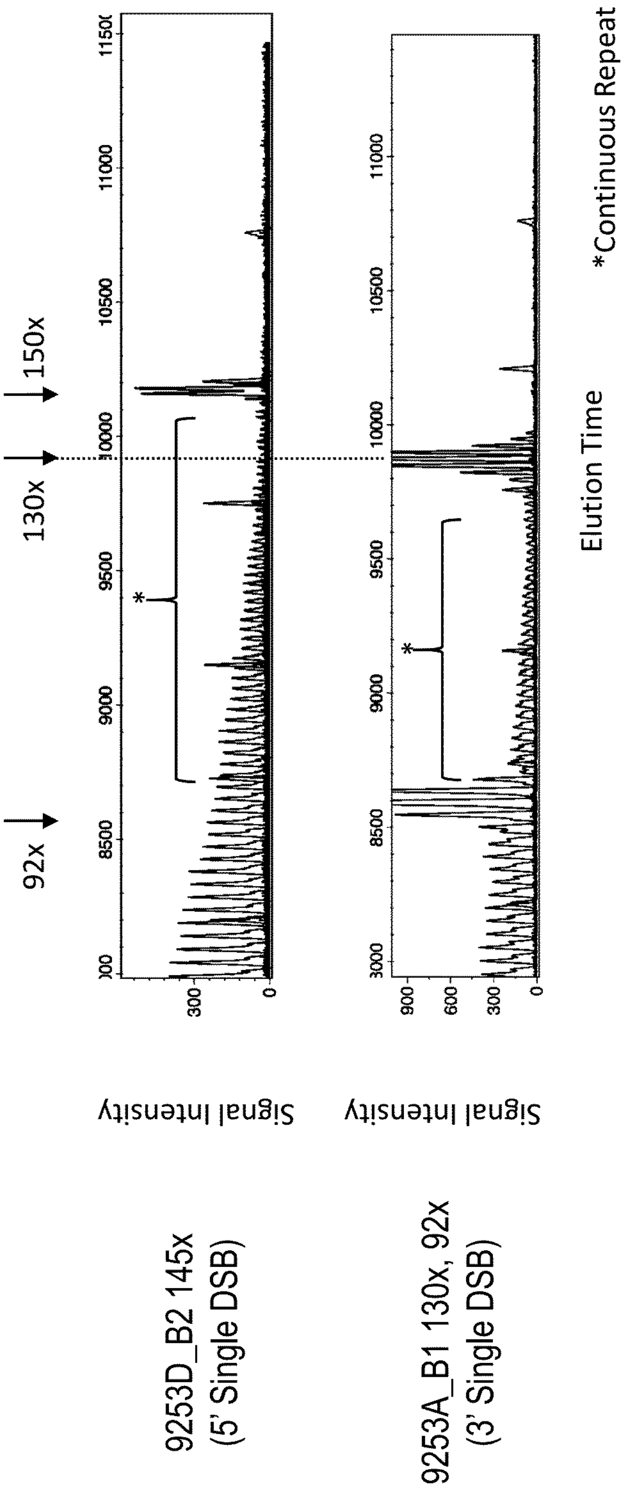
FIG. 9 shows the results of prime PCR to confirm the number of repeats in one of the clones from FIG. 7A and one of the clones from FIG. 7B.

Introducing a DSB at either side of the repeat resulted in size alteration at the repeat area as demonstrated using conventional two-primer PCR. See FIGS. 7A and 7B. Results for 16 out of 88 colonies for each condition are shown in FIGS. 7A and 7B. The 5' single DSB clone and the 3' single DSB clone with the largest expansions were chosen for further analysis using prime PCR to confirm repeat expansion. Prime PCR confirmed that clone 9253D-B2 (5' single DSB) had 145 repeat and that clone 9253A-B1 (3' single DSB) had 130 repeats and 92 repeats. See FIGS. 8 and 9. FIG. 8 shows results from capillary electrophoresis. Signal intensity is on the Y axis, and PCR product size is on the X axis. The readout is the number of peaks. The top panel is from the 92× parental clone, and there are 92 peaks. One hundred fifty peaks were counted in the middle panel and 130× peaks in the bottom panel. Two high peaks were observed in the bottom panel. This is likely because the ES cell colonies we picked were not a homogenous clone.

Figure 10:
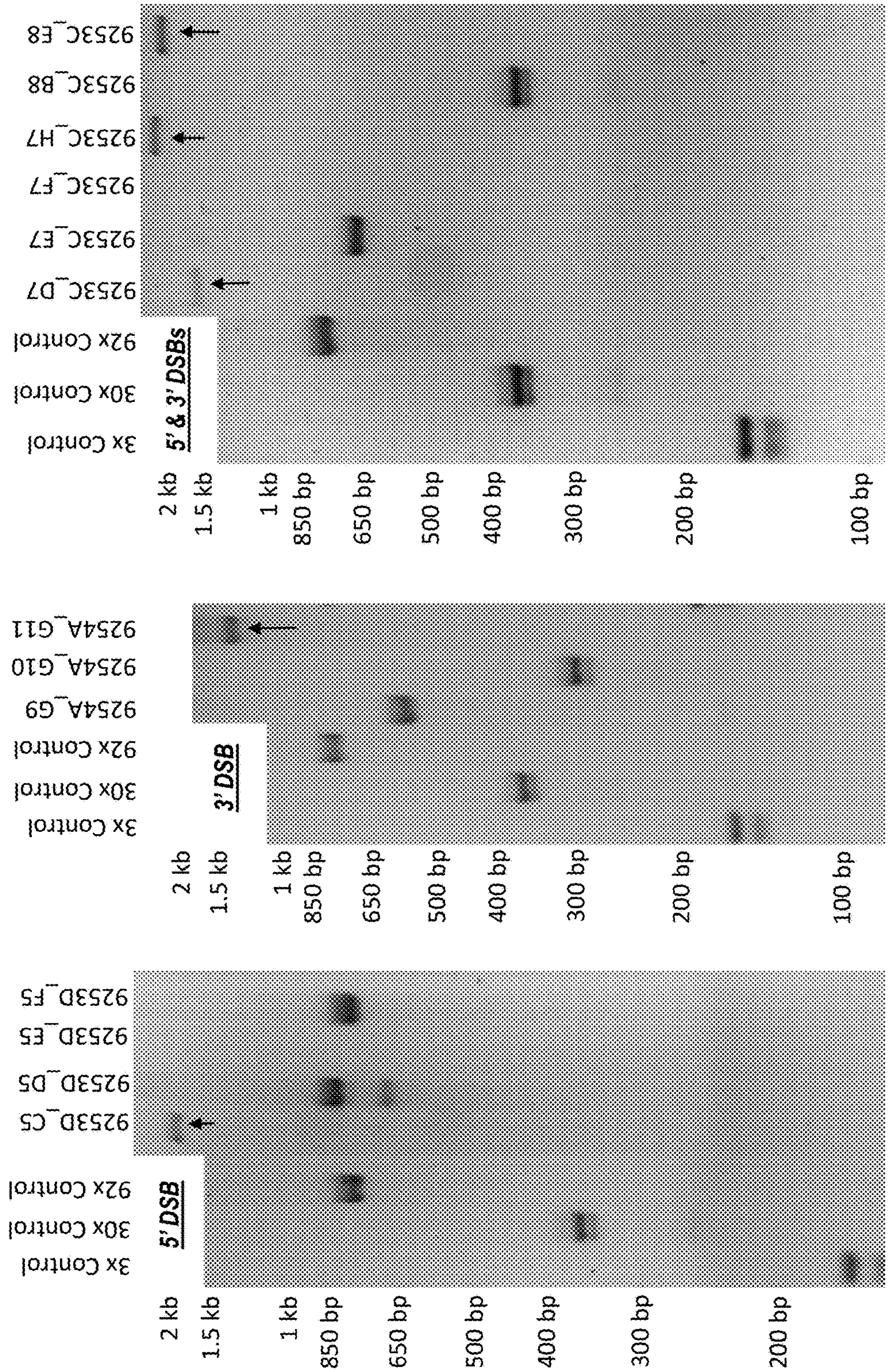
FIG. 10 shows the results of conventional PCR of the C9orf72 locus to assess the size of the repeat area following cleavage near of the 5' end of the 92× repeat expansion sequence, cleavage near the 3' end of the 92× repeat expansion sequence, or cleavage near both the 5' and 3' ends of the 92× repeat expansion sequence. Expanded repeats are marked by arrows.

The same experiment was repeated again with similar results. See FIG. 10. For each condition (single 5' DSB, single 3' DSB, or both 5' and 3' DSBs), 88 clones were tested. DSBs at the repeat caused repeat instability. DSBs at either side or both sides of the repeat led to repeat expansion (from 92× up to ~300×). A complete analysis of the expansions or contractions in the different clones is provided in Table 6. Full contraction was called either by TAQMAN assay or Asuragen AmplideX PCR/CE C9orf72 Kit.

TABLE 6

Assessment of Repeat Expansion or Contraction after First Repeat Expansion.

| Rearrangement | 5' & 3' DSB (%) | Single 5' DSB (%) | Single 3' DSB (%) |
|---|---|---|---|
| Expansion (>750 bp = 92×) | 4.5 | 18.2 | 5.6 |
| Partial contraction (<750 bp, >200 bp) | 9.1 | 9.1 | 9.1 |
| Retained (750 bp) | 19.3 | 36.4(51.1)* | 5.6(28.4)* |
| Full contraction (<200 bp) | 46.6 | 21.6 | 55.8 |
| Not detected | 20.5 | 14.8 | 27.3 |
| Total | 100 | 100 | 100 |

*Multiple bands observed

Figure 11A:
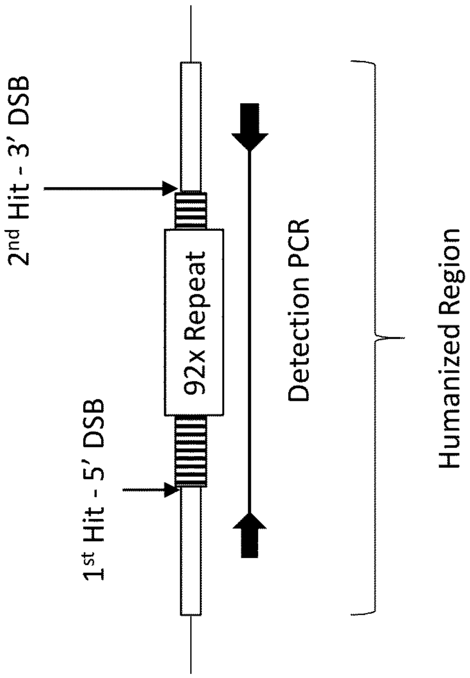
FIG. 11A (not to scale) shows a schematic of the scheme for expanding a 92× repeat in mouse ES cells by first introducing a double-strand break near the 5' end of the 92× repeat expansion sequence to generate a first expanded clone and then introducing a double-strand break near the 3' end of the repeat expansion sequence in the first expanded clone to generate a second expanded clone. The humanized region is indicated by a label and the white boxes). The locations of the 5' DSB and the 3' DSB are indicated, along with the locations of the primers for detection by PCR.
Figure 11B:
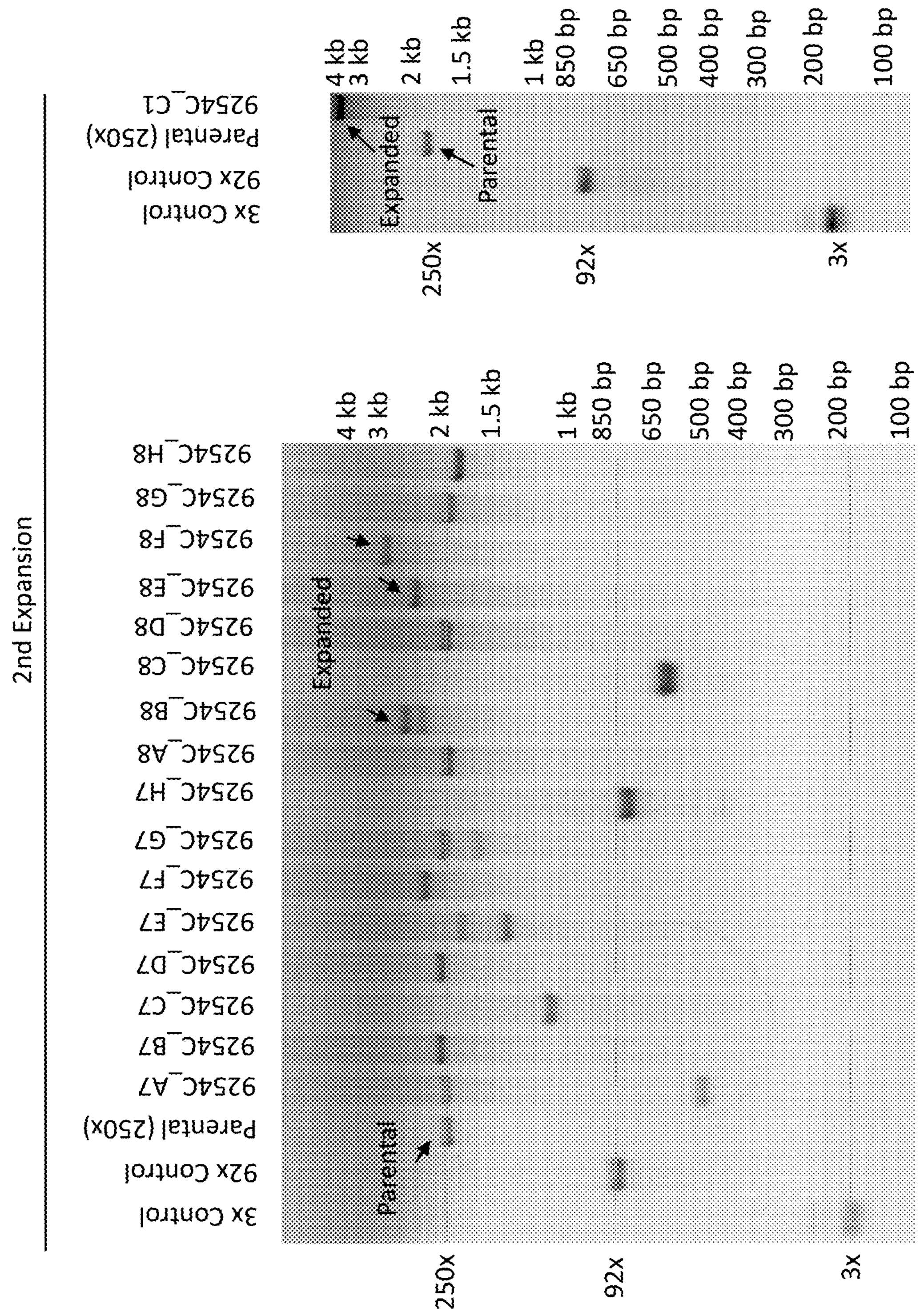
FIG. 11B shows the results of conventional PCR of the C9orf72 locus to assess the size of the repeat area following a second expansion after cleavage of a 250× repeat expansion sequence clone near the 3' end of the 250× repeat expansion sequence. Expanded repeats and parental repeats are marked by labeled arrows.

The biggest repeat was obtained by introducing both 5' and 3' DSBs together. The biggest repeat obtained by introducing a single DSB was approximately 250×, in which the 3' gRNA site was still intact and the repeat expandable. To further expand that repeat, the 250× repeat clone (MAID9253D-05) was used and a DSB was introduced at the 3' end through introduction of the Cas9/gRNA RNP as described above. Using the 250× allele, the repeat was further expanded to approximately the size of ~600×. See FIGS. 11A and 11B and Table 7.

TABLE 7

Assessment of Repeat Expansion or Contraction after Second Repeat Expansion with Single 3' DSB.

| Parental clone | 8029, 92× (%) | 9253D-C5, 250× (%) |
|---|---|---|
| Expansion (>parental clone) | 5.6 | 13.6 |
| Partial contraction (<parental clone, >200 bp) | 9.1 | 43.2 |
| Retained (= parental clone) | 5.6(28.4)* | 30.7(43.2)* |
| Full contraction (<200 bp) | 55.8 | 4.5 |
| Not detected | 27.3 | 2.3 |
| Total | 100 | 100 |

*Multiple bands observed

Example 2. Analysis of Motor Neurons or Brain Tissues Comprising Hexanucleotide Repeat Expansion at the C9orf72 Gene Locus The stability of the size of the hexanucleotide repeat in the mice is confirmed using AmplideX PCR/CE C9orf72 Kit (Asuragen) as described above.

RNA transcripts in mouse embryonic-stem-cell-derived motor neurons (ESMNs) comprising a wildtype C9orf72 locus (control) or a genetically modified C9orf72 locus from Example 1 were examined as described in US 2018/0094267 and WO 2018/064600, each of which is herein incorporated by reference in its entirety for all purposes. RNA foci and dipeptide repeat protein levels were evaluated in ESMNs derived from parental embryonic stem cells comprising a wildtype C9orf72 locus (control) or a genetically modified C9orf72 locus from Example 1. The materials and methods are described below.

Additionally, RNA transcripts in mouse brain tissues and parental embryonic stem cells comprising a wildtype C9orf72 locus (control) or a genetically modified C9orf72 locus from Example 1 are examined as described in US 2018/0094267 and WO 2018/064600, each of which is herein incorporated by reference in its entirety for all purposes. RNA foci and dipeptide repeat protein levels are evaluated in ESMNs derived from parental embryonic stem cells comprising a wildtype C9orf72 locus (control) or a genetically modified C9orf72 locus from Examples 1 and 2. The materials and methods are described below.

Embryonic-Stem-Cell-Derived Motor Neurons

Embryonic stem cells (ESCs) from Example 1 were cultured in embryonic stem cell medium (ESM; DMEM+15% fetal bovine serum+penicillin/streptomycin+glutamine+non-essential amino acids+nucleosides+β-mercaptoethanol+sodium pyruvate+LIF) for 2 days, during which the medium was changed daily. ES medium was replaced with 7 mL of ADFNK medium (advanced DMEM/F12+neurobasal medium+10% knockout serum+penicillin/streptomycin+glutamine+β-mercaptoethanol) 1 hour before trypsinization. ADFNK medium was aspirated, and ESCs were trypsinized with 0.05% trypsin—EDTA. Pelleted cells were resuspended in 12 mL of ADFNK and grown for two days in suspension. Cells were cultured for a further 4 days in ADFNK supplemented with retinoic acid (RA), smoothened agonist, and purmorphamine to obtain limb-like motor neurons (ESMNs). Dissociated motor neurons were plated and matured in embryonic-stem-cell-derived motor neuron medium (ESMN; neurobasal medium+2% horse serum+B27+glutamine+penicillin/streptomycin+β-mercaptoethanol+10 ng/mL GDNF, BDNF, CNTF).

Quantitative Polymerase Chain Reaction

Total RNA from each sample was extracted and reverse transcribed using primers that flank various regions and probes that detect those regions of the modified C9orf72 locus. Detectable regions include those that span the junction of mouse and human sequences, only human sequences, or only mouse sequences. qPCR of GAPDH, DROSHA, or 132-microglobulin was performed using probes and primers of readily available kits.

Specifically, RNA was isolated from embryonic-stem-cell-derived motor neurons (ESMN) comprising a wild type (WT) C9orf72 locus (control) or a genetically modified C9orf72 locus. In other experiments, RNA is also isolated from parental embryonic stem (ES) cells or total brains isolated from mice comprising a wild type (WT) C9orf72 locus (control) or a genetically modified C9orf72 locus.

Total RNA was isolated using Direct-zol RNA Miniprep plus kit according to the manufacturer's protocol (Zymo Research). Total RNA was treated with DNase using Turbo DNA-free kit according to the manufacturer's protocol (Invitrogen) and diluted to 20 ng/μL. Reverse transcription (RT) and PCR were performed in a one-step reaction with Quantitect Probe RT-PCR kit (Qiagen). The qRT-PCR reaction contained 2 μL RNA and 8 μL mixture containing RT-PCR Master mix, ROX dye, RT-mix, and 20× gene specific primer-probe mix to make a final volume of 10 μL.

Unless otherwise noted, final primer and probe concentrations were 0.5 μM and 0.25 μM, respectively. qRT-PCR was performed on a ViiA™ 7 Real-Time PCR Detection System (ThermoFisher). PCR reactions were done in quadruplicates with RT-step at 45° C. 10 min followed by 95° C. 10 min and 2-step cycling 95° C. 5s, 60° C. 30s for 45 cycles in an optical 384-well plate. The sequences of the primers and probes and SEQ ID NO used in each analysis (A, B, C, D, E, F, G, H, I, and J) are provided in Table 8.

TABLE 8

| Primers and Probes. | |
|---|---|
| **Analysis A** | |
| Forward Primer | CATCCCAATTGCCCTTTCC (SEQ ID NO: 61) |
| Reverse Primer | CCCACACCTGCTCTTGCTAGA (SEQ ID NO: 62) |
| Probe | TCTAGGTGGAAAGTGGG (SEQ ID NO: 63) |
| **Analysis B** | |
| Forward Primer | GAGCAGGTGTGGGTTTAGGA (SEQ ID NO: 64) |
| Reverse Primer | CCAGGTCTCACTGCATTCCA (SEQ ID NO: 65) |
| Probe | ATTGCAAGCGTTCGGATAATGTGAGA (SEQ ID NO: 66) |
| **Analysis C** | |
| Forward Primer | GATAGTCGACATCCCTGCATC (SEQ ID NO: 95) |
| Reverse Primer | GGTGGCGAGTGGCTATTG (SEQ ID NO: 96) |
| Probe | AAGCGTTCGGATAATGTGAGACCTGG (SEQ ID NO: 97) |
| **Analysis D** | |
| Forward Primer | GCTGTCACGAAGGCTTTCTTC (SEQ ID NO: 67) |
| Reverse Primer | GCACTGCTGCCAACTACAAC(SEQ ID NO: 68) |
| Probe | TCAATGCCATCAGCTCACACCTGC(SEQ ID NO: 69) |
| **Analysis E** | |
| Forward Primer | TCTCACAGTACTCGCTGAGGGTGA (SEQ ID NO: 98) |
| Reverse Primer | AAGAGCAGGTGTGGGTTTAG (SEQ ID NO: 99) |
| Probe | CGGTTGTTTCCCTCCTTGT (SEQ ID NO: 100) |
| **Analysis F** | |
| Forward Primer | CCCACTACTTGCTCTCACAG (SEQ ID NO: 101) |
| Reverse Primer | TACAGGCTGCGGTTGTTT (SEQ ID NO: 102) |
| Probe | ACTCGCTGAGGGTGAACAAGAAA (SEQ ID NO: 103) |
| **Analysis G** | |
| Forward Primer | AAGAGGCGCGGGTAGAA (SEQ ID NO: 70) |
| Reverse Primer | CAGCTTCGGTCAGAGAAATGAG (SEQ ID NO: 71) |
| Probe | CTCTCCTCAGAGCTCGACGCATTT (SEQ ID NO: 72) |
| **Analysis H** | |
| Forward Primer | CTGCACAATTTCAGCCCAAG (SEQ ID NO: 73) |
| Reverse Primer | CAGGTCATGTCCCACAGAAT (SEQ ID NO: 74) |
| Probe | CATATGAGGGCAGCAATGCAAGTC (SEQ ID NO: 75) |
| **Analysis I** | |
| Forward Primer | CGAGTGGGTGAGTGAGGA (SEQ ID NO: 104) |
| Reverse Primer | TTCTACCCGCGCCTCTT (SEQ ID NO: 105) |
| Probe | ATCCTGGCGGGTGGCTGTTT (SEQ ID NO: 106) |

TABLE 8-continued

| Primers and Probes. | |
|---|---|
| Analysis J | |
| Forward Primer | CGGATAATGTGAGACCTGGAAT (SEQ ID NO: 107) |
| Reverse Primer | AAAGGTAGCCGCCAACAA (SEQ ID NO: 108) |
| Probe | ACCATCTCCTGCTGTTGCCAAGA (SEQ ID NO: 109) |

Western Blot Analysis

Differentiated embryoid bodies (EBs) were collected and homogenized in SDS sample buffer (2% SDS, 10% glycerol, 5% β-mercaptoethanol, 60 mM TrisHCl, pH 6.8, bromophenol blue). Protein extracts were quantified using the RC DC protein assay (BioRad). Extracts (10 μg) were run on a 4-20% SDS-PAGE gel (ThermoFisher) and transferred onto a nitrocellulose membrane using an iBLOT transfer unit (ThermoFisher) Immunoblots were probed with primary antibodies against C9orf72 and GAPDH (Millipore). Bound antibody was detected by incubation with secondary antibodies conjugated to horseradish peroxidase (Abcam) followed by chemiluminescence using a SuperSignal West Pico chemiluminescent substrate (Thermo Scientific). Signal was detected by autoradiography using Full Speed Blue sensitive medical X-Ray film (Ewen Parker XRay Corporation). Relative protein levels were calculated using ImageJ. Data not shown.

Fluorescent In Situ Hybridization (FISH) for Detection of Sense or Antisense RNA Transcription Products Fluorescent in situ hybridization (FISH) was used to determine the location of RNA transcribed from the hexanucleotide repeat sequence set forth as SEQ ID NO: 1 in embryonic-stem-cell-derived motor neurons (ESMNs) generated as described above. Briefly, ESMNs were grown in four-well chamber slides (Lab-Tek II chamber slide system, ThermoFisher Scientific) and fixed with 4% PFA (Electron Microscopy Sciences) in PBS. Cells were then permeabilized with diethyl pyrocarbonate (DEPC) PBS/0.2% Triton X-100 (Fisher Scientific, catalog #BP151) and washed with DEPC-PBS, blocked and stained with LNA oligonucleotides for the detection of RNA transcription products, as described below. After staining, slides were subsequently incubated with an appropriate fluorescent dye, mounted with Fluoromount G (Southern Biotech) and visualized using confocal microscopy.

Slides were pre-hybridized with buffer consisting of 50% formamide (IBI Scientific, catalog #IB72020), DEPC 2×SSC [300 mM sodium chloride, 30 mM sodium citrate (pH 7.0)], 10% (w/v) dextran sulfate (Sigma-Aldrich, catalog #D8960), and DEPC 50 mM sodium phosphate (pH 7.0) for 30 min at 66° C. for LNA probes. The hybridization buffer was then drained off, and 400 μL of 40 nM LNA probe mix in hybridization buffer was added to each of the slides and incubated in the dark for 3 hours at 66° C. (for LNA probes). Slides incubated with LNA probes were rinsed once in DEPC 2× SSC/0.1% Tween 20 (Fisher Scientific, catalog no. BP337) at room temperature and in DEPC 0.1× SSC three times at 65° C. Slides were subsequently incubated with 1 μg/mL DAPI (Molecular Probes Inc.).

In another experiment, slides are pre-hybridized with buffer consisting of 50% formamide (IBI Scientific, catalog #IB72020), DEPC 2×SSC [300 mM sodium chloride, 30 mM sodium citrate (pH 7.0)], 10% (w/v) dextran sulfate (Sigma-Aldrich, catalog #D8960), and DEPC 50 mM sodium phosphate (pH 7.0) for 30 min at 66° C. (for LNA probes) or 55° C. (for DNA probes). The hybridization buffer is then drained off, and 400 μL of 200 ng/mL of DNA probe mix in hybridization buffer is added to each of the slides and incubated in the dark for 3 hours at 55° C. Slides incubated with DNA probes are washed three times with 40% formamide in 2×SSC and briefly washed one time in PBS. Slides are subsequently incubated with 1 μg/mL DAPI (Molecular Probes Inc.).

The sequences and SEQ ID NOS of the LNA and DNA oligonucleotide probes used in this example, as well as the hybridization conditions of the probes, are provided in Table 9 below. A locked nucleic acid (LNA) is a nucleic acid analog in which the ribose moiety is modified with an extra bridge connecting the 2' oxygen and the 4' carbon.

TABLE 9

LNA and DNA Probes.

| Probe | Sequence (SEQ ID NO) | Hybridization Method |
|---|---|---|
| LNA sense $G_4C_2$ RNA | TYE563-CCCCGGCCCCGGCCCC (SEQ ID NO: 38) | 66° C. hybridization and washes in 0.1 X SSC |
| LNA antisense $G_4C_2$ RNA | TYE563-GGGGCCGGGGCCGGGGGCC CC (SEQ ID NO: 39) | 66° C. hybridization and washes in 0.1 X SSC |
| DNA sense $G_4C_2$ RNA | CCCCGGCCCCGGCCCCGG-Cy3 (SEQ ID NO: 44) | 55° C. hybridization and washes in 2 X SSC |
| DNA antisense $G_4C_2$ RNA | GGGGCCGGGGCCGGGGC-Cy3 (SEQ ID NO: 45) | 55° C. hybridization and washes in 2 X SSC |

Detection of Dipeptide Repeat Protein Products (Immunofluorescence and Western Slot Blot) Immunofluorescence was used to assess dipeptide repeat protein production in embryonic-stem-cell-derived motor neurons (ESMNs) generated as described above. Briefly, ESMNs were grown in four-well chamber slides (Lab-Tek II chamber slide system, ThermoFisher Scientific) and fixed with 4% PFA (Electron Microscopy Sciences) in PBS. Cells were then permeabilized with diethyl pyrocarbonate (DEPC) PBS/0.2% Triton X-100 (Fisher Scientific, catalog #BP151) and washed with DEPC-PBS, blocked and stained with anti-polyGA antibody for the detection of RAN translation products, as described below. After staining, slides were subsequently incubated with an appropriate fluorescent dye, mounted with Fluoromount G (Southern Biotech) and visualized using confocal microscopy.

After permeabilization, slides were blocked with 5% normal donkey serum diluted in Tris buffered saline (pH 7.4) with 0.2% Triton X100 (TBS-T). Slides were incubated overnight at 4° C. with primary antibodies against poly-GA (Millipore) diluted in TBS-T with 5% normal donkey. After washing 3 times with TBS-T, slides were incubated with species-specific secondary antibodies coupled to Alexa 488 or 555 (1:1000 in TBS-T, ThermoFisher) and DAPI (1 µg/mL) (Molecular Probes Inc.) for 1 hr at room temperature. After washing 3 times with TBS-T, slides were mounted with Fluoromount G (Southern Biotech) and visualized using confocal microscopy.

For slot blot assays, differentiated embryoid bodies (EBs) were collected and homogenized in SDS sample buffer (2% SDS, 10% glycerol, 5% β-mercaptoethanol, 60 mM TrisHCl, pH 6.8, bromophenol blue). Protein extracts were quantified using the RC DC protein assay (BioRad). Lysates containing 0 µg, 1.25 µg, 2.5 µg, 5 µg, 10 µg, or 20 µg were immobilized onto nitrocellulose membranes with Bio-Slot 48-well microfiltration system (Bio-Rad) under vacuum. The membranes were washed in TBS-T and blotted with an antibody against poly(GP) (1:5,000, Novus biologicals) and poly GA (1:5000, Millipore). After the membrane was incubated with HRP conjugated secondary antibody, bands were visualized by the ECL plus Western Blotting Detection System (Pierce).

Results

Figure 12A:
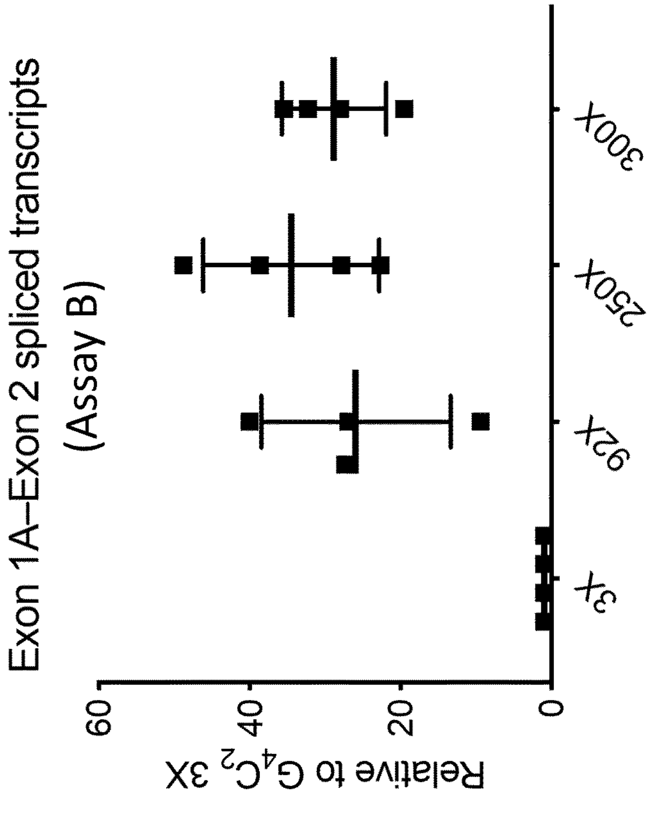
FIGS. 12A-12D are bar graphs showing expression levels (as determined by the TAQMAN® quantitative reverse transcription-coupled PCR (RT-qPCR) assays shown in the depiction of the C9orf72 locus at the top of each figure) of transcripts from the C9orf72 locus (y-axis) that are exon 1A-exon 2 spliced transcripts (FIG. 12A), that are exon 1B-exon 2 spliced transcripts (FIG. 12B), that contain intron sequence near exon 1A (FIG. 12C), and the retain intron sequence near exon 1B (FIG. 12D) in embryonic-stem-cell-derived motor neurons (ESMNs) that are heterozygous for a modified C9orf72 locus comprising 3, 92, 250, or 300 repeats of the hexanucleotide sequence set forth as SEQ ID NO: 1 relative to ESMNs comprising 3 repeats of the hexanucleotide sequence set forth as SEQ ID NO: 1.
Figure 12B:
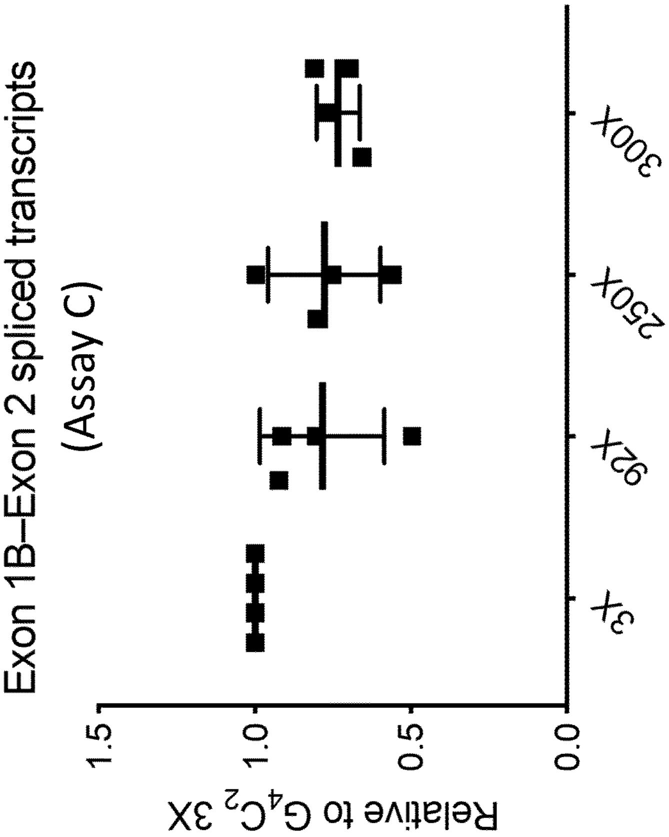
Figure 12D:
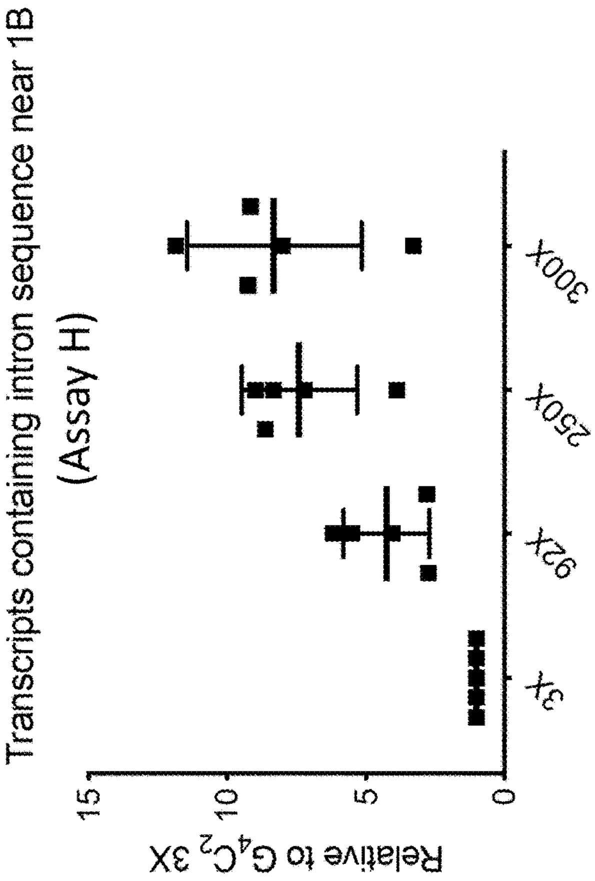
Figure 12C:
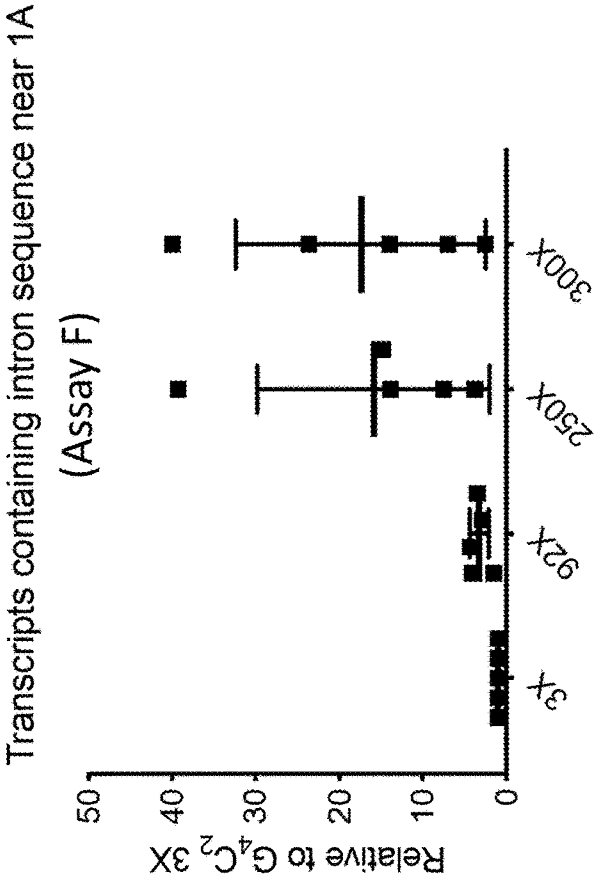
Figure 12E:
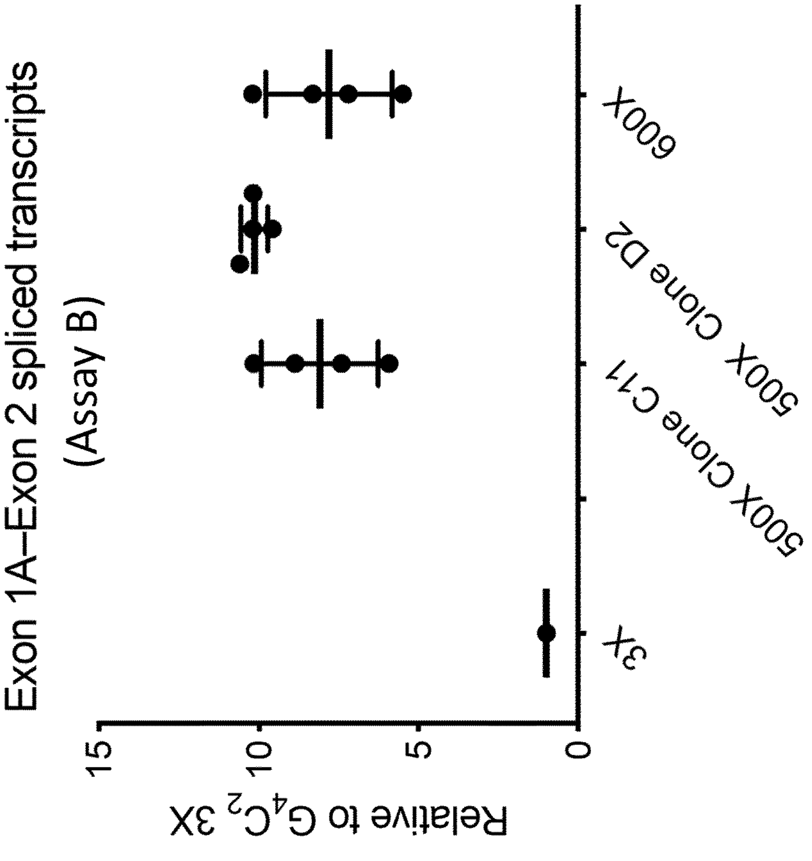
FIGS. 12E-12H are bar graphs showing expression levels (as determined by the TAQMAN® quantitative reverse transcription-coupled PCR (RT-qPCR) assays shown in the depiction of the C9orf72 locus at the top of each figure) of transcripts from the C9orf72 locus (y-axis) that are exon 1A-exon 2 spliced transcripts (FIG. 12E), that are exon 1B-exon 2 spliced transcripts (FIG. 12F), that contain intron sequence near exon 1A (FIG. 12G), and the retain intron sequence near exon 1B (FIG. 12H) in embryonic-stem-cell-derived motor neurons (ESMNs) that are heterozygous for a modified C9orf72 locus comprising 3, 500, or 600 repeats of the hexanucleotide sequence set forth as SEQ ID NO: 1 relative to ESMNs comprising 3 repeats of the hexanucleotide sequence set forth as SEQ ID NO: 1.
Figure 12F:
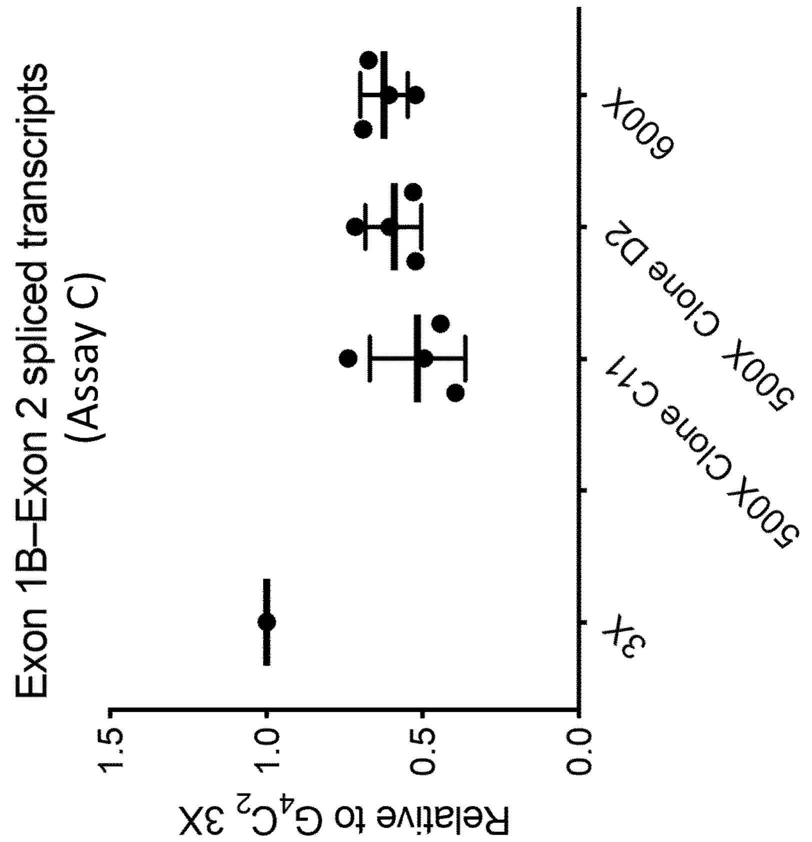
Figure 12G:
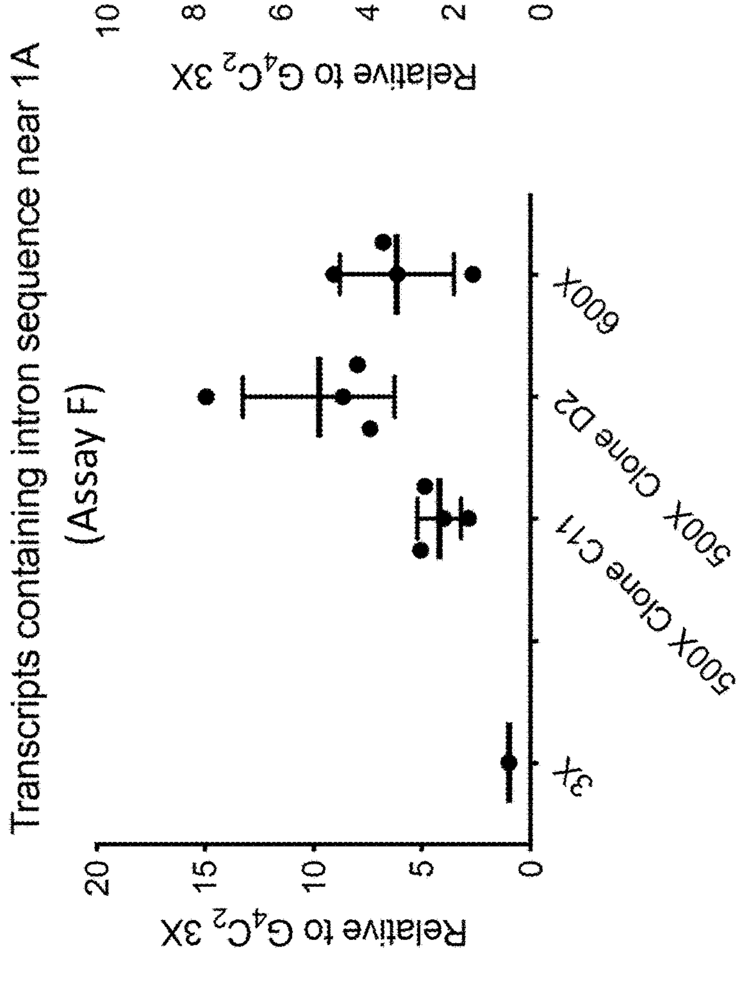
Figure 12H:
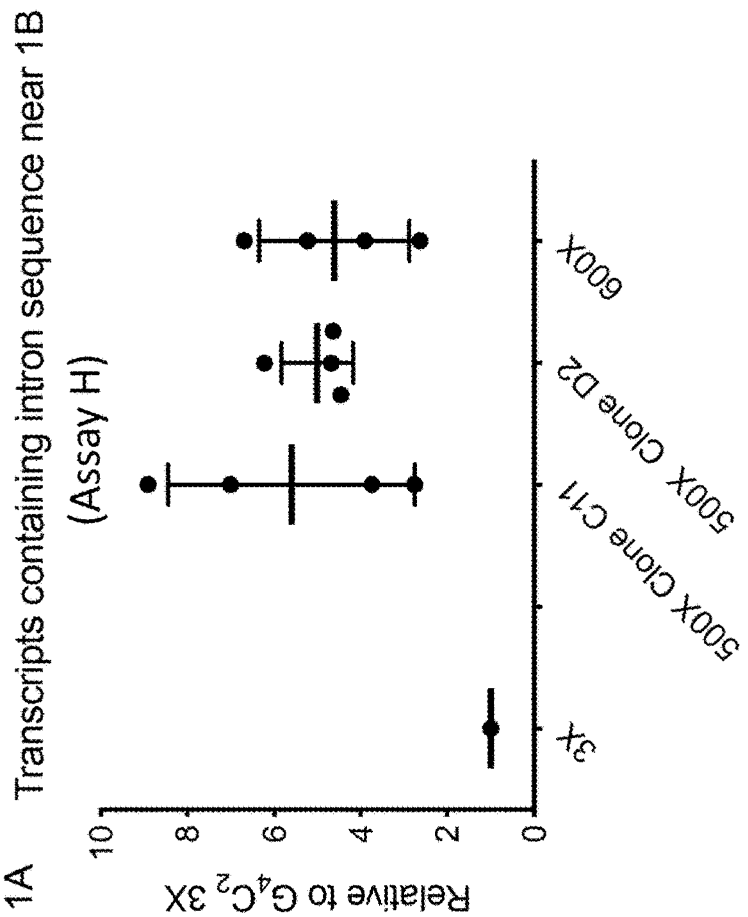
Figure 13:
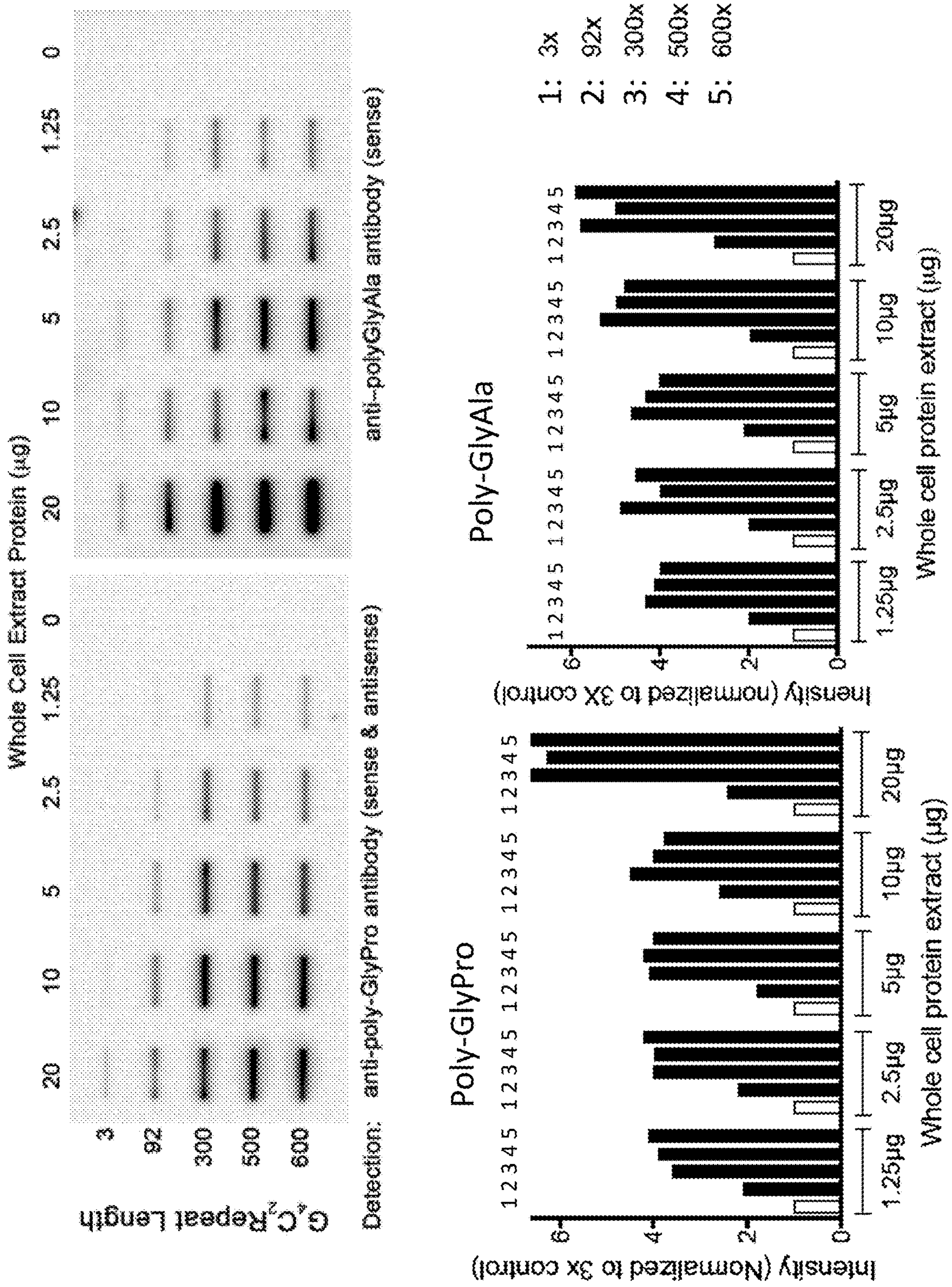
FIG. 13 (top) is a western slot blot image of lysates of from embryonic-stem-cell-derived motor neurons (ESMNs) heterozygous for a modified C9orf72 locus comprising 3, 92, 300, 500, or 600 repeats of the hexanucleotide sequence set forth as SEQ ID NO: 1. Lysates containing 0 μg, 1.25 μg, 2.5 μg, 5 μg, 10 μg, or 20 μg total proteins were blotted with anti-poly-GlyPro antibody or anti-poly-GlyAla antibody.

Embryonic-stem-cell-derived motor neurons (ESMNs) comprising an allelic series of humanized C9orf72 allele with 3 repeats, 92 repeats, 250 repeats, 300 repeats, 500 repeats, or 600 repeats of the $G_4C_2$ hexanucleotide sequence were tested ("G4C2" repeats disclosed as SEQ ID NOS 140-141, 145, and 142-144, respectively, in order of appearance). As shown in FIG. 12C, FIG. 12D, FIG. 12G, and FIG. 12H, ESMNs comprising the hexanucleotide repeat expansion sequence at the C9orf72 locus showed increased expression of C9orf72 mRNA transcripts that retain intron 1 sequences. In addition, larger $G_4C_2$ repeat (SEQ ID NO: 1) expansions had increased use of exon 1A and decreased use of exon 1B. See FIGS. 12A and 12B, respectively, and FIGS. 12E and 12F, respectively. The ESMNs containing $G_4C_2$ repeat (SEQ ID NO: 1) expansions also contained nuclear and cytoplasmic sense and antisense C9orf72 RNA foci (data not shown). The sense G4C2 (SEQ ID NO: 1) foci were larger and distributed to the nucleolus (data not shown). The localization of RNA foci with nucleoli in ESMNs with repeat expansions greater than 300 reproduces pathological findings in ALS-patient-derived cells. In addition, an increased number of repeats of the G4C2 hexanucleotide sequence (SEQ ID NO: 1) directly correlated with the presence of increased dipeptide repeat proteins (polyGA and polyGP) translated (through RAN translation, a non-AUG mechanism) from transcripts of the hexanucleotide repeat sequence. See, e.g., FIG. 13. In summary, motor neurons derived from the allelic series ES cells reproduce molecular hallmarks of ALS disease (sense and antisense repeat RNA foci, repeat RNA foci localized to nucleoli, at least two of the five forms of dipeptide repeat proteins, and increased accumulation of intron-containing transcripts, supporting the use of the non-human animals disclosed herein as a disease model for neurodegenerative disease.

The quantitative PCR reactions for assays C, B, F, H, E, and D in Table 8 were repeated in two types of ESMNs: hypaxial-like motor neurons (MNs) and limb-like motor neurons (MNs). Hypaxial-like MNs innervate hypaxial MNs in models. Examples of muscles innervated by hypaxial MNs include the intercostal muscles, diaphragm, and muscles of the abdominal wall. Limb-like MNs are those which arise from the lateral motor column and innervate distal limb muscles such as those in the forelimb and hindlimb (Tibialis anterior, gastrocnemius and the gluteal muscles). Primarily hypaxial MNs are generated by the protocol that adds retinoic acid (RA) and sonic hedgehog agonist (SAG). Limb-like MNs can be generated by adding 1 µM purmorphamine on top of the RA and SAG we can generate limb-like MNs.

Figures 15A, 15B:
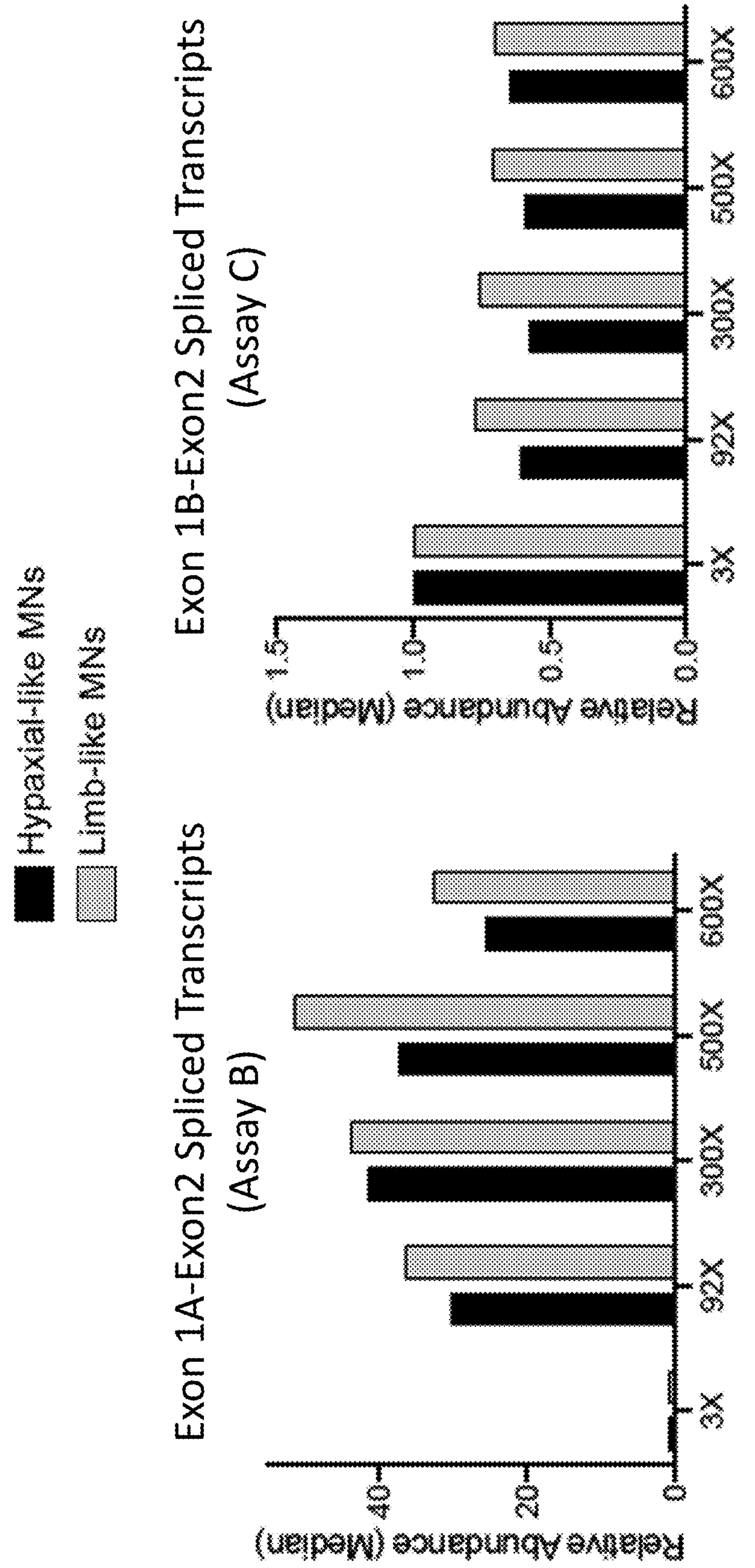
FIGS. 15A-15D are bar graphs showing expression levels (as determined by the TAQMAN® quantitative reverse transcription-coupled PCR (RT-qPCR) assays shown in the depiction of the C9orf72 locus at the top of each figure) of transcripts from the C9orf72 locus (y-axis) that are exon 1A-exon 2 spliced transcripts (FIG. 15A), that are exon 1B-exon 2 spliced transcripts (FIG. 15B), that contain intron sequence near exon 1A (FIG. 15C), and the retain intron sequence near exon 1B (FIG. 15D) in embryonic-stem-cellderived motor neurons (ESMNs) that are hypaxial-like motor neurons or limb-like motor neurons and are heterozygous for a modified C9orf72 locus comprising 3, 92, 300, 500, or 600 repeats of the hexanucleotide sequence set forth as SEQ ID NO: 1 relative to ESMNs comprising 3 repeats of the hexanucleotide sequence set forth as SEQ ID NO: 1.
Figures 15C, 15D:
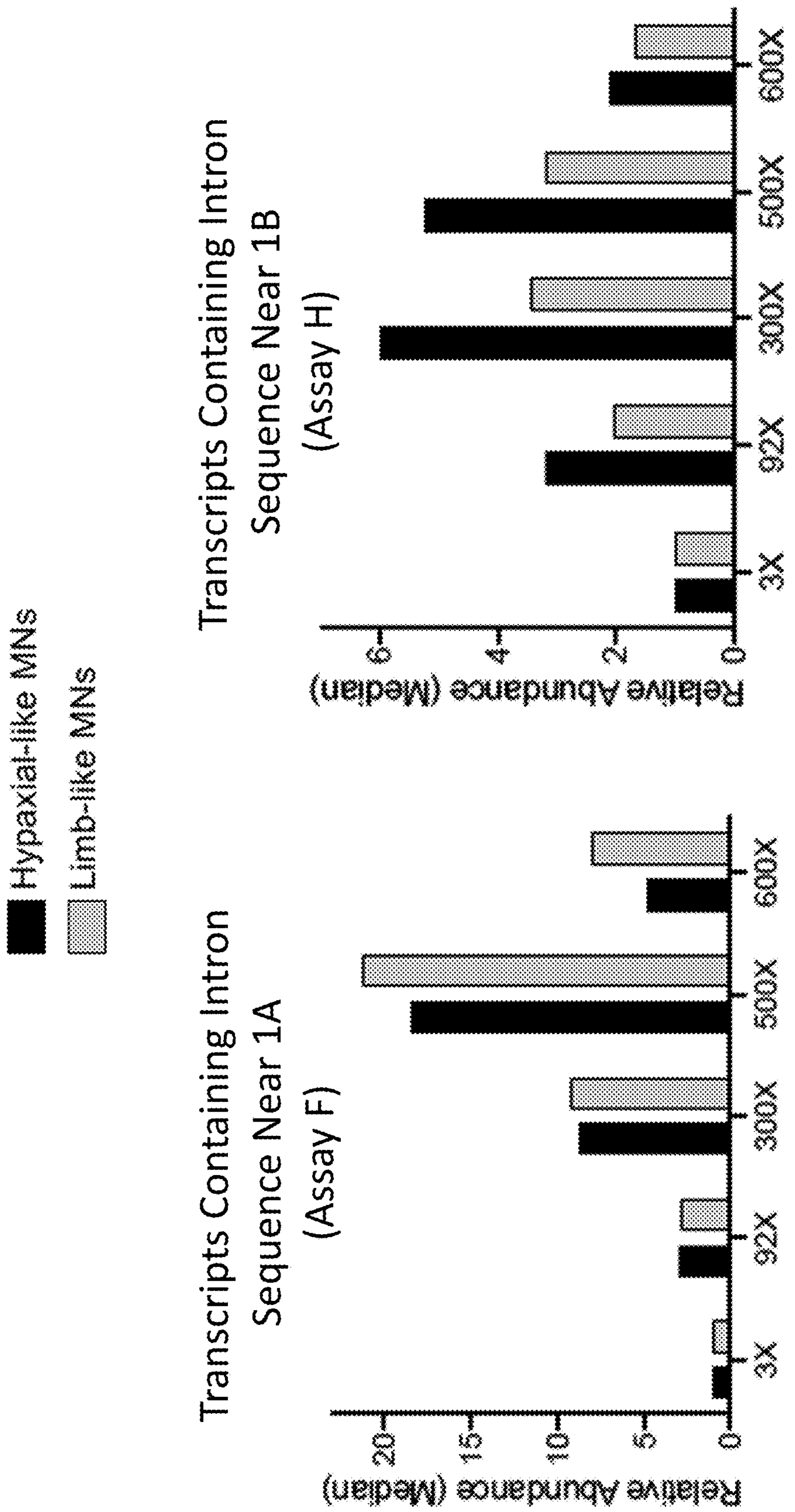
Figures 15E, 15F:
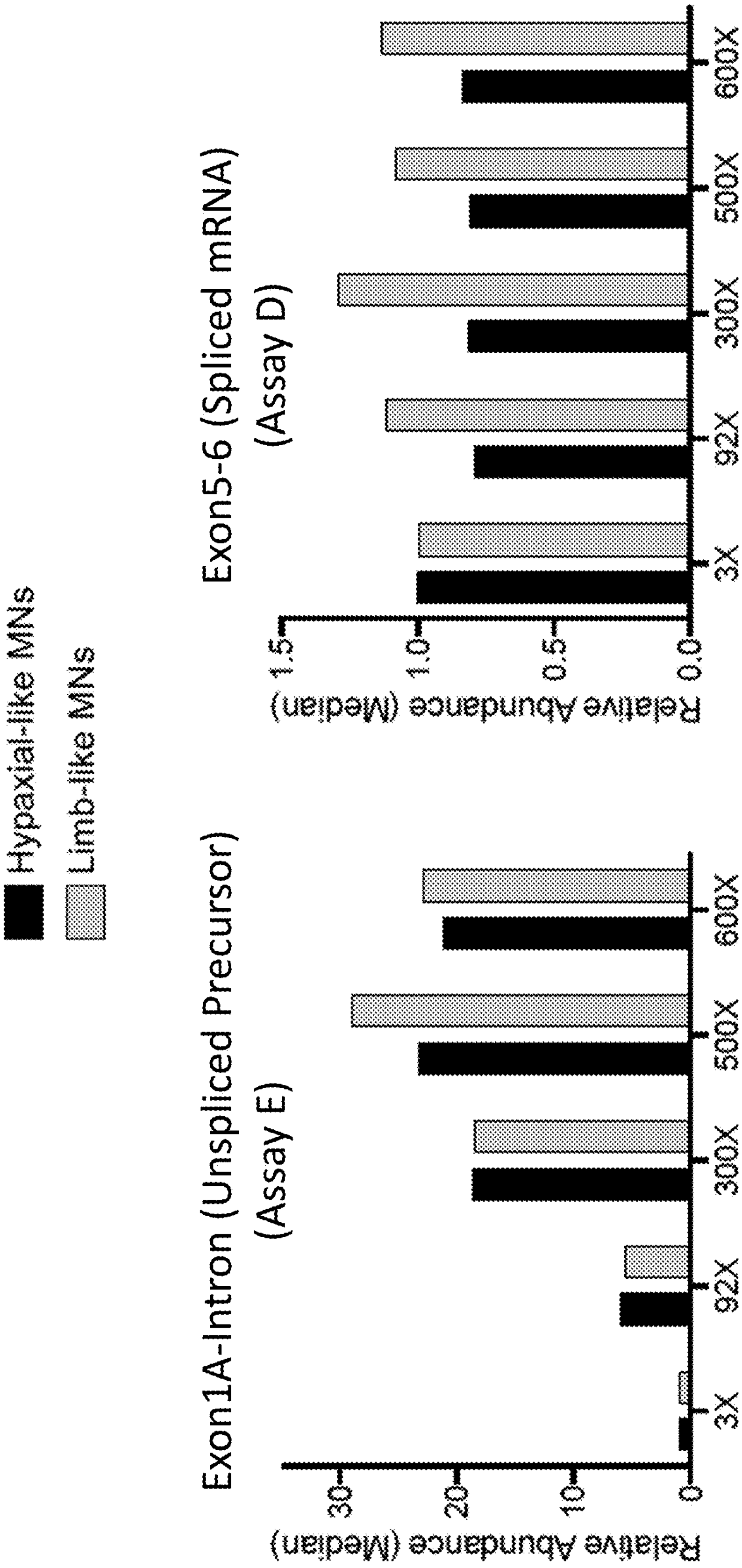
FIGS. 15E-15F are bar graphs showing expression levels (as determined by the TAQMAN® quantitative reverse transcription-coupled PCR (RT-qPCR) assays shown in the depiction of the C9orf72 locus at the top of each figure) of transcripts from the C9orf72 locus (y-axis) that are unspliced precursor transcripts (FIG. 15E) or spliced C9orf72 mRNAs (FIG. 15F) in embryonic-stem-cell-derived motor neurons (ESMNs) that are hypaxial-like motor neurons or limb-like motor neurons and are heterozygous for a modified C9orf72 locus comprising 3, 92, 300, 500, or 600 repeats of the hexanucleotide sequence set forth as SEQ ID NO: 1 relative to ESMNs comprising 3 repeats of the hexanucleotide sequence set forth as SEQ ID NO: 1.

Motor neurons comprising an allelic series of humanized C9orf72 allele with 3 repeats, 92 repeats, 300 repeats, 500 repeats, or 600 repeats of the $G_4C_2$ hexanucleotide sequence were tested ("G4C2" repeats disclosed as SEQ ID NOS 140-144, respectively, in order of appearance). As shown in FIG. 15A and FIG. 15B, larger $G_4C_2$ repeat (SEQ ID NO: 1) expansions had increased use of exon 1A and decreased use of exon 1B. As shown in FIG. 15C and FIG. 15D, ESMNs comprising the hexanucleotide repeat expansion sequence at the C9orf72 locus showed increased expression of C9orf72 mRNA transcripts that retain intron 1 sequences. As shown in FIG. 15E, larger G4C2 repeat (SEQ ID NO: 1) expansions had increased expression of unspliced precursors. As shown in FIG. 15F, expression of spliced C9orf72 mRNA did not change much with repeat size.

Example 3. Generation of Mice Comprising Hexanucleotide Repeat Expansion at the C9orf72 Gene Locus F0 mice were generated using the VELOCIMOUSE® method using the 300× repeat ES cell clones described in Example 1. See, e.g., U.S. Pat. Nos. 7,576,259; 7,659,442; 7,294,754; US 2008/0078000; and Poueymirou et al. (2007) *Nat. Biotechnol.* 25(1):91-99, each of which is herein incorporated by reference in its entirety for all purposes. In the VELOCIMOUSE® method, targeted mouse embryonic stem (ES) cells are injected through laser-assisted injection into pre-morula stage embryos, e.g., eight-cell-stage embryos, which efficiently yields F0 generation mice that are fully ES-cell-derived.

Figure 14A:
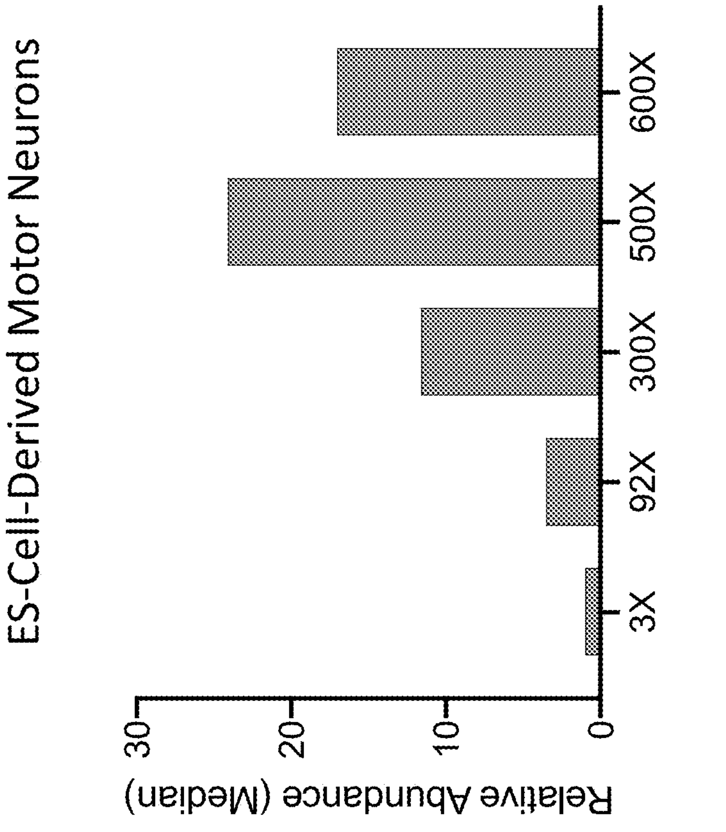
FIGS. 14A-14B are bar graphs showing expression levels (as determined by the TAQMAN® quantitative reverse transcription-coupled PCR (RT-qPCR) assays shown in the depiction of the C9orf72 locus at the top of each figure) of transcripts from the C9orf72 locus (y-axis) that contain intron sequence near exon 1A in embryonic-stem-cell-derived motor neurons (ESMNs) that are heterozygous for a modified C9orf72 locus comprising 3, 92, 300, 500, or 600 repeats of the hexanucleotide sequence set forth as SEQ ID NO: 1 relative to ESMNs comprising 3 repeats of the hexanucleotide sequence set forth as SEQ ID NO: 1 (FIG. 14A) or in brain stem and spinal cord samples from mice that are heterozygous for a modified (humanized) C9orf72 locus comprising 3 or 300 repeats of the hexanucleotide sequence set forth as SEQ ID NO: 1 relative to brain stem and spinal cord samples from mice comprising 3 repeats of the hexanucleotide sequence set forth as SEQ ID NO: 1 (FIG. 14B).
Figure 14B:
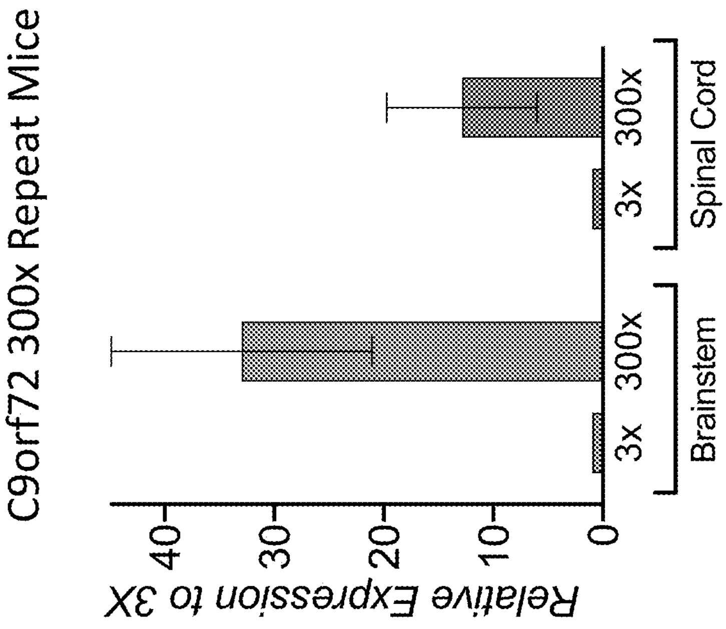

RNA transcripts from brain stem and spinal cord samples from the C9orf72 300× repeat mice (i.e., the humanized C9orf72 allele with 300 repeats of the $G_4C_2$ hexanucleotide sequence) (SEQ ID NO: 142) and control C9orf72 3× repeat mice (i.e., the humanized C9orf72 allele with 3 repeats of the $G_4C_2$ hexanucleotide sequence (SEQ ID NO: 140)) were tested as in Example 3. RNA foci and dipeptide repeat protein levels were evaluated in brain stem and spinal cord samples from the C9orf72 300× repeat mice as in Example 3. As shown in FIG. 14B, brain stem and spinal cord samples from the C9orf72 300× repeat mice showed increased expression of C9orf72 mRNA transcripts that retain intron 1 sequences. In addition, the spinal cord samples (i.e., L4/L5 lumbar spinal cord motor neurons) were tested for and were shown to contain nuclear and cytoplasmic sense and antisense C9orf72 RNA foci (data not shown). Similarly, these samples had an increased presence of dipeptide repeat proteins (polyGA) translated (through RAN translation, a non-AUG mechanism) from transcripts of the hexanucleotide repeat sequence (data not shown).

Likewise, embryonic-stem-cell-derived motor neurons (ESMNs) comprising an allelic series of humanized C9orf72 allele with 3 repeats, 92 repeats, 300 repeats, 500 repeats, or 600 repeats of the $G_4C_2$ hexanucleotide sequence were tested ("G4C2" repeats disclosed as SEQ ID NOS 140-144, respectively, in order of appearance). As shown in FIG. 14A, ESMNs comprising the hexanucleotide repeat expansion sequence at the C9orf72 locus showed increased expression of C9orf72 mRNA transcripts that retain intron 1 sequences. The ESMNs containing $G_4C_2$ repeat (SEQ ID NO: 1) expansions also contained nuclear and cytoplasmic sense and antisense C9orf72 RNA foci and an increased presence of dipeptide repeat proteins (polyGA) translated (through RAN translation, a non-AUG mechanism) from transcripts of the hexanucleotide repeat sequence (data not shown).

F0 mice were also generated having a mouse C9orf72 gene locus replaced with a human counterpart containing approximately 500 repeats or approximately 600 repeats of the GGGGCC (SEQ ID NO: 1) hexanucleotide using known methods.

Example 4. siRNAs Targeting C9orf72-Repeat-Adjacent Intron Sequences Reduce Intron-Containing RNA and Dipeptide Repeat Proteins Amyotrophic lateral sclerosis (ALS) and frontotemporal lobar degeneration (FTLD) are devastating neurodegenerative diseases that cause motor neuron disease in the case of ALS and dementia in the case of FTLD. Both are invariably fatal. ALS and FTLD can present as either a spontaneous or familial (i.e., genetic) disease. The most common genetic cause of ALS and FTLD is an expansion of a hexanucleotide repeat (GGGGCC; SEQ ID NO: 1) in the 5' non-coding part of the C9orf72 gene, which encodes a protein whose function is not fully understood. Unaffected people usually have between a few and a few dozen hexanucleotide repeats in their C9orf72 genes, while those that develop ALS and FTLD inherit a repeat expansion of hundreds to thousands of copies of the hexanucleotide repeat from only one of their parents. No mutations predicted to cause a loss of function of the C9orf72 protein have been linked to ALS and FTLD. These genetic observations suggest that C9orf72 ALS and FTLD are dominant genetic diseases that result from a gain of pathological function.

It is not known how the C9orf72 hexanucleotide repeat expansion causes motor neuron disease and dementia, but two universal postmortem pathological findings in C9orf72 ALS and FTLD patients are associated with the repeat expansion: (1) sense and antisense repeat-containing RNA can be visualized as distinct foci in neurons and other cells by fluorescent in situ hybridization; and (2) dipeptide repeat proteins—poly(glycine-alanine), poly(glycine-proline), poly(glycine-arginine), poly(alanine-proline), and poly(proline-arginine)—synthesized by repeat-associated non-AUG-dependent translation from the sense and antisense repeat-containing RNAs—can be detected in cells by immunohistochemistry. One disease hypothesis proposes that the repeat-containing RNAs, visualized as foci, disrupt cellular RNA metabolism by sequestering RNA binding proteins. A second disease hypothesis posits that the dipeptide repeat proteins exert wide-spread toxic effects on RNA metabolism, proteostasis, and nucleocytoplasmic transport. Both pathogenic mechanisms could contribute to disease. If C9orf72 repeat-containing RNA transcripts, either on their own or as templates for translation of dipeptide repeat proteins, promote pathogenesis in ALS and FTLD, then a general therapeutic strategy would be to destroy GGGGCC-repeat-containing RNA ("GGGGCC" disclosed as SEQ ID NO: 1) or abolish its ability to be translated into dipeptide repeat protein.

The C9orf72 gene produces transcripts from two transcription initiation sites. The upstream site initiates transcription with alternative non-coding exon 1A, while the downstream site initiates transcription with alternative exon 1B. Both exons 1A and 1B can be spliced to exon 2, which contains the start of the protein-coding sequence. Because the pathogenic hexanucleotide repeat expansion is located between exons 1A and 1B, transcription initiated from exon 1A can produce repeat-containing RNAs, while initiation from exon 1B cannot.

To model C9orf72 repeat expansion disease in mice, an allelic series was created in mouse embryonic stem (ES) cells in which a fragment from the human C9orf72 gene, including part of exon 1A, the intron sequence between 1A and 1B, all of exon 1B and part of the downstream intron, was placed precisely at its homologous position in one allele of the mouse C9orf72 gene. See, e.g., US 2018/0094267 and WO 2018/064600, each of which is herein incorporated by reference in its entirety for all purposes. A series of GGGGCC (SEQ ID NO: 1) repeat expansions were placed at the position found in the human gene that ranged from the normal three repeats up to the pathological 600 repeats. See Example 1.

Mouse ES cell clones carrying the different repeat expansions were differentiated into motor neurons in culture to study the effects of the expansions on a cell type relevant to ALS. See Example 3. In examining the transcripts produced from the genetically modified humanized C9orf72 alleles it was found that there was a switch from exon 1B spliced transcripts, which predominate in the three repeat normal control, to increased appearance of exon 1A spliced transcripts in the alleles with longer repeat expansions. See FIG. 12A, FIG. 12B, FIG. 12E, and FIG. 12F. It was also observed the accumulation of unspliced intron-containing transcripts whose abundance was directly correlated with the length of the hexanucleotide repeat, suggesting a selfish feed-forward loop in which the longer the repeat expansion, the more repeat-containing transcripts are produced from the C9orf72 gene. See FIG. 12C, FIG. 12D, FIG. 12G, and FIG. 12H. Targeting the repeat-containing intronic transcripts for destruction or inactivation as templates for dipeptide repeat protein synthesis while sparing synthesis of the normal C9orf72 mRNA and protein would be expected to be a safe and effective therapeutic strategy for C9orf72 repeat expansion disease.

One possible approach to reducing C9orf72 repeat-containing RNAs is through the natural process of RNA interference, in which siRNAs direct cleavage of the target RNAs by the RNA-induced silencing complex followed by degradation of the RNA cleavage fragments by cellular nucleases. RNA interference is, however, a predominantly cytoplasmic process that would not be expected to act on RNAs retained in the nucleus. Intron-containing RNAs are usually short-lived, either as mRNA precursors, which are rapidly spliced into mature mRNAs, or as spliced-out introns, which are rapidly degraded in the nucleus. It is reasonable, therefore, to expect that intron-containing RNAs would not be available for targeting by RNA interference.

Figure 16A:
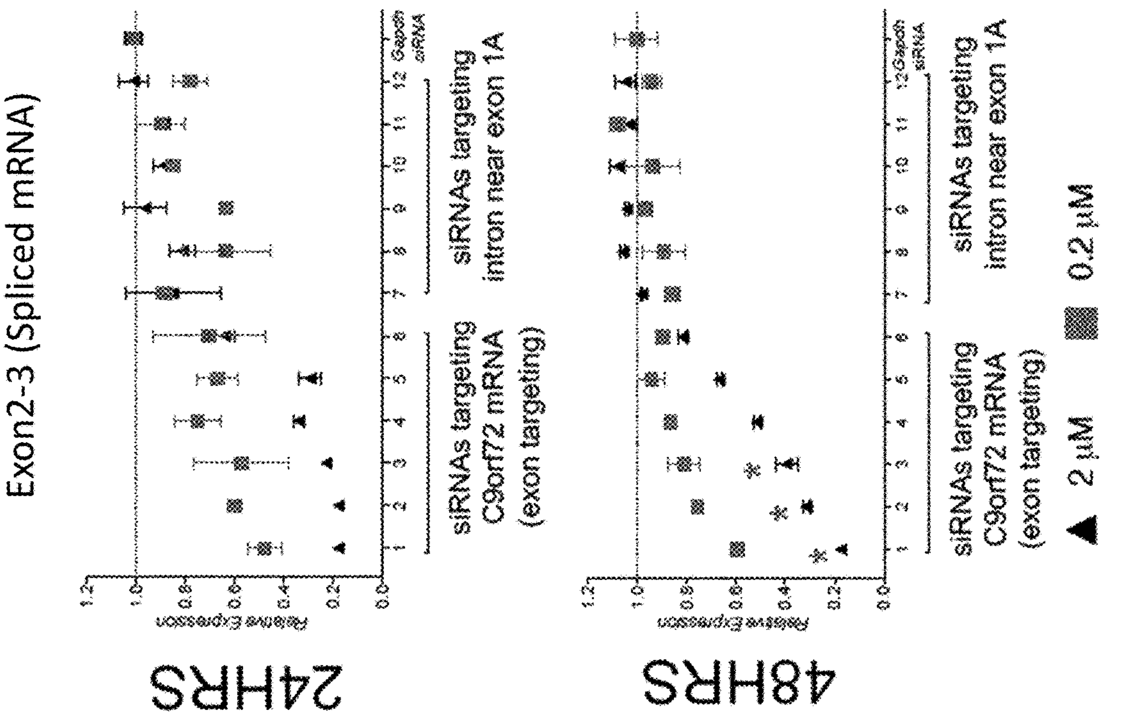
FIGS. 16A-16B are bar graphs showing expression levels (as determined by the TAQMAN® quantitative reverse transcription-coupled PCR (RT-qPCR) assays shown in the depiction of the C9orf72 locus at the top of each figure) of transcripts from the C9orf72 locus (y-axis) that are exon2-3 spliced transcripts (FIG. 16A) or that contain intron sequence near exon 1A (FIG. 16B) in embryonic-stem-cell-derived motor neurons (ESMNs) that are heterozygous for a modified C9orf72 locus comprising 300 repeats of the hexanucleotide sequence set forth as SEQ ID NO: 1 and were treated with siRNAs targeting intron 1 of C9orf72, with siRNAs targeting the spliced C9orf72 mRNA (exon 11 (siRNA 1), exon 5 (siRNAs 2 and 6), or exon 2 (siRNAs 3 and 5), or exon 9 (siRNA4)), or a control GAPDH siRNA at 24 hours and 48 hours after treatment. The asterisks indicate which samples correspond to those in the western blots in FIGS. 17A and 17B.
Figure 16B:
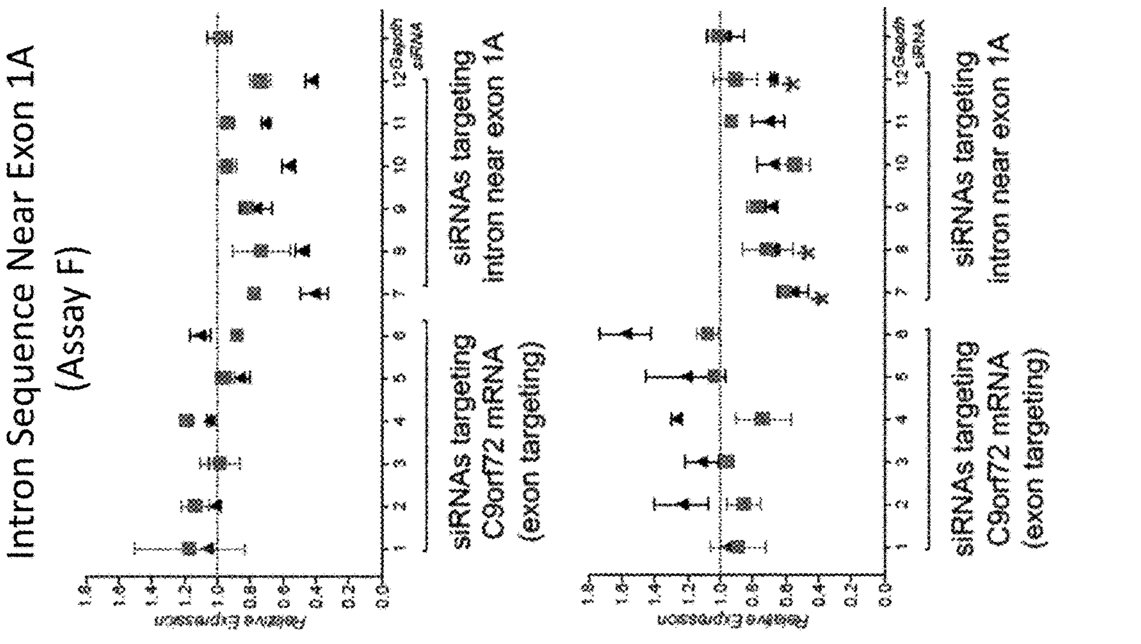

However, in an experiment in which mouse embryonic stem cells carrying a humanized C9orf72 gene having 300 repeats of the GGGGCC hexanucleotide (SEQ ID NO: 142) were treated with siRNAs that targeted C9orf72 RNA sequences, it was demonstrated that siRNAs that targeted intron sequences adjacent to the GGGGCC (SEQ ID NO: 1) repeat expansion promoted reduced accumulation of intron-containing C9orf72 RNAs by at least 60% (see FIG. 16B) while having no effect on the C9orf72 mature mRNA (see FIG. 16A).

The primers and probe used for the intron-containing RT-qPCR assay, measuring transcripts containing intron sequence near exon 1A, is assay F from Table 8. The primers and probe used for the exon2-3 RT-qPCR assay were purchased from ThermoFisher (assay Mm01216829_m1). The control GAPDH siRNA was purchased from ThermoFisher (Product #4390849).

siRNAs targeting the C9orf72 mature mRNA or the C9orf72 intron 5' of the hexanucleotide repeat were designed, synthesized, and assayed for activity in single dose screens in Neuro2a or BE(2)C cells as described in Examples 5 and 6.

The unmodified nucleotide sequence of the sense strand and the antisense strands of the siRNAs used to treat mouse embryonic stem cells carrying a humanized C9orf72 gene having 300 repeats of the GGGGCC hexanucleotide (SEQ ID NO: 142) in this example are shown in Table 10A. The modified nucleotide sequence of the sense strand and the antisense strands of the siRNAs used to treat mouse embryonic stem cells carrying a humanized C9orf72 gene having 300 repeats of the GGGGCC hexanucleotide (SEQ ID NO: 142) in this example are shown in Table 10B.

Figure 17B:
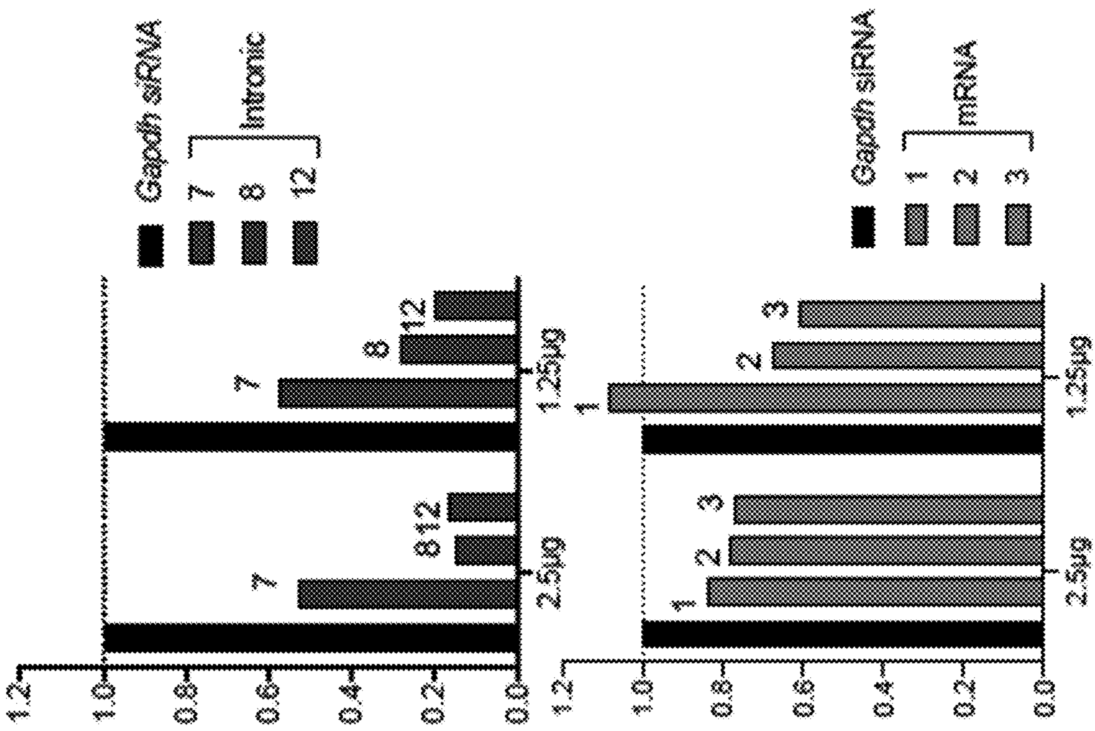
FIG. 17B shows quantification of the western slot blots in FIG. 17A.
Figure 17A:
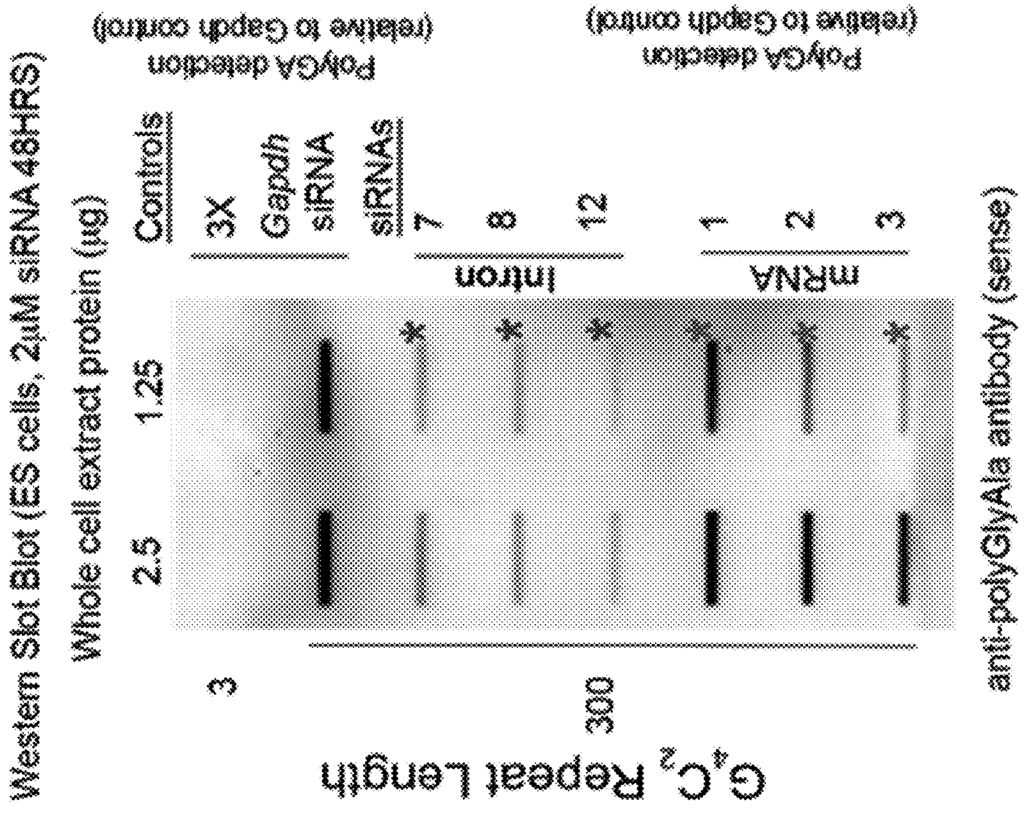
FIG. 17A is a western slot blot image of lysates of from embryonic-stem-cell-derived motor neurons (ESMNs) heterozygous for a modified C9orf72 locus comprising 300 repeats of the hexanucleotide sequence set forth as SEQ ID NO: 1 and treated with siRNAs targeting intron 1 of C9orf72, with siRNAs targeting the spliced C9orf72 mRNA (exon 11 (siRNA 1), exon 5 (siRNA 2), or exon 2 (siRNA 3)), or a control GAPDH siRNA at 48 hours after treatment. Lysates containing 1.25 μg or 2.5 μg total proteins were blotted with anti-poly-GlyAla antibody.

The intron-targeting siRNAs also reduced production of dipeptide repeat proteins by as much as 75%. See FIGS. 17A-17B. These unexpected experimental results indicate that the intron-containing RNAs that accumulate in cells with a C9orf72 hexanucleotide repeat expansion are susceptible to RNA interference. The results demonstrate that a significant fraction of the intron-containing C9orf72 RNAs responsible for dipeptide repeat protein synthesis resides in the cytoplasm. In contrast, siRNAs that targeted the C9orf72 mRNA protein coding sequence produced a strong knock down of the mRNA but had no effect on the intron-containing transcripts and did not appreciably reduce dipeptide repeat protein synthesis. See FIGS. 16A-16B. The divergence in results between the intron-targeting and mRNA-targeting siRNAs suggests that the two classes of targeted sequences are present on separate RNAs that are not covalently linked.

TABLE 10A

C9orf72 siRNAs.

| # | Duplex ID | Region Targeted | Sense Strand Sequence 5' to 3' | Antisense Strand Sequence 5' to 3' |
|---|---|---|---|---|
| 1 | AD-348904 | Exon 11 | GAAGACCUUUCUACACUAGUU (SEQ ID NO: 14) | AACUAGUGUAGAAAGGUCUUCCA (SEQ ID NO: 15) |
| 2 | AD-348136 | Exon 5 | UAGCUGAUACAGUACUCAAUU (SEQ ID NO: 16) | AAUUGAGUACUGUAUCAGCUAUA (SEQ ID NO: 17) |
| 3 | AD-347612 | Exon 2 | CAAGACAGAGAUUGCUUUAAU (SEQ ID NO: 18) | AUUAAAGCAAUCUCUGUCUUGGC (SEQ ID NO: 19) |
| 4 | AD-348639 | Exon 9 | GUCUUACACAGAGACACUCUA (SEQ ID NO: 20) | UAGAGUGUCUCUGUGUAAGACAU (SEQ ID NO: 21) |
| 5 | AD-347606 | Exon 2 | UGUUGCCAAGACAGAGAUUGU (SEQ ID NO: 22) | ACAAUCUCUGUCUUGGCAACAGC (SEQ ID NO: 23) |
| 6 | AD-348140 | Exon 5 | UGAUACAGUACUCAAUGAUGA (SEQ ID NO: 24) | UCAUCAUUGAGUACUGUAUCAGC (SEQ ID NO: 25) |
| 7 | AD-463863 | Intron 1 | AAAGACCUGAUAAAGAUUAAU (SEQ ID NO: 2) | AUUAAUCUUUAUCAGGUCUUUUC (SEQ ID NO: 3) |
| 8 | AD-463862 | Intron 1 | AAAAGACCUGAUAAAGAUUAA (SEQ ID NO: 4) | UUAAUCUUUAUCAGGUCUUUUCU (SEQ ID NO: 5) |
| 9 | AD-463869 | Intron 1 | CUGAUAAAGAUUAACCAGAAU (SEQ ID NO: 6) | AUUCUGGUUAAUCUUUAUCAGGU (SEQ ID NO: 7) |
| 10 | AD-463873 | Intron 1 | AAAGAUUAACCAGAAGAAAAU (SEQ ID NO: 8) | AUUUUCUUCUGGUUAAUCUUUAU (SEQ ID NO: 9) |
| 11 | AD-463872 | Intron 1 | AUAAAGAUUAACCAGAAGAAA (SEQ ID NO: 10) | UUUCUUCUGGUUAAUCUUUAUCA (SEQ ID NO: 11) |
| 12 | AD-463860 | Intron 1 | AGAAAAGACCUGAUAAAGAUU (SEQ ID NO: 12) | AAUCUUUAUCAGGUCUUUUCUUG (SEQ ID NO: 13) |

TABLE 10B

| C9orf72 siRNAs. | | | | | |
|---|---|---|---|---|---|
| Duplex ID | Name | Target | Strand | Sequence 5' to 3' | SEQ ID NO: |
| AD-347606 | siRNA #5 | Exon 2 | sense | usgsuugcCfaAfGfAfcagagauuguL96 | 146 |
| | | | antis | asCfsaauc(Tgn)cugucuUfgGfcaacasgsc | 147 |
| AD-347612 | siRNA #3 | Exon 2 | sense | csasagacAfgAfGfAfuugcuuuaauL96 | 148 |
| | | | antis | asUfsuaaa(Ggn)caaucuCfuGfucuugsgsc | 149 |
| AD-348136 | siRNA #2 | Exon 5 | sense | usasgcugAfuAfCfAfguacucaauuL96 | 150 |
| | | | antis | asAfsuuga(Ggn)uacuguAfuCfagcuasusa | 151 |
| AD-348140 | siRNA #6 | Exon 5 | sense | usgsauacAfgUfAfCfucaaugaugaL96 | 152 |
| | | | antis | usCfsauca(Tgn)ugaguaCfuGfuaucasgsc | 153 |
| AD-348639 | siRNA #4 | Exon 9 | sense | gsuscuuaCfaCfAfGfagacacucuaL96 | 154 |
| | | | antis | usAfsgagu(Ggn)ucucugUfgUfaagacsasu | 155 |
| AD-348904 | siRNA #1 | Exon 11 | sense | gsasagacCfuUfUfCfuacacuaguuL96 | 156 |
| | | | antis | asAfscuag(Tgn)guagaaAfgGfucuucscsa | 157 |
| AD-463860 | siRNA #12 | Intron 1A | sense | asgsaaaaGfaCfCfUfgauaaagauuL96 | 158 |
| | | | antis | asAfsucuUfuAfUfcaggUfcUfuuucusug | 159 |
| AD-463862 | siRNA #8 | Intron 1A | sense | asasaagaCfcUfGfAfuaaagauuaaL96 | 160 |
| | | | antis | usUfsaauCfuUfUfaucaGfgUfcuuuuscsu | 161 |
| AD-463863 | siRNA #7 | Intron 1A | sense | asasagacCfuGfAfUfaaagauuaauL96 | 162 |
| | | | antis | asUfsuaaUfcUfUfuaucAfgGfucuuusus c | 163 |
| AD-463869 | siRNA #9 | Intron 1A | sense | csusgauaAfaGfAfUfuaaccagaauL96 | 164 |
| | | | antis | asUfsucuGfgUfUfaaucUfuUfaucagsgsu | 165 |
| AD-463872 | siRNA #11 | Intron 1A | sense | asusaaagAfuUfAfAfccagaagaaaL96 | 166 |
| | | | antis | usUfsucuUfcUfGfguuaAfuCfuuuauscsa | 167 |
| AD-463873 | siRNA #10 | Intron 1A | sense | asasagauUfaAfCfCfagaagaaaauL96 | 168 |
| | | | antis | asUfsuuuCfuUfCfugguUfaAfucuuusasu | 169 |

The sense strands of SEQ ID NOs: 2, 4, 6, 8, 10, 12, 14, 16, 18, 20, 22, and 24 comprised all of the following characteristics/modifications: (a) a length of 21 nucleotides, (b) 2'-O-methyl modifications at positions 1-6, 8, and 12-21 (counting from the 5' end); (c) 2'-F modifications at positions 7 and 9-11 (counting from the 5' end); (d) phosphorothioate internucleotide linkages between nucleotide positions 1 and 2 and between nucleotide positions 2 and 3 (counting from the 5' end), and (e) an asialoglycoprotein receptor (ASGPR) ligand attached to the 3'-end, wherein the ASGPR ligand comprises three GalNAc derivatives attached through a trivalent branched linker.

The antisense strands of SEQ ID NOS: 3, 5, 7, 9, 11, and 13 comprised all of the following characteristics/modifications: (a) a length of 23 nucleotides; (b) 2'-O-methyl modifications at positions 1, 3-5, 7, 10-13, 15, and 17-23 (counting from the 5' end); (c) 2'-F modifications at positions 2, 6, 8, 9, 14, and 16 (counting from the 5' end); and (d) phosphorothioate internucleotide linkages between nucleotide positions 1 and 2, between nucleotide positions 2 and 3, between nucleotide positions 21 and 22, and between nucleotide positions 22 and 23 (counting from the 5' end).

The antisense strands of SEQ ID NOS: 15, 17, 19, 21, 23, and 25 comprised all of the following characteristics/modifications: (a) a length of 23 nucleotides; (b) 2'-O-methyl modifications at positions 1, 3-6, 8-13, 15, and 17-23; (c) 2'-F modifications at positions 2, 14, and 16; (d) a glycol nucleic acid (GNA) at position 7; and (e) phosphorothioate internucleotide linkages between nucleotide positions 1 and 2, between nucleotide positions 2 and 3, between nucleotide positions 21 and 22, and between nucleotide positions 22 and 23 (counting from the 5' end).

Each of the double-stranded RNAi agents in Tables 10A and 10B comprised a two-nucleotide overhang at the 3'-end of the antisense strand and a blunt end at the 5' end of the antisense strand.

Example 5. RNAi Agent Design, Synthesis, Selection, and In Vitro Evaluation

This Example describes methods for the design, synthesis, selection, and in vitro evaluation of C9orf72 RNAi agents.

Source of Reagents

Where the source of a reagent is not specifically given herein, such reagent can be obtained from any supplier of reagents for molecular biology at a quality/purity standard for application in molecular biology.

Bioinformatics siRNAs targeting the human C9orf72 transcript (C9orf72; human NCBI refseqID NM_001256054; NCBI GeneID: 203228) were designed using custom R and Python scripts. The human NM_001256054 mRNA has a length of 3356 bases.

Detailed lists of the unmodified C9orf72 sense and antisense strand nucleotide sequences are shown in Table 12. Detailed lists of the modified C9orf72 sense and antisense strand nucleotide sequences are shown in Table 13.

siRNAs targeting the intron between exons 1a and 1b in the human C9orf72 gene (GenBank Accession Number NC_000009.12) were designed using custom R and Python scripts. Detailed lists of the unmodified C9orf72 sense and antisense strand nucleotide sequences are shown in Tables 14 and 19. Detailed lists of the modified C9orf72 sense and antisense strand nucleotide sequences are shown in Tables 15 and 20.

It is to be understood that, throughout the application, a duplex name without a decimal is equivalent to a duplex name with a decimal which merely references the batch number of the duplex. For example, AD-347430 is equivalent to AD-347430.1.

In Vitro Cos-7 (Dual-Luciferase psiCHECK2 Vector), BE(2)-C, and Neuro-2a Screening Cell Culture and Transfections:

Cos-7 (ATCC) were transfected by adding 5 µl of 1 ng/ul, diluted in Opti-MEM, C9orf72 intron 1 psiCHECK2 vector (Blue Heron Biotechnology), 4.9 µl of Opti-MEM plus 0.1 µl of Lipofectamine 2000 per well (Invitrogen, Carlsbad Calif. cat #11668-019) to 5 µl of siRNA duplexes per well, with 4 replicates of each siRNA duplex, into a 384-well plate, and incubated at room temperature for 15 minutes. Thirty-five µl of Dulbecco's Modified Eagle Medium (ThermoFisher) containing ~$5\times10^3$ cells were then added to the siRNA mixture. Cells were incubated for 48 hours followed by Firefly (transfection control) and Renilla (fused to target sequence) luciferase measurements. Three dose experiments were performed at 10 nM, 1 nM, and 0.1 nM.

BE(2)-C(ATCC) were transfected by adding 4.9 µl of Opti-MEM plus 0.1 µl of RNAiMAX per well (Invitrogen, Carlsbad Calif. cat #13778-150) to 5 µl of siRNA duplexes per well, with 4 replicates of each siRNA duplex, into a 384-well plate, and incubated at room temperature for 15 minutes. Forty µl of 1:1 mixture of Minimum Essential Medium and F12 Medium (ThermoFisher) containing ~$5\times10^3$ cells were then added to the siRNA mixture. Cells were incubated for 48 hours prior to RNA purification. Two dose experiments were performed at 10 nM and 0.1 nM.

Neuro-2a (ATCC) were transfected by adding 4.9 µl of Opti-MEM plus 0.1 µl of RNAiMAX per well (Invitrogen, Carlsbad Calif. cat #13778-150) to 5 µl of siRNA duplexes per well, with 4 replicates of each siRNA duplex, into a 384-well plate, and incubated at room temperature for 15 minutes. Forty µl of Minimum Essential Medium (ThermoFisher) containing ~$5\times10^3$ cells were then added to the siRNA mixture. Cells were incubated for 48 hours prior to RNA purification. Two dose experiments were performed at 10 nM and 0.1 nM.

Total RNA Isolation Using DYNABEADS mRNA Isolation Kit:

RNA was isolated using an automated protocol on a BioTek-EL406 platform using DYNABEADs (Invitrogen, cat #61012). Briefly, 70 µl of Lysis/Binding Buffer and 10 ul of lysis buffer containing 3 µl of magnetic beads were added to the plate with cells. Plates were incubated on an electromagnetic shaker for 10 minutes at room temperature and then magnetic beads were captured and the supernatant was removed. Bead-bound RNA was then washed 2 times with 150 µl Wash Buffer A and once with Wash Buffer B. Beads were then washed with 150 µl Elution Buffer, re-captured and supernatant removed.

cDNA Synthesis Using ABI High Capacity cDNA Reverse Transcription Kit (Applied Biosystems, Foster City, CA, Cat #4368813):

Ten µl of a master mix containing 1 µl× Buffer, 0.4 ul 25× dNTPs, 1 µl 10× Random primers, 0.5 µl Reverse Transcriptase, 0.5 µl RNase inhibitor and 6.6 µl of $H_2O$ per reaction was added to RNA isolated above. Plates were sealed, mixed, and incubated on an electromagnetic shaker for 10 minutes at room temperature, followed by 2h 37° C.

Real Time PCR:

Two µl of cDNA and 5 µl Lightcycler 480 probe master mix (Roche Cat #04887301001) were added to either 0.5 µl of Human GAPDH TaqMan Probe (4326317E) and 0.5 µl C9orf72 Human probe (Hs00376619_ml, Thermo) or 0.5 µl Mouse GAPDH TaqMan Probe (4352339E) and 0.5 µl C9orf72 Mouse probe (Mm01216837_ml, Thermo) per well in a 384 well plates (Roche cat #04887301001). Real time PCR was done in a LightCycler480 Real Time PCR system (Roche). Each duplex was tested at least two times and data were normalized to cells transfected with a non-targeting control siRNA. To calculate relative fold change, real time data were analyzed using the ΔΔCt method and normalized to assays performed with cells transfected with a non-targeting control siRNA.

The results of the screening of the dsRNA agents listed in Tables 12 and 13 in Neuro2a cells are shown in Table 16. The results of the screening of the dsRNA agents listed in Tables 12 and 13 in BE(2)c cells are shown in Table 17. The results of the screening of the dsRNA agents listed in Tables 14 and 15 in Cos7 cells are shown in Table 18.

TABLE 11

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | Adenosine-3'-phosphate |
| Ab | beta-L-adenosine-3'-phosphate |
| Abs | beta-L-adenosine-3'-phosphorothioate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cbs | beta-L-cytidine-3'-phosphorothioate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide, modified or unmodified |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol Hyp-(GalNAc-alkyl)3 |
| Y34 | 2-hydroxymethyl-tetrahydrofurane-4-methoxy-3-phosphate (abasic 2'-OMe furanose) |
| Y44 | inverted abasic DNA (2-hydroxymethyl-tetrahydrofurane-5-phosphate) |
| (Agn) | Adenosine-glycol nucleic acid (GNA) |
| (Cgn) | Cytidine-glycol nucleic acid (GNA) |
| (Ggn) | Guanosine-glycol nucleic acid (GNA) |

TABLE 11-continued

| Abbreviations of nucleotide monomers used in nucleic acid sequence representation. It will be understood that these monomers, when present in an oligonucleotide, are mutually linked by 5'-3'-phosphodiester bonds. | |
|---|---|
| Abbreviation | Nucleotide(s) |
| (Tgn) | Thymidine-glycol nucleic acid (GNA) S-Isomer |
| P | Phosphate |
| VP | Vinyl-phosphonate |
| dA | 2'-deoxyadenosine-3'-phosphate |
| dAs | 2'-deoxyadenosine-3'-phosphorothioate |
| dC | 2'-deoxycytidine-3'-phosphate |
| dCs | 2'-deoxycytidine-3'-phosphorothioate |
| dG | 2'-deoxyguanosine-3'-phosphate |
| dGs | 2'-deoxyguanosine-3'-phosphorothioate |
| dT | 2'-deoxythymidine-3'-phosphate |
| dTs | 2'-deoxythymidine-3'-phosphorothioate |
| dU | 2'-deoxyuridine |
| dUs | 2'-deoxyuridine-3'-phosphorothioate |
| (Ahd) | 2'-O-hexadecyl-adenosine-3'-phosphate |
| (Ahds) | 2'-O-hexadecyl-adenosine-3'-phosphorothioate |
| (Chd) | 2'-O-hexadecyl-cytidine-3'-phosphate |
| (Chds) | 2'-O-hexadecyl-cytidine-3'-phosphorothioate |
| (Ghd) | 2'-O-hexadecyl-guanosine-3'-phosphate |
| (Ghds) | 2'-O-hexadecyl-guanosine-3'-phosphorothioate |
| (Uhd) | 2'-O-hexadecyl-uridine-3'-phosphate |
| (Uhds) | 2'-O-hexadecyl-uridine-3'-phosphorothioate |

TABLE 12

Unmodified Sense and Antisense Strand Sequences of dsRNA Agents Targeting the Coding Region of C9orf72

| Duplex Name | Sense Sequence 5' to 3' | SEQ ID NO: | Source and Range | Range in NM_ 001256054.2 | Antisense Sequence 5' to 3' | SEQ ID NO: | Source and Range | Range in NM_ 001256054.2 |
|---|---|---|---|---|---|---|---|---|
| AD-347430.1 | UGCGUCAAACAGCGACAAGUU | 170 | NM_001256054.2_35-55_s | 35-55 | AACUUGTCGCUGUUUGACGCACC | 171 | NM_001256054.2_33-55_as | 33-55 |
| AD-347432.1 | CGUCAAACAGCGACAAGUUCU | 172 | NM_001256054.2_37-57_C21U_s | 37-57 | AGAACUTGUCGCUGUUUGACGCA | 173 | NM_001256054.2_35-57_G1A_as | 35-57 |
| AD-347454.1 | CCCACGUAAAAGAUGACGCUU | 174 | NM_001256054.2_59-79_s | 59-79 | AAGCGUCAUCUUUUACGUGGGCG | 175 | NM_001256054.2_57-79_as | 57-79 |
| AD-347455.1 | CCACGUAAAAGAUGACGCUUU | 176 | NM_001256054.2_60-80_G21U_s | 60-80 | AAAGCGTCAUCUUUUACGUGGGC | 177 | NM_001256054.2_58-80_C1A_as | 58-80 |
| AD-347570.1 | AGUGAUGUCGACUCUUUGCCU | 178 | NM_001256054.2_199-219_C21U_s | 199-219 | AGGCAAAGAGUCGACAUCACUGC | 179 | NM_001256054.2_197-219_G1A_as | 197-219 |
| AD-347602.1 | CAGCUGUUGCCAAGACAGAGA | 180 | NM_001256054.2_231-251_s | 231-251 | UCUCUGTCUUGGCAACAGCUGGA | 181 | NM_001256054.2_229-251_as | 229-251 |
| AD-347603.1 | AGCUGUUGCCAAGACAGAGAU | 182 | NM_001256054.2_232-252_s | 232-252 | AUCUCUGUCUUGGCAACAGCUGG | 183 | NM_001256054.2_230-252_as | 230-252 |
| AD-347606.1 | UGUUGCCAAGACAGAGAUUGU | 22 | NM_001256054.2_235-255_C21U_s | 235-255 | ACAAUCTCUGUCUUGGCAACAGC | 23 | NM_001256054.2_233-255_G1A_as | 233-255 |
| AD-347610.1 | GCCAAGACAGAGAUUGCUUUA | 184 | NM_001256054.2_239-259_s | 239-259 | UAAAGCAAUCUCUGUCUUGGCAA | 185 | NM_001256054.2_237-259_as | 237-259 |
| AD-347612.1 | CAAGACAGAGAUUGCUUUAAU | 18 | NM_001256054.2_241-261_G21U_s | 241-261 | AUUAAAGCAAUCUCUGUCUUGGC | 19 | NM_001256054.2_239-261_C1A_as | 239-261 |
| AD-347613.1 | AAGACAGAGAUUGCUUUAAGU | 186 | NM_001256054.2_242-262_s | 242-262 | ACUUAAAGCAAUCUCUGUCUUGG | 187 | NM_001256054.2_240-262_as | 240-262 |
| AD-347614.1 | AGACAGAGAUUGCUUUAAGUU | 188 | NM_001256054.2_243-263_G21U_s | 243-263 | AACUUAAAGCAAUCUCUGUCUUG | 189 | NM_001256054.2_241-263_C1A_as | 241-263 |
| AD-347615.1 | GACAGAGAUUGCUUUAAGUGU | 190 | NM_001256054.2_244-264_G21U_s | 244-264 | ACACUUAAAGCAAUCUCUGUCUU | 191 | NM_001256054.2_242-264_C1A_as | 242-264 |
| AD-347650.1 | UAGCAGCUACUUUUGCUUACU | 192 | NM_001256054.2_279-299_s | 279-299 | AGUAAGCAAAAGUAGCUGCUAAU | 193 | NM_001256054.2_277-299_as | 277-299 |
| AD-347674.1 | ACAAUAUUCUUGGUCCUAGAU | 194 | NM_001256054.2_303-323_G21U_s | 303-323 | AUCUAGGACCAAGAAUAUUGUCC | 195 | NM_001256054.2_301-323_C1A_as | 301-323 |

TABLE 12-continued

Unmodified Sense and Antisense Strand Sequences of dsRNA Agents Targeting the Coding Region of C9orf72

| Duplex Name | Sense Sequence 5' to 3' | SEQ ID NO: | Source and Range | Range in NM_ 001256054.2 | Antisense Sequence 5' to 3' | SEQ ID NO: | Source and Range | Range in NM_ 001256054.2 |
|---|---|---|---|---|---|---|---|---|
| AD-347676.1 | AAUAUUCUUGGUC CUAGAGUA | 196 | NM_001256054.2_305-325_s | 305-325 | UACUCUAGGACCAAGA AUAUUGU | 197 | NM_001256054.2_ 303-325_as | 303-325 |
| AD-347677.1 | AUAUUCUUGGUCC UAGAGUAA | 198 | NM_001256054.2_306-326_s | 306-326 | UUACUCTAGGACCAAG AAUAUUG | 199 | NM_001256054.2_ 304-326_as | 304-326 |
| AD-347716.1 | AGACAGAACAGGU ACUUCUCA | 200 | NM_001256054.2_345-365_s | 345-365 | UGAGAAGUACCUGUUC UGUCUUU | 201 | NM_001256054.2_ 343-365_as | 343-365 |
| AD-347773.1 | UAAAUGGAGAAAU CCUUCGAA | 202 | NM_001256054.2_402-422_s | 402-422 | UUCGAAGGAUUUCUCC AUUUAGA | 203 | NM_001256054.2_ 400-422_as | 400-422 |
| AD-347778.1 | GGAGAAAUCCUUC GAAAUGCA | 204 | NM_001256054.2_407-427_s | 407-427 | UGCAUUTCGAAGGAUU UCUCCAU | 205 | NM_001256054.2_ 405-427_as | 405-427 |
| AD-347842.1 | CAUUAAUCUUUGA UGGAAACU | 206 | NM_001256054.2_489-509_s | 489-509 | AGUUUCCAUCAAAGAU UAAUGAA | 207 | NM_001256054.2_ 487-509_as | 487-509 |
| AD-347843.1 | AUUAAUCUUUGAU GGAAACUU | 208 | NM_001256054.2_490-510_G21U_s | 490-510 | AAGUUUCCAUCAAAGA UUAAUGA | 209 | NM_001256054.2_ 488-510_C1A_as | 488-510 |
| AD-347863.1 | CAUAUGGACUAUC AAUUAUAU | 210 | NM_001256054.2_528-548_C21U_s | 528-548 | AUAUAATUGAUAGUCC AUAUGUG | 211 | NM_001256054.2_ 526-548_G1A_as | 526-548 |
| AD-347865.1 | UAUGGACUAUCAA UUAUACUU | 212 | NM_001256054.2_530-550_s | 530-550 | AAGUAUAAUUGAUAG UCCAUAUG | 213 | NM_001256054.2_ 528-550_as | 528-550 |
| AD-347867.1 | UGGACUAUCAAUU AUACUUCU | 214 | NM_001256054.2_532-552_C21U_s | 532-552 | AGAAGUAUAAUUGAU AGUCCAUA | 215 | NM_001256054.2_ 530-552_G1A_as | 530-552 |
| AD-347874.1 | UCAAUUAUACUUC CACAGACA | 216 | NM_001256054.2_539-559_s | 539-559 | UGUCUGTGGAAGUAUA AUUGAUA | 217 | NM_001256054.2_ 537-559_as | 537-559 |
| AD-347892.1 | ACAGAACUUAGUU UCUACCUU | 218 | NM_001256054.2_557-577_C21U_s | 557-577 | AAGGUAGAAACUAAG UUCUGUCU | 219 | NM_001256054.2_ 555-577_G1A_as | 555-577 |
| AD-347893.1 | CAGAACUUAGUUU CUACCUCU | 220 | NM_001256054.2_558-578_C21U_s | 558-578 | AGAGGUAGAAACUAA GUUCUGUC | 221 | NM_001256054.2_ 556-578_G1A_as | 556-578 |
| AD-347923.1 | GAGUGUGUGUUGA UAGAUUAA | 222 | NM_001256054.2_588-608_s | 588-608 | UUAAUCTAUCAACACA CACUCUA | 223 | NM_001256054.2_ 586-608_as | 586-608 |
| AD-347924.1 | AGUGUGUGUUGAU AGAUUAAU | 224 | NM_001256054.2_589-609_C21U_s | 589-609 | AUUAAUCUAUCAACAC ACACUCU | 225 | NM_001256054.2_ 587-609_G1A_as | 587-609 |
| AD-347926.1 | UGUGUGUUGAUAG AUUAACAU | 226 | NM_001256054.2_591-611_C21U_s | 591-611 | AUGUUAAUCUAUCAAC ACACACU | 227 | NM_001256054.2_ 589-611_G1A_as | 589-611 |

TABLE 12-continued

Unmodified Sense and Antisense Strand Sequences of dsRNA Agents Targeting the Coding Region of C9orf72

| Duplex Name | Sense Sequence 5' to 3' | SEQ ID NO: | Source and Range | Range in NM_ 001256054.2 | Antisense Sequence 5' to 3' | SEQ ID NO: | Source and Range | Range in NM_ 001256054.2 |
|---|---|---|---|---|---|---|---|---|
| AD-347942.1 | AACACAUAUAAUC CGGAAAGU | 228 | NM_001256054.2_607-627_G21U_s | 607-627 | ACUUUCCGGAUUAUAU GUGUUAA | 229 | NM_001256054.2_ 605-627_C1A_as | 605-627 |
| AD-347993.1 | UGUCCAGAAGAUU AUCUUAGA | 230 | NM_001256054.2_661-681_s | 661-681 | UCUAAGAUAAUCUUCU GGACAUU | 231 | NM_001256054.2_ 659-68 1_as | 659-681 |
| AD-348087.1 | GAACUGCUUUCAU CUAUGAAA | 232 | NM_001256054.2_755-775_s | 755-775 | UUUCAUAGAUGAAAGC AGUUCCA | 233 | NM_001256054.2_ 753-775_as | 753-775 |
| AD-348136.1 | UAGCUGAUACAGU ACUCAAUU | 16 | NM_001256054.2_804-824_G21U_s | 804-824 | AAUUGAGUACUGUAUC AGCUAUA | 17 | NM_001256054.2_ 802-824_C1A_as | 802-824 |
| AD-348140.1 | UGAUACAGUACUC AAUGAUGA | 24 | NM_001256054.2_808-828_s | 808-828 | UCAUCAUUGAGUACUG UAUCAGC | 25 | NM_001256054.2_ 806-828_as | 806-828 |
| AD-348176.1 | CUGUCAUGAAGGC UUUCUUCU | 234 | NM_001256054.2_844-864_s | 844-864 | AGAAGAAAGCCUUCAU GACAGCU | 235 | NM_001256054.2_ 842-864_as | 842-864 |
| AD-348231.1 | UGUUCCGUUGUAG UAGGUAGU | 236 | NM_001256054.2_899-919_C21U_s | 899-919 | ACUACCUACUACAACG GAACAGC | 237 | NM_001256054.2_ 897-919_G1A_as | 897-919 |
| AD-348341.1 | AUCAUUUAAAUAU GAGUCAGU | 238 | NM_001256054.2_1012-1032_G21U_s | 1012-1032 | ACUGACTCAUAUUUAA AUGAUGA | 239 | NM_001256054.2_ 1010-1032_C1A_as | 1010-1032 |
| AD-348377.1 | CCUGCUAAAGGAU UCAACUGU | 240 | NM_001256054.2_1048-1068_G21U_s | 1048-1068 | ACAGUUGAAUCCUUUA GCAGGCC | 241 | NM_001256054.2_ 1046-1068_C1A_as | 1046-1068 |
| AD-348487.1 | CACCCUGUCAUGA ACAUAUUU | 242 | NM_001256054.2_1158-1178_s | 1158-1178 | AAAUAUGUUCAUGACA GGGUGGC | 243 | NM_001256054.2_ 1156-1178_as | 1156-1178 |
| AD-348497.1 | UGAACAUAUUUAU AAUCAGCU | 244 | NM_001256054.2_1168-1188_G21U_s | 1168-1188 | AGCUGATUAUAAAUAU GUUCAUG | 245 | NM_001256054.2_ 1166-1188_C1A_as | 1166-1188 |
| AD-348500.1 | ACAUAUUUAUAAU CAGCGUAU | 246 | NM_001256054.2_1171-1191_G21U_s | 1171-1191 | AUACGCTGAUUAUAAA UAUGUUC | 247 | NM_001256054.2_ 1169-1191_C1A_as | 1169-1191 |
| AD-348502.1 | AUAUUUAUAAUCA GCGUAGAU | 248 | NM_001256054.2_1173-1193_s | 1173-1193 | AUCUACGCUGAUUAUA AAUAUGU | 249 | NM_001256054.2_ 1171-1193_as | 1171-1193 |
| AD-348578.1 | UCAGGAUACGAUC AUCUACAU | 250 | NM_001256054.2_1249-1269_C21U_s | 1249-1269 | AUGUAGAUGAUCGUA UCCUGAGC | 251 | NM_001256054.2_ 1247-1269_G1A_as | 1247-1269 |
| AD-348588.1 | AUCAUCUACACUG ACGAAAGU | 252 | NM_001256054.2_1259-1279_C21U_s | 1259-1279 | ACUUUCGUCAGUGUAG AUGAUCG | 253 | NM_001256054.2_ 1257-1279_G1A_as | 1257-1279 |
| AD-348590.1 | CAUCUACACUGAC | 254 | NM_001256054.2_1261- | 1261-1281 | AAGCUUTCGUCAGUGU | 255 | NM_001256054.2_ | 1259-1281 |

TABLE 12-continued

Unmodified Sense and Antisense Strand Sequences of dsRNA Agents Targeting the Coding Region of C9orf72

| Duplex Name | Sense Sequence 5' to 3' | SEQ ID NO: | Source and Range | Range in NM_ 001256054.2 | Antisense Sequence 5' to 3' | SEQ ID NO: | Source and Range | Range in NM_ 001256054.2 |
|---|---|---|---|---|---|---|---|---|
| | GAAAGCUU | | 1281_s | | AGAUGAU | | 1259-1281_as | |
| AD-348591.1 | AUCUACACUGACG AAAGCUUU | 256 | NM_001256054.2_1262-1282_s | 1262-1282 | AAAGCUTUCGUCAGUG UAGAUGA | 257 | NM_001256054.2_1260-1282_as | 1260-1282 |
| AD-348596.1 | CACUGACGAAAGC UUUACUCU | 258 | NM_001256054.2_1267-1287_C21U_s | 1267-1287 | AGAGUAAAGCUUUCGU CAGUGUA | 259 | NM_001256054.2_1265-1287_G1A_as | 1265-1287 |
| AD-348597.1 | ACUGACGAAAGCU UUACUCCU | 260 | NM_001256054.2_1268-1288_s | 1268-1288 | AGGAGUAAAGCUUUCG UCAGUGU | 261 | NM_001256054.2_1266-1288_as | 1266-1288 |
| AD-348598.1 | CUGACGAAAGCUU UACUCCUU | 262 | NM_001256054.2_1269-1289_G21U_s | 1269-1289 | AAGGAGTAAAGCUUUC GUCAGUG | 263 | NM_001256054.2_1267-1289_C1A_as | 1267-1289 |
| AD-348630.1 | UUUCAAGAUGUCU UACACAGA | 264 | NM_001256054.2_1301-1321_s | 1301-1321 | UCUGUGTAAGACAUCU UGAAAAA | 265 | NM_001256054.2_1299-1321_as | 1299-1321 |
| AD-348639.1 | GUCUUACACAGAG ACACUCUA | 20 | NM_001256054.2_1310-1330_s | 1310-1330 | UAGAGUGUCUCUGUGU AAGACAU | 21 | NM_001256054.2_1308-1330_as | 1308-1330 |
| AD-348672.1 | CUGGAUCAGGUCU UUCAGCUU | 266 | NM_001256054.2_1343-1363_G21U_s | 1343-1363 | AAGCUGAAAGACCUGA UCCAGGA | 267 | NM_001256054.2_1341-1363_C1A_as | 1341-1363 |
| AD-348708.1 | CUCAGAAGUACUU UCCUUGCA | 268 | NM_001256054.2_1379-1399_s | 1379-1399 | UGCAAGGAAAGUACUU CUGAGAG | 269 | NM_001256054.2_1377-1399_as | 1377-1399 |
| AD-348734.1 | UCUACUUGUCCUU CACAGAAA | 270 | NM_001256054.2_1405-1425_s | 1405-1425 | UUUCUGTGAAGGACAA GUAGAAA | 271 | NM_001256054.2_1403-1425_as | 1403-1425 |
| AD-348751.1 | GAAAAGCCUUGAC ACUAAUAA | 272 | NM_001256054.2_1422-1442_s | 1422-1442 | UUAUUAGUGUCAAGGC UUUUCUG | 273 | NM_001256054.2_1420-1442_as | 1420-1442 |
| AD-348787.1 | CCUUUAAAUCUCU UCGGAACU | 274 | NM_001256054.2_1479-1499_C21U_s | 1479-1499 | AGUUCCGAAGAGAUUU AAAGGGC | 275 | NM_001256054.2_1477-1499_G1A_as | 1477-1499 |
| AD-348788.1 | CUUUAAAUCUCUU CGGAACCU | 276 | NM_001256054.2_1480-1500_s | 1480-1500 | AGGUUCCGAAGAGAUU UAAAGGG | 277 | NM_001256054.2_1478-1500_as | 1478-1500 |
| AD-348789.1 | UUUAAAUCUCUUC GGAACCUU | 278 | NM_001256054.2_1481-1501_G21U_s | 1481-1501 | AAGGUUCCGAAGAGAU UUAAAGG | 279 | NM_001256054.2_1479-1501_C1A_as | 1479-1501 |
| AD-348836.1 | GGGCGAUCUUAAC AUAAUAAU | 280 | NM_001256054.2_1528-1548_s | 1528-1548 | AUUAUUAUGUUAAGA UCGCCCUC | 281 | NM_001256054.2_1526-1548_as | 1526-1548 |
| AD-348842.1 | UCUUAACAUAAUA AUGGCUCU | 282 | NM_001256054.2_1534-1554_s | 1534-1554 | AGAGCCAUUAUUAUGU UAAGAUC | 283 | NM_001256054.2_1532-1554_as | 1532-1554 |

TABLE 12-continued

Unmodified Sense and Antisense Strand Sequences of dsRNA Agents Targeting the Coding Region of C9orf72

| Duplex Name | Sense Sequence 5' to 3' | SEQ ID NO: | Source and Range | Range in NM_ 001256054.2 | Antisense Sequence 5' to 3' | SEQ ID NO: | Source and Range | Range in NM_ 001256054.2 |
|---|---|---|---|---|---|---|---|---|
| AD-348895.1 | UUAUCUUUGGAAGACCUUUCU | 284 | NM_001256054.2_1587-1607_s | 1587-1607 | AGAAAGGUCUUCCAAAGAUAAAA | 285 | NM_001256054.2_1585-1607_as | 1585-1607 |
| AD-348904.1 | GAAGACCUUUCUACACUAGUU | 14 | NM_001256054.2_1596-1616_G21U_s | 1596-1616 | AACUAGTGUAGAAAGGUCUUCCA | 15 | NM_001256054.2_1594-1616_C1A_as | 1594-1616 |
| AD-348905.1 | AAGACCUUUCUACACUAGUGU | 286 | NM_001256054.2_1597-1617_s | 1597-1617 | ACACUAGUGUAGAAAGGUCUUCC | 287 | NM_001256054.2_1595-1617_as | 1595-1617 |
| AD-348906.1 | AGACCUUUCUACACUAGUGUU | 288 | NM_001256054.2_1598-1618_G21U_s | 1598-1618 | AACACUAGUGUAGAAAGGUCUUC | 289 | NM_001256054.2_1596-1618_C1A_as | 1596-1618 |
| AD-348926.1 | GCAAGAACGAGAUGUUCUAAU | 290 | NM_001256054.2_1618-1638_s | 1618-1638 | AUUAGAACAUCUCGUUCUUGCAC | 291 | NM_001256054.2_1616-1638_as | 1616-1638 |
| AD-348930.1 | GAACGAGAUGUUCUAAUGACU | 292 | NM_001256054.2_1622-1642_s | 1622-1642 | AGUCAUTAGAACAUCUCGUUCUU | 293 | NM_001256054.2_1620-1642_as | 1620-1642 |
| AD-348931.1 | AACGAGAUGUUCUAAUGACUU | 294 | NM_001256054.2_1623-1643_s | 1623-1643 | AAGUCATUAGAACAUCUCGUUCU | 295 | NM_001256054.2_1621-1643_as | 1621-1643 |
| AD-348932.1 | ACGAGAUGUUCUAAUGACUUU | 296 | NM_001256054.2_1624-1644_s | 1624-1644 | AAAGUCAUUAGAACAUCUCGUUC | 297 | NM_001256054.2_1622-1644_as | 1622-1644 |
| AD-348957.1 | AUGUGUAACUUAAUAAGCCUA | 298 | NM_001256054.2_1649-1669_s | 1649-1669 | UAGGCUTAUUAAGUUACACAUUU | 299 | NM_001256054.2_1647-1669_as | 1647-1669 |
| AD-348959.1 | GUGUAACUUAAUAAGCCUAUU | 300 | NM_001256054.2_1651-1671_s | 1651-1671 | AAUAGGCUUAUUAAGUUACACAU | 301 | NM_001256054.2_1649-1671_as | 1649-1671 |
| AD-348961.1 | GUAACUUAAUAAGCCUAUUCU | 302 | NM_001256054.2_1653-1673_C21U_s | 1653-1673 | AGAAUAGGCUUAUUAAGUUACAC | 303 | NM_001256054.2_1651-1673_G1A_as | 1651-1673 |
| AD-348962.1 | UAACUUAAUAAGCCUAUUCCA | 304 | NM_001256054.2_1654-1674_s | 1654-1674 | UGGAAUAGGCUUAUUAAGUUACA | 305 | NM_001256054.2_1652-1674_as | 1652-1674 |
| AD-348963.1 | AACUUAAUAAGCCUAUUCCAU | 306 | NM_001256054.2_1655-1675_s | 1655-1675 | AUGGAATAGGCUUAUUAAGUUAC | 307 | NM_001256054.2_1653-1675_as | 1653-1675 |
| AD-349042.1 | GUUAAGUAAGUUACACUACAU | 308 | NM_001256054.2_1765-1785_G21U_s | 1765-1785 | AUGUAGTGUAACUUACUUAACUG | 309 | NM_001256054.2_1763-1785_C1A_as | 1763-1785 |
| AD-349048.1 | UAAGUUACACUACAGUUCUCA | 310 | NM_001256054.2_1771-1791_s | 1771-1791 | UGAGAACUGUAGUGUAACUUACU | 311 | NM_001256054.2_1769-1791_as | 1769-1791 |
| AD-349051.1 | GUUACACUACAGUUCUCACAA | 312 | NM_001256054.2_1774-1794_s | 1774-1794 | UUGUGAGAACUGUAGUGUAACUU | 313 | NM_001256054.2_1772-1794_as | 1772-1794 |

TABLE 12-continued

| Unmodified Sense and Antisense Strand Sequences of dsRNA Agents Targeting the Coding Region of C9orf72 | | | | | | | | |
|---|---|---|---|---|---|---|---|---|
| Duplex Name | Sense Sequence 5' to 3' | SEQ ID NO: | Source and Range | Range in NM_ 001256054.2 | Antisense Sequence 5' to 3' | SEQ ID NO: | Source and Range | Range in NM_ 001256054.2 |
| AD-349126.1 | CAGACCUAUGUUUACAAUAUA | 314 | NM_001256054.2_1867-1887_s | 1867-1887 | UAUAUUGUAAACAUAGGUCUGUA | 315 | NM_001256054.2_1865-1887_as | 1865-1887 |
| AD-349127.1 | AGACCUAUGUUUACAAUAUAA | 316 | NM_001256054.2_1868-1888_s | 1868-1888 | UUAUAUTGUAAACAUAGGUCUGU | 317 | NM_001256054.2_1866-1888_as | 1866-1888 |
| AD-349395.1 | GAUCAAGCAGAUGUUUAAUUU | 318 | NM_001256054.2_2165-2185_G21U_s | 2165-2185 | AAAUUAAACAUCUGCUUGAUCAA | 319 | NM_001256054.2_2163-2185_C1A_as | 2163-2185 |
| AD-349454.1 | UGGGAUUCAGUCUGUAGAAAU | 320 | NM_001256054.2_2224-2244_s | 2224-2244 | AUUUCUACAGACUGAAUCCCAGG | 321 | NM_001256054.2_2222-2244_as | 2222-2244 |
| AD-349474.1 | UGUCUAAUAGUUCUCUAUAGU | 322 | NM_001256054.2_2244-2264_s | 2244-2264 | ACUAUAGAGAACUAUUAGACAUU | 323 | NM_001256054.2_2242-2264_as | 2242-2264 |
| AD-349477.1 | CUAAUAGUUCUCUAUAGUCCU | 324 | NM_001256054.2_2247-2267_s | 2247-2267 | AGGACUAUAGAGAACUAUUAGAC | 325 | NM_001256054.2_2245-2267_as | 2245-2267 |
| AD-349610.1 | AGCCAAAUUGAAAUGUGCACU | 326 | NM_001256054.2_2419-2439_C21U_s | 2419-2439 | AGUGCACAUUUCAAUUUGGCUCA | 327 | NM_001256054.2_2417-2439_G1A_as | 2417-2439 |
| AD-349692.1 | UUCUUGCUAAGUCUUACCAUU | 328 | NM_001256054.2_2524-2544_G21U_s | 2524-2544 | AAUGGUAAGACUUAGCAAGAAGA | 329 | NM_001256054.2_2522-2544_C1A_as | 2522-2544 |
| AD-349847.1 | UGCAAUAGGCUAUAAGGAAUA | 330 | NM_001256054.2_2699-2719_s | 2699-2719 | UAUUCCTUAUAGCCUAUUGCAGG | 331 | NM_001256054.2_2697-2719_as | 2697-2719 |
| AD-349848.1 | GCAAUAGGCUAUAAGGAAUAU | 332 | NM_001256054.2_2700-2720_G21U_s | 2700-2720 | AUAUUCCUUAUAGCCUAUUGCAG | 333 | NM_001256054.2_2698-2720_C1A_as | 2698-2720 |
| AD-350108.1 | GAAAGGUCAUAAUAGCUUUCU | 334 | NM_001256054.2_3013-3033_C21U_s | 3013-3033 | AGAAAGCUAUUAUGACCUUUCAC | 335 | NM_001256054.2_3011-3033_G1A_as | 3011-3033 |
| AD-350109.1 | AAAGGUCAUAAUAGCUUUCCU | 336 | NM_001256054.2_3014-3034_C21U_s | 3014-3034 | AGGAAAGCUAUUAUGACCUUUCA | 337 | NM_001256054.2_3012-3034_G1A_as | 3012-3034 |
| AD-350179.1 | AACUAGAUGACUGUUGUACUU | 338 | NM_001256054.2_3084-3104_G21U_s | 3084-3104 | AAGUACAACAGUCAUCUAGUUCA | 339 | NM_001256054.2_3082-3104_C1A_as | 3082-3104 |
| AD-350197.1 | CUGUAGCUCAGUCAUUUAAAA | 340 | NM_001256054.2_3102-3122_s | 3102-3122 | UUUUAAAUGACUGAGCUACAGUA | 341 | NM_001256054.2_3100-3122_as | 3100-3122 |
| AD-350270.1 | CUGGUUUAUUGUACUGUUAUA | 342 | NM_001256054.2_3211-3231_s | 3211-3231 | UAUAACAGUACAAUAAACCAGCC | 343 | NM_001256054.2_3209-3231_as | 3209-3231 |
| AD-350329.1 | AUGUGUAAACAUU | 344 | NM_001256054.2_3270- | 3270-3290 | UAUAUAACAAUGUUU | 345 | NM_001256054.2_ | 3268-3290 |

TABLE 12-continued

| Unmodified Sense and Antisense Strand Sequences of dsRNA Agents Targeting the Coding Region of C9orf72 | | | | | | | | |
|---|---|---|---|---|---|---|---|---|
| Duplex Name | Sense Sequence 5' to 3' | SEQ ID NO: | Source and Range | Range in NM_ 001256054.2 | Antisense Sequence 5' to 3' | SEQ ID NO: | Source and Range | Range in NM_ 001256054.2 |
| | GUUAUAUA | | 3290_s | | ACACAUGC | | 3268-3290_as | |

TABLE 13

Modified Sense and Antisense Strand Sequences of of dsRNA Agents Targeting the Coding Region of C9orf72

| Duplex ID | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-347430.1 | usgscgucAfaAfCfAfgcgacaaguuL96 | 346 | asAfscuug(Tgn)cgcuguUfuGfacgcascsc | 347 | GGUGCGUCAAACAGCGACAAGUU | 348 |
| AD-347432.1 | csgsucaaAfcAfGfCfgacaaguucuL96 | 349 | asGfsaacu(Tgn)gucgcuGfuUfugacgscsa | 350 | UGCGUCAAACAGCGACAAGUUCC | 351 |
| AD-347454.1 | cscscacgUfaAfAfAfgaugacgcuuL96 | 352 | asAfsgcgu(Cgn)aucuuuUfaCfgugggscsg | 353 | CGCCCACGUAAAAGAUGACGCUU | 354 |
| AD-347455.1 | cscsacguAfaAfAfGfaugacgcuuuL96 | 355 | asAfsagcg(Tgn)caucuuUfuAfcguggsgsc | 356 | GCCCACGUAAAAGAUGACGCUUG | 357 |
| AD-347570.1 | asgsugauGfuCfGfAfcucuuugccuL96 | 358 | asGfsgcaa(Agn)gagucgAfcAfucacusgsc | 359 | GCAGUGAUGUCGACUCUUUGCCC | 360 |
| AD-347602.1 | csasgcugUfuGfCfCfaagacagagaL96 | 361 | usCfsucug(Tgn)cuuggcAfaCfagcugsgsa | 362 | UCCAGCUGUUGCCAAGACAGAGA | 363 |
| AD-347603.1 | asgscuguUfgCfCfAfagacagagauL96 | 364 | asUfscucu(Ggn)ucuuggCfaAfcagcusgsg | 365 | CCAGCUGUUGCCAAGACAGAGAU | 366 |
| AD-347606.1 | usgsuugcCfaAfGfAfcagagauuguL96 | 146 | asCfsaauc(Tgn)cugucuUfgGfcaacasgsc | 147 | GCUGUUGCCAAGACAGAGAUUGC | 367 |
| AD-347610.1 | gscscaagAfcAfGfAfgauugcuuuaL96 | 368 | usAfsaagc(Agn)aucucuGfuCfuuggcsasa | 369 | UUGCCAAGACAGAGAUUGCUUUA | 370 |
| AD-347612.1 | csasagacAfgAfGfAfuugcuuuaauL96 | 148 | asUfsuaaa(Ggn)caaucuCfuGfucuugsgsc | 149 | GCCAAGACAGAGAUUGCUUUAAG | 371 |
| AD-347613.1 | asasgacaGfaGfAfUfugcuuuaaguL96 | 372 | asCfsuuaa(Agn)gcaaucUfcUfgucuusgsg | 373 | CCAAGACAGAGAUUGCUUUAAGU | 374 |
| AD-347614.1 | asgsacagAfgAfUfUfgcuuuaaguuL96 | 375 | asAfscuua(Agn)agcaauCfuCfugucususg | 376 | CAAGACAGAGAUUGCUUUAAGUG | 377 |
| AD-347615.1 | gsascagaGfaUfUfGfcuuuaaguguL96 | 378 | asCfsacuu(Agn)aagcaaUfcUfcugucsusu | 379 | AAGACAGAGAUUGCUUUAAGUGG | 380 |
| AD-347650.1 | usasgcagCfuAfCfUfuuugcuuacuL96 | 381 | asGfsuaag(Cgn)aaaaguAfgCfugcuasasu | 382 | AUUAGCAGCUACUUUUGCUUACU | 383 |
| AD-347674.1 | ascsaauaUfuCfUfUfgguccuagauL96 | 384 | asUfscuag(Ggn)accaagAfaUfauuguscsc | 385 | GGACAAUAUUCUUGGUCCUAGAG | 386 |
| AD-347676.1 | asasuauuCfuUfGfGfuccuagaguaL96 | 387 | usAfscucu(Agn)ggaccaAfgAfauauusgsu | 388 | ACAAUAUUCUUGGUCCUAGAGUA | 389 |
| AD-347677.1 | asusauucUfuGfGfUfccuagaguaaL96 | 390 | usUfsacuc(Tgn)aggaccAfaGfaauaususg | 391 | CAAUAUUCUUGGUCCUAGAGUAA | 392 |
| AD-347716.1 | asgsacagAfaCfAfGfguacuucucaL96 | 393 | usGfsagaa(Ggn)uaccugUfuCfugucususu | 394 | AAAGACAGAACAGGUACUUCUCA | 395 |
| AD-347773.1 | usasaaugGfaGfAfAfauccuucgaaL96 | 396 | usUfscgaa(Ggn)gauuucUfcCfauuuasgsa | 397 | UCUAAAUGGAGAAAUCCUUCGAA | 398 |
| AD-347778.1 | gsgsagaaAfuCfCfUfucgaaaugcaL96 | 399 | usGfscauu(Tgn)cgaaggAfuUfucuccsasu | 400 | AUGGAGAAAUCCUUCGAAAUGCA | 401 |
| AD-347842.1 | csasuuaaUfcUfUfUfgauggaaacuL96 | 402 | asGfsuuuc(Cgn)aucaaaGfaUfuaaugsasa | 403 | UUCAUUAAUCUUUGAUGGAAACU | 404 |
| AD-347843.1 | asusuaauCfuUfUfGfauggaaacuuL96 | 405 | asAfsguuu(Cgn)caucaaAfgAfuuaausgsa | 406 | UCAUUAAUCUUUGAUGGAAACUG | 407 |
| AD-347863.1 | csasuaugGfaCfUfAfucaauuauauL96 | 408 | asUfsauaa(Tgn)ugauagUfcCfauaugsusg | 409 | CACAUAUGGACUAUCAAUUAUAC | 410 |

TABLE 13-continued

| Modified Sense and Antisense Strand Sequences of of dsRNA Agents Targeting the Coding Region of C9orf72 | | | | | | |
|---|---|---|---|---|---|---|
| Duplex ID | Sense Sequence 5' to 3' | SEQ ID NO: | Antisense Sequence 5' to 3' | SEQ ID NO: | mRNA Target Sequence 5' to 3' | SEQ ID NO: |
| AD-347865.1 | usasuggaCfuAfUfCfaauuauacuuL96 | 411 | asAfsguau(Agn)auugauAfgUfccauasusg | 412 | CAUAUGGACUAUCAAUUAUACUU | 413 |
| AD-347867.1 | usgsgacuAfuCfAfAfuuauacuucuL96 | 414 | asGfsaagu(Agn)uaauugAfuAfguccasusa | 415 | UAUGGACUAUCAAUUAUACUUCC | 416 |
| AD-347874.1 | uscsaauuAfuAfCfUfuccacagacaL96 | 417 | usGfsucug(Tgn)ggaaguAfuAfauugasusa | 418 | UAUCAAUUAUACUUCCACAGACA | 419 |
| AD-347892.1 | ascsagaaCfuUfAfGfuuucuaccuuL96 | 420 | asAfsggua(Ggn)aaacuaAfgUfucuguscsu | 421 | AGACAGAACUUAGUUUCUACCUC | 422 |
| AD-347893.1 | csasgaacUfuAfGfUfuucuaccucuL96 | 423 | asGfsaggu(Agn)gaaacuAfaGfuucugsusc | 424 | GACAGAACUUAGUUUCUACCUCC | 425 |
| AD-347923.1 | gsasguguGfuGfUfUfgauagauuaaL96 | 426 | usUfsaauc(Tgn)aucaacAfcAfcacucsusa | 427 | UAGAGUGUGUGUUGAUAGAUUAA | 428 |
| AD-347924.1 | asgsugugUfgUfUfGfauagauuaauL96 | 429 | asUfsuaau(Cgn)uaucaaCfaCfacacuscsu | 430 | AGAGUGUGUGUUGAUAGAUUAAC | 431 |
| AD-347926.1 | usgsugugUfuGfAfUfagauuaacauL96 | 432 | asUfsguua(Agn)ucuaucAfaCfacacascsu | 433 | AGUGUGUGUUGAUAGAUUAACAC | 434 |
| AD-347942.1 | asascacaUfaUfAfAfuccggaaaguL96 | 435 | asCfsuuuc(Cgn)ggauuaUfaUfguguusasa | 436 | UUAACACAUAUAAUCCGGAAAGG | 437 |
| AD-347993.1 | usgsuccaGfaAfGfAfuuaucuuagaL96 | 438 | usCfsuaag(Agn)uaaucuUfcUfggacasusu | 439 | AAUGUCCAGAAGAUUAUCUUAGA | 440 |
| AD-348087.1 | gsasacugCfuUfUfCfaucuaugaaaL96 | 441 | usUfsucau(Agn)gaugaaAfgCfaguucscsa | 442 | UGGAACUGCUUUCAUCUAUGAAA | 443 |
| AD-348136.1 | usasgcugAfuAfCfAfguacucaauuL96 | 150 | asAfsuuga(Ggn)uacuguAfuCfagcuasusa | 151 | UAUAGCUGAUACAGUACUCAAUG | 444 |
| AD-348140.1 | usgsauacAfgUfAfCfucaaugaugaL96 | 152 | usCfsauca(Tgn)ugaguaCfuGfuaucasgsc | 153 | GCUGAUACAGUACUCAAUGAUGA | 445 |
| AD-348176.1 | csusgucaUfgAfAfGfgcuuucuucuL96 | 446 | asGfsaaga(Agn)agccuuCfaUfgacagscsu | 447 | AGCUGUCAUGAAGGCUUUCUUCU | 448 |
| AD-348231.1 | usgsuuccGfuUfGfUfaguagguaguL96 | 449 | asCfsuacc(Tgn)acuacaAfcGfgaacasgsc | 450 | GCUGUUCCGUUGUAGUAGGUAGC | 451 |
| AD-348341.1 | asuscauuUfaAfAfUfaugagucaguL96 | 452 | asCfsugac(Tgn)cauauuUfaAfaugausgsa | 453 | UCAUCAUUUAAAUAUGAGUCAGG | 454 |
| AD-348377.1 | cscsugcuAfaAfGfGfauucaacuguL96 | 455 | asCfsaguu(Ggn)aauccuUfuAfgcaggscsc | 456 | GGCCUGCUAAAGGAUUCAACUGG | 457 |
| AD-348487.1 | csascccuGfuCfAfUfgaacauauuuL96 | 458 | asAfsauau(Ggn)uucaugAfcAfgggugsgsc | 459 | GCCACCCUGUCAUGAACAUAUUU | 460 |
| AD-348497.1 | usgsaacaUfaUfUfUfauaaucagcuL96 | 461 | asGfscuga(Tgn)uauaaaUfaUfguucasusg | 462 | CAUGAACAUAUUUAUAAUCAGCG | 463 |
| AD-348500.1 | ascsauauUfuAfUfAfaucagcguauL96 | 464 | asUfsacgc(Tgn)gauuauAfaAfuaugusgsc | 465 | GAACAUAUUUAUAAUCAGCGUAG | 466 |
| AD-348502.1 | asusauuuAfuAfAfUfcagcguagauL96 | 467 | asUfscuac(Ggn)cugauuAfuAfaauausgsu | 468 | ACAUAUUUAUAAUCAGCGUAGAU | 469 |
| AD-348578.1 | uscsaggaUfaCfGfAfucaucuacauL96 | 470 | asUfsguag(Agn)ugaucgUfaUfccugasgsc | 471 | GCUCAGGAUACGAUCAUCUACAC | 472 |
| AD-348588.1 | asuscaucUfaCfAfCfugacgaaaguL96 | 473 | asCfsuuuc(Ggn)ucagugUfaGfaugauscsg | 474 | CGAUCAUCUACACUGACGAAAGC | 475 |

TABLE 13-continued

Modified Sense and Antisense Strand Sequences of of dsRNA Agents Targeting the Coding Region of C9orf72

| Duplex ID | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-348590.1 | csasucuaCfaCfUfGfacgaaagcuuL96 | 476 | asAfsgcuu(Tgn)cgucagUfgUfagaugsasu | 477 | AUCAUCUACACUGACGAAAGCUU | 478 |
| AD-348591.1 | asuscuacAfcUfGfAfcgaaagcuuuL96 | 479 | asAfsagcu(Tgn)ucgucaGfuGfuagausgsa | 480 | UCAUCUACACUGACGAAAGCUUU | 481 |
| AD-348596.1 | csascugaCfgAfAfAfgcuuuacucuL96 | 482 | asGfsagua(Agn)agcuuuCfgUfcagugsusa | 483 | UACACUGACGAAAGCUUUACUCC | 484 |
| AD-348597.1 | ascsugacGfaAfAfGfcuuuacuccuL96 | 485 | asGfsgagu(Agn)aagcuuUfcGfucagusgsu | 486 | ACACUGACGAAAGCUUUACUCCU | 487 |
| AD-348598.1 | csusgacgAfaAfGfCfuuuacuccuuL96 | 488 | asAfsggag(Tgn)aaagcuUfuCfgucagsusg | 489 | CACUGACGAAAGCUUUACUCCUG | 490 |
| AD-348630.1 | ususucaaGfaUfGfUfcuuacacagaL96 | 491 | usCfsugug(Tgn)aagacaUfcUfugaaasasa | 492 | UUUUUCAAGAUGUCUUACACAGA | 493 |
| AD-348639.1 | gsuscuuaCfaCfAfGfagacacucuaL96 | 154 | usAfsgagu(Ggn)ucucugUfgUfaagacsasu | 155 | AUGUCUUACACAGAGACACUCUA | 494 |
| AD-348672.1 | csusggauCfaGfGfUfcuuucagcuuL96 | 495 | asAfsgcug(Agn)aagaccUfgAfuccagsgsa | 496 | UCCUGGAUCAGGUCUUUCAGCUG | 497 |
| AD-348708.1 | csuscagaAfgUfAfCfuuuccuugcaL96 | 498 | usGfscaag(Ggn)aaaguaCfuUfcugagsasg | 499 | CUCUCAGAAGUACUUUCCUUGCA | 500 |
| AD-348734.1 | uscsuacuUfgUfCfCfuucacagaaaL96 | 501 | usUfsucug(Tgn)gaaggaCfaAfguagasasa | 502 | UUUCUACUUGUCCUUCACAGAAA | 503 |
| AD-348751.1 | gsasaaagCfcUfUfGfacacuaauaaL96 | 504 | usUfsauua(Ggn)ugucaaGfgCfuuuucsusg | 505 | CAGAAAAGCCUUGACACUAAUAA | 506 |
| AD-348787.1 | cscsuuuaAfaUfCfUfcuucggaacuL96 | 507 | asGfsuucc(Ggn)aagagaUfuUfaaaggsgsc | 508 | GCCCUUUAAAUCUCUUCGGAACC | 509 |
| AD-348788.1 | csusuuaaAfuCfUfCfuucggaaccuL96 | 510 | asGfsguuc(Cgn)gaagagAfuUfuaaagsgsg | 511 | CCCUUUAAAUCUCUUCGGAACCU | 512 |
| AD-348789.1 | ususuaaaUfcUfCfUfucggaaccuuL96 | 513 | asAfsgguu(Cgn)cgaagaGfaUfuuaaasgsg | 514 | CCUUUAAAUCUCUUCGGAACCUG | 515 |
| AD-348836.1 | gsgsgcgaUfcUfUfAfacauaauaauL96 | 516 | asUfsuauu(Agn)uguuaaGfaUfcgcccsusc | 517 | GAGGGCGAUCUUAACAUAAUAAU | 518 |
| AD-348842.1 | uscsuuaaCfaUfAfAfuaauggcucuL96 | 519 | asGfsagcc(Agn)uuauuaUfgUfuaagasusc | 520 | GAUCUUAACAUAAUAAUGGCUCU | 521 |
| AD-348895.1 | ususaucuUfuGfGfAfagaccuuucuL96 | 522 | asGfsaaag(Ggn)ucuuccAfaAfgauaasasa | 523 | UUUUAUCUUUGGAAGACCUUUCU | 524 |
| AD-348904.1 | gsasagacCfuUfUfCfuacacuaguuL96 | 156 | asAfscuag(Tgn)guagaaAfgGfucuucscsa | 157 | UGGAAGACCUUUCUACACUAGUG | 525 |
| AD-348905.1 | asasgaccUfuUfCfUfacacuaguguL96 | 526 | asCfsacua(Ggn)uguagaAfaGfgucuuscsc | 527 | GGAAGACCUUUCUACACUAGUGU | 528 |
| AD-348906.1 | asgsaccuUfuCfUfAfcacuaguguuL96 | 529 | asAfscacu(Agn)guguagAfaAfggucusus c | 530 | GAAGACCUUUCUACACUAGUGUG | 531 |
| AD-348926.1 | gscsaagaAfcGfAfGfauguucuaauL96 | 532 | asUfsuaga(Agn)caucucGfuUfcuugcsasc | 533 | GUGCAAGAACGAGAUGUUCUAAU | 534 |
| AD-348930.1 | gsasacgaGfaUfGfUfucuaaugacuL96 | 535 | asGfsucau(Tgn)agaacaUfcUfcguucsusu | 536 | AAGAACGAGAUGUUCUAAUGACU | 537 |
| AD-348931.1 | asascgagAfuGfUfUfcuaaugacuuL96 | 538 | asAfsguca(Tgn)uagaacAfuCfucguuscsu | 539 | AGAACGAGAUGUUCUAAUGACUU | 540 |
| AD-348932.1 | ascsgagaUfgUfUfCfuaaugacuuuL96 | 541 | asAfsaguc(Agn)uuagaaCfaUfcucgususc | 542 | GAACGAGAUGUUCUAAUGACUUU | 543 |

TABLE 13-continued

Modified Sense and Antisense Strand Sequences of of dsRNA Agents Targeting the Coding Region of C9orf72

| Duplex ID | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-348957.1 | asusguguAfaCfUfUfaauaagccuaL96 | 544 | usAfsggcu(Tgn)auuaagUfuAfcacaususu | 545 | AAAUGUGUAACUUAAUAAGCCUA | 546 |
| AD-348959.1 | gsusguaaCfuUfAfAfuaagccuauuL96 | 547 | asAfsuagg(Cgn)uuauuaAfgUfuacacsasu | 548 | AUGUGUAACUUAAUAAGCCUAUU | 549 |
| AD-348961.1 | gsusaacuUfaAfUfAfagccuauucuL96 | 550 | asGfsaaua(Ggn)gcuuauUfaAfguuacsasc | 551 | GUGUAACUUAAUAAGCCUAUUCC | 552 |
| AD-348962.1 | usasacuuAfaUfAfAfgccuauuccaL96 | 553 | usGfsgaau(Agn)ggcuuaUfuAfaguuascsa | 554 | UGUAACUUAAUAAGCCUAUUCCA | 555 |
| AD-348963.1 | asascuuaAfuAfAfGfccuauuccauL96 | 556 | asUfsggaa(Tgn)aggcuuAfuUfaaguusasc | 557 | GUAACUUAAUAAGCCUAUUCCAU | 558 |
| AD-349042.1 | gsusuaagUfaAfGfUfuacacuacauL96 | 559 | asUfsguag(Tgn)guaacuUfaCfuuaacsusg | 560 | CAGUUAAGUAAGUUACACUACAG | 561 |
| AD-349048.1 | usasaguuAfcAfCfUfacaguucucaL96 | 562 | usGfsagaa(Cgn)uguaguGfuAfacuuascsu | 563 | AGUAAGUUACACUACAGUUCUCA | 564 |
| AD-349051.1 | gsusuacaCfuAfCfAfguucucacaaL96 | 565 | usUfsguga(Ggn)aacuguAfgUfguaacsusu | 566 | AAGUUACACUACAGUUCUCACAA | 567 |
| AD-349126.1 | csasgaccUfaUfGfUfuuacaauauaL96 | 568 | usAfsuauu(Ggn)uaaacaUfaGfgucugsusa | 569 | UACAGACCUAUGUUUACAAUAUA | 570 |
| AD-349127.1 | asgsaccuAfuGfUfUfuacaauauaaL96 | 571 | usUfsauau(Tgn)guaaacAfuAfggucusgsu | 572 | ACAGACCUAUGUUUACAAUAUAA | 573 |
| AD-349395.1 | gsasucaaGfcAfGfAfuguuuaauuuL96 | 574 | asAfsauua(Agn)acaucuGfcUfugaucsasa | 575 | UUGAUCAAGCAGAUGUUUAAUUG | 576 |
| AD-349454.1 | usgsggauUfcAfGfUfcuguagaaauL96 | 577 | asUfsuucu(Agn)cagacuGfaAfucccasgsg | 578 | CCUGGGAUUCAGUCUGUAGAAAU | 579 |
| AD-349474.1 | usgsucuaAfuAfGfUfucucuauaguL96 | 580 | asCfsuaua(Ggn)agaacuAfuUfagacasusu | 581 | AAUGUCUAAUAGUUCUCUAUAGU | 582 |
| AD-349477.1 | csusaauaGfuUfCfUfcuauaguccuL96 | 583 | asGfsgacu(Agn)uagagaAfcUfauuagsasc | 584 | GUCUAAUAGUUCUCUAUAGUCCU | 585 |
| AD-349610.1 | asgsccaaAfuUfGfAfaaugugcacuL96 | 586 | asGfsugca(Cgn)auuucaAfuUfuggcuscsa | 587 | UGAGCCAAAUUGAAAUGUGCACC | 588 |
| AD-349692.1 | ususcuugCfuAfAfGfucuuaccauuL96 | 589 | asAfsuggu(Agn)agacuuAfgCfaagaasgsa | 590 | UCUUCUUGCUAAGUCUUACCAUG | 591 |
| AD-349847.1 | usgscaauAfgGfCfUfauaaggaauaL96 | 592 | usAfsuucc(Tgn)uauagcCfuAfuugcasgsg | 593 | CCUGCAAUAGGCUAUAAGGAAUA | 594 |
| AD-349848.1 | gscsaauaGfgCfUfAfuaaggaauauL96 | 595 | asUfsauuc(Cgn)uuauagCfcUfauugcsasg | 596 | CUGCAAUAGGCUAUAAGGAAUAG | 597 |
| AD-350108.1 | gsasaaggUfcAfUfAfauagcuuucuL96 | 598 | asGfsaaag(Cgn)uauuauGfaCfcuuucsasc | 599 | GUGAAAGGUCAUAAUAGCUUUCC | 600 |
| AD-350109.1 | asasagguCfaUfAfAfuagcuuuccuL96 | 601 | asGfsgaaa(Ggn)cuauuaUfgAfccuuuscsa | 602 | UGAAAGGUCAUAAUAGCUUUCCC | 603 |
| AD-350179.1 | asascuagAfuGfAfCfuguuguacuuL96 | 604 | asAfsguac(Agn)acagucAfuCfuaguuscsa | 605 | UGAACUAGAUGACUGUUGUACUG | 606 |
| AD-350197.1 | csusguagCfuCfAfGfucauuuaaaaL96 | 607 | usUfsuuaa(Agn)ugacugAfgCfuacagsusa | 608 | UACUGUAGCUCAGUCAUUUAAAA | 609 |
| AD-350270.1 | csusgguuUfaUfUfGfuacuguuauaL96 | 610 | usAfsuaac(Agn)guacaaUfaAfaccagscsc | 611 | GGCUGGUUUAUUGUACUGUUAUA | 612 |

TABLE 13-continued

| Modified Sense and Antisense Strand Sequences of of dsRNA Agents Targeting the Coding Region of C9orf72 | | | | | | |
|---|---|---|---|---|---|---|
| Duplex ID | Sense Sequence 5' to 3' | SEQ ID NO: | Antisense Sequence 5' to 3' | SEQ ID NO: | mRNA Target Sequence 5' to 3' | SEQ ID NO: |
| AD-350329.1 | asusguguAfaAfCfAfuuguuauauaL96 | 613 | usAfsuaua(Agn)caauguUfuAfcacausgsc | 614 | GCAUGUGUAAACAUUGUUAUAUA | 615 |

TABLE 14

C9orf72 Unmodified Sense and Antisense Strand Sequences of dsRNA Agents Targeting the Intron Between Exons 1a and 1b

| Duplex ID | Sense Sequence 5' to 3' | SEQ ID NO: | Antisense Sequence 5' to 3' | SEQ ID NO: |
|---|---|---|---|---|
| AD-463863.1 | AAAGACCUGAUAAAGAUUAAU | 2 | AUUAAUCUUUAUCAGGUCUUUUC | 3 |
| AD-463862.1 | AAAAGACCUGAUAAAGAUUAA | 4 | UUAAUCUUUAUCAGGUCUUUUCU | 5 |
| AD-463869.1 | CUGAUAAAGAUUAACCAGAAU | 6 | AUUCUGGUUAAUCUUUAUCAGGU | 7 |
| AD-463873.1 | AAAGAUUAACCAGAAGAAAAU | 8 | AUUUUCUUCUGGUUAAUCUUUAU | 9 |
| AD-463872.1 | AUAAAGAUUAACCAGAAGAAA | 10 | UUUCUUCUGGUUAAUCUUUAUCA | 11 |
| AD-463860.1 | AGAAAAGACCUGAUAAAGAUU | 12 | AAUCUUUAUCAGGUCUUUUCUUG | 13 |
| AD-463847.1 | GCUGAGGGUGAACAAGAAAAU | 616 | AUUUUCUUGUUCACCCUCAGCGA | 617 |
| AD-463871.1 | GAUAAAGAUUAACCAGAAGAA | 618 | UUCUUCUGGUUAAUCUUUAUCAG | 619 |
| AD-463878.1 | AACCAGAAGAAAACAAGGAGU | 620 | ACUCCUUGUUUUCUUCUGGUUAA | 621 |
| AD-463875.1 | AUUAACCAGAAGAAAACAAGU | 622 | ACUUGUUUUCUUCUGGUUAAUCU | 623 |
| AD-463877.1 | UAACCAGAAGAAAACAAGGAU | 624 | AUCCUUGUUUUCUUCUGGUUAAU | 625 |
| AD-463857.1 | AACAAGAAAAGACCUGAUAAA | 626 | UUUAUCAGGUCUUUUCUUGUUCA | 627 |
| AD-463861.1 | GAAAAGACCUGAUAAAGAUUA | 628 | UAAUCUUUAUCAGGUCUUUUCUU | 629 |
| AD-463858.1 | ACAAGAAAAGACCUGAUAAAU | 630 | AUUUAUCAGGUCUUUUCUUGUUC | 631 |
| AD-463864.1 | AAGACCUGAUAAAGAUUAACU | 632 | AGUUAAUCUUUAUCAGGUCUUUU | 633 |
| AD-463866.1 | GACCUGAUAAAGAUUAACCAU | 634 | AUGGUUAAUCUUUAUCAGGUCUU | 635 |
| AD-463870.1 | UGAUAAAGAUUAACCAGAAGA | 636 | UCUUCUGGUUAAUCUUUAUCAGG | 637 |
| AD-463867.1 | ACCUGAUAAAGAUUAACCAGA | 638 | UCUGGUUAAUCUUUAUCAGGUCU | 639 |
| AD-463859.1 | AAGAAAAGACCUGAUAAAGAU | 640 | AUCUUUAUCAGGUCUUUUCUUGU | 641 |
| AD-463848.1 | CUGAGGGUGAACAAGAAAAGA | 642 | UCUUUUCUUGUUCACCCUCAGCG | 643 |
| AD-463855.1 | UGAACAAGAAAAGACCUGAUA | 644 | UAUCAGGUCUUUUCUUGUUCACC | 645 |
| AD-463850.1 | GAGGGUGAACAAGAAAAGACU | 646 | AGUCUUUUCUUGUUCACCCUCAG | 647 |
| AD-463854.1 | GUGAACAAGAAAAGACCUGAU | 648 | AUCAGGUCUUUUCUUGUUCACCC | 649 |
| AD-463874.1 | AAGAUUAACCAGAAGAAAACA | 650 | UGUUUUCUUCUGGUUAAUCUUUA | 651 |
| AD-463851.1 | AGGGUGAACAAGAAAAGACCU | 652 | AGGUCUUUUCUUGUUCACCCUCA | 653 |
| AD-463868.1 | CCUGAUAAAGAUUAACCAGAA | 654 | UUCUGGUUAAUCUUUAUCAGGUC | 655 |
| AD-463832.1 | UGCUCUCACAGUACUCGCUGA | 656 | UCAGCGAGUACUGUGAGAGCAAG | 657 |
| AD-463853.1 | GGUGAACAAGAAAAGACCUGA | 658 | UCAGGUCUUUUCUUGUUCACCCU | 659 |
| AD-463844.1 | CUCGCUGAGGGUGAACAAGAA | 660 | UUCUUGUUCACCCUCAGCGAGUA | 661 |
| AD-463846.1 | CGCUGAGGGUGAACAAGAAAA | 662 | UUUUCUUGUUCACCCUCAGCGAG | 663 |
| AD-463839.1 | CAGUACUCGCUGAGGGUGAAU | 664 | AUUCACCCUCAGCGAGUACUGUG | 665 |
| AD-463845.1 | UCGCUGAGGGUGAACAAGAAA | 666 | UUUCUUGUUCACCCUCAGCGAGU | 667 |
| AD-463820.1 | CUCCCCACUACUUGCUCUCAU | 668 | AUGAGAGCAAGUAGUGGGGAGAG | 669 |
| AD-463884.1 | ACAACCGCAGCCUGUAGCAAU | 670 | AUUGCUACAGGCUGCGGUUGUUU | 671 |
| AD-463831.1 | UUGCUCUCACAGUACUCGCUU | 672 | AAGCGAGUACUGUGAGAGCAAGU | 673 |
| AD-463842.1 | UACUCGCUGAGGGUGAACAAU | 674 | AUUGUUCACCCUCAGCGAGUACU | 675 |
| AD-463893.1 | GUAGCAAGCUCUGGAACUCAU | 676 | AUGAGUUCCAGAGCUUGCUACAG | 677 |

TABLE 14-continued

C9orf72 Unmodified Sense and Antisense Strand Sequences of dsRNA Agents Targeting the Intron Between Exons 1a and 1b

| Duplex ID | Sense Sequence 5' to 3' | SEQ ID NO: | Antisense Sequence 5' to 3' | SEQ ID NO: |
|---|---|---|---|---|
| AD-463899.1 | AGCUCUGGAACUCAGGAGUCU | 678 | AGACUCCUGAGUUCCAGAGCUUG | 679 |
| AD-463822.1 | CCCCACUACUUGCUCUCACAU | 680 | AUGUGAGAGCAAGUAGUGGGGAG | 681 |
| AD-463834.1 | CUCUCACAGUACUCGCUGAGU | 682 | ACUCAGCGAGUACUGUGAGAGCA | 683 |
| AD-463815.1 | UGUGUUUUUGUUUUUCCCACU | 684 | AGUGGGAAAAACAAAAACACACA | 685 |
| AD-463856.1 | GAACAAGAAAAGACCUGAUAA | 686 | UUAUCAGGUCUUUUCUUGUUCAC | 687 |
| AD-463879.1 | ACCAGAAGAAAACAAGGAGGU | 688 | ACCUCCUUGUUUUCUUCUGGUUA | 689 |
| AD-463894.1 | UAGCAAGCUCUGGAACUCAGU | 690 | ACUGAGUUCCAGAGCUUGCUACA | 691 |
| AD-463865.1 | AGACCUGAUAAAGAUUAACCA | 692 | UGGUUAAUCUUUAUCAGGUCUUU | 693 |
| AD-463841.1 | GUACUCGCUGAGGGUGAACAA | 694 | UUGUUCACCCUCAGCGAGUACUG | 695 |
| AD-463829.1 | ACUUGCUCUCACAGUACUCGU | 696 | ACGAGUACUGUGAGAGCAAGUAG | 697 |
| AD-463889.1 | GCCUGUAGCAAGCUCUGGAAU | 698 | AUUCCAGAGCUUGCUACAGGCUG | 699 |
| AD-463897.1 | CAAGCUCUGGAACUCAGGAGU | 700 | ACUCCUGAGUUCCAGAGCUUGCU | 701 |
| AD-463814.1 | GUGUGUUUUUGUUUUUCCCAU | 702 | AUGGGAAAAACAAAAACACACAC | 703 |
| AD-463825.1 | CACUACUUGCUCUCACAGUAU | 704 | AUACUGUGAGAGCAAGUAGUGGG | 705 |
| AD-463898.1 | AAGCUCUGGAACUCAGGAGUU | 706 | AACUCCUGAGUUCCAGAGCUUGC | 707 |
| AD-463827.1 | CUACUUGCUCUCACAGUACUU | 708 | AAGUACUGUGAGAGCAAGUAGUG | 709 |
| AD-463828.1 | UACUUGCUCUCACAGUACUCU | 710 | AGAGUACUGUGAGAGCAAGUAGU | 711 |
| AD-463885.1 | CAACCGCAGCCUGUAGCAAGU | 712 | ACUUGCUACAGGCUGCGGUUGUU | 713 |
| AD-463852.1 | GGGUGAACAAGAAAAGACCUU | 714 | AAGGUCUUUUCUUGUUCACCCUC | 715 |
| AD-463830.1 | CUUGCUCUCACAGUACUCGCU | 716 | AGCGAGUACUGUGAGAGCAAGUA | 717 |
| AD-463876.1 | UUAACCAGAAGAAAACAAGGA | 718 | UCCUUGUUUUCUUCUGGUUAAUC | 719 |
| AD-463819.1 | UCUCCCCACUACUUGCUCUCA | 720 | UGAGAGCAAGUAGUGGGGAGAGA | 721 |
| AD-463833.1 | GCUCUCACAGUACUCGCUGAU | 722 | AUCAGCGAGUACUGUGAGAGCAA | 723 |
| AD-463900.1 | GCUCUGGAACUCAGGAGUCGU | 724 | ACGACUCCUGAGUUCCAGAGCUU | 725 |
| AD-463838.1 | ACAGUACUCGCUGAGGGUGAA | 726 | UUCACCCUCAGCGAGUACUGUGA | 727 |
| AD-463886.1 | AACCGCAGCCUGUAGCAAGCU | 728 | AGCUUGCUACAGGCUGCGGUUGU | 729 |
| AD-463821.1 | UCCCCACUACUUGCUCUCACA | 730 | UGUGAGAGCAAGUAGUGGGGAGA | 731 |
| AD-463826.1 | ACUACUUGCUCUCACAGUACU | 732 | AGUACUGUGAGAGCAAGUAGUGG | 733 |
| AD-463881.1 | GGAAACAACCGCAGCCUGUAU | 734 | AUACAGGCUGCGGUUGUUUCCCU | 735 |
| AD-463890.1 | CCUGUAGCAAGCUCUGGAACU | 736 | AGUUCCAGAGCUUGCUACAGGCU | 737 |
| AD-463849.1 | UGAGGGUGAACAAGAAAAGAU | 738 | AUCUUUUCUUGUUCACCCUCAGC | 739 |
| AD-463892.1 | UGUAGCAAGCUCUGGAACUCA | 740 | UGAGUUCCAGAGCUUGCUACAGG | 741 |
| AD-463840.1 | AGUACUCGCUGAGGGUGAACA | 742 | UGUUCACCCUCAGCGAGUACUGU | 743 |
| AD-463823.1 | CCCACUACUUGCUCUCACAGU | 744 | ACUGUGAGAGCAAGUAGUGGGGA | 745 |
| AD-463888.1 | AGCCUGUAGCAAGCUCUGGAA | 746 | UUCCAGAGCUUGCUACAGGCUGC | 747 |
| AD-463835.1 | CUCACAGUACUCGCUGAGGGU | 748 | ACCCUCAGCGAGUACUGUGAGAG | 749 |

TABLE 14-continued

C9orf72 Unmodified Sense and Antisense Strand Sequences of dsRNA Agents Targeting the Intron Between Exons 1a and 1b

| Duplex ID | Sense Sequence 5' to 3' | SEQ ID NO: | Antisense Sequence 5' to 3' | SEQ ID NO: |
|---|---|---|---|---|
| AD-463824.1 | CCACUACUUGCUCUCACAGUA | 750 | UACUGUGAGAGCAAGUAGUGGGG | 751 |
| AD-463896.1 | GCAAGCUCUGGAACUCAGGAU | 752 | AUCCUGAGUUCCAGAGCUUGCUA | 753 |
| AD-463891.1 | CUGUAGCAAGCUCUGGAACUU | 754 | AAGUUCCAGAGCUUGCUACAGGC | 755 |
| AD-463887.1 | CCGCAGCCUGUAGCAAGCUCU | 756 | AGAGCUUGCUACAGGCUGCGGUU | 757 |
| AD-463843.1 | ACUCGCUGAGGGUGAACAAGA | 758 | UCUUGUUCACCCUCAGCGAGUAC | 759 |
| AD-463901.1 | UCAGGAGUCGCGCGCUAGGGU | 760 | ACCCUAGCGCGCGACUCCUGAGU | 761 |
| AD-463895.1 | AGCAAGCUCUGGAACUCAGGA | 762 | UCCUGAGUUCCAGAGCUUGCUAC | 763 |
| AD-463817.1 | GUUUUUGUUUUUCCCACCCUU | 764 | AAGGGUGGGAAAAACAAAAACAC | 765 |
| AD-463816.1 | GUGUUUUUGUUUUUCCCACCU | 766 | AGGUGGGAAAAACAAAAACACAC | 767 |
| AD-463883.1 | AACAACCGCAGCCUGUAGCAA | 768 | UUGCUACAGGCUGCGGUUGUUUC | 769 |
| AD-463902.1 | CAGGAGUCGCGCGCUAGGGGU | 770 | ACCCCUAGCGCGCGACUCCUGAG | 771 |
| AD-463904.1 | GGAGUCGCGCGCUAGGGGCCU | 772 | AGGCCCCUAGCGCGCGACUCCUG | 773 |
| AD-463837.1 | CACAGUACUCGCUGAGGGUGA | 774 | UCACCCUCAGCGAGUACUGUGAG | 775 |
| AD-463880.1 | GGGAAACAACCGCAGCCUGUA | 776 | UACAGGCUGCGGUUGUUUCCCUC | 777 |
| AD-463903.1 | AGGAGUCGCGCGCUAGGGGCU | 778 | AGCCCCUAGCGCGCGACUCCUGA | 779 |
| AD-463882.1 | AAACAACCGCAGCCUGUAGCA | 780 | UGCUACAGGCUGCGGUUGUUUCC | 781 |
| AD-463905.1 | GAGUCGCGCGCUAGGGGCCGU | 782 | ACGGCCCCUAGCGCGCGACUCCU | 783 |
| AD-463906.1 | AGUCGCGCGCUAGGGGCCGGU | 784 | ACCGGCCCCUAGCGCGCGACUCC | 785 |

TABLE 15

Modified Sense and Antisense Strand Sequences of C9orf72 dsRNA Agents

| Duplex ID | Sense Sequence 5' to 3' | SEQ ID NO: | Antisense Sequence 5' to 3' | SEQ ID NO: |
|---|---|---|---|---|
| AD-463863.1 | asasagacCfuGfAfUfaaagauuaauL96 | 162 | asUfsuaaUfcUfUfuaucAfgGfucuuusuc | 163 |
| AD-463862.1 | asasaagaCfcUfGfAfuaaagauuaaL96 | 160 | usUfsaauCfuUfUfaucaGfgUfcuuuuscsu | 161 |
| AD-463869.1 | csusgauaAfaGfAfUfuaaccagaauL96 | 164 | asUfsucuGfgUfUfaaucUfuUfaucagsgsu | 165 |
| AD-463873.1 | asasagauUfaAfCfCfagaagaaaauL96 | 168 | asUfsuuuCfuUfCfugguUfaAfucuuusasu | 169 |
| AD-463872.1 | asusaaagAfuUfAfAfccagaagaaaL96 | 166 | usUfsucuUfcUfGfguuaAfuCfuuuauscsa | 167 |
| AD-463860.1 | asgsaaaaGfaCfCfUfgauaaagauuL96 | 158 | asAfsucuUfuAfUfcaggUfcUfuuucusug | 159 |
| AD-463847.1 | gscsugagGfgUfGfAfacaagaaaauL96 | 786 | asUfsuuuCfuUfGfuucaCfcCfucagcsgsa | 787 |
| AD-463871.1 | gsasuaaaGfaUfUfAfaccagaagaaL96 | 788 | usUfscuuCfuGfGfuuaaUfcUfuuaucsasg | 789 |
| AD-463878.1 | asasccagAfaGfAfAfaacaaggaguL96 | 790 | asCfsuccUfuGfUfuuucUfuCfugguusasa | 791 |
| AD-463875.1 | asusuaacCfaGfAfAfgaaaacaaguL96 | 792 | asCfsuugUfuUfUfcuucUfgGfuuaauscsu | 793 |
| AD-463877.1 | usasaccaGfaAfGfAfaaacaaggauL96 | 794 | asUfsccuUfgUfUfuucuUfcUfgguuasasu | 795 |
| AD-463857.1 | asascaagAfaAfAfGfaccugauaaaL96 | 796 | usUfsuauCfaGfGfucuuUfuCfuuguuscsa | 797 |
| AD-463861.1 | gsasaaagAfcCfUfGfauaaagauuaL96 | 798 | usAfsaucUfuUfAfucagGfuCfuuuucsusu | 799 |

TABLE 15-continued

Modified Sense and Antisense Strand Sequences of C9orf72 dsRNA Agents

| Duplex ID | Sense Sequence 5' to 3' | SEQ ID NO: | Antisense Sequence 5' to 3' | SEQ ID NO: |
|---|---|---|---|---|
| AD-463858.1 | ascsaagaAfaAfGfAfccugauaaauL96 | 800 | asUfsuuaUfcAfGfgucuUfuUfcuugususc | 801 |
| AD-463864.1 | asasgaccUfgAfUfAfaagauuaacuL96 | 802 | asGfsuuaAfuCfUfuuauCfaGfgucuususu | 803 |
| AD-463866.1 | gsasccugAfuAfAfAfgauuaaccauL96 | 804 | asUfsgguUfaAfUfcuuuAfuCfaggucsusu | 805 |
| AD-463870.1 | usgsauaaAfgAfUfUfaaccagaagaL96 | 806 | usCfsuucUfgGfUfuaauCfuUfuaucasgsg | 807 |
| AD-463867.1 | ascscugaUfaAfAfGfauuaaccagaL96 | 808 | usCfsuggUfuAfAfucuuUfaUfcaggusesu | 809 |
| AD-463859.1 | asasgaaaAfgAfCfCfugauaaagauL96 | 810 | asUfscuuUfaUfCfagguCfuUfuucuusgsu | 811 |
| AD-463848.1 | csusgaggGfuGfAfAfcaagaaaagaL96 | 812 | usCfsuuuUfcUfUfguucAfcCfcucagscsg | 813 |
| AD-463855.1 | usgsaacaAfgAfAfAfagaccugauaL96 | 814 | usAfsucaGfgUfCfuuuuCfuUfguucascsc | 815 |
| AD-463850.1 | gsasggguGfaAfCfAfagaaaagacuL96 | 816 | asGfsucuUfuUfCfuuguUfcAfcccucsasg | 817 |
| AD-463854.1 | gsusgaacAfaGfAfAfaagaccugauL96 | 818 | asUfscagGfuCfUfuuucUfuGfuucacscsc | 819 |
| AD-463874.1 | asasgauuAfaCfCfAfgaagaaaacaL96 | 820 | usGfsuuuUfcUfUfcuggUfuAfaucuususa | 821 |
| AD-463851.1 | asgsggugAfaCfAfAfgaaaagaccuL96 | 822 | asGfsgucUfuUfUfcuugUfuCfacccuscsa | 823 |
| AD-463868.1 | cscsugauAfaAfGfAfuuaaccagaaL96 | 824 | usUfscugGfuUfAfaucuUfuAfucaggsusc | 825 |
| AD-463832.1 | usgscucuCfaCfAfGfuacucgcugaL96 | 826 | usCfsagcGfaGfUfacugUfgAfgagcasasg | 827 |
| AD-463853.1 | gsgsugaaCfaAfGfAfaaagaccugaL96 | 828 | usCfsaggUfcUfUfuucuUfgUfucaccscsu | 829 |
| AD-463844.1 | csuscgcuGfaGfGfGfugaacaagaaL96 | 830 | usUfscuuGfuUfCfacccUfcAfgcgagsusa | 831 |
| AD-463846.1 | csgscugaGfgGfUfGfaacaagaaaaL96 | 832 | usUfsuucUfuGfUfucacCfcUfcagcgsasg | 833 |
| AD-463839.1 | csasguacUfcGfCfUfgagggugaauL96 | 834 | asUfsucaCfcCfUfcagcGfaGfuacugsusg | 835 |
| AD-463845.1 | uscsgcugAfgGfGfUfgaacaagaaaL96 | 836 | usUfsucuUfgUfUfcaccCfuCfagcgasgsu | 837 |
| AD-463820.1 | csuscccсAfcUfAfCfuugcucucauL96 | 838 | asUfsgagAfgCfAfaguaGfuGfgggagsasg | 839 |
| AD-463884.1 | ascsaaccGfcAfGfCfcuguagcaauL96 | 840 | asUfsugcUfaCfAfggcuGfcGfguugususu | 841 |
| AD-463831.1 | ususgcucUfcAfCfAfguacucgcuuL96 | 842 | asAfsgcgAfgUfAfcuguGfaGfagcaasgsu | 843 |
| AD-463842.1 | usascucgCfuGfAfGfggugaacaauL96 | 844 | asUfsuguUfcAfCfccucAfgCfgaguascsu | 845 |
| AD-463893.1 | gsusagcaAfgCfUfCfuggaacucauL96 | 846 | asUfsgagUfuCfCfagagCfuUfgcuacsasg | 847 |
| AD-463899.1 | asgscucuGfgAfAfCfucaggagucuL96 | 848 | asGfsacuCfcUfGfaguuCfcAfgagcusUsg | 849 |
| AD-463822.1 | cscsccacUfaCfUfUfgcucucacauL96 | 850 | asUfsgugAfgAfGfcaagUfaGfuggggsasg | 851 |
| AD-463834.1 | csuscucaCfaGfUfAfcucgcugaguL96 | 852 | asCfsucaGfcGfAfguacUfgUfgagagscsa | 853 |
| AD-463815.1 | usgsuguuUfuUfGfUfuuuucccacuL96 | 854 | asGfsuggGfaAfAfaacaAfaAfacacascsa | 855 |
| AD-463856.1 | gsasacaaGfaAfAfAfgaccugauaaL96 | 856 | usUfsaucAfgGfUfcuuuUfcUfuguucsasc | 857 |
| AD-463879.1 | ascscagaAfgAfAfAfacaaggagguL96 | 858 | asCfscucCfuUfGfuuuuCfuUfcuggususa | 859 |
| AD-463894.1 | usasgcaaGfcUfCfUfggaacucaguL96 | 860 | asCfsugaGfuUfCfcagaGfcUfugcuascsa | 861 |
| AD-463865.1 | asgsaccuGfaUfAfAfagauuaaccaL96 | 862 | usGfsguuAfaUfCfuuuaUfcAfggucususu | 863 |
| AD-463841.1 | gsusacucGfcUfGfAfgggugaacaaL96 | 864 | usUfsguuCfaCfCfcucaGfcGfaguacsusg | 865 |
| AD-463829.1 | ascsuugcUfcUfCfAfcaguacucguL96 | 866 | asCfsgagUfaCfUfgugaGfaGfcaagusasg | 867 |
| AD-463889.1 | gscscuguAfgCfAfAfgcucuggaauL96 | 868 | asUfsuccAfgAfGfcuugCfuAfcaggcsusg | 869 |
| AD-463897.1 | csasagcuCfuGfGfAfacucaggaguL96 | 870 | asCfsuccUfgAfGfuuccAfgAfgcuugscsu | 871 |
| AD-463814.1 | gsusguguUfuUfUfGfuuuuucccauL96 | 872 | asUfsgggAfaAfAfacaaAfaAfcacacsasc | 873 |

TABLE 15-continued

Modified Sense and Antisense Strand Sequences of C9orf72 dsRNA Agents

| Duplex ID | Sense Sequence 5' to 3' | SEQ ID NO: | Antisense Sequence 5' to 3' | SEQ ID NO: |
|---|---|---|---|---|
| AD-463825.1 | csascuacUfuGfCfUfcucacaguauL96 | 874 | asUfsacuGfuGfAfgagcAfaGfuagugsgsg | 875 |
| AD-463898.1 | asasgcucUfgGfAfAfcucaggaguuL96 | 876 | asAfscucCfuGfAfguucCfaGfagcuusgsc | 877 |
| AD-463827.1 | csusacuuGfcUfCfUfcacaguacuuL96 | 878 | asAfsguaCfuGfUfgagaGfcAfaguagsusg | 879 |
| AD-463828.1 | usascuugCfuCfUfCfacaguacucuL96 | 880 | asGfsaguAfcUfGfugagAfgCfaaguasgsu | 881 |
| AD-463885.1 | csasaccgCfaGfCfCfuguagcaaguL96 | 882 | asCfsuugCfuAfCfaggcUfgCfgguugsusu | 883 |
| AD-463852.1 | gsgsgugaAfcAfAfGfaaaagaccuuL96 | 884 | asAfsgguCfuUfUfucuuGfuUfcacccsusc | 885 |
| AD-463830.1 | csusugcuCfuCfAfCfaguacucgcuL96 | 886 | asGfscgaGfuAfCfugugAfgAfgcaagsusa | 887 |
| AD-463876.1 | ususaaccAfgAfAfGfaaaacaaggaL96 | 888 | usCfscuuGfuUfUfucuuCfuGfguuaasusc | 889 |
| AD-463819.1 | uscsucccCfaCfUfAfcuugcucucaL96 | 890 | usGfsagaGfcAfAfguagUfgGfggagasgsa | 891 |
| AD-463833.1 | gscsucucAfcAfGfUfacucgcugauL96 | 892 | asUfscagCfgAfGfuacuGfuGfagagcsasa | 893 |
| AD-463900.1 | gscsucugGfaAfCfUfcaggagucguL96 | 894 | asCfsgacUfcCfUfgaguUfcCfagagcsusu | 895 |
| AD-463838.1 | ascsaguaCfuCfGfCfugagggugaaL96 | 896 | usUfscacCfcUfCfagcgAfgUfacugusgsa | 897 |
| AD-463886.1 | asasccgcAfgCfCfUfguagcaagcuL96 | 898 | asGfscuuGfcUfAfcaggCfuGfcgguusgsu | 899 |
| AD-463821.1 | uscscccaCfuAfCfUfugcucucacaL96 | 900 | usGfsugaGfaGfCfaaguAfgUfggggasgsa | 901 |
| AD-463826.1 | ascsuacuUfgCfUfCfucacaguacuL96 | 902 | asGfsuacUfgUfGfagagCfaAfguagusgsg | 903 |
| AD-463881.1 | gsgsaaacAfaCfCfGfcagccuguauL96 | 904 | asUfsacaGfgCfUfgcggUfuGfuuuccscsu | 905 |
| AD-463890.1 | cscsuguaGfcAfAfGfcucuggaacuL96 | 906 | asGfsuucCfaGfAfgcuuGfcUfacaggscsu | 907 |
| AD-463849.1 | usgsagggUfgAfAfCfaagaaaagauL96 | 908 | asUfscuuUfuCfUfuguuCfaCfccucasgsc | 909 |
| AD-463892.1 | usgsuagcAfaGfCfUfcuggaacucaL96 | 910 | usGfsaguUfcCfAfgagcUfuGfcuacasgsg | 911 |
| AD-463840.1 | asgsuacuCfgCfUfGfagggugaacaL96 | 912 | usGfsuucAfcCfCfucagCfgAfguacusgsu | 913 |
| AD-463823.1 | cscscacuAfcUfUfGfcucucacaguL96 | 914 | asCfsuguGfaGfAfgcaaGfuAfgugggsgsa | 915 |
| AD-463888.1 | asgsccugUfaGfCfAfagcucuggaaL96 | 916 | usUfsccaGfaGfCfuugcUfaCfaggcusgsc | 917 |
| AD-463835.1 | csuscacaGfuAfCfUfcgcugaggguL96 | 918 | asCfscccuCfaGfCfgaguAfcUfgugagsasg | 919 |
| AD-463824.1 | cscsacuaCfuUfGfCfucucacaguaL96 | 920 | usAfscugUfgAfGfagcaAfgUfaguggsgsg | 921 |
| AD-463896.1 | gscsaagcUfcUfGfGfaacucaggauL96 | 922 | asUfsccuGfaGfUfuccaGfaGfcuugcsusa | 923 |
| AD-463891.1 | csusguagCfaAfGfCfucuggaacuuL96 | 924 | asAfsguuCfcAfGfagcuUfgCfuacagsgsc | 925 |
| AD-463887.1 | cscsgcagCfcUfGfUfagcaagcucuL96 | 926 | asGfsagcUfuGfCfuacaGfgCfugcggsusu | 927 |
| AD-463843.1 | ascsucgcUfgAfGfGfgugaacaagaL96 | 928 | usCfsuugUfuCfAfcccuCfaGfcgagusasc | 929 |
| AD-463901.1 | uscsaggaGfuCfGfCfgcgcuagguL96 | 930 | asCfsccuAfgCfGfcgcgAfcUfccugasgsu | 931 |
| AD-463895.1 | asgscaagCfuCfUfGfgaacucaggaL96 | 932 | usCfscugAfgUfUfccagAfgCfuugcusasc | 933 |
| AD-463817.1 | gsusuuuuGfuUfUfUfucccacccuuL96 | 934 | asAfsgggUfgGfGfaaaaAfcAfaaaacsasc | 935 |
| AD-463816.1 | gsusguuuUfuGfUfUfuuucccaccuL96 | 936 | asGfsgugGfgAfAfaaacAfaAfaacacsasc | 937 |
| AD-463883.1 | asascaacCfgCfAfGfccuguagcaaL96 | 938 | usUfsgcuAfcAfGfgcugCfgGfuuguusus c | 939 |
| AD-463902.1 | csasggagUfcGfCfGfcgcuaggguL96 | 940 | asCfscccUfaGfCfgcgcGfaCfuccugsasg | 941 |
| AD-463904.1 | gsgsagucGfcGfCfGfcuaggggccuL96 | 942 | asGfsgccCfcUfAfgcgcGfcGfacuccsusg | 943 |
| AD-463837.1 | csascaguAfcUfCfGfcugagggugaL96 | 944 | usCfsaccCfuCfAfgcgaGfuAfcugugsasg | 945 |
| AD-463880.1 | gsgsgaaaCfaAfCfCfgcagccuguaL96 | 946 | usAfscagGfcUfGfcgguUfgUfuucccsusc | 947 |

TABLE 15-continued

| Modified Sense and Antisense Strand Sequences of C9orf72 dsRNA Agents | | | | |
|---|---|---|---|---|
| Duplex ID | Sense Sequence 5' to 3' | SEQ ID NO: | Antisense Sequence 5' to 3' | SEQ ID NO: |
| AD-463903.1 | asgsgaguCfgCfGfCfgcuaggggcuL96 | 948 | asGfscccCfuAfGfcgcgCfgAfcuccusgsa | 949 |
| AD-463882.1 | asasacaaCfcGfCfAfgccuguagcaL96 | 950 | usGfscuaCfaGfGfcugcGfgUfuguuuscsc | 951 |
| AD-463905.1 | gsasgucgCfgCfGfCfuaggggccguL96 | 952 | asCfsggcCfcCfUfagcgCfgCfgacucscsu | 953 |
| AD-463906.1 | asgsucgcGfcGfCfUfaggggccgguL96 | 954 | asCfscggCfcCfCfuagcGfcGfcgacuscsc | 955 |

TABLE 16

| C9orf72 Single Dose Screens in Neuro2a Cells | | | | |
|---|---|---|---|---|
| | 10 nM Dose | | 0.1 nM Dose | |
| Duplex | Avg % C9orf72 mRNA Remaining | SD | Avg % C9orf72 mRNA Remaining | SD |
| AD-347430.1 | 108.1586 | 9.776762 | 102.926461 | 9.844402 |
| AD-347432.1 | 80.82998 | 7.685495 | 93.4467535 | 3.707112 |
| AD-347454.1 | 101.7639 | 6.31874 | 96.0559772 | 3.124197 |
| AD-347455.1 | 93.96188 | 12.4245 | 103.672652 | 14.9392 |
| AD-347570.1 | 100.9925 | 14.11266 | 97.2382292 | 3.232345 |
| AD-347602.1 | 50.61606 | 2.769283 | 90.9130248 | 14.80726 |
| AD-347603.1 | 36.75218 | 3.59788 | 91.2130671 | 9.217747 |
| AD-347606.1 | 14.03328 | 0.575122 | 82.1811557 | 11.31506 |
| AD-347610.1 | 16.84431 | 3.344733 | 84.438968 | 18.13649 |
| AD-347612.1 | 11.30135 | 1.222139 | 64.3047238 | 9.535823 |
| AD-347613.1 | 16.45266 | 1.644385 | 87.0981976 | 4.857487 |
| AD-347614.1 | 47.69549 | 7.728849 | 85.9734577 | 6.335515 |
| AD-347615.1 | 40.87763 | 6.263038 | 95.9572664 | 10.7571 |
| AD-347650.1 | 101.8945 | 13.09817 | 94.8255195 | 10.59428 |
| AD-347674.1 | 65.11115 | 6.153852 | 99.7925784 | 3.061382 |
| AD-347676.1 | 55.2216 | 6.538367 | 92.3882432 | 8.410176 |
| AD-347677.1 | 76.39543 | 7.73141 | 98.5375449 | 9.261759 |
| AD-347716.1 | 101.7214 | 5.417192 | 101.563557 | 4.413121 |
| AD-347773.1 | 25.37153 | 5.786308 | 90.5692411 | 9.346695 |
| AD-347778.1 | 67.86754 | 25.22616 | 88.9278585 | 9.809726 |
| AD-347842.1 | 83.67195 | 9.396759 | 106.321112 | 12.30094 |
| AD-347843.1 | 99.14834 | 12.88462 | 93.3342087 | 12.02222 |
| AD-347863.1 | 43.93743 | 5.498079 | 92.8893809 | 5.933657 |
| AD-347865.1 | 83.32648 | 17.19332 | 112.817387 | 7.794245 |
| AD-347867.1 | 69.77927 | 4.708071 | 97.6185534 | 10.16772 |
| AD-347874.1 | 76.30515 | 13.31293 | 111.290499 | 17.68477 |

TABLE 16-continued

| C9orf72 Single Dose Screens in Neuro2a Cells | | | | |
|---|---|---|---|---|
| | 10 nM Dose | | 0.1 nM Dose | |
| Duplex | Avg % C9orf72 mRNA Remaining | SD | Avg % C9orf72 mRNA Remaining | SD |
| AD-347892.1 | 96.22058 | 7.665784 | 92.4547627 | 11.2075 |
| AD-347893.1 | 101.5948 | 8.86735 | 105.607076 | 10.04238 |
| AD-347923.1 | 82.3263 | 13.52911 | 100.608981 | 17.91672 |
| AD-347924.1 | 90.86273 | 9.373496 | 94.7441667 | 7.274829 |
| AD-347926.1 | 82.85491 | 21.92686 | 89.7017391 | 9.976171 |
| AD-347942.1 | 93.69591 | 12.95754 | 91.8512716 | 17.41955 |
| AD-347993.1 | 95.05716 | 13.84628 | 110.698325 | 20.13021 |
| AD-348087.1 | 64.2739 | 3.190526 | 98.6940059 | 13.94537 |
| AD-348136.1 | 11.22875 | 0.70978 | 54.5425144 | 5.936783 |
| AD-348140.1 | 20.23686 | 3.421909 | 84.7820238 | 11.42362 |
| AD-348176.1 | 62.68142 | 6.009446 | 97.6143802 | 19.28814 |
| AD-348231.1 | 84.50123 | 10.95544 | 88.6877429 | 6.371108 |
| AD-348341.1 | 96.09791 | 12.62484 | 96.4581518 | 12.15386 |
| AD-348377.1 | 100.1362 | 8.605203 | 110.137549 | 16.89486 |
| AD-348487.1 | 75.55589 | 10.21049 | 86.2374386 | 0.392865 |
| AD-348497.1 | 82.80696 | 14.32393 | 88.5415729 | 2.818069 |
| AD-348500.1 | 75.31347 | 7.550983 | 95.8111343 | 11.06454 |
| AD-348502.1 | 84.82139 | 14.11956 | 88.7596585 | 9.557181 |
| AD-348578.1 | 70.79848 | 11.44325 | 95.3600129 | 6.623138 |
| AD-348588.1 | 90.28763 | 10.19408 | 94.5206354 | 6.193889 |
| AD-348590.1 | 85.64384 | 22.17813 | 94.23508 | 14.42933 |
| AD-348591.1 | 88.27091 | 9.957384 | 97.8838666 | 13.20964 |
| AD-348596.1 | 102.3846 | 15.30875 | 87.3876578 | 4.606803 |
| AD-348597.1 | 90.49934 | 9.265808 | 96.2475161 | 4.061686 |
| AD-348598.1 | 94.34813 | 9.170095 | 106.768924 | 17.55944 |
| AD-348630.1 | 78.77815 | 12.8725 | 95.328952 | 8.85476 |

TABLE 16-continued

| C9orf72 Single Dose Screens in Neuro2a Cells | | | | |
|---|---|---|---|---|
| | 10 nM Dose | | 0.1 nM Dose | |
| Duplex | Avg % C9orf72 mRNA Remaining | SD | Avg % C9orf72 mRNA Remaining | SD |
| AD-348639.1 | 13.70135 | 2.886124 | 75.7676877 | 5.843324 |
| AD-348672.1 | 89.88466 | 14.53998 | 98.09215 | 18.3019 |
| AD-348708.1 | 61.84377 | 5.055461 | 107.413925 | 21.38253 |
| AD-348734.1 | 95.86399 | 15.87249 | 98.3209181 | 10.69515 |
| AD-348751.1 | 31.79708 | 4.66811 | 101.630492 | 5.905301 |
| AD-348787.1 | 49.79092 | 5.894205 | 86.9442769 | 22.10655 |
| AD-348788.1 | 51.1666 | 11.20645 | 109.857745 | 12.05388 |
| AD-348789.1 | 80.88218 | 8.107075 | 99.5021731 | 10.52775 |
| AD-348836.1 | 32.20706 | 2.883623 | 92.794671 | 9.647938 |
| AD-348842.1 | 16.61415 | 3.691673 | 98.511271 | 24.0038 |
| AD-348895.1 | 71.62264 | 15.37766 | 96.3016163 | 14.16359 |
| AD-348904.1 | 9.257562 | 2.22834 | 53.4658877 | 12.09395 |
| AD-348905.1 | 15.74941 | 1.840235 | 80.898199 | 5.782131 |
| AD-348906.1 | 52.90698 | 5.482321 | 89.0445935 | 4.202231 |
| AD-348926.1 | 89.17682 | 4.958206 | 99.7640306 | 1.997126 |
| AD-348930.1 | 20.24304 | 4.668287 | 87.9325289 | 10.38548 |
| AD-348931.1 | 21.64584 | 1.151471 | 86.5235896 | 8.119257 |
| AD-348932.1 | 65.4211 | 6.171016 | 98.0124995 | 6.290356 |
| AD-348957.1 | 99.11614 | 5.422021 | 98.130978 | 17.98878 |
| AD-348959.1 | 98.72032 | 18.18334 | 85.5950571 | 9.305798 |
| AD-348961.1 | 95.63409 | 14.86035 | 88.1861421 | 8.042136 |
| AD-348962.1 | 93.07311 | 17.28878 | 96.4886467 | 20.13191 |
| AD-348963.1 | 93.0378 | 6.249871 | 98.5325806 | 9.378936 |
| AD-349042.1 | 87.08801 | 5.943891 | 97.8928314 | 13.51528 |
| AD-349048.1 | 90.07839 | 9.309048 | 97.0782319 | 9.82998 |
| AD-349051.1 | 72.66003 | 12.19094 | 97.0614884 | 14.31408 |
| AD-349126.1 | 102.9632 | 4.735787 | 101.144929 | 11.55466 |
| AD-349127.1 | 88.62489 | 11.91672 | 91.8250081 | 2.66611 |
| AD-349395.1 | 95.46553 | 16.43203 | 97.6042107 | 4.227649 |
| AD-349454.1 | 88.26711 | 5.092706 | 105.115217 | 3.470468 |
| AD-349474.1 | 89.97248 | 8.272942 | 100.835274 | 12.23494 |
| AD-349477.1 | 101.5282 | 12.84979 | 106.139698 | 6.558009 |
| AD-349610.1 | 103.9541 | 15.77276 | 107.645445 | 12.40821 |
| AD-349692.1 | 108.9096 | 12.64303 | 101.695084 | 10.31383 |
| AD-349847.1 | 90.23518 | 13.76773 | 88.8762369 | 3.801429 |
| AD-349848.1 | 93.67591 | 6.621208 | 100.159587 | 4.107114 |
| AD-350108.1 | 112.3379 | 10.06486 | 98.3414867 | 5.841237 |
| AD-350109.1 | 96.98935 | 9.710059 | 101.154071 | 9.850331 |
| AD-350179.1 | 83.68433 | 16.73609 | 102.259228 | 4.069927 |
| AD-350197.1 | 83.4485 | 6.210923 | 85.9923746 | 3.243041 |
| AD-350270.1 | 99.62824 | 14.44672 | 90.0604061 | 6.15077 |
| AD-350329.1 | 17.11297 | 2.798394 | 77.8753892 | 13.18545 |

TABLE 17

| C9orf72 Single Dose Screens in BE(2)C Cells | | | | |
|---|---|---|---|---|
| | 10 nM Dose | | 0.1 nM Dose | |
| Duplex | Avg % C9orf72 mRNA Remaining | SD | Avg % C9orf72 mRNA Remaining | SD |
| AD-347430.1 | 82.88227 | 13.77676 | 100.4073 | 8.711257 |
| AD-347432.1 | 60.10642 | 2.72119 | 70.0206 | 13.68082 |
| AD-347454.1 | 110.2161 | 8.732283 | 107.3506 | 1.973967 |
| AD-347455.1 | 96.54231 | 10.72406 | 92.79051 | 12.60443 |
| AD-347570.1 | 43.18622 | 2.33787 | 98.16339 | 10.7447 |
| AD-347602.1 | 60.48774 | 16.01064 | 75.41154 | 5.907048 |
| AD-347603.1 | 44.44516 | 5.422459 | 60.93898 | 12.51016 |
| AD-347606.1 | 20.66731 | 2.206332 | 43.31785 | 3.515035 |
| AD-347610.1 | 43.78379 | 10.3912 | 81.08617 | 2.536212 |
| AD-347612.1 | 22.41886 | 2.722727 | 60.50788 | 7.288639 |
| AD-347613.1 | 46.6743 | 8.170093 | 65.21552 | 12.51711 |
| AD-347614.1 | 72.20537 | 23.59788 | 78.17678 | 20.28306 |
| AD-347615.1 | 61.48894 | 5.138911 | 79.37615 | 21.31636 |
| AD-347650.1 | 47.99727 | 2.522146 | 104.3003 | 4.790927 |
| AD-347674.1 | 80.53007 | 22.51517 | 76.06062 | 17.77269 |
| AD-347676.1 | 64.25803 | 19.85368 | 58.46471 | 21.36364 |
| AD-347677.1 | 103.7541 | 4.87836 | 89.38045 | 18.31084 |
| AD-347716.1 | 39.16332 | 3.009752 | 71.40257 | 4.309919 |
| AD-347773.1 | 22.79971 | 3.801035 | 82.8196 | 6.565303 |
| AD-347778.1 | 55.45244 | 10.03663 | 103.55 | 10.88137 |
| AD-347842.1 | 85.20458 | 15.02426 | 81.30493 | 11.86813 |
| AD-347843.1 | 94.05675 | 18.541 | 111.0976 | 13.02574 |
| AD-347863.1 | 17.14299 | 1.434336 | 77.74684 | 4.954083 |
| AD-347865.1 | 90.51911 | 8.09217 | 96.69731 | 5.84892 |
| AD-347867.1 | 37.10558 | 11.16917 | 88.67657 | 15.57378 |
| AD-347874.1 | 49.26003 | 4.158059 | 100.6093 | 5.739901 |
| AD-347892.1 | 30.89859 | 7.317843 | 71.88334 | 6.283385 |
| AD-347893.1 | 30.20136 | 5.660424 | 86.78551 | 13.85252 |
| AD-347923.1 | 21.31491 | 3.326146 | 78.04297 | 5.51637 |
| AD-347924.1 | 71.07692 | 5.337269 | 99.36227 | 4.570199 |
| AD-347926.1 | 27.58301 | 4.30096 | 83.90653 | 5.447661 |
| AD-347942.1 | 86.30598 | 10.22092 | 97.86192 | 8.429688 |
| AD-347993.1 | 31.66535 | 5.027872 | 85.81969 | 5.542086 |
| AD-348087.1 | 39.38533 | 8.883016 | 72.86883 | 3.669532 |
| AD-348136.1 | 24.30857 | 5.274965 | 58.90466 | 5.373379 |
| AD-348140.1 | 14.39598 | 2.368607 | 67.3472 | 11.30915 |
| AD-348176.1 | 78.32646 | 2.522093 | 88.55116 | 10.30097 |
| AD-348231.1 | 53.4932 | 4.021274 | 92.7088 | 9.539667 |
| AD-348341.1 | 83.89848 | 17.44643 | 86.34048 | 6.96364 |
| AD-348377.1 | 50.84853 | 9.656333 | 84.3215 | 11.23426 |
| AD-348487.1 | 41.47418 | 6.787419 | 75.41429 | 17.5351 |
| AD-348497.1 | 66.49273 | 13.48261 | 86.63238 | 17.01784 |
| AD-348500.1 | 19.22007 | 3.385975 | 62.65074 | 10.7548 |

TABLE 17-continued

| C9orf72 Single Dose Screens in BE(2)C Cells | | | | |
|---|---|---|---|---|
| | 10 nM Dose | | 0.1 nM Dose | |
| Duplex | Avg % C9orf72 mRNA Remaining | SD | Avg % C9orf72 mRNA Remaining | SD |
| AD-348502.1 | 64.79465 | 11.59712 | 81.20134 | 15.65802 |
| AD-348578.1 | 20.69829 | 2.038162 | 65.04362 | 4.226679 |
| AD-348588.1 | 22.64718 | 2.226235 | 66.52442 | 6.439306 |
| AD-348590.1 | 53.82448 | 9.0131 | 99.50188 | 12.42381 |
| AD-348591.1 | 46.04985 | 9.076041 | 72.44525 | 7.061754 |
| AD-348596.1 | 36.92846 | 7.643471 | 84.48218 | 9.605091 |
| AD-348597.1 | 19.59032 | 4.186554 | 60.80839 | 9.97145 |
| AD-348598.1 | 39.93177 | 3.173106 | 80.63123 | 12.4441 |
| AD-348630.1 | 71.52849 | 10.66853 | 78.44949 | 9.348965 |
| AD-348639.1 | 15.6934 | 2.226095 | 52.72726 | 3.204068 |
| AD-348672.1 | 26.3175 | 6.176373 | 61.14771 | 6.371119 |
| AD-348708.1 | 35.99064 | 7.287375 | 88.86058 | 10.105 |
| AD-348734.1 | 31.97164 | 4.916142 | 76.4496 | 8.004687 |
| AD-348751.1 | 26.67156 | 2.862387 | 71.02257 | 4.224371 |
| AD-348787.1 | 35.22187 | 5.595156 | 75.23651 | 8.51262 |
| AD-348788.1 | 33.69843 | 3.577929 | 70.47266 | 7.116083 |
| AD-348789.1 | 60.60725 | 1.970527 | 110.8428 | 5.584758 |
| AD-348836.1 | 67.48432 | 9.387845 | 104.4636 | 8.446368 |
| AD-348842.1 | 36.89163 | 3.29892 | 99.32988 | 11.88113 |
| AD-348895.1 | 32.91338 | 3.743304 | 89.36052 | 6.64023 |
| AD-348904.1 | 28.80843 | 3.433009 | 52.81576 | 9.948805 |
| AD-348905.1 | 31.06881 | 5.086494 | 95.81619 | 8.079109 |
| AD-348906.1 | 67.75211 | 3.326577 | 104.8576 | 23.53051 |
| AD-348926.1 | 81.0301 | 4.95746 | 104.3321 | 11.46042 |
| AD-348930.1 | 58.13332 | 18.52752 | 101.5076 | 15.73369 |
| AD-348931.1 | 34.92576 | 7.411208 | 74.78969 | 28.27697 |
| AD-348932.1 | 27.96506 | 4.683937 | 77.32319 | 10.11088 |
| AD-348957.1 | 85.18783 | 9.584405 | 95.68012 | 5.275668 |
| AD-348959.1 | 29.52378 | 3.036392 | 71.73005 | 6.004029 |
| AD-348961.1 | 44.05841 | 5.454327 | 114.1652 | 14.95256 |
| AD-348962.1 | 86.72846 | 11.99514 | 89.64847 | 8.637003 |
| AD-348963.1 | 107.1386 | 12.93197 | 107.867 | 7.059721 |
| AD-349042.1 | 25.83698 | 6.208601 | 73.0493 | 11.32439 |
| AD-349048.1 | 51.92857 | 12.09663 | 93.208 | 7.767345 |
| AD-349051.1 | 32.54422 | 7.917884 | 55.10166 | 12.73971 |
| AD-349126.1 | 38.02445 | 8.158304 | 65.81213 | 8.34951 |
| AD-349127.1 | 44.34683 | 4.329469 | 61.37972 | 8.434831 |
| AD-349395.1 | 38.72672 | 9.143905 | 73.90281 | 6.509425 |
| AD-349454.1 | 25.74301 | 1.818085 | 63.89429 | 7.087295 |
| AD-349474.1 | 54.35402 | 5.785511 | 104.8446 | 8.454144 |
| AD-349477.1 | 35.84411 | 5.102722 | 91.68584 | 6.502661 |
| AD-349610.1 | 44.55332 | 5.64699 | 95.48529 | 16.9582 |
| AD-349692.1 | 26.64121 | 3.550501 | 71.19351 | 4.976952 |
| AD-349847.1 | 42.44005 | 9.583344 | 100.7526 | 8.318353 |
| AD-349848.1 | 26.44739 | 2.337312 | 72.32507 | 7.431502 |
| AD-350108.1 | 77.7291 | 11.47368 | 110.5336 | 20.27915 |
| AD-350109.1 | 26.81206 | 6.729989 | 70.7082 | 8.645896 |
| AD-350179.1 | 28.94105 | 4.109557 | 85.93683 | 4.82879 |
| AD-350197.1 | 24.61377 | 2.991152 | 48.15037 | 5.130792 |
| AD-350270.1 | 34.99259 | 9.000575 | 80.03001 | 11.82625 |
| AD-350329.1 | 29.75514 | 4.619727 | 57.08563 | 7.22942 |

TABLE 18

| C9orf72 Single Dose Screens | | | | | | |
|---|---|---|---|---|---|---|
| | 10 nM Dose | | 1 nM Dose | | 0.1 nM Dose | |
| Duplex | Avg % C9orf72 Target RNA Remaining | SD | Avg % C9orf72 Target RNA Remaining | SD | Avg % C9orf72 Target RNA Remaining | SD |
| AD-463863.1 | 6.895104 | 1.887372 | 17.990786 | 3.581209 | 47.74899 | 9.608242 |
| AD-463862.1 | 11.71756 | 1.624716 | 25.6975889 | 4.69844 | 69.58064 | 11.48016 |
| AD-463869.1 | 11.89178 | 1.13751 | 21.4449784 | 5.258391 | 78.90809 | 4.527617 |
| AD-463873.1 | 13.12453 | 1.926293 | 17.3532715 | 3.624777 | 56.40397 | 14.57048 |
| AD-463872.1 | 14.31053 | 2.347295 | 33.8387941 | 7.887076 | 68.98069 | 9.630744 |
| AD-463860.1 | 14.38719 | 4.174403 | 25.6651884 | 4.012716 | 69.34006 | 8.603515 |
| AD-463847.1 | 15.94532 | 2.910257 | 40.3177154 | 10.98583 | 74.72245 | 3.797427 |
| AD-463871.1 | 16.59102 | 3.60679 | 43.8501782 | 9.795528 | 78.33788 | 11.04167 |
| AD-463878.1 | 17.44205 | 6.330127 | 30.7611339 | 2.808117 | 78.51312 | 2.360064 |
| AD-463875.1 | 18.06926 | 5.250411 | 47.7505591 | 6.339073 | 80.28471 | 4.643024 |
| AD-463877.1 | 19.76524 | 2.463983 | 32.3670028 | 5.565999 | 91.14105 | 4.419216 |
| AD-463857.1 | 19.92302 | 5.089927 | 30.2229624 | 7.222642 | 64.72521 | 12.13353 |
| AD-463861.1 | 20.76325 | 3.866795 | 44.4845299 | 4.859767 | 92.14849 | 6.749253 |
| AD-463858.1 | 21.82364 | 7.846073 | 34.3701191 | 10.6661 | 82.0841 | 8.566596 |
| AD-463864.1 | 21.8246 | 3.66252 | 49.6302605 | 9.716144 | 78.01891 | 3.071723 |
| AD-463866.1 | 24.0353 | 4.42879 | 46.1919626 | 3.599353 | 84.54992 | 5.048781 |
| AD-463870.1 | 25.46799 | 4.006128 | 58.2570405 | 4.729279 | 90.10873 | 4.873256 |
| AD-463867.1 | 27.63503 | 6.322693 | 52.584482 | 10.57925 | 93.01992 | 8.170161 |
| AD-463859.1 | 27.9419 | 6.237851 | 48.112763 | 4.317608 | 88.26397 | 8.121303 |
| AD-463848.1 | 31.208 | 7.399623 | 59.3237856 | 6.602048 | 78.3498 | 9.343049 |
| AD-463855.1 | 31.6721 | 3.178719 | 52.1362368 | 5.292684 | 86.86777 | 6.307716 |
| AD-463850.1 | 31.72366 | 9.046134 | 61.457552 | 7.846478 | 89.91207 | 9.559405 |
| AD-463854.1 | 33.99302 | 4.494354 | 50.3642249 | 6.049553 | 98.50773 | 8.755903 |
| AD-463874.1 | 34.28805 | 4.662807 | 46.9952482 | 9.765255 | 81.63979 | 9.244761 |
| AD-463851.1 | 36.38047 | 5.665975 | 59.8831826 | 7.846382 | 88.63486 | 4.023827 |
| AD-463868.1 | 37.85565 | 2.293403 | 64.9907705 | 3.362285 | 86.97633 | 8.633561 |
| AD-463832.1 | 40.05936 | 7.066138 | 77.1665714 | 3.454563 | 88.75029 | 7.540446 |
| AD-463853.1 | 40.80135 | 7.554402 | 65.5474235 | 6.99034 | 87.30056 | 8.121754 |
| AD-463844.1 | 41.73267 | 9.685821 | 63.364797 | 9.218938 | 93.14991 | 11.03547 |
| AD-463846.1 | 42.64359 | 6.597737 | 62.4440201 | 5.458658 | 100.4715 | 2.361336 |
| AD-463839.1 | 42.98393 | 13.02984 | 68.9062633 | 2.531826 | 94.36524 | 8.202007 |

TABLE 18-continued

C9orf72 Single Dose Screens

| Duplex | 10 nM Dose Avg % C9orf72 Target RNA Remaining | 10 nM Dose SD | 1 nM Dose Avg % C9orf72 Target RNA Remaining | 1 nM Dose SD | 0.1 nM Dose Avg % C9orf72 Target RNA Remaining | 0.1 nM Dose SD |
|---|---|---|---|---|---|---|
| AD-463845.1 | 43.30533 | 6.617779 | 67.6577722 | 3.438657 | 96.3938 | 15.75012 |
| AD-463820.1 | 43.91113 | 7.978728 | 69.81747 | 12.4481 | 94.38236 | 4.783487 |
| AD-463884.1 | 44.73481 | 8.68839 | 66.0916778 | 4.521927 | 88.30249 | 4.150882 |
| AD-463831.1 | 45.28 | 4.393546 | 87.4988878 | 6.794657 | 96.65482 | 9.742692 |
| AD-463842.1 | 47.94548 | 2.6434 | 68.3097157 | 10.49513 | 89.12627 | 6.732591 |
| AD-463893.1 | 48.024 | 4.50011 | 70.6327049 | 14.83107 | 101.2062 | 4.477603 |
| AD-463899.1 | 48.93584 | 4.533855 | 79.60743 | 4.808234 | 99.56349 | 7.167818 |
| AD-463822.1 | 49.22299 | 11.77449 | 61.7869785 | 9.385718 | 104.7792 | 5.326017 |
| AD-463834.1 | 50.54416 | 7.157611 | 67.6085094 | 6.51823 | 95.15348 | 6.00028 |
| AD-463815.1 | 50.7322 | 8.15209 | 85.8836494 | 5.801274 | 93.306 | 2.133296 |
| AD-463856.1 | 52.09708 | 9.292538 | 71.6208025 | 4.402486 | 83.66283 | 7.512359 |
| AD-463879.1 | 52.29238 | 12.31902 | 91.3354901 | 5.701787 | 87.11167 | 8.476857 |
| AD-463894.1 | 53.83841 | 5.300078 | 78.519777 | 10.16316 | 98.54044 | 7.394306 |
| AD-463865.1 | 53.89827 | 7.734349 | 76.9058342 | 13.81802 | 90.7827 | 4.899252 |
| AD-463841.1 | 55.34068 | 14.6004 | 75.3676484 | 3.249612 | 86.74545 | 7.197606 |
| AD-463829.1 | 55.65741 | 7.327545 | 76.05587 | 5.933388 | 87.68048 | 3.095124 |
| AD-463889.1 | 57.15583 | 4.218506 | 79.8912749 | 10.87685 | 105.7882 | 1.681391 |
| AD-463897.1 | 57.28436 | 11.24736 | 78.1815484 | 3.395568 | 107.6228 | 8.576143 |
| AD-463814.1 | 57.48673 | 10.52274 | 76.0543605 | 6.494248 | 108.132 | 15.95589 |
| AD-463825.1 | 57.72945 | 9.281364 | 69.2059288 | 11.50281 | 94.58803 | 7.275608 |
| AD-463898.1 | 57.81877 | 7.668013 | 84.2611527 | 2.724986 | 101.0082 | 5.448219 |
| AD-463827.1 | 57.94463 | 7.138324 | 70.5072119 | 7.704315 | 96.08478 | 2.721961 |
| AD-463828.1 | 58.4669 | 6.262051 | 78.0817792 | 15.02007 | 94.57042 | 6.224673 |
| AD-463885.1 | 59.80305 | 6.187644 | 79.434974 | 8.667472 | 102.3 | 8.49886 |
| AD-463852.1 | 60.87121 | 8.593189 | 85.2019462 | 7.875974 | 90.30217 | 7.204589 |
| AD-463830.1 | 61.33072 | 7.241431 | 88.4420867 | 4.450489 | 102.3726 | 4.326917 |
| AD-463876.1 | 62.82897 | 0.59753 | 89.6575968 | 7.218984 | 98.10649 | 9.501475 |
| AD-463819.1 | 64.15961 | 7.129148 | 85.4054309 | 15.43181 | 97.1615 | 4.038406 |
| AD-463833.1 | 64.41388 | 7.336112 | 82.4725601 | 7.028475 | 95.57842 | 3.279038 |
| AD-463900.1 | 64.46457 | 2.572698 | 83.954137 | 8.818046 | 97.58683 | 11.33522 |
| AD-463838.1 | 64.65207 | 5.639705 | 82.4582348 | 5.243051 | 106.8135 | 10.45547 |
| AD-463886.1 | 65.06557 | 11.70007 | 88.8179271 | 6.667204 | 87.75141 | 6.017168 |
| AD-463821.1 | 65.36418 | 10.33992 | 81.1393994 | 13.84006 | 95.46494 | 7.125634 |
| AD-463826.1 | 65.52606 | 15.25068 | 88.6539653 | 8.213642 | 94.64711 | 10.77663 |
| AD-463881.1 | 65.66246 | 7.881975 | 77.5301467 | 1.659743 | 97.81026 | 5.112844 |
| AD-463890.1 | 66.23927 | 5.466641 | 90.2130612 | 5.662899 | 102.2023 | 6.763745 |
| AD-463849.1 | 67.84639 | 19.69218 | 85.5657586 | 5.003069 | 93.71145 | 5.923616 |
| AD-463892.1 | 69.13546 | 9.358767 | 80.4149188 | 5.170864 | 94.32616 | 7.351974 |
| AD-463840.1 | 69.45808 | 7.728181 | 87.7588532 | 8.442319 | 95.12692 | 10.12238 |
| AD-463823.1 | 69.87365 | 14.23887 | 98.4007125 | 8.297397 | 92.44274 | 8.161986 |
| AD-463888.1 | 70.24116 | 9.876654 | 94.9620706 | 1.396841 | 91.30081 | 3.123677 |
| AD-463835.1 | 73.50516 | 17.24816 | 94.6762699 | 11.00273 | 98.88008 | 1.234605 |
| AD-463824.1 | 74.94413 | 8.910127 | 100.838579 | 4.251858 | 87.97097 | 5.900965 |
| AD-463896.1 | 75.15816 | 6.626289 | 92.2732663 | 2.956882 | 91.34906 | 9.34084 |
| AD-463891.1 | 75.89363 | 4.932301 | 84.3316467 | 11.76645 | 101.5825 | 10.64198 |
| AD-463887.1 | 77.00152 | 4.720732 | 92.3937763 | 8.106755 | 107.5829 | 9.283113 |
| AD-463843.1 | 77.18108 | 8.475728 | 88.0193493 | 7.350552 | 101.6992 | 8.130878 |
| AD-463901.1 | 79.69214 | 3.554174 | 91.3385601 | 5.151392 | 99.21389 | 6.067914 |
| AD-463895.1 | 84.04935 | 11.39932 | 97.3393402 | 8.076027 | 99.30656 | 7.939733 |
| AD-463817.1 | 85.08871 | 13.20444 | 89.5576574 | 4.128533 | 87.36462 | 5.78227 |
| AD-463816.1 | 85.70303 | 9.912715 | 105.472774 | 10.27543 | 104.2863 | 13.51739 |
| AD-463883.1 | 85.71968 | 8.035838 | 94.1941814 | 5.718514 | 92.57683 | 8.285562 |
| AD-463902.1 | 86.39055 | 12.69315 | 98.0579662 | 6.445276 | 95.96132 | 11.12554 |
| AD-463904.1 | 87.02583 | 6.485768 | 90.3248342 | 10.19339 | 92.35205 | 0.545498 |
| AD-463837.1 | 87.17962 | 6.005932 | 91.36949 | 4.836236 | 101.3081 | 19.91605 |
| AD-463880.1 | 94.4352 | 10.15591 | 93.0563793 | 7.156635 | 93.58439 | 3.276504 |
| AD-463903.1 | 98.01208 | 9.460806 | 92.2505023 | 13.5983 | 110.9407 | 9.669494 |
| AD-463882.1 | 102.1867 | 8.188831 | 98.739041 | 3.554669 | 93.32284 | 9.663378 |
| AD-463905.1 | 102.8622 | 17.44574 | 95.432284 | 8.163072 | 109.1775 | 7.124329 |
| AD-463906.1 | 104.3926 | 5.265817 | 98.6778108 | 8.880539 | 103.8829 | 10.47854 |

Example 6. In Vivo Evaluation in Transgenic Mice

This Example describes methods for the in vivo evaluation of C9orf72 RNAi agents in transgenic mice expressing human C9orf72 RNAs with up to, e.g., 450 GGGGCC repeats (SEQ ID NO: 135) (see, e.g., Jiang, et al. (supra).

The ability of selected dsRNA agents designed and assayed in Example 5 are assessed for their ability to reduce the level of both sense- or antisense-containing foci in mice expressing human C9orf72 RNAs with up to 450 GGGGCC repeats (SEQ ID NO: 135).

Briefly, control littermates, mice heterozygous for the human C9orf72 RNA with up to 450 GGGGCC repeats (SEQ ID NO: 135), and mice homozygous for the human C9orf72 RNA with up to 450 GGGGCC repeats (SEQ ID NO: 135) are administered intrathecally or subcutaneously a single dose of the dsRNA agents of interest, including duplexes AD-463863.1, AD-463862.1, AD-463869.1, AD-463873.1, AD-463872.1, or AD-463860.1, or a placebo. Two weeks post-administration, animals are sacrificed, blood and tissue samples, including cerebral cortex, spinal cord, liver, spleen, and cervical lymph nodes, are collected.

As discussed above, there are three C9orf72 transcripts generated by differential use of transcription alternative start and termination sites generates. Therefore, to determine the effect of administration of the dsRNA agents on the level of detrimental repeat-containing mRNA, the levels of repeat-containing C9orf 72 mRNA, total C9orf72 mRNA, and exon 1b-containing, mRNA levels are determined in cortex and spinal cord samples by qRT-PCR (see, e.g., above and Jiang, supra).

The results demonstrate that administration of a single dose of the dsRNA agents inhibits the production of repeat-containing C9orf 72 mRNA but has only a minimal impact on the level of total C9orf72 mRNA and no effect on exon 1b-containing mRNA levels.

In order to determine the effect of the dsRNA agents to reduce the number and/or formation of both C9orf72 sense strand- and antisense strand-containing foci, the FISH methods described in Jiang, supra are employed in samples obtained from the animals administered the duplexes of interest from above. The probes that are used include those that are against the sense and antisense RNA hexanucleotide repeat (Exiqon, Inc.). All hybridization steps are performed under RNase-free conditions. Fifteen micrometer brain and spinal cord OCT frozen sections are permeabi-lized and the sections are blocked. The sections are then hybridized with denatured probes. After hybridization, slides are washed. Autofluorescence of lipofuscin is quenched and cell nuclei are stained with DAPI. Quantitation of sense and antisense RNA foci in mouse frontal cortex, hippocampal dentate gyrus, retrosplenial cortex and cerebellar molecular layer is performed by a blinded investigator. Three to six random pictures are taken by confocal microscopy under 100× magnification and 200-400 cells are counted.

The results demonstrate that administration of a single dose of the dsRNA agents reduce the level of sense strand- and antisense strand-containing foci in the frontal cortex, hippocampal dentate gyrus, retrosplenial cortex and cerebellar molecular layer.

The effect of administration of the agents on the level of aberrant dipeptide repeat protein level and poly(GP) and poly(GA) burden and size is also assessed as described in, for example, Jiang, supra) in the animals administered the duplexes of interest above.

Immunohistochemistryis used to identify and assess aberrant dipeptide repeat protein level in mouse hemibrain and spinal cord. Briefly, eight to ten micron thick sagittal slices of mouse hemibrain or coronal slices of spinal cord are cut from formalin-fixed, paraffin-embedded blocks and mounted on glass slides. After drying, slides are deparaffinized and rehydrated in xylene and alcohol washes before washing. Then slides are steamed and blocked. After staining with commercially available antibodies against poly (GP), poly(GA), poly(GR), poly(PA), poly(PR), GFAP, IBA-1, CD3, F4/80, and CD45R/B220 overnight, HRP-conjugated secondary antibody is applied and peroxidase activity is developed with substrate. Sections are counterstained with Harris' modified hematoxylin and coverslipped.

To quantify poly(GP) and poly(GA) inclusion burden and size, mice hemibrain sections immunostained for poly(GP) or poly(GA) are scanned at 40× magnification to obtain high-resolution digitized images. Using suitable software, the number of inclusions in the hippocampus or a delineated area in the retrosplenial cortex are counted. To measure the size of inclusions in these regions, images are taken with a microscope under 63× magnification. Although each inclusion in a given field is only analyzed once, multiple images of the field may be taken to ensure the analysis is done only on inclusions that are in focus. Images are opened and enlarged, and an outline tool is used to trace each inclusion to determine its area (μm$^2$). For each mouse, the average size of inclusions in μm2 within each tested region is calculated.

The data is used to determine whether administration of a single dose of the dsRNA agents reduces the level of aberrant dipeptide repeat protein levels, in particular the level of poly(GP) and poly(GA) inclusion burden and size.

TABLE 19

Unmodified Sense and Antisense Strand Sequences of C9orf72 dsRNA Agents (Ensembl Gene ID: ENSG00000147894)

| Target Coordinates in Human Chromosome 9 build 38 (hg38) | Sense Sequence 5' to 3' | SEQ ID NO: | Sense Source Name from Ensembl Gene ID: ENSG00000147894 | Antisense Sequence 5' to 3' | SEQ ID NO: | Antisense Source Name from Ensembl Gene ID: ENSG00000147894 |
|---|---|---|---|---|---|---|
| (hg38) chr9:27573685-27573707:- | GUGUGUUUUUGUUUUUCCCAU | 702 | ENSG00000147894_394-414_C21U_s | AUGGGAAAAACAAAAACACACAC | 703 | ENSG00000147894_392-414_G1A_as |
| (hg38) chr9:27573684-27573706:- | UGUGUUUUUGUUUUUCCCACU | 684 | ENSG00000147894_393-413_C21U_s | AGUGGGAAAAACAAAAACACACA | 685 | ENSG00000147894_391-413_G1A_as |
| (hg38) chr9:27573683-27573705:- | GUGUUUUUGUUUUUCCCACCU | 766 | ENSG00000147894_392-412_C21U_s | AGGUGGGAAAAACAAAAACACAC | 767 | ENSG00000147894_390-412_G1A_as |
| (hg38) chr9:27573681-27573703:- | GUUUUUGUUUUUCCCACCCUU | 764 | ENSG00000147894_390-410_C21U_s | AAGGGUGGGAAAAACAAAAACAC | 765 | ENSG00000147894_388-410_G1A_as |
| (hg38) chr9:27573664-27573686:- | CCUCUCUCCCCACUACUUGCU | 956 | ENSG00000147894_373-393_s | AGCAAGUAGUGGGGAGAGAGGGU | 957 | ENSG00000147894_371-393_as |
| (hg38) chr9:27573660-27573682:- | UCUCCCCACUACUUGCUCUCA | 720 | ENSG00000147894_369-389_s | UGAGAGCAAGUAGUGGGGAGAGA | 721 | ENSG00000147894_367-389_as |
| (hg38) chr9:27573659-27573681:- | CUCCCCACUACUUGCUCUCAU | 668 | ENSG00000147894_368-388_C21U_s | AUGAGAGCAAGUAGUGGGGAGAG | 669 | ENSG00000147894_366-388_G1A_as |
| (hg38) chr9:27573658-27573680:- | UCCCCACUACUUGCUCUCACA | 730 | ENSG00000147894_367-387_s | UGUGAGAGCAAGUAGUGGGGAGA | 731 | ENSG00000147894_365-387_as |
| (hg38) chr9:27573657-27573679:- | CCCCACUACUUGCUCUCACAU | 680 | ENSG00000147894_366-386_G21U_s | AUGUGAGAGCAAGUAGUGGGGAG | 681 | ENSG00000147894_364-386_C1A_as |
| (hg38) chr9:27573656-27573678:- | CCCACUACUUGCUCUCACAGU | 744 | ENSG00000147894_365-385_s | ACUGUGAGAGCAAGUAGUGGGGA | 745 | ENSG00000147894_363-385_as |
| (hg38) chr9:27573655-27573677:- | CCACUACUUGCUCUCACAGUA | 750 | ENSG00000147894_364-384_s | UACUGUGAGAGCAAGUAGUGGGG | 751 | ENSG00000147894_362-384_as |

TABLE 19-continued

Unmodified Sense and Antisense Strand Sequences of C9orf72 dsRNA Agents (Ensembl Gene ID: ENSG00000147894)

| Target Coordinates in Human Chromosome 9 build 38 (hg38) | Sense Sequence 5' to 3' | SEQ ID NO: | Sense Source Name from Ensembl Gene ID: ENSG00000147894 | Antisense Sequence 5' to 3' | SEQ ID NO: | Antisense Source Name from Ensembl Gene ID: ENSG00000147894 |
|---|---|---|---|---|---|---|
| (hg38) chr9:27573654-27573676:- | CACUACUUGCUCUCACAGUAU | 704 | ENSG00000147894_363-383_C21U_s | AUACUGUGAGAGCAAGUAGUGG | 705 | ENSG00000147894_361-383_G1A_as |
| (hg38) chr9:27573653-27573675:- | ACUACUUGCUCUCACAGUACU | 732 | ENSG00000147894_362-382_s | AGUACUGUGAGAGCAAGUAGUGG | 733 | ENSG00000147894_360-382_as |
| (hg38) chr9:27573652-27573674:- | CUACUUGCUCUCACAGUACUU | 708 | ENSG00000147894_361-381_C21U_s | AAGUACUGUGAGAGCAAGUAGUG | 709 | ENSG00000147894_359-381_G1A_as |
| (hg38) chr9:27573651-27573673:- | UACUUGCUCUCACAGUACUCU | 710 | ENSG00000147894_360-380_G21U_s | AGAGUACUGUGAGAGCAAGUAGU | 711 | ENSG00000147894_358-380_C1A_as |
| (hg38) chr9:27573650-27573672:- | ACUUGCUCUCACAGUACUCGU | 696 | ENSG00000147894_359-379_C21U_s | ACGAGUACUGUGAGAGCAAGUAG | 697 | ENSG00000147894_357-379_G1A_as |
| (hg38) chr9:27573649-27573671:- | CUUGCUCUCACAGUACUCGCU | 716 | ENSG00000147894_358-378_s | AGCGAGUACUGUGAGAGCAAGUA | 717 | ENSG00000147894_356-378_as |
| (hg38) chr9:27573648-27573670:- | UUGCUCUCACAGUACUCGCUU | 672 | ENSG00000147894_357-377_G21U_s | AAGCGAGUACUGUGAGAGCAAGU | 673 | ENSG00000147894_355-377_C1A_as |
| (hg38) chr9:27573647-27573669:- | UGCUCUCACAGUACUCGCUGA | 656 | ENSG00000147894_356-376_s | UCAGCGAGUACUGUGAGAGCAAG | 657 | ENSG00000147894_354-376_as |
| (hg38) chr9:27573646-27573668:- | GCUCUCACAGUACUCGCUGAU | 722 | ENSG00000147894_355-375_G21U_s | AUCAGCGAGUACUGUGAGAGCAA | 723 | ENSG00000147894_353-375_C1A_as |
| (hg38) chr9:27573645-27573667:- | CUCUCACAGUACUCGCUGAGU | 682 | ENSG00000147894_354-374_G21U_s | ACUCAGCGAGUACUGUGAGAGCA | 683 | ENSG00000147894_352-374_C1A_as |
| (hg38) chr9:27573643-27573665:- | CUCACAGUACUCGCUGAGGGU | 748 | ENSG00000147894_352-372_s | ACCCUCAGCGAGUACUGUGAGAG | 749 | ENSG00000147894350-372_as |
| (hg38) chr9:27573642- | UCACAGUACUCGCUGAGGGUU | 958 | ENSG00000147894_351-371_G21U_s | AACCCUCAGCGAGUACUGUGAGA | 959 | ENSG00000147894_349-371_C1A_as |

TABLE 19-continued

| Unmodified Sense and Antisense Strand Sequences of C9orf72 dsRNA Agents (Ensembl Gene ID: ENSG00000147894) | | | | | | |
|---|---|---|---|---|---|---|
| Target Coordinates in Human Chromosome 9 build 38 (hg38) | Sense Sequence 5' to 3' | SEQ ID NO: | Sense Source Name from Ensembl Gene ID: ENSG00000147894 | Antisense Sequence 5' to 3' | SEQ ID NO: | Antisense Source Name from Ensembl Gene ID: ENSG00000147894 |
| 27573664:- | | | | | | |
| (hg38) chr9:27573641-27573663:- | CACAGUACUCGCUGAGGGUGA | 774 | ENSG00000147894_350-370_s | UCACCCUCAGCGAGUACUGUGAG | 775 | ENSG00000147894_348-370_as |
| (hg38) chr9:27573640-27573662:- | ACAGUACUCGCUGAGGGUGAA | 726 | ENSG00000147894_349-369_s | UUCACCCUCAGCGAGUACUGUGA | 727 | ENSG00000147894347-369_as |
| (hg38) chr9:27573639-27573661:- | CAGUACUCGCUGAGGGUGAAU | 664 | ENSG00000147894_348-368_C21U_s | AUUCACCCUCAGCGAGUACUGUG | 665 | ENSG00000147894_346-368_G1A_as |
| (hg38) chr9:27573638-27573660:- | AGUACUCGCUGAGGGUGAACA | 742 | ENSG00000147894_347-367_s | UGUUCACCCUCAGCGAGUACUGU | 743 | ENSG00000147894_345-367_as |
| (hg38) chr9:27573637-27573659:- | GUACUCGCUGAGGGUGAACAA | 694 | ENSG00000147894_346-366_s | UUGUUCACCCUCAGCGAGUACUG | 695 | ENSG00000147894344-366_as |
| (hg38) chr9:27573636-27573658:- | UACUCGCUGAGGGUGAACAAU | 674 | ENSG00000147894_345-365_G21U_s | AUUGUUCACCCUCAGCGAGUACU | 675 | ENSG00000147894_343-365_C1A_as |
| (hg38) chr9:27573635-27573657:- | ACUCGCUGAGGGUGAACAAGA | 758 | ENSG00000147894_344-364_s | UCUUGUUCACCCUCAGCGAGUAC | 759 | ENSG00000147894_342-364_as |
| (hg38) chr9:27573634-27573656:- | CUCGCUGAGGGUGAACAAGAA | 660 | ENSG00000147894_343-363_s | UUCUUGUUCACCCUCAGCGAGUA | 661 | ENSG00000147894_341-363_as |
| (hg38) chr9:27573633-27573655:- | UCGCUGAGGGUGAACAAGAAA | 666 | ENSG00000147894_342-362_s | UUUCUUGUUCACCCUCAGCGAGU | 667 | ENSG00000147894_340-362_as |
| (hg38) chr9:27573632-27573654:- | CGCUGAGGGUGAACAAGAAAA | 662 | ENSG00000147894_341-361_s | UUUUCUUGUUCACCCUCAGCGAG | 663 | ENSG00000147894_339-361_as |
| (hg38) chr9:27573631-27573653:- | GCUGAGGGUGAACAAGAAAAU | 616 | ENSG00000147894_340-360_G21U_s | AUUUUCUUGUUCACCCUCAGCGA | 617 | ENSG00000147894_338-360_C1A_as |

TABLE 19-continued

| Unmodified Sense and Antisense Strand Sequences of C9orf72 dsRNA Agents (Ensembl Gene ID: ENSG00000147894) | | | | | | |
|---|---|---|---|---|---|---|
| Target Coordinates in Human Chromosome 9 build 38 (hg38) | Sense Sequence 5' to 3' | SEQ ID NO: | Sense Source Name from Ensembl Gene ID: ENSG00000147894 | Antisense Sequence 5' to 3' | SEQ ID NO: | Antisense Source Name from Ensembl Gene ID: ENSG00000147894 |
| (hg38) chr9:27573630-27573652:- | CUGAGGGUGAACAAGAAAAGA | 642 | ENSG00000147894_339-359_s | UCUUUUCUUGUUCACCCUCAGCG | 643 | ENSG00000147894_337-359_as |
| (hg38) chr9:27573629-27573651:- | UGAGGGUGAACAAGAAAAGAU | 738 | ENSG00000147894_338-358_C21U_s | AUCUUUUCUUGUUCACCCUCAGC | 739 | ENSG00000147894_336-358_G1A_as |
| (hg38) chr9:27573628-27573650:- | GAGGGUGAACAAGAAAAGACU | 646 | ENSG00000147894_337-357_C21U_s | AGUCUUUUCUUGUUCACCCUCAG | 647 | ENSG00000147894_335-357_G1A_as |
| (hg38) chr9:27573627-27573649:- | AGGGUGAACAAGAAAAGACCU | 652 | ENSG00000147894_336-356_s | AGGUCUUUUCUUGUUCACCCUCA | 653 | ENSG00000147894_334-356_as |
| (hg38) chr9:27573626-27573648:- | GGGUGAACAAGAAAAGACCUU | 714 | ENSG00000147894_335-355_G21U_s | AAGGUCUUUUCUUGUUCACCCUC | 715 | ENSG00000147894_333-355_C1A_as |
| (hg38) chr9:27573625-27573647:- | GGUGAACAAGAAAAGACCUGA | 658 | ENSG00000147894_334-354_s | UCAGGUCUUUUCUUGUUCACCCU | 659 | ENSG00000147894_332-354_as |
| (hg38) chr9:27573624-27573646:- | GUGAACAAGAAAAGACCUGAU | 648 | ENSG00000147894_333-353_s | AUCAGGUCUUUUCUUGUUCACCC | 649 | ENSG00000147894_331-353_as |
| (hg38) chr9:27573623-27573645:- | UGAACAAGAAAAGACCUGAUA | 644 | ENSG00000147894_332-352_s | UAUCAGGUCUUUUCUUGUUCACC | 645 | ENSG00000147894_330-352_as |
| (hg38) chr9:27573622-27573644:- | GAACAAGAAAAGACCUGAUAA | 686 | ENSG00000147894_331-351_s | UUAUCAGGUCUUUUCUUGUUCAC | 687 | ENSG00000147894_329-351_as |
| (hg38) chr9:27573621-27573643:- | AACAAGAAAAGACCUGAUAAA | 626 | ENSG00000147894_330-350_s | UUUAUCAGGUCUUUUCUUGUUCA | 627 | ENSG00000147894_328-350_as |
| (hg38) chr9:27573620-27573642:- | ACAAGAAAAGACCUGAUAAAU | 630 | ENSG00000147894_329-349_G21U_s | AUUUAUCAGGUCUUUUCUUGUUC | 631 | ENSG00000147894_327-349_C1A_as |
| (hg38) chr9:27573618- | AAGAAAAGACCUGAUAAAGAU | 640 | ENSG00000147894_327-347_s | AUCUUUAUCAGGUCUUUUCUUGU | 641 | ENSG00000147894_325-347_as |

TABLE 19-continued

| Unmodified Sense and Antisense Strand Sequences of C9orf72 dsRNA Agents (Ensembl Gene ID: ENSG00000147894) | | | | | | |
|---|---|---|---|---|---|---|
| Target Coordinates in Human Chromosome 9 build 38 (hg38) | Sense Sequence 5' to 3' | SEQ ID NO: | Sense Source Name from Ensembl Gene ID: ENSG00000147894 | Antisense Sequence 5' to 3' | SEQ ID NO: | Antisense Source Name from Ensembl Gene ID: ENSG00000147894 |
| 27573640:- | | | | | | |
| (hg38) chr9:27573617-27573639:- | AGAAAAGACCUGAUAAAGAUU | 12 | ENSG00000147894_326-346_s | AAUCUUUAUCAGGUCUUUUCUUG | 13 | ENSG00000147894_324-346_as |
| (hg38) chr9:27573616-27573638:- | GAAAAGACCUGAUAAAGAUUA | 628 | ENSG00000147894_325-345_s | UAAUCUUUAUCAGGUCUUUUCUU | 629 | ENSG00000147894_323-345_as |
| (hg38) chr9:27573615-27573637:- | AAAAGACCUGAUAAAGAUUAA | 4 | ENSG00000147894_324-344_s | UUAAUCUUUAUCAGGUCUUUUCU | 5 | ENSG00000147894_322-344_as |
| (hg38) chr9:27573614-27573636:- | AAAGACCUGAUAAAGAUUAAU | 2 | ENSG00000147894_323-343_C21U_s | AUUAAUCUUUAUCAGGucuuuuc | 3 | ENSG00000147894_321-343_G1A_as |
| (hg38) chr9:27573613-27573635:- | AAGACCUGAUAAAGAUUAACU | 632 | ENSG00000147894_322-342_C21U_s | AGUUAAUCUUUAUCAGGUCUUUU | 633 | ENSG00000147894_320-342_G1A_as |
| (hg38) chr9:27573612-27573634:- | AGACCUGAUAAAGAUUAACCA | 692 | ENSG00000147894_321-341_s | UGGUUAAUCUUUAUCAGGUCUUU | 693 | ENSG00000147894_319-341_as |
| (hg38) chr9:27573611-27573633:- | GACCUGAUAAAGAUUAACCAU | 634 | ENSG00000147894_320-340_G21U_s | AUGGUUAAUCUUUAUCAGGUCUU | 635 | ENSG00000147894_318-340_C1A_as |
| (hg38) chr9:27573610-27573632:- | ACCUGAUAAAGAUUAACCAGA | 638 | ENSG00000147894_319-339_s | UCUGGUUAAUCUUUAUCAGGUCU | 639 | ENSG00000147894_317-339_as |
| (hg38) chr9:27573609-27573631:- | CCUGAUAAAGAUUAACCAGAA | 654 | ENSG00000147894_318-338_s | UUCUGGUUAAUCUUUAUCAGGUC | 655 | ENSG00000147894_316-338_as |
| (hg38) chr9:27573608-27573630:- | CUGAUAAAGAUUAACCAGAAU | 6 | ENSG00000147894_317-337_G21U_s | AUUCUGGUUAAUCUUUAUCAGGU | 7 | ENSG00000147894_315-337_C1A_as |
| (hg38) chr9:27573607-27573629:- | UGAUAAAGAUUAACCAGAAGA | 636 | ENSG00000147894_316-336_s | UCUUCUGGUUAAUCUUUAUCAGG | 637 | ENSG00000147894_314-336_as |

TABLE 19-continued

Unmodified Sense and Antisense Strand Sequences of C9orf72 dsRNA Agents (Ensembl Gene ID: ENSG00000147894)

| Target Coordinates in Human Chromosome 9 build 38 (hg38) | Sense Sequence 5' to 3' | SEQ ID NO: | Sense Source Name from Ensembl Gene ID: ENSG00000147894 | Antisense Sequence 5' to 3' | SEQ ID NO: | Antisense Source Name from Ensembl Gene ID: ENSG00000147894 |
|---|---|---|---|---|---|---|
| (hg38) chr9:27573606-27573628:- | GAUAAAGAUUAACCAGAAGAA | 618 | ENSG00000147894_315-335_s | UUCUUCUGGUUAAUCUUUAUCAG | 619 | ENSG00000147894_313-335_as |
| (hg38) chr9:27573605-27573627:- | AUAAAGAUUAACCAGAAGAAA | 10 | ENSG00000147894_314-334_s | UUUCUUCUGGUUAAUCUUUAUCA | 11 | ENSG00000147894_312-334_as |
| (hg38) chr9:27573603-27573625:- | AAAGAUUAACCAGAAGAAAAU | 8 | ENSG00000147894_312-332_C21U_s | AUUUUCUUCUGGUUAAUCUUUAU | 9 | ENSG00000147894_310-332_G1A_as |
| (hg38) chr9:27573602-27573624:- | AAGAUUAACCAGAAGAAAACA | 650 | ENSG00000147894_311-331_s | UGUUUUCUUCUGGUUAAUCUUUA | 651 | ENSG00000147894_309-331_as |
| (hg38) chr9:27573599-27573621:- | AUUAACCAGAAGAAAACAAGU | 622 | ENSG00000147894_308-328_G21U_s | ACUUGUUUUCUUCUGGUUAAUCU | 623 | ENSG00000147894_306-328_C1A_as |
| (hg38) chr9:27573598-27573620:- | UUAACCAGAAGAAAACAAGGA | 718 | ENSG00000147894_307-327_s | UCCUUGUUUUCUUCUGGUUAAUC | 719 | ENSG00000147894305-327_as |
| (hg38) chr9:27573597-27573619:- | UAACCAGAAGAAAACAAGGAU | 624 | ENSG00000147894_306-326_G21U_s | AUCCUUGUUUUCUUCUGGUUAAU | 625 | ENSG00000147894_304-326_C1A_as |
| (hg38) chr9:27573596-27573618:- | AACCAGAAGAAAACAAGGAGU | 620 | ENSG00000147894_305-325_G21U_s | ACUCCUUGUUUUCUUCUGGUUAA | 621 | ENSG00000147894_303-325_C1A_as |
| (hg38) chr9:27573595-27573617:- | ACCAGAAGAAAACAAGGAGGU | 688 | ENSG00000147894_304-324_G21U_s | ACCUCCUUGUUUUCUUCUGGUUA | 689 | ENSG00000147894_302-324_C1A_as |
| (hg38) chr9:27573577-27573599:- | GGGAAACAACCGCAGCCUGUA | 776 | ENSG00000147894_286-306_s | UACAGGCUGCGGUUGUUUCCCUC | 777 | ENSG00000147894_284-306_as |
| (hg38) chr9:27573576-27573598:- | GGAAACAACCGCAGCCUGUAU | 734 | ENSG00000147894_285-305_G21U_s | AUACAGGCUGCGGUUGUUUCCCU | 735 | ENSG00000147894_283-305_C1A_as |
| (hg38) chr9:27573574- | AAACAACCGCAGCCUGUAGCA | 780 | ENSG00000147894_283-303_s | UGCUACAGGCUGCGGUUGUUUCC | 781 | ENSG00000147894_281-303_as |

TABLE 19-continued

Unmodified Sense and Antisense Strand Sequences of C9orf72 dsRNA Agents (Ensembl Gene ID: ENSG00000147894)

| Target Coordinates in Human Chromosome 9 build 38 (hg38) | Sense Sequence 5' to 3' | SEQ ID NO: | Sense Source Name from Ensembl Gene ID: ENSG00000147894 | Antisense Sequence 5' to 3' | SEQ ID NO: | Antisense Source Name from Ensembl Gene ID: ENSG00000147894 |
|---|---|---|---|---|---|---|
| 27573596:- | | | | | | |
| (hg38) chr9:27573573-27573595:- | AACAACCGCAGCCUGUAGCAA | 768 | ENSG00000147894_282-302_s | UUGCUACAGGCUGCGGUUGUUUC | 769 | ENSG00000147894_280-302_as |
| (hg38) chr9:27573572-27573594:- | ACAACCGCAGCCUGUAGCAAU | 670 | ENSG00000147894_281-301_G21U_s | AUUGCUACAGGCUGCGGUUGUUU | 671 | ENSG00000147894_279-301_C1A_as |
| (hg38) chr9:27573571-27573593:- | CAACCGCAGCCUGUAGCAAGU | 712 | ENSG00000147894_280-300_C21U_s | ACUUGCUACAGGCUGCGGUUGUU | 713 | ENSG00000147894_278-300_G1A_as |
| (hg38) chr9:27573570-27573592:- | AACCGCAGCCUGUAGCAAGCU | 728 | ENSG00000147894_279-299_s | AGCUUGCUACAGGCUGCGGUUGU | 729 | ENSG00000147894_277-299_as |
| (hg38) chr9:27573568-27573590:- | CCGCAGCCUGUAGCAAGCUCU | 756 | ENSG00000147894_277-297_s | AGAGCUUGCUACAGGCUGCGGUU | 757 | ENSG00000147894_275-297_as |
| (hg38) chr9:27573564-27573586:- | AGCCUGUAGCAAGCUCUGGAA | 746 | ENSG00000147894_273-293_s | UUCCAGAGCUUGCUACAGGCUGC | 747 | ENSG00000147894_271-293_as |
| (hg38) chr9:27573563-27573585:- | GCCUGUAGCAAGCUCUGGAAU | 698 | ENSG00000147894_272-292_C21U_s | AUUCCAGAGCUUGCUACAGGCUG | 699 | ENSG00000147894_270-292_G1A_as |
| (hg38) chr9:27573562-27573584:- | CCUGUAGCAAGCUCUGGAACU | 736 | ENSG00000147894_271-291_s | AGUUCCAGAGCUUGCUACAGGCU | 737 | ENSG00000147894_269-291_as |
| (hg38) chr9:27573561-27573583:- | CUGUAGCAAGCUCUGGAACUU | 754 | ENSG00000147894_270-290_C21U_s | AAGUUCCAGAGCUUGCUACAGGC | 755 | ENSG00000147894_268-290_G1A_as |
| (hg38) chr9:27573560-27573582:- | UGUAGCAAGCUCUGGAACUCA | 740 | ENSG00000147894_269-289_s | UGAGUUCCAGAGCUUGCUACAGG | 741 | ENSG00000147894_267-289_as |
| (hg38) chr9:27573559-27573581:- | GUAGCAAGCUCUGGAACUCAU | 676 | ENSG00000147894_268-288_G21U_s | AUGAGUUCCAGAGCUUGCUACAG | 677 | ENSG00000147894_266-288_C1A_as |

TABLE 19-continued

| Unmodified Sense and Antisense Strand Sequences of C9orf72 dsRNA Agents (Ensembl Gene ID: ENSG00000147894) | | | | | | |
|---|---|---|---|---|---|---|
| Target Coordinates in Human Chromosome 9 build 38 (hg38) | Sense Sequence 5' to 3' | SEQ ID NO: | Sense Source Name from Ensembl Gene ID: ENSG00000147894 | Antisense Sequence 5' to 3' | SEQ ID NO: | Antisense Source Name from Ensembl Gene ID: ENSG00000147894 |
| (hg38) chr9:27573558-27573580:- | UAGCAAGCUCUGGAACUCAGU | 690 | ENSG00000147894_267-287_G21U_s | ACUGAGUUCCAGAGCUUGCUACA | 691 | ENSG00000147894_265-287_C1A_as |
| (hg38) chr9:27573557-27573579:- | AGCAAGCUCUGGAACUCAGGA | 762 | ENSG00000147894_266-286_s | UCCUGAGUUCCAGAGCUUGCUAC | 763 | ENSG00000147894_264-286_as |
| (hg38) chr9:27573556-27573578:- | GCAAGCUCUGGAACUCAGGAU | 752 | ENSG00000147894_265-285_G21U_s | AUCCUGAGUUCCAGAGCUUGCUA | 753 | ENSG00000147894_263-285_C1A_as |
| (hg38) chr9:27573555-27573577:- | CAAGCUCUGGAACUCAGGAGU | 700 | ENSG00000147894_264-284_s | ACUCCUGAGUUCCAGAGCUUGCU | 701 | ENSG00000147894_262-284_as |
| (hg38) chr9:27573554-27573576:- | AAGCUCUGGAACUCAGGAGUU | 706 | ENSG00000147894_263-283_C21U_s | AACUCCUGAGUUCCAGAGCUUGC | 707 | ENSG00000147894_261-283_G1A_as |
| (hg38) chr9:27573553-27573575:- | AGCUCUGGAACUCAGGAGUCU | 678 | ENSG00000147894_262-282_G21U_s | AGACUCCUGAGUUCCAGAGCUUG | 679 | ENSG00000147894_260-282_C1A_as |
| (hg38) chr9:27573552-27573574:- | GCUCUGGAACUCAGGAGUCGU | 724 | ENSG00000147894_261-281_C21U_s | ACGACUCCUGAGUUCCAGAGCUU | 725 | ENSG00000147894_259-281_G1A_as |
| (hg38) chr9:27573542-27573564:- | UCAGGAGUCGCGCGCUAGGGU | 760 | ENSG00000147894_251-271_G21U_s | ACCCUAGCGCGCGACUCCUGAGU | 761 | ENSG00000147894_249-271_C1A_as |
| (hg38) chr9:27573541-27573563:- | CAGGAGUCGCGCGCUAGGGGU | 770 | ENSG00000147894_250-270_C21U_s | ACCCCUAGCGCGCGACUCCUGAG | 771 | ENSG00000147894_248-270_G1A_as |
| (hg38) chr9:27573540-27573562:- | AGGAGUCGCGCGCUAGGGGCU | 778 | ENSG00000147894_249-269_C21U_s | AGCCCCUAGCGCGCGACUCCUGA | 779 | ENSG00000147894_247-269_G1A_as |
| (hg38) chr9:27573539-27573561:- | GGAGUCGCGCGCUAGGGGCCU | 772 | ENSG00000147894_248-268_G21U_s | AGGCCCCUAGCGCGCGACUCCUG | 773 | ENSG00000147894_246-268_C1A_as |
| (hg38) chr9:27573538- | GAGUCGCGCGCUAGGGGCCGU | 782 | ENSG00000147894_247-267_G21U_s | ACGGCCCCUAGCGCGCGACUCCU | 783 | ENSG00000147894_245-267_C1A_as |

TABLE 19-continued

| Unmodified Sense and Antisense Strand Sequences of C9orf72 dsRNA Agents (Ensembl Gene ID: ENSG00000147894) | | | | | | |
|---|---|---|---|---|---|---|
| Target Coordinates in Human Chromosome 9 build 38 (hg38) | Sense Sequence 5' to 3' | SEQ ID NO: | Sense Source Name from Ensembl Gene ID: ENSG00000147894 | Antisense Sequence 5' to 3' | SEQ ID NO: | Antisense Source Name from Ensembl Gene ID: ENSG00000147894 |
| 27573560:- | | | | | | |
| (hg38) chr9:27573537-27573559:- | AGUCGCGCGCUAGGGGCCGGU | 784 | ENSG00000147894_246-266_G21U_s | ACCGGCCCCUAGCGCGCGACUCC | 785 | ENSG00000147894_244-266_C1A_as |

TABLE 20

| Modified Sense and Antisense Strand Sequences of C9orf72 dsRNA Agents (Ensembl Gene ID: ENSG00000147894) | | | | | | |
|---|---|---|---|---|---|---|
| Target Coordinates in Human Chromosome 9 build 38 (hg38) | Target mRNA Sequence | SEQ ID NO: | Antisense Sequence 5' to 3' | SEQ ID NO: | Sense Sequence 5' to 3' | SEQ ID NO: |
| (hg38) chr9:27573685-27573707:- | GUGUGUGUUUUUGUUUUUCCCAC | 960 | asUfsgggAfaAfAfacaaAfaAfcacacsasc | 873 | gsusguguUfuUfUfGfuuuuucccauL96 | 872 |
| (hg38) chr9:27573684-27573706:- | UGUGUGUUUUUGUUUUUCCCACC | 961 | asGfsuggGfaAfAfaacaAfaAfacacascsa | 855 | usgsuguuUfuUfGfUfuuuucccacuL96 | 854 |
| (hg38) chr9:27573683-27573705:- | GUGUGUUUUUGUUUUUCCCACCC | 962 | asGfsgugGfgAfAfaaacAfaAfaacacsasc | 937 | gsusguuuUfuGfUfUfuuucccaccuL96 | 936 |
| (hg38) chr9:27573681-27573703:- | GUGUUUUUGUUUUUCCCACCCUC | 963 | asAfsgggUfgGfGfaaaaAfcAfaaaacsasc | 935 | gsusuuuuGfuUfUfUfucccacccuuL96 | 934 |
| (hg38) chr9:27573664-27573686:- | ACCCUCUCUCCCCACUACUUGCU | 964 | asGfscaaGfuAfGfugggGfaGfagaggsgsu | 965 | cscsucucUfcCfCfCfacuacuugcuL96 | 966 |
| (hg38) chr9:27573660-27573682:- | UCUCUCCCCACUACUUGCUCUCA | 967 | usGfsagaGfcAfAfguagUfgGfggagasgsa | 891 | uscsucccCfaCfUfAfcuugcucucaL96 | 890 |
| (hg38) chr9:27573659-27573681:- | CUCUCCCCACUACUUGCUCUCAC | 968 | asUfsgagAfgCfAfaguaGfuGfgggagsasg | 839 | csusccccAfcUfAfCfuugcucucauL96 | 838 |
| (hg38) chr9:27573658-27573680:- | UCUCCCCACUACUUGCUCUCACA | 969 | usGfsugaGfaGfCfaaguAfgUfggggasgsa | 901 | uscscccaCfuAfCfUfugcucucacaL96 | 900 |
| (hg38) chr9:27573657-27573679:- | CUCCCCACUACUUGCUCUCACAG | 970 | asUfsgugAfgAfGfcaagUfaGfugggsasg | 851 | cscsccacUfaCfUfUfgcucucacauL96 | 850 |
| (hg38) chr9:27573656-27573678:- | UCCCCACUACUUGCUCUCACAGU | 971 | asCfsuguGfaGfAfgcaaGfuAfgugggsgsa | 915 | cscscacuAfcUfUfGfcucucacaguL96 | 914 |
| (hg38) chr9:27573655-27573677:- | CCCCACUACUUGCUCUCACAGUA | 972 | usAfscugUfgAfGfagcaAfgUfaguggsgsg | 921 | cscsacuaCfuUfGfCfucucacaguaL96 | 920 |

TABLE 20-continued

| Modified Sense and Antisense Strand Sequences of C9orf72 dsRNA Agents (Ensembl Gene ID: ENSG00000147894) | | | | | | |
|---|---|---|---|---|---|---|
| Target Coordinates in Human Chromosome 9 build 38 (hg38) | Target mRNA Sequence | SEQ ID NO: | Antisense Sequence 5' to 3' | SEQ ID NO: | Sense Sequence 5' to 3' | SEQ ID NO: |
| (hg38) chr9:27573654-27573676:- | CCCACUACUUGCUCUCACAGUAC | 973 | asUfsacuGfuGfAfgagcAfaGfuagugsgsg | 875 | csascuacUfuGfCfUfcucacaguauL96 | 874 |
| (hg38) chr9:27573653-27573675:- | CCACUACUUGCUCUCACAGUACu | 974 | asGfsuacUfgUfGfagagCfaAfguagusgsg | 903 | ascsuacuUfgCfUfCfucacaguacuL96 | 902 |
| (hg38) chr9:27573652-27573674:- | CACUACUUGCUCUCACAGUACUC | 975 | asAfsguaCfuGfUfgagaGfcAfaguagsusg | 879 | csusacuuGfcUfCfUfcacaguacuuL96 | 878 |
| (hg38) chr9:27573651-27573673:- | ACUACUUGCUCUCACAGUACUCG | 976 | asGfsaguAfcUfGfugagAfgCfaaguasgsu | 881 | usascuugCfuCfUfCfacaguacucuL96 | 880 |
| (hg38) chr9:27573650-27573672:- | CUACUUGCUCUCACAGUACUCGC | 977 | asCfsgagUfaCfUfgugaGfaGfcaagusasg | 867 | ascsuugcUfcUfCfAfcaguacucguL96 | 866 |
| (hg38) chr9:27573649-27573671:- | UACUUGCUCUCACAGUACUCGCU | 978 | asGfscgaGfuAfCfugugAfgAfgcaagsusa | 887 | csusugcuCfuCfAfCfaguacucgcuL96 | 886 |
| (hg38) chr9:27573648-27573670:- | ACUUGCUCUCACAGUACUCGCUG | 979 | asAfsgcgAfgUfAfcuguGfaGfagcaasgsu | 843 | ususgcucUfcAfCfAfguacucgcuuL96 | 842 |
| (hg38) chr9:27573647-27573669:- | CUUGCUCUCACAGUACUCGCUGA | 980 | usCfsagcGfaGfUfacugUfgAfgagcasasg | 827 | usgscucuCfaCfAfGfuacucgcugaL96 | 826 |
| (hg38) chr9:27573646-27573668:- | UUGCUCUCACAGUACUCGCUGAG | 981 | asUfscagCfgAfGfuacuGfuGfagagcsasa | 893 | gscsucucAfcAfGfUfacucgcugauL96 | 892 |
| (hg38) chr9:27573645-27573667:- | UGCUCUCACAGUACUCGCUGAGG | 982 | asCfsucaGfcGfAfguacUfgUfgagagscsa | 853 | csuscucaCfaGfUfAfcucgcugaguL96 | 852 |
| (hg38) chr9:27573643-27573665:- | CUCUCACAGUACUCGCUGAGGGU | 983 | asCfsccuCfaGfCfgaguAfcUfgugagsasg | 919 | csuscacaGfuAfCfUfcgcugaggguL96 | 918 |
| (hg38) chr9:27573642- | UCUCACAGUACUCGCUGAGGGUG | 984 | asAfscccUfcAfGfcgagUfaCfugugasgsa | 985 | uscsacagUfaCfUfCfgcugaggguuL96 | 986 |

TABLE 20-continued

| Modified Sense and Antisense Strand Sequences of C9orf72 dsRNA Agents (Ensembl Gene ID: ENSG00000147894) | | | | | | |
|---|---|---|---|---|---|---|
| Target Coordinates in Human Chromosome 9 build 38 (hg38) | Target mRNA Sequence | SEQ ID NO: | Antisense Sequence 5' to 3' | SEQ ID NO: | Sense Sequence 5' to 3' | SEQ ID NO: |
| 27573664:- | | | | | | |
| (hg38) chr9:27573641-27573663:- | CUCACAGUACUCGCUGAGGGUGA | 987 | usCfsaccCfuCfAfgcgaGfuAfcugugsasg | 945 | csascaguAfcUfCfGfcugagggugaL96 | 944 |
| (hg38) chr9:27573640-27573662:- | UCACAGUACUCGCUGAGGGUGAA | 988 | usUfscacCfcUfCfagcgAfgUfacugusgsa | 897 | ascsaguaCfuCfGfCfugagggugaaL96 | 896 |
| (hg38) chr9:27573639-27573661:- | CACAGUACUCGCUGAGGGUGAAC | 989 | asUfsucaCfcCfUfcagcGfaGfuacugsusg | 835 | csasguacUfcGfCfUfgagggugaauL96 | 834 |
| (hg38) chr9:27573638-27573660:- | ACAGUACUCGCUGAGGGUGAACA | 990 | usGfsuucAfcCfCfucagCfgAfguacusgsu | 913 | asgsuacuCfgCfUfGfagggugaacaL96 | 912 |
| (hg38) chr9:27573637-27573659:- | CAGUACUCGCUGAGGGUGAACAA | 991 | usUfsguuCfaCfCfcucaGfcGfaguacsusg | 865 | gsusacucGfcUfGfAfgggugaacaaL96 | 864 |
| (hg38) chr9:27573636-27573658:- | AGUACUCGCUGAGGGUGAACAAG | 992 | asUfsuguUfcAfCfccucAfgCfgaguascsu | 845 | usascucgCfuGfAfGfggugaacaauL96 | 844 |
| (hg38) chr9:27573635-27573657:- | GUACUCGCUGAGGGUGAACAAGA | 993 | usCfsuugUfuCfAfcccuCfaGfcgagusasc | 929 | ascsucgcUfgAfGfGfgugaacaagaL96 | 928 |
| (hg38) chr9:27573634-27573656:- | UACUCGCUGAGGGUGAACAAGAA | 994 | usUfscuuGfuUfCfacccUfcAfgegagsusa | 831 | csuscgcuGfaGfGfGfugaacaagaaL96 | 830 |
| (hg38) chr9:27573633-27573655:- | ACUCGCUGAGGGUGAACAAGAAA | 995 | usUfsucuUfgUfUfcaccCfuCfagcgasgsu | 837 | uscsgcugAfgGfGfUfgaacaagaaaL96 | 836 |
| (hg38) chr9:27573632-27573654:- | CUCGCUGAGGGUGAACAAGAAAA | 996 | usUfsuucUfuGfUfucacCfcUfcagcgsasg | 833 | csgscugaGfgGfUfGfaacaagaaaaL96 | 832 |
| (hg38) chr9:27573631-27573653:- | UCGCUGAGGGUGAACAAGAAAAG | 997 | asUfsuuuCfuUfGfuucaCfcCfucagcsgsa | 787 | gscsugagGfgUfGfAfacaagaaaauL96 | 786 |

TABLE 20-continued

| Modified Sense and Antisense Strand Sequences of C9orf72 dsRNA Agents (Ensembl Gene ID: ENSG00000147894) | | | | | | |
|---|---|---|---|---|---|---|
| Target Coordinates in Human Chromosome 9 build 38 (hg38) | Target mRNA Sequence | SEQ ID NO: | Antisense Sequence 5' to 3' | SEQ ID NO: | Sense Sequence 5' to 3' | SEQ ID NO: |
| (hg38) chr9:27573630-27573652:- | CGCUGAGGGUGAACAAGAAAAGA | 998 | usCfsuuuUfcUfUfguucAfcCfcucagscsg | 813 | csusgaggGfuGfAfAfcaagaaaagaL96 | 812 |
| (hg38) chr9:27573629-27573651:- | GCUGAGGGUGAACAAGAAAAGAC | 999 | asUfscuuUfuCfUfuguuCfaCfccucasgsc | 909 | usgsagggUfgAfAfCfaagaaaagauL96 | 908 |
| (hg38) chr9:27573628-27573650:- | CUGAGGGUGAACAAGAAAAGACC | 1000 | asGfsucuUfuUfCfuuguUfcAfcccucsasg | 817 | gsasggguGfaAfCfAfagaaaagacuL96 | 816 |
| (hg38) chr9:27573627-27573649:- | UGAGGGUGAACAAGAAAAGACCU | 1001 | asGfsgucUfuUfUfcuugUfuCfacccuscsa | 823 | asgsggugAfaCfAfAfgaaaagaccuL96 | 822 |
| (hg38) chr9:27573626-27573648:- | GAGGGUGAACAAGAAAAGACCUG | 1002 | asAfsgguCfuUfUfucuuGfuUfcacccsusc | 885 | gsgsgugaAfcAfAfGfaaaagaccuuL96 | 884 |
| (hg38) chr9:27573625-27573647:- | AGGGUGAACAAGAAAAGACCUGA | 1003 | usCfsaggUfcUfUfuucuUfgUfucaccscsu | 829 | gsgsugaaCfaAfGfAfaaagaccugaL96 | 828 |
| (hg38) chr9:27573624-27573646:- | GGGUGAACAAGAAAAGACCUGAU | 1004 | asUfscagGfuCfUfuuucUfuGfuucacscsc | 819 | gsusgaacAfaGfAfAfaagaccugauL96 | 818 |
| (hg38) chr9:27573623-27573645:- | GGUGAACAAGAAAAGACCUGAUA | 1005 | usAfsucaGfgUfCfuuuuCfuUfguucascsc | 815 | usgsaacaAfgAfAfAfagaccugauaL96 | 814 |
| (hg38) chr9:27573622-27573644:- | GUGAACAAGAAAAGACCUGAUAA | 1006 | usUfsaucAfgGfUfcuuuUfcUfuguucsasc | 857 | gsasacaaGfaAfAfAfgaccugauaaL96 | 856 |
| (hg38) chr9:27573621-27573643:- | UGAACAAGAAAAGACCUGAUAAA | 1007 | usUfsuauCfaGfGfucuuUfuCfuuguuscsa | 797 | asascaagAfaAfAfGfaccugauaaaL96 | 796 |
| (hg38) chr9:27573620-27573642:- | GAACAAGAAAAGACCUGAUAAAG | 1008 | asUfsuuaUfcAfGfgucuUfuUfcuugususc | 801 | ascsaagaAfaAfGfAfccugauaaauL96 | 800 |
| (hg38) chr9:27573618- | ACAAGAAAAGACCUGAUAAAGAU | 1009 | asUfscuuUfaUfCfagguCfuUfuucuusgsu | 811 | asasgaaaAfgAfCfCfugauaaagauL96 | 810 |

TABLE 20-continued

| Modified Sense and Antisense Strand Sequences of C9orf72 dsRNA Agents (Ensembl Gene ID: ENSG00000147894) | | | | | | |
|---|---|---|---|---|---|---|
| Target Coordinates in Human Chromosome 9 build 38 (hg38) | Target mRNA Sequence | SEQ ID NO: | Antisense Sequence 5' to 3' | SEQ ID NO: | Sense Sequence 5' to 3' | SEQ ID NO: |
| 27573640:- | | | | | | |
| (hg38) chr9:27573617-27573639:- | CAAGAAAAGACCUGAUAAAGAUU | 1010 | asAfsucuUfuAfUfcaggUfcUfuuucususg | 159 | asgsaaaaGfaCfCfUfgauaaagauuL96 | 158 |
| (hg38) chr9:27573616-27573638:- | AAGAAAAGACCUGAUAAAGAUUA | 1011 | usAfsaucUfuUfAfucagGfuCfuuuucsusu | 799 | gsasaaagAfcCfUfGfauaaagauuaL96 | 798 |
| (hg38) chr9:27573615-27573637:- | AGAAAAGACCUGAUAAAGAUUAA | 1012 | usUfsaauCfuUfUfaucaGfgUfcuuUUSCSU | 161 | asasaagaCfcUfGfAfuaaagauuaaL96 | 160 |
| (hg38) chr9:27573614-27573636:- | GAAAAGACCUGAUAAAGAUUAAC | 1013 | asUfsuaaUfcUfUfuaucAfgGfucuUUSUSC | 163 | asasagacCfuGfAfUfaaagauuaauL96 | 162 |
| (hg38) chr9:27573613-27573635:- | AAAAGACCUGAUAAAGAUUAACC | 1014 | asGfsuuaAfuCfUfuuauCfaGfgucuusus u | 803 | asasgaccUfgAfUfAfaagauuaacuL96 | 802 |
| (hg38) chr9:27573612-27573634:- | AAAGACCUGAUAAAGAUUAACCA | 1015 | usGfsguuAfaUfCfuuuaUfcAfggucususu | 863 | asgsaccuGfaUfAfAfagauuaaccaL96 | 862 |
| (hg38) chr9:27573611-27573633:- | AAGACCUGAUAAAGAUUAACCAG | 1016 | asUfsgguUfaAfUfcuuuAfuCfaggucsusu | 805 | gsasccugAfuAfAfAfgauuaaccauL96 | 804 |
| (hg38) chr9:27573610-27573632:- | AGACCUGAUAAAGAUUAACCAGA | 1017 | usCfsuggUfuAfAfucuuUfaUfcagguscsu | 809 | ascscugaUfaAfAfGfauuaaccagaL96 | 808 |
| (hg38) chr9:27573609-27573631:- | GACCUGAUAAAGAUUAACCAGAA | 1018 | usUfscugGfuUfAfaucuUfuAfucaggusc | 825 | cscsugauAfaAfGfAfuuaaccagaaL96 | 824 |
| (hg38) chr9:27573608-27573630:- | ACCUGAUAAAGAUUAACCAGAAG | 1019 | asUfsucuGfgUfUfaaucUfuUfaucagsgsu | 165 | csusgauaAfaGfAfUfuaaccagaauL96 | 164 |
| (hg38) chr9:27573607-27573629:- | CCUGAUAAAGAUUAACCAGAAGA | 1020 | usCfsuucUfgGfUfuaauCfuUfuaucasgsg | 807 | usgsauaaAfgAfUfUfaaccagaagaL96 | 806 |

TABLE 20-continued

Modified Sense and Antisense Strand Sequences of C9orf72 dsRNA Agents (Ensembl Gene ID: ENSG00000147894)

| Target Coordinates in Human Chromosome 9 build 38 (hg38) | Target mRNA Sequence | SEQ ID NO: | Antisense Sequence 5' to 3' | SEQ ID NO: | Sense Sequence 5' to 3' | SEQ ID NO: |
|---|---|---|---|---|---|---|
| (hg38) chr9:27573606-27573628:- | CUGAUAAAGAUUAACCAGAAGAA | 1021 | usUfscuuCfuGfGfuuaaUfcUfuuaucsasg | 789 | gsasuaaaGfaUfUfAfaccagaagaaL96 | 788 |
| (hg38) chr9:27573605-27573627:- | UGAUAAAGAUUAACCAGAAGAAA | 1022 | usUfsucuUfcUfGfguuaAfuCfuuuauscsa | 167 | asusaaagAfuUfAfAfccagaagaaaL96 | 166 |
| (hg38) chr9:27573603-27573625:- | AUAAAGAUUAACCAGAAGAAAAC | 1023 | asUfsuuuCfuUfCfugguUfaAfucuuusasu | 169 | asasagauUfaAfCfCfagaagaaaauL96 | 168 |
| (hg38) chr9:27573602-27573624:- | UAAAGAUUAACCAGAAGAAAACA | 1024 | usGfsuuuUfcUfUfcuggUfuAfaucuusua | 821 | asasgauuAfaCfCfAfgaagaaaacaL96 | 820 |
| (hg38) chr9:27573599-27573621:- | AGAUUAACCAGAAGAAAACAAGG | 1025 | asCfsuugUfuUfUfcuucUfgGfuuaauscsu | 793 | asusuaacCfaGfAfAfgaaaacaaguL96 | 792 |
| (hg38) chr9:27573598-27573620:- | GAUUAACCAGAAGAAAACAAGGA | 1026 | usCfscuuGfuUfUfucuuCfuGfguuaasusc | 889 | ususaaccAfgAfAfGfaaaacaaggaL96 | 888 |
| (hg38) chr9:27573597-27573619:- | AUUAACCAGAAGAAAACAAGGAG | 1027 | asUfsccuUfgUfUfuucuUfcUfgguuasasu | 795 | usasaccaGfaAfGfAfaaacaaggauL96 | 794 |
| (hg38) chr9:27573596-27573618:- | UUAACCAGAAGAAAACAAGGAGG | 1028 | asCfsuccUfuGfUfuuucUfuCfugguusasa | 791 | asasccagAfaGfAfAfaacaaggaguL96 | 790 |
| (hg38) chr9:27573595-27573617:- | UAACCAGAAGAAAACAAGGAGGG | 1029 | asCfscucCfuUfGfuuuuCfuUfcuggusua | 859 | ascscagaAfgAfAfAfacaaggagguL96 | 858 |
| (hg38) chr9:27573577-27573599:- | GAGGGAAACAACCGCAGCCUGUA | 1030 | usAfscagGfcUfGfcgguUfgUfuucccsusc | 947 | gsgsgaaaCfaAfCfCfgcagccuguaL96 | 946 |
| (hg38) chr9:27573576-27573598:- | AGGGAAACAACCGCAGCCUGUAG | 1031 | asUfsacaGfgCfUfgcggUfuGfuuUCCSCSU | 905 | gsgsaaacAfaCfCfGfcagccuguauL96 | 904 |
| (hg38) chr9:27573574- | GGAAACAACCGCAGCCUGUAGCA | 1032 | usGfscuaCfaGfGfcugcGfgUfuguuuscsc | 951 | asasacaaCfcGfCfAfgccuguagcaL96 | 950 |

TABLE 20-continued

| Modified Sense and Antisense Strand Sequences of C9orf72 dsRNA Agents (Ensembl Gene ID: ENSG00000147894) | | | | | | |
|---|---|---|---|---|---|---|
| Target Coordinates in Human Chromosome 9 build 38 (hg38) | Target mRNA Sequence | SEQ ID NO: | Antisense Sequence 5' to 3' | SEQ ID NO: | Sense Sequence 5' to 3' | SEQ ID NO: |
| 27573596:- | | | | | | |
| (hg38) chr9:27573573-27573595:- | GAAACAACCGCAGCCUGUAGCAA | 1033 | usUfsgcuAfcAfGfgcugCfgGfuuguususc | 939 | asascaacCfgCfAfGfccuguagcaaL96 | 938 |
| (hg38) chr9:27573572-27573594:- | AAACAACCGCAGCCUGUAGCAAG | 1034 | asUfsugcUfaCfAfggcuGfGfguugususu | 841 | ascsaaccGfcAfGfCfcuguagcaauL96 | 840 |
| (hg38) chr9:27573571-27573593:- | AACAACCGCAGCCUGUAGCAAGC | 1035 | asCfsuugCfuAfCfaggcUfgCfgguugsusu | 883 | csasaccgCfaGfCfCfuguagcaaguL96 | 882 |
| (hg38) chr9:27573570-27573592:- | ACAACCGCAGCCUGUAGCAAGCU | 1036 | asGfscuuGfcUfAfcaggCfuGfcgguusgsu | 899 | asasccgcAfgCfCfUfguagcaagcuL96 | 898 |
| (hg38) chr9:27573568-27573590:- | AACCGCAGCCUGUAGCAAGCUCU | 1037 | asGfsagcUfuGfCfuacaGfgCfugcggsusu | 927 | cscsgcagCfcUfGfUfagcaagcucuL96 | 926 |
| (hg38) chr9:27573564-27573586:- | GCAGCCUGUAGCAAGCUCUGGAA | 1038 | usUfsccaGfaGfCfuugcUfaCfaggcusgsc | 917 | asgsccugUfaGfCfAfagcucuggaaL96 | 916 |
| (hg38) chr9:27573563-27573585:- | CAGCCUGUAGCAAGCUCUGGAAC | 1039 | asUfsuccAfgAfGfcuugCfuAfcaggcsusg | 869 | gscscuguAfgCfAfAfgcucuggaauL96 | 868 |
| (hg38) chr9:27573562-27573584:- | AGCCUGUAGCAAGCUCUGGAACU | 1040 | asGfsuucCfaGfAfgcuuGfcUfacaggscsu | 907 | cscsuguaGfcAfAfGfcucuggaacuL96 | 906 |
| (hg38) chr9:27573561-27573583:- | GCCUGUAGCAAGCUCUGGAACUC | 1041 | asAfsguuCfcAfGfagcuUfgCfuacagsgsc | 925 | csusguagCfaAfGfCfucuggaacuuL96 | 924 |
| (hg38) chr9:27573560-27573582:- | CCUGUAGCAAGCUCUGGAACUCA | 1042 | usGfsaguUfcCfAfgagcUfuGfcuacasgsg | 911 | usgsuagcAfaGfCfUfcuggaacucaL96 | 910 |
| (hg38) chr9:27573559-27573581:- | CUGUAGCAAGCUCUGGAACUCAG | 1043 | asUfsgagUfuCfCfagagCfuUfgcuacsasg | 847 | gsusagcaAfgCfUfCfuggaacucauL96 | 846 |

TABLE 20-continued

Modified Sense and Antisense Strand Sequences of C9orf72 dsRNA Agents (Ensembl Gene ID: ENSG00000147894)

| Target Coordinates in Human Chromosome 9 build 38 (hg38) | Target mRNA Sequence | SEQ ID NO: | Antisense Sequence 5' to 3' | SEQ ID NO: | Sense Sequence 5' to 3' | SEQ ID NO: |
|---|---|---|---|---|---|---|
| (hg38) chr9:27573558-27573580:- | UGUAGCAAGCUCUGGAACUCAGG | 1044 | asCfsugaGfuUfCfcagaGfcUfugcuascsa | 861 | usasgcaaGfcUfCfUfggaacucaguL96 | 860 |
| (hg38) chr9:27573557-27573579:- | GUAGCAAGCUCUGGAACUCAGGA | 1045 | usCfscugAfgUfUfccagAfgCfuugcusasc | 933 | asgscaagCfuCfUfGfgaacucaggaL96 | 932 |
| (hg38) chr9:27573556-27573578:- | UAGCAAGCUCUGGAACUCAGGAG | 1046 | asUfsccuGfaGfUfuccaGfaGfcuugesusa | 923 | gscsaagcUfcUfGfGfaacucaggauL96 | 922 |
| (hg38) chr9:27573555-27573577:- | AGCAAGCUCUGGAACUCAGGAGU | 1047 | asCfsuccUfgAfGfuuccAfgAfgcuugscsu | 871 | csasagcuCfuGfGfAfacucaggaguL96 | 870 |
| (hg38) chr9:27573554-27573576:- | GCAAGCUCUGGAACUCAGGAGUC | 1048 | asAfscucCfuGfAfguucCfaGfagcuusgsc | 877 | asasgcucUfgGfAfAfcucaggaguuL96 | 876 |
| (hg38) chr9:27573553-27573575:- | CAAGCUCUGGAACUCAGGAGUCG | 1049 | asGfsacuCfcUfGfaguuCfcAfgagcusnsg | 849 | asgscucuGfgAfAfCfucaggagucuL96 | 848 |
| (hg38) chr9:27573552-27573574:- | AAGCUCUGGAACUCAGGAGUCGC | 1050 | asCfsgacUfcCfUfgaguUfcCfagagcsusu | 895 | gscsucugGfaAfCfUfcaggagucguL96 | 894 |
| (hg38) chr9:27573542-27573564:- | ACUCAGGAGUCGCGCGCUAGGGG | 1051 | asCfsccuAfgCfGfcgcgAfcUfccugasgsu | 931 | uscsaggaGfuCfGfCfgcgcuaggguL96 | 930 |
| (hg38) chr9:27573541-27573563:- | CUCAGGAGUCGCGCGCUAGGGGC | 1052 | asCfscccUfaGfCfgcgcGfaCfuccugsasg | 941 | csasggagUfcGfCfGfcgcuagggguL96 | 940 |
| (hg38) chr9:27573540-27573562:- | UCAGGAGUCGCGCGCUAGGGGCC | 1053 | asGfsccccCfuAfGfcgcgCfgAfcuccusgsa | 949 | asgsgaguCfgCfGfCfgcuaggggcuL96 | 948 |
| (hg38) chr9:27573539-27573561:- | CAGGAGUCGCGCGCUAGGGGCCG | 1054 | asGfsgccCfcUfAfgcgcGfcGfacuccsusg | 943 | gsgsagucGfcGfCfGfcuaggggccuL96 | 942 |
| (hg38) chr9:27573538- | AGGAGUCGCGCGCUAGGGGCCGG | 1055 | asCfsggcCfcCfUfagcgCfgCfgacUCSCSU | 953 | gsasgucgCfgCfGfCfuagggggccguL96 | 952 |

TABLE 20-continued

Modified Sense and Antisense Strand Sequences of C9orf72 dsRNA Agents (Ensembl Gene ID: ENSG00000147894)

| Target Coordinates in Human Chromosome 9 build 38 (hg38) | Target mRNA Sequence | SEQ ID NO: | Antisense Sequence 5' to 3' | SEQ ID NO: | Sense Sequence 5' to 3' | SEQ ID NO: |
|---|---|---|---|---|---|---|
| 27573560:- | | | | | | |
| (hg38) chr9:27573537-27573559:- | GGAGUCGCGCGCUAGGGGCCGGG | 1056 | asCfscggCfcCfCfuagcGfcGfcgacuscsc | 955 | asgsucgcGfcGfCfUfaggggccgguL96 | 954 |

Example 7. C9orf72 siRNAs Targeting Exon 1A, Intron 1A, and Intron 1B

Figure 18A:
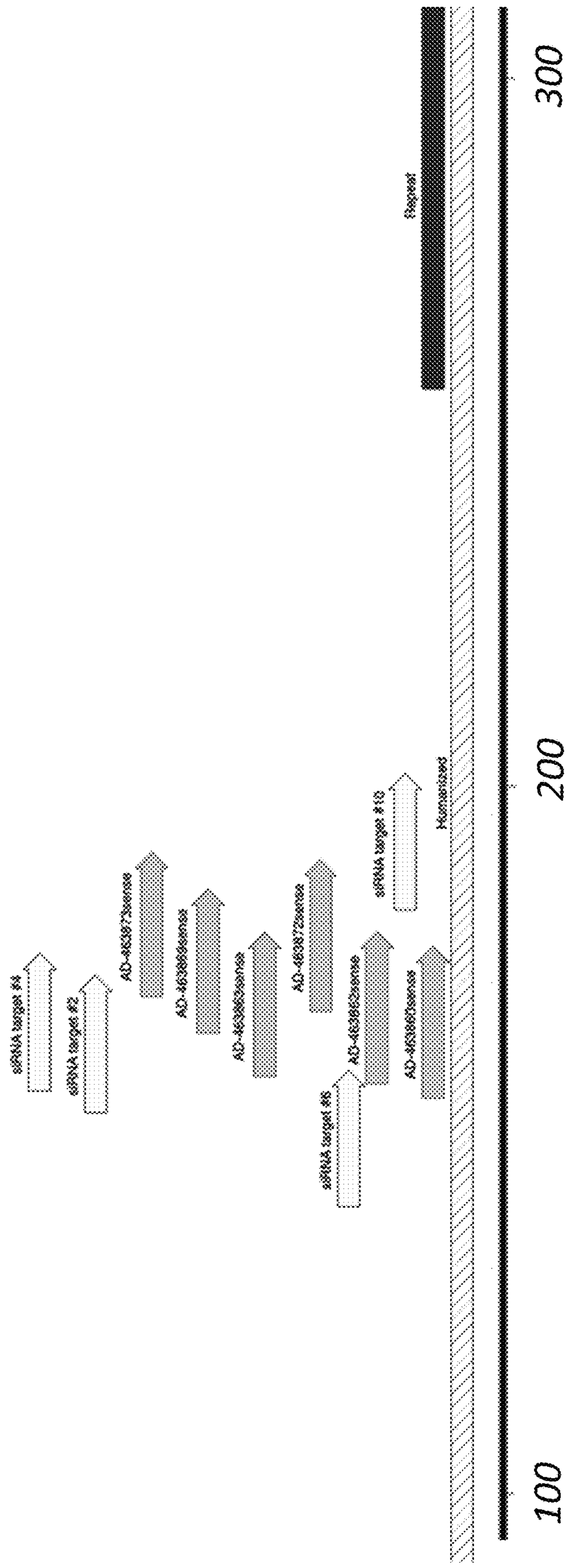
FIG. 18A is a schematic (not to scale) of siRNAs targeting intron 1A of C9orf72.
Figure 18B:
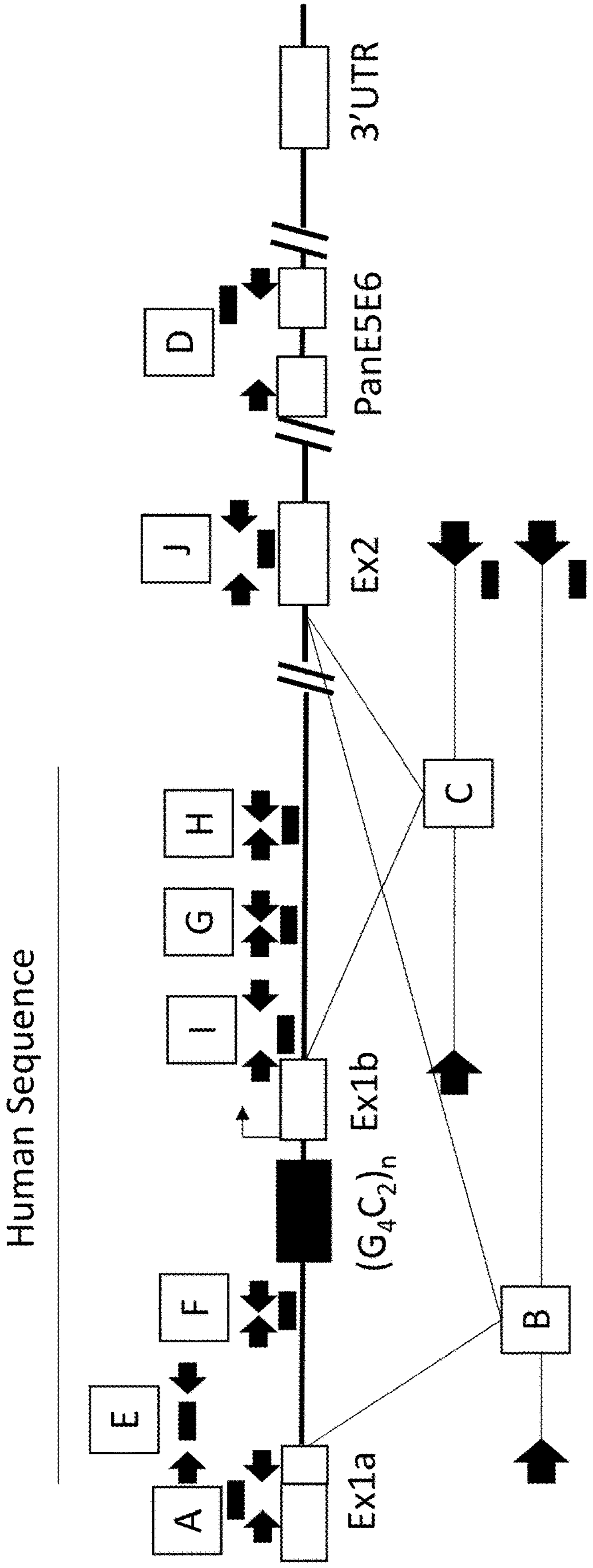
FIG. 18B is a schematic (not to scale) of TAQMAN® qualitative PCR assays A, B, C, D, E, F, G, H, I, and J spanning different sections of the C9orf72 pre-mRNA. Sequences for the primers and probes are shown in Table 8.
Figure 19A:
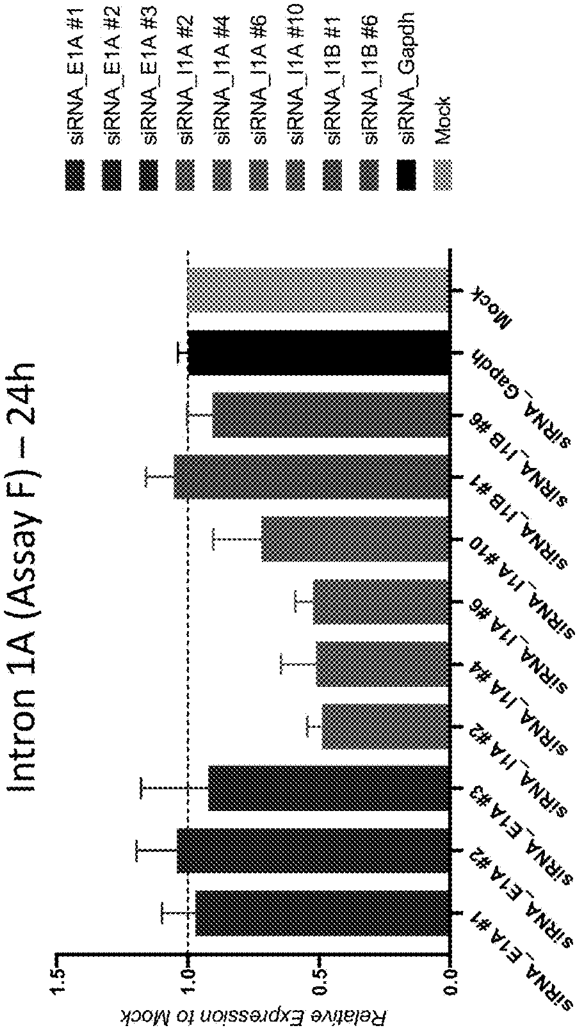
FIGS. 19A-19C are bar graphs showing relative expression levels (as determined by the TAQMAN® quantitative reverse transcription-coupled PCR (RT-qPCR) assays) of transcripts from the C9orf72 locus (y-axis) that contain C9orf72 intron 1A sequence (FIG. 19A; Assay F), that are C9orf72 exon 2-3 spliced transcripts (FIG. 19B), or that are C9orf72 exon 1a-2 spliced transcripts (FIG. 19C; Assay B) 24 hours after transfection with siRNAs targeting exon 1A (siRNAs E1A #1, E1A #2, and E1A #3), intron 1A upstream of the hexanucleotide repeat (siRNAs I1A #2, I1A #4, I1A #6, and I1A #10), or intron 1B downstream of the hexanucleotide repeat and downstream of exon 1B (siRNAs I1B #1 and I1B #6) in mouse embryonic stem cells comprising a modified C9orf72 locus comprising 300 repeats of the hexanucleotide sequence set forth as SEQ ID NO: 1. Gapdh siRNAs were used as a control, and mock was used as a negative control.
Figure 19B:
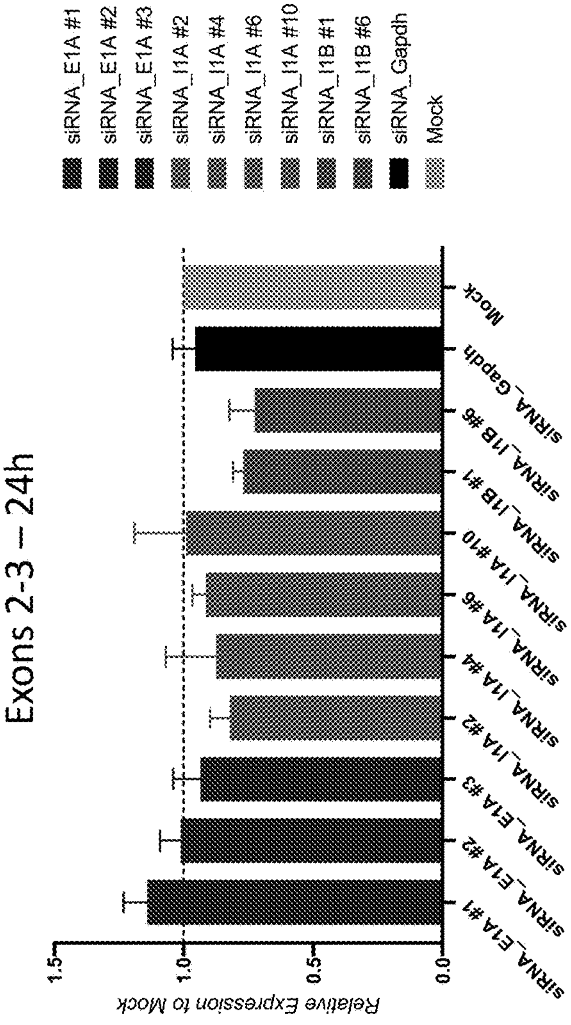
Figure 19C:
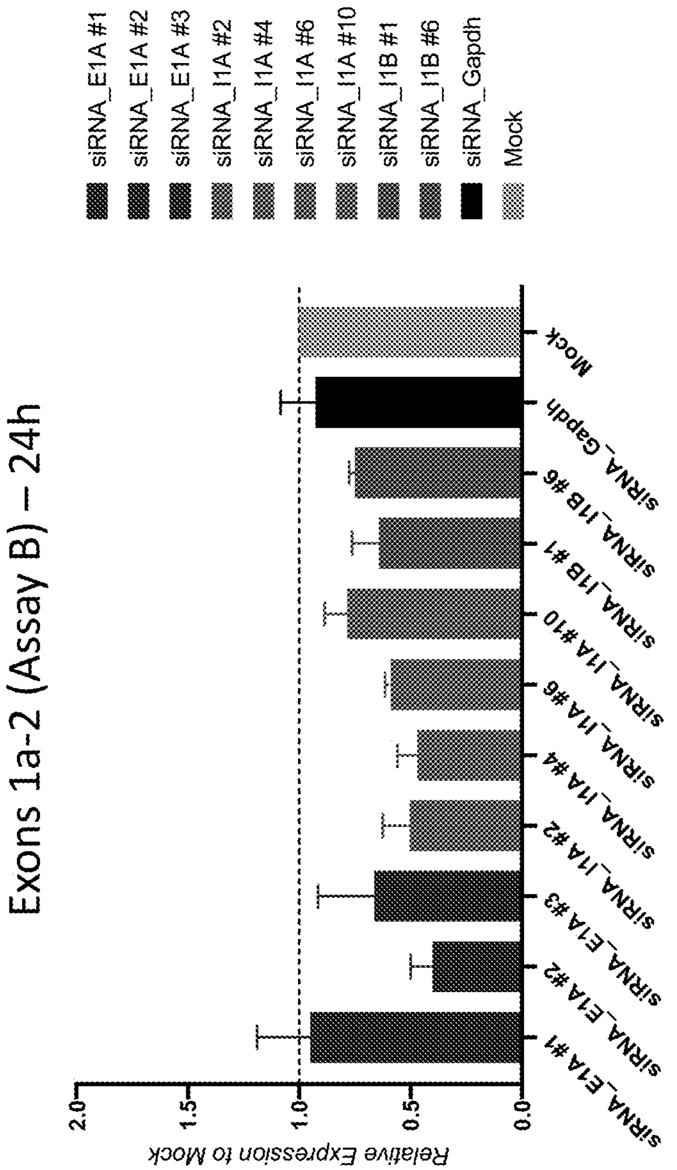
Figure 20A:
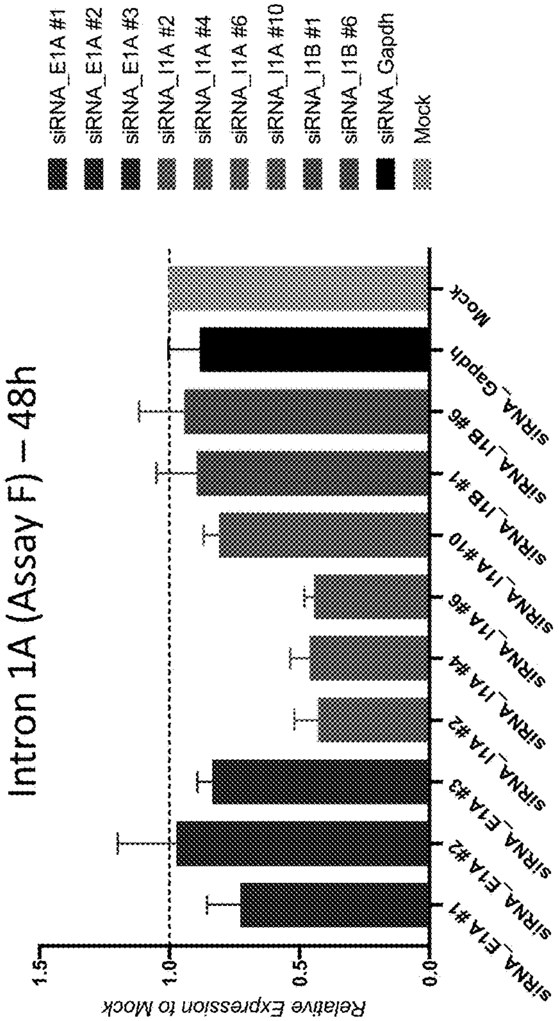
FIGS. 20A-20C are bar graphs showing relative expression levels (as determined by the TAQMAN® quantitative reverse transcription-coupled PCR (RT-qPCR) assays) of transcripts from the C9orf72 locus (y-axis) that contain C9orf72 intron 1A (FIG. 20A; Assay F), that are C9orf72 exon 2-3 spliced transcripts (FIG. 20B), or that are C9orf72 exon 1a-2 spliced transcripts (FIG. 20C; Assay B) 48 hours after transfection with siRNAs targeting exon 1A (siRNAs E1A #1, E1A #2, and E1A #3), intron 1A upstream of the hexanucleotide repeat (siRNAs I1A #2, I1A #4, I1A #6, and I1A #10), or intron 1B downstream of the hexanucleotide repeat and downstream of exon 1B (siRNAs I1B #1 and I1B #6) in mouse embryonic stem cells comprising a modified C9orf72 locus comprising 300 repeats of the hexanucleotide sequence set forth as SEQ ID NO: 1. Gapdh siRNAs were used as a control, and mock was used as a negative control.
Figure 20B:
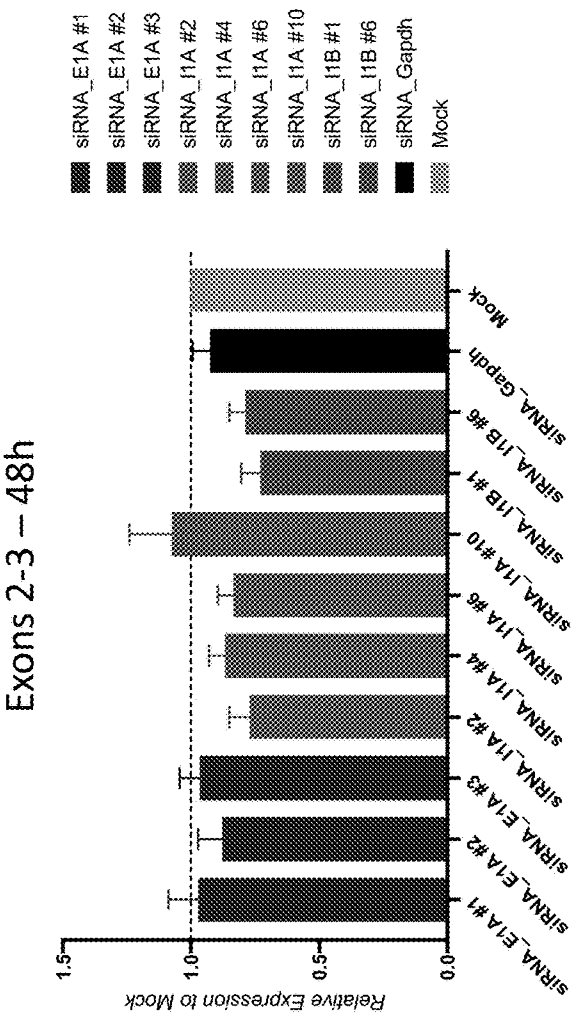
Figure 20C:
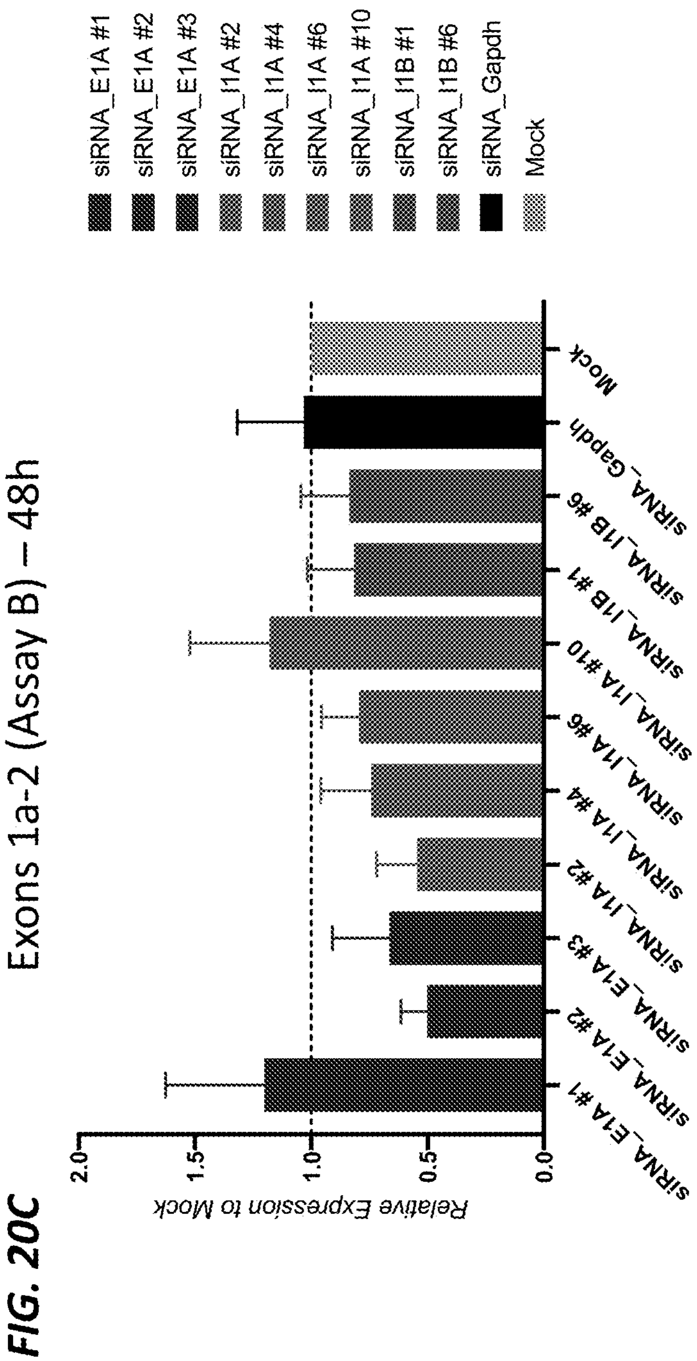
Figure 21A:
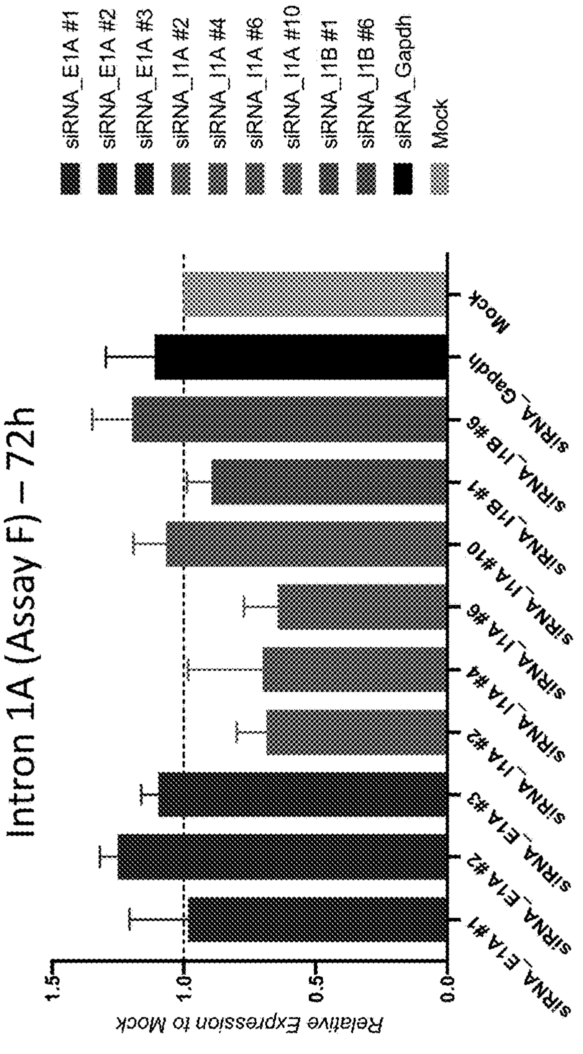
FIGS. 21A-21C are bar graphs showing relative expression levels (as determined by the TAQMAN® quantitative reverse transcription-coupled PCR (RT-qPCR) assays) of transcripts from the C9orf72 locus (y-axis) that contain C9orf72 intron 1A (FIG. 21A; Assay F), that are C9orf72 exon 2-3 spliced transcripts (FIG. 21B), or that are C9orf72 exon 1a-2 spliced transcripts (FIG. 21C; Assay B) 72 hours after transfection with siRNAs targeting exon 1A (siRNAs E1A #1, E1A #2, and E1A #3), intron 1A upstream of the hexanucleotide repeat (siRNAs I1A #2, I1A #4, I1A #6, and I1A #10), or intron 1B downstream of the hexanucleotide repeat and downstream of exon 1B (siRNAs I1B #1 and I1B #6) in mouse embryonic stem cells comprising a modified C9orf72 locus comprising 300 repeats of the hexanucleotide sequence set forth as SEQ ID NO: 1. Gapdh siRNAs were used as a control, and mock was used as a negative control.
Figure 21B:
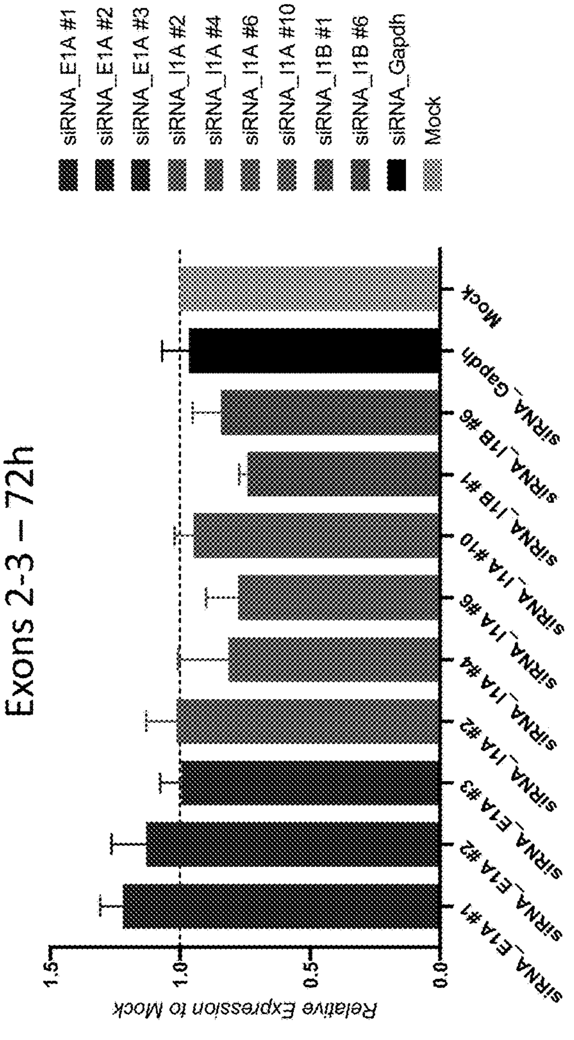
Figure 21C:
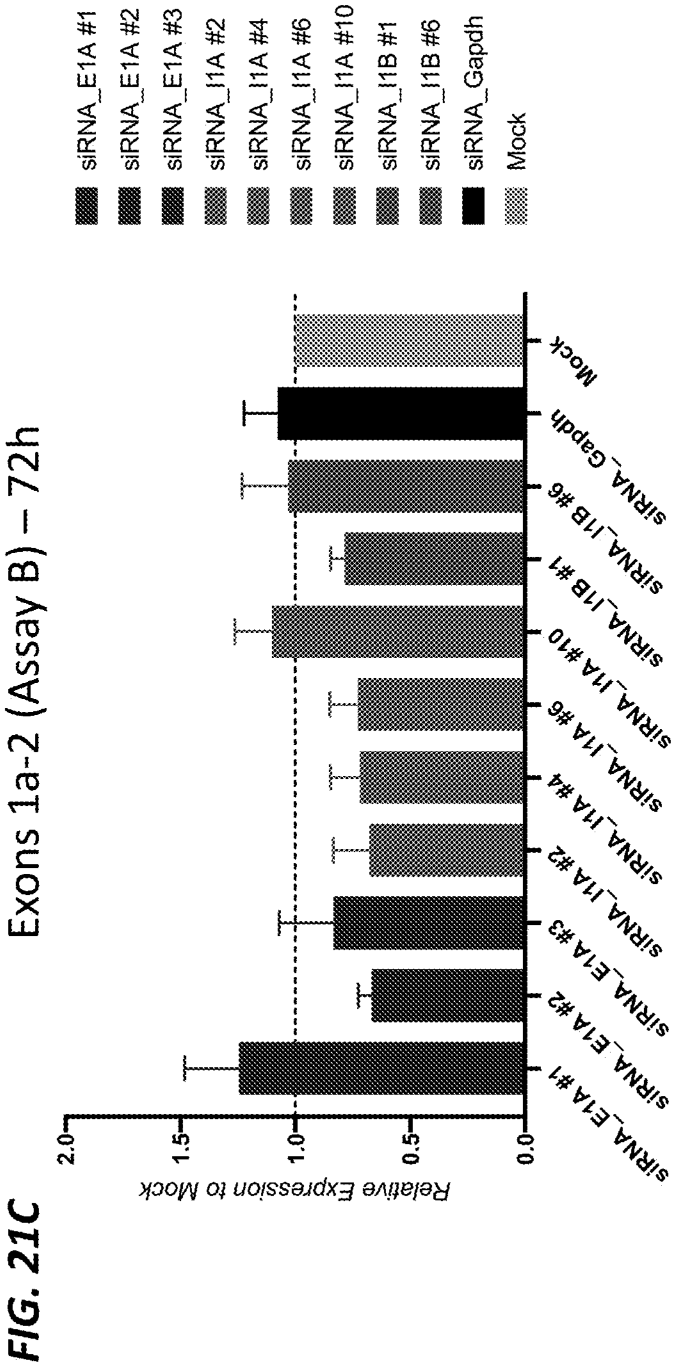

To further explore the phenomenon observed in Example 4, mouse embryonic stem cells carrying a humanized C9orf72 gene having 300 repeats of the GGGGCC hexanucleotide (SEQ ID NO: 142) were treated with siRNAs that targeted C9orf72 RNA sequences in exon 1A, intron 1A (upstream of hexanucleotide repeat expansion), and intron 1B (downstream of hexanucleotide repeat expansion and downstream of exon 1B). Three siRNAs targeted exon 1A (siRNAs E1A #1, E1A #2, and E1A #3), four siRNAs targeted intron 1A upstream of the hexanucleotide repeat (siRNAs I1A #2, I1A #4, I1A #6, and I1A #10), and two siRNAs targeted intron 1B downstream of the hexanucleotide repeat and downstream of exon 1B (siRNAs I1B #1 and I1B #6). Table 21 provides the sense strand and antisense strand nucleotide sequences of these agents. The C9orf72 regions targeted by the four siRNAs targeting intron 1A are shown in FIG. 18A along with the siRNAs used in Example 4. A Gapdh siRNA was used as a positive control, and a TAQMAN® qualitative PCR assay for Gapdh expression confirmed knockdown of Gapdh expression (data not shown). Mock was used as a negative control. Gene expression was evaluated at 24 hours, 48 hours, and 72 hours post-transfection with 25 nM siRNA. TAQMAN® qualitative PCR assays were then performed using primers that flank various regions and probes that detect those regions of the modified C9orf72 locus. The primers and probes are shown in FIG. 18B and in Table 8. It was demonstrated that siRNAs that targeted intron sequences in intron 1A (upstream of the GGGGCC repeat (SEQ ID NO: 1) expansion) promoted reduced accumulation of intron-1A-containing C9orf72 RNAs (assay F; see FIGS. 19A, 20A, and 21A for the 24 h, 48h, and 72h time points, respectively) while having little effect on the C9orf72 mature mRNA (exon 2-3 assay ID Mm01216829 ml from Thermo Fisher Scientific; see FIGS. 19B, 20B, and 21B for the 24 h, 48h, and 72h time points, respectively). In contrast, siRNAs targeting exon 1A or intron 1B (downstream of the GGGGCC repeat (SEQ ID NO: 1) expansion and downstream of exon 1B) did not reduce accumulation of intron-1A-containing C9orf72 RNAs (see FIGS. 19A, 20A, and 21A for the 24 h, 48h, and 72h time points, respectively). The Gapdh siRNA control shows that the specific knock down of C9orf72 RNAs is not simply the result of general RNA interference activity in the cells.

Figure 22A:
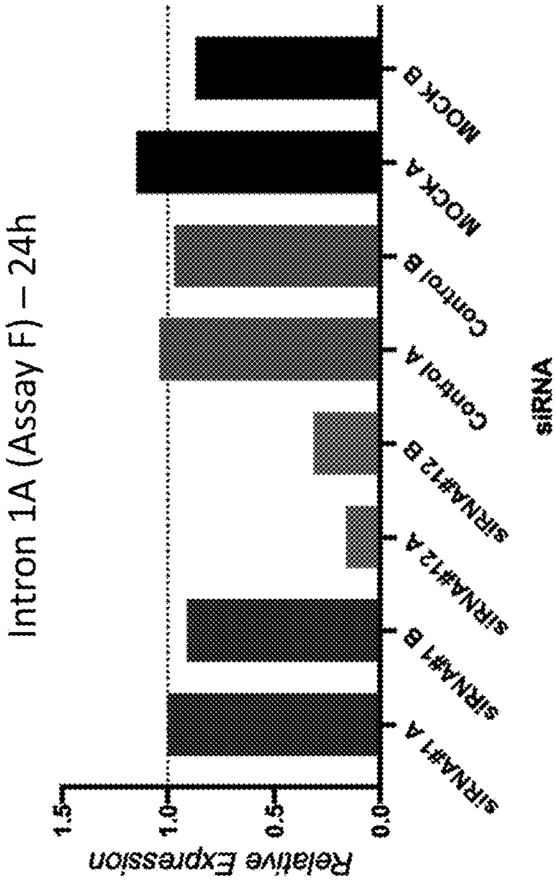
FIGS. 22A-22E are bar graphs showing relative expression levels (as determined by the TAQMAN® quantitative reverse transcription-coupled PCR (RT-qPCR) assays) of transcripts from the C9orf72 locus (y-axis) that contain C9orf72 intron 1A sequence (FIG. 22A; Assay F), that contain C9orf72 intron 1A sequence linked to exon 1A (FIG. 22B; Assay E), that are C9orf72 exon 1a-2 spliced transcripts (FIG. 22C; Assay B), that are C9orf72 exon 1b-2 spliced transcripts (FIG. 22D; Assay C), or that are C9orf72 exon 5-6 spliced transcripts (FIG. 22E; Assay D) 24 hours after electroporation with siRNAs targeting mature C9orf72 mRNA (siRNA #1) or intron 1A upstream of the hexanucleotide repeat (siRNA #12) in mouse embryonic stem cells comprising a modified C9orf72 locus comprising 300 repeats of the hexanucleotide sequence set forth as SEQ ID NO: 1. A Gapdh siRNA and a mock sample were used as negative controls.
Figure 22B:
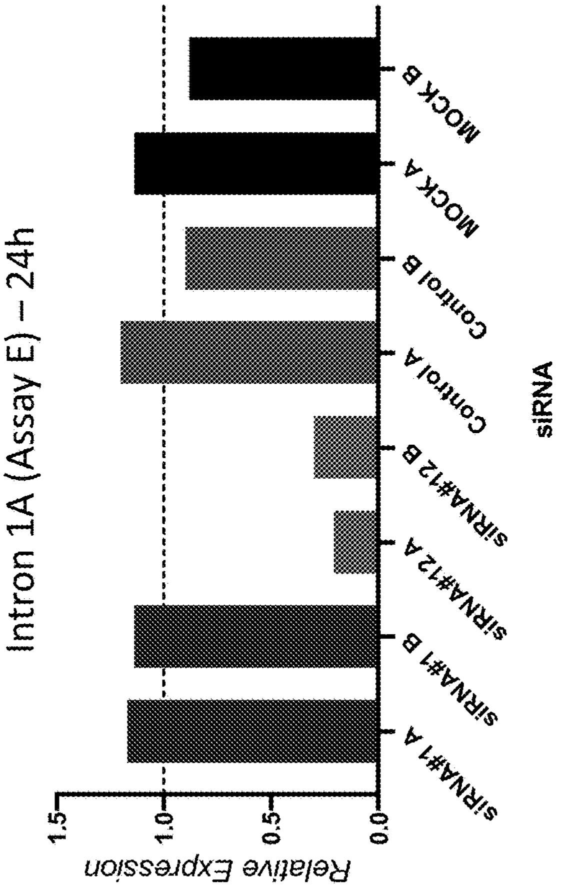
Figure 22C:
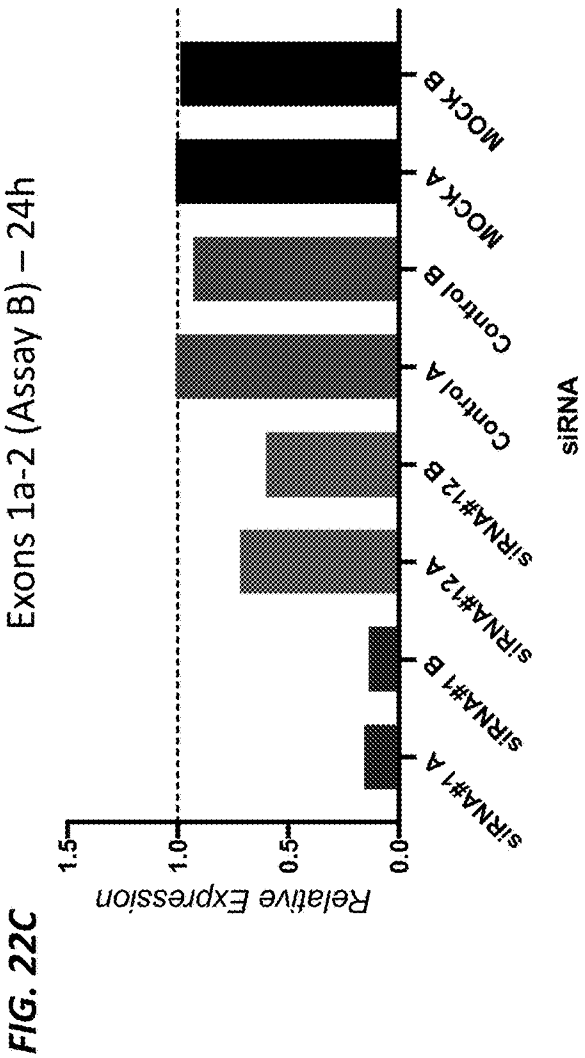
Figure 22D:
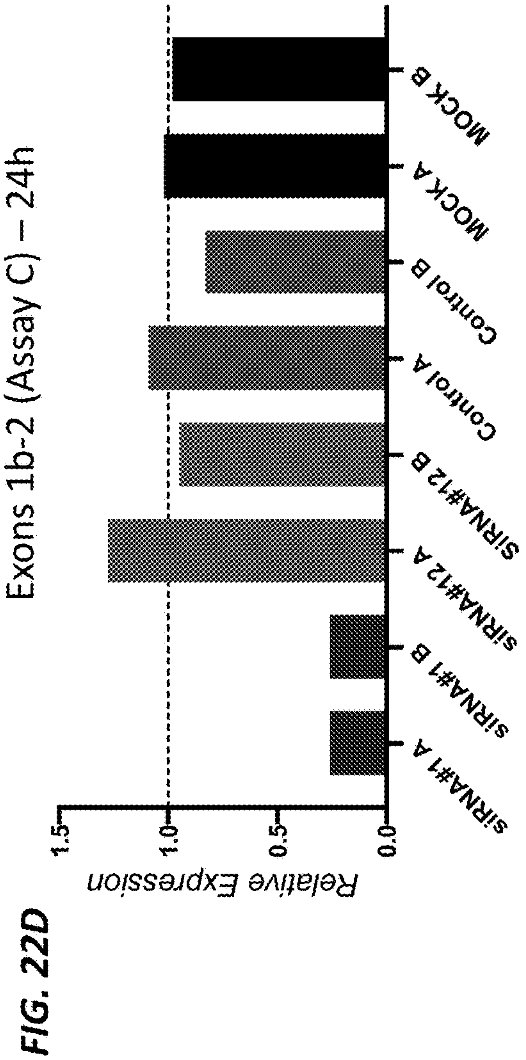
Figure 22E:
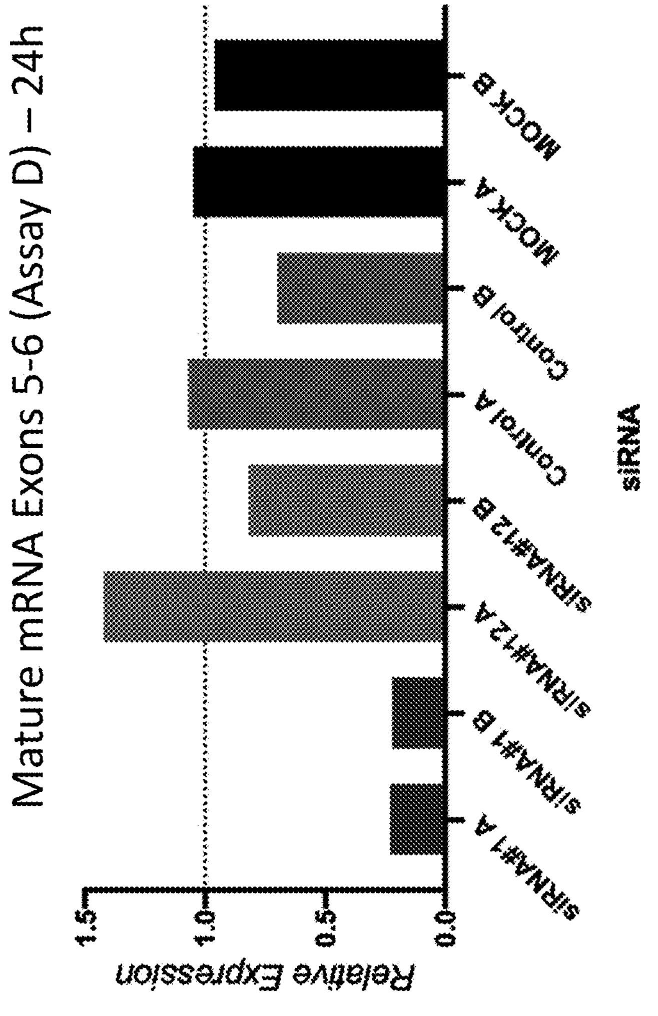
Figure 23A:
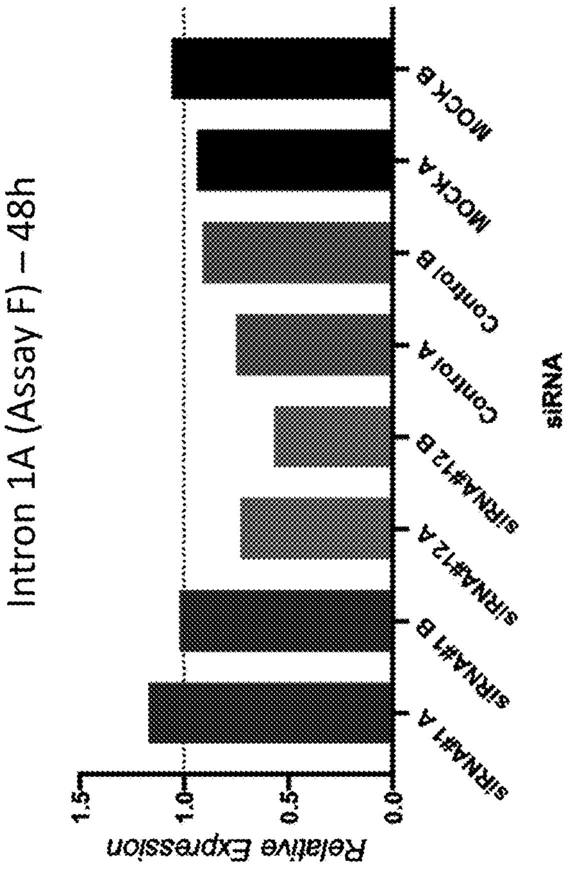
FIGS. 23A-23E are bar graphs showing relative expression levels (as determined by the TAQMAN® quantitative reverse transcription-coupled PCR (RT-qPCR) assays) of transcripts from the C9orf72 locus (y-axis) that contain C9orf72 intron 1A sequence (FIG. 23A; Assay F), that contain C9orf72 intron 1A sequence linked to exon 1A (FIG. 23B; Assay E), that are C9orf72 exon 1a-2 spliced transcripts (FIG. 23C; Assay B), that are C9orf72 exon 1b-2 spliced transcripts (FIG. 23D; Assay C), or that are C9orf72 exon 5-6 spliced transcripts (FIG. 23E; Assay D) 48 hours after electroporation with siRNAs targeting mature C9orf72 mRNA (siRNA #1) or intron 1A upstream of the hexanucleotide repeat (siRNA #12) in mouse embryonic stem cells comprising a modified C9orf72 locus comprising 300 repeats of the hexanucleotide sequence set forth as SEQ ID NO: 1. A Gapdh siRNA and a mock sample were used as negative controls.
Figure 23B:
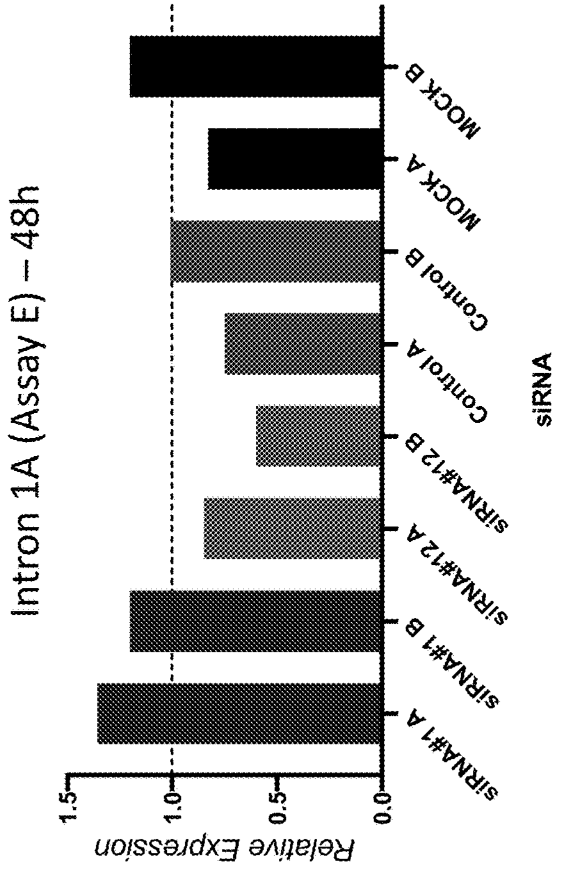
Figure 23C:
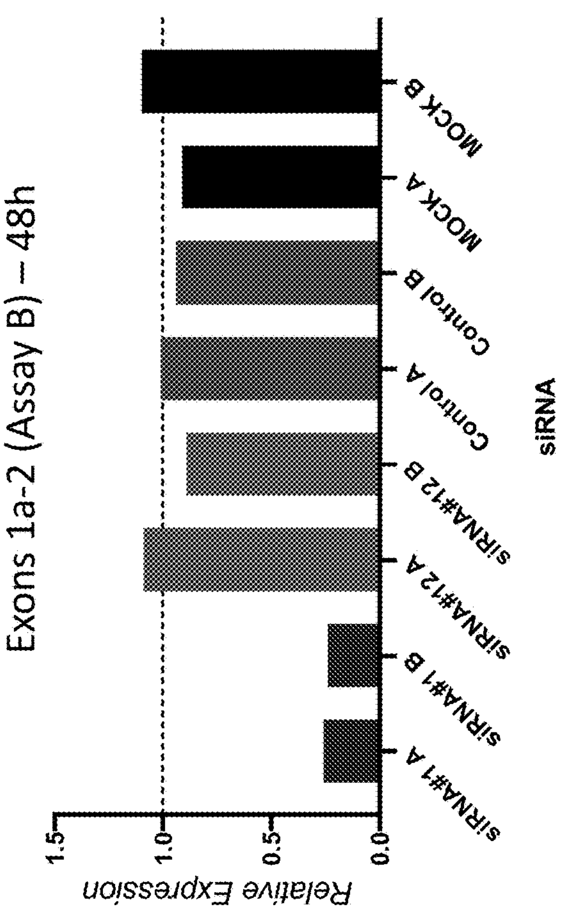
Figure 23D:
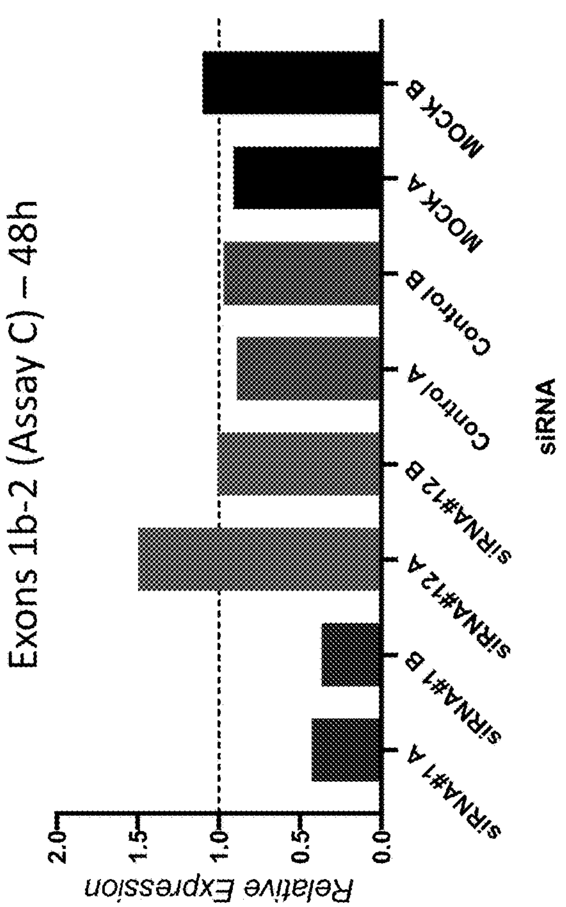
Figure 23E:
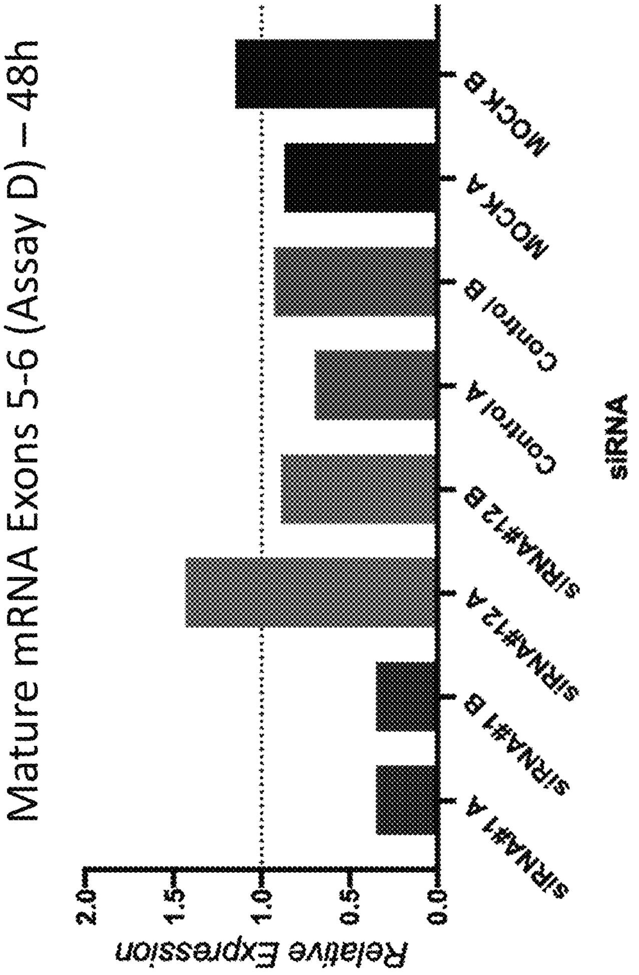

The effects of siRNAs targeting C9orf72 mature RNA were compared with the effects of siRNAs targeting C9orf72 intron 1A in mouse embryonic stem cells carrying a humanized C9orf72 gene having 300 repeats of the GGGGCC hexanucleotide (SEQ ID NO: 142). The siRNAs were electroporated into the cells, and gene expression was evaluated at 24 hours and 48 hours after electroporation. One siRNA targeting the C9orf72 mature RNA was used (siRNA #1), and one siRNA targeting C9orf72 intron 1A was used (siRNA #12). TAQMAN® qualitative PCR assays were then performed using primers that flank various regions and probes that detect those regions of the modified C9orf72 locus. The primers and probes are shown in FIG. 18B and in Table 8. The siRNA data were tight and reproduced the previous results of selective knockdown of intron-1A-containing C9orf72 RNAs (assay F) when targeting intron 1A (see siRNA #12 in FIGS. 22A and 23A) while having little effect on the C9orf72 mature RNA (assay D) (see siRNA #12 in FIGS. 22E and 23E). The siRNA targeting the C9orf72 mature RNA had the opposite effect.

In addition, siRNAs that target the body of the mature mRNA knocked down C9orf72 exon 1A-exon 2 spliced mRNAs (assay B), indicating they are covalently linked. In contrast, siRNAs targeting C9orf72 intron 1A (upstream of the hexanucleotide repeat) did not significantly affect the expression of exon 1A-exon 2 spliced mRNAs. See FIGS. 22C and 23C.

The intron-1A-targeting siRNAs also did not knock down the predominant normal C9orf72 mRNAs that initiate at exon 1B, as demonstrated by the assay C results. See FIGS. 22D and 23D. Assay C (exon 1B-exon 2 splicing) demonstrated that siRNAs that knock down intron-1A-containing RNAs adjacent to the hexanucleotide repeat (presumably the pathogenic repeat-containing RNAs) spare the normal mRNAs and, therefore, do not appreciably reduce C9orf72 protein translated from the most abundant forms of the C9orf72 mRNA.

Assay E shows that the intron-1A-targeting siRNAs also knock down RNAs that retain the intron sequences upstream of the hexanucleotide repeat and are linked to exon 1A. See FIGS. 22B and 23B. This type of transcript could be one in which transcription initiates at exon 1A, extends through the repeat sequence to exon 1B and then is spliced from exon 1B to exon 2 and the body of the mRNA. Such an RNA could serve as a template for dipeptide repeat protein synthesis encoded by the hexanucleotide repeat. Our results show that the intron-1A-targeting siRNAs would destroy such transcripts and contribute to the reduction in DPR protein synthesis, at least for poly(Gly-Ala), that we observe upon treatment with this siRNA. In summary, siRNAs targeting the intron upstream of the hexanucleotide repeat spare the mature C9orf72 mRNA. They are very specific for the intron-containing C9orf72 transcripts, including RNAs that have exon 1A linked to the adjacent intron.

TABLE 21

| Target | Name | Sequence 5' to 3' | SEQ ID NO: |
|---|---|---|---|
| mouse/human Exon1A | siRNA_E1A#1 | Sense: 5' GGAAAGUGGGGUCUAGCAAUU 3' | 1057 |
| | | Antisense: 5' UUGCUAGACCCCACUUUCCUU 3' | 1058 |
| human Exon 1A | siRNA_E1A#2 | Sense: 5' CAAGAGCAGGUGUGGGUUUUU 3' | 1059 |
| | | Antisense: 5' AAACCCACACCUGCUCUUGUU 3' | 1060 |
| mouse Exon 1A | siRNA_E1A#3 | Sense: 5' CCUUCUAGGUGGAAAGUGGUU 3' | 1061 |
| | | Antisense: 5'-PCCACUUUCCACCUAGAAGGUU 3' | 1062 |
| human intron 1A | siRNA_HA#2 | Sense: 5' CAAGAAAAGACCUGAUAAAUU 3' | 1063 |
| | | Antisense: 5' UUUAUCAGGUCUUUUCUUGUU 3' | 1064 |

TABLE 21-continued

| Target | Name | Sequence 5' to 3' | SEQ ID NO: |
|---|---|---|---|
| | siRNA_HA#4 | Sense: 5' GAAAAGACCUGAUAAAGAUUU 3' | 1065 |
| | | Antisense: 5' AUCUUUAUCAGGUCUUUUCUU 3' | 1066 |
| | siRNA_HA#6 | Sense: 5' CGCUGAGGGUGAACAAGAAUU 3' | 1067 |
| | | Antisense: 5' UUCUUGUUCACCCUCAGCGUU 3' | 1068 |
| | siRNA_HA#10 | Sense: 5' GAAGAAAACAAGGAGGGAAUU 3' | 1069 |
| | | Antisense: 5' UUCCCUCCUUGUUUUCUUCUU 3' | 1070 |
| human intron 1B | siRNA_HB#1 | Sense: 5' CCUCAGAGCUCGACGCAUUUU 3' | 1071 |
| | | Antisense: 5' AAUGCGUCGAGCUCUGAGGUU 3' | 1072 |
| | siRNA HB#6 | Sense: 5' UCUAGCGACUGGUGGAAUUUU 3' | 1073 |
| | | Antisense: 5' AAUUCCACCAGUCGCUAGAUU 3' | 1074 |

We claim:

1. A double stranded ribonucleic acid (dsRNA) agent for inhibiting expression of C9orf72, or a salt thereof,
   - wherein the dsRNA agent, or a salt thereof, comprises a sense strand and an antisense strand forming a double stranded region,
   - wherein the sense strand and the antisense strand are each independently 17-25 nucleotides in length,
   - wherein the antisense strand comprises at least 17 contiguous nucleotides from the nucleotide sequence 5'-AUUAAUCUUUAUCAGGUCUUUUC-3' of SEQ ID NO:3,
   - wherein all of the nucleotides of the sense strand and all of the nucleotides of the antisense strand independently comprise a nucleotide modification selected from the group consisting of a 2'-O-methyl nucleotide modification and a 2'-fluoro nucleotide modification,
   - wherein the dsRNA agent, or a salt thereof, comprises 6-8 phosphorothioate internucleotide linkages; and
   - wherein a lipophilic moiety containing a saturated or unsaturated C6-C18 hydrocarbon chain is conjugated to one or more internal positions selected from the group consisting of positions 4-8 and 13-18 on the sense strand, counting from the 5'-end of the strand.

2. The dsRNA agent, or a salt thereof, of claim 1, wherein the lipophilic moiety is conjugated via a linker or carrier.

3. The dsRNA agent, or a salt thereof, of claim 1, wherein each strand is independently 19-25 nucleotides in length.

4. The dsRNA agent, or a salt thereof, of claim 1, wherein at least one strand comprises a 3' overhang of at least 1 nucleotide.

5. The dsRNA agent, or a salt thereof, of claim 1, wherein the double stranded region is 17-25 nucleotide pairs in length.

6. The dsRNA agent, or a salt thereof, of claim 1, wherein the lipophilic moiety contains a saturated or unsaturated C16 hydrocarbon chain.

7. The dsRNA agent, or a salt thereof, of claim 6, wherein the saturated or unsaturated C16 hydrocarbon chain is conjugated to position 6, counting from the 5'-end of the strand.

8. The dsRNA agent, or a salt thereof, of claim 1, further comprising a phosphate or phosphate mimic at the 5'-end of the antisense strand.

9. An isolated cell containing the dsRNA agent, or a salt thereof, of claim 1.

10. A pharmaceutical composition for inhibiting expression of a C9orf72, comprising the dsRNA agent, or a salt thereof, of claim 1.

11. A kit comprising the dsRNA agent, or a salt thereof, of claim 1.

12. A vial comprising the dsRNA agent, or a salt thereof, of claim 1.

13. A syringe comprising the dsRNA agent, or a salt thereof, of claim 1.

14. The dsRNA agent, or a salt thereof, of claim 1, wherein the antisense strand comprises at least 18 contiguous nucleotides from the nucleotide sequence 5'-AUUAAUCUUUAUCAGGUCUUUUC-3' of SEQ ID NO: 3.

15. The dsRNA agent, or a salt thereof, of claim 1, wherein the antisense strand comprises at least 19 contiguous nucleotides from the nucleotide sequence 5'-AUUAAUCUUUAUCAGGUCUUUUC-3' of SEQ ID NO: 3.

16. The dsRNA agent, or a salt thereof, of claim 1, wherein the sense strand comprises at least 17 contiguous nucleotides from the nucleotide sequence 5'-AAAGACCUGAUAAAGAUUAAU-3' of SEQ ID NO: 2.

17. The dsRNA agent of claim 1, which is in salt form.

18. The dsRNA agent of claim 1, which is in sodium salt form.

19. The dsRNA agent, or a salt thereof, of claim 1, wherein each strand is independently 19-23 nucleotides in length.

20. The dsRNA agent, or a salt thereof, of claim 1, wherein each strand is independently 21-23 nucleotides in length.

21. The dsRNA agent, or a salt thereof, of claim 1, wherein the one or more lipophilic moieties moiety is conjugated to the dsRNA agent, or a salt thereof, via a linker containing an ether, thioether, urea, carbonate, amine, amide, maleimide-thioether, disulfide, phosphodiester, sulfonamide linkage, a product of a click reaction, or carbamate.

22. The dsRNA agent, or a salt thereof, of claim 1, wherein the lipophilic moiety is conjugated to a nucleobase, sugar moiety, or internucleosidic linkage.

23. The dsRNA agent, or a salt thereof, of claim 2, wherein the carrier is a cyclic group selected from the group consisting of pyrrolidinyl, pyrazolinyl, pyrazolidinyl, imidazolinyl, imidazolidinyl, piperidinyl, piperazinyl, [1,3]dioxolanyl, oxazolidinyl, isoxazolidinyl, morpholinyl, thiazolidinyl, isothiazolidinyl, quinoxalinyl, pyridazinonyl, tetrahydrofuranyl, and decalinyl; or is an acyclic moiety based on a serinol backbone or a diethanolamine backbone.

24. The dsRNA agent, or a salt thereof, of claim 1, wherein the 3' end of the sense strand is protected via an end cap which is a cyclic group having an amine, said cyclic group being selected from the group consisting of pyrrolidinyl, pyrazolinyl, pyrazolidinyl, imidazolinyl, imidazolidinyl, piperidinyl, piperazinyl, [1,3]dioxolanyl, oxazolidinyl, isoxazolidinyl, morpholinyl, thiazolidinyl, isothiazolidinyl, quinoxalinyl, pyridazinonyl, tetrahydrofuranyl, and decalinyl.

25. The dsRNA agent, or a salt thereof, of claim 8, wherein the phosphate mimic is a 5'-vinyl phosphonate (VP).

* * * * *

SEQUENCE LISTING

<160> NUMBER OF SEQ ID NOS: 1074

<210> SEQ ID NO 1
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1 ggggcc 6

<210> SEQ ID NO 2
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 2
aaagaccuga uaaagauuaa u 21

<210> SEQ ID NO 3
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 3
auuaaucuuu aucaggucuu uuc 23

<210> SEQ ID NO 4
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 4
aaaagaccug auaaagauua a 21

<210> SEQ ID NO 5
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5
uuaaucuuua ucaggucuuu ucu 23

<210> SEQ ID NO 6
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 6
cugauaaaga uuaaccagaa u 21

<210> SEQ ID NO 7
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 7
auucugguua aucuuuauca ggu 23

<210> SEQ ID NO 8
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 8
aaagauuaac cagaagaaaa u 21

<210> SEQ ID NO 9
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 9
auuuucuucu gguuaaucuu uau 23

<210> SEQ ID NO 10
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 10
auaaagauua accagaagaa a 21

<210> SEQ ID NO 11
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 11
uuucuucugg uuaaucuuua uca 23

<210> SEQ ID NO 12
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 12
agaaaagacc ugauaaagau u 21

<210> SEQ ID NO 13
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 13
aaucuuuauc aggucuuuuc uug 23

<210> SEQ ID NO 14
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 14
gaagaccuuu cuacacuagu u 21

<210> SEQ ID NO 15
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 15
aacuagtgua gaaaggucuu cca 23

-continued

<210> SEQ ID NO 16
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 16
uagcugauac aguacucaau u 21

<210> SEQ ID NO 17
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 17
aauugaguac uguaucagcu aua 23

<210> SEQ ID NO 18
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 18
caagacagag auugcuuuaa u 21

<210> SEQ ID NO 19
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 19
auuaaagcaa ucucugucuu ggc 23

<210> SEQ ID NO 20
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 20
gucuuacaca gagacacucu a 21

<210> SEQ ID NO 21
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 21
uagagugucu cuguguaaga cau 23

<210> SEQ ID NO 22
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 22
uguugccaag acagagauug u 21

<210> SEQ ID NO 23
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 23
acaauctcug ucuuggcaac agc 23

<210> SEQ ID NO 24
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 24
ugauacagua cucaaugaug a 21

<210> SEQ ID NO 25
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 25
ucaucatuga guacuguauc agc 23

<210> SEQ ID NO 26
<211> LENGTH: 3261
<212> TYPE: DNA
<213> ORGANISM: Homo sapiens

<400> SEQUENCE: 26
gggcggggct gcggttgcgg tgcctgcgcc cgcggcggcg gaggcgcagg cggtggcgag 60
tggatatctc cggagcattt ggataatgtg acagttggaa tgcagtgatg tcgactcttt 120
gcccaccgcc atctccagct gttgccaaga cagagattgc tttaagtggc aaatcacctt 180
tattagcagc tacttttgct tactgggaca atattcttgg tcctagagta aggcacattt 240
gggctccaaa gacagaacag gtacttctca gtgatggaga aataactttt cttgccaacc 300
acactctaaa tggagaaatc cttcgaaatg cagagagtgg tgctatagat gtaaagtttt 360
ttgtcttgtc tgaaaaggga gtgattattg tttcattaat ctttgatgga aactggaatg 420
gggatcgcag cacatatgga ctatcaatta tacttccaca gacagaactt agtttctacc 480
tcccacttca tagagtgtgt gttgatagat taacacatat aatccggaaa ggaagaatat 540
ggatgcataa ggaaagacaa gaaaatgtcc agaagattat cttagaaggc acagagagaa 600
tggaagatca gggtcagagt attattccaa tgcttactgg agaagtgatt cctgtaatgg 660
aactgctttc atctatgaaa tcacacagtg ttcctgaaga aatagatata gctgatacag 720
tactcaatga tgatgatatt ggtgacagct gtcatgaagg ctttcttctc aatgccatca 780
gctcacactt gcaaacctgt ggctgttccg ttgtagtagg tagcagtgca gagaaagtaa 840
ataagatagt cagaacatta tgcctttttc tgactccagc agagagaaaa tgctccaggt 900
tatgtgaagc agaatcatca tttaaatatg agtcagggct ctttgtacaa ggcctgctaa 960
aggattcaac tggaagcttt gtgctgcctt tccggcaagt catgtatgct ccatatccca 1020
ccacacacat agatgtggat gtcaatactg tgaagcagat gccaccctgt catgaacata 1080
tttataatca gcgtagatac atgagatccg agctgacagc cttctggaga gccacttcag 1140
aagaagacat ggctcaggat acgatcatct acactgacga aagctttact cctgatttga 1200
atatttttca agatgtctta cacagagaca ctctagtgaa agccttcctg gatcaggtct 1260
ttcagctgaa acctggctta tctctcagaa gtactttcct tgcacagttt ctacttgtcc 1320
ttcacagaaa agccttgaca ctaataaaat atatagaaga cgatacgcag aagggaaaaa 1380
agccctttaa atctcttcgg aacctgaaga tagaccttga tttaacagca gagggcgatc 1440
ttaacataat aatggctctg gctgagaaaa ttaaaccagg cctacactct tttatctttg 1500
gaagaccttt ctacactagt gtgcaagaac gagatgttct aatgactttt taaatgtgta 1560
acttaataag cctattccat cacaatcatg atcgctggta aagtagctca gtggtgtggg 1620
gaaacgttcc cctggatcat actccagaat tctgctctca gcaattgcag ttaagtaagt 1680
tacactacag ttctcacaag agcctgtgag ggatgtcag gtgcatcatt acattgggtg 1740
tctcttttcc tagatttatg cttttgggat acagacctat gtttacaata taataaatat 1800
tattgctatc ttttaaagat ataataatag gatgtaaact tgaccacaac tactgttttt 1860
ttgaaataca tgattcatgg tttacatgtg tcaaggtgaa atctgagttg gcttttacag 1920
atagttgact ttctatcttt tggcattctt tggtgtgtag aattactgta atacttctgc 1980
aatcaactga aaactagagc ctttaaatga tttcaattcc acagaaagaa agtgagcttg 2040
aacataggat gagctttaga aagaaaattg atcaagcaga tgtttaattg gaattgatta 2100
ttagatccta ctttgtggat ttagtccctg ggattcagtc tgtagaaatg tctaatagtt 2160
ctctatagtc cttgttcctg gtgaaccaca gttagggtgt tttgtttatt ttattgttct 2220
tgctattgtt gatattctat gtagttgagc tctgtaaaag gaaattgtat tttatgtttt 2280

```
agtaattgtt gccaactttt taaattaatt ttcattattt ttgagccaaa ttgaaatgtg   2340
cacctcctgt gccttttttc tccttagaaa atctaattac ttggaacaag ttcagatttc   2400
actggtcagt cattttcatc ttgttttctt cttgctaagt cttaccatgt acctgctttg   2460
gcaatcattg caactctgag attataaaat gccttagaga atatactaac taataagatc   2520
ttttttttcag aaacagaaaa tagttccttg agtacttcct tcttgcattt ctgcctatgt   2580
ttttgaagtt gttgctgttt gcctgcaata ggctataagg aatagcagga gaaattttac   2640
tgaagtgctg ttttcctagg tgctactttg gcagagctaa gttatctttt gttttcttaa   2700
tgcgtttgga ccattttgct ggctataaaa taactgatta atataattct aacacaatgt   2760
tgacattgta gttacacaaa cacaaataaa tattttattt aaaattctgg aagtaatata   2820
aaagggaaaa tatatttata agaaagggat aaaggtaata gagcccttct gccccccacc   2880
caccaaattt acacaacaaa atgacatgtt cgaatgtgaa aggtcataat agctttccca   2940
tcatgaatca gaaagatgtg gacagcttga tgttttagac aaccactgaa ctagatgact   3000
gttgtactgt agctcagtca tttaaaaaat atataaatac taccttgtag tgtcccatac   3060
tgtgtttttt acatggtaga ttcttattta agtgctaact ggttattttc tttggctggt   3120
ttattgtact gttatacaga atgtaagttg tacagtgaaa taagttatta aagcatgtgt   3180
aaacattgtt atatatcttt tctcctaaat ggagaatttt gaataaaata tatttgaaat   3240
tttaaaaaaa aaaaaaaaaa a                                              3261
```

<210> SEQ ID NO 27
<211> LENGTH: 481
<212> TYPE: PRT
<213> ORGANISM: Homo sapiens

<400> SEQUENCE: 27

```
Met Ser Thr Leu Cys Pro Pro Pro Ser Pro Ala Val Ala Lys Thr Glu
1               5                   10                  15

Ile Ala Leu Ser Gly Lys Ser Pro Leu Leu Ala Ala Thr Phe Ala Tyr
            20                  25                  30

Trp Asp Asn Ile Leu Gly Pro Arg Val Arg His Ile Trp Ala Pro Lys
        35                  40                  45

Thr Glu Gln Val Leu Leu Ser Asp Gly Glu Ile Thr Phe Leu Ala Asn
    50                  55                  60

His Thr Leu Asn Gly Glu Ile Leu Arg Asn Ala Glu Ser Gly Ala Ile
65                  70                  75                  80

Asp Val Lys Phe Phe Val Leu Ser Glu Lys Gly Val Ile Ile Val Ser
                85                  90                  95

Leu Ile Phe Asp Gly Asn Trp Asn Gly Asp Arg Ser Thr Tyr Gly Leu
            100                 105                 110

Ser Ile Ile Leu Pro Gln Thr Glu Leu Ser Phe Tyr Leu Pro Leu His
        115                 120                 125

Arg Val Cys Val Asp Arg Leu Thr His Ile Ile Arg Lys Gly Arg Ile
    130                 135                 140

Trp Met His Lys Glu Arg Gln Glu Asn Val Gln Lys Ile Ile Leu Glu
145                 150                 155                 160

Gly Thr Glu Arg Met Glu Asp Gln Gly Gln Ser Ile Ile Pro Met Leu
                165                 170                 175

Thr Gly Glu Val Ile Pro Val Met Glu Leu Leu Ser Ser Met Lys Ser
            180                 185                 190
```

```
His Ser Val Pro Glu Glu Ile Asp Ile Ala Asp Thr Val Leu Asn Asp
        195                 200                 205

Asp Asp Ile Gly Asp Ser Cys His Glu Gly Phe Leu Leu Asn Ala Ile
    210                 215                 220

Ser Ser His Leu Gln Thr Cys Gly Cys Ser Val Val Val Gly Ser Ser
225                 230                 235                 240

Ala Glu Lys Val Asn Lys Ile Val Arg Thr Leu Cys Leu Phe Leu Thr
                245                 250                 255

Pro Ala Glu Arg Lys Cys Ser Arg Leu Cys Glu Ala Glu Ser Ser Phe
            260                 265                 270

Lys Tyr Glu Ser Gly Leu Phe Val Gln Gly Leu Leu Lys Asp Ser Thr
        275                 280                 285

Gly Ser Phe Val Leu Pro Phe Arg Gln Val Met Tyr Ala Pro Tyr Pro
    290                 295                 300

Thr Thr His Ile Asp Val Asp Val Asn Thr Val Lys Gln Met Pro Pro
305                 310                 315                 320

Cys His Glu His Ile Tyr Asn Gln Arg Arg Tyr Met Arg Ser Glu Leu
                325                 330                 335

Thr Ala Phe Trp Arg Ala Thr Ser Glu Glu Asp Met Ala Gln Asp Thr
            340                 345                 350

Ile Ile Tyr Thr Asp Glu Ser Phe Thr Pro Asp Leu Asn Ile Phe Gln
        355                 360                 365

Asp Val Leu His Arg Asp Thr Leu Val Lys Ala Phe Leu Asp Gln Val
    370                 375                 380

Phe Gln Leu Lys Pro Gly Leu Ser Leu Arg Ser Thr Phe Leu Ala Gln
385                 390                 395                 400

Phe Leu Leu Val Leu His Arg Lys Ala Leu Thr Leu Ile Lys Tyr Ile
                405                 410                 415

Glu Asp Asp Thr Gln Lys Gly Lys Lys Pro Phe Lys Ser Leu Arg Asn
            420                 425                 430

Leu Lys Ile Asp Leu Asp Leu Thr Ala Glu Gly Asp Leu Asn Ile Ile
        435                 440                 445

Met Ala Leu Ala Glu Lys Ile Lys Pro Gly Leu His Ser Phe Ile Phe
    450                 455                 460

Gly Arg Pro Phe Tyr Thr Ser Val Gln Glu Arg Asp Val Leu Met Thr
465                 470                 475                 480

Phe
```

<210> SEQ ID NO 28
<211> LENGTH: 3356
<212> TYPE: DNA
<213> ORGANISM: Homo sapiens

<400> SEQUENCE: 28

```
acgtaaccta cggtgtcccg ctaggaaaga gaggtgcgtc aaacagcgac aagttccgcc      60

cacgtaaaag atgacgcttg gtgtgtcagc cgtccctgct gcccggttgc ttctcttttg     120

ggggcggggt ctagcaagag caggtgtggg tttaggagat atctccggag catttggata     180

atgtgacagt tggaatgcag tgatgtcgac tctttgccca ccgccatctc cagctgttgc     240

caagacagag attgctttaa gtggcaaatc acctttatta gcagctactt ttgcttactg     300

ggacaatatt cttggtccta gagtaaggca catttgggct ccaaagacag aacaggtact     360

tctcagtgat ggagaaataa cttttcttgc caaccacact ctaaatggag aaatccttcg     420
```

```
aaatgcagag agtggtgcta tagatgtaaa gttttttgtc ttgtctgaaa agggagtgat     480
tattgtttca ttaatctttg atggaaactg gaatggggat cgcagcacat atggactatc     540
aattatactt ccacagacag aacttagttt ctacctccca cttcatagag tgtgtgttga     600
tagattaaca catataatcc ggaaaggaag aatatggatg cataaggaaa gacaagaaaa     660
tgtccagaag attatcttag aaggcacaga gagaatggaa gatcagggtc agagtattat     720
tccaatgctt actggagaag tgattcctgt aatggaactg ctttcatcta tgaaatcaca     780
cagtgttcct gaagaaatag atatagctga tacagtactc aatgatgatg atattggtga     840
cagctgtcat gaaggctttc ttctcaatgc catcagctca cacttgcaaa cctgtggctg     900
ttccgttgta gtaggtagca gtgcagagaa agtaaataag atagtcagaa cattatgcct     960
ttttctgact ccagcagaga gaaaatgctc caggttatgt gaagcagaat catcatttaa    1020
atatgagtca gggctctttg tacaaggcct gctaaaggat tcaactggaa gctttgtgct    1080
gcctttccgg caagtcatgt atgctccata tcccaccaca cacatagatg tggatgtcaa    1140
tactgtgaag cagatgccac cctgtcatga acatatttat aatcagcgta gatacatgag    1200
atccgagctg acagccttct ggagagccac ttcagaagaa gacatggctc aggatacgat    1260
catctacact gacgaaagct ttactcctga tttgaatatt tttcaagatg tcttacacag    1320
agacactcta gtgaaagcct tcctggatca ggtctttcag ctgaaacctg gcttatctct    1380
cagaagtact ttccttgcac agtttctact tgtccttcac agaaaagcct tgacactaat    1440
aaaatatata gaagacgata cgcagaaggg aaaaaagccc tttaaatctc ttcggaacct    1500
gaagatagac cttgatttaa cagcagaggg cgatcttaac ataataatgg ctctggctga    1560
gaaaattaaa ccaggcctac actcttttat ctttggaaga cctttctaca ctagtgtgca    1620
agaacgagat gttctaatga ctttttaaat gtgtaactta ataagcctat tccatcacaa    1680
tcatgatcgc tggtaaagta gctcagtggt gtggggaaac gttcccctgg atcatactcc    1740
agaattctgc tctcagcaat tgcagttaag taagttacac tacagttctc acaagagcct    1800
gtgaggggat gtcaggtgca tcattacatt gggtgtctct tttcctagat ttatgctttt    1860
gggatacaga cctatgttta caatataata aatattattg ctatctttta aagatataat    1920
aataggatgt aaacttgacc acaactactg ttttttttgaa atacatgatt catggtttac    1980
atgtgtcaag gtgaaatctg agttggcttt tacagatagt tgactttcta tcttttggca    2040
ttctttggtg tgtagaatta ctgtaatact tctgcaatca actgaaaact agagccttta    2100
aatgatttca attccacaga aagaaagtga gcttgaacat aggatgagct ttagaaagaa    2160
aattgatcaa gcagatgttt aattggaatt gattattaga tcctactttg tggatttagt    2220
ccctgggatt cagtctgtag aaatgtctaa tagttctcta tagtccttgt tcctggtgaa    2280
ccacagttag ggtgttttgt ttattttatt gttcttgcta ttgttgatat tctatgtagt    2340
tgagctctgt aaaaggaaat tgtattttat gttttagtaa ttgttgccaa ctttttaaat    2400
taattttcat tatttttgag ccaaattgaa atgtgcacct cctgtgcctt ttttctcctt    2460
agaaaatcta attacttgga acaagttcag atttcactgg tcagtcattt tcatcttgtt    2520
ttcttcttgc taagtcttac catgtacctg ctttggcaat cattgcaact ctgagattat    2580
aaaatgcctt agagaatata ctaactaata agatcttttt ttcagaaaca gaaaatagtt    2640
ccttgagtac ttccttcttg catttctgcc tatgtttttg aagttgttgc tgtttgcctg    2700
caataggcta taaggaatag caggagaaat tttactgaag tgctgttttc ctaggtgcta    2760
ctttggcaga gctaagttat cttttgtttt cttaatgcgt ttggaccatt ttgctggcta    2820
```

taaaataact gattaatata attctaacac aatgttgaca ttgtagttac acaaacacaa 2880
ataaatattt tatttaaaat tctggaagta atataaaagg gaaaatatat ttataagaaa 2940
gggataaagg taatagagcc cttctgcccc ccacccacca aatttacaca acaaaatgac 3000
atgttcgaat gtgaaaggtc ataatagctt tcccatcatg aatcagaaag atgtggacag 3060
cttgatgttt tagacaacca ctgaactaga tgactgttgt actgtagctc agtcatttaa 3120
aaaatatata aatactacct tgtagtgtcc catactgtgt tttttacatg gtagattctt 3180
atttaagtgc taactggtta ttttctttgg ctggtttatt gtactgttat acagaatgta 3240
agttgtacag tgaaataagt tattaaagca tgtgtaaaca ttgttatata tcttttctcc 3300
taaatggaga attttgaata aaatatattt gaaattttaa aaaaaaaaaa aaaaaa 3356

<210> SEQ ID NO 29
<211> LENGTH: 481
<212> TYPE: PRT
<213> ORGANISM: Homo sapiens

<400> SEQUENCE: 29

Met Ser Thr Leu Cys Pro Pro Pro Ser Pro Ala Val Ala Lys Thr Glu
1 5 10 15

Ile Ala Leu Ser Gly Lys Ser Pro Leu Leu Ala Ala Thr Phe Ala Tyr
20 25 30

Trp Asp Asn Ile Leu Gly Pro Arg Val Arg His Ile Trp Ala Pro Lys
35 40 45

Thr Glu Gln Val Leu Leu Ser Asp Gly Glu Ile Thr Phe Leu Ala Asn
50 55 60

His Thr Leu Asn Gly Glu Ile Leu Arg Asn Ala Glu Ser Gly Ala Ile
65 70 75 80

Asp Val Lys Phe Phe Val Leu Ser Glu Lys Gly Val Ile Ile Val Ser
85 90 95

Leu Ile Phe Asp Gly Asn Trp Asn Gly Asp Arg Ser Thr Tyr Gly Leu
100 105 110

Ser Ile Ile Leu Pro Gln Thr Glu Leu Ser Phe Tyr Leu Pro Leu His
115 120 125

Arg Val Cys Val Asp Arg Leu Thr His Ile Ile Arg Lys Gly Arg Ile
130 135 140

Trp Met His Lys Glu Arg Gln Glu Asn Val Gln Lys Ile Ile Leu Glu
145 150 155 160

Gly Thr Glu Arg Met Glu Asp Gln Gly Gln Ser Ile Ile Pro Met Leu
165 170 175

Thr Gly Glu Val Ile Pro Val Met Glu Leu Leu Ser Ser Met Lys Ser
180 185 190

His Ser Val Pro Glu Glu Ile Asp Ile Ala Asp Thr Val Leu Asn Asp
195 200 205

Asp Asp Ile Gly Asp Ser Cys His Glu Gly Phe Leu Leu Asn Ala Ile
210 215 220

Ser Ser His Leu Gln Thr Cys Gly Cys Ser Val Val Val Gly Ser Ser
225 230 235 240

Ala Glu Lys Val Asn Lys Ile Val Arg Thr Leu Cys Leu Phe Leu Thr
245 250 255

Pro Ala Glu Arg Lys Cys Ser Arg Leu Cys Glu Ala Glu Ser Ser Phe
260 265 270

```
Lys Tyr Glu Ser Gly Leu Phe Val Gln Gly Leu Leu Lys Asp Ser Thr
        275                 280                 285

Gly Ser Phe Val Leu Pro Phe Arg Gln Val Met Tyr Ala Pro Tyr Pro
    290                 295                 300

Thr Thr His Ile Asp Val Asp Val Asn Thr Val Lys Gln Met Pro Pro
305                 310                 315                 320

Cys His Glu His Ile Tyr Asn Gln Arg Arg Tyr Met Arg Ser Glu Leu
                325                 330                 335

Thr Ala Phe Trp Arg Ala Thr Ser Glu Glu Asp Met Ala Gln Asp Thr
            340                 345                 350

Ile Ile Tyr Thr Asp Glu Ser Phe Thr Pro Asp Leu Asn Ile Phe Gln
        355                 360                 365

Asp Val Leu His Arg Asp Thr Leu Val Lys Ala Phe Leu Asp Gln Val
    370                 375                 380

Phe Gln Leu Lys Pro Gly Leu Ser Leu Arg Ser Thr Phe Leu Ala Gln
385                 390                 395                 400

Phe Leu Leu Val Leu His Arg Lys Ala Leu Thr Leu Ile Lys Tyr Ile
                405                 410                 415

Glu Asp Asp Thr Gln Lys Gly Lys Lys Pro Phe Lys Ser Leu Arg Asn
            420                 425                 430

Leu Lys Ile Asp Leu Asp Leu Thr Ala Glu Gly Asp Leu Asn Ile Ile
        435                 440                 445

Met Ala Leu Ala Glu Lys Ile Lys Pro Gly Leu His Ser Phe Ile Phe
    450                 455                 460

Gly Arg Pro Phe Tyr Thr Ser Val Gln Glu Arg Asp Val Leu Met Thr
465                 470                 475                 480

Phe
```

<210> SEQ ID NO 30
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 30
gctatgcgat cgccgtctcg 20

<210> SEQ ID NO 31
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 31
ccccggcccc ggccccgaga 20

<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 32
cgccgtctcg gggccggggc 20

<210> SEQ ID NO 33
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 33
ccgtctcggg gccggggccg 20

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 34
cggccggccc tcgagggtct 20

<210> SEQ ID NO 35
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 35
ggccggggcc gagaccctcg 20

<210> SEQ ID NO 36
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 36
gagggtctcg gccccggccc 20

<210> SEQ ID NO 37
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 37
ctcggccccg gccccggccc 20

<210> SEQ ID NO 38
<211> LENGTH: 16
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
ccccggcccc ggcccc 16

<210> SEQ ID NO 39
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
ggggccgggg ccggggggcc cc 22

<210> SEQ ID NO 40
<211> LENGTH: 3198
<212> TYPE: DNA
<213> ORGANISM: Mus musculus

<400> SEQUENCE: 40
gtgtccgggg cggggcggtc ccggggcggg gcccggagcg ggctgcggtt gcggtccctg 60
cgccggcggt gaaggcgcag cagcggcgag tggctattgc aagcgttcgg ataatgtgag 120
acctggaatg cagtgagacc tgggatgcag ggatgtcgac tatctgcccc ccaccatctc 180
ctgctgttgc caagacagag attgctttaa gtggtgaatc acccttgttg gcggctacct 240
ttgcttactg ggataatatt cttggtccta gagtaaggca tatttgggct ccaaagacag 300
accaagtgct tctcagtgat ggagaaataa cttttcttgc caaccacact ctaaatggag 360
aaattcttcg aaatgcagag agtggggcta tagatgtaaa attttttgtc ttatctgaaa 420
aaggggtaat tattgtttca ttaatcttcg acggaaactg gaatggagat cggagcactt 480
atggactatc aattatactg ccgcagacag agctgagctt ctacctccca cttcacagag 540
tgtgtgttga caggctaaca cacattattc gaaaaggaag aatatggatg cataaggaaa 600
gacaagaaaa tgtccagaaa attgtcttgg aaggcacaga gaggatggaa gatcagggtc 660
agagtatcat tcccatgctt actggggaag tcattcctgt aatggagctg cttgcatcta 720
tgaaatccca cagtgttcct gaagacattg atatagctga tacagtgctc aatgatgatg 780
acattggtga cagctgtcac gaaggctttc ttctcaatgc catcagctca cacctgcaga 840
cctgtggctg ttccgttgta gttggcagca gtgcagagaa agtaaataag atagtaagaa 900
cgctgtgcct ttttctgaca ccagcagaga ggaaatgctc caggctgtgt gaagcagaat 960
cgtcctttaa gtacgaatcg ggactctttg tgcaaggctt gctaaaggat gcaacaggca 1020
gttttgtcct acccttccgg caagttatgt atgccccgta ccccaccacg cacattgatg 1080
tggatgtcaa cactgtcaag cagatgccac cgtgtcatga acatatttat aatcaacgca 1140
gatacatgag gtcagagctg acagccttct ggagggcaac ttcagaagag gacatggcgc 1200
aggacaccat catctacaca gatgagagct tcactcctga tttgaatatt ttccaagatg 1260
tcttacacag agacactcta gtgaaagcct tcctggatca ggtcttccat ttgaagcctg 1320
gcctgtctct caggagtact ttccttgcac agttcctcct cattcttcac agaaaagcct 1380
tgacactaat caagtacatc gaggatgata cgcagaaggg gaaaaagccc tttaagtctc 1440

```
ttcggaacct gaagatagat cttgatttaa cagcagaggg cgatcttaac ataataatgg   1500
ctctagctga gaaaattaag ccaggcctac actctttcat ctttgggaga cctttctaca   1560
ctagtgtaca agaacgtgat gttctaatga ccttttgacc gtgtggtttg ctgtgtctgt   1620
ctcttcacag tcacacctgc tgttacagtg tctcagcagt gtgtgggcac atccttcctc   1680
ccgagtcctg ctgcaggaca gggtacacta cacttgtcag tagaagtctg tacctgatgt   1740
caggtgcatc gttacagtga atgactcttc ctagaataga tgtactcttt tagggcctta   1800
tgtttacaat tatcctaagt actattgctg tcttttaaag atatgaatga tggaatatac   1860
acttgaccat aactgctgat tggtttttttg ttttgttttg tttgttttct tggaaactta   1920
tgattcctgg tttacatgta ccacactgaa accctcgtta gctttacaga taaagtgtga   1980
gttgacttcc tgcccctctg tgttctgtgg tatgtccgat tacttctgcc acagctaaac   2040
attagagcat ttaaagtttg cagttcctca gaaaggaact tagtctgact acagattagt   2100
tcttgagaga agacactgat agggcagagc tgtaggtgaa atcagttgtt agcccttcct   2160
ttatagacgt agtccttcag attcggtctg tacagaaatg ccgaggggtc atgcatgggc   2220
cctgagtatc gtgacctgtg acaagttttt tgttggttta ttgtagttct gtcaaagaaa   2280
gtggcatttg tttttataat tgttgccaac ttttaaggtt aattttcatt atttttgagc   2340
cgaattaaaa tgcgcacctc ctgtgccttt cccaatcttg gaaaatataa tttcttggca   2400
gagggtcaga tttcagggcc cagtcacttt catctgacca ccctttgcac ggctgccgtg   2460
tgcctggctt agattagaag tccttgttaa gtatgtcaga gtacattcgc tgataagatc   2520
tttgaagagc agggaagcgt cttgcctctt tcctttggtt tctgcctgta ctctggtgtt   2580
tcccgtgtca cctgcatcat aggaacagca gagaaatctg acccagtgct atttttctag   2640
gtgctactat ggcaaactca agtggtctgt ttctgttcct gtaacgttcg actatctcgc   2700
tagctgtgaa gtactgatta gtggagttct gtgcaacagc agtgtaggag tatacacaaa   2760
cacaaatatg tgtttctatt taaaactgtg gacttagcat aaaaagggag aatatattta   2820
ttttttacaa aagggataaa aatgggcccc gttcctcacc caccagattt agcgagaaaa   2880
agctttctat tctgaaaggt cacggtggct ttggcattac aaatcagaac aacacacact   2940
gaccatgatg gcttgtgaac taactgcaag gcactccgtc atggtaagcg agtaggtccc   3000
acctcctagt gtgccgctca ttgctttaca cagtagaatc ttatttgagt gctaattgtt   3060
gtctttgctg ctttactgtg ttgttataga aaatgtaagc tgtacagtga ataagttatt   3120
gaagcatgtg taaacactgt tatatatctt ttctcctaga tggggaattt tgaataaaat   3180
acctttgaaa ttctgtgt                                                 3198
```

<210> SEQ ID NO 41
<211> LENGTH: 481
<212> TYPE: PRT
<213> ORGANISM: Mus musculus

<400> SEQUENCE: 41

```
Met Ser Thr Ile Cys Pro Pro Pro Ser Pro Ala Val Ala Lys Thr Glu
1               5                   10                  15

Ile Ala Leu Ser Gly Glu Ser Pro Leu Leu Ala Ala Thr Phe Ala Tyr
            20                  25                  30

Trp Asp Asn Ile Leu Gly Pro Arg Val Arg His Ile Trp Ala Pro Lys
        35                  40                  45
```

-continued

```
Thr Asp Gln Val Leu Leu Ser Asp Gly Glu Ile Thr Phe Leu Ala Asn
    50                  55                  60

His Thr Leu Asn Gly Glu Ile Leu Arg Asn Ala Glu Ser Gly Ala Ile
65                  70                  75                  80

Asp Val Lys Phe Phe Val Leu Ser Glu Lys Gly Val Ile Ile Val Ser
                85                  90                  95

Leu Ile Phe Asp Gly Asn Trp Asn Gly Asp Arg Ser Thr Tyr Gly Leu
            100                 105                 110

Ser Ile Ile Leu Pro Gln Thr Glu Leu Ser Phe Tyr Leu Pro Leu His
        115                 120                 125

Arg Val Cys Val Asp Arg Leu Thr His Ile Ile Arg Lys Gly Arg Ile
    130                 135                 140

Trp Met His Lys Glu Arg Gln Glu Asn Val Gln Lys Ile Val Leu Glu
145                 150                 155                 160

Gly Thr Glu Arg Met Glu Asp Gln Gly Gln Ser Ile Ile Pro Met Leu
                165                 170                 175

Thr Gly Glu Val Ile Pro Val Met Glu Leu Leu Ala Ser Met Lys Ser
            180                 185                 190

His Ser Val Pro Glu Asp Ile Asp Ile Ala Asp Thr Val Leu Asn Asp
        195                 200                 205

Asp Asp Ile Gly Asp Ser Cys His Glu Gly Phe Leu Leu Asn Ala Ile
    210                 215                 220

Ser Ser His Leu Gln Thr Cys Gly Cys Ser Val Val Val Gly Ser Ser
225                 230                 235                 240

Ala Glu Lys Val Asn Lys Ile Val Arg Thr Leu Cys Leu Phe Leu Thr
                245                 250                 255

Pro Ala Glu Arg Lys Cys Ser Arg Leu Cys Glu Ala Glu Ser Ser Phe
            260                 265                 270

Lys Tyr Glu Ser Gly Leu Phe Val Gln Gly Leu Leu Lys Asp Ala Thr
        275                 280                 285

Gly Ser Phe Val Leu Pro Phe Arg Gln Val Met Tyr Ala Pro Tyr Pro
    290                 295                 300

Thr Thr His Ile Asp Val Asp Val Asn Thr Val Lys Gln Met Pro Pro
305                 310                 315                 320

Cys His Glu His Ile Tyr Asn Gln Arg Arg Tyr Met Arg Ser Glu Leu
                325                 330                 335

Thr Ala Phe Trp Arg Ala Thr Ser Glu Glu Asp Met Ala Gln Asp Thr
            340                 345                 350

Ile Ile Tyr Thr Asp Glu Ser Phe Thr Pro Asp Leu Asn Ile Phe Gln
        355                 360                 365

Asp Val Leu His Arg Asp Thr Leu Val Lys Ala Phe Leu Asp Gln Val
    370                 375                 380

Phe His Leu Lys Pro Gly Leu Ser Leu Arg Ser Thr Phe Leu Ala Gln
385                 390                 395                 400

Phe Leu Leu Ile Leu His Arg Lys Ala Leu Thr Leu Ile Lys Tyr Ile
                405                 410                 415

Glu Asp Asp Thr Gln Lys Gly Lys Lys Pro Phe Lys Ser Leu Arg Asn
            420                 425                 430

Leu Lys Ile Asp Leu Asp Leu Thr Ala Glu Gly Asp Leu Asn Ile Ile
        435                 440                 445

Met Ala Leu Ala Glu Lys Ile Lys Pro Gly Leu His Ser Phe Ile Phe
    450                 455                 460
```

```
Gly Arg Pro Phe Tyr Thr Ser Val Gln Glu Arg Asp Val Leu Met Thr
465                 470                 475                 480

Phe


<210> SEQ ID NO 42
<211> LENGTH: 3435
<212> TYPE: DNA
<213> ORGANISM: Rattus norvegicus

<400> SEQUENCE: 42

cgtttgtagt gtcagccatc ccaattgcct gttccttctc tgtgggagtg gtgtctagac     60

agtccaggca gggtatgcta ggcaggtgcg ttttggttgc ctcagatcgc aacttgactc    120

cataacggtg accaaagaca aaagaaggaa accagattaa aaagaaccgg acacagaccc    180

ctgcagaatc tggagcggcc gtggttgggg gcggggctac gacggggcgg actcgggggc    240

gtgggagggc ggggccgggg cggggcccgg agccggctgc ggttgcggtc cctgcgccgg    300

cggtgaaggc gcagcggcgg cgagtggcta ttgcaagcgt ttggataatg tgagacctgg    360

gatgcaggga tgtcgactat ctgcccccca ccatctcctg ctgttgccaa gacagagatt    420

gctttaagtg gtgaatcacc cttgttggcg gctacctttg cttactggga taatattctt    480

ggtcctagag taaggcacat ttgggctcca aagacagacc aagtactcct cagtgatgga    540

gaaatcactt ttcttgccaa ccacactctg aatggagaaa ttcttcggaa tgcggagagt    600

ggggcaatag atgtaaagtt ttttgtctta tctgaaaagg gcgtcattat tgtttcatta    660

atcttcgacg ggaactggaa cggagatcgg agcacttacg gactatcaat tatactgccg    720

cagacggagc tgagtttcta cctcccactg cacagagtgt gtgttgacag gctaacgcac    780

atcattcgaa aaggaaggat atggatgcac aaggaaagac aagaaaatgt ccagaaaatt    840

gtcttggaag gcaccgagag gatggaagat cagggtcaga gtatcatccc tatgcttact    900

ggggaggtca tccctgtgat ggagctgctt gcgtctatga gatcacacag tgttcctgaa    960

gacctcgata tagctgatac agtactcaat gatgatgaca ttggtgacag ctgtcatgaa   1020

ggctttcttc tcaatgccat cagctcacat ctgcagacct gcggctgttc tgtggtggta   1080

ggcagcagtg cagagaaagt aaataagata gtaagaacac tgtgcctttt tctgacacca   1140

gcagagagga agtgctccag gctgtgtgaa gccgaatcgt cctttaaata cgaatctgga   1200

ctctttgtac aaggcttgct aaaggatgcg actggcagtt ttgtactacc tttccggcaa   1260

gttatgtatg ccccttatcc caccacacac atcgatgtgg atgtcaacac tgtcaagcag   1320

atgccaccgt gtcatgaaca tatttataat caacgcagat acatgaggtc agagctgaca   1380

gccttctgga gggcaacttc agaagaggac atggctcagg acaccatcat ctacacagat   1440

gagagcttca ctcctgattt gaatattttc caagatgtct tacacagaga cactctagtg   1500

aaagcctttc tggatcaggt cttccatttg aagcctggcc tgtctctcag gagtactttc   1560

cttgcacagt tcctcctcat tcttcacaga aaagccttga cactaatcaa gtacatagag   1620

gatgacacgc agaaggggaa aaagcccttt aagtctcttc ggaacctgaa gatagatctt   1680

gatttaacag cagagggcga ccttaacata ataatggctc tagctgagaa aattaagcca   1740

ggcctacact ctttcatctt cgggagacct ttctacacta gtgtccaaga acgtgatgtt   1800

ctaatgactt tttaaacatg tggtttgctc cgtgtgtctc atgacagtca cacttgctgt   1860

tacagtgtct cagcgctttg gacacatcct tcctccaggg tcctgccgca ggacacgtta   1920

cactacactt gtcagtagag gtctgtacca gatgtcaggt acatcgttgt agtgaatgtc   1980
```

```
tcttttccta gactagatgt accctcgtag ggacttatgt ttacaaccct cctaagtact   2040

agtgctgtct tgtaaggata cgaatgaagg gatgtaaact tcaccacaac tgctggttgg   2100

ttttgttgtt tttgtttttt gaaacttata attcatggtt tacatgcatc acactgaaac   2160

cctagttagc tttttacagg taagctgtga gttgactgcc tgtccctgtg ttctctggcc   2220

tgtacgatct gtggcgtgta ggatcacttt tgcaacaact aaaaactaaa gcactttgtt   2280

tgcagttcta cagaaagcaa cttagtctgt ctgcagattc gtttttgaaa gaagacatga   2340

gaaagcggag ttttaggtga agtcagttgt tggatcttcc tttatagact tagtccttta   2400

gatgtggtct gtatagacat gcccaaccat catgcatggg cactgaatat cgtgaactgt   2460

ggtatgcttt ttgttggttt attgtacttc tgtcaaagaa agtggcattg gtttttataa   2520

ttgttgccaa gttttaaggt taattttcat tatttttgag ccaaattaaa atgtgcacct   2580

cctgtgcctt tcccaatctt ggaaaatata atttcttggc agaaggtcag atttcagggc   2640

ccagtcactt tcgtctgact tccctttgca cagtccgcca tgggcctggc ttagaagttc   2700

ttgtaaacta tgccagagag tacattcgct gataaaatct tctttgcaga gcaggagagc   2760

ttcttgcctc tttcctttca tttctgcctg gactttggtg ttctccacgt tccctgcatc   2820

ctaaggacag caggagaact ctgaccccag tgctatttct ctaggtgcta ttgtggcaaa   2880

ctcaagcggt ccgtctctgt ccctgtaacg ttcgtacctt gctggctgtg aagtactgac   2940

tggtaaagct ccgtgctaca gcagtgtagg gtatacacaa acacaagtaa gtgttttatt   3000

taaaactgtg gacttagcat aaaaagggag actatattta ttttttacaa aagggataaa   3060

aatggaaccc tttcctcacc caccagattt agtcagaaaa aaacattcta ttctgaaagg   3120

tcacagtggt tttgacatga cacatcagaa caacgcacac tgtccatgat ggcttatgaa   3180

ctccaagtca ctccatcatg gtaaatgggt agatccctcc ttctagtgtg ccacaccatt   3240

gcttcccaca gtagaatctt atttaagtgc taagtgttgt ctctgctggt ttactctgtt   3300

gttttagaga atgtaagttg tatagtgaat aagttattga agcatgtgta aacactgtta   3360

tacatctttt ctcctagatg gggaatttgg aataaaatac ctttaaaatt caaaaaaaaa   3420

aaaaaaaaaa aaaaa                                                    3435
```

<210> SEQ ID NO 43
<211> LENGTH: 481
<212> TYPE: PRT
<213> ORGANISM: Rattus norvegicus

<400> SEQUENCE: 43

```
Met Ser Thr Ile Cys Pro Pro Pro Ser Pro Ala Val Ala Lys Thr Glu
1               5                   10                  15

Ile Ala Leu Ser Gly Glu Ser Pro Leu Leu Ala Ala Thr Phe Ala Tyr
            20                  25                  30

Trp Asp Asn Ile Leu Gly Pro Arg Val Arg His Ile Trp Ala Pro Lys
        35                  40                  45

Thr Asp Gln Val Leu Leu Ser Asp Gly Glu Ile Thr Phe Leu Ala Asn
    50                  55                  60

His Thr Leu Asn Gly Glu Ile Leu Arg Asn Ala Glu Ser Gly Ala Ile
65                  70                  75                  80

Asp Val Lys Phe Phe Val Leu Ser Glu Lys Gly Val Ile Ile Val Ser
                85                  90                  95

Leu Ile Phe Asp Gly Asn Trp Asn Gly Asp Arg Ser Thr Tyr Gly Leu
            100                 105                 110
```

-continued

```
Ser Ile Ile Leu Pro Gln Thr Glu Leu Ser Phe Tyr Leu Pro Leu His
        115                 120                 125

Arg Val Cys Val Asp Arg Leu Thr His Ile Ile Arg Lys Gly Arg Ile
    130                 135                 140

Trp Met His Lys Glu Arg Gln Glu Asn Val Gln Lys Ile Val Leu Glu
145                 150                 155                 160

Gly Thr Glu Arg Met Glu Asp Gln Gly Gln Ser Ile Ile Pro Met Leu
                165                 170                 175

Thr Gly Glu Val Ile Pro Val Met Glu Leu Leu Ala Ser Met Arg Ser
            180                 185                 190

His Ser Val Pro Glu Asp Leu Asp Ile Ala Asp Thr Val Leu Asn Asp
        195                 200                 205

Asp Asp Ile Gly Asp Ser Cys His Glu Gly Phe Leu Leu Asn Ala Ile
    210                 215                 220

Ser Ser His Leu Gln Thr Cys Gly Cys Ser Val Val Val Gly Ser Ser
225                 230                 235                 240

Ala Glu Lys Val Asn Lys Ile Val Arg Thr Leu Cys Leu Phe Leu Thr
                245                 250                 255

Pro Ala Glu Arg Lys Cys Ser Arg Leu Cys Glu Ala Glu Ser Ser Phe
            260                 265                 270

Lys Tyr Glu Ser Gly Leu Phe Val Gln Gly Leu Leu Lys Asp Ala Thr
        275                 280                 285

Gly Ser Phe Val Leu Pro Phe Arg Gln Val Met Tyr Ala Pro Tyr Pro
    290                 295                 300

Thr Thr His Ile Asp Val Asp Val Asn Thr Val Lys Gln Met Pro Pro
305                 310                 315                 320

Cys His Glu His Ile Tyr Asn Gln Arg Arg Tyr Met Arg Ser Glu Leu
                325                 330                 335

Thr Ala Phe Trp Arg Ala Thr Ser Glu Glu Asp Met Ala Gln Asp Thr
            340                 345                 350

Ile Ile Tyr Thr Asp Glu Ser Phe Thr Pro Asp Leu Asn Ile Phe Gln
        355                 360                 365

Asp Val Leu His Arg Asp Thr Leu Val Lys Ala Phe Leu Asp Gln Val
    370                 375                 380

Phe His Leu Lys Pro Gly Leu Ser Leu Arg Ser Thr Phe Leu Ala Gln
385                 390                 395                 400

Phe Leu Leu Ile Leu His Arg Lys Ala Leu Thr Leu Ile Lys Tyr Ile
                405                 410                 415

Glu Asp Asp Thr Gln Lys Gly Lys Lys Pro Phe Lys Ser Leu Arg Asn
            420                 425                 430

Leu Lys Ile Asp Leu Asp Leu Thr Ala Glu Gly Asp Leu Asn Ile Ile
        435                 440                 445

Met Ala Leu Ala Glu Lys Ile Lys Pro Gly Leu His Ser Phe Ile Phe
    450                 455                 460

Gly Arg Pro Phe Tyr Thr Ser Val Gln Glu Arg Asp Val Leu Met Thr
465                 470                 475                 480

Phe
```

<210> SEQ ID NO 44
<211> LENGTH: 18
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 44
ccccggcccc ggccccgg 18

<210> SEQ ID NO 45
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
ggggccgggg ccggggc 17

<210> SEQ ID NO 46
<211> LENGTH: 198
<212> TYPE: DNA
<213> ORGANISM: Homo sapiens

<400> SEQUENCE: 46
gggtctagca agagcaggtg tgggtttagg aggtgtgtgt ttttgttttt cccaccctct 60
ctccccacta cttgctctca cagtactcgc tgagggtgaa caagaaaaga cctgataaag 120
attaaccaga agaaaacaag gagggaaaca accgcagcct gtagcaagct ctggaactca 180
ggagtcgcgc gctatgcg 198

<210> SEQ ID NO 47
<211> LENGTH: 118
<212> TYPE: DNA
<213> ORGANISM: Homo sapiens

<400> SEQUENCE: 47
gcgatcgcgg ggcgtggtcg gggcgggccc gggggcgggc ccggggcggg gctgcggttg 60
cggtgcctgc gcccgcggcg gcggaggcgc aggcggtggc gagtgggtga gtgaggag 118

<210> SEQ ID NO 48
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
ggccccggcc ccggcccc 18

<210> SEQ ID NO 49
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
agtcagtcag tc 12

-continued

<210> SEQ ID NO 50
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 50
ggggccgggg ccggggccgg ggccggggcc ggggccagtc agtcagtca 49

<210> SEQ ID NO 51
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 51 tgactgact 9

<210> SEQ ID NO 52
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 52
ccccggcccc ggccccgaga 20

<210> SEQ ID NO 53
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 53
cggccggccc tcgagggtct 20

<210> SEQ ID NO 54
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 54
gagggtctcg gccccggccc 20

<210> SEQ ID NO 55
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 55
ctcggccccg gccccggccc 20

<210> SEQ ID NO 56
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 56
gcuaugcgau cgccgucucg guuuuagagc uaugcuguuu ug 42

<210> SEQ ID NO 57
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 57
ccccggcccc ggccccgaga guuuuagagc uaugcuguuu ug 42

<210> SEQ ID NO 58
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 58
gcgcgctatg cgatcgccgt ctcggggccg gggccggggc cgg 43

<210> SEQ ID NO 59
<211> LENGTH: 62
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 59
ccggggccgg ggccggggcc gagaccctcg agggccggcc gctagcgcga tcgcggggcg 60
tg 62

<210> SEQ ID NO 60
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 60
ggggccgggg ccggggccgg ggccggggcc ggggcc 36

<210> SEQ ID NO 61
<211> LENGTH: 19

-continued

<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 61
catcccaatt gccctttcc 19

<210> SEQ ID NO 62
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 62
cccacacctg ctcttgctag a 21

<210> SEQ ID NO 63
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 63
tctaggtgga aagtggg 17

<210> SEQ ID NO 64
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 64
gagcaggtgt gggtttagga 20

<210> SEQ ID NO 65
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 65
ccaggtctca ctgcattcca 20

<210> SEQ ID NO 66
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 66
attgcaagcg ttcggataat gtgaga 26

<210> SEQ ID NO 67
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 67
gctgtcacga aggctttctt c 21

<210> SEQ ID NO 68
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 68
gcactgctgc caactacaac 20

<210> SEQ ID NO 69
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 69
tcaatgccat cagctcacac ctgc 24

<210> SEQ ID NO 70
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 70
aagaggcgcg ggtagaa 17

<210> SEQ ID NO 71
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 71
cagcttcggt cagagaaatg ag 22

<210> SEQ ID NO 72
<211> LENGTH: 24
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 72
ctctcctcag agctcgacgc attt 24

<210> SEQ ID NO 73
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 73
ctgcacaatt tcagcccaag 20

<210> SEQ ID NO 74
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 74
caggtcatgt cccacagaat 20

<210> SEQ ID NO 75
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 75
catatgaggg cagcaatgca agtc 24

<210> SEQ ID NO 76
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 76
cgccgucucg gggccggggc guuuuagagc uaugcuguuu ug 42

<210> SEQ ID NO 77
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 77
ccgucucggg gccggggccg guuuuagagc uaugcuguuu ug 42

<210> SEQ ID NO 78
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 78
cggccggccc ucgagggucu guuuuagagc uaugcuguuu ug 42

<210> SEQ ID NO 79
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 79
ggccggggcc gagacccucg guuuuagagc uaugcuguuu ug 42

<210> SEQ ID NO 80
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 80
gagggucucg gccccggccc guuuuagagc uaugcuguuu ug 42

<210> SEQ ID NO 81
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 81
cucggccccg gccccggccc guuuuagagc uaugcuguuu ug 42

<210> SEQ ID NO 82
<211> LENGTH: 89
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 82
guuggaacca uucaaaacag cauagcaagu uaaaauaagg cuaguccguu aucaacuuga 60
aaaaguggca ccgagucggu gcuuuuuuu 89

<210> SEQ ID NO 83
<211> LENGTH: 5
<212> TYPE: RNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 83 gggguㅤ5

<210> SEQ ID NO 84
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 84
gcuaugcgau cgccgucucg 20

<210> SEQ ID NO 85
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 85
ccccggcccc ggccccgaga 20

<210> SEQ ID NO 86
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 86
cgccgucucg gggccggggc 20

<210> SEQ ID NO 87
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 87
ccgucucggg gccggggccg 20

<210> SEQ ID NO 88
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 88
cggccggccc ucgagggucu 20

<210> SEQ ID NO 89
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 89
ggccggggcc gagacccucg 20

<210> SEQ ID NO 90
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 90
gagggucucg gccccggccc 20

<210> SEQ ID NO 91
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 91
cucggccccg gccccggccc 20

<210> SEQ ID NO 92
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 92
tgcgcctccg ccgccgcggg cgcaggcacc gcaaccgca 39

<210> SEQ ID NO 93
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 93
cgcagcctgt agcaagctct ggaactcagg agtcg 35

<210> SEQ ID NO 94
<211> LENGTH: 1957
<212> TYPE: DNA
<213> ORGANISM: Homo sapiens

<400> SEQUENCE: 94

```
acgtaaccta cggtgtcccg ctaggaaaga gaggtgcgtc aaacagcgac aagttccgcc     60
cacgtaaaag atgacgcttg atatctccgg agcatttgga taatgtgaca gttggaatgc    120
agtgatgtcg actctttgcc caccgccatc tccagctgtt gccaagacag agattgcttt    180
aagtggcaaa tcacctttat tagcagctac ttttgcttac tgggacaata ttcttggtcc    240
tagagtaagg cacatttggg ctccaaagac agaacaggta cttctcagtg atggagaaat    300
aacttttctt gccaaccaca ctctaaatgg agaaatcctt cgaaatgcag agagtggtgc    360
tatagatgta aagtttttg tcttgtctga aaagggagtg attattgttt cattaatctt     420
tgatggaaac tggaatgggg atcgcagcac atatggacta tcaattatac ttccacagac    480
agaacttagt ttctacctcc cacttcatag agtgtgtgtt gatagattaa cacatataat    540
ccggaaagga agaatatgga tgcataagga aagacaagaa aatgtccaga agattatctt    600
agaaggcaca gagagaatgg aagatcaggg tcagagtatt attccaatgc ttactggaga    660
agtgattcct gtaatggaac tgctttcatc tatgaaatca cacagtgttc ctgaagaaat    720
agatatagct gatacagtac tcaatgatga tgatattggt gacagctgtc atgaaggctt    780
tcttctcaag taagaatttt tcttttcata aaagctggat gaagcagata ccatcttatg    840
ctcacctatg acaagatttg gaagaaagaa aataacagac tgtctactta gattgttcta    900
gggacattac gtatttgaac tgttgcttaa atttgtgtta tttttcactc attatatttc    960
tatatatatt tggtgttatt ccatttgcta tttaaagaaa ccgagtttcc atcccagaca   1020
agaaatcatg gccccttgct tgattctggt ttcttgtttt acttctcatt aaagctaaca   1080
gaatcctttc atattaagtt gtactgtaga tgaacttaag ttatttaggc gtagaacaaa   1140
attattcata tttatactga tctttttcca tccagcagtg gagtttagta cttaagagtt   1200
tgtgccctta aaccagactc cctggattaa tgctgtgtac ccgtgggcaa ggtgcctgaa   1260
ttctctatac acctatttcc tcatctgtaa aatggcaata atagtaatag tacctaatgt   1320
gtagggttgt tataagcatt gagtaagata aataatataa agcacttaga acagtgcctg   1380
gaacataaaa acacttaata atagctcata gctaacattt cctatttaca tttcttctag   1440
aaatagccag tatttgttga gtgcctacat gttagttcct ttactagttg ctttacatgt   1500
attatcttat attctgtttt aaagtttctt cacagttaca gattttcatg aaattttact   1560
tttaataaaa gagaagtaaa agtataaagt attcactttt atgttcacag tcttttcctt   1620
taggctcatg atggagtatc agaggcatga gtgtgtttaa cctaagagcc ttaatggctt   1680
gaatcagaag cactttagtc ctgtatctgt tcagtgtcag cctttcatac atcattttaa   1740
atcccatttg actttaagta agtcacttaa tctctctaca tgtcaatttc ttcagctata   1800
aaatgatggt atttcaataa ataaatacat taattaaatg atattatact gactaattgg   1860
gctgttttaa ggctcaataa gaaaatttct gtgaaaggtc tctagaaaat gtaggttcct   1920
atacaaataa aagataacat tgtgcttata aaaaaaa                            1957
```

<210> SEQ ID NO 95
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 95
gatagtcgac atccctgcat c 21

<210> SEQ ID NO 96
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 96
ggtggcgagt ggctattg 18

<210> SEQ ID NO 97
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 97
aagcgttcgg ataatgtgag acctgg 26

<210> SEQ ID NO 98
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 98
tctcacagta ctcgctgagg gtga 24

<210> SEQ ID NO 99
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 99
aagagcaggt gtgggtttag 20

<210> SEQ ID NO 100
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 100
cggttgtttc cctccttgt 19

<210> SEQ ID NO 101
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 101
cccactactt gctctcacag 20

<210> SEQ ID NO 102
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 102
tacaggctgc ggttgttt 18

<210> SEQ ID NO 103
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 103
actcgctgag ggtgaacaag aaa 23

<210> SEQ ID NO 104
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 104
cgagtgggtg agtgagga 18

<210> SEQ ID NO 105
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 105
ttctacccgc gcctctt 17

<210> SEQ ID NO 106
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 106
atcctggcgg gtggctgttt 20

<210> SEQ ID NO 107
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 107
cggataatgt gagacctgga at 22

<210> SEQ ID NO 108
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 108
aaaggtagcc gccaacaa 18

<210> SEQ ID NO 109
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 109
accatctcct gctgttgcca aga 23

<210> SEQ ID NO 110
<211> LENGTH: 222
<212> TYPE: PRT
<213> ORGANISM: Homo sapiens

<400> SEQUENCE: 110

```
Met Ser Thr Leu Cys Pro Pro Pro Ser Pro Ala Val Ala Lys Thr Glu
1               5                   10                  15

Ile Ala Leu Ser Gly Lys Ser Pro Leu Leu Ala Ala Thr Phe Ala Tyr
            20                  25                  30

Trp Asp Asn Ile Leu Gly Pro Arg Val Arg His Ile Trp Ala Pro Lys
        35                  40                  45

Thr Glu Gln Val Leu Leu Ser Asp Gly Glu Ile Thr Phe Leu Ala Asn
    50                  55                  60

His Thr Leu Asn Gly Glu Ile Leu Arg Asn Ala Glu Ser Gly Ala Ile
65                  70                  75                  80

Asp Val Lys Phe Phe Val Leu Ser Glu Lys Gly Val Ile Ile Val Ser
                85                  90                  95

Leu Ile Phe Asp Gly Asn Trp Asn Gly Asp Arg Ser Thr Tyr Gly Leu
            100                 105                 110

Ser Ile Ile Leu Pro Gln Thr Glu Leu Ser Phe Tyr Leu Pro Leu His
        115                 120                 125

Arg Val Cys Val Asp Arg Leu Thr His Ile Ile Arg Lys Gly Arg Ile
    130                 135                 140

Trp Met His Lys Glu Arg Gln Glu Asn Val Gln Lys Ile Ile Leu Glu
145                 150                 155                 160
```

```
Gly Thr Glu Arg Met Glu Asp Gln Gly Gln Ser Ile Ile Pro Met Leu
                165                 170                 175

Thr Gly Glu Val Ile Pro Val Met Glu Leu Leu Ser Ser Met Lys Ser
            180                 185                 190

His Ser Val Pro Glu Glu Ile Asp Ile Ala Asp Thr Val Leu Asn Asp
        195                 200                 205

Asp Asp Ile Gly Asp Ser Cys His Glu Gly Phe Leu Leu Lys
    210                 215                 220


<210> SEQ ID NO 111
<211> LENGTH: 6702
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(158)
<223> OTHER INFORMATION: /note="Exon 1A"
<220> FEATURE:
<221> NAME/KEY: misc_feature
<222> LOCATION: (321)..(338)
<223> OTHER INFORMATION: /note="3x Hexanucleotide Repeat"
<220> FEATURE:
<221> NAME/KEY: misc_feature
<222> LOCATION: (374)..(436)
<223> OTHER INFORMATION: /note="Exon 1B"

<400> SEQUENCE: 111

acguaaccua cggugucccg cuaggaaaga gaggugcguc aaacagcgac aaguuccgcc     60

cacguaaaag augacgcuug gugugucagc cgucccugcu gcccgguugc uucucuuuug    120

ggggcggggu cuagcaagag caggugtggg uuuaggaggu gugugutuuu guuuuuccca    180

cccucucucc ccacuacuug cucucacagu acucgcugag ggugaacaag aaaagaccug    240

auaaagauua accagaagaa aacaaggagg gaaacaaccg cagccuguag caagcucugg    300

aacucaggag ucgcgcgcua ggggccgggg ccggggccgg ggcguggucg gggcgggccc    360

gggggcgggc ccggggcggg gcugcgguug cggugccugc gcccgcggcg gcggaggcgc    420

aggcgguggc gaguggguga gugaggaggc ggcauccugg cggguggcug uuuggggguuc   480

ggcugccggg aagaggcgcg gguagaagcg ggggcucucc ucagagcucg acgcauuuuu    540

acuuucccuc ucauuucucu gaccgaagcu gggugucggg cuuucgccuc uagcgacugg    600

uggaauugcc ugcauccggg ccccgggcuu cccggcggcg gcggcggcgg cggcggcgca    660

gggacaaggg auggggaucu ggccucuucc uugcuuuccc gcccucagua cccgagcugu    720

cuccuucccg gggacccgcu gggagcgcug ccgcugcggg cucgagaaaa gggagccucg    780

gguacugaga ggccucgccu gggggaaggc cggagggugg gcggcgcgcg gcuucugcgg    840

accaagucgg gguucgcuag gaacccgaga cggucccugc cggcgaggag aucaugcggg    900

augagauggg ggugugggaga cgccugcaca auuucagccc aagcuucuag agaguggugua   960

ugacuugcau augagggcag caaugcaagu cggugugcuc cccauucugu gggacaugac   1020

cugguugcuu cacagcuccg agaugacaca gacuugcuua aaggaaguga cuauugugac   1080

uugggcauca cuugacugau gguaaucagu ugucuaaaga agugcacaga uuacaugucc   1140

gugugcucau ugggucuauc uggccgcguu gaacaccacc aggcuuugua uucagaaaca   1200

ggagggaggu ccugcacuuu cccaggaggg guggcccuuu cagaugcaau cgagauuguu   1260
```

-continued aggcucuggg agaguaguug ccugguugug gcaguuggua aauuucuauu caaacaguug 1320
ccaugcacca guuguucaca acaaggguac guaaucuguc uggcauuacu ucuacuuuug 1380
uacaaaggau caaaaaaaaa aaagauacug uuaagauaug auuuuucuca gacuuuggga 1440
aacuuuuaac auaaucugug aauaucacag aaacaagacu aucauauagg ggauauuaau 1500
aaccuggagu cagaauacuu gaaauacggu gucauuugac acgggcauug uugucaccac 1560
cucugccaag gccugccacu uuaggaaaac ccugaaucag uuggaaacug cuacaugcug 1620
auaguacauc ugaaacaaga acgagaguaa uuaccacauu ccagauuguu cacuaagcca 1680
gcauuuaccu gcuccaggaa aaaauuacaa gcaccuuaug aaguugauaa aauauuuugu 1740
uuggcuaugu uggcacucca caauuugcuu ucagagaaac aaaguaaacc aaggaggacu 1800
ucuguuuuuc aagucugccc ucggguucua uucuacguua auuagauagu ucccaggagg 1860
acuagguuag ccuaccuauu gucugagaaa cuuggaacug ugagaaaugg ccagauagug 1920
auaugaacuu caccuuccag ucuucccuga uguugaagau ugagaaagug uugugaacuu 1980
ucugguacug uaaacaguuc acuguccuug aagugguccu gggcagcucc uguuguggaa 2040
aguggacggu uuaggauccu gcuucucuuu gggcugggag aaaauaaaca gcaugguuac 2100
aaguauugag agccagguug gagaaggugg cuuacaccug uaaugccaga gcuuugggag 2160
gcggaggcaa gaggaucacu ugaagccagg aguucaagcu caaccugggc aacguagacc 2220
cugucucuac aaaaaauuaa aaacuuagcc gggcguggug augugcaccu guaguccuag 2280
cuacuuggga ggcugaggca ggagggucau uugagcccaa gaguuugaag uuaccgagag 2340
cuaugauccu gccagugcau uccagccugg augacaaaac gagacccugu cucuaaaaaa 2400
caagaaguga gggcuuuaug auuguagaau uuucacuaca auagcagugg accaaccacc 2460
uuucuaaaua ccaaucaggg aagagauggu ugauuuuuua acagacguuu aaagaaaaag 2520
caaaaccuca aacuuagcac ucuacuaaca guuuuagcag auguuaauua auguaaucau 2580
gucugcaugu augggauuau uuccagaaag uguauuggga aaccucucau gaacccugug 2640
agcaagccac cgucucacuc aauuugaauc uuggcuuccc ucaaaagacu ggcuaauguu 2700
ugguaacucu cuggaguaga cagcacuaca uguacguaag auagguacau aaacaacuau 2760
ugguuuugag cugauuuuuu ucagcugcau uugcauguau ggauuuuucu caccaaagac 2820
gaugacuuca aguauuagua aaauaauugu acagcucucc ugauuauacu ucucugugac 2880
auuucauuuc ccaggcuauu ucuuuuggua ggauuuaaaa cuaagcaauu caguaugauc 2940
uuuguccuuc auuuucuuuc uuauucuuuu uguuuguuug uuuguuuguu uuuuucuuga 3000
ggcagagucu cucucugucg cccaggcugg agugcagugg cgccaucuca gcucauugca 3060
accucugcca ccuccggguu caagagauuc uccugccuca gccucccgag uagcugggau 3120
uacaggugcc caccaccaca cccggcuaau uuuuuguauu uuuaguagag guggguuuc 3180 accauguugg ccaggcuggu cuugagcucc ugaccucagg ugauccaccu gccucggccu 3240
accaaagagc ugggauaaca ggugugaccc accaugcccg gcccauuuuu uuuuucuuau 3300
ucuguuagga gugagagugu aacuagcagu auaauaguuc aauuuucaca acgugguaaa 3360
aguuucccua uaauucaauc agauuuugcu ccaggguuca guucuguuuu aggaaauacu 3420
uuuauuuuca guuuaaugau gaaauauuag aguuguaaua uugccuuuau gauuauccac 3480
cuuuuuaacc uaaaagaaug aaagaaaaau auguuugcaa uauaauuuua ugguuguaug 3540
uuaacuuaau ucauuauguu ggccuccagu uugcuguugu uaguuaugac agcaguagug 3600
ucauuaccau uucaauucag auuacauucc uauauuugau cauuguaaac ugacugcuua 3660
cauuguauua aaaacagugg auauuuuaaa gaagcuguac ggcuuauauc uagugcuguc 3720
ucuuaagacu auuaaauuga uacaacauau uuaaaaguaa auauuaccua aaugaauuuu 3780
ugaaauuaca aauacacgug uuaaaacugu cguuguguuc aaccauuucu guacauacuu 3840
agaguuaacu guuuugccag gcucuguaug ccuacucaua auaugauaaa agcacucauc 3900
uaaugcucug uaaauagaag ucagugcuuu ccaucagacu gaacucucuu gacaagaugu 3960
ggaugaaauu cuuuaaguaa aauuguuuac uuugucauac auuuacagau caaauguuag 4020
cucccaaagc aaucauaugg caaagauagg uauaucauag uuugccuauu agcugcuuug 4080
uauugcuauu auuauaaaua gacuucacag uuuuagacuu gcuuaggugua aauugcaauu 4140
cuuuuuacuu ucagucuuag auaacaaguc uucaauuaua guacaaucac acauugcuua 4200
ggaaugcauc auuaggcgau uuugucauua ugcaaacauc auagagugua cuuacacaaa 4260
ccuagauagu auagccuuua uguaccuagg ccguauggua uagucuguug cuccuaggcc 4320
acaaaccugu acaacuguua cuguacugaa uacuauagac aguuguaaca cagugguaaa 4380
uauuuaucua aauauaugca aacagagaaa agguacagua aaaguauggu auaaaagaua 4440
augguauacc uguguaggcc acuuaccacg aauggagcuu gcaggacuag aaguugcucu 4500
gggugaguca gugagugagu ggugaauuaa ugugaaggcc uagaacacug uacaccacug 4560
uagacuauaa acacaguacg cugaagcuac accaaauuua ucuuaacagu uuuucuucaa 4620
uaaaaaauua uaacuuuuua acuuuguaaa cuuuuuaauu uuuuaacuuu uaaaauacuu 4680
agcuugaaac acaaauacau uguauagcua uacaaaaaua uuuuuucuuu guauccuuau 4740
ucuagaagcu uuuuucuauu uucuauuuua aauuuuuuuu uuuacuuguu agucguuuuu 4800
guuaaaaacu aaaacacaca cacuuucacc uaggcauaga caggauuagg aucaucagua 4860
ucacucccuu ccaccucacu gccuuccacc uccacaucuu gucccacugg aagguuuuua 4920
ggggcaauaa cacacaugua gcugucaccu augauaacag ugcuuucugu ugaauaccuc 4980
cugaaggacu ugccugaggc uguuuuacau uuaacuuaaa aaaaaaaaaa guagaaggag 5040
ugcacucuaa aauaacaaua aaaggcauag uauagugaau acauaaacca gcaauguagu 5100
aguuuauuau caaguguugu acacuguaau aauuguaugu gcuauacuuu aaauaacuug 5160
caaaauagua cuaagaccuu augaugguua cagugucacu aaggcaauag cauauuuuca 5220
gguccauugu aaucuaaugg gacuaccauc auauaugcag ucuaccauug acugaaacgu 5280
uacauggcac auaacuguau uugcaagaau gauuuguuuu acauuaauau cacauaggau 5340
guaccuuuuu agagugguau guuuaugugg auuaagaugu acaaguugag caaggggacc 5400
aagagcccug gguucugucu uggaugugag cguuuauguu cuucuccuca ugucuguuuu 5460
cucauuaaau ucaaaggcuu gaacgggccc uauuuagccc uucuguuuuc uacguguucu 5520
aaauaacuaa agcuuuuaaa uucuagccau uuaguguaga acucucuuug cagugaugaa 5580
augcuguauu gguuucuugg cuagcauauu aaauauuuuu aucuuugucu ugauacuuca 5640
augucguuuu aaacaucagg aucgggcuuc aguauucuca uaaccagaga guucacugag 5700
gauacaggac uguuugccca uuuuuuguua uggcuccaga cuugugguau uuccaugucu 5760
uuuuuuuuuu uuuuuuuuuu gaccuuuuag cggcuuuaaa guauuucugu uguuaggugu 5820
uguauuacuu uucuaagauu acuuaacaaa gcaccacaaa cugaguggcu uuaaacaaca 5880
gcaauuuauu cucucacaau ucuagaagcu agaaguccga aaucaaagug uugacagggg 5940
caugaucuuc aagagagaag acucuuuccu ugccucuucc uggcuucugg ugguuaccag 6000
caauccugag uguuccuuuc uugccuugua guuucaacaa uccaguaucu gccuuuuguc 6060
uucacauggc ugucuaccau uugucucugu gucuccaaau cucucuccuu auaaacacag 6120
caguuauugg auuaggcccc acucuaaucc aguaugaccc cauuuuaaca ugauuacacu 6180
uauuucuaga uaaggucaca uucacguaca ccaaggguua ggaauugaac auaucuuuuu 6240
gggggacaca auucaaccca caagugucag ucucuagcug agccuuuccc uuccuguuuu 6300
ucuccuuuuu aguugcuaug gguuaggggc caaaucucca gucauacuag aauugcacau 6360
ggacuggaua uuugggaaua cugcgggucu auucuaugag cuuuaguaug uaacauuuaa 6420
uaucagugua aagaagcccu uuuuuaaguu auuucuuuga auuucuaaau guaugcccug 6480
aauauaagua acaaguuacc augucuugua aaaugaucau aucaacaaac auuuaaugug 6540
caccuacugu gcuaguugaa ugucuuuauc cugauaggag auaacaggau uccacaucuu 6600
ugacuuaaga ggacaaacca aauaugucua aaucauuugg gguuuugaug gauaucuuua 6660
aauugcugaa ccuaaucauu gguuucauau gucauuguuu ag 6702

<210> SEQ ID NO 112
<211> LENGTH: 6702
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (6267)..(6329)
<223> OTHER INFORMATION: /note="Exon 1B"
<220> FEATURE:
<221> NAME/KEY: misc_feature
<222> LOCATION: (6365)..(6382)
<223> OTHER INFORMATION: /note="3x Hexanucleotide Repeat"
<220> FEATURE:
<221> NAME/KEY: misc_feature
<222> LOCATION: (6545)..(6702)
<223> OTHER INFORMATION: /note="Exon 1A"

<400> SEQUENCE: 112
cuaaacaaug acauaugaaa ccaaugauua gguucagcaa uuuaaagaua uccaucaaaa 60
ccccaaauga uuuagacaua uuugguuugu ccucuuaagu caaagaugug gaauccuguu 120
aucuccuauc aggauaaaga cauucaacua gcacaguagg ugcacauuaa auguuuguug 180
auaugaucau uuuacaagac augguaacuu guuacuuaua uucagggcau acauuuagaa 240
auucaaagaa auaacuuaaa aaagggcuuc uuuacacuga uauuaaaugu uacauacuaa 300
agcucauaga auagacccgc aguauuccca aauauccagu ccaugugcaa uucuaguaug 360
acuggagauu uggccccuaa cccauagcaa cuaaaaagga gaaaaacagg aagggaaagg 420
cucagcuaga gacugacacu uguggguuga auugugucccc ccaaaaagau auguucaauu 480
ccuaacccuu gguguacgug aaugugaccu uaucuagaaa uaaguguaau cauguuaaaa 540
uggggucaua cuggauuaga guggggccua auccaauaac ugcuguguuu auaaggagag 600
agauuuggag acacagagac aaaugguaga cagccaugug aagacaaaag gcagauacug 660
gauuguugaa acuacaaggc aagaaaggaa cacucaggau ugcugguaac caccagaagc 720
caggaagagg caaggaaaga gucuucucuc uugaagauca ugccccuguc aacacuuuga 780
uuucggacuu cuagcuucua gaauugugag agaauaaauu gcuguuguuu aaagccacuc 840
aguuuguggu gcuuuguuaa guaaucuuag aaaaguaaua caacaccuaa caacagaaau 900
acuuuaaagc cgcuaaaagg ucaaaaaaaa aaaaaaaaaa aaagacaugg aaauaccaca 960

-continued

```
agucuggagc cauaacaaaa aaugggcaaa caguccugua ucccucagug a acucucuggu   1020
```

agucuggagc cauaacaaaa aaugggcaaa caguccugua ucccucaguga acucucuggu 1020 uaugagaaua cugaagcccg auccugaugu uuaaaacgac auugaaguau caagacaaag 1080
auaaaaauau uuaauaugcu agccaagaaa ccaauacagc auuucaucac ugcaaagaga 1140
guucuacacu aaauggcuag aauuuaaaag cuuuaguuau uuagaacacg uagaaaacag 1200
aagggcuaaa uagggcccgu ucaagccuuu gaauuuaaug agaaaacaga caugaggaga 1260
agaacauaaa cgcucacauc caagacagaa cccagggcuc uugguccccu ugcucaacuu 1320
guacaucuua auccacauaa acauaccacu cuaaaaaggu acauccuaug ugauauuaau 1380
guaaaacaaa ucauucuugc aaauacaguu augugccaug uaacguuuca gucaauggua 1440
gacugcauau augaugguag ucccauuaga uuacaaugga ccugaaaaua ugcuauugcc 1500
uuagugacac uguaaccauc auaaggucuu aguacuauuu ugcaaguuau uuaaaguaua 1560
gcacauacaa uuauuacagu guacaacacu ugauaauaaa cuacuacauu gcugguuuau 1620
guauucacua uacuaugccu uuuauuguua uuuuagagug cacuccuucu acuuuuuuuu 1680
uuuuuaaguu aaauguaaaa cagccucagg caaguccuuc aggagguauu caacagaaag 1740
cacuguuauc auaggugaca gcuacaugug uguuauugcc ccuaaaaacc uuccaguggg 1800
acaagaugug gagguggaag gcagugaggu ggaagggagu gauacugaug auccuaaucc 1860
ugucuaugcc uaggugaaag uguguguguu uuaguuuuua acaaaaacga cuaacaagua 1920
aaaaaaaaaa uuuaaaauag aaaauagaaa aaagcuucua gaauaaggau acaaagaaaa 1980
aauauuuuug uauagcuaua caauguauuu guguuucaag cuaaguauuu uaaaaguuaa 2040
aaaauuaaaa aguuuacaaa guuaaaaagu uauaauuuuu uauugaagaa aaacuguuaa 2100
gauaaauuug guguagcuuc agcguacugu guuuauaguc uacaguggug uacaguguuc 2160
uaggccuuca cauuaauuca ccacucacuc acugacucac ccagagcaac uucuaguccu 2220
gcaagcucca uucgugguaa guggccuaca cagguauacc auuaucuuuu auaccauacu 2280
uuuacuguac cuuuucucug uuugcauaua uuuagauaaa uauuuaccac uguguuacaa 2340
cugucuauag uauucaguac aguaacaguu guacagguuu guggccuagg agcaacagac 2400
uauaccauac ggccuaggua cauaaaggcu auacuaucua gguuugugua aguacacucu 2460
augauguuug cauaaugaca aaaucgccua augaugcauu ccuaagcaau gugugauugu 2520
acuauaauug aagacuuguu aucuaagacu gaaaguaaaa agaauugcaa uuucaccuaa 2580
gcaagucuaa aacugugaag ucuauuuaua auaauagcaa uacaaagcag cuaauaggca 2640
aacuaugaua uaccuaucuu ugccauauga uugcuuuggg agcuaacauu ugaucuguaa 2700
auguaugaca aaguaaacaa uuuuacuuaa agaauuucau ccacaucuug ucaagagagu 2760
ucagucugau ggaaagcacu gacuucuauu uacagagcau uagaugagug cuuuuaucau 2820
auuaugagua ggcauacaga gccuggcaaa acaguuaacu cuaaguaugu acagaaaugg 2880
uugaacacaa cgacaguuuu aacacgugua uuuguaauuu caaaaauuca uuuagguaau 2940
auuuacuuuu aaauauguug uaucaauuua auagucuuaa gagacagcac uagauauaag 3000
ccguacagcu ucuuuaaaau auccacuguu uuuaauacaa uguaagcagu caguuuacaa 3060
ugaucaaaua uaggaaugua aucugaauug aaaugguaau gacacuacug cugucauaac 3120
uaacaacagc aaacuggagg ccaacauaau gaauuaaguu aacauacaac cauaaaauua 3180
uauugcaaac auauuuuucu uucauucuuu uagguuaaaa agguggauaa ucauaaaggc 3240
aauauuacaa cucuaauauu ucaucauuaa acugaaaaua aaaguauuuc cuaaaacaga 3300

-continued

```
acugaacccu ggagcaaaau cugauugaau uauagggaaa cuuuuaccac guugugaaaa   3360

uugaacuauu auacugcuag uuacacucuc acuccuaaca gaauaagaaa aaaaaaaugg   3420

gccgggcaug gugggucaca ccuguuaucc cagcucuuug guaggccgag gcagguggau   3480

caccugaggu caggagcuca agaccagccu ggccaacaug gugaaacccc accucuacua   3540

aaaauacaaa aaauuagccg ggugugguggg uggacaccug uaaucccagc uacucgggag   3600

gcugaggcag gagaaucucu ugaacccgga gguggcagag guugcaauga gcugagaugg   3660

cgccacugca cuccagccug ggcgacagag agagacucug ccucaagaaa aaaacaaaca   3720

aacaaacaaa caaaaagaau aagaaagaaa augaaggaca aagaucauac ugaauugcuu   3780

aguuuuaaau ccuaccaaaa gaaauagccu gggaaaugaa augucacaga gaaguauaau   3840

caggagagcu guacaauuau uuuacuaaua cuugaaguca ucgucuuugg ugagaaaaau   3900

ccauacaugc aaaugcagcu gaaaaaaauc agcucaaaac caauaguugu uuauguaccu   3960

aucuuacgua cauguagugc ugucuacucc agagaguuac caaacauuag ccagucuuuu   4020

gagggaagcc aagauucaaa uugagugaga cgguggcuug cucacagggu ucaugagagg   4080

uuucccaaua cacuuucugg aaauaauccc auacaugcag acaugauuac auuaauuaac   4140

aucugcuaaa acuguuagua gagugcuaag uuugagguuu ugcuuuuucu uuaaacgucu   4200

guuaaaaaau caaccaucuc uucccugauu gguauuuaga aaggugguug guccacugcu   4260

auuguaguga aaauucuaca aucauaaagc ccucacuucu uguuuuuuag agacaggguc   4320

ucguuuuguc auccaggcug gaaugcacug gcaggaucau agcucucggu aacuucaaac   4380

ucuugggcuc aaaugacccu ccugccucag ccucccaagu agcuaggacu acaggugcac   4440

aucaccacgc ccggcuaagu uuuuaauuuu uuguagagac agggucuacg uugcccaggu   4500

ugagcuugaa cuccuggcuu caagugaucc ucuugccucc gccucccaaa gcucuggcau   4560

uacaggugua agccaccuuc uccaaccugg cucucaauac uuguaaccau gcuguuuauu   4620

uucucccagc ccaaagagaa gcaggauccu aaaccgucca cuuuccacaa caggagcugc   4680

ccaggaccac uucaaggaca gugaacuguu uacaguacca gaaaguucac aacacuuucu   4740

caaucuucaa caucagggaa gacuggaagg ugaaguucau aucacuaucu ggccauuucu   4800

cacaguucca aguuucucag acaauaggua ggcuaaccua guccuccugg gaacuaucua   4860

auuaacguag aauagaaccc gagggcagac uugaaaaaca gaaguccucc uugguuuacu   4920

uuguuucucu gaaagcaaau uguggagugc caacauagcc aaacaaaaua uuuuaucaac   4980

uucauaaggu gcuuguaauu uuuuccugga gcagguaaau gcuggcuuag ugaacaaucu   5040

ggaaugugguu aauuacucuc guucuuguuu cagauguacu aucagcaugu agcaguuucc   5100

aacugauuca ggguuuuccu aaaguggcag gccuuggcag agguggugac aacaaugccc   5160

gugucaaaug acaccguauu ucaaguauuc ugacuccagg uuauuaauau ccccuauaug   5220

auagucuugu uucugugaua uucacagauu auguuaaaag uuucccaaag ucugagaaaa   5280

aucauaucuu aacaguaucu uuuuuuuuuu ugauccuuug uacaaaagua gaaguaaugc   5340

cagacagauu acguacccuu guugugaaca acuggugcau ggcaacuguu ugaauagaaa   5400

uuuaccaacu gccacaacca ggcaacuacu cucccagagc cuaacaaucu cgauugcauc   5460

ugaaagggcc accccuccug ggaaagugca ggaccucccu ccuguuucug aauacaaagc   5520

cuggugguguu ucaacgcggc cagauagacc caaugagcac acggacaugu aaucugugca   5580

cuucuuuaga caacugauua ccaucaguca agugaugccc aagucacaau agucacuucc   5640

uuuaagcaag ucugugucau cucggagcug ugaagcaacc aggucauguc ccacagaaug   5700
```

gggagcacac cgacuugcau ugcugcccuc auaugcaagu caucaccacu cucuagaagc 5760
uugggcugaa auugugcagg cgucuccaca cccccaucuc aucccgcaug aucuccucgc 5820
cggcagggac cgucucgggu ucccuagcgaa ccccgacuug guccgcagaa gccgcgcgcc 5880
gcccacccuc cggccuuccc ccaggcgagg ccucucagua cccgaggcuc ccuuuucucg 5940
agcccgcagc ggcagcgcuc ccagcgggucc cccgggaagg agacagcucg gguacugagg 6000
gcgggaaagc aaggaagagg ccagaucccc aucccuuguc ccugcgccgc cgccgccgcc 6060
gccgccgccg ggaagcccgg ggcccggaug caggcaauuc caccagucgc uagaggcgaa 6120
agcccgacac ccagcuucgg ucagagaaau gagagggaaa guaaaaaugc gucgagcucu 6180
gaggagagcc cccgcuucua cccgcgccuc uucccggcag ccgaacccca aacagccacc 6240
cgccaggaug ccgccuccuc acucacccac ucgccaccgc cugcgccucc gccgccgcgg 6300
gcgcaggcac cgcaaccgca gccccgcccc gggcccgccc ccgggcccgc cccgaccacg 6360
ccccggcccc ggccccggcc ccuagcgcgc gacuccugag uuccagagcu ugcuacaggc 6420
ugcgguuguu ucccuccuug uuuucuucug guuaaucuuu aucaggucuu uucuuguuca 6480
cccucagcga guacugugag agcaaguagu ggggagagag ggugggaaaa acaaaaacac 6540
acaccuccua aacccacacc ugcucuugcu agaccccgcc cccaaaagag aagcaaccgg 6600
gcagcaggga cggcugacac accaagcguc aucuuuuacg ugggcggaac uugucgcugu 6660
uugacgcacc ucucuuuccu agcgggacac cguagguuac gu 6702

<210> SEQ ID NO 113
<211> LENGTH: 215
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (163)..(180)
<223> OTHER INFORMATION: /note="3x Hexanucleotide Repeat"

<400> SEQUENCE: 113 gugugugguuu uuguuuuucc cacccucucu ccccacuacu ugcucucaca guacucgcug 60
agggugaaca agaaaagacc ugauaaagau uaaccagaag aaaacaagga gggaaacaac 120
cgcagccugu agcaagcucu ggaacucagg agucgcgcgc uaggggccgg ggccggggcc 180
ggggcguggu cggggcgggc ccgggggcgg gcccg 215

<210> SEQ ID NO 114
<211> LENGTH: 215
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (36)..(53)
<223> OTHER INFORMATION: /note="3x Hexanucleotide Repeat"

<400> SEQUENCE: 114
cgggcccgcc cccgggcccg ccccgaccac gccccggccc cggccccggc cccuagcgcg 60
cgacuccuga guuccagagc uugcuacagg cugcgguugu uucccuccuu guuuucuucu 120
gguuaaucuu uaucaggucu uuucuuguuc acccucagcg aguacuguga gagcaaguag 180
uggggagaga gggugggaaa aacaaaaaca cacac 215

<210> SEQ ID NO 115
<211> LENGTH: 162
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 115 gugugugu uu uuguuuuucc cacccucucu ccccacuacu ugcucucaca guacucgcug 60
agggugaaca agaaaagacc ugauaaagau uaaccagaag aaaacaagga gggaaacaac 120
cgcagccugu agcaagcucu ggaacucagg agucgcgcgc ua 162

<210> SEQ ID NO 116
<211> LENGTH: 162
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 116
uagcgcgcga cuccugaguu ccagagcuug cuacaggcug cgguuguuuc ccuccuuguu 60
uucuucuggu uaaucuuuau caggucuuuu cuuguucacc cucagcgagu acugugagag 120
caaguagugg ggagagaggg ugggaaaaac aaaaacacac ac 162

<210> SEQ ID NO 117
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 117
caagaaaaga ccugauaaag auuaaccaga agaaaa 36

<210> SEQ ID NO 118
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 118
uuuucuucug guuaaucuuu aucaggucuu uucuug 36

<210> SEQ ID NO 119

<400> SEQUENCE: 119

000

<210> SEQ ID NO 120

<400> SEQUENCE: 120

000

<210> SEQ ID NO 121
<211> LENGTH: 3356
<212> TYPE: DNA
<213> ORGANISM: Homo sapiens

<400> SEQUENCE: 121

```
acgtaaccta cggtgtcccg ctaggaaaga gaggtgcgtc aaacagcgac aagttccgcc     60
cacgtaaaag atgacgcttg gtgtgtcagc cgtccctgct gcccggttgc ttctcttttg    120
ggggcggggt ctagcaagag caggtgtggg tttaggagat atctccggag catttggata    180
atgtgacagt tggaatgcag tgatgtcgac tctttgccca ccgccatctc cagctgttgc    240
caagacagag attgctttaa gtggcaaatc acctttatta gcagctactt ttgcttactg    300
ggacaatatt cttggtccta gagtaaggca catttgggct ccaaagacag aacaggtact    360
tctcagtgat ggagaaataa cttttcttgc caaccacact ctaaatggag aaatccttcg    420
aaatgcagag agtggtgcta tagatgtaaa gtttttgtc ttgtctgaaa agggagtgat     480
tattgtttca ttaatctttg atggaaactg gaatggggat cgcagcacat atggactatc    540
aattatactt ccacagacag aacttagttt ctacctccca cttcatagag tgtgtgttga    600
tagattaaca catataatcc ggaaaggaag aatatggatg cataaggaaa gacaagaaaa    660
tgtccagaag attatcttag aaggcacaga gagaatggaa gatcagggtc agagtattat    720
tccaatgctt actggagaag tgattcctgt aatggaactg ctttcatcta tgaaatcaca    780
cagtgttcct gaagaaatag atatagctga tacagtactc aatgatgatg atattggtga    840
cagctgtcat gaaggctttc ttctcaatgc catcagctca cacttgcaaa cctgtggctg    900
ttccgttgta gtaggtagca gtgcagagaa agtaaataag atagtcagaa cattatgcct    960
ttttctgact ccagcagaga gaaaatgctc caggttatgt gaagcagaat catcatttaa   1020
atatgagtca gggctctttg tacaaggcct gctaaaggat tcaactggaa gctttgtgct   1080
gcctttccgg caagtcatgt atgctccata tcccaccaca cacatagatg tggatgtcaa   1140
tactgtgaag cagatgccac cctgtcatga acatatttat aatcagcgta gatacatgag   1200
atccgagctg acagccttct ggagagccac ttcagaagaa gacatggctc aggatacgat   1260
catctacact gacgaaagct ttactcctga tttgaatatt tttcaagatg tcttacacag   1320
agacactcta gtgaaagcct tcctggatca ggtctttcag ctgaaacctg gcttatctct   1380
cagaagtact ttccttgcac agtttctact tgtccttcac agaaaagcct tgacactaat   1440
aaaatatata gaagacgata cgcagaaggg aaaaaagccc tttaaatctc ttcggaacct   1500
gaagatagac cttgatttaa cagcagaggg cgatcttaac ataataatgg ctctggctga   1560
gaaaattaaa ccaggcctac actcttttat ctttggaaga cctttctaca ctagtgtgca   1620
agaacgagat gttctaatga ctttttaaat gtgtaactta ataagcctat tccatcacaa   1680
tcatgatcgc tggtaaagta gctcagtggt gtggggaaac gttcccctgg atcatactcc   1740
agaattctgc tctcagcaat tgcagttaag taagttacac tacagttctc acaagagcct   1800
gtgaggggat gtcaggtgca tcattacatt gggtgtctct tttcctagat ttatgctttt   1860
gggatacaga cctatgttta caatataata aatattattg ctatctttta aagatataat   1920
```

```
aataggatgt aaacttgacc acaactactg ttttttgaa atacatgatt catggtttac   1980
atgtgtcaag gtgaaatctg agttggcttt tacagatagt tgactttcta tcttttggca   2040
ttctttggtg tgtagaatta ctgtaatact tctgcaatca actgaaaact agagccttta   2100
aatgatttca attccacaga aagaaagtga gcttgaacat aggatgagct ttagaaagaa   2160
aattgatcaa gcagatgttt aattggaatt gattattaga tcctactttg tggatttagt   2220
ccctgggatt cagtctgtag aaatgtctaa tagttctcta tagtccttgt tcctggtgaa   2280
ccacagttag ggtgttttgt ttattttatt gttcttgcta ttgttgatat tctatgtagt   2340
tgagctctgt aaaaggaaat tgtattttat gttttagtaa ttgttgccaa ctttttaaat   2400
taattttcat tatttttgag ccaaattgaa atgtgcacct cctgtgcctt ttttctcctt   2460
agaaaatcta attacttgga acaagttcag atttcactgg tcagtcattt tcatcttgtt   2520
ttcttcttgc taagtcttac catgtacctg ctttggcaat cattgcaact ctgagattat   2580
aaaatgcctt agagaatata ctaactaata agatcttttt ttcagaaaca gaaaatagtt   2640
ccttgagtac ttccttcttg catttctgcc tatgtttttg aagttgttgc tgtttgcctg   2700
caataggcta taaggaatag caggagaaat tttactgaag tgctgttttc ctaggtgcta   2760
ctttggcaga gctaagttat cttttgtttt cttaatgcgt ttggaccatt ttgctggcta   2820
taaaataact gattaatata attctaacac aatgttgaca ttgtagttac acaaacacaa   2880
ataaatattt tatttaaaat tctggaagta atataaaagg gaaaatatat ttataagaaa   2940
gggataaagg taatagagcc cttctgcccc ccacccacca aatttacaca acaaaatgac   3000
atgttcgaat gtgaaaggtc ataatagctt tcccatcatg aatcagaaag atgtggacag   3060
cttgatgttt tagacaacca ctgaactaga tgactgttgt actgtagctc agtcatttaa   3120
aaaatatata aatactacct tgtagtgtcc catactgtgt tttttacatg gtagattctt   3180
atttaagtgc taactggtta ttttctttgg ctggtttatt gtactgttat acagaatgta   3240
agttgtacag tgaaataagt tattaaagca tgtgtaaaca ttgttatata tcttttctcc   3300
taaatggaga attttgaata aaatatattt gaaattttaa aaaaaaaaaa aaaaaa       3356
```

```
<210> SEQ ID NO 122
<211> LENGTH: 3339
<212> TYPE: DNA
<213> ORGANISM: Macaca fascicularis

<400> SEQUENCE: 122
```

```
acgtaaccta cggtgtcccg ctaggaaaga gaggcgcgtc aaacagcgac aagttccgcc     60
cacgtaaaag atgacgcttg gtgcgtcagc cgtccctgct gcccggttcc ttctctctgg    120
gggcggggcc tggctagagc aggtgtgggt ttaggagata tctcaggagc atttggataa    180
tgtgacagtt ggaatgcagt gatgtcgact ctttgcccac cgccatctcc agctgttgcc    240
aagacagaga ttgctttaag tggtgaatca cctttattag cagctacttt tgcttactgg    300
gacaatattc ttggtcctag agtaaggcac atttgggctc caaagacaga acaggtactt    360
ctcagtgacg gagaaataac ttttcttgcc aaccacactc taaatggaga aatccttcga    420
aatgcagaga gtggtgctat agatgtaaag ttttttgtct tgtctgaaaa gggagtgatt    480
attgtttcat taatctttga tggaaactgg aatggggatc gcagcacata cggactatca    540
attatacttc cacagacaga acttagtttc tacctcccac ttcatagagt gtgtgttgat    600
agattaacac atataatccg gaaaggaaga atatggatgc ataaggaaag acaagaaaat    660
```

-continued

```
gtccagaaga ttatcttaga aggcacagag agaatggaag atcagggtca gagtattatt     720
ccaatgctta ctggagaagt gattcctgta atggaactgc tttcatctat gaaatcacac     780
agtgttcctg aagaaataga tatagctgat acagtactca atgatgatga tattggtgac     840
agttgtcatg aaggctttct tctcaatgcc atcagctcac acttgcaaac ctgtggctgt     900
tccgttgtag taggtagcag tgcagagaaa gtaaataaga tagtcagaac attatgcctt     960
tttctgactg cagcagagag aaaatgctcc aggttatgtg aagcagaatc atcatttaaa    1020
tatgagtcag ggctctttgt acagggcctg ctaaaggatt caactggaag ctttgtgctg    1080
cctttccggc aagtcatgta tgctccatat cccaccacac acatagatgt ggatgtcaat    1140
actgtgaagc agatgccacc ctgtcatgaa catatttata atcagcgtag atacatgaga    1200
tccgagctga cagccttctg gagagccact tcagaagaag acatggctca ggatacgatc    1260
atctacactg acgaaagctt tactcctgat ttgaatattt ttcaagatgt cttacacaga    1320
gacactctag tgaaagcctt cctggatcag gtctttcagc tgaaacctgg cttatctctc    1380
aggagtactt tccttgcaca gtttttactt gtccttcaca gaaaagcctt gacactaata    1440
aaatatatag aagatgatac gcagaaggga aaaaagccct ttaaatctct tcggaacctg    1500
aagatagacc ttgatttaac agcagagggc gatcttaaca taataatggc tctggctgag    1560
aaaattaaac caggcctaca ctcttttatc tttggaagac ctttctacac tagtgtacaa    1620
gaacgagatg ttctaatgac tttttaaatg tgtaacttaa taagcctatt ccatcacaat    1680
cgtgatcgct gctaaagtag ctcggtggtg tggggaaaca ttcccctgga tcatactcca    1740
gagctctgct cggcagttgc agttaagtta gttacactac agttctcaca agagtctgtg    1800
aggggatgtc aggtgcatca ttacattgga tgtctctttt cctagattta tgcttttggg    1860
atacagacct atgtttacaa tataataggt attattgctg tcttttaaat atataataat    1920
aggatataaa cttgaccaca actgctgttt ttttgaaata tatgattcat ggtttacatg    1980
tattaaggtg aaatccgagt tcgcttttac agatattagt tgactttcta tcttttggca    2040
ttctttggtg tgtggaatta ctgtaatact tctgcaatca actgaaaatt agagccttta    2100
aatgatttca gttccacaga aagaaagtga gcttcaacat aggataagct ttagaaagag    2160
aattgatcaa gcagatgttt aattggaatt gattattaga tcctgctttg tggatttagc    2220
cctcgggatt cagtctgtag aaatgtctga tagttctcta tagtccctgc tcatggtgaa    2280
ccacagttag gatgttttgt ttgttttatt gttgttgcta ttgttgatgt tctatatagt    2340
tgagctctgt aaaaggaaat tgtattttat gttttagtag ttgttgccaa ctttttaaat    2400
taattttcat tatttttgag ccaaattgaa atgtgcacct cctgtgcctt ttttttcctt    2460
ggaaaatcga attacttgga agaagttcag atttcactgg tcagtcgttt tcatcttgtt    2520
ttcttcttgc agagtcttac catgtacctg ctttggcaat cattgtaact ctgagattat    2580
aaaatgcatt agagaatata ttaactaata agatcttttt tttcaggaac agaaaatagt    2640
tccttgagta cttccttctt acatttctgc ccatgttttt gaagttgttg ccatttgcct    2700
gcaataggct ataaggaata gcaggagaaa ttttactgaa gtgctatttt tctaggtgct    2760
actttggcag agctaagtgg tctgtttctt ttgtttcctt aatgcgtttg gaccattttg    2820
ctggctgtaa aataactgat taatataatt ctaacacaat attgacattg tagtgtacac    2880
aaacacaaat attttattta aaactggaag taacataaaa gggaaaatat atttataaga    2940
aaggaataaa ggtaatagag ctcttctgtc ccccagccac caaatttaca caacaaaatg    3000
atatgttcta atgtgaaagg tcataatagc tttcccatca ttaatcagaa agatgtggca    3060
```

-continued

```
gcttgatttt tcagacaacc cctgaactag atgactgttg tactgtagct cagtcattta   3120

aaaaatatat aaatactatc tcgtagtgtc ccatactatg tttttacat gatagattct   3180

tatttaagtg ctacctggtt attttctttg gctggtttat tgtactgtta tatagaatgt   3240

aagttgtaca gtgaaataag ttattaaagc atgtgtaaac attgttatat atcttttctc   3300

ctagatggag aattttgaat aaaatatatt tgaaatttt                          3339
```

```
<210> SEQ ID NO 123
<211> LENGTH: 3151
<212> TYPE: DNA
<213> ORGANISM: Mus musculus

<400> SEQUENCE: 123

gcggttgcgg tccctgcgcc ggcggtgaag gcgcagcagc ggcgagtggc tattgcaagc     60

gttcggataa tgtgagacct ggaatgcagt gagacctggg atgcagggat gtcgactatc    120

tgccccccac catctcctgc tgttgccaag acagagattg ctttaagtgg tgaatcaccc    180

ttgttggcgg ctacctttgc ttactgggat aatattcttg gtcctagagt aaggcatatt    240

tgggctccaa agacagacca agtgcttctc agtgatggag aaataacttt tcttgccaac    300

cacactctaa atggagaaat tcttcgaaat gcagagagtg gggctataga tgtaaaattt    360

tttgtcttat ctgaaaaagg ggtaattatt gtttcattaa tcttcgacgg aaactggaat    420

ggagatcgga gcacttatgg actatcaatt atactgccgc agacagagct gagcttctac    480

ctcccacttc acagagtgtg tgttgacagg ctaacacaca ttattcgaaa aggaagaata    540

tggatgcata aggaaagaca agaaaatgtc cagaaaattg tcttggaagg cacagagagg    600

atggaagatc agggtcagag tatcattccc atgcttactg ggaagtcat tcctgtaatg     660

gagctgcttg catctatgaa atcccacagt gttcctgaag acattgatat agctgataca    720

gtgctcaatg atgatgacat tggtgacagc tgtcacgaag gctttcttct caatgccatc    780

agctcacacc tgcagacctg tggctgttcc gttgtagttg gcagcagtgc agagaaagta    840

aataagatag taagaacgct gtgccttttt ctgacaccag cagagaggaa atgctccagg    900

ctgtgtgaag cagaatcgtc ctttaagtac gaatcgggac tctttgtgca aggcttgcta    960

aaggatgcaa caggcagttt tgtcctaccc ttccggcaag ttatgtatgc cccgtacccc   1020

accacgcaca ttgatgtgga tgtcaacact gtcaagcaga tgccaccgtg tcatgaacat   1080

atttataatc aacgcagata catgaggtca gagctgacag ccttctggag ggcaacttca   1140

gaagaggaca tggcgcagga caccatcatc tacacagatg agagcttcac tcctgatttg   1200

aatattttcc aagatgtctt acacagagac actctagtga aagccttcct ggatcaggtc   1260

ttccatttga agcctggcct gtctctcagg agtactttcc ttgcacagtt cctcctcatt   1320

cttcacagaa aagccttgac actaatcaag tacatcgagg atgatacgca gaaggggaaa   1380

aagcccttta agtctcttcg gaacctgaag atagatcttg atttaacagc agagggcgat   1440

cttaacataa taatggctct agctgagaaa attaagccag gcctacactc tttcatcttt   1500

gggagacctt tctacactag tgtacaagaa cgtgatgttc taatgacctt ttgaccgtgt   1560

ggtttgctgt gtctgtctct tcacagtcac acctgctgtt acagtgtctc agcagtgtgt   1620

gggcacatcc ttcctcccga gtcctgctgc aggacagggt acactacact tgtcagtaga   1680

agtctgtacc tgatgtcagg tgcatcgtta cagtgaatga ctcttcctag aatagatgta   1740

ctcttttagg gccttatgtt tacaattatc ctaagtacta ttgctgtctt ttaaagatat   1800
```

-continued

```
gaatgatgga atatacactt gaccataact gctgattggt tttttgtttt gttttgtttg   1860
ttttcttgga aacttatgat tcctggttta catgtaccac actgaaaccc tcgttagctt   1920
tacagataaa gtgtgagttg acttcctgcc cctctgtgtt ctgtggtatg tccgattact   1980
tctgccacag ctaaacatta gagcatttaa agtttgcagt tcctcagaaa ggaacttagt   2040
ctgactacag attagttctt gagagaagac actgataggg cagagctgta ggtgaaatca   2100
gttgttagcc cttcctttat agacgtagtc cttcagattc ggtctgtaca gaaatgccga   2160
ggggtcatgc atgggccctg agtatcgtga cctgtgacaa gtttttgtt ggtttattgt    2220
agttctgtca aagaaagtgg catttgtttt tataattgtt gccaactttt aaggttaatt   2280
ttcattattt ttgagccgaa ttaaaatgcg cacctcctgt gcctttccca atcttggaaa   2340
atataatttc ttggcagagg gtcagatttc agggcccagt cactttcatc tgaccaccct   2400
ttgcacggct gccgtgtgcc tggcttagat tagaagtcct tgttaagtat gtcagagtac   2460
attcgctgat aagatctttg aagagcaggg aagcgtcttg cctctttcct ttggtttctg   2520
cctgtactct ggtgtttccc gtgtcacctg catcatagga acagcagaga aatctgaccc   2580
agtgctattt ttctaggtgc tactatggca aactcaagtg gtctgtttct gttcctgtaa   2640
cgttcgacta tctcgctagc tgtgaagtac tgattagtgg agttctgtgc aacagcagtg   2700
taggagtata cacaaacaca aatatgtgtt tctatttaaa actgtggact tagcataaaa   2760
agggagaata tatttatttt ttacaaaagg gataaaaatg ggccccgttc ctcacccacc   2820
agatttagcg agaaaaagct ttctattctg aaaggtcacg gtggctttgg cattacaaat   2880
cagaacaaca cacactgacc atgatggctt gtgaactaac tgcaaggcac tccgtcatgg   2940
taagcgagta ggtcccacct cctagtgtgc cgctcattgc tttacacagt agaatcttat   3000
ttgagtgcta attgttgtct ttgctgcttt actgtgttgt tatagaaaat gtaagctgta   3060
cagtgaataa gttattgaag catgtgtaaa cactgttata tatcttttct cctagatggg   3120
gaattttgaa taaaatacct ttgaaattct g                                  3151
```

<210> SEQ ID NO 124
<211> LENGTH: 3435
<212> TYPE: DNA
<213> ORGANISM: Rattus norvegicus

<400> SEQUENCE: 124

```
cgtttgtagt gtcagccatc ccaattgcct gttccttctc tgtgggagtg gtgtctagac     60
agtccaggca gggtatgcta ggcaggtgcg ttttggttgc ctcagatcgc aacttgactc    120
cataacggtg accaaagaca aaagaaggaa accagattaa aaagaaccgg acacagaccc    180
ctgcagaatc tggagcggcc gtggttgggg gcggggctac gacggggcgg actcgggggc    240
gtgggagggc ggggccgggg cggggcccgg agccggctgc ggttgcggtc cctgcgccgg    300
cggtgaaggc gcagcggcgg cgagtggcta ttgcaagcgt ttggataatg tgagacctgg    360
gatgcaggga tgtcgactat ctgcccccca ccatctcctg ctgttgccaa gacagagatt    420
gctttaagtg gtgaatcacc cttgttggcg gctacctttg cttactggga taatattctt    480
ggtcctagag taaggcacat ttgggctcca aagacagacc aagtactcct cagtgatgga    540
gaaatcactt ttcttgccaa ccacactctg aatggagaaa ttcttcggaa tgcggagagt    600
ggggcaatag atgtaaagtt ttttgtctta tctgaaaagg gcgtcattat tgtttcatta    660
atcttcgacg ggaactggaa cggagatcgg agcacttacg gactatcaat tatactgccg    720
cagacggagc tgagtttcta cctcccactg cacagagtgt gtgttgacag gctaacgcac    780
```

```
atcattcgaa aaggaaggat atggatgcac aaggaaagac aagaaaatgt ccagaaaatt    840
gtcttggaag gcaccgagag gatggaagat cagggtcaga gtatcatccc tatgcttact    900
ggggaggtca tccctgtgat ggagctgctt gcgtctatga gatcacacag tgttcctgaa    960
gacctcgata tagctgatac agtactcaat gatgatgaca ttggtgacag ctgtcatgaa   1020
ggctttcttc tcaatgccat cagctcacat ctgcagacct gcggctgttc tgtggtggta   1080
ggcagcagtg cagagaaagt aaataagata gtaagaacac tgtgcctttt tctgacacca   1140
gcagagagga agtgctccag gctgtgtgaa gccgaatcgt cctttaaata cgaatctgga   1200
ctctttgtac aaggcttgct aaaggatgcg actggcagtt ttgtactacc tttccggcaa   1260
gttatgtatg ccccttatcc caccacacac atcgatgtgg atgtcaacac tgtcaagcag   1320
atgccaccgt gtcatgaaca tatttataat caacgcagat acatgaggtc agagctgaca   1380
gccttctgga gggcaacttc agaagaggac atggctcagg acaccatcat ctacacagat   1440
gagagcttca ctcctgattt gaatattttc caagatgtct tacacagaga cactctagtg   1500
aaagcctttc tggatcaggt cttccatttg aagcctggcc tgtctctcag gagtactttc   1560
cttgcacagt tcctcctcat tcttcacaga aaagccttga cactaatcaa gtacatagag   1620
gatgacacgc agaaggggaa aaagcccttt aagtctcttc ggaacctgaa gatagatctt   1680
gatttaacag cagagggcga ccttaacata ataatggctc tagctgagaa aattaagcca   1740
ggcctacact ctttcatctt cgggagacct ttctacacta gtgtccaaga acgtgatgtt   1800
ctaatgactt tttaaacatg tggtttgctc cgtgtgtctc atgacagtca cacttgctgt   1860
tacagtgtct cagcgctttg gacacatcct tcctccaggg tcctgccgca ggacacgtta   1920
cactacactt gtcagtagag gtctgtacca gatgtcaggt acatcgttgt agtgaatgtc   1980
tcttttccta gactagatgt accctcgtag ggacttatgt ttacaaccct cctaagtact   2040
agtgctgtct tgtaaggata cgaatgaagg gatgtaaact tcaccacaac tgctggttgg   2100
ttttgttgtt tttgtttttt gaaacttata attcatggtt tacatgcatc acactgaaac   2160
cctagttagc tttttacagg taagctgtga gttgactgcc tgtccctgtg ttctctggcc   2220
tgtacgatct gtggcgtgta ggatcacttt tgcaacaact aaaaactaaa gcactttgtt   2280
tgcagttcta cagaaagcaa cttagtctgt ctgcagattc gtttttgaaa gaagacatga   2340
gaaagcggag ttttaggtga agtcagttgt tggatcttcc tttatagact tagtccttta   2400
gatgtggtct gtatagacat gcccaaccat catgcatggg cactgaatat cgtgaactgt   2460
ggtatgcttt ttgttggttt attgtacttc tgtcaaagaa agtggcattg gtttttataa   2520
ttgttgccaa gttttaaggt taattttcat tatttttgag ccaaattaaa atgtgcacct   2580
cctgtgcctt tcccaatctt ggaaaatata atttcttggc agaaggtcag atttcagggc   2640
ccagtcactt tcgtctgact tccctttgca cagtccgcca tgggcctggc ttagaagttc   2700
ttgtaaacta tgccagagag tacattcgct gataaaatct tctttgcaga gcaggagagc   2760
ttcttgcctc tttcctttca tttctgcctg gactttggtg ttctccacgt tccctgcatc   2820
ctaaggacag caggagaact ctgaccccag tgctatttct ctaggtgcta ttgtggcaaa   2880
ctcaagcggt ccgtctctgt ccctgtaacg ttcgtacctt gctggctgtg aagtactgac   2940
tggtaaagct ccgtgctaca gcagtgtagg gtatacacaa acacaagtaa gtgttttatt   3000
taaaactgtg gacttagcat aaaaagggag actatattta ttttttacaa aagggataaa   3060
aatggaaccc tttcctcacc caccagattt agtcagaaaa aaacattcta ttctgaaagg   3120
```

```
tcacagtggt tttgacatga cacatcagaa caacgcacac tgtccatgat ggcttatgaa   3180

ctccaagtca ctccatcatg gtaaatgggt agatccctcc ttctagtgtg ccacaccatt   3240

gcttcccaca gtagaatctt atttaagtgc taagtgttgt ctctgctggt ttactctgtt   3300

gttttagaga atgtaagttg tatagtgaat aagttattga agcatgtgta aacactgtta   3360

tacatctttt ctcctagatg gggaatttgg aataaaatac ctttaaaatt caaaaaaaaa   3420

aaaaaaaaaa aaaaa                                                    3435
```

<210> SEQ ID NO 125
<211> LENGTH: 3356
<212> TYPE: DNA
<213> ORGANISM: Homo sapiens

<400> SEQUENCE: 125

```
ttttttttt ttttttttaa aatttcaaat atattttatt caaaattctc catttaggag     60

aaaagatata taacaatgtt tacacatgct ttaataactt atttcactgt acaacttaca    120

ttctgtataa cagtacaata aaccagccaa agaaaataac cagttagcac ttaaataaga    180

atctaccatg taaaaaacac agtatgggac actacaaggt agtatttata tattttttaa    240

atgactgagc tacagtacaa cagtcatcta gttcagtggt tgtctaaaac atcaagctgt    300

ccacatcttt ctgattcatg atgggaaagc tattatgacc tttcacattc gaacatgtca    360

ttttgttgtg taaatttggt gggtgggggg cagaagggct ctattacctt tatccctttc    420

ttataaatat attttccctt ttatattact tccagaattt taaataaaat atttatttgt    480

gtttgtgtaa ctacaatgtc aacattgtgt tagaattata ttaatcagtt attttatagc    540

cagcaaaatg gtccaaacgc attaagaaaa caaaagataa cttagctctg ccaaagtagc    600

acctaggaaa acagcacttc agtaaaattt ctcctgctat tccttatagc ctattgcagg    660

caaacagcaa caacttcaaa aacataggca gaaatgcaag aaggaagtac tcaaggaact    720

attttctgtt tctgaaaaaa agatcttatt agttagtata ttctctaagg cattttataa    780

tctcagagtt gcaatgattg ccaaagcagg tacatggtaa gacttagcaa gaagaaaaca    840

agatgaaaat gactgaccag tgaaatctga acttgttcca agtaattaga ttttctaagg    900

agaaaaaagg cacaggaggt gcacatttca atttggctca aaaataatga aaattaattt    960

aaaaagttgg caacaattac taaaacataa aatacaattt ccttttacag agctcaacta   1020

catagaatat caacaatagc aagaacaata aaataaacaa aacaccctaa ctgtggttca   1080

ccaggaacaa ggactataga gaactattag acatttctac agactgaatc ccagggacta   1140

aatccacaaa gtaggatcta ataatcaatt ccaattaaac atctgcttga tcaattttct   1200

ttctaaagct catcctatgt tcaagctcac tttctttctg tggaattgaa atcatttaaa   1260

ggctctagtt ttcagttgat tgcagaagta ttacagtaat tctacacacc aaagaatgcc   1320

aaaagataga aagtcaacta tctgtaaaag ccaactcaga tttcaccttg acacatgtaa   1380

accatgaatc atgtatttca aaaaaacagt agttgtggtc aagtttacat cctattatta   1440

tatctttaaa agatagcaat aatatttatt atattgtaaa cataggtctg tatcccaaaa   1500

gcataaatct aggaaaagag acacccaatg taatgatgca cctgacatcc cctcacaggc   1560

tcttgtgaga actgtagtgt aacttactta actgcaattg ctgagagcag aattctggag   1620

tatgatccag gggaacgttt ccccacacca ctgagctact ttaccagcga tcatgattgt   1680

gatggaatag gcttattaag ttacacattt aaaaagtcat tagaacatct cgttcttgca   1740

cactagtgta gaaaggtctt ccaaagataa aagagtgtag gcctggttta attttctcag   1800
```

```
ccagagccat tattatgtta agatcgccct ctgctgttaa atcaaggtct atcttcaggt   1860

tccgaagaga tttaaagggc ttttttccct tctgcgtatc gtcttctata tattttatta   1920

gtgtcaaggc ttttctgtga aggacaagta gaaactgtgc aaggaaagta cttctgagag   1980

ataagccagg tttcagctga aagacctgat ccaggaaggc tttcactaga gtgtctctgt   2040

gtaagacatc ttgaaaaata ttcaaatcag gagtaaagct ttcgtcagtg tagatgatcg   2100

tatcctgagc catgtcttct tctgaagtgg ctctccagaa ggctgtcagc tcggatctca   2160

tgtatctacg ctgattataa atatgttcat gacagggtgg catctgcttc acagtattga   2220

catccacatc tatgtgtgtg gtgggatatg gagcatacat gacttgccgg aaaggcagca   2280

caaagcttcc agttgaatcc tttagcaggc cttgtacaaa gagccctgac tcatatttaa   2340

atgatgattc tgcttcacat aacctggagc attttctctc tgctggagtc agaaaaaggc   2400

ataatgttct gactatctta tttactttct ctgcactgct acctactaca acggaacagc   2460

cacaggtttg caagtgtgag ctgatggcat tgagaagaaa gccttcatga cagctgtcac   2520

caatatcatc atcattgagt actgtatcag ctatatctat ttcttcagga acactgtgtg   2580

atttcataga tgaaagcagt tccattacag gaatcacttc tccagtaagc attggaataa   2640

tactctgacc ctgatcttcc attctctctg tgccttctaa gataatcttc tggacatttt   2700

cttgtctttc cttatgcatc catattcttc ctttccggat tatatgtgtt aatctatcaa   2760

cacacactct atgaagtggg aggtagaaac taagttctgt ctgtggaagt ataattgata   2820

gtccatatgt gctgcgatcc ccattccagt ttccatcaaa gattaatgaa acaataatca   2880

ctccctttc agacaagaca aaaaacttta catctatagc accactctct gcatttcgaa   2940

ggatttctcc atttagagtg tggttggcaa gaaaagttat ttctccatca ctgagaagta   3000

cctgttctgt ctttggagcc caaatgtgcc ttactctagg accaagaata ttgtcccagt   3060

aagcaaaagt agctgctaat aaaggtgatt tgccacttaa agcaatctct gtcttggcaa   3120

cagctggaga tggcggtggg caaagagtcg acatcactgc attccaactg tcacattatc   3180

caaatgctcc ggagatatct cctaaaccca cacctgctct tgctagaccc cgccccccaaa   3240

agagaagcaa ccgggcagca gggacggctg acacaccaag cgtcatcttt tacgtgggcg   3300

gaacttgtcg ctgtttgacg cacctctctt tcctagcggg acaccgtagg ttacgt       3356
```

<210> SEQ ID NO 126
<211> LENGTH: 3339
<212> TYPE: DNA
<213> ORGANISM: Macaca fascicularis

<400> SEQUENCE: 126

```
aaaatttcaa atatatttta ttcaaaattc tccatctagg agaaaagata tataacaatg     60

tttacacatg ctttaataac ttatttcact gtacaactta cattctatat aacagtacaa    120

taaaccagcc aaagaaaata accaggtagc acttaaataa gaatctatca tgtaaaaaac    180

atagtatggg acactacgag atagtattta tatatttttt aaatgactga gctacagtac    240

aacagtcatc tagttcaggg gttgtctgaa aaatcaagct gccacatctt tctgattaat    300

gatgggaaag ctattatgac ctttcacatt agaacatatc attttgttgt gtaaatttgg    360

tggctggggg acagaagagc tctattacct ttattccttt cttataaata tattttccct    420

tttatgttac ttccagtttt aaataaaata tttgtgtttg tgtacactac aatgtcaata    480

ttgtgttaga attatattaa tcagttattt tacagccagc aaaatggtcc aaacgcatta    540
```

aggaaacaaa agaaacagac cacttagctc tgccaaagta gcacctagaa aaatagcact 600
tcagtaaaat ttctcctgct attccttata gcctattgca ggcaaatggc aacaacttca 660
aaaacatggg cagaaatgta agaaggaagt actcaaggaa ctattttctg ttcctgaaaa 720
aaaagatctt attagttaat atattctcta atgcatttta taatctcaga gttacaatga 780
ttgccaaagc aggtacatgg taagactctg caagaagaaa acaagatgaa aacgactgac 840
cagtgaaatc tgaacttctt ccaagtaatt cgattttcca aggaaaaaaa aggcacagga 900
ggtgcacatt tcaatttggc tcaaaaataa tgaaaattaa tttaaaaagt tggcaacaac 960
tactaaaaca taaaatacaa tttcctttta cagagctcaa ctatatagaa catcaacaat 1020
agcaacaaca ataaaacaaa caaaacatcc taactgtggt tcaccatgag cagggactat 1080
agagaactat cagacatttc tacagactga atcccgaggg ctaaatccac aaagcaggat 1140
ctaataatca attccaatta aacatctgct tgatcaattc tctttctaaa gcttatccta 1200
tgttgaagct cactttcttt ctgtggaact gaaatcattt aaaggctcta attttcagtt 1260
gattgcagaa gtattacagt aattccacac accaaagaat gccaaaagat agaaagtcaa 1320
ctaatatctg taaaagcgaa ctcggatttc accttaatac atgtaaacca tgaatcatat 1380
atttcaaaaa aacagcagtt gtggtcaagt ttatatccta ttattatata tttaaaagac 1440
agcaataata cctattatat tgtaaacata ggtctgtatc ccaaaagcat aaatctagga 1500
aaagagacat ccaatgtaat gatgcacctg acatcccctc acagactctt gtgagaactg 1560
tagtgtaact aacttaactg caactgccga gcagagctct ggagtatgat ccaggggaat 1620
gtttccccac accaccgagc tactttagca gcgatcacga ttgtgatgga ataggcttat 1680
taagttacac atttaaaaag tcattagaac atctcgttct tgtacactag tgtagaaagg 1740
tcttccaaag ataaaagagt gtaggcctgg tttaattttc tcagccagag ccattattat 1800
gttaagatcg ccctctgctg ttaaatcaag gtctatcttc aggttccgaa gagatttaaa 1860
gggctttttt cccttctgcg tatcatcttc tatatatttt attagtgtca aggcttttct 1920
gtgaaggaca agtaaaaact gtgcaaggaa agtactcctg agagataagc caggtttcag 1980
ctgaaagacc tgatccagga aggctttcac tagagtgtct ctgtgtaaga catcttgaaa 2040
aatattcaaa tcaggagtaa agctttcgtc agtgtagatg atcgtatcct gagccatgtc 2100
ttcttctgaa gtggctctcc agaaggctgt cagctcggat ctcatgtatc tacgctgatt 2160
ataaatatgt tcatgacagg gtggcatctg cttcacagta ttgacatcca catctatgtg 2220
tgtggtggga tatggagcat acatgacttg ccggaaaggc agcacaaagc ttccagttga 2280
atcctttagc aggccctgta caaagagccc tgactcatat ttaaatgatg attctgcttc 2340
acataacctg gagcattttc tctctgctgc agtcagaaaa aggcataatg ttctgactat 2400
cttatttact ttctctgcac tgctacctac tacaacggaa cagccacagg tttgcaagtg 2460
tgagctgatg gcattgagaa gaaagccttc atgacaactg tcaccaatat catcatcatt 2520
gagtactgta tcagctatat ctatttcttc aggaacactg tgtgatttca tagatgaaag 2580
cagttccatt acaggaatca cttctccagt aagcattgga ataatactct gaccctgatc 2640
ttccattctc tctgtgcctt ctaagataat cttctggaca ttttcttgtc tttccttatg 2700
catccatatt cttcctttcc ggattatatg tgttaatcta tcaacacaca ctctatgaag 2760
tgggaggtag aaactaagtt ctgtctgtgg aagtataatt gatagtccgt atgtgctgcg 2820
atccccattc cagtttccat caaagattaa tgaaacaata atcactccct tttcagacaa 2880
gacaaaaaac tttacatcta tagcaccact ctctgcattt cgaaggattt ctccatttag 2940

```
agtgtggttg gcaagaaaag ttatttctcc gtcactgaga agtacctgtt ctgtctttgg   3000

agcccaaatg tgccttactc taggaccaag aatattgtcc cagtaagcaa aagtagctgc   3060

taataaaggt gattcaccac ttaaagcaat ctctgtcttg gcaacagctg gagatggcgg   3120

tgggcaaaga gtcgacatca ctgcattcca actgtcacat tatccaaatg ctcctgagat   3180

atctcctaaa cccacacctg ctctagccag gccccgcccc cagagagaag gaaccgggca   3240

gcagggacgg ctgacgcacc aagcgtcatc ttttacgtgg gcggaacttg tcgctgtttg   3300

acgcgcctct ctttcctagc gggacaccgt aggttacgt                          3339
```

<210> SEQ ID NO 127
<211> LENGTH: 3151
<212> TYPE: DNA
<213> ORGANISM: Mus musculus

<400> SEQUENCE: 127

```
cagaatttca aaggtatttt attcaaaatt ccccatctag gagaaaagat atataacagt     60

gtttacacat gcttcaataa cttattcact gtacagctta cattttctat aacaacacag    120

taaagcagca aagacaacaa ttagcactca aataagattc tactgtgtaa agcaatgagc    180

ggcacactag gaggtgggac ctactcgctt accatgacgg agtgccttgc agttagttca    240

caagccatca tggtcagtgt gtgttgttct gatttgtaat gccaaagcca ccgtgacctt    300

tcagaataga aagctttttc tcgctaaatc tggtgggtga ggaacggggc ccatttttat    360

cccttttgta aaaaataaat atattctccc tttttatgct aagtccacag ttttaaatag    420

aaacacatat ttgtgtttgt gtatactcct acactgctgt tgcacagaac tccactaatc    480

agtacttcac agctagcgag atagtcgaac gttacaggaa cagaaacaga ccacttgagt    540

ttgccatagt agcacctaga aaaatagcac tgggtcagat ttctctgctg ttcctatgat    600

gcaggtgaca cgggaaacac cagagtacag gcagaaacca aaggaaagag gcaagacgct    660

tccctgctct tcaaagatct tatcagcgaa tgtactctga catacttaac aaggacttct    720

aatctaagcc aggcacacgg cagccgtgca aagggtggtc agatgaaagt gactgggccc    780

tgaaatctga ccctctgcca agaaattata ttttccaaga ttgggaaagg cacaggaggt    840

gcgcatttta attcggctca aaaataatga aaattaacct taaaagttgg caacaattat    900

aaaaacaaat gccactttct ttgacagaac tacaataaac caacaaaaaa cttgtcacag    960

gtcacgatac tcagggccca tgcatgaccc ctcggcattt ctgtacagac cgaatctgaa   1020

ggactacgtc tataaaggaa gggctaacaa ctgatttcac ctacagctct gccctatcag   1080

tgtcttctct caagaactaa tctgtagtca gactaagttc ctttctgagg aactgcaaac   1140

tttaaatgct ctaatgttta gctgtggcag aagtaatcgg acataccaca gaacacagag   1200

gggcaggaag tcaactcaca ctttatctgt aaagctaacg agggtttcag tgtggtacat   1260

gtaaaccagg aatcataagt ttccaagaaa acaaacaaaa caaaacaaaa aaccaatcag   1320

cagttatggt caagtgtata ttccatcatt catatcttta aaagacagca atagtactta   1380

ggataattgt aaacataagg ccctaaaaga gtacatctat tctaggaaga gtcattcact   1440

gtaacgatgc acctgacatc aggtacagac ttctactgac aagtgtagtg taccctgtcc   1500

tgcagcagga ctcgggagga aggatgtgcc cacacactgc tgagacactg taacagcagg   1560

tgtgactgtg aagagacaga cacagcaaac cacacggtca aaaggtcatt agaacatcac   1620

gttcttgtac actagtgtag aaaggtctcc caaagatgaa agagtgtagg cctggcttaa   1680
```

```
ttttctcagc tagagccatt attatgttaa gatcgccctc tgctgttaaa tcaagatcta   1740

tcttcaggtt ccgaagagac ttaaagggct tttccccctt ctgcgtatca tcctcgatgt   1800

acttgattag tgtcaaggct tttctgtgaa gaatgaggag gaactgtgca aggaaagtac   1860

tcctgagaga caggccaggc ttcaaatgga agacctgatc caggaaggct ttcactagag   1920

tgtctctgtg taagacatct tggaaaatat tcaaatcagg agtgaagctc tcatctgtgt   1980

agatgatggt gtcctgcgcc atgtcctctt ctgaagttgc cctccagaag gctgtcagct   2040

ctgacctcat gtatctgcgt tgattataaa tatgttcatg acacggtggc atctgcttga   2100

cagtgttgac atccacatca atgtgcgtgg tggggtacgg ggcatacata acttgccgga   2160

agggtaggac aaaactgcct gttgcatcct ttagcaagcc ttgcacaaag agtcccgatt   2220

cgtacttaaa ggacgattct gcttcacaca gcctggagca tttcctctct gctggtgtca   2280

gaaaaaggca cagcgttctt actatcttat ttactttctc tgcactgctg ccaactacaa   2340

cggaacagcc acaggtctgc aggtgtgagc tgatggcatt gagaagaaag ccttcgtgac   2400

agctgtcacc aatgtcatca tcattgagca ctgtatcagc tatatcaatg tcttcaggaa   2460

cactgtggga tttcatagat gcaagcagct ccattacagg aatgacttcc ccagtaagca   2520

tgggaatgat actctgaccc tgatcttcca tcctctctgt gccttccaag acaattttct   2580

ggacattttc ttgtctttcc ttatgcatcc atattcttcc ttttcgaata atgtgtgtta   2640

gcctgtcaac acacactctg tgaagtggga ggtagaagct cagctctgtc tgcggcagta   2700

taattgatag tccataagtg ctccgatctc cattccagtt tccgtcgaag attaatgaaa   2760

caataattac cccttttca gataagacaa aaaattttac atctatagcc ccactctctg   2820

catttcgaag aatttctcca tttagagtgt ggttggcaag aaaagttatt tctccatcac   2880

tgagaagcac ttggtctgtc tttggagccc aaatatgcct tactctagga ccaagaatat   2940

tatcccagta agcaaaggta gccgccaaca agggtgattc accacttaaa gcaatctctg   3000

tcttggcaac agcaggagat ggtgggggc agatagtcga catccctgca tcccaggtct   3060

cactgcattc caggtctcac attatccgaa cgcttgcaat agccactcgc cgctgctgcg   3120

ccttcaccgc cggcgcaggg accgcaaccg c                                  3151
```

<210> SEQ ID NO 128
<211> LENGTH: 3435
<212> TYPE: DNA
<213> ORGANISM: Rattus norvegicus

<400> SEQUENCE: 128

```
tttttttttt tttttttttt ttttgaattt taaaggtatt ttattccaaa ttccccatct     60

aggagaaaag atgtataaca gtgtttacac atgcttcaat aacttattca ctatacaact    120

tacattctct aaaacaacag agtaaaccag cagagacaac acttagcact taaataagat    180

tctactgtgg gaagcaatgg tgtggcacac tagaaggagg gatctaccca tttaccatga    240

tggagtgact tggagttcat aagccatcat ggacagtgtg cgttgttctg atgtgtcatg    300

tcaaaaccac tgtgaccttt cagaatagaa tgttttttc tgactaaatc tggtgggtga    360

ggaaagggtt ccatttttat cccttttgta aaaaataaat atagtctccc tttttatgct    420

aagtccacag ttttaaataa aacacttact tgtgtttgtg tataccctac actgctgtag    480

cacggagctt taccagtcag tacttcacag ccagcaaggt acgaacgtta cagggacaga    540

gacggaccgc ttgagtttgc cacaatagca cctagagaaa tagcactggg gtcagagttc    600

tcctgctgtc cttaggatgc agggaacgtg gagaacacca aagtccaggc agaaatgaaa    660
```

-continued

```
ggaaagaggc aagaagctct cctgctctgc aaagaagatt ttatcagcga atgtactctc    720
tggcatagtt tacaagaact tctaagccag gcccatggcg gactgtgcaa agggaagtca    780
gacgaaagtg actgggccct gaaatctgac cttctgccaa gaaattatat tttccaagat    840
tgggaaaggc acaggaggtg cacattttaa tttggctcaa aaataatgaa aattaacctt    900
aaaacttggc aacaattata aaaaccaatg ccactttctt tgacagaagt acaataaacc    960
aacaaaaagc ataccacagt tcacgatatt cagtgcccat gcatgatggt tgggcatgtc   1020
tatacagacc acatctaaag gactaagtct ataaaggaag atccaacaac tgacttcacc   1080
taaaactccg ctttctcatg tcttctttca aaaacgaatc tgcagacaga ctaagttgct   1140
ttctgtagaa ctgcaaacaa agtgctttag tttttagttg ttgcaaaagt gatcctacac   1200
gccacagatc gtacaggcca gagaacacag ggacaggcag tcaactcaca gcttacctgt   1260
aaaaagctaa ctagggtttc agtgtgatgc atgtaaacca tgaattataa gtttcaaaaa   1320
acaaaaacaa caaaaccaac cagcagttgt ggtgaagttt acatcccttc attcgtatcc   1380
ttacaagaca gcactagtac ttaggagggt tgtaaacata agtccctacg agggtacatc   1440
tagtctagga aaagagacat tcactacaac gatgtacctg acatctggta cagacctcta   1500
ctgacaagtg tagtgtaacg tgtcctgcgg caggaccctg gaggaaggat gtgtccaaag   1560
cgctgagaca ctgtaacagc aagtgtgact gtcatgagac acacggagca aaccacatgt   1620
ttaaaaagtc attagaacat cacgttcttg gacactagtg tagaaaggtc tcccgaagat   1680
gaaagagtgt aggcctggct taattttctc agctagagcc attattatgt taaggtcgcc   1740
ctctgctgtt aaatcaagat ctatcttcag gttccgaaga gacttaaagg gctttttccc   1800
cttctgcgtg tcatcctcta tgtacttgat tagtgtcaag gcttttctgt gaagaatgag   1860
gaggaactgt gcaaggaaag tactcctgag agacaggcca ggcttcaaat ggaagacctg   1920
atccagaaag gctttcacta gagtgtctct gtgtaagaca tcttggaaaa tattcaaatc   1980
aggagtgaag ctctcatctg tgtagatgat ggtgtcctga gccatgtcct cttctgaagt   2040
tgccctccag aaggctgtca gctctgacct catgtatctg cgttgattat aaatatgttc   2100
atgacacggt ggcatctgct tgacagtgtt gacatccaca tcgatgtgtg tggtgggata   2160
aggggcatac ataacttgcc ggaaaggtag tacaaaactg ccagtcgcat cctttagcaa   2220
gccttgtaca aagagtccag attcgtattt aaaggacgat tcggcttcac acagcctgga   2280
gcacttcctc tctgctggtg tcagaaaaag gcacagtgtt cttactatct tatttacttt   2340
ctctgcactg ctgcctacca ccacagaaca gccgcaggtc tgcagatgtg agctgatggc   2400
attgagaaga aagccttcat gacagctgtc accaatgtca tcatcattga gtactgtatc   2460
agctatatcg aggtcttcag gaacactgtg tgatctcata gacgcaagca gctccatcac   2520
agggatgacc tccccagtaa gcatagggat gatactctga ccctgatctt ccatcctctc   2580
ggtgccttcc aagacaattt tctggacatt ttcttgtctt tccttgtgca tccatatcct   2640
tccttttcga atgatgtgcg ttagcctgtc aacacacact ctgtgcagtg ggaggtagaa   2700
actcagctcc gtctgcggca gtataattga tagtccgtaa gtgctccgat ctccgttcca   2760
gttcccgtcg aagattaatg aaacaataat gacgcccttt tcagataaga caaaaaactt   2820
tacatctatt gccccactct ccgcattccg aagaatttct ccattcagag tgtggttggc   2880
aagaaaagtg atttctccat cactgaggag tacttggtct gtctttggag cccaaatgtg   2940
ccttactcta ggaccaagaa tattatccca gtaagcaaag gtagccgcca acaagggtga   3000
```

-continued

```
ttcaccactt aaagcaatct ctgtcttggc aacagcagga gatggtgggg ggcagatagt   3060

cgacatccct gcatcccagg tctcacatta tccaaacgct tgcaatagcc actcgccgcc   3120

gctgcgcctt caccgccggc gcagggaccg caaccgcagc cggctccggg ccccgccccg   3180

gccccgccct cccacgcccc cgagtccgcc ccgtcgtagc cccgccccca accacggccg   3240

ctccagattc tgcaggggtc tgtgtccggt tctttttaat ctggtttcct tcttttgtct   3300

ttggtcaccg ttatggagtc aagttgcgat ctgaggcaac caaaacgcac ctgcctagca   3360

taccctgcct ggactgtcta gacaccactc ccacagagaa ggaacaggca attgggatgg   3420

ctgacactac aaacg                                                    3435
```

```
<210> SEQ ID NO 129
<211> LENGTH: 1957
<212> TYPE: DNA
<213> ORGANISM: Homo sapiens

<400> SEQUENCE: 129

acgtaaccta cggtgtcccg ctaggaaaga gaggtgcgtc aaacagcgac aagttccgcc     60

cacgtaaaag atgacgcttg atatctccgg agcatttgga taatgtgaca gttggaatgc    120

agtgatgtcg actctttgcc caccgccatc tccagctgtt gccaagacag agattgcttt    180

aagtggcaaa tcacctttat tagcagctac ttttgcttac tgggacaata ttcttggtcc    240

tagagtaagg cacatttggg ctccaaagac agaacaggta cttctcagtg atggagaaat    300

aacttttctt gccaaccaca ctctaaatgg agaaatcctt cgaaatgcag agagtggtgc    360

tatagatgta aagtttttg tcttgtctga aaagggagtg attattgttt cattaatctt    420

tgatggaaac tggaatgggg atcgcagcac atatggacta tcaattatac ttccacagac    480

agaacttagt ttctacctcc cacttcatag agtgtgtgtt gatagattaa cacatataat    540

ccggaaagga agaatatgga tgcataagga aagacaagaa aatgtccaga agattatctt    600

agaaggcaca gagagaatgg aagatcaggg tcagagtatt attccaatgc ttactggaga    660

agtgattcct gtaatggaac tgctttcatc tatgaaatca cacagtgttc ctgaagaaat    720

agatatagct gatacagtac tcaatgatga tgatattggt gacagctgtc atgaaggctt    780

tcttctcaag taagaatttt tcttttcata aaagctggat gaagcagata ccatcttatg    840

ctcacctatg acaagatttg gaagaaagaa aataacagac tgtctactta gattgttcta    900

gggacattac gtatttgaac tgttgcttaa atttgtgtta tttttcactc attatatttc    960

tatatatatt tggtgttatt ccatttgcta tttaaagaaa ccgagtttcc atcccagaca   1020

agaaatcatg gccccttgct tgattctggt ttcttgtttt acttctcatt aaagctaaca   1080

gaatcctttc atattaagtt gtactgtaga tgaacttaag ttatttaggc gtagaacaaa   1140

attattcata tttatactga tctttttcca tccagcagtg gagtttagta cttaagagtt   1200

tgtgccctta aaccagactc cctggattaa tgctgtgtac ccgtgggcaa ggtgcctgaa   1260

ttctctatac acctatttcc tcatctgtaa aatggcaata atagtaatag tacctaatgt   1320

gtagggttgt tataagcatt gagtaagata aataatataa agcacttaga acagtgcctg   1380

gaacataaaa acacttaata atagctcata gctaacattt cctatttaca tttcttctag   1440

aaatagccag tatttgttga gtgcctacat gttagttcct ttactagttg ctttacatgt   1500

attatcttat attctgtttt aaagtttctt cacagttaca gattttcatg aaattttact   1560

tttaataaaa gagaagtaaa agtataaagt attcactttt atgttcacag tcttttcctt   1620

taggctcatg atggagtatc agaggcatga gtgtgtttaa cctaagagcc ttaatggctt   1680
```

gaatcagaag cactttagtc ctgtatctgt tcagtgtcag cctttcatac atcattttaa 1740
atcccatttg actttaagta agtcacttaa tctctctaca tgtcaatttc ttcagctata 1800
aaatgatggt atttcaataa ataaatacat taattaaatg atattatact gactaattgg 1860
gctgttttaa ggctcaataa gaaaatttct gtgaaaggtc tctagaaaat gtaggttcct 1920
atacaaataa aagataacat tgtgcttata aaaaaaa 1957

<210> SEQ ID NO 130
<211> LENGTH: 1957
<212> TYPE: DNA
<213> ORGANISM: Homo sapiens

<400> SEQUENCE: 130
ttttttttat aagcacaatg ttatctttta tttgtatagg aacctacatt ttctagagac 60
ctttcacaga aattttctta ttgagcctta aaacagccca attagtcagt ataatatcat 120
ttaattaatg tatttattta ttgaaatacc atcattttat agctgaagaa attgacatgt 180
agagagatta agtgacttac ttaaagtcaa atgggattta aaatgatgta tgaaaggctg 240
acactgaaca gatacaggac taaagtgctt ctgattcaag ccattaaggc tcttaggtta 300
aacacactca tgcctctgat actccatcat gagcctaaag gaaaagactg tgaacataaa 360
agtgaatact ttatactttt acttctcttt tattaaaagt aaaatttcat gaaaatctgt 420
aactgtgaag aaactttaaa acagaatata agataataca tgtaaagcaa ctagtaaagg 480
aactaacatg taggcactca acaaatactg gctatttcta gaagaaatgt aaataggaaa 540
tgttagctat gagctattat taagtgtttt tatgttccag gcactgttct aagtgcttta 600
tattatttat cttactcaat gcttataaca accctacaca ttaggtacta ttactattat 660
tgccatttta cagatgagga aataggtgta tagagaattc aggcaccttg cccacgggta 720
cacagcatta atccagggag tctggtttaa gggcacaaac tcttaagtac taaactccac 780
tgctggatgg aaaaagatca gtataaatat gaataatttt gttctacgcc taaataactt 840
aagttcatct acagtacaac ttaatatgaa aggattctgt tagctttaat gagaagtaaa 900
acaagaaacc agaatcaagc aaggggccat gatttcttgt ctgggatgga aactcggttt 960
ctttaaatag caaatggaat aacaccaaat atatatagaa atataatgag tgaaaaataa 1020
cacaaattta agcaacagtt caaatacgta atgtccctag aacaatctaa gtagacagtc 1080 tgttatttc tttcttccaa atcttgtcat aggtgagcat aagatggtat ctgcttcatc 1140
cagcttttat gaaaagaaaa attcttactt gagaagaaag ccttcatgac agctgtcacc 1200
aatatcatca tcattgagta ctgtatcagc tatatctatt tcttcaggaa cactgtgtga 1260
tttcatagat gaaagcagtt ccattacagg aatcacttct ccagtaagca ttggaataat 1320
actctgaccc tgatcttcca ttctctctgt gccttctaag ataatcttct ggacattttc 1380
ttgtctttcc ttatgcatcc atattcttcc tttccggatt atatgtgtta atctatcaac 1440
acacactcta tgaagtggga ggtagaaact aagttctgtc tgtggaagta taattgatag 1500
tccatatgtg ctgcgatccc cattccagtt tccatcaaag attaatgaaa caataatcac 1560 tccctttca gacaagacaa aaaactttac atctatagca ccactctctg catttcgaag 1620
gatttctcca tttagagtgt ggttggcaag aaaagttatt tctccatcac tgagaagtac 1680
ctgttctgtc tttggagccc aaatgtgcct tactctagga ccaagaatat tgtcccagta 1740
agcaaaagta gctgctaata aaggtgattt gccacttaaa gcaatctctg tcttggcaac 1800
agctggagat ggcggtgggc aaagagtcga catcactgca ttccaactgt cacattatcc 1860
aaatgctccg gagatatcaa gcgtcatctt ttacgtgggc ggaacttgtc gctgtttgac 1920
gcacctctct ttcctagcgg gacaccgtag gttacgt 1957

<210> SEQ ID NO 131
<211> LENGTH: 3231
<212> TYPE: DNA
<213> ORGANISM: Homo sapiens

<400> SEQUENCE: 131
ggttgcggtg cctgcgcccg cggcggcgga ggcgcaggcg gtggcgagtg gatatctccg 60
gagcatttgg ataatgtgac agttggaatg cagtgatgtc gactctttgc ccaccgccat 120
ctccagctgt tgccaagaca gagattgctt taagtggcaa atcaccttta ttagcagcta 180
cttttgctta ctgggacaat attcttggtc ctagagtaag gcacatttgg gctccaaaga 240
cagaacaggt acttctcagt gatggagaaa taacttttct tgccaaccac actctaaatg 300
gagaaatcct tcgaaatgca gagagtggtg ctatagatgt aaagtttttt gtcttgtctg 360
aaaagggagt gattattgtt tcattaatct ttgatggaaa ctggaatggg gatcgcagca 420
catatggact atcaattata cttccacaga cagaacttag tttctacctc ccacttcata 480
gagtgtgtgt tgatagatta acacatataa tccggaaagg aagaatatgg atgcataagg 540
aaagacaaga aaatgtccag aagattatct tagaaggcac agagagaatg gaagatcagg 600
gtcagagtat tattccaatg cttactggag aagtgattcc tgtaatggaa ctgctttcat 660
ctatgaaatc acacagtgtt cctgaagaaa tagatatagc tgatacagta ctcaatgatg 720
atgatattgg tgacagctgt catgaaggct ttcttctcaa tgccatcagc tcacacttgc 780
aaacctgtgg ctgttccgtt gtagtaggta gcagtgcaga gaaagtaaat aagatagtca 840
gaacattatg cctttttctg actccagcag agagaaaatg ctccaggtta tgtgaagcag 900
aatcatcatt taaatatgag tcagggctct ttgtacaagg cctgctaaag gattcaactg 960
gaagctttgt gctgcctttc cggcaagtca tgtatgctcc atatcccacc acacacatag 1020
atgtggatgt caatactgtg aagcagatgc caccctgtca tgaacatatt tataatcagc 1080
gtagatacat gagatccgag ctgacagcct tctggagagc cacttcagaa gaagacatgg 1140
ctcaggatac gatcatctac actgacgaaa gctttactcc tgatttgaat atttttcaag 1200
atgtcttaca cagagacact ctagtgaaag ccttcctgga tcaggtcttt cagctgaaac 1260
ctggcttatc tctcagaagt actttccttg cacagtttct acttgtcctt cacagaaaag 1320
ccttgacact aataaaatat atagaagacg atacgcagaa gggaaaaaag ccctttaaat 1380
ctcttcggaa cctgaagata gaccttgatt taacagcaga gggcgatctt aacataataa 1440
tggctctggc tgagaaaatt aaaccaggcc tacactcttt tatctttgga agacctttct 1500
acactagtgt gcaagaacga gatgttctaa tgactttta aatgtgtaac ttaataagcc 1560
tattccatca caatcatgat cgctggtaaa gtagctcagt ggtgtgggga aacgttcccc 1620
tggatcatac tccagaattc tgctctcagc aattgcagtt aagtaagtta cactacagtt 1680
ctcacaagag cctgtgaggg gatgtcaggt gcatcattac attgggtgtc tcttttccta 1740
gatttatgct tttgggatac agacctatgt ttacaatata ataaatatta ttgctatctt 1800
ttaaagatat aataatagga tgtaaacttg accacaacta ctgttttttt gaaatacatg 1860
attcatggtt tacatgtgtc aaggtgaaat ctgagttggc ttttacagat agttgacttt 1920
ctatcttttg gcattctttg gtgtgtagaa ttactgtaat acttctgcaa tcaactgaaa 1980

-continued

```
actagagcct ttaaatgatt tcaattccac agaaagaaag tgagcttgaa cataggatga   2040

gctttagaaa gaaaattgat caagcagatg tttaattgga attgattatt agatcctact   2100

ttgtggattt agtccctggg attcagtctg tagaaatgtc taatagttct ctatagtcct   2160

tgttcctggt gaaccacagt tagggtgttt tgtttatttt attgttcttg ctattgttga   2220

tattctatgt agttgagctc tgtaaaagga aattgtattt tatgttttag taattgttgc   2280

caacttttta aattaatttt cattattttt gagccaaatt gaaatgtgca cctcctgtgc   2340

ctttttctc cttagaaaat ctaattactt ggaacaagtt cagatttcac tggtcagtca   2400

ttttcatctt gttttcttct tgctaagtct taccatgtac ctgctttggc aatcattgca   2460

actctgagat tataaaatgc cttagagaat atactaacta ataagatctt tttttcagaa   2520

acagaaaata gttccttgag tacttccttc ttgcatttct gcctatgttt ttgaagttgt   2580

tgctgtttgc ctgcaatagg ctataaggaa tagcaggaga aattttactg aagtgctgtt   2640

ttcctaggtg ctactttggc agagctaagt tatcttttgt tttcttaatg cgtttggacc   2700

attttgctgg ctataaaata actgattaat ataattctaa cacaatgttg acattgtagt   2760

tacacaaaca caaataaata ttttatttaa aattctggaa gtaatataaa agggaaaata   2820

tatttataag aaagggataa aggtaataga gcccttctgc cccccaccca ccaaatttac   2880

acaacaaaat gacatgttcg aatgtgaaag gtcataatag ctttcccatc atgaatcaga   2940

aagatgtgga cagcttgatg ttttagacaa ccactgaact agatgactgt tgtactgtag   3000

ctcagtcatt taaaaaatat ataaatacta ccttgtagtg tcccatactg tgtttttttac   3060

atggtagatt cttatttaag tgctaactgg ttattttctt tggctggttt attgtactgt   3120

tatacagaat gtaagttgta cagtgaaata agttattaaa gcatgtgtaa acattgttat   3180

atatcttttc tcctaaatgg agaattttga ataaaatata tttgaaattt t            3231
```

<210> SEQ ID NO 132
<211> LENGTH: 3231
<212> TYPE: DNA
<213> ORGANISM: Homo sapiens

<400> SEQUENCE: 132

```
aaaatttcaa atatatttta ttcaaaattc tccatttagg agaaaagata tataacaatg     60

tttacacatg ctttaataac ttatttcact gtacaactta cattctgtat aacagtacaa    120

taaaccagcc aaagaaaata accagttagc acttaaataa gaatctacca tgtaaaaaac    180

acagtatggg acactacaag gtagtattta tatatttttt aaatgactga gctacagtac    240

aacagtcatc tagttcagtg gttgtctaaa acatcaagct gtccacatct ttctgattca    300

tgatgggaaa gctattatga cctttcacat tcgaacatgt cattttgttg tgtaaatttg    360

gtgggtgggg ggcagaaggg ctctattacc tttatccctt tcttataaat atattttccc    420

ttttatatta cttccagaat tttaaataaa atatttattt gtgtttgtgt aactacaatg    480

tcaacattgt gttagaatta tattaatcag ttattttata gccagcaaaa tggtccaaac    540

gcattaagaa aacaaaagat aacttagctc tgccaaagta gcacctagga aaacagcact    600

tcagtaaaat ttctcctgct attccttata gcctattgca ggcaaacagc aacaacttca    660

aaaacatagg cagaaatgca agaaggaagt actcaaggaa ctattttctg tttctgaaaa    720

aaagatctta ttagttagta tattctctaa ggcattttat aatctcagag ttgcaatgat    780

tgccaaagca ggtacatggt aagacttagc aagaagaaaa caagatgaaa atgactgacc    840
```

-continued

```
agtgaaatct gaacttgttc caagtaatta gattttctaa ggagaaaaaa ggcacaggag    900
gtgcacattt caatttggct caaaaataat gaaaattaat ttaaaaagtt ggcaacaatt    960
actaaaacat aaaatacaat ttccttttac agagctcaac tacatagaat atcaacaata   1020
gcaagaacaa taaaataaac aaaacaccct aactgtggtt caccaggaac aaggactata   1080
gagaactatt agacatttct acagactgaa tcccagggac taaatccaca aagtaggatc   1140
taataatcaa ttccaattaa acatctgctt gatcaatttt ctttctaaag ctcatcctat   1200
gttcaagctc actttctttc tgtggaattg aaatcattta aaggctctag ttttcagttg   1260
attgcagaag tattacagta attctacaca ccaaagaatg ccaaaagata gaaagtcaac   1320
tatctgtaaa agccaactca gatttcacct tgacacatgt aaaccatgaa tcatgtattt   1380
caaaaaaaca gtagttgtgg tcaagtttac atcctattat tatatcttta aaagatagca   1440
ataatattta ttatattgta aacataggtc tgtatcccaa aagcataaat ctaggaaaag   1500
agacacccaa tgtaatgatg cacctgacat cccctcacag gctcttgtga gaactgtagt   1560
gtaacttact taactgcaat tgctgagagc agaattctgg agtatgatcc aggggaacgt   1620
ttccccacac cactgagcta ctttaccagc gatcatgatt gtgatggaat aggcttatta   1680
agttacacat ttaaaaagtc attagaacat ctcgttcttg cacactagtg tagaaaggtc   1740
ttccaaagat aaaagagtgt aggcctggtt taattttctc agccagagcc attattatgt   1800
taagatcgcc ctctgctgtt aaatcaaggt ctatcttcag gttccgaaga gatttaaagg   1860
gctttttcc cttctgcgta tcgtcttcta tatattttat tagtgtcaag gcttttctgt   1920
gaaggacaag tagaaactgt gcaaggaaag tacttctgag agataagcca ggtttcagct   1980
gaaagacctg atccaggaag gctttcacta gagtgtctct gtgtaagaca tcttgaaaaa   2040
tattcaaatc aggagtaaag ctttcgtcag tgtagatgat cgtatcctga gccatgtctt   2100
cttctgaagt ggctctccag aaggctgtca gctcggatct catgtatcta cgctgattat   2160
aaatatgttc atgacagggt ggcatctgct tcacagtatt gacatccaca tctatgtgtg   2220
tggtgggata tggagcatac atgacttgcc ggaaaggcag cacaaagctt ccagttgaat   2280
cctttagcag gccttgtaca aagagccctg actcatattt aaatgatgat tctgcttcac   2340
ataacctgga gcattttctc tctgctggag tcagaaaaag gcataatgtt ctgactatct   2400
tatttacttt ctctgcactg ctacctacta caacggaaca gccacaggtt tgcaagtgtg   2460
agctgatggc attgagaaga aagccttcat gacagctgtc accaatatca tcatcattga   2520
gtactgtatc agctatatct atttcttcag gaacactgtg tgatttcata gatgaaagca   2580
gttccattac aggaatcact tctccagtaa gcattggaat aatactctga ccctgatctt   2640
ccattctctc tgtgccttct aagataatct tctggacatt ttcttgtctt tccttatgca   2700
tccatattct tcctttccgg attatatgtg ttaatctatc aacacacact ctatgaagtg   2760
ggaggtagaa actaagttct gtctgtggaa gtataattga tagtccatat gtgctgcgat   2820
ccccattcca gtttccatca aagattaatg aaacaataat cactcccttt tcagacaaga   2880
caaaaaactt tacatctata gcaccactct ctgcatttcg aaggatttct ccatttagag   2940
tgtggttggc aagaaaagtt atttctccat cactgagaag tacctgttct gtctttggag   3000
cccaaatgtg ccttactcta ggaccaagaa tattgtccca gtaagcaaaa gtagctgcta   3060
ataaaggtga tttgccactt aaagcaatct ctgtcttggc aacagctgga gatggcggtg   3120
ggcaaagagt cgacatcact gcattccaac tgtcacatta tccaaatgct ccggagatat   3180
ccactcgcca ccgcctgcgc ctccgccgcc gcgggcgcag gcaccgcaac c            3231
```

<210> SEQ ID NO 133
<211> LENGTH: 27321
<212> TYPE: DNA
<213> ORGANISM: Homo sapiens

<400> SEQUENCE: 133
acgtaaccta cggtgtcccg ctaggaaaga gaggtgcgtc aaacagcgac aagttccgcc 60
cacgtaaaag atgacgcttg gtgtgtcagc cgtccctgct gcccggttgc ttctcttttg 120
ggggcggggt ctagcaagag caggtgtggg tttaggaggt gtgtgttttt gtttttccca 180
ccctctctcc ccactacttg ctctcacagt actcgctgag ggtgaacaag aaaagacctg 240
ataaagatta accagaagaa aacaaggagg gaaacaaccg cagcctgtag caagctctgg 300
aactcaggag tcgcgcgcta ggggccgggg ccggggccgg ggcgtggtcg gggcgggccc 360
gggggcgggc ccggggcggg gctgcggttg cggtgcctgc gcccgcggcg gcggaggcgc 420
aggcggtggc gagtgggtga gtgaggaggc ggcatcctgg cgggtggctg tttggggttc 480
ggctgccggg aagaggcgcg ggtagaagcg gggggctctcc tcagagctcg acgcattttt 540
actttccctc tcatttctct gaccgaagct gggtgtcggg ctttcgcctc tagcgactgg 600
tggaattgcc tgcatccggg ccccgggctt cccggcggcg gcggcggcgg cggcggcgca 660
gggacaaggg atggggatct ggcctcttcc ttgctttccc gccctcagta cccgagctgt 720
ctccttcccg gggacccgct gggagcgctg ccgctgcggg ctcgagaaaa gggagcctcg 780
ggtactgaga ggcctcgcct gggggaaggc cggagggtgg gcggcgcgcg gcttctgcgg 840
accaagtcgg ggttcgctag gaacccgaga cggtccctgc cggcgaggag atcatgcggg 900
atgagatggg ggtgtggaga cgcctgcaca atttcagccc aagcttctag agagtggtga 960
tgacttgcat atgagggcag caatgcaagt cggtgtgctc cccattctgt gggacatgac 1020
ctggttgctt cacagctccg agatgacaca gacttgctta aaggaagtga ctattgtgac 1080
ttgggcatca cttgactgat ggtaatcagt tgtctaaaga agtgcacaga ttacatgtcc 1140
gtgtgctcat tgggtctatc tggccgcgtt gaacaccacc aggctttgta ttcagaaaca 1200
ggagggaggt cctgcacttt cccaggaggg gtggcccttt cagatgcaat cgagattgtt 1260
aggctctggg agagtagttg cctggttgtg gcagttggta aatttctatt caaacagttg 1320
ccatgcacca gttgttcaca acaagggtac gtaatctgtc tggcattact tctacttttg 1380
tacaaaggat caaaaaaaaa aaagatactg ttaagatatg atttttctca gactttggga 1440
aacttttaac ataatctgtg aatatcacag aaacaagact atcatatagg ggatattaat 1500
aacctggagt cagaatactt gaaatacggt gtcatttgac acgggcattg ttgtcaccac 1560
ctctgccaag gcctgccact ttaggaaaac cctgaatcag ttggaaactg ctacatgctg 1620
atagtacatc tgaaacaaga acgagagtaa ttaccacatt ccagattgtt cactaagcca 1680
gcatttacct gctccaggaa aaaattacaa gcaccttatg aagttgataa aatattttgt 1740
ttggctatgt tggcactcca caatttgctt tcagagaaac aaagtaaacc aaggaggact 1800
tctgtttttc aagtctgccc tcgggttcta ttctacgtta attagatagt tcccaggagg 1860
actaggttag cctacctatt gtctgagaaa cttggaactg tgagaaatgg ccagatagtg 1920
atatgaactt caccttccag tcttccctga tgttgaagat tgagaaagtg ttgtgaactt 1980
tctggtactg taaacagttc actgtccttg aagtggtcct gggcagctcc tgttgtggaa 2040
agtggacggt ttaggatcct gcttctcttt gggctgggag aaaataaaca gcatggttac 2100

```
aagtattgag agccaggttg gagaaggtgg cttacacctg taatgccaga gctttgggag   2160
gcggaggcaa gaggatcact tgaagccagg agttcaagct caacctgggc aacgtagacc   2220
ctgtctctac aaaaaattaa aaacttagcc gggcgtggtg atgtgcacct gtagtcctag   2280
ctacttggga ggctgaggca ggagggtcat ttgagcccaa gagtttgaag ttaccgagag   2340
ctatgatcct gccagtgcat tccagcctgg atgacaaaac gagaccctgt ctctaaaaaa   2400
caagaagtga gggctttatg attgtagaat tttcactaca atagcagtgg accaaccacc   2460
tttctaaata ccaatcaggg aagagatggt tgattttta acagacgttt aaagaaaaag   2520
caaaacctca aacttagcac tctactaaca gttttagcag atgttaatta atgtaatcat   2580
gtctgcatgt atgggattat ttccagaaag tgtattggga aacctctcat gaaccctgtg   2640
agcaagccac cgtctcactc aatttgaatc ttggcttccc tcaaaagact ggctaatgtt   2700
tggtaactct ctggagtaga cagcactaca tgtacgtaag ataggtacat aaacaactat   2760
tggttttgag ctgatttttt tcagctgcat ttgcatgtat ggatttttct caccaaagac   2820
gatgacttca agtattagta aaataattgt acagctctcc tgattatact tctctgtgac   2880
atttcatttc ccaggctatt tcttttggta ggatttaaaa ctaagcaatt cagtatgatc   2940
tttgtccttc attttctttc ttattctttt tgtttgtttg tttgtttgtt tttttcttga   3000
ggcagagtct ctctctgtcg cccaggctgg agtgcagtgg cgccatctca gctcattgca   3060
acctctgcca cctccgggtt caagagattc tcctgcctca gcctcccgag tagctgggat   3120
tacaggtgtc caccaccaca cccggctaat tttttgtatt tttagtagag gtggggtttc   3180
accatgttgg ccaggctggt cttgagctcc tgacctcagg tgatccacct gcctcggcct   3240
accaaagagc tgggataaca ggtgtgaccc accatgcccg gcccattttt tttttcttat   3300
tctgttagga gtgagagtgt aactagcagt ataatagttc aattttcaca acgtggtaaa   3360
agtttcccta taattcaatc agattttgct ccagggttca gttctgtttt aggaaatact   3420
tttattttca gtttaatgat gaaatattag agttgtaata ttgcctttat gattatccac   3480
ctttttaacc taaaagaatg aaagaaaaat atgtttgcaa tataatttta tggttgtatg   3540
ttaacttaat tcattatgtt ggcctccagt ttgctgttgt tagttatgac agcagtagtg   3600
tcattaccat ttcaattcag attacattcc tatatttgat cattgtaaac tgactgctta   3660
cattgtatta aaaacagtgg atattttaaa gaagctgtac ggcttatatc tagtgctgtc   3720
tcttaagact attaaattga tacaacatat ttaaaagtaa atattaccta aatgaatttt   3780
tgaaattaca aatacacgtg ttaaaactgt cgttgtgttc aaccatttct gtacatactt   3840
agagttaact gttttgccag gctctgtatg cctactcata atatgataaa agcactcatc   3900
taatgctctg taaatagaag tcagtgcttt ccatcagact gaactctctt gacaagatgt   3960
ggatgaaatt ctttaagtaa aattgtttac tttgtcatac atttacagat caaatgttag   4020
ctcccaaagc aatcatatgg caaagatagg tatatcatag tttgcctatt agctgctttg   4080
tattgctatt attataaata gacttcacag ttttagactt gcttaggtga aattgcaatt   4140
ctttttactt tcagtcttag ataacaagtc ttcaattata gtacaatcac acattgctta   4200
ggaatgcatc attaggcgat tttgtcatta tgcaaacatc atagagtgta cttacacaaa   4260
cctagatagt atagccttta tgtacctagg ccgtatggta tagtctgttg ctcctaggcc   4320
acaaacctgt acaactgtta ctgtactgaa tactatagac agttgtaaca cagtggtaaa   4380
tatttatcta aatatatgca aacagagaaa aggtacagta aaagtatggt ataaaagata   4440
atggtatacc tgtgtaggcc acttaccacg aatggagctt gcaggactag aagttgctct   4500
```

gggtgagtca gtgagtgagt ggtgaattaa tgtgaaggcc tagaacactg tacaccactg 4560
tagactataa acacagtacg ctgaagctac accaaattta tcttaacagt ttttcttcaa 4620
taaaaaatta taacttttta actttgtaaa ctttttaatt ttttaacttt taaaatactt 4680
agcttgaaac acaaatacat tgtatagcta tacaaaaata tttttctttt gtatccttat 4740
tctagaagct tttttctatt ttctatttta aatttttttt tttacttgtt agtcgttttt 4800
gttaaaaact aaaacacaca cactttcacc taggcataga caggattagg atcatcagta 4860
tcactccctt ccacctcact gccttccacc tccacatctt gtcccactgg aaggttttta 4920
ggggcaataa cacacatgta gctgtcacct atgataacag tgctttctgt tgaatacctc 4980
ctgaaggact tgcctgaggc tgttttacat ttaacttaaa aaaaaaaaaa gtagaaggag 5040
tgcactctaa aataacaata aaaggcatag tatagtgaat acataaacca gcaatgtagt 5100
agtttattat caagtgttgt acactgtaat aattgtatgt gctatacttt aaataacttg 5160
caaaatagta ctaagacctt atgatggtta cagtgtcact aaggcaatag catattttca 5220
ggtccattgt aatctaatgg gactaccatc atatatgcag tctaccattg actgaaacgt 5280
tacatggcac ataactgtat ttgcaagaat gatttgtttt acattaatat cacataggat 5340
gtaccttttt agagtggtat gtttatgtgg attaagatgt acaagttgag caaggggacc 5400
aagagccctg ggttctgtct tggatgtgag cgtttatgtt cttctcctca tgtctgtttt 5460
ctcattaaat tcaaaggctt gaacgggccc tatttagccc ttctgttttc tacgtgttct 5520
aaataactaa agcttttaaa ttctagccat ttagtgtaga actctctttg cagtgatgaa 5580
atgctgtatt ggtttcttgg ctagcatatt aaatattttt atctttgtct tgatacttca 5640
atgtcgtttt aaacatcagg atcgggcttc agtattctca taaccagaga gttcactgag 5700
gatacaggac tgtttgccca ttttttgtta tggctccaga cttgtggtat ttccatgtct 5760
tttttttttt tttttttttt gaccttttag cggctttaaa gtatttctgt tgttaggtgt 5820
tgtattactt ttctaagatt acttaacaaa gcaccacaaa ctgagtggct ttaaacaaca 5880
gcaatttatt ctctcacaat tctagaagct agaagtccga aatcaaagtg ttgacagggg 5940
catgatcttc aagagagaag actctttcct tgcctcttcc tggcttctgg tggttaccag 6000
caatcctgag tgttcctttc ttgccttgta gtttcaacaa tccagtatct gccttttgtc 6060
ttcacatggc tgtctaccat ttgtctctgt gtctccaaat ctctctcctt ataaacacag 6120
cagttattgg attaggcccc actctaatcc agtatgaccc cattttaaca tgattacact 6180
tatttctaga taaggtcaca ttcacgtaca ccaagggtta ggaattgaac atatcttttt 6240
gggggacaca attcaaccca caagtgtcag tctctagctg agcctttccc ttcctgtttt 6300
tctccttttt agttgctatg ggttaggggc caaatctcca gtcatactag aattgcacat 6360
ggactggata tttgggaata ctgcgggtct attctatgag ctttagtatg taacatttaa 6420
tatcagtgta aagaagccct tttttaagtt atttctttga atttctaaat gtatgccctg 6480
aatataagta acaagttacc atgtcttgta aaatgatcat atcaacaaac atttaatgtg 6540
cacctactgt gctagttgaa tgtctttatc ctgataggag ataacaggat tccacatctt 6600
tgacttaaga ggacaaacca aatatgtcta aatcatttgg ggttttgatg gatatcttta 6660
aattgctgaa cctaatcatt ggtttcatat gtcattgttt agatatctcc ggagcatttg 6720
gataatgtga cagttggaat gcagtgatgt cgactctttg cccaccgcca tctccagctg 6780
ttgccaagac agagattgct ttaagtggca aatcaccttt attagcagct acttttgctt 6840

-continued actgggacaa tattcttggt cctagagtaa ggcacatttg ggctccaaag acagaacagg 6900
tacttctcag tgatggagaa ataacttttc ttgccaacca cactctaaat ggagaaatcc 6960
ttcgaaatgc agagagtggt gctatagatg taaagttttt tgtcttgtct gaaaagggag 7020
tgattattgt ttcattaatc tttgatggaa actggaatgg ggatcgcagc acatatggac 7080
tatcaattat acttccacag acagaactta gtttctacct cccacttcat agagtgtgtg 7140
ttgatagatt aacacatata atccggaaag gaagaatatg gatgcataag gtaagtgatt 7200
tttcagctta ttaatcatgt taacctatct gttgaaagct tattttctgg tacatataaa 7260
tcttattttt ttaattatat gcagtgaaca tcaaacaata aatgttattt attttgcatt 7320
taccctatta gatacaaata catctggtct gatacctgtc atcttcatat taactgtgga 7380
aggtacgaaa tggtagctcc acattataga tgaaaagcta aagcttagac aaataaagaa 7440
acttttagac cctggattct tcttgggagc ctttgactct aataccttttt gtttcccttt 7500
cattgcacaa ttctgtcttt tgcttactac tatgtgtaag tataacagtt caaagtaata 7560
gtttcataag ctgttggtca tgtagccttt ggtctcttta acctctttgc caagttccca 7620
ggttcataaa atgaggaggt tgaatggaat ggttcccaag agaattcctt ttaatcttac 7680
agaaattatt gttttcctaa atcctgtagt tgaatatata atgctattta catttcagta 7740
tagttttgat gtatctaaag aacacattga attctccttc ctgtgttcca gtttgatact 7800
aacctgaaag tccattaagc attaccagtt ttaaaaggct tttgcccaat agtaaggaaa 7860
aataatatct tttaaaagaa taattttttta ctatgtttgc aggcttactt cctttttttct 7920
cacattatga aactcttaaa atcaggagaa tcttttaaac aacatcataa tgtttaattt 7980
gaaaagtgca agtcattctt ttcctttttg aaactatgca gatgttacat tgactgtttt 8040
ctgtgaagtt atcttttttt cactgcagaa taaaggttgt tttgatttta ttttgtattg 8100
tttatgagaa catgcatttg ttgggttaat ttcctacccc tgccccccatt ttttccctaa 8160
agtagaaagt atttttcttg tgaactaaat tactacacaa gaacatgtct attgaaaaat 8220
aagcaagtat caaaatgttg tgggttgttt ttttaaataa attttctctt gctcaggaaa 8280
gacaagaaaa tgtccagaag attatcttag aaggcacaga gagaatggaa gatcaggtat 8340
atgcaaattg catactgtca aatgtttttc tcacagcatg tatctgtata aggttgatgg 8400
ctacatttgt caaggccttg gagacatacg aataagcctt taatggagct tttatggagg 8460
tgtacagaat aaactggagg aagatttcca tatcttaaac ccaaagagtt aaatcagtaa 8520
acaaaggaaa atagtaattg catctacaaa ttaatatttg ctccctttttt ttttctgttt 8580
gcccagaata aattttggat aacttgttca tagtaaaaat aaaaaaaatt gtctctgata 8640
tgttctttaa ggtactactt ctcgaacctt tccctagaag tagctgtaac agaaggagag 8700
catatgtacc cctgaggtat ctgtctgggg tgtaggccca ggtccacaca atatttcttc 8760
taagtcttat gttgtatcgt taagactcat gcaatttaca ttttattcca taactatttt 8820
agtattaaaa tttgtcagtg atatttctta ccctctcctc taggaaaatg tgccatgttt 8880
atcccttggc tttgaatgcc cctcaggaac agacactaag agtttgagaa gcatggttac 8940
aagggtgtgg cttcccctgc ggaaactaag tacagactat ttcactgtaa agcagagaag 9000
ttcttttgaa ggagaatctc cagtgaagaa agagttcttc acttttactt ccatttcctc 9060
ttgtgggtga ccctcaatgc tccttgtaaa actccaatat tttaaacatg gctgttttgc 9120
ctttctttgc ttctttttag catgaatgag acagatgata ctttaaaaaa gtaattaaaa 9180
aaaaaaactt gtgaaaatac atggccataa tacagaaccc aatacaatga tctcctttac 9240
caaattgtta tgtttgtact tttgtagata gctttccaat tcagagacag ttattctgtg 9300
taaaggtctg acttaacaag aaaagatttc cctttaccca aagaatccca gtccttattt 9360
gctggtcaat aagcagggtc cccaggaatg gggtaacttt cagcaccctc taacccacta 9420
gttattagta gactaattaa gtaaacttat cgcaagttga ggaaacttag aaccaactaa 9480
aattctgctt ttactgggat tttgtttttt caaaccagaa acctttactt aagttgacta 9540
ctattaatga attttggtct ctcttttaag tgctcttctt aaaaatgtta tcttactgct 9600
gagaagttca agtttgggaa gtacaaggag gaatagaaac ttaagagatt ttcttttaga 9660
gcctcttctg tatttagccc tgtaggattt tttttttttt tttttttttt ggtgttgttg 9720
agcttcagtg aggctattca ttcacttata ctgataatgt ctgagatact gtgaatgaaa 9780
tactatgtat gcttaaacct aagaggaaat attttcccaa aattattctt cccgaaaagg 9840
aggagttgcc ttttgattga gttcttgcaa atctcacaac gactttattt tgaacaatac 9900
tgtttgggga tgatgcatta gtttgaaaca acttcagttg tagctgtcat ctgataaaat 9960
tgcttcacag ggaaggaaat ttaacacgga tctagtcatt attcttgtta gattgaatgt 10020
gtgaattgta attgtaaaca ggcatgataa ttattacttt aaaaactaaa aacagtgaat 10080
agttagttgt ggaggttact aaaggatggt tttttttaa ataaaacttt cagcattatg 10140
caaatgggca tatggcttag gataaaactt ccagaagtag catcacattt aaattctcaa 10200
gcaacttaat aatatggggc tctgaaaaac tggttaaggt tactccaaaa atggccctgg 10260
gtctgacaaa gattctaact taaagatgct tatgaagact ttgagtaaaa tcatttcata 10320
aaataagtga ggaaaaacaa ctagtattaa attcatctta aataatgtat gatttaaaaa 10380
atatgtttag ctaaaaatgc atagtcattt gacaatttca tttatatctc aaaaaattta 10440
cttaaccaag ttggtcacaa aactgatgag actggtggtg gtagtgaata aatgagggac 10500
catccatatt tgagacactt tacatttgtg atgtgttata ctgaattttc agtttgattc 10560
tatagactac aaatttcaaa attacaattt caagatgtaa taagtagtaa tatcttgaaa 10620
tagctctaaa gggaattttt ctgttttatt gattcttaaa atatatgtgc tgattttgat 10680
ttgcatttgg gtagattata cttttatgag tatggaggtt aggtattgat tcaagttttc 10740
cttacctatt tggtaaggat ttcaaagtct ttttgtgctt ggttttcctc atttttaaat 10800
atgaaatata ttgatgacct ttaacaaatt ttttttatct caaattttaa aggagatctt 10860
ttctaaaaga ggcatgatga cttaatcatt gcatgtaaca gtaaacgata aaccaatgat 10920
tccatactct ctaaagaata aaagtgagct ttagggccgg gcatggtcag aaatttgaca 10980
ccaacctggc caacatggcg aaaccccgtc tctactaaaa atacaaaaat cagccgggca 11040
tggtggcggc acctatagtc ccagctactt gggaggatga gacaggagag tcacttgaac 11100
ctgggaggag aggttgcagt gagctgagat cacgccattg cactccagcc tgagcaatga 11160
aagcaaaact ccatctcaaa aaaaaaaaaa gaaaagaaag aataaaagtg agctttggat 11220
tgcatataaa tcctttagac atgtagtaga cttgtttgat actgtgtttg aacaaattac 11280
gaagtatttt catcaaagaa tgttattgtt tgatgttatt tttatttttt attgcccagc 11340
ttctctcata ttacgtgatt ttcttcactt catgtcactt tattgtgcag ggtcagagta 11400
ttattccaat gcttactgga gaagtgattc ctgtaatgga actgctttca tctatgaaat 11460
cacacagtgt tcctgaagaa atagatgtaa gtttaaatga gagcaattat acactttatg 11520
agttttttgg ggttatagta ttattatgta tattattaat attctaattt taatagtaag 11580

-continued gactttgtca tacatactat tcacatacag tattagccac tttagcaaat aagcacacac 11640
aaaatcctgg attttatggc aaaacagagg catttttgat cagtgatgac aaaattaaat 11700
tcattttgtt tatttcatta cttttataat tcctaaaagt gggaggatcc cagctcttat 11760
aggagcaatt aatatttaat gtagtgtctt ttgaaacaaa actgtgtgcc aaagtagtaa 11820
ccattaatgg aagtttactt gtagtcacaa atttagtttc cttaatcatt tgttgaggac 11880
gttttgaatc acacactatg agtgttaaga gataccttta ggaaactatt cttgttgttt 11940
tctgattttg tcatttaggt tagtctcctg attctgacag ctcagaagag gaagttgttc 12000
ttgtaaaaat tgtttaacct gcttgaccag ctttcacatt tgttcttctg aagtttatgg 12060
tagtgcacag agattgtttt ttggggagtc ttgattctcg gaaatgaagg cagtgtgtta 12120
tattgaatcc agacttccga aaacttgtat attaaaagtg ttatttcaac actatgttac 12180
agccagacta attttttat tttttgatgc attttagata gctgatacag tactcaatga 12240
tgatgatatt ggtgacagct gtcatgaagg ctttcttctc aagtaagaat ttttcttttc 12300
ataaaagctg gatgaagcag ataccatctt atgctcacct atgacaagat ttggaagaaa 12360
gaaaataaca gactgtctac ttagattgtt ctagggacat tacgtatttg aactgttgct 12420
taaatttgtg ttatttttca ctcattatat ttctatatat atttggtgtt attccatttg 12480
ctatttaaag aaaccgagtt tccatcccag acaagaaatc atggcccctt gcttgattct 12540
ggtttcttgt tttacttctc attaaagcta acagaatcct ttcatattaa gttgtactgt 12600
agatgaactt aagttattta ggcgtagaac aaaattattc atatttatac tgatcttttt 12660
ccatccagca gtggagttta gtacttaaga gtttgtgccc ttaaaccaga ctccctggat 12720
taatgctgtg tacccgtggg caaggtgcct gaattctcta tacacctatt tcctcatctg 12780
taaaatggca ataatagtaa tagtacctaa tgtgtagggt tgttataagc attgagtaag 12840
ataaataata taaagcactt agaacagtgc ctggaacata aaaacactta ataatagctc 12900
atagctaaca tttcctattt acatttcttc tagaaatagc cagtatttgt tgagtgccta 12960
catgttagtt cctttactag ttgctttaca tgtattatct tatattctgt tttaaagttt 13020
cttcacagtt acagattttc atgaaatttt acttttaata aaagagaagt aaaagtataa 13080
agtattcact tttatgttca cagtcttttc ctttaggctc atgatggagt atcagaggca 13140
tgagtgtgtt taacctaaga gccttaatgg cttgaatcag aagcacttta gtcctgtatc 13200
tgttcagtgt cagcctttca tacatcattt taaatcccat ttgactttaa gtaagtcact 13260
taatctctct acatgtcaat ttcttcagct ataaaatgat ggtatttcaa taaataaata 13320
cattaattaa atgatattat actgactaat tgggctgttt taaggctcaa taagaaaatt 13380
tctgtgaaag gtctctagaa aatgtaggtt cctatacaaa taaaagataa cattgtgctt 13440
atagcttcgg tgtttatcat ataaagctat tctgagttat ttgaagagct cacctacttt 13500
tttttgtttt tagtttgtta aattgtttta taggcaatgt ttttaatctg ttttctttaa 13560
cttacagtgc catcagctca cacttgcaaa cctgtggctg ttccgttgta gtaggtagca 13620
gtgcagagaa agtaaataag gtagtttatt ttataatcta gcaaatgatt tgactcttta 13680
agactgatga tatatcatgg attgtcattt aaatggtagg ttgcaattaa aatgatctag 13740
tagtataagg aggcaatgta atctcatcaa attgctaaga caccttgtgg caacagtgag 13800
tttgaaataa actgagtaag aatcatttat cagtttattt tgatagctcg gaaataccag 13860
tgtcagtagt gtataaatgg ttttgagaat atattaaaat cagatatata aaaaaaatta 13920
ctcttctatt tcccaatgtt atctttaaca aatctgaaga tagtcatgta cttttggtag 13980

```
tagttccaaa gaaatgttat ttgtttattc atcttgattt cattgtcttc gctttccttc  14040
taaatctgtc ccttctaggg agctattggg attaagtggt cattgattat tatactttat  14100
tcagtaatgt ttctgaccct ttccttcagt gctacttgag ttaattaagg attaatgaac  14160
agttacattt ccaagcatta gctaataaac taaaggattt tgcacttttc ttcactgacc  14220
attagttaga aagagttcag agataagtat gtgtatcttt caatttcagc aaacctaatt  14280
ttttaaaaaa agttttacat aggaaatatg ttggaaatga tactttacaa agatattcat  14340
aatttttttt tgtaatcagc tactttgtat atttacatga gccttaattt atatttctca  14400
tataaccatt tatgagagct tagtatacct gtgtcattat attgcatcta cgaactagtg  14460
accttattcc ttctgttacc tcaaacaggt ggctttccat ctgtgatctc caaagcctta  14520
ggttgcacag agtgactgcc gagctgcttt atgaagggag aaaggctcca tagttggagt  14580
gttttttttt ttttttttaa acatttttcc catcctccat cctcttgagg gagaatagct  14640
taccttttat cttgttttaa tttgagaaag aagttgccac cactctaggt tgaaaaccac  14700
tcctttaaca taataactgt ggatatggtt tgaatttcaa gatagttaca tgccttttta  14760
tttttcctaa tagagctgta ggtcaaatat tattagaatc agatttctaa atcccaccca  14820
atgacctgct tattttaaat caaattcaat aattaattct cttctttttg gaggatctgg  14880
acattctttg atatttctta caacgaattt catgtgtaga cccactaaac agaagctata  14940
aaagttgcat ggtcaaataa gtctgagaaa gtctgcagat gatataattc acctgaagag  15000
tcacagtatg tagccaaatg ttaaaggttt tgagatgcca tacagtaaat ttaccaagca  15060
ttttctaaat ttatttgacc acagaatccc tattttaagc aacaactgtt acatcccatg  15120
gattccaggt gactaaagaa tacttatttc ttaggatatg ttttattgat aataacaatt  15180
aaaatttcag atatctttca taagcaaatc agtggtcttt ttacttcatg ttttaatgct  15240
aaaatatttt cttttataga tagtcagaac attatgcctt tttctgactc cagcagagag  15300
aaaatgctcc aggttatgtg aagcagaatc atcatttaaa tatgagtcag ggctctttgt  15360
acaaggcctg ctaaaggtat agtttctagt tatcacaagt gaaaccactt ttctaaaatc  15420
atttttgaga ctctttatag acaaatctta aatattagca tttaatgtat ctcatattga  15480
catgcccaga gactgacttc ctttacacag ttctgcacat agactatatg tcttatggat  15540
ttatagttag tatcatcagt gaaacaccat agaataccct ttgtgttcca ggtgggtccc  15600
tgttcctaca tgtctagcct caggactttt ttttttttaa cacatgctta aatcaggttg  15660
cacatcaaaa ataagatcat ttctttttaa ctaaatagat ttgaatttta ttgaaaaaaa  15720
attttaaaca tctttaagaa gcttatagga tttaagcaat tcctatgtat gtgtactaaa  15780
atatatatat ttctatatat aatatatatt agaaaaaaat tgtatttttc ttttatttga  15840
gtctactgtc aaggagcaaa acagagaaat gtaaattagc aattatttat aatacttaaa  15900
gggaagaaag ttgttcacct tgttgaatct attattgtta tttcaattat agtcccaaga  15960
cgtgaagaaa tagctttcct aatggttatg tgattgtctc atagtgacta ctttcttgag  16020
gatgtagcca cggcaaaatg aaataaaaaa atttaaaaat tgttgcaaat acaagttata  16080
ttaggctttt gtgcattttc aataatgtgc tgctatgaac tcagaatgat agtatttaaa  16140
tatagaaact agttaaagga aacgtagttt ctatttgagt tatacatatc tgtaaattag  16200
aacttctcct gttaaaggca taataaagtg cttaatactt ttgtttcctc agcaccctct  16260
catttaatta tataatttta gttctgaaag ggacctatac cagatgccta gaggaaattt  16320
```

caaaactatg atctaatgaa aaaatattta atagttctcc atgcaaatac aaatcatata 16380
gttttccaga aaatacccttt gacattatac aaagatgatt atcacagcat tataatagta 16440
aaaaaatgga aatagcctct ttcttctgtt ctgttcatag cacagtgcct catacgcagt 16500
aggttattat tacatggtaa ctggctaccc caactgatta ggaaagaagt aaatttgttt 16560
tataaaaata catactcatt gaggtgcata gaataattaa gaaattaaaa gacacttgta 16620
attttgaatc cagtgaatac ccactgttaa tatttggtat atctctttct agtctttttt 16680 tccctttttgc atgtattttc tttaagactc ccaccccccac tggatcatct ctgcatgttc 16740
taatctgctt ttttcacagc agattctaag cctctttgaa tatcaacaca aacttcaaca 16800
acttcatcta tagatgccaa ataataaatt catttttatt tacttaacca cttcctttgg 16860
atgcttaggt cattctgatg ttttgctatt gaaaccaatg ctatactgaa cacttctgtc 16920
actaaaactt tgcacacact catgaatagc ttcttaggat aaatttttag agatggattt 16980
gctaaatcag agaccatttt ttaaaattaa aaaacaatta ttcatatcgt ttggcatgta 17040
agacagtaaa ttttcctttt attttgacag gattcaactg gaagctttgt gctgcctttc 17100
cggcaagtca tgtatgctcc atatcccacc acacacatag atgtggatgt caatactgtg 17160
aagcagatgc caccctgtca tgaacatatt tataatcagc gtagatacat gagatccgag 17220
ctgacagcct tctggagagc cacttcagaa gaagacatgg ctcaggatac gatcatctac 17280
actgacgaaa gctttactcc tgatttgtac gtaatgctct gcctgctggt actgtagtca 17340
agcaatatga aattgtgtct tttacgaata aaaacaaaac agaagttgca tttaaaaaga 17400
aagaaatatt accagcagaa ttatgcttga agaaacattt aatcaagcat tttttctta 17460 aatgttcttc tttttccata caattgtgtt taccctaaaa taggtaagat taacccttaa 17520
agtaaatatt taactatttg tttaataaat atatattgag ctcctaggca ctgttctagg 17580
taccgggctt aatagtggcc aaccagacag ccccagcccc agcccctaca ttgtgtatag 17640
tctattatgt aacagttatt gaatggactt attaacaaaa ccaaagaagt aattctaagt 17700
cttttttttc ttgacatatg aatataaaat acagcaaaac tgttaaaata tattaatgga 17760
acattttttt actttgcatt ttatattgtt attcacttct tattttttttt taaaaaaaaa 17820 agcctgaaca gtaaattcaa aaggaaaagt aatgataatt aattgttgag catggaccca 17880
acttgaaaaa aaaaatgatg atgataaatc tataatccta aaaccctaag taaacactta 17940
aaagatgttc tgaaatcagg aaaagaatta tagtatactt ttgtgtttct cttttatcag 18000
ttgaaaaaag gcacagtagc tcatgcctgt aagaacagag ctttgggagt gcaaggcagg 18060
cggatcactt gaggccagga gttccagacc agcctgggca acatagtgaa accccatctc 18120
tacaaaaaat aaaaaagaat tattggaatg tgtttctgtg tgcctgtaat cctagctatt 18180
ccgaaagctg aggcaggagg atcttttgag cccaggagtt tgaggttaca gggagttatg 18240
atgtgccagt gtactccagc ctggggaaca ccgagactct gtcttattta aaaaaaaaaa 18300
aaaaaaaatg cttgcaataa tgcctggcac atagaaggta acagtaagtg ttaactgtaa 18360
taacccaggt ctaagtgtgt aaggcaatag aaaaattggg gcaaataagc ctgacctatg 18420
tatctacaga atcagtttga gcttaggtaa cagacctgtg gagcaccagt aattacacag 18480
taagtgttaa ccaaaagcat agaataggaa tatcttgttc aagggacccc cagccttata 18540
catctcaagg tgcagaaaga tgacttaata taggacccat tttttcctag ttctccagag 18600
tttttattgg ttcttgagaa agtagtaggg gaatgtttta gaaaatgaat tggtccaact 18660
gaaattacat gtcagtaagt ttttatatat tggtaaattt tagtagacat gtagaagttt 18720
tctaattaat ctgtgccttg aaacattttc ttttttccta aagtgcttag tatttttttcc 18780
gtttttgat tggttacttg ggagcttttt tgaggaaatt tagtgaactg cagaatgggt 18840
ttgcaaccat ttggtatttt tgttttgttt tttagaggat gtatgtgtat tttaacattt 18900
cttaatcatt tttagccagc tatgtttgtt ttgctgattt gacaaactac agttagacag 18960
ctattctcat tttgctgatc atgacaaaat aatatcctga atttttaaat tttgcatcca 19020
gctctaaatt ttctaaacat aaaattgtcc aaaaaatagt attttcagcc actagattgt 19080
gtgttaagtc tattgtcaca gagtcatttt acttttaagt atatgttttt acatgttaat 19140
tatgtttgtt atttttaatt ttaacttttt aaaataattc cagtcactgc caatacatga 19200
aaaattggtc actggaattt tttttttgac ttttatttta ggttcatgtg tacatgtgca 19260
ggtgtgttat acaggtaaat tgcgtgtcat gagggtttgg tgtacaggtg atttcattac 19320
ccaggtaata agcatagtac ccaataggta gttttttgat cctcaccctt ctcccaccct 19380
caagtaggcc ctggtgttgc tgtttccttc tttgtgtcca tgtatactca gtgtttagct 19440
cccacttaga agtgagaaca tgcggtagtt ggttttctgt tcctggatta gttcacttag 19500
gataatgacc tctagctcca tctggttttt atggctgcat agtattccat ggtgtatatg 19560
tatcacattt tctttatcca gtctaccatt gataggcatt taggttgatt ccctgtcttt 19620
gttatcatga atagtgctgt gatgaacata cacatgcatg tgtctttatg gtagaaaaat 19680
ttgtattcct ttaggtacat atagaataat ggggttgcta gggtgaatgg tagttctatt 19740
ttcagttatt tgagaaatct tcaaactgct tttcataata gctaaactaa tttacagtcc 19800
cgccagcagt gtataagtgt tccctttct ccacaacctt gccaacatct gtgatttttt 19860
gactttttaa taatagccat tcctagagaa ttgatttgca attctctatt agtgatatta 19920
agcatttttt catatgcttt ttagctgtct gtatatattc ttctgaaaaa ttttcatgtc 19980
ctttgcccag tttgtagtgg ggtgggttgt tttttgcttg ttaattagtt ttaagttcct 20040
tccagattct gcatatccct ttgttggata catggtttgc agatattttt ctcccattgt 20100
gtaggttgtc ttttactctg ttgatagttt cttttgccat gcaggagctc gttaggtccc 20160
atttgtgttt gtttttgttg cagttgcttt tggcgtcttc atcataaaat ctgtgccagg 20220
gcctatgtcc agaatggtat ttcctaggtt gtcttccagg gtttttacaa ttttagattt 20280
tacgtttatg tctttaatcc atcttgagtt gatttttgta tatggcacaa ggaaggggtc 20340
cagtttcact ccaattccta tggctagcaa ttatcccagc accatttatt gaatacggag 20400
tcctttcccc attgcttgtt ttttgtcaac tttgttgaag atcagatggt tgtaagtgtg 20460
tggctttatt tcttggctct ctattctcca ttggtctatg tgtctgtttt tataacagta 20520
ccctgctgtt caggttccta tagcctttta gtataaaatc ggctaatgtg atgcctccag 20580
ctttgttctt tttgcttagg attgctttgg ctatttgggc tcctttttgg gtccatatta 20640
attttaaaac agtttttttct ggttttgtga aggatatcat tggtagttta taggaatagc 20700
attgaatctg tagattgctt tgggcagtat ggccatttta acaatattaa ttcttcctat 20760
ctatgaatat ggaatgtttt tccatgtgtt tgtgtcatct ctttatacct gatgtataaa 20820
gaaaagctgg tattattcct actcaatctg ttccaaaaaa ttgaggagga ggaactcttc 20880
cctaatgagg ccagcatcat tctgatacca aaacctggca gagacacaac agaaaaaaga 20940
aaacttcagg ccaatatcct tgatgaatat agatgcaaaa atcctcaaca aaatactagc 21000
aaaccaaatc cagcagcaca tcaaaaagct gatctacttt gatcaagtag gctttatccc 21060

-continued

```
tgggatgcaa ggttggttca acatacacaa atcaataagt gtgattcatc acataaacag  21120
agctaaaaac aaaaaccaca agattatctc aataggtaga gaaaaggttg tcaataaaat  21180
ttaacatcct ccatgttaaa aaccttcagt aggtcaggtg tagtgactca cacctgtaat  21240
cccagcactt tgggaggcca aggcgggcat atctcttaag cccaggagtt caagacgagc  21300
ctaggcagca tggtgaaacc ccatctctac aaaaaaaaaa aaaaaaaaaa attagcttgg  21360
tatggtgaca tgcacctata gtcccagcta ttcaggaggt tgaggtggga ggattgtttg  21420
agcccgggag gcagaggttg gcagcgagct gagatcatgc caccgcactc cagcctgggc  21480
aacggagtga gaccctgtct caaaaaagaa aaatcacaaa caatcctaaa caaactaggc  21540
attgaaggaa catgcctcaa aaaaataaga accatctatg acagacccat agccaatatc  21600
ttaccaaatg ggcaaaagct ggaagtattc tccttgagaa ccgtaacaag acaaggatgt  21660
ccactctcac cactcctttt cagcatagtt ctggaagtcc tagccagagc aatcaggaaa  21720
gagaaagaaa gaaagacatt cagataggaa gagaagaagt caaactattt ctgtttgcag  21780
gcagtataat tctgtaccta gaaaatctca tagtctctgc ccagaaactc ctaaatctgt  21840
taaaaatttc agcaaagttt tggcattctc tatactccaa caccttccaa agtgagagca  21900
aaatcaagaa cacagtccca ttcacaatag ccgcaaaacg aataaaatac ctaggaatcc  21960
agctaaccag ggaggtgaaa gatctctatg agaattacaa aacactgctg aaagaaatca  22020
gagatgacac aaacaaatgg aaatgttctt ttttaacacc ttgctttatc taattcactt  22080
atgatgaaga tactcattca gtggaacagg tataataagt ccactcgatt aaatataagc  22140
cttattctct ttccagagcc caagaagggg cactatcagt gcccagtcaa taatgacgaa  22200
atgctaatat ttttcccctt tacggtttct ttcttctgta gtgtggtaca ctcgtttctt  22260
aagataagga aacttgaact accttcctgt ttgcttctac acatacccat tctctttttt  22320
tgccactctg gtcaggtata ggatgatccc taccactttc agttaaaaac tcctcctctt  22380
actaaatgtt ctcttaccct ctggcctgag tagaacctag ggaaaatgga agagaaaaag  22440
atgaaaggga ggtggggcct gggaagggaa taagtagtcc tgtttgtttg tgtgtttgct  22500
ttagcacctg ctatatccta ggtgctgtgt taggcacaca ttattttaag tggccattat  22560
attactacta ctcactctgg tcgttgccaa ggtaggtagt actttcttgg atagttggtt  22620
catgttactt acagatggtg ggcttgttga ggcaaaccca gtggataatc atcggagtgt  22680
gttctctaat ctcactcaaa tttttcttca catttttgg tttgttttgg tttttgatgg  22740
tagtggctta tttttgttgc tggtttgttt tttgtttttt tttgagatgg caagaattgg  22800
tagttttatt tattaattgc ctaagggtct ctactttttt taaaagatga gagtagtaaa  22860
atagattgat agatacatac atacccttac tggggactgc ttatattctt tagagaaaaa  22920
attacatatt agcctgacaa acaccagtaa aatgtaaata tatccttgag taaataaatg  22980
aatgtatatt ttgtgtctcc aaatatatat atctatattc ttacaaatgt gtttatatgt  23040
aatatcaatt tataagaact taaaatgttg gctcaagtga gggattgtgg aaggtagcat  23100
tatatggcca tttcaacatt tgaacttttt tcttttcttc attttcttct tttcttcagg  23160
aatatttttc aagatgtctt acacagagac actctagtga aagccttcct ggatcaggta  23220
aatgttgaac ttgagattgt cagagtgaat gatatgacat gttttctttt ttaatatatc  23280
ctacaatgcc tgttctatat atttatattc ccctggatca tgccccagag ttctgctcag  23340
caattgcagt taagttagtt acactacagt tctcagaaga gtctgtgagg gcatgtcaag  23400
tgcatcatta cattggttgc ctcttgtcct agatttatgc ttcgggaatt cagacctttg  23460
```

```
tttacaatat aataaatatt attgctatct tttaaagata taataataag atataaagtt 23520
gaccacaact actgtttttt gaaacataga attcctggtt tacatgtatc aaagtgaaat 23580
ctgacttagc ttttacagat ataatatata catatatata tcctgcaatg cttgtactat 23640
atatgtagta caagtatata tatatgtttg tgtgtgtata tatatatagt acgagcatat 23700
atacatatta ccagcattgt aggatatata tatgtttata tattaaaaaa aagttataaa 23760
cttaaaaccc tattatgtta tgtagagtat atgttatata tgatatgtaa aatatataac 23820
atatactcta tgatagagtg taatatattt tttatatata ttttaacatt tataaaatga 23880
tagaattaag aattgagtcc taatctgttt tattaggtgc tttttgtagt gtctggtctt 23940
tctaaagtgt ctaaatgatt tttccttttg acttattaat ggggaagagc ctgtatatta 24000
acaattaaga gtgcagcatt ccatacgtca aacaacaaac attttaattc aagcattaac 24060
ctataacaag taagtttttt tttttttttt gagaaaggga ggttgtttat ttgcctgaaa 24120
tgactcaaaa atatttttga aacatagtgt acttatttaa ataacatctt tattgtttca 24180
ttcttttaaa aaatatctac ttaattacac agttgaagga aatcgtagat tatatggaac 24240
ttatttctta atatattaca gtttgttata ataacattct ggggatcagg ccaggaaact 24300
gtgtcataga taaagctttg aaataatgag atccttatgt ttactagaaa ttttggattg 24360
agatctatga ggtctgtgac atattgcgaa gttcaaggaa aattcgtagg cctggaattt 24420
catgcttctc aagctgacat aaaatccctc ccactctcca cctcatcata tgcacacatt 24480
ctactcctac ccacccactc cacccccctgc aaaagtacag gtatatgaat gtctcaaaac 24540
cataggctca tcttctagga gcttcaatgt tatttgaaga tttgggcaga aaaaattaag 24600
taatacgaaa taacttatgt atgagtttta aaagtgaagt aaacatggat gtattctgaa 24660
gtagaatgca aaatttgaat gcatttttaa agataaatta gaaaacttct aaaaactgtc 24720
agattgtctg ggcctggtgg cttatgcctg taatcccagc actttgggag tccgaggtgg 24780
gtggatcaca aggtcaggag atcgagacca tcctgccaac atggtgaaac cccgtctcta 24840
ctaagtatac aaaaattagc tgggcgtggc agcgtgtgcc tgtaatccca gctacctggg 24900
aggctgaggc aggagaatcg cttgaaccca ggaggtgtag gttgcagtga gtcaagatcg 24960
cgccactgca ctttagcctg gtgacagagc tagactccgt ctcaaaaaaa aaaaaaaata 25020
tcagattgtt cctacaccta gtgcttctat accacactcc tgttaggggg catcagtgga 25080
aatggttaag gagatgttta gtgtgtattg tctgccaagc actgtcaaca ctgtcataga 25140
aacttctgta cgagtagaat gtgagcaaat tatgtgttga aatggttcct ctccctgcag 25200
gtctttcagc tgaaacctgg cttatctctc agaagtactt tccttgcaca gtttctactt 25260
gtccttcaca gaaaagcctt gacactaata aaatatatag aagacgatac gtgagtaaaa 25320
ctcctacacg gaagaaaaac ctttgtacat tgtttttttg ttttgtttcc tttgtacatt 25380
ttctatatca taatttttgc gcttcttttt tttttttttt tttttttttt tccattattt 25440
ttaggcagaa gggaaaaaag ccctttaaat ctcttcggaa cctgaagata gaccttgatt 25500
taacagcaga gggcgatctt aacataataa tggctctggc tgagaaaatt aaaccaggcc 25560
tacactcttt tatctttgga agacctttct acactagtgt gcaagaacga gatgttctaa 25620
tgactttttta aatgtgtaac ttaataagcc tattccatca caatcatgat cgctggtaaa 25680
gtagctcagt ggtgtgggga aacgttcccc tggatcatac tccagaattc tgctctcagc 25740
aattgcagtt aagtaagtta cactacagtt ctcacaagag cctgtgaggg gatgtcaggt 25800
```

```
gcatcattac attgggtgtc tcttttccta gatttatgct tttgggatac agacctatgt  25860
ttacaatata ataaatatta ttgctatctt ttaaagatat aataatagga tgtaaacttg  25920
accacaacta ctgttttttt gaaatacatg attcatggtt tacatgtgtc aaggtgaaat  25980
ctgagttggc ttttacagat agttgacttt ctatcttttg gcattctttg gtgtgtagaa  26040
ttactgtaat acttctgcaa tcaactgaaa actagagcct ttaaatgatt tcaattccac  26100
agaaagaaag tgagcttgaa cataggatga gctttagaaa gaaaattgat caagcagatg  26160
tttaattgga attgattatt agatcctact ttgtggattt agtccctggg attcagtctg  26220
tagaaatgtc taatagttct ctatagtcct tgttcctggt gaaccacagt tagggtgttt  26280
tgtttatttt attgttcttg ctattgttga tattctatgt agttgagctc tgtaaaagga  26340
aattgtattt tatgttttag taattgttgc caacttttta aattaatttt cattattttt  26400
gagccaaatt gaaatgtgca cctcctgtgc ctttttttctc cttagaaaat ctaattactt  26460
ggaacaagtt cagatttcac tggtcagtca ttttcatctt gttttcttct tgctaagtct  26520
taccatgtac ctgctttggc aatcattgca actctgagat tataaaatgc cttagagaat  26580
atactaacta ataagatctt tttttcagaa acagaaaata gttccttgag tacttccttc  26640
ttgcatttct gcctatgttt ttgaagttgt tgctgtttgc ctgcaatagg ctataaggaa  26700
tagcaggaga aattttactg aagtgctgtt ttcctaggtg ctactttggc agagctaagt  26760
tatcttttgt tttcttaatg cgtttggacc attttgctgg ctataaaata actgattaat  26820
ataattctaa cacaatgttg acattgtagt tacacaaaca caaataaata ttttatttaa  26880
aattctggaa gtaatataaa agggaaaata tatttataag aaagggataa aggtaataga  26940
gcccttctgc cccccaccca ccaaatttac acaacaaaat gacatgttcg aatgtgaaag  27000
gtcataatag ctttcccatc atgaatcaga aagatgtgga cagcttgatg ttttagacaa  27060
ccactgaact agatgactgt tgtactgtag ctcagtcatt taaaaaaatat ataaatacta  27120
ccttgtagtg tcccatactg tgtttttttac atggtagatt cttatttaag tgctaactgg  27180
ttattttctt tggctggttt attgtactgt tatacagaat gtaagttgta cagtgaaata  27240
agttattaaa gcatgtgtaa acattgttat atatcttttc tcctaaatgg agaattttga  27300
ataaaatata tttgaaattt t                                            27321
```

<210> SEQ ID NO 134
<211> LENGTH: 27321
<212> TYPE: DNA
<213> ORGANISM: Homo sapiens

<400> SEQUENCE: 134

```
aaaatttcaa atatatttta ttcaaaattc tccatttagg agaaaagata tataacaatg     60
tttacacatg ctttaataac ttatttcact gtacaactta cattctgtat aacagtacaa    120
taaaccagcc aaagaaaata accagttagc acttaaataa gaatctacca tgtaaaaaac    180
acagtatggg acactacaag gtagtattta tatatttttt aaatgactga gctacagtac    240
aacagtcatc tagttcagtg gttgtctaaa acatcaagct gtccacatct ttctgattca    300
tgatgggaaa gctattatga cctttcacat tcgaacatgt cattttgttg tgtaaatttg    360
gtgggtgggg ggcagaaggg ctctattacc tttatccctt tcttataaat atattttccc    420
ttttatatta cttccagaat tttaaataaa atatttattt gtgtttgtgt aactacaatg    480
tcaacattgt gttagaatta tattaatcag ttattttata gccagcaaaa tggtccaaac    540
gcattaagaa aacaaaagat aacttagctc tgccaaagta gcacctagga aaacagcact    600
```

-continued

```
tcagtaaaat ttctcctgct attccttata gcctattgca ggcaaacagc aacaacttca    660
aaaacatagg cagaaatgca agaaggaagt actcaaggaa ctattttctg tttctgaaaa    720
aaagatctta ttagttagta tattctctaa ggcattttat aatctcagag ttgcaatgat    780
tgccaaagca ggtacatggt aagacttagc aagaagaaaa caagatgaaa atgactgacc    840
agtgaaatct gaacttgttc caagtaatta gattttctaa ggagaaaaaa ggcacaggag    900
gtgcacattt caatttggct caaaaataat gaaaattaat ttaaaaagtt ggcaacaatt    960
actaaaacat aaaatacaat ttccttttac agagctcaac tacatagaat atcaacaata   1020
gcaagaacaa taaaataaac aaaacaccct aactgtggtt caccaggaac aaggactata   1080
gagaactatt agacatttct acagactgaa tcccagggac taaatccaca aagtaggatc   1140
taataatcaa ttccaattaa acatctgctt gatcaatttt ctttctaaag ctcatcctat   1200
gttcaagctc actttctttc tgtggaattg aaatcattta aaggctctag ttttcagttg   1260
attgcagaag tattacagta attctacaca ccaaagaatg ccaaaagata gaaagtcaac   1320
tatctgtaaa agccaactca gatttcacct tgacacatgt aaaccatgaa tcatgtattt   1380
caaaaaaaca gtagttgtgg tcaagtttac atcctattat tatatcttta aaagatagca   1440
ataatattta ttatattgta aacataggtc tgtatcccaa aagcataaat ctaggaaaag   1500
agacacccaa tgtaatgatg cacctgacat cccctcacag gctcttgtga gaactgtagt   1560
gtaacttact taactgcaat tgctgagagc agaattctgg agtatgatcc aggggaacgt   1620
ttccccacac cactgagcta ctttaccagc gatcatgatt gtgatggaat aggcttatta   1680
agttacacat ttaaaaagtc attagaacat ctcgttcttg cacactagtg tagaaaggtc   1740
ttccaaagat aaaagagtgt aggcctggtt taattttctc agccagagcc attattatgt   1800
taagatcgcc ctctgctgtt aaatcaaggt ctatcttcag gttccgaaga gatttaaagg   1860
gctttttttcc cttctgccta aaaataatgg aaaaaaaaaa aaaaaaaaaa aaaaaagaag   1920
cgcaaaaatt atgatataga aaatgtacaa aggaaacaaa acaaaaaaac aatgtacaaa   1980
ggtttttctt ccgtgtagga gttttactca cgtatcgtct tctatatatt ttattagtgt   2040
caaggctttt ctgtgaagga caagtagaaa ctgtgcaagg aaagtacttc tgagagataa   2100
gccaggtttc agctgaaaga cctgcaggga gaggaaccat ttcaacacat aatttgctca   2160
cattctactc gtacagaagt ttctatgaca gtgttgacag tgcttggcag acaatacaca   2220
ctaaacatct ccttaaccat ttccactgat gccccctaac aggagtgtgg tatagaagca   2280
ctaggtgtag gaacaatctg atattttttt tttttttga gacggagtct agctctgtca   2340
ccaggctaaa gtgcagtggc gcgatcttga ctcactgcaa cctacacctc ctgggttcaa   2400
gcgattctcc tgcctcagcc tcccaggtag ctgggattac aggcacacgc tgccacgccc   2460
agctaatttt tgtatactta gtagagacgg ggtttcacca tgttggcagg atggtctcga   2520
tctcctgacc ttgtgatcca cccacctcgg actcccaaag tgctgggatt acaggcataa   2580
gccaccaggc ccagacaatc tgacagtttt tagaagtttt ctaatttatc tttaaaaatg   2640
cattcaaatt ttgcattcta cttcagaata catccatgtt tacttcactt ttaaaactca   2700
tacataagtt atttcgtatt acttaatttt ttctgcccaa atcttcaaat aacattgaag   2760
ctcctagaag atgagcctat ggttttgaga cattcatata cctgtacttt tgcagggggt   2820
ggagtgggtg ggtaggagta gaatgtgtgc atatgatgag gtggagagtg ggagggattt   2880
tatgtcagct tgagaagcat gaaattccag gcctacgaat tttccttgaa cttcgcaata   2940
```

-continued

```
tgtcacagac ctcatagatc tcaatccaaa atttctagta aacataagga tctcattatt   3000
tcaaagcttt atctatgaca cagtttcctg gcctgatccc cagaatgtta ttataacaaa   3060
ctgtaatata ttaagaaata agttccatat aatctacgat ttccttcaac tgtgtaatta   3120
agtagatatt ttttaaaaga atgaaacaat aaagatgtta tttaaataag tacactatgt   3180
ttcaaaaata tttttgagtc atttcaggca aataaacaac ctccctttct caaaaaaaaa   3240
aaaaaaactt acttgttata ggttaatgct tgaattaaaa tgtttgttgt ttgacgtatg   3300
gaatgctgca ctcttaattg ttaatataca ggctcttccc cattaataag tcaaaaggaa   3360
aaatcattta gacactttag aaagaccaga cactacaaaa agcacctaat aaaacagatt   3420
aggactcaat tcttaattct atcattttat aaatgttaaa atatatataa aaaatatatt   3480
acactctatc atagagtata tgttatatat tttacatatc atatataaca tatactctac   3540
ataacataat agggttttaa gtttataact ttttttaat atataaacat atatatatcc   3600
tacaatgctg gtaatatgta tatatgctcg tactatatat atatacacac acaaacatat   3660
atatatactt gtactacata tatagtacaa gcattgcagg atatatatat gtatatatta   3720
tatctgtaaa agctaagtca gatttcactt tgatacatgt aaaccaggaa ttctatgttt   3780
caaaaaacag tagttgtggt caactttata tcttattatt atatctttaa aagatagcaa   3840
taatatttat tatattgtaa acaaaggtct gaattcccga agcataaatc taggacaaga   3900
ggcaaccaat gtaatgatgc acttgacatg ccctcacaga ctcttctgag aactgtagtg   3960
taactaactt aactgcaatt gctgagcaga actctggggc atgatccagg ggaatataaa   4020
tatatagaac aggcattgta ggatatatta aaaaagaaaa catgtcatat cattcactct   4080
gacaatctca agttcaacat ttacctgatc caggaaggct ttcactagag tgtctctgtg   4140
taagacatct tgaaaaatat tcctgaagaa aagaagaaaa tgaagaaaag aaaaaagttc   4200
aaatgttgaa atggccatat aatgctacct tccacaatcc ctcacttgag ccaacatttt   4260
aagttcttat aaattgatat tacatataaa cacatttgta agaatataga tatatatatt   4320
tggagacaca aaatatacat tcatttattt actcaaggat atatttacat tttactggtg   4380
tttgtcaggc taatatgtaa ttttttctct aaagaatata agcagtcccc agtaagggta   4440
tgtatgtatc tatcaatcta ttttactact ctcatctttt aaaaaaagta gagaccctta   4500
ggcaattaat aaataaaact accaattctt gccatctcaa aaaaaaacaa aaaacaaacc   4560
agcaacaaaa ataagccact accatcaaaa accaaaacaa accaaaaaat gtgaagaaaa   4620
atttgagtga gattagagaa cacactccga tgattatcca ctgggtttgc ctcaacaagc   4680
ccaccatctg taagtaacat gaaccaacta tccaagaaag tactacctac cttggcaacg   4740
accagagtga gtagtagtaa tataatggcc acttaaaata atgtgtgcct aacacagcac   4800
ctaggatata gcaggtgcta aagcaaacac acaaacaaac aggactactt attcccttcc   4860
caggccccac ctccctttca tctttttctc ttccattttc cctaggttct actcaggcca   4920
gagggtaaga gaacatttag taagaggagg agtttttaac tgaaagtggt agggatcatc   4980
ctatacctga ccagagtggc aaaaaaagag aatgggtatg tgtagaagca aacaggaagg   5040
tagttcaagt ttccttatct taagaaacga gtgtaccaca ctacagaaga aagaaaccgt   5100
aaaggggaaa aatattagca tttcgtcatt attgactggg cactgatagt gccccttctt   5160
gggctctgga aagagaataa ggcttatatt taatcgagtg gacttattat acctgttcca   5220
ctgaatgagt atcttcatca taagtgaatt agataaagca aggtgttaaa aaagaacatt   5280
tccatttgtt tgtgtcatct ctgatttctt tcagcagtgt tttgtaattc tcatagagat   5340
```

ctttcacctc cctggttagc tggattccta ggtattttat tcgttttgcg gctattgtga 5400
atgggactgt gttcttgatt ttgctctcac tttggaaggt gttggagtat agagaatgcc 5460
aaaactttgc tgaaattttt aacagattta ggagtttctg ggcagagact atgagatttt 5520
ctaggtacag aattatactg cctgcaaaca gaaatagttt gacttcttct cttcctatct 5580
gaatgtcttt ctttctttct ctttcctgat tgctctggct aggacttcca gaactatgct 5640
gaaaaggagt ggtgagagtg gacatccttg tcttgttacg gttctcaagg agaatacttc 5700
cagcttttgc ccatttggta agatattggc tatgggtctg tcatagatgg ttcttatttt 5760
tttgaggcat gttccttcaa tgcctagttt gtttaggatt gtttgtgatt tttctttttt 5820
gagacagggt ctcactccgt tgcccaggct ggagtgcggt ggcatgatct cagctcgctg 5880
ccaacctctg cctcccgggc tcaaacaatc ctcccacctc aacctcctga atagctggga 5940
ctataggtgc atgtcaccat accaagctaa tttttttttt tttttttttt tgtagagatg 6000
gggtttcacc atgctgccta ggctcgtctt gaactcctgg gcttaagaga tatgcccgcc 6060
ttggcctccc aaagtgctgg gattacaggt gtgagtcact acacctgacc tactgaaggt 6120
ttttaacatg gaggatgtta aattttattg acaacctttt ctctacctat tgagataatc 6180
ttgtggtttt tgtttttagc tctgtttatg tgatgaatca cacttattga tttgtgtatg 6240
ttgaaccaac cttgcatccc agggataaag cctacttgat caaagtagat cagctttttg 6300
atgtgctgct ggatttggtt tgctagtatt ttgttgagga tttttgcatc tatattcatc 6360
aaggatattg gcctgaagtt ttcttttttc tgttgtgtct ctgccaggtt ttggtatcag 6420
aatgatgctg gcctcattag ggaagagttc ctcctcctca attttttgga acagattgag 6480
taggaataat accagctttt ctttatacat caggtataaa gagatgacac aaacacatgg 6540
aaaaacattc catattcata gataggaaga attaatattg ttaaaatggc catactgccc 6600
aaagcaatct acagattcaa tgctattcct ataaactacc aatgatatcc ttcacaaaac 6660
cagaaaaaac tgttttaaaa ttaatatgga cccaaaaagg agcccaaata gccaaagcaa 6720
tcctaagcaa aaagaacaaa gctggaggca tcacattagc cgattttata ctaaaaggct 6780
ataggaacct gaacagcagg gtactgttat aaaaacagac acatagacca atggagaata 6840
gagagccaag aaataaagcc acacacttac aaccatctga tcttcaacaa agttgacaaa 6900
aaacaagcaa tggggaaagg actccgtatt caataaatgg tgctgggata attgctagcc 6960
ataggaattg gagtgaaact ggaccccttc cttgtgccat atacaaaaat caactcaaga 7020
tggattaaag acataaacgt aaaatctaaa attgtaaaaa ccctggaaga caacctagga 7080
aataccattc tggacatagg ccctggcaca gattttatga tgaagacgcc aaaagcaact 7140
gcaacaaaaa caaacacaaa tgggacctaa cgagctcctg catggcaaaa gaaactatca 7200
acagagtaaa agacaaccta cacaatggga gaaaaatatc tgcaaaccat gtatccaaca 7260
aagggatatg cagaatctgg aaggaactta aaactaatta acaagcaaaa aacaacccac 7320
cccactacaa actgggcaaa ggacatgaaa atttttcaga agaatatata cagacagcta 7380
aaaagcatat gaaaaaatgc ttaatatcac taatagagaa ttgcaaatca attctctagg 7440
aatggctatt attaaaaagt caaaaaatca cagatgttgg caaggttgtg gagaaaaggg 7500
aacacttata cactgctggc gggactgtaa attagtttag ctattatgaa aagcagtttg 7560
aagatttctc aaataactga aaatagaact accattcacc ctagcaaccc cattattcta 7620
tatgtaccta aaggaataca aatttttcta ccataaagac acatgcatgt gtatgttcat 7680

-continued

```
cacagcacta ttcatgataa caaagacagg gaatcaacct aaatgcctat caatggtaga   7740
ctggataaag aaaatgtgat acatatacac catggaatac tatgcagcca taaaaaccag   7800
atggagctag aggtcattat cctaagtgaa ctaatccagg aacagaaaac caactaccgc   7860
atgttctcac ttctaagtgg gagctaaaca ctgagtatac atggacacaa agaaggaaac   7920
agcaacacca gggcctactt gagggtggga gaagggtgag gatcaaaaaa ctacctattg   7980
ggtactatgc ttattacctg ggtaatgaaa tcacctgtac accaaaccct catgacacgc   8040
aatttacctg tataacacac ctgcacatgt acacatgaac ctaaaataaa agtcaaaaaa   8100
aaaattccag tgaccaattt ttcatgtatt ggcagtgact ggaattattt taaaaagtta   8160
aaattaaaaa taacaaacat aattaacatg taaaaacata tacttaaaag taaaatgact   8220
ctgtgacaat agacttaaca cacaatctag tggctgaaaa tactattttt tggacaattt   8280
tatgtttaga aaatttagag ctggatgcaa aatttaaaaa ttcaggatat tattttgtca   8340
tgatcagcaa aatgagaata gctgtctaac tgtagtttgt caaatcagca aaacaaacat   8400
agctggctaa aaatgattaa gaaatgttaa aatacacata catcctctaa aaaacaaaac   8460
aaaaatacca aatggttgca aacccattct gcagttcact aaatttcctc aaaaaagctc   8520
ccaagtaacc aatcaaaaaa cggaaaaaat actaagcact ttaggaaaaa agaaaatgtt   8580
tcaaggcaca gattaattag aaaacttcta catgtctact aaaatttacc aatatataaa   8640
aacttactga catgtaattt cagttggacc aattcatttt ctaaaacatt cccctactac   8700
tttctcaaga accaataaaa actctggaga actaggaaaa aatgggtcct atattaagtc   8760
atctttctgc accttgagat gtataaggct gggggtccct tgaacaagat attcctattc   8820
tatgcttttg gttaacactt actgtgtaat tactggtgct ccacaggtct gttacctaag   8880
ctcaaactga ttctgtagat acataggtca ggcttatttg ccccaatttt tctattgcct   8940
tacacactta gacctgggtt attacagtta acacttactg ttaccttcta tgtgccaggc   9000
attattgcaa gcattttttt tttttttttt ttaaataaga cagagtctcg gtgttcccca   9060
ggctggagta cactggcaca tcataactcc ctgtaacctc aaactcctgg gctcaaaaga   9120
tcctcctgcc tcagctttcg gaatagctag gattacaggc acacagaaac acattccaat   9180
aattcttttt tattttttgt agagatgggg tttcactatg ttgcccaggc tggtctggaa   9240
ctcctggcct caagtgatcc gcctgccttg cactcccaaa gctctgttct tacaggcatg   9300
agctactgtg ccttttttca actgataaaa gagaaacaca aaagtatact ataattcttt   9360
tcctgatttc agaacatctt ttaagtgttt acttagggtt ttaggattat agatttatca   9420
tcatcatttt ttttttcaag ttgggtccat gctcaacaat taattatcat tacttttcct   9480
tttgaattta ctgttcaggc tttttttttt aaaaaaaaat aagaagtgaa taacaatata   9540
aaatgcaaag taaaaaaatg ttccattaat atattttaac agttttgctg tattttatat   9600
tcatatgtca agaaaaaaaa gacttagaat tacttctttg gttttgttaa taagtccatt   9660
caataactgt tacataatag actatacaca atgtaggggc tggggctggg gctgtctggt   9720
tggccactat taagcccggt acctagaaca gtgcctagga gctcaatata tatttattaa   9780
acaaatagtt aaatatttac tttaagggtt aatcttacct attttagggt aaacacaatt   9840
gtatggaaaa agaagaacat ttaagaaaaa aatgcttgat taaatgtttc ttcaagcata   9900
attctgctgg taatatttct ttctttttaa atgcaacttc tgttttgttt ttattcgtaa   9960
aagacacaat ttcatattgc ttgactacag taccagcagg cagagcatta cgtacaaatc  10020
aggagtaaag ctttcgtcag tgtagatgat cgtatcctga gccatgtctt cttctgaagt  10080
```

ggctctccag aaggctgtca gctcggatct catgtatcta cgctgattat aaatatgttc 10140
atgacagggt ggcatctgct tcacagtatt gacatccaca tctatgtgtg tggtgggata 10200
tggagcatac atgacttgcc ggaaaggcag cacaaagctt ccagttgaat cctgtcaaaa 10260
taaaaggaaa atttactgtc ttacatgcca aacgatatga ataattgttt tttaatttta 10320
aaaaatggtc tctgatttag caaatccatc tctaaaaatt tatcctaaga agctattcat 10380
gagtgtgtgc aaagttttag tgacagaagt gttcagtata gcattggttt caatagcaaa 10440
acatcagaat gacctaagca tccaaaggaa gtggttaagt aaataaaaat gaatttatta 10500
tttggcatct atagatgaag ttgttgaagt ttgtgttgat attcaaagag gcttagaatc 10560
tgctgtgaaa aaagcagatt agaacatgca gagatgatcc agtgggggtg ggagtcttaa 10620
agaaaataca tgcaaaaggg aaaaaaagac tagaaagaga tataccaaat attaacagtg 10680
ggtattcact ggattcaaaa ttacaagtgt cttttaattt cttaattatt ctatgcacct 10740
caatgagtat gtatttttat aaaacaaatt tacttctttc ctaatcagtt ggggtagcca 10800
gttaccatgt aataataacc tactgcgtat gaggcactgt gctatgaaca gaacagaaga 10860
aagaggctat ttccattttt ttactattat aatgctgtga taatcatctt tgtataatgt 10920
caaaggtatt ttctggaaaa ctatatgatt tgtatttgca tggagaacta ttaaatattt 10980
tttcattaga tcatagtttt gaaatttcct ctaggcatct ggtataggtc cctttcagaa 11040
ctaaaattat ataattaaat gagagggtgc tgaggaaaca aaagtattaa gcactttatt 11100
atgcctttaa caggagaagt tctaatttac agatatgtat aactcaaata gaaactacgt 11160
ttcctttaac tagtttctat atttaaatac tatcattctg agttcatagc agcacattat 11220
tgaaaatgca caaaagccta atataacttg tatttgcaac aatttttaaa ttttttttatt 11280
tcattttgcc gtggctacat cctcaagaaa gtagtcacta tgagacaatc acataaccat 11340
taggaaagct atttcttcac gtcttgggac tataattgaa ataacaataa tagattcaac 11400
aaggtgaaca actttcttcc ctttaagtat tataaataat tgctaattta catttctctg 11460
ttttgctcct tgacagtaga ctcaaataaa agaaaaatac aattttttttc taatatatat 11520
tatatataga aatatatata ttttagtaca catacatagg aattgcttaa atcctataag 11580
cttcttaaag atgtttaaaa ttttttttca ataaaattca aatctattta gttaaaaaga 11640
aatgatctta tttttgatgt gcaacctgat ttaagcatgt gttaaaaaaa aaaaagtcct 11700
gaggctagac atgtaggaac agggacccac ctggaacaca aagggtattc tatggtgttt 11760
cactgatgat actaactata aatccataag acatatagtc tatgtgcaga actgtgtaaa 11820
ggaagtcagt ctctgggcat gtcaatatga gatacattaa atgctaatat ttaagatttg 11880
tctataaaga gtctcaaaaa tgattttaga aaagtggttt cacttgtgat aactagaaac 11940
tataccttta gcaggccttg tacaaagagc cctgactcat atttaaatga tgattctgct 12000
tcacataacc tggagcattt tctctctgct ggagtcagaa aaaggcataa tgttctgact 12060
atctataaaa gaaaatattt tagcattaaa acatgaagta aaaagaccac tgatttgctt 12120
atgaaagata tctgaaattt taattgttat tatcaataaa acatatccta agaaataagt 12180
attctttagt cacctggaat ccatgggatg taacagttgt tgcttaaaat agggattctg 12240
tggtcaaata aatttagaaa atgcttggta aatttactgt atggcatctc aaaaccttta 12300
acatttggct acatactgtg actcttcagg tgaattatat catctgcaga ctttctcaga 12360
cttatttgac catgcaactt ttatagcttc tgtttagtgg gtctacacat gaaattcgtt 12420

-continued

```
gtaagaaata tcaaagaatg tccagatcct ccaaaaagaa gagaattaat tattgaattt  12480
gatttaaaat aagcaggtca ttgggtggga tttagaaatc tgattctaat aatatttgac  12540
ctacagctct attaggaaaa ataaaaaggc atgtaactat cttgaaattc aaaccatatc  12600
cacagttatt atgttaaagg agtggttttc aacctagagt ggtggcaact tctttctcaa  12660
attaaaacaa gataaaaggt aagctattct ccctcaagag gatggaggat gggaaaaatg  12720
tttaaaaaaa aaaaaaaaaa cactccaact atggagcctt tctcccttca taaagcagct  12780
cggcagtcac tctgtgcaac ctaaggcttt ggagatcaca gatggaaagc cacctgtttg  12840
aggtaacaga aggaataagg tcactagttc gtagatgcaa tataatgaca caggtatact  12900
aagctctcat aaatggttat atgagaaata taaattaagg ctcatgtaaa tatacaaagt  12960
agctgattac aaaaaaaaat tatgaatatc tttgtaaagt atcatttcca acatatttcc  13020
tatgtaaaac ttttttttaaa aaattaggtt tgctgaaatt gaaagataca catacttatc  13080
tctgaactct ttctaactaa tggtcagtga agaaaagtgc aaaatccttt agtttattag  13140
ctaatgcttg gaaatgtaac tgttcattaa tccttaatta actcaagtag cactgaagga  13200
aagggtcaga aacattactg aataaagtat aataatcaat gaccacttaa tcccaatagc  13260
tccctagaag ggacagattt agaaggaaag cgaagacaat gaaatcaaga tgaataaaca  13320
aataacattt ctttggaact actaccaaaa gtacatgact atcttcagat ttgttaaaga  13380
taacattggg aaatagaaga gtaatttttt ttatatatct gattttaata tattctcaaa  13440
accatttata cactactgac actggtattt ccgagctatc aaaataaact gataaatgat  13500
tcttactcag tttatttcaa actcactgtt gccacaaggt gtcttagcaa tttgatgaga  13560
ttacattgcc tccttatact actagatcat tttaattgca acctaccatt taaatgacaa  13620
tccatgatat atcatcagtc ttaaagagtc aaatcatttg ctagattata aaataaacta  13680
ccttatttac tttctctgca ctgctaccta ctacaacgga acagccacag gtttgcaagt  13740
gtgagctgat ggcactgtaa gttaaagaaa acagattaaa aacattgcct ataaaacaat  13800
ttaacaaact aaaaacaaaa aaaagtaggt gagctcttca aataactcag aatagcttta  13860
tatgataaac accgaagcta taagcacaat gttatctttt atttgtatag gaacctacat  13920
tttctagaga cctttcacag aaattttctt attgagcctt aaaacagccc aattagtcag  13980
tataatatca tttaattaat gtatttattt attgaaatac catcatttta tagctgaaga  14040
aattgacatg tagagagatt aagtgactta cttaaagtca aatgggattt aaaatgatgt  14100
atgaaaggct gacactgaac agatacagga ctaaagtgct tctgattcaa gccattaagg  14160
ctcttaggtt aaacacactc atgcctctga tactccatca tgagcctaaa ggaaaagact  14220
gtgaacataa aagtgaatac tttatacttt tacttctctt ttattaaaag taaaatttca  14280
tgaaaatctg taactgtgaa gaaactttaa aacagaatat aagataatac atgtaaagca  14340
actagtaaag gaactaacat gtaggcactc aacaaatact ggctatttct agaagaaatg  14400
taaataggaa atgttagcta tgagctatta ttaagtgttt ttatgttcca ggcactgttc  14460
taagtgcttt atattattta tcttactcaa tgcttataac aaccctacac attaggtact  14520
attactatta ttgccatttt acagatgagg aaataggtgt atagagaatt caggcacctt  14580
gcccacgggt acacagcatt aatccaggga gtctggttta agggcacaaa ctcttaagta  14640
ctaaactcca ctgctggatg gaaaaagatc agtataaata tgaataattt tgttctacgc  14700
ctaaataact taagttcatc tacagtacaa cttaatatga aaggattctg ttagctttaa  14760
tgagaagtaa aacaagaaac cagaatcaag caaggggcca tgatttcttg tctgggatgg  14820
```

aaactcggtt tctttaaata gcaaatggaa taacaccaaa tatatataga aatataatga 14880
gtgaaaaata acacaaattt aagcaacagt tcaaatacgt aatgtcccta gaacaatcta 14940
agtagacagt ctgttatttt ctttcttcca aatcttgtca taggtgagca taagatggta 15000
tctgcttcat ccagctttta tgaaaagaaa aattcttact tgagaagaaa gccttcatga 15060
cagctgtcac caatatcatc atcattgagt actgtatcag ctatctaaaa tgcatcaaaa 15120
aataaaaaaa ttagtctggc tgtaacatag tgttgaaata acacttttaa tatacaagtt 15180
ttcggaagtc tggattcaat ataacacact gccttcattt ccgagaatca agactcccca 15240
aaaaacaatc tctgtgcact accataaact tcagaagaac aaatgtgaaa gctggtcaag 15300
caggttaaac aatttttaca agaacaactt cctcttctga gctgtcagaa tcaggagact 15360
aacctaaatg acaaaatcag aaaacaacaa gaatagtttc ctaaaggtat ctcttaacac 15420
tcatagtgtg tgattcaaaa cgtcctcaac aaatgattaa ggaaactaaa tttgtgacta 15480
caagtaaact tccattaatg gttactactt tggcacacag ttttgtttca aaagacacta 15540
cattaaatat taattgctcc tataagagct gggatcctcc cacttttagg aattataaaa 15600
gtaatgaaat aaacaaaatg aatttaattt tgtcatcact gatcaaaaat gcctctgttt 15660
tgccataaaa tccaggattt tgtgtgtgct tatttgctaa agtggctaat actgtatgtg 15720
aatagtatgt atgacaaagt ccttactatt aaaattagaa tattaataat atacataata 15780
atactataac cccaaaaaac tcataaagtg tataattgct ctcatttaaa cttacatcta 15840
tttcttcagg aacactgtgt gatttcatag atgaaagcag ttccattaca ggaatcactt 15900
ctccagtaag cattggaata atactctgac cctgcacaat aaagtgacat gaagtgaaga 15960
aaatcacgta atatgagaga agctgggcaa taaaaaataa aaataacatc aaacaataac 16020
attctttgat gaaaatactt cgtaatttgt tcaaacacag tatcaaacaa gtctactaca 16080
tgtctaaagg atttatatgc aatccaaagc tcacttttat tctttctttt cttttttttt 16140
ttttgagatg gagttttgct ttcattgctc aggctggagt gcaatggcgt gatctcagct 16200
cactgcaacc tctcctccca ggttcaagtg actctcctgt ctcatcctcc caagtagctg 16260
ggactatagg tgccgccacc atgcccggct gatttttgta tttttagtag agacggggtt 16320
tcgccatgtt ggccaggttg gtgtcaaatt tctgaccatg cccggcccta aagctcactt 16380
ttattcttta gagagtatgg aatcattggt ttatcgttta ctgttacatg caatgattaa 16440
gtcatcatgc ctcttttaga aaagatctcc tttaaaattt gagataaaaa aaatttgtta 16500
aaggtcatca atatatttca tatttaaaaa tgaggaaaac caagcacaaa aagactttga 16560
aatccttacc aaataggtaa ggaaaacttg aatcaatacc taacctccat actcataaaa 16620
gtataatcta cccaaatgca aatcaaaatc agcacatata ttttaagaat caataaaaca 16680
gaaaaattcc ctttagagct atttcaagat attactactt attacatctt gaaattgtaa 16740
ttttgaaatt tgtagtctat agaatcaaac tgaaaattca gtataacaca tcacaaatgt 16800
aaagtgtctc aaatatggat ggtccctcat ttattcacta ccaccaccag tctcatcagt 16860
tttgtgacca acttggttaa gtaaattttt tgagatataa atgaaattgt caaatgacta 16920
tgcattttta gctaaacata ttttttaaat catacattat ttaagatgaa tttaatacta 16980
gttgtttttc ctcacttatt ttatgaaatg attttactca aagtcttcat aagcatcttt 17040
aagttagaat ctttgtcaga cccagggcca tttttggagt aaccttaacc agtttttcag 17100
agccccatat tattaagttg cttgagaatt taaatgtgat gctacttctg gaagttttat 17160

```
cctaagccat atgcccattt gcataatgct gaaagtttta tttaaaaaaa aaccatcctt  17220
tagtaacctc cacaactaac tattcactgt ttttagtttt taaagtaata attatcatgc  17280
ctgtttacaa ttacaattca cacattcaat ctaacaagaa taatgactag atccgtgtta  17340
aatttccttc cctgtgaagc aattttatca gatgacagct acaactgaag ttgtttcaaa  17400
ctaatgcatc atccccaaac agtattgttc aaaataaagt cgttgtgaga tttgcaagaa  17460
ctcaatcaaa aggcaactcc tccttttcgg gaagaataat tttgggaaaa tatttcctct  17520
taggtttaag catacatagt atttcattca cagtatctca gacattatca gtataagtga  17580
atgaatagcc tcactgaagc tcaacaacac caaaaaaaaa aaaaaaaaaa aaaatcctac  17640
agggctaaat acagaagagg ctctaaaaga aaatctctta agtttctatt cctccttgta  17700
cttcccaaac ttgaacttct cagcagtaag ataacatttt taagaagagc acttaaaaga  17760
gagaccaaaa ttcattaata gtagtcaact taagtaaagg tttctggttt gaaaaaacaa  17820
aatcccagta aaagcagaat tttagttggt tctaagtttc ctcaacttgc gataagttta  17880
cttaattagt ctactaataa ctagtgggtt agagggtgct gaaagttacc ccattcctgg  17940
ggaccctgct tattgaccag caaataagga ctgggattct ttgggtaaag ggaaatcttt  18000
tcttgttaag tcagaccttt acacagaata actgtctctg aattggaaag ctatctacaa  18060
aagtacaaac ataacaattt ggtaaaggag atcattgtat tgggttctgt attatggcca  18120
tgtattttca caagtttttt tttttaatta ctttttaaa gtatcatctg tctcattcat  18180
gctaaaaaga agcaaagaaa ggcaaaacag ccatgtttaa aatattggag ttttacaagg  18240
agcattgagg gtcacccaca agaggaaatg gaagtaaaag tgaagaactc tttcttcact  18300
ggagattctc cttcaaaaga acttctctgc tttacagtga aatagtctgt acttagtttc  18360
cgcaggggaa gccacaccct tgtaaccatg cttctcaaac tcttagtgtc tgttcctgag  18420
gggcattcaa agccaaggga taaacatggc acattttcct agaggagagg gtaagaaata  18480
tcactgacaa attttaatac taaaatagtt atggaataaa atgtaaattg catgagtctt  18540
aacgatacaa cataagactt agaagaaata ttgtgtggac ctgggcctac accccagaca  18600
gatacctcag ggtacatat gctctccttc tgttacagct acttctaggg aaaggttcga  18660
gaagtagtac cttaaagaac atatcagaga caattttttt tatttttact atgaacaagt  18720
tatccaaaat ttattctggg caaacagaaa aaaaaaggga gcaaatatta atttgtagat  18780
gcaattacta ttttcctttg tttactgatt taactctttg ggtttaagat atggaaatct  18840
tcctccagtt tattctgtac acctccataa aagctccatt aaaggcttat tcgtatgtct  18900
ccaaggcctt gacaaatgta gccatcaacc ttatacagat acatgctgtg agaaaaacat  18960
ttgacagtat gcaatttgca tatacctgat cttccattct ctctgtgcct tctaagataa  19020
tcttctggac attttcttgt ctttcctgag caagagaaaa tttatttaaa aaaacaaccc  19080
acaacatttt gatacttgct tatttttcaa tagacatgtt cttgtgtagt aatttagttc  19140
acaagaaaaa tactttctac tttagggaaa aaatgggggc aggggtagga aattaaccca  19200
acaaatgcat gttctcataa acaatacaaa ataaaatcaa aacaaccttt attctgcagt  19260
gaaaaaaaga taacttcaca gaaaacagtc aatgtaacat ctgcatagtt tcaaaaagga  19320
aaagaatgac ttgcactttt caaattaaac attatgatgt tgtttaaaag attctcctga  19380
ttttaagagt ttcataatgt gagaaaaaag gaagtaagcc tgcaaacata gtaaaaaatt  19440
attcttttaa aagatattat ttttccttac tattgggcaa aagcctttta aaactggtaa  19500
tgcttaatgg actttcaggt tagtatcaaa ctggaacaca ggaaggagaa ttcaatgtgt  19560
```

```
tctttagata catcaaaact atactgaaat gtaaatagca ttatatattc aactacagga  19620
tttaggaaaa caataatttc tgtaagatta aaaggaattc tcttgggaac cattccattc  19680
aacctcctca ttttatgaac ctgggaactt ggcaaagagg ttaaagagac caaaggctac  19740
atgaccaaca gcttatgaaa ctattacttt gaactgttat acttacacat agtagtaagc  19800
aaaagacaga attgtgcaat gaaagggaaa caaaaggtat tagagtcaaa ggctcccaag  19860
aagaatccag ggtctaaaag tttctttatt tgtctaagct ttagcttttc atctataatg  19920
tggagctacc atttcgtacc ttccacagtt aatatgaaga tgacaggtat cagaccagat  19980
gtatttgtat ctaatagggt aaatgcaaaa taaataacat ttattgtttg atgttcactg  20040
catataatta aaaaaataag atttatatgt accagaaaat aagctttcaa cagataggtt  20100
aacatgatta ataagctgaa aaatcactta ccttatgcat ccatattctt cctttccgga  20160
ttatatgtgt taatctatca acacacactc tatgaagtgg gaggtagaaa ctaagttctg  20220
tctgtggaag tataattgat agtccatatg tgctgcgatc cccattccag tttccatcaa  20280
agattaatga aacaataatc actccctttt cagacaagac aaaaaacttt acatctatag  20340
caccactctc tgcatttcga aggatttctc catttagagt gtggttggca agaaaagtta  20400
tttctccatc actgagaagt acctgttctg tctttggagc ccaaatgtgc cttactctag  20460
gaccaagaat attgtcccag taagcaaaag tagctgctaa taaaggtgat ttgccactta  20520
aagcaatctc tgtcttggca acagctggag atggcggtgg gcaaagagtc gacatcactg  20580
cattccaact gtcacattat ccaaatgctc cggagatatc taaacaatga catatgaaac  20640
caatgattag gttcagcaat ttaaagatat ccatcaaaac cccaaatgat ttagacatat  20700
ttggtttgtc ctcttaagtc aaagatgtgg aatcctgtta tctcctatca ggataaagac  20760
attcaactag cacagtaggt gcacattaaa tgtttgttga tatgatcatt ttacaagaca  20820
tggtaacttg ttacttatat tcagggcata catttagaaa ttcaaagaaa taacttaaaa  20880
aagggcttct ttacactgat attaaatgtt acatactaaa gctcatagaa tagacccgca  20940
gtattcccaa atatccagtc catgtgcaat tctagtatga ctggagattt ggcccctaac  21000
ccatagcaac taaaaaggag aaaaacagga agggaaaggc tcagctagag actgacactt  21060
gtgggttgaa ttgtgtcccc caaaaagata tgttcaattc ctaacccttg gtgtacgtga  21120
atgtgacctt atctagaaat aagtgtaatc atgttaaaat ggggtcatac tggattagag  21180
tggggcctaa tccaataact gctgtgttta taaggagaga gatttggaga cacagagaca  21240
aatggtagac agccatgtga agacaaaagg cagatactgg attgttgaaa ctacaaggca  21300
agaaaggaac actcaggatt gctggtaacc accagaagcc aggaagaggc aaggaaagag  21360
tcttctctct tgaagatcat gcccctgtca acactttgat ttcggacttc tagcttctag  21420
aattgtgaga gaataaattg ctgttgttta aagccactca gtttgtggtg ctttgttaag  21480
taatcttaga aaagtaatac aacacctaac aacagaaata ctttaaagcc gctaaaaggt  21540
caaaaaaaaa aaaaaaaaaa aagacatgga aataccacaa gtctggagcc ataacaaaaa  21600
atgggcaaac agtcctgtat cctcagtgaa ctctctggtt atgagaatac tgaagcccga  21660
tcctgatgtt taaaacgaca ttgaagtatc aagacaaaga taaaaatatt taatatgcta  21720
gccaagaaac caatacagca tttcatcact gcaaagagag ttctacacta aatggctaga  21780
atttaaaagc tttagttatt tagaacacgt agaaaacaga agggctaaat agggcccgtt  21840
caagcctttg aatttaatga gaaaacagac atgaggagaa gaacataaac gctcacatcc  21900
```

aagacagaac ccagggctct tggtcccctt gctcaacttg tacatcttaa tccacataaa 21960
cataccactc taaaaaggta catcctatgt gatattaatg taaaacaaat cattcttgca 22020
aatacagtta tgtgccatgt aacgtttcag tcaatggtag actgcatata tgatggtagt 22080
cccattagat tacaatggac ctgaaaatat gctattgcct tagtgacact gtaaccatca 22140
taaggtctta gtactatttt gcaagttatt taaagtatag cacatacaat tattacagtg 22200
tacaacactt gataataaac tactacattg ctggtttatg tattcactat actatgcctt 22260
ttattgttat tttagagtgc actccttcta cttttttttt ttttaagtta aatgtaaaac 22320
agcctcaggc aagtccttca ggaggtattc aacagaaagc actgttatca taggtgacag 22380
ctacatgtgt gttattgccc ctaaaaacct tccagtggga caagatgtgg aggtggaagg 22440
cagtgaggtg gaagggagtg atactgatga tcctaatcct gtctatgcct aggtgaaagt 22500
gtgtgtgttt tagtttttaa caaaaacgac taacaagtaa aaaaaaaaat ttaaaataga 22560
aaatagaaaa aagcttctag aataaggata caaagaaaaa atatttttgt atagctatac 22620
aatgtatttg tgtttcaagc taagtatttt aaaagttaaa aaattaaaaa gtttacaaag 22680
ttaaaaagtt ataatttttt attgaagaaa aactgttaag ataaatttgg tgtagcttca 22740
gcgtactgtg tttatagtct acagtggtgt acagtgttct aggccttcac attaattcac 22800
cactcactca ctgactcacc cagagcaact tctagtcctg caagctccat tcgtggtaag 22860
tggcctacac aggtatacca ttatctttta taccatactt ttactgtacc ttttctctgt 22920
ttgcatatat ttagataaat atttaccact gtgttacaac tgtctatagt attcagtaca 22980
gtaacagttg tacaggtttg tggcctagga gcaacagact ataccatacg gcctaggtac 23040
ataaaggcta tactatctag gtttgtgtaa gtacactcta tgatgtttgc ataatgacaa 23100
aatcgcctaa tgatgcattc ctaagcaatg tgtgattgta ctataattga agacttgtta 23160
tctaagactg aaagtaaaaa gaattgcaat ttcacctaag caagtctaaa actgtgaagt 23220
ctatttataa taatagcaat acaaagcagc taataggcaa actatgatat acctatcttt 23280
gccatatgat tgctttggga gctaacattt gatctgtaaa tgtatgacaa agtaaacaat 23340
tttacttaaa gaatttcatc cacatcttgt caagagagtt cagtctgatg gaaagcactg 23400
acttctattt acagagcatt agatgagtgc ttttatcata ttatgagtag gcatacagag 23460
cctggcaaaa cagttaactc taagtatgta cagaaatggt tgaacacaac gacagtttta 23520
acacgtgtat ttgtaatttc aaaaattcat ttaggtaata tttactttta aatatgttgt 23580
atcaatttaa tagtcttaag agacagcact agatataagc cgtacagctt ctttaaaata 23640
tccactgttt ttaatacaat gtaagcagtc agtttacaat gatcaaatat aggaatgtaa 23700
tctgaattga aatggtaatg acactactgc tgtcataact aacaacagca aactggaggc 23760
caacataatg aattaagtta acatacaacc ataaaattat attgcaaaca tatttttctt 23820
tcattctttt aggttaaaaa ggtggataat cataaaggca atattacaac tctaatattt 23880
catcattaaa ctgaaaataa aagtatttcc taaaacagaa ctgaaccctg gagcaaaatc 23940
tgattgaatt atagggaaac ttttaccacg ttgtgaaaat tgaactatta tactgctagt 24000
tacactctca ctcctaacag aataagaaaa aaaaaatggg ccgggcatgg tgggtcacac 24060
ctgttatccc agctctttgg taggccgagg caggtggatc acctgaggtc aggagctcaa 24120
gaccagcctg gccaacatgg tgaaacccca cctctactaa aaatacaaaa aattagccgg 24180
gtgtggtggt ggacacctgt aatcccagct actcgggagg ctgaggcagg agaatctctt 24240
gaacccggag gtggcagagg ttgcaatgag ctgagatggc gccactgcac tccagcctgg 24300
gcgacagaga gagactctgc ctcaagaaaa aaacaaacaa acaaacaaac aaaaagaata 24360
agaaagaaaa tgaaggacaa agatcatact gaattgctta gttttaaatc ctaccaaaag 24420
aaatagcctg ggaaatgaaa tgtcacagag aagtataatc aggagagctg tacaattatt 24480
ttactaatac ttgaagtcat cgtctttggt gagaaaaatc catacatgca aatgcagctg 24540
aaaaaaatca gctcaaaacc aatagttgtt tatgtaccta tcttacgtac atgtagtgct 24600
gtctactcca gagagttacc aaacattagc cagtcttttg agggaagcca agattcaaat 24660
tgagtgagac ggtggcttgc tcacagggtt catgagaggt ttcccaatac actttctgga 24720
aataatccca tacatgcaga catgattaca ttaattaaca tctgctaaaa ctgttagtag 24780
agtgctaagt ttgaggtttt gctttttctt taaacgtctg ttaaaaaatc aaccatctct 24840
tccctgattg gtatttagaa aggtggttgg tccactgcta ttgtagtgaa aattctacaa 24900
tcataaagcc ctcacttctt gtttttttaga gacagggtct cgttttgtca tccaggctgg 24960
aatgcactgg caggatcata gctctcggta acttcaaact cttgggctca aatgaccctc 25020
ctgcctcagc ctcccaagta gctaggacta caggtgcaca tcaccacgcc cggctaagtt 25080
tttaattttt tgtagagaca gggtctacgt tgcccaggtt gagcttgaac tcctggcttc 25140
aagtgatcct cttgcctccg cctcccaaag ctctggcatt acaggtgtaa gccaccttct 25200
ccaacctggc tctcaatact tgtaaccatg ctgtttattt tctcccagcc caaagagaag 25260
caggatccta aaccgtccac tttccacaac aggagctgcc caggaccact tcaaggacag 25320
tgaactgttt acagtaccag aaagttcaca acactttctc aatcttcaac atcagggaag 25380
actggaaggt gaagttcata tcactatctg gccatttctc acagttccaa gtttctcaga 25440
caataggtag gctaacctag tcctcctggg aactatctaa ttaacgtaga atagaacccg 25500
agggcagact tgaaaaacag aagtcctcct tggtttactt tgtttctctg aaagcaaatt 25560
gtggagtgcc aacatagcca aacaaaatat tttatcaact tcataaggtg cttgtaattt 25620
tttcctggag caggtaaatg ctggcttagt gaacaatctg gaatgtggta attactctcg 25680
ttcttgtttc agatgtacta tcagcatgta gcagtttcca actgattcag ggttttccta 25740
aagtggcagg ccttggcaga ggtggtgaca acaatgcccg tgtcaaatga caccgtattt 25800
caagtattct gactccaggt tattaatatc ccctatatga tagtcttgtt tctgtgatat 25860
tcacagatta tgttaaaagt ttcccaaagt ctgagaaaaa tcatatctta acagtatctt 25920
tttttttttt gatcctttgt acaaaagtag aagtaatgcc agacagatta cgtacccttg 25980
ttgtgaacaa ctggtgcatg gcaactgttt gaatagaaat ttaccaactg ccacaaccag 26040
gcaactactc tcccagagcc taacaatctc gattgcatct gaaagggcca cccctcctgg 26100
gaaagtgcag gacctccctc ctgtttctga atacaaagcc tggtggtgtt caacgcggcc 26160
agatagaccc aatgagcaca cggacatgta atctgtgcac ttctttagac aactgattac 26220
catcagtcaa gtgatgccca agtcacaata gtcacttcct ttaagcaagt ctgtgtcatc 26280
tcggagctgt gaagcaacca ggtcatgtcc cacagaatgg ggagcacacc gacttgcatt 26340
gctgccctca tatgcaagtc atcaccactc tctagaagct tgggctgaaa ttgtgcaggc 26400
gtctccacac ccccatctca tcccgcatga tctcctcgcc ggcagggacc gtctcgggtt 26460
cctagcgaac cccgacttgg tccgcagaag ccgcgcgccg cccaccctcc ggccttcccc 26520
caggcgaggc ctctcagtac ccgaggctcc cttttctcga gcccgcagcg gcagcgctcc 26580
cagcgggtcc ccgggaagga gacagctcgg gtactgaggg cgggaaagca aggaagaggc 26640

```
cagatcccca tcccttgtcc ctgcgccgcc gccgccgccg ccgccgccgg gaagcccggg  26700

gcccggatgc aggcaattcc accagtcgct agaggcgaaa gcccgacacc cagcttcggt  26760

cagagaaatg agagggaaag taaaaatgcg tcgagctctg aggagagccc ccgcttctac  26820

ccgcgcctct tcccggcagc cgaaccccaa acagccaccc gccaggatgc cgcctcctca  26880

ctcacccact cgccaccgcc tgcgcctccg ccgccgcggg cgcaggcacc gcaaccgcag  26940

ccccgccccg ggcccgcccc cgggcccgcc ccgaccacgc cccggccccg gccccggccc  27000

ctagcgcgcg actcctgagt tccagagctt gctacaggct gcggttgttt ccctccttgt  27060

tttcttctgg ttaatcttta tcaggtcttt tcttgttcac cctcagcgag tactgtgaga  27120

gcaagtagtg gggagagagg gtgggaaaaa caaaaacaca cacctcctaa acccacacct  27180

gctcttgcta gaccccgccc ccaaaagaga agcaaccggg cagcagggac ggctgacaca  27240

ccaagcgtca tcttttacgt gggcggaact tgtcgctgtt tgacgcacct ctctttccta  27300

gcgggacacc gtaggttacg t                                             27321


<210> SEQ ID NO 135
<211> LENGTH: 2700
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 135

ggggccgggg ccggggccgg ggccggggcc ggggccgggg ccggggccgg ggccggggcc     60

ggggccgggg ccggggccgg ggccggggcc ggggccgggg ccggggccgg ggccggggcc    120

ggggccgggg ccggggccgg ggccggggcc ggggccgggg ccggggccgg ggccggggcc    180

ggggccgggg ccggggccgg ggccggggcc ggggccgggg ccggggccgg ggccggggcc    240

ggggccgggg ccggggccgg ggccggggcc ggggccgggg ccggggccgg ggccggggcc    300

ggggccgggg ccggggccgg ggccggggcc ggggccgggg ccggggccgg ggccggggcc    360

ggggccgggg ccggggccgg ggccggggcc ggggccgggg ccggggccgg ggccggggcc    420

ggggccgggg ccggggccgg ggccggggcc ggggccgggg ccggggccgg ggccggggcc    480

ggggccgggg ccggggccgg ggccggggcc ggggccgggg ccggggccgg ggccggggcc    540

ggggccgggg ccggggccgg ggccggggcc ggggccgggg ccggggccgg ggccggggcc    600

ggggccgggg ccggggccgg ggccggggcc ggggccgggg ccggggccgg ggccggggcc    660

ggggccgggg ccggggccgg ggccggggcc ggggccgggg ccggggccgg ggccggggcc    720

ggggccgggg ccggggccgg ggccggggcc ggggccgggg ccggggccgg ggccggggcc    780

ggggccgggg ccggggccgg ggccggggcc ggggccgggg ccggggccgg ggccggggcc    840

ggggccgggg ccggggccgg ggccggggcc ggggccgggg ccggggccgg ggccggggcc    900

ggggccgggg ccggggccgg ggccggggcc ggggccgggg ccggggccgg ggccggggcc    960

ggggccgggg ccggggccgg ggccggggcc ggggccgggg ccggggccgg ggccggggcc   1020

ggggccgggg ccggggccgg ggccggggcc ggggccgggg ccggggccgg ggccggggcc   1080

ggggccgggg ccggggccgg ggccggggcc ggggccgggg ccggggccgg ggccggggcc   1140

ggggccgggg ccggggccgg ggccggggcc ggggccgggg ccggggccgg ggccggggcc   1200

ggggccgggg ccggggccgg ggccggggcc ggggccgggg ccggggccgg ggccggggcc   1260

ggggccgggg ccggggccgg ggccggggcc ggggccgggg ccggggccgg ggccggggcc   1320
```

gggccgggg ccggggccgg ggccggggcc ggggccgggg ccggggccgg ggccggggcc 1380
ggggccgggg ccggggccgg ggccggggcc ggggccgggg ccggggccgg ggccggggcc 1440
ggggccgggg ccggggccgg ggccggggcc ggggccgggg ccggggccgg ggccggggcc 1500
ggggccgggg ccggggccgg ggccggggcc ggggccgggg ccggggccgg ggccggggcc 1560
ggggccgggg ccggggccgg ggccggggcc ggggccgggg ccggggccgg ggccggggcc 1620
ggggccgggg ccggggccgg ggccggggcc ggggccgggg ccggggccgg ggccggggcc 1680
ggggccgggg ccggggccgg ggccggggcc ggggccgggg ccggggccgg ggccggggcc 1740
ggggccgggg ccggggccgg ggccggggcc ggggccgggg ccggggccgg ggccggggcc 1800
ggggccgggg ccggggccgg ggccggggcc ggggccgggg ccggggccgg ggccggggcc 1860
ggggccgggg ccggggccgg ggccggggcc ggggccgggg ccggggccgg ggccggggcc 1920
ggggccgggg ccggggccgg ggccggggcc ggggccgggg ccggggccgg ggccggggcc 1980
ggggccgggg ccggggccgg ggccggggcc ggggccgggg ccggggccgg ggccggggcc 2040
ggggccgggg ccggggccgg ggccggggcc ggggccgggg ccggggccgg ggccggggcc 2100
ggggccgggg ccggggccgg ggccggggcc ggggccgggg ccggggccgg ggccggggcc 2160
ggggccgggg ccggggccgg ggccggggcc ggggccgggg ccggggccgg ggccggggcc 2220
ggggccgggg ccggggccgg ggccggggcc ggggccgggg ccggggccgg ggccggggcc 2280
ggggccgggg ccggggccgg ggccggggcc ggggccgggg ccggggccgg ggccggggcc 2340
ggggccgggg ccggggccgg ggccggggcc ggggccgggg ccggggccgg ggccggggcc 2400
ggggccgggg ccggggccgg ggccggggcc ggggccgggg ccggggccgg ggccggggcc 2460
ggggccgggg ccggggccgg ggccggggcc ggggccgggg ccggggccgg ggccggggcc 2520
ggggccgggg ccggggccgg ggccggggcc ggggccgggg ccggggccgg ggccggggcc 2580
ggggccgggg ccggggccgg ggccggggcc ggggccgggg ccggggccgg ggccggggcc 2640
ggggccgggg ccggggccgg ggccggggcc ggggccgggg ccggggccgg ggccggggcc 2700

<210> SEQ ID NO 136
<211> LENGTH: 16
<212> TYPE: PRT
<213> ORGANISM: Unknown
<220> FEATURE:
<221> NAME/KEY: source
<223> OTHER INFORMATION: /note="Description of Unknown:
RFGF peptide"

<400> SEQUENCE: 136

Ala Ala Val Ala Leu Leu Pro Ala Val Leu Leu Ala Leu Leu Ala Pro
1 5 10 15

<210> SEQ ID NO 137
<211> LENGTH: 11
<212> TYPE: PRT
<213> ORGANISM: Unknown
<220> FEATURE:
<221> NAME/KEY: source
<223> OTHER INFORMATION: /note="Description of Unknown:
RFGF analogue peptide"

<400> SEQUENCE: 137

Ala Ala Leu Leu Pro Val Leu Leu Ala Ala Pro
1 5 10

<210> SEQ ID NO 138

<211> LENGTH: 13
<212> TYPE: PRT
<213> ORGANISM: Human immunodeficiency virus

<400> SEQUENCE: 138

Gly Arg Lys Lys Arg Arg Gln Arg Arg Arg Pro Pro Gln
1 5 10

<210> SEQ ID NO 139
<211> LENGTH: 16
<212> TYPE: PRT
<213> ORGANISM: Drosophila sp.

<400> SEQUENCE: 139

Arg Gln Ile Lys Ile Trp Phe Gln Asn Arg Arg Met Lys Trp Lys Lys
1 5 10 15

<210> SEQ ID NO 140
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 140
ggggccgggg ccggggcc 18

<210> SEQ ID NO 141
<211> LENGTH: 552
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 141
ggggccgggg ccggggccgg ggccggggcc ggggccgggg ccggggccgg ggccggggcc 60
ggggccgggg ccggggccgg ggccggggcc ggggccgggg ccggggccgg ggccggggcc 120
ggggccgggg ccggggccgg ggccggggcc ggggccgggg ccggggccgg ggccggggcc 180
ggggccgggg ccggggccgg ggccggggcc ggggccgggg ccggggccgg ggccggggcc 240
ggggccgggg ccggggccgg ggccggggcc ggggccgggg ccggggccgg ggccggggcc 300
ggggccgggg ccggggccgg ggccggggcc ggggccgggg ccggggccgg ggccggggcc 360
ggggccgggg ccggggccgg ggccggggcc ggggccgggg ccggggccgg ggccggggcc 420
ggggccgggg ccggggccgg ggccggggcc ggggccgggg ccggggccgg ggccggggcc 480
ggggccgggg ccggggccgg ggccggggcc ggggccgggg ccggggccgg ggccggggcc 540
ggggccgggg cc 552

<210> SEQ ID NO 142
<211> LENGTH: 1800
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 142

```
ggggccgggg ccggggccgg ggccggggcc ggggccgggg ccggggccgg ggccggggcc     60
ggggccgggg ccggggccgg ggccggggcc ggggccgggg ccggggccgg ggccggggcc    120
ggggccgggg ccggggccgg ggccggggcc ggggccgggg ccggggccgg ggccggggcc    180
ggggccgggg ccggggccgg ggccggggcc ggggccgggg ccggggccgg ggccggggcc    240
ggggccgggg ccggggccgg ggccggggcc ggggccgggg ccggggccgg ggccggggcc    300
ggggccgggg ccggggccgg ggccggggcc ggggccgggg ccggggccgg ggccggggcc    360
ggggccgggg ccggggccgg ggccggggcc ggggccgggg ccggggccgg ggccggggcc    420
ggggccgggg ccggggccgg ggccggggcc ggggccgggg ccggggccgg ggccggggcc    480
ggggccgggg ccggggccgg ggccggggcc ggggccgggg ccggggccgg ggccggggcc    540
ggggccgggg ccggggccgg ggccggggcc ggggccgggg ccggggccgg ggccggggcc    600
ggggccgggg ccggggccgg ggccggggcc ggggccgggg ccggggccgg ggccggggcc    660
ggggccgggg ccggggccgg ggccggggcc ggggccgggg ccggggccgg ggccggggcc    720
ggggccgggg ccggggccgg ggccggggcc ggggccgggg ccggggccgg ggccggggcc    780
ggggccgggg ccggggccgg ggccggggcc ggggccgggg ccggggccgg ggccggggcc    840
ggggccgggg ccggggccgg ggccggggcc ggggccgggg ccggggccgg ggccggggcc    900
ggggccgggg ccggggccgg ggccggggcc ggggccgggg ccggggccgg ggccggggcc    960
ggggccgggg ccggggccgg ggccggggcc ggggccgggg ccggggccgg ggccggggcc   1020
ggggccgggg ccggggccgg ggccggggcc ggggccgggg ccggggccgg ggccggggcc   1080
ggggccgggg ccggggccgg ggccggggcc ggggccgggg ccggggccgg ggccggggcc   1140
ggggccgggg ccggggccgg ggccggggcc ggggccgggg ccggggccgg ggccggggcc   1200
ggggccgggg ccggggccgg ggccggggcc ggggccgggg ccggggccgg ggccggggcc   1260
ggggccgggg ccggggccgg ggccggggcc ggggccgggg ccggggccgg ggccggggcc   1320
ggggccgggg ccggggccgg ggccggggcc ggggccgggg ccggggccgg ggccggggcc   1380
ggggccgggg ccggggccgg ggccggggcc ggggccgggg ccggggccgg ggccggggcc   1440
ggggccgggg ccggggccgg ggccggggcc ggggccgggg ccggggccgg ggccggggcc   1500
ggggccgggg ccggggccgg ggccggggcc ggggccgggg ccggggccgg ggccggggcc   1560
ggggccgggg ccggggccgg ggccggggcc ggggccgggg ccggggccgg ggccggggcc   1620
ggggccgggg ccggggccgg ggccggggcc ggggccgggg ccggggccgg ggccggggcc   1680
ggggccgggg ccggggccgg ggccggggcc ggggccgggg ccggggccgg ggccggggcc   1740
ggggccgggg ccggggccgg ggccggggcc ggggccgggg ccggggccgg ggccggggcc   1800
```

<210> SEQ ID NO 143
<211> LENGTH: 3000
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 143

```
ggggccgggg ccggggccgg ggccggggcc ggggccgggg ccggggccgg ggccggggcc     60
ggggccgggg ccggggccgg ggccggggcc ggggccgggg ccggggccgg ggccggggcc    120
```

-continued

```
ggggccgggg ccggggccgg ggccggggcc ggggccgggg ccggggccgg ggccggggcc    180
ggggccgggg ccggggccgg ggccggggcc ggggccgggg ccggggccgg ggccggggcc    240
ggggccgggg ccggggccgg ggccggggcc ggggccgggg ccggggccgg ggccggggcc    300
ggggccgggg ccggggccgg ggccggggcc ggggccgggg ccggggccgg ggccggggcc    360
ggggccgggg ccggggccgg ggccggggcc ggggccgggg ccggggccgg ggccggggcc    420
ggggccgggg ccggggccgg ggccggggcc ggggccgggg ccggggccgg ggccggggcc    480
ggggccgggg ccggggccgg ggccggggcc ggggccgggg ccggggccgg ggccggggcc    540
ggggccgggg ccggggccgg ggccggggcc ggggccgggg ccggggccgg ggccggggcc    600
ggggccgggg ccggggccgg ggccggggcc ggggccgggg ccggggccgg ggccggggcc    660
ggggccgggg ccggggccgg ggccggggcc ggggccgggg ccggggccgg ggccggggcc    720
ggggccgggg ccggggccgg ggccggggcc ggggccgggg ccggggccgg ggccggggcc    780
ggggccgggg ccggggccgg ggccggggcc ggggccgggg ccggggccgg ggccggggcc    840
ggggccgggg ccggggccgg ggccggggcc ggggccgggg ccggggccgg ggccggggcc    900
ggggccgggg ccggggccgg ggccggggcc ggggccgggg ccggggccgg ggccggggcc    960
ggggccgggg ccggggccgg ggccggggcc ggggccgggg ccggggccgg ggccggggcc   1020
ggggccgggg ccggggccgg ggccggggcc ggggccgggg ccggggccgg ggccggggcc   1080
ggggccgggg ccggggccgg ggccggggcc ggggccgggg ccggggccgg ggccggggcc   1140
ggggccgggg ccggggccgg ggccggggcc ggggccgggg ccggggccgg ggccggggcc   1200
ggggccgggg ccggggccgg ggccggggcc ggggccgggg ccggggccgg ggccggggcc   1260
ggggccgggg ccggggccgg ggccggggcc ggggccgggg ccggggccgg ggccggggcc   1320
ggggccgggg ccggggccgg ggccggggcc ggggccgggg ccggggccgg ggccggggcc   1380
ggggccgggg ccggggccgg ggccggggcc ggggccgggg ccggggccgg ggccggggcc   1440
ggggccgggg ccggggccgg ggccggggcc ggggccgggg ccggggccgg ggccggggcc   1500
ggggccgggg ccggggccgg ggccggggcc ggggccgggg ccggggccgg ggccggggcc   1560
ggggccgggg ccggggccgg ggccggggcc ggggccgggg ccggggccgg ggccggggcc   1620
ggggccgggg ccggggccgg ggccggggcc ggggccgggg ccggggccgg ggccggggcc   1680
ggggccgggg ccggggccgg ggccggggcc ggggccgggg ccggggccgg ggccggggcc   1740
ggggccgggg ccggggccgg ggccggggcc ggggccgggg ccggggccgg ggccggggcc   1800
ggggccgggg ccggggccgg ggccggggcc ggggccgggg ccggggccgg ggccggggcc   1860
ggggccgggg ccggggccgg ggccggggcc ggggccgggg ccggggccgg ggccggggcc   1920
ggggccgggg ccggggccgg ggccggggcc ggggccgggg ccggggccgg ggccggggcc   1980
ggggccgggg ccggggccgg ggccggggcc ggggccgggg ccggggccgg ggccggggcc   2040
ggggccgggg ccggggccgg ggccggggcc ggggccgggg ccggggccgg ggccggggcc   2100
ggggccgggg ccggggccgg ggccggggcc ggggccgggg ccggggccgg ggccggggcc   2160
ggggccgggg ccggggccgg ggccggggcc ggggccgggg ccggggccgg ggccggggcc   2220
ggggccgggg ccggggccgg ggccggggcc ggggccgggg ccggggccgg ggccggggcc   2280
ggggccgggg ccggggccgg ggccggggcc ggggccgggg ccggggccgg ggccggggcc   2340
ggggccgggg ccggggccgg ggccggggcc ggggccgggg ccggggccgg ggccggggcc   2400
ggggccgggg ccggggccgg ggccggggcc ggggccgggg ccggggccgg ggccggggcc   2460
ggggccgggg ccggggccgg ggccggggcc ggggccgggg ccggggccgg ggccggggcc   2520
```

ggggccgggg ccggggccgg ggccggggcc ggggccgggg ccggggccgg ggccggggcc 2580
ggggccgggg ccggggccgg ggccggggcc ggggccgggg ccggggccgg ggccggggcc 2640
ggggccgggg ccggggccgg ggccggggcc ggggccgggg ccggggccgg ggccggggcc 2700
ggggccgggg ccggggccgg ggccggggcc ggggccgggg ccggggccgg ggccggggcc 2760
ggggccgggg ccggggccgg ggccggggcc ggggccgggg ccggggccgg ggccggggcc 2820
ggggccgggg ccggggccgg ggccggggcc ggggccgggg ccggggccgg ggccggggcc 2880
ggggccgggg ccggggccgg ggccggggcc ggggccgggg ccggggccgg ggccggggcc 2940
ggggccgggg ccggggccgg ggccggggcc ggggccgggg ccggggccgg ggccggggcc 3000

<210> SEQ ID NO 144
<211> LENGTH: 3600
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 144
ggggccgggg ccggggccgg ggccggggcc ggggccgggg ccggggccgg ggccggggcc 60
ggggccgggg ccggggccgg ggccggggcc ggggccgggg ccggggccgg ggccggggcc 120
ggggccgggg ccggggccgg ggccggggcc ggggccgggg ccggggccgg ggccggggcc 180
ggggccgggg ccggggccgg ggccggggcc ggggccgggg ccggggccgg ggccggggcc 240
ggggccgggg ccggggccgg ggccggggcc ggggccgggg ccggggccgg ggccggggcc 300
ggggccgggg ccggggccgg ggccggggcc ggggccgggg ccggggccgg ggccggggcc 360
ggggccgggg ccggggccgg ggccggggcc ggggccgggg ccggggccgg ggccggggcc 420
ggggccgggg ccggggccgg ggccggggcc ggggccgggg ccggggccgg ggccggggcc 480
ggggccgggg ccggggccgg ggccggggcc ggggccgggg ccggggccgg ggccggggcc 540
ggggccgggg ccggggccgg ggccggggcc ggggccgggg ccggggccgg ggccggggcc 600
ggggccgggg ccggggccgg ggccggggcc ggggccgggg ccggggccgg ggccggggcc 660
ggggccgggg ccggggccgg ggccggggcc ggggccgggg ccggggccgg ggccggggcc 720
ggggccgggg ccggggccgg ggccggggcc ggggccgggg ccggggccgg ggccggggcc 780
ggggccgggg ccggggccgg ggccggggcc ggggccgggg ccggggccgg ggccggggcc 840
ggggccgggg ccggggccgg ggccggggcc ggggccgggg ccggggccgg ggccggggcc 900
ggggccgggg ccggggccgg ggccggggcc ggggccgggg ccggggccgg ggccggggcc 960
ggggccgggg ccggggccgg ggccggggcc ggggccgggg ccggggccgg ggccggggcc 1020
ggggccgggg ccggggccgg ggccggggcc ggggccgggg ccggggccgg ggccggggcc 1080
ggggccgggg ccggggccgg ggccggggcc ggggccgggg ccggggccgg ggccggggcc 1140
ggggccgggg ccggggccgg ggccggggcc ggggccgggg ccggggccgg ggccggggcc 1200
ggggccgggg ccggggccgg ggccggggcc ggggccgggg ccggggccgg ggccggggcc 1260
ggggccgggg ccggggccgg ggccggggcc ggggccgggg ccggggccgg ggccggggcc 1320
ggggccgggg ccggggccgg ggccggggcc ggggccgggg ccggggccgg ggccggggcc 1380
ggggccgggg ccggggccgg ggccggggcc ggggccgggg ccggggccgg ggccggggcc 1440
ggggccgggg ccggggccgg ggccggggcc ggggccgggg ccggggccgg ggccggggcc 1500
ggggccgggg ccggggccgg ggccggggcc ggggccgggg ccggggccgg ggccggggcc 1560
ggggccgggg ccggggccgg ggccggggcc ggggccgggg ccggggccgg ggccggggcc 1620
ggggccgggg ccggggccgg ggccggggcc ggggccgggg ccggggccgg ggccggggcc 1680
ggggccgggg ccggggccgg ggccggggcc ggggccgggg ccggggccgg ggccggggcc 1740
ggggccgggg ccggggccgg ggccggggcc ggggccgggg ccggggccgg ggccggggcc 1800
ggggccgggg ccggggccgg ggccggggcc ggggccgggg ccggggccgg ggccggggcc 1860
ggggccgggg ccggggccgg ggccggggcc ggggccgggg ccggggccgg ggccggggcc 1920
ggggccgggg ccggggccgg ggccggggcc ggggccgggg ccggggccgg ggccggggcc 1980
ggggccgggg ccggggccgg ggccggggcc ggggccgggg ccggggccgg ggccggggcc 2040
ggggccgggg ccggggccgg ggccggggcc ggggccgggg ccggggccgg ggccggggcc 2100
ggggccgggg ccggggccgg ggccggggcc ggggccgggg ccggggccgg ggccggggcc 2160
ggggccgggg ccggggccgg ggccggggcc ggggccgggg ccggggccgg ggccggggcc 2220
ggggccgggg ccggggccgg ggccggggcc ggggccgggg ccggggccgg ggccggggcc 2280
ggggccgggg ccggggccgg ggccggggcc ggggccgggg ccggggccgg ggccggggcc 2340
ggggccgggg ccggggccgg ggccggggcc ggggccgggg ccggggccgg ggccggggcc 2400
ggggccgggg ccggggccgg ggccggggcc ggggccgggg ccggggccgg ggccggggcc 2460
ggggccgggg ccggggccgg ggccggggcc ggggccgggg ccggggccgg ggccggggcc 2520
ggggccgggg ccggggccgg ggccggggcc ggggccgggg ccggggccgg ggccggggcc 2580
ggggccgggg ccggggccgg ggccggggcc ggggccgggg ccggggccgg ggccggggcc 2640
ggggccgggg ccggggccgg ggccggggcc ggggccgggg ccggggccgg ggccggggcc 2700
ggggccgggg ccggggccgg ggccggggcc ggggccgggg ccggggccgg ggccggggcc 2760
ggggccgggg ccggggccgg ggccggggcc ggggccgggg ccggggccgg ggccggggcc 2820
ggggccgggg ccggggccgg ggccggggcc ggggccgggg ccggggccgg ggccggggcc 2880
ggggccgggg ccggggccgg ggccggggcc ggggccgggg ccggggccgg ggccggggcc 2940
ggggccgggg ccggggccgg ggccggggcc ggggccgggg ccggggccgg ggccggggcc 3000
ggggccgggg ccggggccgg ggccggggcc ggggccgggg ccggggccgg ggccggggcc 3060
ggggccgggg ccggggccgg ggccggggcc ggggccgggg ccggggccgg ggccggggcc 3120
ggggccgggg ccggggccgg ggccggggcc ggggccgggg ccggggccgg ggccggggcc 3180
ggggccgggg ccggggccgg ggccggggcc ggggccgggg ccggggccgg ggccggggcc 3240
ggggccgggg ccggggccgg ggccggggcc ggggccgggg ccggggccgg ggccggggcc 3300
ggggccgggg ccggggccgg ggccggggcc ggggccgggg ccggggccgg ggccggggcc 3360
ggggccgggg ccggggccgg ggccggggcc ggggccgggg ccggggccgg ggccggggcc 3420
ggggccgggg ccggggccgg ggccggggcc ggggccgggg ccggggccgg ggccggggcc 3480
ggggccgggg ccggggccgg ggccggggcc ggggccgggg ccggggccgg ggccggggcc 3540
ggggccgggg ccggggccgg ggccggggcc ggggccgggg ccggggccgg ggccggggcc 3600

<210> SEQ ID NO 145
<211> LENGTH: 1500
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 145
ggggccgggg ccggggccgg ggccggggcc ggggccgggg ccggggccgg ggccggggcc 60
ggggccgggg ccggggccgg ggccggggcc ggggccgggg ccggggccgg ggccggggcc 120
ggggccgggg ccggggccgg ggccggggcc ggggccgggg ccggggccgg ggccggggcc 180
ggggccgggg ccggggccgg ggccggggcc ggggccgggg ccggggccgg ggccggggcc 240
ggggccgggg ccggggccgg ggccggggcc ggggccgggg ccggggccgg ggccggggcc 300
ggggccgggg ccggggccgg ggccggggcc ggggccgggg ccggggccgg ggccggggcc 360
ggggccgggg ccggggccgg ggccggggcc ggggccgggg ccggggccgg ggccggggcc 420
ggggccgggg ccggggccgg ggccggggcc ggggccgggg ccggggccgg ggccggggcc 480
ggggccgggg ccggggccgg ggccggggcc ggggccgggg ccggggccgg ggccggggcc 540
ggggccgggg ccggggccgg ggccggggcc ggggccgggg ccggggccgg ggccggggcc 600
ggggccgggg ccggggccgg ggccggggcc ggggccgggg ccggggccgg ggccggggcc 660
ggggccgggg ccggggccgg ggccggggcc ggggccgggg ccggggccgg ggccggggcc 720
ggggccgggg ccggggccgg ggccggggcc ggggccgggg ccggggccgg ggccggggcc 780
ggggccgggg ccggggccgg ggccggggcc ggggccgggg ccggggccgg ggccggggcc 840
ggggccgggg ccggggccgg ggccggggcc ggggccgggg ccggggccgg ggccggggcc 900
ggggccgggg ccggggccgg ggccggggcc ggggccgggg ccggggccgg ggccggggcc 960
ggggccgggg ccggggccgg ggccggggcc ggggccgggg ccggggccgg ggccggggcc 1020
ggggccgggg ccggggccgg ggccggggcc ggggccgggg ccggggccgg ggccggggcc 1080
ggggccgggg ccggggccgg ggccggggcc ggggccgggg ccggggccgg ggccggggcc 1140
ggggccgggg ccggggccgg ggccggggcc ggggccgggg ccggggccgg ggccggggcc 1200
ggggccgggg ccggggccgg ggccggggcc ggggccgggg ccggggccgg ggccggggcc 1260
ggggccgggg ccggggccgg ggccggggcc ggggccgggg ccggggccgg ggccggggcc 1320
ggggccgggg ccggggccgg ggccggggcc ggggccgggg ccggggccgg ggccggggcc 1380
ggggccgggg ccggggccgg ggccggggcc ggggccgggg ccggggccgg ggccggggcc 1440
ggggccgggg ccggggccgg ggccggggcc ggggccgggg ccggggccgg ggccggggcc 1500

<210> SEQ ID NO 146
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 146
uguugccaag acagagauug u 21

<210> SEQ ID NO 147
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:

<221> NAME/KEY: source
<223> OTHER INFORMATION: /note="Description of Combined DNA/RNA
Molecule: Synthetic oligonucleotide"

<400> SEQUENCE: 147
acaauctcug ucuuggcaac agc 23

<210> SEQ ID NO 148
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 148
caagacagag auugcuuuaa u 21

<210> SEQ ID NO 149
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 149
auuaaagcaa ucucugucuu ggc 23

<210> SEQ ID NO 150
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 150
uagcugauac aguacucaau u 21

<210> SEQ ID NO 151
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 151
aauugaguac uguaucagcu aua 23

<210> SEQ ID NO 152
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 152
ugauacagua cucaaugaug a 21

<210> SEQ ID NO 153
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 153
ucaucatuga guacuguauc agc 23

<210> SEQ ID NO 154
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 154
gucuuacaca gagacacucu a 21

<210> SEQ ID NO 155
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 155
uagagugucu cuguguaaga cau 23

<210> SEQ ID NO 156
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 156
gaagaccuuu cuacacuagu u 21

<210> SEQ ID NO 157
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 157
aacuagtgua gaaaggucuu cca 23

<210> SEQ ID NO 158

<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 158
agaaaagacc ugauaaagau u 21

<210> SEQ ID NO 159
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 159
aaucuuuauc aggucuuuuc uug 23

<210> SEQ ID NO 160
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 160
aaaagaccug auaaagauua a 21

<210> SEQ ID NO 161
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 161
uuaaucuuua ucaggucuuu ucu 23

<210> SEQ ID NO 162
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 162
aaagaccuga uaaagauuaa u 21

<210> SEQ ID NO 163
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 163
auuaaucuuu aucaggucuu uuc 23

<210> SEQ ID NO 164
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 164
cugauaaaga uuaaccagaa u 21

<210> SEQ ID NO 165
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 165
auucugguua aucuuuauca ggu 23

<210> SEQ ID NO 166
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 166
auaaagauua accagaagaa a 21

<210> SEQ ID NO 167
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 167
uuucuucugg uuaaucuuua uca 23

<210> SEQ ID NO 168
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 168
aaagauuaac cagaagaaaa u 21

<210> SEQ ID NO 169
<211> LENGTH: 23
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169

auuuucuucu gguuaaucuu uau                                          23


<210> SEQ ID NO 170
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170

ugcgucaaac agcgacaagu u                                            21


<210> SEQ ID NO 171
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 171

aacuugtcgc uguuugacgc acc                                          23


<210> SEQ ID NO 172
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172

cgucaaacag cgacaaguuc u                                            21


<210> SEQ ID NO 173
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 173

agaacutguc gcuguuugac gca                                          23


<210> SEQ ID NO 174
<211> LENGTH: 21
<212> TYPE: RNA
<213> ORGANISM: Artificial Sequence
```

<220> FEATURE:
<221> NAME/KEY: source
<223> OTHER INFORMATION: /note="Description of Artificial Sequence:
Synthetic oligonucleotide"

<400> SEQUENCE: 174
cccacguaaa agaugacgcu u 21

<210> SEQ ID NO 175
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 175
aagcgucauc uuuuacgugg gcg 23

<210> SEQ ID NO 176
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 176
ccacguaaaa gaugacgcuu u 21

<210> SEQ ID NO 177
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 177
aaagcgtcau cuuuuacgug ggc 23

<210> SEQ ID NO 178
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 178
agugaugucg acucuuugcc u 21

<210> SEQ ID NO 179
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 179
aggcaaagag ucgacaucac ugc 23

<210> SEQ ID NO 180
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 180
cagcuguugc caagacagag a 21

<210> SEQ ID NO 181
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 181
ucucugtcuu ggcaacagcu gga 23

<210> SEQ ID NO 182
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 182
agcuguugcc aagacagaga u 21

<210> SEQ ID NO 183
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 183
aucucugucu uggcaacagc ugg 23

<210> SEQ ID NO 184
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 184
gccaagacag agauugcuuu a 21

<210> SEQ ID NO 185
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 185
uaaagcaauc ucugucuugg caa 23

<210> SEQ ID NO 186
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 186
aagacagaga uugcuuuaag u 21

<210> SEQ ID NO 187
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 187
acuuaaagca aucucugucu ugg 23

<210> SEQ ID NO 188
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 188
agacagagau ugcuuuaagu u 21

<210> SEQ ID NO 189
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 189
aacuuaaagc aaucucuguc uug 23

<210> SEQ ID NO 190
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 190
gacagagauu gcuuuaagug u 21

<210> SEQ ID NO 191
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 191
acacuuaaag caaucucugu cuu 23

<210> SEQ ID NO 192
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 192
uagcagcuac uuuugcuuac u 21

<210> SEQ ID NO 193
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 193
aguaagcaaa aguagcugcu aau 23

<210> SEQ ID NO 194
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 194
acaauauucu ugguccuaga u 21

<210> SEQ ID NO 195
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 195
aucuaggacc aagaauauug ucc 23

<210> SEQ ID NO 196
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 196
aauauucuug guccuagagu a 21

<210> SEQ ID NO 197
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 197
uacucuagga ccaagaauau ugu 23

<210> SEQ ID NO 198
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 198
auauucuugg uccuagagua a 21

<210> SEQ ID NO 199
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 199
uuacuctagg accaagaaua uug 23

<210> SEQ ID NO 200
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 200
agacagaaca gguacuucuc a 21

<210> SEQ ID NO 201
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 201
ugagaaguac cuguucuguc uuu 23

<210> SEQ ID NO 202
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 202
uaaauggaga aauccuucga a 21

<210> SEQ ID NO 203
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 203
uucgaaggau uucuccauuu aga 23

<210> SEQ ID NO 204
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 204
ggagaaaucc uucgaaaugc a 21

<210> SEQ ID NO 205
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 205
ugcauutcga aggauuucuc cau 23

<210> SEQ ID NO 206
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 206
cauuaaucuu ugauggaaac u 21

<210> SEQ ID NO 207
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 207
aguuuccauc aaagauuaau gaa 23

<210> SEQ ID NO 208
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 208
auuaaucuuu gauggaaacu u 21

<210> SEQ ID NO 209
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 209
aaguuuccau caaagauuaa uga 23

<210> SEQ ID NO 210
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 210
cauauggacu aucaauuaua u 21

<210> SEQ ID NO 211
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 211
auauaatuga uaguccauau gug 23

<210> SEQ ID NO 212
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 212
uauggacuau caauuauacu u 21

<210> SEQ ID NO 213
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 213
aaguauaauu gauaguccau aug 23

<210> SEQ ID NO 214
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 214
uggacuauca auuauacuuc u 21

<210> SEQ ID NO 215
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 215
agaaguauaa uugauagucc aua 23

<210> SEQ ID NO 216
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 216
ucaauuauac uuccacagac a 21

<210> SEQ ID NO 217
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 217
ugucugtgga aguauaauug aua 23

<210> SEQ ID NO 218
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 218
acagaacuua guuucuaccu u 21

<210> SEQ ID NO 219
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 219
aagguagaaa cuaaguucug ucu 23

<210> SEQ ID NO 220
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 220
cagaacuuag uuucuaccuc u 21

<210> SEQ ID NO 221
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 221
agagguagaa acuaaguucu guc 23

<210> SEQ ID NO 222
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 222
gagugugugu ugauagauua a 21

<210> SEQ ID NO 223
<211> LENGTH: 23
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 223
uuaauctauc aacacacacu cua 23

<210> SEQ ID NO 224
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 224 agugugugu gauagauuaa u 21

<210> SEQ ID NO 225
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 225
auuaaucuau caacacacac ucu 23

<210> SEQ ID NO 226
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 226 ugugugguuga uagauuaaca u 21

<210> SEQ ID NO 227
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 227
auguuaaucu aucaacacac acu 23

<210> SEQ ID NO 228
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 228
aacacauaua auccggaaag u 21

<210> SEQ ID NO 229
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 229
acuuuccgga uuauaugugu uaa 23

<210> SEQ ID NO 230
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 230
uguccagaag auuaucuuag a 21

<210> SEQ ID NO 231
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 231
ucuaagauaa ucuucuggac auu 23

<210> SEQ ID NO 232
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 232
gaacugcuuu caucuaugaa a 21

<210> SEQ ID NO 233
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 233
uuucauagau gaaagcaguu cca 23

<210> SEQ ID NO 234
<211> LENGTH: 21
<212> TYPE: RNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 234
cugucaugaa ggcuuucuuc u 21

<210> SEQ ID NO 235
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 235
agaagaaagc cuucaugaca gcu 23

<210> SEQ ID NO 236
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 236
uguuccguug uaguagguag u 21

<210> SEQ ID NO 237
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 237
acuacctacu acaacggaac agc 23

<210> SEQ ID NO 238
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 238
aucauuuaaa uaugagucag u 21

<210> SEQ ID NO 239
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<220> FEATURE:
<221> NAME/KEY: source
<223> OTHER INFORMATION: /note="Description of Combined DNA/RNA
Molecule: Synthetic oligonucleotide"

<400> SEQUENCE: 239
acugactcau auuuaaauga uga 23

<210> SEQ ID NO 240
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 240
ccugcuaaag gauucaacug u 21

<210> SEQ ID NO 241
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 241
acaguugaau ccuuuagcag gcc 23

<210> SEQ ID NO 242
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 242
cacccuguca ugaacauauu u 21

<210> SEQ ID NO 243
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 243
aaauauguuc augacagggu ggc 23

<210> SEQ ID NO 244
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 244
ugaacauauu uauaaucagc u 21

<210> SEQ ID NO 245
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 245
agcugatuau aaauauguuc aug 23

<210> SEQ ID NO 246
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 246
acauauuuau aaucagcgua u 21

<210> SEQ ID NO 247
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 247
auacgctgau uauaaauaug uuc 23

<210> SEQ ID NO 248
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 248
auauuuauaa ucagcguaga u 21

<210> SEQ ID NO 249
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 249
aucuacgcug auuauaaaua ugu 23

-continued

<210> SEQ ID NO 250
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 250
ucaggauacg aucaucuaca u 21

<210> SEQ ID NO 251
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 251
auguagauga ucguauccug agc 23

<210> SEQ ID NO 252
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 252
aucaucuaca cugacgaaag u 21

<210> SEQ ID NO 253
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 253
acuuucguca guguagauga ucg 23

<210> SEQ ID NO 254
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 254
caucuacacu gacgaaagcu u 21

<210> SEQ ID NO 255
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:

<221> NAME/KEY: source
<223> OTHER INFORMATION: /note="Description of Combined DNA/RNA
Molecule: Synthetic oligonucleotide"

<400> SEQUENCE: 255
aagcuutcgu caguguagau gau 23

<210> SEQ ID NO 256
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 256
aucuacacug acgaaagcuu u 21

<210> SEQ ID NO 257
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 257
aaagcutucg ucaguguaga uga 23

<210> SEQ ID NO 258
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 258
cacugacgaa agcuuuacuc u 21

<210> SEQ ID NO 259
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 259
agaguaaagc uuucgucagu gua 23

<210> SEQ ID NO 260
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 260
acugacgaaa gcuuuacucc u 21

<210> SEQ ID NO 261
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 261
aggaguaaag cuuucgucag ugu 23

<210> SEQ ID NO 262
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 262
cugacgaaag cuuuacuccu u 21

<210> SEQ ID NO 263
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 263
aaggagtaaa gcuuucguca gug 23

<210> SEQ ID NO 264
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 264
uuucaagaug ucuuacacag a 21

<210> SEQ ID NO 265
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 265
ucugugtaag acaucuugaa aaa 23

<210> SEQ ID NO 266
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 266
cuggaucagg ucuuucagcu u 21

<210> SEQ ID NO 267
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 267
aagcugaaag accugaucca gga 23

<210> SEQ ID NO 268
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 268
cucagaagua cuuuccuugc a 21

<210> SEQ ID NO 269
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 269
ugcaaggaaa guacuucuga gag 23

<210> SEQ ID NO 270
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 270
ucuacuuguc cuucacagaa a 21

<210> SEQ ID NO 271
<211> LENGTH: 23
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 271

uuucugtgaa ggacaaguag aaa                                          23


<210> SEQ ID NO 272
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272

gaaaagccuu gacacuaaua a                                            21


<210> SEQ ID NO 273
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273

uuauuagugu caaggcuuuu cug                                          23


<210> SEQ ID NO 274
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274

ccuuuaaauc ucuucggaac u                                            21


<210> SEQ ID NO 275
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275

aguuccgaag agauuuaaag ggc                                          23


<210> SEQ ID NO 276
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 276
cuuuaaaucu cuucggaacc u 21

<210> SEQ ID NO 277
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 277
agguuccgaa gagauuuaaa ggg 23

<210> SEQ ID NO 278
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 278
uuuaaaucuc uucggaaccu u 21

<210> SEQ ID NO 279
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 279
aagguuccga agagauuuaa agg 23

<210> SEQ ID NO 280
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 280
gggcgaucuu aacauaauaa u 21

<210> SEQ ID NO 281
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 281
auuauuaugu uaagaucgcc cuc 23

<210> SEQ ID NO 282
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 282
ucuuaacaua auaauggcuc u 21

<210> SEQ ID NO 283
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 283
agagccauua uuauguuaag auc 23

<210> SEQ ID NO 284
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 284
uuaucuuugg aagaccuuuc u 21

<210> SEQ ID NO 285
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 285
agaaaggucu uccaaagaua aaa 23

<210> SEQ ID NO 286
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 286
aagaccuuuc uacacuagug u 21

<210> SEQ ID NO 287
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 287
acacuagugu agaaaggucu ucc 23

<210> SEQ ID NO 288
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 288
agaccuuucu acacuagugu u 21

<210> SEQ ID NO 289
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 289
aacacuagug uagaaagguc uuc 23

<210> SEQ ID NO 290
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 290
gcaagaacga gauguucuaa u 21

<210> SEQ ID NO 291
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 291
auuagaacau cucguucuug cac 23

<210> SEQ ID NO 292
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 292
gaacgagaug uucuaaugac u 21

<210> SEQ ID NO 293
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<220> FEATURE:
<221> NAME/KEY: source
<223> OTHER INFORMATION: /note="Description of Combined DNA/RNA
Molecule: Synthetic oligonucleotide"

<400> SEQUENCE: 293
agucautaga acaucucguu cuu 23

<210> SEQ ID NO 294
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 294
aacgagaugu ucuaaugacu u 21

<210> SEQ ID NO 295
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 295
aagucatuag aacaucucgu ucu 23

<210> SEQ ID NO 296
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 296
acgagauguu cuaaugacuu u 21

<210> SEQ ID NO 297
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 297
aaagucauua gaacaucucg uuc 23

<210> SEQ ID NO 298
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 298
auguguaacu uaauaagccu a 21

<210> SEQ ID NO 299
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 299
uaggcutauu aaguuacaca uuu 23

<210> SEQ ID NO 300
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 300
guguaacuua auaagccuau u 21

<210> SEQ ID NO 301
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 301
aauaggcuua uuaaguuaca cau 23

<210> SEQ ID NO 302
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 302
guaacuuaau aagccuauuc u 21

<210> SEQ ID NO 303
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 303
agaauaggcu uauuaaguua cac 23

<210> SEQ ID NO 304
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 304
uaacuuaaua agccuauucc a 21

<210> SEQ ID NO 305
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 305
uggaauaggc uuauuaaguu aca 23

<210> SEQ ID NO 306
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 306
aacuuaauaa gccuauucca u 21

<210> SEQ ID NO 307
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 307
auggaatagg cuuauuaagu uac 23

<210> SEQ ID NO 308
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 308
guuaaguaag uuacacuaca u 21

<210> SEQ ID NO 309
<211> LENGTH: 23
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 309

auguagtgua acuuacuuaa cug                                            23


<210> SEQ ID NO 310
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310

uaaguuacac uacaguucuc a                                              21


<210> SEQ ID NO 311
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311

ugagaacugu aguguaacuu acu                                            23


<210> SEQ ID NO 312
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312

guuacacuac aguucucaca a                                              21


<210> SEQ ID NO 313
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313

uugugagaac uguaguguaa cuu                                            23


<210> SEQ ID NO 314
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 314
cagaccuaug uuuacaauau a 21

<210> SEQ ID NO 315
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 315
uauauuguaa acauaggucu gua 23

<210> SEQ ID NO 316
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 316
agaccuaugu uuacaauaua a 21

<210> SEQ ID NO 317
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 317
uuauautgua aacauagguc ugu 23

<210> SEQ ID NO 318
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 318
gaucaagcag auguuuaauu u 21

<210> SEQ ID NO 319
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 319
aaauuaaaca ucugcuugau caa 23

-continued

<210> SEQ ID NO 320
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 320
ugggauucag ucuguagaaa u 21

<210> SEQ ID NO 321
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 321
auuucuacag acugaauccc agg 23

<210> SEQ ID NO 322
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 322
ugucuaauag uucucuauag u 21

<210> SEQ ID NO 323
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 323
acuauagaga acuauuagac auu 23

<210> SEQ ID NO 324
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 324
cuaauaguuc ucuauagucc u 21

<210> SEQ ID NO 325
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 325
aggacuauag agaacuauua gac 23

<210> SEQ ID NO 326
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 326
agccaaauug aaaugugcac u 21

<210> SEQ ID NO 327
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 327
agugcacauu ucaauuuggc uca 23

<210> SEQ ID NO 328
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 328
uucuugcuaa gucuuaccau u 21

<210> SEQ ID NO 329
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 329
aaugguaaga cuuagcaaga aga 23

<210> SEQ ID NO 330
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 330
ugcaauaggc uauaaggaau a 21

<210> SEQ ID NO 331
<211> LENGTH: 23
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 331
uauucctuau agccuauugc agg 23

<210> SEQ ID NO 332
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 332
gcaauaggcu auaaggaaua u 21

<210> SEQ ID NO 333
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 333
auauuccuua uagccuauug cag 23

<210> SEQ ID NO 334
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 334
gaaaggucau aauagcuuuc u 21

<210> SEQ ID NO 335
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 335
agaaagcuau uaugaccuuu cac 23

<210> SEQ ID NO 336
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 336
aaaggucaua auagcuuucc u 21

<210> SEQ ID NO 337
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 337
aggaaagcua uuaugaccuu uca 23

<210> SEQ ID NO 338
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 338
aacuagauga cuguuguacu u 21

<210> SEQ ID NO 339
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 339
aaguacaaca gucaucuagu uca 23

<210> SEQ ID NO 340
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 340
cuguagcuca gucauuuaaa a 21

<210> SEQ ID NO 341
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 341
uuuuaaauga cugagcuaca gua 23

<210> SEQ ID NO 342
<211> LENGTH: 21
<212> TYPE: RNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 342
cugguuuauu guacuguuau a 21

<210> SEQ ID NO 343
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 343
uauaacagua caauaaacca gcc 23

<210> SEQ ID NO 344
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 344
auguguaaac auuguuauau a 21

<210> SEQ ID NO 345
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 345
uauauaacaa uguuuacaca ugc 23

<210> SEQ ID NO 346
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 346
ugcgucaaac agcgacaagu u 21

<210> SEQ ID NO 347
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 347
aacuugtcgc uguuugacgc acc 23

<210> SEQ ID NO 348
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 348
ggugcgucaa acagcgacaa guu 23

<210> SEQ ID NO 349
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 349
cgucaaacag cgacaaguuc u 21

<210> SEQ ID NO 350
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 350
agaacutguc gcuguuugac gca 23

<210> SEQ ID NO 351
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 351
ugcgucaaac agcgacaagu ucc 23

<210> SEQ ID NO 352
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 352
cccacguaaa agaugacgcu u 21

<210> SEQ ID NO 353
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 353
aagcgucauc uuuuacgugg gcg 23

<210> SEQ ID NO 354
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 354
cgcccacgua aaagaugacg cuu 23

<210> SEQ ID NO 355
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 355
ccacguaaaa gaugacgcuu u 21

<210> SEQ ID NO 356
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 356
aaagcgtcau cuuuuacgug ggc 23

<210> SEQ ID NO 357
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 357
gcccacguaa aagaugacgc uug 23

<210> SEQ ID NO 358
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 358
agugaugucg acucuuugcc u 21

<210> SEQ ID NO 359
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 359
aggcaaagag ucgacaucac ugc 23

<210> SEQ ID NO 360
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 360
gcagugaugu cgacucuuug ccc 23

<210> SEQ ID NO 361
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 361
cagcuguugc caagacagag a 21

<210> SEQ ID NO 362
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 362
ucucugtcuu ggcaacagcu gga 23

<210> SEQ ID NO 363
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 363
uccagcuguu gccaagacag aga 23

<210> SEQ ID NO 364
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 364
agcuguugcc aagacagaga u 21

<210> SEQ ID NO 365
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 365
aucucugucu uggcaacagc ugg 23

<210> SEQ ID NO 366
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 366
ccagcuguug ccaagacaga gau 23

<210> SEQ ID NO 367
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 367
gcuguugcca agacagagau ugc 23

<210> SEQ ID NO 368
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 368
gccaagacag agauugcuuu a 21

<210> SEQ ID NO 369
<211> LENGTH: 23
<212> TYPE: RNA
<213> ORGANISM: Artificial Sequence -continued
<220> FEATURE:
<221> NAME/KEY: source
<223> OTHER INFORMATION: /note="Description of Artificial Sequence: Synthetic oligonucleotide"

<400> SEQUENCE: 369
uaaagcaauc ucugucuugg caa 23

<210> SEQ ID NO 370
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 370
uugccaagac agagauugcu uua 23

<210> SEQ ID NO 371
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 371
gccaagacag agauugcuuu aag 23

<210> SEQ ID NO 372
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 372
aagacagaga uugcuuuaag u 21

<210> SEQ ID NO 373
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 373
acuuaaagca aucucugucu ugg 23

<210> SEQ ID NO 374
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 374
ccaagacaga gauugcuuua agu 23

<210> SEQ ID NO 375
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 375
agacagagau ugcuuuaagu u 21

<210> SEQ ID NO 376
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 376
aacuuaaagc aaucucuguc uug 23

<210> SEQ ID NO 377
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 377
caagacagag auugcuuuaa gug 23

<210> SEQ ID NO 378
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 378
gacagagauu gcuuuaagug u 21

<210> SEQ ID NO 379
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 379
acacuuaaag caaucucugu cuu 23

<210> SEQ ID NO 380
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 380
aagacagaga uugcuuuaag ugg 23

<210> SEQ ID NO 381
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 381
uagcagcuac uuuugcuuac u 21

<210> SEQ ID NO 382
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 382
aguaagcaaa aguagcugcu aau 23

<210> SEQ ID NO 383
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 383
auuagcagcu acuuuugcuu acu 23

<210> SEQ ID NO 384
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 384
acaauauucu ugguccuaga u 21

<210> SEQ ID NO 385
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 385
aucuaggacc aagaauauug ucc 23

<210> SEQ ID NO 386
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 386
ggacaauauu cuugguccua gag 23

<210> SEQ ID NO 387
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 387
aauauucuug guccuagagu a 21

<210> SEQ ID NO 388
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 388
uacucuagga ccaagaauau ugu 23

<210> SEQ ID NO 389
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 389
acaauauucu ugguccuaga gua 23

<210> SEQ ID NO 390
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 390
auauucuugg uccuagagua a 21

<210> SEQ ID NO 391
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 391
uuacuctagg accaagaaua uug 23

<210> SEQ ID NO 392
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 392
caauauucuu gguccuagag uaa 23

<210> SEQ ID NO 393
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 393
agacagaaca gguacuucuc a 21

<210> SEQ ID NO 394
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 394
ugagaaguac cuguucuguc uuu 23

<210> SEQ ID NO 395
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 395
aaagacagaa cagguacuuc uca 23

<210> SEQ ID NO 396
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 396
uaaauggaga aauccuucga a 21

<210> SEQ ID NO 397
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 397
uucgaaggau uucuccauuu aga 23

<210> SEQ ID NO 398
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 398
ucuaaaugga gaaauccuuc gaa 23

<210> SEQ ID NO 399
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 399
ggagaaaucc uucgaaaugc a 21

<210> SEQ ID NO 400
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 400
ugcauutcga aggauuucuc cau 23

<210> SEQ ID NO 401
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 401
auggagaaau ccuucgaaau gca 23

<210> SEQ ID NO 402
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 402
cauuaaucuu ugauggaaac u 21

<210> SEQ ID NO 403
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 403
aguuuccauc aaagauuaau gaa 23

<210> SEQ ID NO 404
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 404
uucauuaauc uuugauggaa acu 23

<210> SEQ ID NO 405
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 405
auuaaucuuu gauggaaacu u 21

<210> SEQ ID NO 406
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 406
aaguuuccau caaagauuaa uga 23

<210> SEQ ID NO 407
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 407
ucauuaaucu uugauggaaa cug 23

<210> SEQ ID NO 408
<211> LENGTH: 21
<212> TYPE: RNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 408
cauauggacu aucaauuaua u 21

<210> SEQ ID NO 409
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 409
auauaatuga uaguccauau gug 23

<210> SEQ ID NO 410
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 410
cacauaugga cuaucaauua uac 23

<210> SEQ ID NO 411
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 411
uauggacuau caauuauacu u 21

<210> SEQ ID NO 412
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 412
aaguauaauu gauaguccau aug 23

<210> SEQ ID NO 413
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 413
cauauggacu aucaauuaua cuu 23

<210> SEQ ID NO 414
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 414
uggacuauca auuauacuuc u 21

<210> SEQ ID NO 415
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 415
agaaguauaa uugauagucc aua 23

<210> SEQ ID NO 416
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 416
uauggacuau caauuauacu ucc 23

<210> SEQ ID NO 417
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 417
ucaauuauac uuccacagac a 21

<210> SEQ ID NO 418
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 418
ugucugtgga aguauaauug aua 23

<210> SEQ ID NO 419
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 419
uaucaauuau acuuccacag aca 23

<210> SEQ ID NO 420
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 420
acagaacuua guuucuaccu u 21

<210> SEQ ID NO 421
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 421
aagguagaaa cuaaguucug ucu 23

<210> SEQ ID NO 422
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 422
agacagaacu uaguuucuac cuc 23

<210> SEQ ID NO 423
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 423
cagaacuuag uuucuaccuc u 21

<210> SEQ ID NO 424
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 424
agagguagaa acuaaguucu guc 23

<210> SEQ ID NO 425
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 425
gacagaacuu aguuucuacc ucc 23

<210> SEQ ID NO 426
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 426
gagugugugu ugauagauua a 21

<210> SEQ ID NO 427
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 427
uuaauctauc aacacacacu cua 23

<210> SEQ ID NO 428
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 428
uagagugugu guugauagau uaa 23

<210> SEQ ID NO 429
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 429 agugugugu gauagauuaa u 21

<210> SEQ ID NO 430
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 430
auuaaucuau caacacacac ucu 23

<210> SEQ ID NO 431
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 431
agagugugug uugauagauu aac 23

<210> SEQ ID NO 432
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 432 ugugguuga uagauuaaca u 21

<210> SEQ ID NO 433
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 433
auguuaaucu aucaacacac acu 23

<210> SEQ ID NO 434
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 434 agugugugu gauagauuaa cac 23

<210> SEQ ID NO 435
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 435
aacacauaua auccggaaag u 21

<210> SEQ ID NO 436
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 436
acuuuccgga uuauaugugu uaa 23

<210> SEQ ID NO 437
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 437
uuaacacaua uaauccggaa agg 23

<210> SEQ ID NO 438
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 438
uguccagaag auuaucuuag a 21

<210> SEQ ID NO 439
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 439
ucuaagauaa ucuucuggac auu 23

<210> SEQ ID NO 440
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 440
aauguccaga agauuaucuu aga 23

<210> SEQ ID NO 441
<211> LENGTH: 21
<212> TYPE: RNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 441
gaacugcuuu caucuaugaa a 21

<210> SEQ ID NO 442
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 442
uuucauagau gaaagcaguu cca 23

<210> SEQ ID NO 443
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 443
uggaacugcu uucaucuaug aaa 23

<210> SEQ ID NO 444
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 444
uauagcugau acaguacuca aug 23

<210> SEQ ID NO 445
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 445
gcugauacag uacucaauga uga 23

<210> SEQ ID NO 446
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 446
cugucaugaa ggcuuucuuc u 21

<210> SEQ ID NO 447
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 447
agaagaaagc cuucaugaca gcu 23

<210> SEQ ID NO 448
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 448
agcugucaug aaggcuuucu ucu 23

<210> SEQ ID NO 449
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 449
uguuccguug uaguagguag u 21

<210> SEQ ID NO 450
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 450
acuacctacu acaacggaac agc 23

<210> SEQ ID NO 451
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 451
gcuguuccgu uguaguaggu agc 23

<210> SEQ ID NO 452
<211> LENGTH: 21
<212> TYPE: RNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 452
aucauuuaaa uaugagucag u 21

<210> SEQ ID NO 453
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 453
acugactcau auuuaaauga uga 23

<210> SEQ ID NO 454
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 454
ucaucauuua aauaugaguc agg 23

<210> SEQ ID NO 455
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 455
ccugcuaaag gauucaacug u 21

<210> SEQ ID NO 456
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 456
acaguugaau ccuuuagcag gcc 23

<210> SEQ ID NO 457
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 457
ggccugcuaa aggauucaac ugg 23

<210> SEQ ID NO 458
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 458
cacccuguca ugaacauauu u 21

<210> SEQ ID NO 459
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 459
aaauauguuc augacagggu ggc 23

<210> SEQ ID NO 460
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 460
gccacccugu caugaacaua uuu 23

<210> SEQ ID NO 461
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 461
ugaacauauu uauaaucagc u 21

<210> SEQ ID NO 462
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 462
agcugatuau aaauauguuc aug 23

<210> SEQ ID NO 463
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 463
caugaacaua uuuauaauca gcg 23

<210> SEQ ID NO 464
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 464
acauauuuau aaucagcgua u 21

<210> SEQ ID NO 465
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 465
auacgctgau uauaaauaug uuc 23

<210> SEQ ID NO 466
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 466
gaacauauuu auaaucagcg uag 23

<210> SEQ ID NO 467
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 467
auauuuauaa ucagcguaga u 21

<210> SEQ ID NO 468
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 468
aucuacgcug auuauaaaua ugu 23

<210> SEQ ID NO 469
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 469
acauauuuau aaucagcgua gau 23

<210> SEQ ID NO 470
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 470
ucaggauacg aucaucuaca u 21

<210> SEQ ID NO 471
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 471
auguagauga ucguauccug agc 23

<210> SEQ ID NO 472
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 472
gcucaggaua cgaucaucua cac 23

<210> SEQ ID NO 473
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 473
aucaucuaca cugacgaaag u 21

<210> SEQ ID NO 474
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 474
acuuucguca guguagauga ucg 23

<210> SEQ ID NO 475
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 475
cgaucaucua cacugacgaa agc 23

<210> SEQ ID NO 476
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 476
caucuacacu gacgaaagcu u 21

<210> SEQ ID NO 477
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 477
aagcuutcgu caguguagau gau 23

<210> SEQ ID NO 478
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 478
aucaucuaca cugacgaaag cuu 23

<210> SEQ ID NO 479
<211> LENGTH: 21
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 479

aucuacacug acgaaagcuu u                                             21


<210> SEQ ID NO 480
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 480

aaagcutucg ucaguguaga uga                                           23


<210> SEQ ID NO 481
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 481

ucaucuacac ugacgaaagc uuu                                           23


<210> SEQ ID NO 482
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482

cacugacgaa agcuuuacuc u                                             21


<210> SEQ ID NO 483
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 483

agaguaaagc uuucgucagu gua                                           23


<210> SEQ ID NO 484
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 484
uacacugacg aaagcuuuac ucc 23

<210> SEQ ID NO 485
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 485
acugacgaaa gcuuuacucc u 21

<210> SEQ ID NO 486
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 486
aggaguaaag cuuucgucag ugu 23

<210> SEQ ID NO 487
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 487
acacugacga aagcuuuacu ccu 23

<210> SEQ ID NO 488
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 488
cugacgaaag cuuuacuccu u 21

<210> SEQ ID NO 489
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 489
aaggagtaaa gcuuucguca gug 23

<210> SEQ ID NO 490
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 490
cacugacgaa agcuuuacuc cug 23

<210> SEQ ID NO 491
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 491
uuucaagaug ucuuacacag a 21

<210> SEQ ID NO 492
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 492
ucugugtaag acaucuugaa aaa 23

<210> SEQ ID NO 493
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 493
uuuuucaaga ugucuuacac aga 23

<210> SEQ ID NO 494
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 494
augucuuaca cagagacacu cua 23

<210> SEQ ID NO 495
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 495
cuggaucagg ucuuucagcu u 21

<210> SEQ ID NO 496
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 496
aagcugaaag accugaucca gga 23

<210> SEQ ID NO 497
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 497
uccuggauca ggucuuucag cug 23

<210> SEQ ID NO 498
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 498
cucagaagua cuuuccuugc a 21

<210> SEQ ID NO 499
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 499
ugcaaggaaa guacuucuga gag 23

<210> SEQ ID NO 500
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 500
cucucagaag uacuuuccuu gca 23

<210> SEQ ID NO 501
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 501
ucuacuuguc cuucacagaa a 21

<210> SEQ ID NO 502
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 502
uuucugtgaa ggacaaguag aaa 23

<210> SEQ ID NO 503
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 503
uuucuacuug uccuucacag aaa 23

<210> SEQ ID NO 504
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 504
gaaaagccuu gacacuaaua a 21

<210> SEQ ID NO 505
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 505
uuauuagugu caaggcuuuu cug 23

<210> SEQ ID NO 506
<211> LENGTH: 23
<212> TYPE: RNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 506
cagaaaagcc uugacacuaa uaa 23

<210> SEQ ID NO 507
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 507
ccuuuaaauc ucuucggaac u 21

<210> SEQ ID NO 508
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 508
aguuccgaag agauuuaaag ggc 23

<210> SEQ ID NO 509
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 509
gcccuuuaaa ucucuucgga acc 23

<210> SEQ ID NO 510
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 510
cuuuaaaucu cuucggaacc u 21

<210> SEQ ID NO 511
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 511
agguuccgaa gagauuuaaa ggg 23

<210> SEQ ID NO 512
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 512
cccuuuaaau cucuucggaa ccu 23

<210> SEQ ID NO 513
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 513
uuuaaaucuc uucggaaccu u 21

<210> SEQ ID NO 514
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 514
aagguuccga agagauuuaa agg 23

<210> SEQ ID NO 515
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 515
ccuuuaaauc ucuucggaac cug 23

<210> SEQ ID NO 516
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 516
gggcgaucuu aacauaauaa u 21

<210> SEQ ID NO 517
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 517
auuauuaugu uaagaucgcc cuc 23

<210> SEQ ID NO 518
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 518
gagggcgauc uuaacauaau aau 23

<210> SEQ ID NO 519
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 519
ucuuaacaua auaauggcuc u 21

<210> SEQ ID NO 520
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 520
agagccauua uuauguuaag auc 23

<210> SEQ ID NO 521
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 521
gaucuuaaca uaauaauggc ucu 23

<210> SEQ ID NO 522
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 522
uuaucuuugg aagaccuuuc u 21

<210> SEQ ID NO 523
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 523
agaaaggucu uccaaagaua aaa 23

<210> SEQ ID NO 524
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 524
uuuuaucuuu ggaagaccuu ucu 23

<210> SEQ ID NO 525
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 525
uggaagaccu uucuacacua gug 23

<210> SEQ ID NO 526
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 526
aagaccuuuc uacacuagug u 21

<210> SEQ ID NO 527
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 527
acacuagugu agaaaggucu ucc 23

<210> SEQ ID NO 528
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 528
ggaagaccuu ucuacacuag ugu 23

<210> SEQ ID NO 529
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 529
agaccuuucu acacuagugu u 21

<210> SEQ ID NO 530
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 530
aacacuagug uagaaagguc uuc 23

<210> SEQ ID NO 531
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 531
gaagaccuuu cuacacuagu gug 23

<210> SEQ ID NO 532
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 532
gcaagaacga gauguucuaa u 21

<210> SEQ ID NO 533
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 533
auuagaacau cucguucuug cac 23

<210> SEQ ID NO 534
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 534
gugcaagaac gagauguucu aau 23

<210> SEQ ID NO 535
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 535
gaacgagaug uucuaaugac u 21

<210> SEQ ID NO 536
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 536
agucautaga acaucucguu cuu 23

<210> SEQ ID NO 537
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 537
aagaacgaga uguucuaaug acu 23

<210> SEQ ID NO 538
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 538
aacgagaugu ucuaaugacu u 21

<210> SEQ ID NO 539
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 539
aagucatuag aacaucucgu ucu 23

<210> SEQ ID NO 540
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 540
agaacgagau guucuaauga cuu 23

<210> SEQ ID NO 541
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 541
acgagauguu cuaaugacuu u 21

<210> SEQ ID NO 542
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 542
aaagucauua gaacaucucg uuc 23

<210> SEQ ID NO 543
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 543
gaacgagaug uucuaaugac uuu 23

<210> SEQ ID NO 544
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 544
auguguaacu uaauaagccu a 21

<210> SEQ ID NO 545
<211> LENGTH: 23
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 545

uaggcutauu aaguuacaca uuu                                              23


<210> SEQ ID NO 546
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 546

aaauguguaa cuuaauaagc cua                                              23


<210> SEQ ID NO 547
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547

guguaacuua auaagccuau u                                                21


<210> SEQ ID NO 548
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548

aauaggcuua uuaaguuaca cau                                              23


<210> SEQ ID NO 549
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549

auguguaacu uaauaagccu auu                                              23


<210> SEQ ID NO 550
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 550
guaacuuaau aagccuauuc u 21

<210> SEQ ID NO 551
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 551
agaauaggcu uauuaaguua cac 23

<210> SEQ ID NO 552
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 552
guguaacuua auaagccuau ucc 23

<210> SEQ ID NO 553
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 553
uaacuuaaua agccuauucc a 21

<210> SEQ ID NO 554
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 554
uggaauaggc uuauuaaguu aca 23

<210> SEQ ID NO 555
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 555
uguaacuuaa uaagccuauu cca 23

<210> SEQ ID NO 556
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 556
aacuuaauaa gccuauucca u 21

<210> SEQ ID NO 557
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 557
auggaatagg cuuauuaagu uac 23

<210> SEQ ID NO 558
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 558
guaacuuaau aagccuauuc cau 23

<210> SEQ ID NO 559
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 559
guuaaguaag uuacacuaca u 21

<210> SEQ ID NO 560
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 560
auguagtgua acuuacuuaa cug 23

<210> SEQ ID NO 561
<211> LENGTH: 23
<212> TYPE: RNA
<213> ORGANISM: Artificial Sequence
<220> FEATURE:

-continued

<221> NAME/KEY: source
<223> OTHER INFORMATION: /note="Description of Artificial Sequence: Synthetic oligonucleotide"

<400> SEQUENCE: 561
caguuaagua aguuacacua cag 23

<210> SEQ ID NO 562
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 562
uaaguuacac uacaguucuc a 21

<210> SEQ ID NO 563
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 563
ugagaacugu aguguaacuu acu 23

<210> SEQ ID NO 564
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 564
aguaaguuac acuacaguuc uca 23

<210> SEQ ID NO 565
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 565
guuacacuac aguucucaca a 21

<210> SEQ ID NO 566
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 566
uugugagaac uguaguguaa cuu 23

<210> SEQ ID NO 567
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 567
aaguuacacu acaguucuca caa 23

<210> SEQ ID NO 568
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 568
cagaccuaug uuuacaauau a 21

<210> SEQ ID NO 569
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 569
uauauuguaa acauaggucu gua 23

<210> SEQ ID NO 570
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 570
uacagaccua uguuuacaau aua 23

<210> SEQ ID NO 571
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 571
agaccuaugu uuacaauaua a 21

<210> SEQ ID NO 572
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:

<221> NAME/KEY: source
<223> OTHER INFORMATION: /note="Description of Combined DNA/RNA
Molecule: Synthetic oligonucleotide"

<400> SEQUENCE: 572
uuauautgua aacauagguc ugu 23

<210> SEQ ID NO 573
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 573
acagaccuau guuuacaaua uaa 23

<210> SEQ ID NO 574
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 574
gaucaagcag auguuuaauu u 21

<210> SEQ ID NO 575
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 575
aaauuaaaca ucugcuugau caa 23

<210> SEQ ID NO 576
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 576
uugaucaagc agauguuuaa uug 23

<210> SEQ ID NO 577
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 577
ugggauucag ucuguagaaa u 21

<210> SEQ ID NO 578
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 578
auuucuacag acugaauccc agg 23

<210> SEQ ID NO 579
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 579
ccugggauuc agucuguaga aau 23

<210> SEQ ID NO 580
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 580
ugucuaauag uucucuauag u 21

<210> SEQ ID NO 581
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 581
acuauagaga acuauuagac auu 23

<210> SEQ ID NO 582
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 582
aaugucuaau aguucucuau agu 23

<210> SEQ ID NO 583
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 583
cuaauaguuc ucuauagucc u 21

<210> SEQ ID NO 584
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 584
aggacuauag agaacuauua gac 23

<210> SEQ ID NO 585
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 585
gucuaauagu ucucuauagu ccu 23

<210> SEQ ID NO 586
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 586
agccaaauug aaaugugcac u 21

<210> SEQ ID NO 587
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 587
agugcacauu ucaauuuggc uca 23

<210> SEQ ID NO 588
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 588
ugagccaaau ugaaaugugc acc 23

<210> SEQ ID NO 589
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
uucuugcuaa gucuuaccau u 21

<210> SEQ ID NO 590
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
aaugguaaga cuuagcaaga aga 23

<210> SEQ ID NO 591
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
ucuucuugcu aagucuuacc aug 23

<210> SEQ ID NO 592
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
ugcaauaggc uauaaggaau a 21

<210> SEQ ID NO 593
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 593
uauucctuau agccuauugc agg 23

<210> SEQ ID NO 594
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
ccugcaauag gcuauaagga aua 23

<210> SEQ ID NO 595
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 595
gcaauaggcu auaaggaaua u 21

<210> SEQ ID NO 596
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 596
auauuccuua uagccuauug cag 23

<210> SEQ ID NO 597
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 597
cugcaauagg cuauaaggaa uag 23

<210> SEQ ID NO 598
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 598
gaaaggucau aauagcuuuc u 21

<210> SEQ ID NO 599
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 599
agaaagcuau uaugaccuuu cac 23

<210> SEQ ID NO 600
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 600
gugaaagguc auaauagcuu ucc 23

<210> SEQ ID NO 601
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 601
aaaggucaua auagcuuucc u 21

<210> SEQ ID NO 602
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 602
aggaaagcua uuaugaccuu uca 23

<210> SEQ ID NO 603
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 603
ugaaagguca uaauagcuuu ccc 23

<210> SEQ ID NO 604
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 604
aacuagauga cuguuguacu u 21

<210> SEQ ID NO 605
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 605
aaguacaaca gucaucuagu uca 23

<210> SEQ ID NO 606
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 606
ugaacuagau gacuguugua cug 23

<210> SEQ ID NO 607
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 607
cuguagcuca gucauuuaaa a 21

<210> SEQ ID NO 608
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 608
uuuuaaauga cugagcuaca gua 23

<210> SEQ ID NO 609
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 609
uacuguagcu cagucauuua aaa 23

<210> SEQ ID NO 610
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 610
cugguuuauu guacuguuau a 21

<210> SEQ ID NO 611
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 611
uauaacagua caauaaacca gcc 23

<210> SEQ ID NO 612
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 612
ggcugguuua uuguacuguu aua 23

<210> SEQ ID NO 613
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 613
auguguaaac auuguuauau a 21

<210> SEQ ID NO 614
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 614
uauauaacaa uguuuacaca ugc 23

<210> SEQ ID NO 615
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 615
gcauguguaa acauuguuau aua 23

<210> SEQ ID NO 616
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 616
gcugagggug aacaagaaaa u 21

<210> SEQ ID NO 617
<211> LENGTH: 23
<212> TYPE: RNA

-continued

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 617
auuuucuugu ucacccucag cga 23

<210> SEQ ID NO 618
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 618
gauaaagauu aaccagaaga a 21

<210> SEQ ID NO 619
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 619
uucuucuggu uaaucuuuau cag 23

<210> SEQ ID NO 620
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 620
aaccagaaga aaacaaggag u 21

<210> SEQ ID NO 621
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 621
acuccuuguu uucuucuggu uaa 23

<210> SEQ ID NO 622
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 622
auuaaccaga agaaaacaag u 21

<210> SEQ ID NO 623
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 623
acuuguuuuc uucugguuaa ucu 23

<210> SEQ ID NO 624
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 624
uaaccagaag aaaacaagga u 21

<210> SEQ ID NO 625
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 625
auccuuguuu ucuucugguu aau 23

<210> SEQ ID NO 626
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 626
aacaagaaaa gaccugauaa a 21

<210> SEQ ID NO 627
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 627
uuuaucaggu cuuuucuugu uca 23

<210> SEQ ID NO 628
<211> LENGTH: 21
<212> TYPE: RNA
<213> ORGANISM: Artificial Sequence
<220> FEATURE:
<221> NAME/KEY:
source <223> OTHER INFORMATION: /note="Description of Artificial Sequence:
      Synthetic oligonucleotide"

<400> SEQUENCE: 628
gaaaagaccu gauaaagauu a 21

<210> SEQ ID NO 629
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629
uaaucuuuau caggucuuuu cuu 23

<210> SEQ ID NO 630
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 630
acaagaaaag accugauaaa u 21

<210> SEQ ID NO 631
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 631
auuuaucagg ucuuuucuug uuc 23

<210> SEQ ID NO 632
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 632
aagaccugau aaagauuaac u 21

<210> SEQ ID NO 633
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 633
aguuaaucuu uaucaggucu uuu 23

<210> SEQ ID NO 634

<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 634
gaccugauaa agauuaacca u 21

<210> SEQ ID NO 635
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 635
augguuaauc uuuaucaggu cuu 23

<210> SEQ ID NO 636
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 636
ugauaaagau uaaccagaag a 21

<210> SEQ ID NO 637
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 637
ucuucugguu aaucuuuauc agg 23

<210> SEQ ID NO 638
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 638
accugauaaa gauuaaccag a 21

<210> SEQ ID NO 639
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 639
ucugguuaau cuuuaucagg ucu 23

<210> SEQ ID NO 640
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 640
aagaaaagac cugauaaaga u 21

<210> SEQ ID NO 641
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 641
aucuuuauca ggucuuuucu ugu 23

<210> SEQ ID NO 642
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 642
cugaggguga acaagaaaag a 21

<210> SEQ ID NO 643
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 643
ucuuuucuug uucacccuca gcg 23

<210> SEQ ID NO 644
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 644
ugaacaagaa aagaccugau a 21

<210> SEQ ID NO 645
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 645
uaucaggucu uuucuuguuc acc 23

<210> SEQ ID NO 646
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 646
gagggugaac aagaaaagac u 21

<210> SEQ ID NO 647
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 647
agucuuuucu uguucacccu cag 23

<210> SEQ ID NO 648
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 648
gugaacaaga aaagaccuga u 21

<210> SEQ ID NO 649
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 649
aucaggucuu uucuuguuca ccc 23

<210> SEQ ID NO 650
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 650
aagauuaacc agaagaaaac a 21

```
<210> SEQ ID NO 651
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 651

uguuuucuuc ugguuaaucu uua                                             23


<210> SEQ ID NO 652
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 652

agggugaaca agaaaagacc u                                               21


<210> SEQ ID NO 653
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653

aggucuuuuc uuguucaccc uca                                             23


<210> SEQ ID NO 654
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 654

ccugauaaag auuaaccaga a                                               21


<210> SEQ ID NO 655
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 655

uucugguuaa ucuuuaucag guc                                             23


<210> SEQ ID NO 656
<211> LENGTH: 21
<212> TYPE: RNA
<213> ORGANISM: Artificial Sequence
<220> FEATURE:
```

-continued

<221> NAME/KEY: source
<223> OTHER INFORMATION: /note="Description of Artificial Sequence:
      Synthetic oligonucleotide"

<400> SEQUENCE: 656
ugcucucaca guacucgcug a 21

<210> SEQ ID NO 657
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 657
ucagcgagua cugugagagc aag 23

<210> SEQ ID NO 658
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 658
ggugaacaag aaaagaccug a 21

<210> SEQ ID NO 659
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 659
ucaggucuuu ucuuguucac ccu 23

<210> SEQ ID NO 660
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 660
cucgcugagg gugaacaaga a 21

<210> SEQ ID NO 661
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 661
uucuuguuca cccucagcga gua 23

<210> SEQ ID NO 662
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 662
cgcugagggu gaacaagaaa a 21

<210> SEQ ID NO 663
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 663
uuuucuuguu cacccucagc gag 23

<210> SEQ ID NO 664
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 664
caguacucgc ugagggugaa u 21

<210> SEQ ID NO 665
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 665
auucacccuc agcgaguacu gug 23

<210> SEQ ID NO 666
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 666
ucgcugaggg ugaacaagaa a 21

<210> SEQ ID NO 667
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 667
uuucuuguuc acccucagcg agu 23

<210> SEQ ID NO 668
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 668
cuccccacua cuugcucuca u 21

<210> SEQ ID NO 669
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 669
augagagcaa guaguggga gag 23

<210> SEQ ID NO 670
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 670
acaaccgcag ccuguagcaa u 21

<210> SEQ ID NO 671
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 671
auugcuacag gcugcgguug uuu 23

<210> SEQ ID NO 672
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 672
uugcucucac aguacucgcu u 21

<210> SEQ ID NO 673
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 673
aagcgaguac ugugagagca agu 23

<210> SEQ ID NO 674
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 674
uacucgcuga gggugaacaa u 21

<210> SEQ ID NO 675
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 675
auuguucacc cucagcgagu acu 23

<210> SEQ ID NO 676
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 676
guagcaagcu cuggaacuca u 21

<210> SEQ ID NO 677
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 677
augaguucca gagcuugcua cag 23

<210> SEQ ID NO 678
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 678
agcucuggaa cucaggaguc u 21

<210> SEQ ID NO 679
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 679
agacuccuga guuccagagc uug 23

<210> SEQ ID NO 680
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 680
ccccacuacu ugcucucaca u 21

<210> SEQ ID NO 681
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 681
augugagagc aaguaguggg gag 23

<210> SEQ ID NO 682
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 682
cucucacagu acucgcugag u 21

<210> SEQ ID NO 683
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 683
acucagcgag uacugugaga gca 23

<210> SEQ ID NO 684
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 684
uguguuuuug uuuuucccac u 21

<210> SEQ ID NO 685
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 685
agugggaaaa acaaaaacac aca 23

<210> SEQ ID NO 686
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 686
gaacaagaaa agaccugaua a 21

<210> SEQ ID NO 687
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 687
uuaucagguc uuuucuuguu cac 23

<210> SEQ ID NO 688
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 688
accagaagaa aacaaggagg u 21

<210> SEQ ID NO 689
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 689
accuccuugu uuucuucugg uua 23

<210> SEQ ID NO 690
<211> LENGTH: 21
<212> TYPE: RNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 690
uagcaagcuc uggaacucag u 21

<210> SEQ ID NO 691
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 691
acugaguucc agagcuugcu aca 23

<210> SEQ ID NO 692
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 692
agaccugaua aagauuaacc a 21

<210> SEQ ID NO 693
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 693
ugguuaaucu uuaucagguc uuu 23

<210> SEQ ID NO 694
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 694
guacucgcug agggugaaca a 21

<210> SEQ ID NO 695
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 695
uuguucaccc ucagcgagua cug 23

<210> SEQ ID NO 696
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 696
acuugcucuc acaguacucg u 21

<210> SEQ ID NO 697
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 697
acgaguacug ugagagcaag uag 23

<210> SEQ ID NO 698
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 698
gccuguagca agcucuggaa u 21

<210> SEQ ID NO 699
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 699
auuccagagc uugcuacagg cug 23

<210> SEQ ID NO 700
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 700
caagcucugg aacucaggag u 21

<210> SEQ ID NO 701
<211> LENGTH: 23
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 701
acuccugagu uccagagcuu gcu 23

<210> SEQ ID NO 702
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 702
guguguuuuu guuuuuccca u 21

<210> SEQ ID NO 703
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 703
augggaaaaa caaaaacaca cac 23

<210> SEQ ID NO 704
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 704
cacuacuugc ucucacagua u 21

<210> SEQ ID NO 705
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 705
auacugugag agcaaguagu ggg 23

<210> SEQ ID NO 706
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 706
aagcucugga acucaggagu u 21

```
<210> SEQ ID NO 707
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 707

aacuccugag uuccagagcu ugc                                              23


<210> SEQ ID NO 708
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 708

cuacuugcuc ucacaguacu u                                                21


<210> SEQ ID NO 709
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 709

aaguacugug agagcaagua gug                                              23


<210> SEQ ID NO 710
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 710

uacuugcucu cacaguacuc u                                                21


<210> SEQ ID NO 711
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 711

agaguacugu gagagcaagu agu                                              23


<210> SEQ ID NO 712
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 712
caaccgcagc cuguagcaag u 21

<210> SEQ ID NO 713
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 713
acuugcuaca ggcugcgguu guu 23

<210> SEQ ID NO 714
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 714
gggugaacaa gaaaagaccu u 21

<210> SEQ ID NO 715
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 715
aaggucuuuu cuuguucacc cuc 23

<210> SEQ ID NO 716
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 716
cuugcucuca caguacucgc u 21

<210> SEQ ID NO 717
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 717
agcgaguacu gugagagcaa gua 23

<210> SEQ ID NO 718
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 718
uuaaccagaa gaaaacaagg a 21

<210> SEQ ID NO 719
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 719
uccuuguuuu cuucugguua auc 23

<210> SEQ ID NO 720
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 720
ucuccccacu acuugcucuc a 21

<210> SEQ ID NO 721
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 721
ugagagcaag uaguggggag aga 23

<210> SEQ ID NO 722
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 722
gcucucacag uacucgcuga u 21

<210> SEQ ID NO 723
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 723
aucagcgagu acugugagag caa 23

<210> SEQ ID NO 724
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 724
gcucuggaac ucaggagucg u 21

<210> SEQ ID NO 725
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 725
acgacuccug aguuccagag cuu 23

<210> SEQ ID NO 726
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 726
acaguacucg cugaggguga a 21

<210> SEQ ID NO 727
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 727
uucacccuca gcgaguacug uga 23

<210> SEQ ID NO 728
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 728
aaccgcagcc uguagcaagc u 21

<210> SEQ ID NO 729
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 729
agcuugcuac aggcugcggu ugu 23

<210> SEQ ID NO 730
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 730
uccccacuac uugcucucac a 21

<210> SEQ ID NO 731
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 731
ugugagagca aguaguggggg aga 23

<210> SEQ ID NO 732
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 732
acuacuugcu cucacaguac u 21

<210> SEQ ID NO 733
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 733
aguacuguga gagcaaguag ugg 23

<210> SEQ ID NO 734
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 734
ggaaacaacc gcagccugua u 21

<210> SEQ ID NO 735
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 735
auacaggcug cgguuguuuc ccu 23

<210> SEQ ID NO 736
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 736
ccuguagcaa gcucuggaac u 21

<210> SEQ ID NO 737
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 737
aguuccagag cuugcuacag gcu 23

<210> SEQ ID NO 738
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 738
ugagggugaa caagaaaaga u 21

<210> SEQ ID NO 739
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 739
aucuuuucuu guucacccuc agc 23

<210> SEQ ID NO 740
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 740
uguagcaagc ucuggaacuc a 21

<210> SEQ ID NO 741
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 741
ugaguuccag agcuugcuac agg 23

<210> SEQ ID NO 742
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 742
aguacucgcu gagggugaac a 21

<210> SEQ ID NO 743
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 743
uguucacccu cagcgaguac ugu 23

<210> SEQ ID NO 744
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 744
cccacuacuu gcucucacag u 21

<210> SEQ ID NO 745
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 745
acugugagag caaguagugg gga 23

<210> SEQ ID NO 746
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 746
agccuguagc aagcucugga a 21

<210> SEQ ID NO 747
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 747
uuccagagcu ugcuacaggc ugc 23

<210> SEQ ID NO 748
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 748
cucacaguac ucgcugaggg u 21

<210> SEQ ID NO 749
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 749
acccucagcg aguacuguga gag 23

<210> SEQ ID NO 750
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 750
ccacuacuug cucucacagu a 21

<210> SEQ ID NO 751
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 751
uacugugaga gcaaguagug ggg 23

<210> SEQ ID NO 752
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 752
gcaagcucug gaacucagga u 21

<210> SEQ ID NO 753
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 753
auccugaguu ccagagcuug cua 23

<210> SEQ ID NO 754
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 754
cuguagcaag cucuggaacu u 21

<210> SEQ ID NO 755
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 755
aaguuccaga gcuugcuaca ggc 23

<210> SEQ ID NO 756
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 756
ccgcagccug uagcaagcuc u 21

<210> SEQ ID NO 757
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 757
agagcuugcu acaggcugcg guu 23

<210> SEQ ID NO 758
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 758
acucgcugag ggugaacaag a 21

<210> SEQ ID NO 759
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 759
ucuuguucac ccucagcgag uac 23

<210> SEQ ID NO 760
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 760
ucaggagucg cgcgcuaggg u 21

<210> SEQ ID NO 761
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 761
acccuagcgc gcgacuccug agu 23

<210> SEQ ID NO 762
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 762
agcaagcucu ggaacucagg a 21

<210> SEQ ID NO 763
<211> LENGTH: 23
<212> TYPE: RNA
<213> ORGANISM: Artificial Sequence -continued
<220> FEATURE:
<221> NAME/KEY: source
<223> OTHER INFORMATION: /note="Description of Artificial Sequence:
      Synthetic oligonucleotide"

<400> SEQUENCE: 763
uccugaguuc cagagcuugc uac 23

<210> SEQ ID NO 764
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 764
guuuuuguuu uucccacccu u 21

<210> SEQ ID NO 765
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 765
aaggguggga aaaacaaaaa cac 23

<210> SEQ ID NO 766
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 766
guguuuuugu uuuucccacc u 21

<210> SEQ ID NO 767
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 767
aggugggaaa aacaaaaaca cac 23

<210> SEQ ID NO 768
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 768
aacaaccgca gccuguagca a 21

<210> SEQ ID NO 769
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 769
uugcuacagg cugcgguugu uuc 23

<210> SEQ ID NO 770
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 770
caggagucgc gcgcuagggg u 21

<210> SEQ ID NO 771
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 771
accccuagcg cgcgacuccu gag 23

<210> SEQ ID NO 772
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 772
ggagucgcgc gcuaggggcc u 21

<210> SEQ ID NO 773
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 773
aggccccuag cgcgcgacuc cug 23

<210> SEQ ID NO 774
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 774
cacaguacuc gcugagggug a 21

<210> SEQ ID NO 775
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 775
ucacccucag cgaguacugu gag 23

<210> SEQ ID NO 776
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 776
gggaaacaac cgcagccugu a 21

<210> SEQ ID NO 777
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 777
uacaggcugc gguuguuucc cuc 23

<210> SEQ ID NO 778
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 778
aggagucgcg cgcuaggggc u 21

<210> SEQ ID NO 779
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 779
agccccuagc gcgcgacucc uga 23

<210> SEQ ID NO 780
<211> LENGTH: 21
<212> TYPE: RNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 780
aaacaaccgc agccuguagc a 21

<210> SEQ ID NO 781
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 781
ugcuacaggc ugcgguuguu ucc 23

<210> SEQ ID NO 782
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 782
gagucgcgcg cuaggggccg u 21

<210> SEQ ID NO 783
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 783
acggccccua gcgcgcgacu ccu 23

<210> SEQ ID NO 784
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 784
agucgcgcgc uaggggccgg u 21

<210> SEQ ID NO 785
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 785
accggccccu agcgcgcgac ucc 23

<210> SEQ ID NO 786
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 786
gcugagggug aacaagaaaa u 21

<210> SEQ ID NO 787
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 787
auuuucuugu ucacccucag cga 23

<210> SEQ ID NO 788
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 788
gauaaagauu aaccagaaga a 21

<210> SEQ ID NO 789
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 789
uucuucuggu uaaucuuuau cag 23

<210> SEQ ID NO 790
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 790
aaccagaaga aaacaaggag u 21

<210> SEQ ID NO 791
<211> LENGTH: 23
<212> TYPE: RNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 791
acuccuuguu uucuucuggu uaa 23

<210> SEQ ID NO 792
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 792
auuaaccaga agaaaacaag u 21

<210> SEQ ID NO 793
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 793
acuuguuuuc uucugguuaa ucu 23

<210> SEQ ID NO 794
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 794
uaaccagaag aaaacaagga u 21

<210> SEQ ID NO 795
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 795
auccuuguuu ucuucugguu aau 23

<210> SEQ ID NO 796
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 796
aacaagaaaa gaccugauaa a 21

<210> SEQ ID NO 797
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 797
uuuaucaggu cuuuucuugu uca 23

<210> SEQ ID NO 798
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 798
gaaaagaccu gauaaagauu a 21

<210> SEQ ID NO 799
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 799
uaaucuuuau caggucuuuu cuu 23

<210> SEQ ID NO 800
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 800
acaagaaaag accugauaaa u 21

<210> SEQ ID NO 801
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 801
auuuaucagg ucuuuucuug uuc 23

<210> SEQ ID NO 802
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 802
aagaccugau aaagauuaac u 21

<210> SEQ ID NO 803
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 803
aguuaaucuu uaucaggucu uuu 23

<210> SEQ ID NO 804
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 804
gaccugauaa agauuaacca u 21

<210> SEQ ID NO 805
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 805
augguuaauc uuuaucaggu cuu 23

<210> SEQ ID NO 806
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 806
ugauaaagau uaaccagaag a 21

<210> SEQ ID NO 807
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 807
ucuucugguu aaucuuuauc agg 23

<210> SEQ ID NO 808
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 808
accugauaaa gauuaaccag a 21

<210> SEQ ID NO 809
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 809
ucugguuaau cuuuaucagg ucu 23

<210> SEQ ID NO 810
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 810
aagaaaagac cugauaaaga u 21

<210> SEQ ID NO 811
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 811
aucuuuauca ggucuuuucu ugu 23

<210> SEQ ID NO 812
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 812
cugaggguga acaagaaaag a 21

<210> SEQ ID NO 813
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 813
ucuuuucuug uucacccuca gcg 23

<210> SEQ ID NO 814
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 814
ugaacaagaa aagaccugau a 21

<210> SEQ ID NO 815
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 815
uaucaggucu uuucuuguuc acc 23

<210> SEQ ID NO 816
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 816
gagggugaac aagaaaagac u 21

<210> SEQ ID NO 817
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 817
agucuuuucu uguucacccu cag 23

<210> SEQ ID NO 818
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 818
gugaacaaga aaagaccuga u 21

<210> SEQ ID NO 819
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 819
aucaggucuu uucuuguuca ccc 23

<210> SEQ ID NO 820
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 820
aagauuaacc agaagaaaac a 21

<210> SEQ ID NO 821
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 821
uguuuucuuc ugguuaaucu uua 23

<210> SEQ ID NO 822
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 822
agggugaaca agaaaagacc u 21

<210> SEQ ID NO 823
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 823
aggucuuuuc uuguucaccc uca 23

<210> SEQ ID NO 824
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 824
ccugauaaag auuaaccaga a 21

<210> SEQ ID NO 825
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 825
uucugguuaa ucuuuaucag guc 23

<210> SEQ ID NO 826
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 826
ugcucucaca guacucgcug a 21

<210> SEQ ID NO 827
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 827
ucagcgagua cugugagagc aag 23

<210> SEQ ID NO 828
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 828
ggugaacaag aaaagaccug a 21

<210> SEQ ID NO 829
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 829
ucaggucuuu ucuuguucac ccu 23

<210> SEQ ID NO 830
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 830
cucgcugagg gugaacaaga a 21

<210> SEQ ID NO 831
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 831
uucuuguuca cccucagcga gua 23

<210> SEQ ID NO 832
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 832
cgcugagggu gaacaagaaa a 21

<210> SEQ ID NO 833
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 833
uuuucuuguu cacccucagc gag 23

<210> SEQ ID NO 834
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 834
caguacucgc ugagggugaa u 21

<210> SEQ ID NO 835
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 835
auucacccuc agcgaguacu gug 23

<210> SEQ ID NO 836
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 836
ucgcugaggg ugaacaagaa a 21

<210> SEQ ID NO 837
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 837
uuucuuguuc acccucagcg agu 23

<210> SEQ ID NO 838
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 838
cuccccacua cuugcucuca u 21

<210> SEQ ID NO 839
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 839
augagagcaa guaguggga gag 23

<210> SEQ ID NO 840
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 840
acaaccgcag ccuguagcaa u 21

<210> SEQ ID NO 841
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 841
auugcuacag gcugcgguug uuu 23

```
<210> SEQ ID NO 842
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 842

uugcucucac aguacucgcu u                                             21


<210> SEQ ID NO 843
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 843

aagcgaguac ugugagagca agu                                           23


<210> SEQ ID NO 844
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 844

uacucgcuga gggugaacaa u                                             21


<210> SEQ ID NO 845
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 845

auuguucacc cucagcgagu acu                                           23


<210> SEQ ID NO 846
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 846

guagcaagcu cuggaacuca u                                             21


<210> SEQ ID NO 847
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 847
augaguucca gagcuugcua cag 23

<210> SEQ ID NO 848
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 848
agcucuggaa cucaggaguc u 21

<210> SEQ ID NO 849
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 849
agacuccuga guuccagagc uug 23

<210> SEQ ID NO 850
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 850
ccccacuacu ugcucucaca u 21

<210> SEQ ID NO 851
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 851
augugagagc aaguaguggg gag 23

<210> SEQ ID NO 852
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 852
cucucacagu acucgcugag u 21

<210> SEQ ID NO 853
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 853
acucagcgag uacugugaga gca 23

<210> SEQ ID NO 854
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 854
uguguuuuug uuuuucccac u 21

<210> SEQ ID NO 855
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 855
agugggaaaa acaaaaacac aca 23

<210> SEQ ID NO 856
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 856
gaacaagaaa agaccugaua a 21

<210> SEQ ID NO 857
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 857
uuaucagguc uuuucuuguu cac 23

<210> SEQ ID NO 858
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 858
accagaagaa aacaaggagg u 21

<210> SEQ ID NO 859
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 859
accuccuugu uuucuucugg uua 23

<210> SEQ ID NO 860
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 860
uagcaagcuc uggaacucag u 21

<210> SEQ ID NO 861
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 861
acugaguucc agagcuugcu aca 23

<210> SEQ ID NO 862
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 862
agaccugaua aagauuaacc a 21

<210> SEQ ID NO 863
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 863
ugguuaaucu uuaucagguc uuu 23

<210> SEQ ID NO 864
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 864
guacucgcug agggugaaca a 21

<210> SEQ ID NO 865
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 865
uuguucaccc ucagcgagua cug 23

<210> SEQ ID NO 866
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 866
acuugcucuc acaguacucg u 21

<210> SEQ ID NO 867
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 867
acgaguacug ugagagcaag uag 23

<210> SEQ ID NO 868
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 868
gccuguagca agcucuggaa u 21

<210> SEQ ID NO 869
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 869
auuccagagc uugcuacagg cug 23

<210> SEQ ID NO 870
<211> LENGTH: 21
<212> TYPE: RNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 870
caagcucugg aacucaggag u 21

<210> SEQ ID NO 871
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 871
acuccugagu uccagagcuu gcu 23

<210> SEQ ID NO 872
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 872
guguguuuuu guuuuuccca u 21

<210> SEQ ID NO 873
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 873
augggaaaaa caaaaacaca cac 23

<210> SEQ ID NO 874
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 874
cacuacuugc ucucacagua u 21

<210> SEQ ID NO 875
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 875
auacugugag agcaaguagu ggg 23

<210> SEQ ID NO 876
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 876
aagcucugga acucaggagu u 21

<210> SEQ ID NO 877
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 877
aacuccugag uuccagagcu ugc 23

<210> SEQ ID NO 878
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 878
cuacuugcuc ucacaguacu u 21

<210> SEQ ID NO 879
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 879
aaguacugug agagcaagua gug 23

<210> SEQ ID NO 880
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 880
uacuugcucu cacaguacuc u 21

<210> SEQ ID NO 881
<211> LENGTH: 23
<212> TYPE: RNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 881
agaguacugu gagagcaagu agu 23

<210> SEQ ID NO 882
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 882
caaccgcagc cuguagcaag u 21

<210> SEQ ID NO 883
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 883
acuugcuaca ggcugcgguu guu 23

<210> SEQ ID NO 884
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 884
gggugaacaa gaaaagaccu u 21

<210> SEQ ID NO 885
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 885
aaggucuuuu cuuguucacc cuc 23

<210> SEQ ID NO 886
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 886
cuugcucuca caguacucgc u 21

<210> SEQ ID NO 887
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 887
agcgaguacu gugagagcaa gua 23

<210> SEQ ID NO 888
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 888
uuaaccagaa gaaaacaagg a 21

<210> SEQ ID NO 889
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 889
uccuuguuuu cuucugguua auc 23

<210> SEQ ID NO 890
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 890
ucuccccacu acuugcucuc a 21

<210> SEQ ID NO 891
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 891
ugagagcaag uaguggggag aga 23

<210> SEQ ID NO 892
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 892
gcucucacag uacucgcuga u 21

<210> SEQ ID NO 893
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 893
aucagcgagu acugugagag caa 23

<210> SEQ ID NO 894
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 894
gcucuggaac ucaggagucg u 21

<210> SEQ ID NO 895
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 895
acgacuccug aguuccagag cuu 23

<210> SEQ ID NO 896
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 896
acaguacucg cugaggguga a 21

<210> SEQ ID NO 897
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 897
uucacccuca gcgaguacug uga 23

<210> SEQ ID NO 898
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 898
aaccgcagcc uguagcaagc u 21

<210> SEQ ID NO 899
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 899
agcuugcuac aggcugcggu ugu 23

<210> SEQ ID NO 900
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 900
uccccacuac uugcucucac a 21

<210> SEQ ID NO 901
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 901
ugugagagca aguaguggggg aga 23

<210> SEQ ID NO 902
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 902
acuacuugcu cucacaguac u 21

<210> SEQ ID NO 903
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 903
aguacuguga gagcaaguag ugg 23

<210> SEQ ID NO 904
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 904
ggaaacaacc gcagccugua u 21

<210> SEQ ID NO 905
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 905
auacaggcug cgguuguuuc ccu 23

<210> SEQ ID NO 906
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 906
ccuguagcaa gcucuggaac u 21

<210> SEQ ID NO 907
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 907
aguuccagag cuugcuacag gcu 23

<210> SEQ ID NO 908
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 908
ugagggugaa caagaaaaga u 21

<210> SEQ ID NO 909
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 909
aucuuuucuu guucacccuc agc 23

<210> SEQ ID NO 910
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 910
uguagcaagc ucuggaacuc a 21

<210> SEQ ID NO 911
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 911
ugaguuccag agcuugcuac agg 23

<210> SEQ ID NO 912
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 912
aguacucgcu gagggugaac a 21

<210> SEQ ID NO 913
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 913
uguucacccu cagcgaguac ugu 23

<210> SEQ ID NO 914
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 914
cccacuacuu gcucucacag u 21

<210> SEQ ID NO 915
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 915
acugugagag caaguagugg gga 23

<210> SEQ ID NO 916
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 916
agccuguagc aagcucugga a 21

<210> SEQ ID NO 917
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 917
uuccagagcu ugcuacaggc ugc 23

<210> SEQ ID NO 918
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 918
cucacaguac ucgcugaggg u 21

<210> SEQ ID NO 919
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 919
acccucagcg aguacuguga gag 23

<210> SEQ ID NO 920
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 920
ccacuacuug cucucacagu a 21

<210> SEQ ID NO 921
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 921
uacugugaga gcaaguagug ggg 23

<210> SEQ ID NO 922
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 922
gcaagcucug gaacucagga u 21

<210> SEQ ID NO 923
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 923
auccugaguu ccagagcuug cua 23

<210> SEQ ID NO 924
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 924
cuguagcaag cucuggaacu u 21

<210> SEQ ID NO 925
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 925
aaguuccaga gcuugcuaca ggc 23

<210> SEQ ID NO 926
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 926
ccgcagccug uagcaagcuc u 21

<210> SEQ ID NO 927
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 927
agagcuugcu acaggcugcg guu 23

<210> SEQ ID NO 928
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 928
acucgcugag ggugaacaag a 21

<210> SEQ ID NO 929
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 929
ucuuguucac ccucagcgag uac 23

<210> SEQ ID NO 930
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 930
ucaggagucg cgcgcuaggg u 21

<210> SEQ ID NO 931
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 931
acccuagcgc gcgacuccug agu 23

-continued

<210> SEQ ID NO 932
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 932
agcaagcucu ggaacucagg a 21

<210> SEQ ID NO 933
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 933
uccugaguuc cagagcuugc uac 23

<210> SEQ ID NO 934
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 934
guuuuuguuu uucccacccu u 21

<210> SEQ ID NO 935
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 935 aagggguggga aaaacaaaaa cac 23

<210> SEQ ID NO 936
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 936
guguuuuugu uuuucccacc u 21

<210> SEQ ID NO 937
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 937
aggugggaaa aacaaaaaca cac 23

<210> SEQ ID NO 938
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 938
aacaaccgca gccuguagca a 21

<210> SEQ ID NO 939
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 939
uugcuacagg cugcgguugu uuc 23

<210> SEQ ID NO 940
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 940
caggagucgc gcgcuagggg u 21

<210> SEQ ID NO 941
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 941
accccuagcg cgcgacuccu gag 23

<210> SEQ ID NO 942
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 942
ggagucgcgc gcuaggggcc u 21

<210> SEQ ID NO 943
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 943
aggccccuag cgcgcgacuc cug 23

<210> SEQ ID NO 944
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 944
cacaguacuc gcugagggug a 21

<210> SEQ ID NO 945
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 945
ucacccucag cgaguacugu gag 23

<210> SEQ ID NO 946
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 946
gggaaacaac cgcagccugu a 21

<210> SEQ ID NO 947
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 947
uacaggcugc gguuguuucc cuc 23

<210> SEQ ID NO 948
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 948
aggagucgcg cgcuaggggc u 21

<210> SEQ ID NO 949
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 949
agccccuagc gcgcgacucc uga 23

<210> SEQ ID NO 950
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 950
aaacaaccgc agccuguagc a 21

<210> SEQ ID NO 951
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 951
ugcuacaggc ugcgguuguu ucc 23

<210> SEQ ID NO 952
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 952
gagucgcgcg cuaggggccg u 21

<210> SEQ ID NO 953
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 953
acggccccua gcgcgcgacu ccu 23

<210> SEQ ID NO 954
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 954
agucgcgcgc uaggggccgg u 21

<210> SEQ ID NO 955
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 955
accggccccu agcgcgcgac ucc 23

<210> SEQ ID NO 956
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 956
ccucucuccc cacuacuugc u 21

<210> SEQ ID NO 957
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 957
agcaaguagu ggggagagag ggu 23

<210> SEQ ID NO 958
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 958
ucacaguacu cgcugagggu u 21

<210> SEQ ID NO 959
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 959
aacccucagc gaguacugug aga 23

<210> SEQ ID NO 960
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 960
guguguguuu uuguuuuucc cac 23

<210> SEQ ID NO 961
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 961
ugugugauuu uguuuuuccc acc 23

<210> SEQ ID NO 962
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 962
guguguuuuu guuuuuccca ccc 23

<210> SEQ ID NO 963
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 963
guguuuuugu uuuucccacc cuc 23

<210> SEQ ID NO 964
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 964
acccucucuc cccacuacuu gcu 23

<210> SEQ ID NO 965
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 965
agcaaguagu ggggagagag ggu 23

<210> SEQ ID NO 966
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 966
ccucucuccc cacuacuugc u 21

<210> SEQ ID NO 967
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 967
ucucucccca cuacuugcuc uca 23

<210> SEQ ID NO 968
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 968
cucuccccac uacuugcucu cac 23

<210> SEQ ID NO 969
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 969
ucuccccacu acuugcucuc aca 23

<210> SEQ ID NO 970
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 970
cuccccacua cuugcucuca cag 23

<210> SEQ ID NO 971
<211> LENGTH: 23
<212> TYPE: RNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 971
uccccacuac uugcucucac agu 23

<210> SEQ ID NO 972
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 972
ccccacuacu ugcucucaca gua 23

<210> SEQ ID NO 973
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 973
cccacuacuu gcucucacag uac 23

<210> SEQ ID NO 974
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 974
ccacuacuug cucucacagu acu 23

<210> SEQ ID NO 975
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 975
cacuacuugc ucucacagua cuc 23

<210> SEQ ID NO 976
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 976
acuacuugcu cucacaguac ucg 23

<210> SEQ ID NO 977
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 977
cuacuugcuc ucacaguacu cgc 23

<210> SEQ ID NO 978
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 978
uacuugcucu cacaguacuc gcu 23

<210> SEQ ID NO 979
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 979
acuugcucuc acaguacucg cug 23

<210> SEQ ID NO 980
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 980
cuugcucuca caguacucgc uga 23

<210> SEQ ID NO 981
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 981
uugcucucac aguacucgcu gag 23

<210> SEQ ID NO 982
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 982
ugcucucaca guacucgcug agg 23

<210> SEQ ID NO 983
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 983
cucucacagu acucgcugag ggu 23

<210> SEQ ID NO 984
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 984
ucucacagua cucgcugagg gug 23

<210> SEQ ID NO 985
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 985
aacccucagc gaguacugug aga 23

<210> SEQ ID NO 986
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 986
ucacaguacu cgcugagggu u 21

<210> SEQ ID NO 987
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 987
cucacaguac ucgcugaggg uga 23

<210> SEQ ID NO 988
<211> LENGTH: 23
<212> TYPE: RNA
<213> ORGANISM: Artificial Sequence -continued
<220> FEATURE:
<221> NAME/KEY: source
<223> OTHER INFORMATION: /note="Description of Artificial Sequence:
Synthetic oligonucleotide"

<400> SEQUENCE: 988
ucacaguacu cgcugagggu gaa 23

<210> SEQ ID NO 989
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 989
cacaguacuc gcugagggug aac 23

<210> SEQ ID NO 990
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 990
acaguacucg cugaggguga aca 23

<210> SEQ ID NO 991
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 991
caguacucgc ugagggugaa caa 23

<210> SEQ ID NO 992
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 992
aguacucgcu gagggugaac aag 23

<210> SEQ ID NO 993
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 993
guacucgcug agggugaaca aga 23

<210> SEQ ID NO 994
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 994
uacucgcuga gggugaacaa gaa 23

<210> SEQ ID NO 995
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 995
acucgcugag ggugaacaag aaa 23

<210> SEQ ID NO 996
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 996
cucgcugagg gugaacaaga aaa 23

<210> SEQ ID NO 997
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 997
ucgcugaggg ugaacaagaa aag 23

<210> SEQ ID NO 998
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 998
cgcugagggu gaacaagaaa aga 23

<210> SEQ ID NO 999
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 999
gcugagggug aacaagaaaa gac 23

<210> SEQ ID NO 1000
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1000
cugaggguga acaagaaaag acc 23

<210> SEQ ID NO 1001
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1001
ugagggugaa caagaaaaga ccu 23

<210> SEQ ID NO 1002
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1002
gagggugaac aagaaaagac cug 23

<210> SEQ ID NO 1003
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1003
agggugaaca agaaaagacc uga 23

<210> SEQ ID NO 1004
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1004
gggugaacaa gaaaagaccu gau 23

<210> SEQ ID NO 1005
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1005
ggugaacaag aaaagaccug aua 23

<210> SEQ ID NO 1006
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1006
gugaacaaga aaagaccuga uaa 23

<210> SEQ ID NO 1007
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1007
ugaacaagaa aagaccugau aaa 23

<210> SEQ ID NO 1008
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1008
gaacaagaaa agaccugaua aag 23

<210> SEQ ID NO 1009
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1009
acaagaaaag accugauaaa gau 23

<210> SEQ ID NO 1010
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1010
caagaaaaga ccugauaaag auu 23

<210> SEQ ID NO 1011
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1011
aagaaaagac cugauaaaga uua 23

<210> SEQ ID NO 1012
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1012
agaaaagacc ugauaaagau uaa 23

<210> SEQ ID NO 1013
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1013
gaaaagaccu gauaaagauu aac 23

<210> SEQ ID NO 1014
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1014
aaaagaccug auaaagauua acc 23

<210> SEQ ID NO 1015
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1015
aaagaccuga uaaagauuaa cca 23

<210> SEQ ID NO 1016
<211> LENGTH: 23
<212> TYPE: RNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 1016
aagaccugau aaagauuaac cag 23

<210> SEQ ID NO 1017
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1017
agaccugaua aagauuaacc aga 23

<210> SEQ ID NO 1018
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1018
gaccugauaa agauuaacca gaa 23

<210> SEQ ID NO 1019
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1019
accugauaaa gauuaaccag aag 23

<210> SEQ ID NO 1020
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1020
ccugauaaag auuaaccaga aga 23

<210> SEQ ID NO 1021
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1021
cugauaaaga uuaaccagaa gaa 23

<210> SEQ ID NO 1022
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1022
ugauaaagau uaaccagaag aaa 23

<210> SEQ ID NO 1023
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1023
auaaagauua accagaagaa aac 23

<210> SEQ ID NO 1024
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1024
uaaagauuaa ccagaagaaa aca 23

<210> SEQ ID NO 1025
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1025
agauuaacca gaagaaaaca agg 23

<210> SEQ ID NO 1026
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1026
gauuaaccag aagaaaacaa gga 23

<210> SEQ ID NO 1027
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1027
auuaaccaga agaaaacaag gag 23

<210> SEQ ID NO 1028
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1028
uuaaccagaa gaaaacaagg agg 23

<210> SEQ ID NO 1029
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1029
uaaccagaag aaaacaagga ggg 23

<210> SEQ ID NO 1030
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1030
gagggaaaca accgcagccu gua 23

<210> SEQ ID NO 1031
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1031
agggaaacaa ccgcagccug uag 23

<210> SEQ ID NO 1032
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1032
ggaaacaacc gcagccugua gca 23

<210> SEQ ID NO 1033
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1033
gaaacaaccg cagccuguag caa 23

<210> SEQ ID NO 1034
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1034
aaacaaccgc agccuguagc aag 23

<210> SEQ ID NO 1035
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1035
aacaaccgca gccuguagca agc 23

<210> SEQ ID NO 1036
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1036
acaaccgcag ccuguagcaa gcu 23

<210> SEQ ID NO 1037
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1037
aaccgcagcc uguagcaagc ucu 23

<210> SEQ ID NO 1038
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1038
gcagccugua gcaagcucug gaa 23

<210> SEQ ID NO 1039
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1039
cagccuguag caagcucugg aac 23

<210> SEQ ID NO 1040
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1040
agccuguagc aagcucugga acu 23

<210> SEQ ID NO 1041
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1041
gccuguagca agcucuggaa cuc 23

<210> SEQ ID NO 1042
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1042
ccuguagcaa gcucuggaac uca 23

<210> SEQ ID NO 1043
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1043
cuguagcaag cucuggaacu cag 23

<210> SEQ ID NO 1044
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1044
uguagcaagc ucuggaacuc agg 23

<210> SEQ ID NO 1045
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1045
guagcaagcu cuggaacuca gga 23

<210> SEQ ID NO 1046
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1046
uagcaagcuc uggaacucag gag 23

<210> SEQ ID NO 1047
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1047
agcaagcucu ggaacucagg agu 23

<210> SEQ ID NO 1048
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1048
gcaagcucug gaacucagga guc 23

<210> SEQ ID NO 1049
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1049
caagcucugg aacucaggag ucg 23

<210> SEQ ID NO 1050
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1050
aagcucugga acucaggagu cgc 23

<210> SEQ ID NO 1051
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1051
acucaggagu cgcgcgcuag ggg 23

<210> SEQ ID NO 1052
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1052
cucaggaguc gcgcgcuagg ggc 23

<210> SEQ ID NO 1053
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1053
ucaggagucg cgcgcuaggg gcc 23

<210> SEQ ID NO 1054
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1054
caggagucgc gcgcuagggg ccg 23

<210> SEQ ID NO 1055
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1055
aggagucgcg cgcuaggggc cgg 23

<210> SEQ ID NO 1056
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1056
ggagucgcgc gcuaggggcc ggg 23

<210> SEQ ID NO 1057
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1057
ggaaaguggg gucuagcaau u 21

<210> SEQ ID NO 1058
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1058
uugcuagacc ccacuuuccu u 21

<210> SEQ ID NO 1059
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1059
caagagcagg ugugguuuu u 21

<210> SEQ ID NO 1060
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1060
aaacccacac cugcucuugu u 21

<210> SEQ ID NO 1061
<211> LENGTH: 21
<212> TYPE: RNA
<213> ORGANISM: Artificial Sequence
<220> FEATURE:

-continued

<221> NAME/KEY: source
<223> OTHER INFORMATION: /note="Description of Artificial Sequence:
Synthetic oligonucleotide"

<400> SEQUENCE: 1061
ccuucuaggu ggaaaguggu u 21

<210> SEQ ID NO 1062
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1062
ccacuuucca ccuagaaggu u 21

<210> SEQ ID NO 1063
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1063
caagaaaaga ccugauaaau u 21

<210> SEQ ID NO 1064
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1064
uuuaucaggu cuuuucuugu u 21

<210> SEQ ID NO 1065
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1065
gaaaagaccu gauaaagauu u 21

<210> SEQ ID NO 1066
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1066
aucuuuauca ggucuuuucu u 21

<210> SEQ ID NO 1067
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1067
cgcugagggu gaacaagaau u 21

<210> SEQ ID NO 1068
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1068
uucuuguuca cccucagcgu u 21

<210> SEQ ID NO 1069
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1069
gaagaaaaca aggagggaau u 21

<210> SEQ ID NO 1070
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1070
uucccuccuu guuuucuucu u 21

<210> SEQ ID NO 1071
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1071
ccucagagcu cgacgcauuu u 21

<210> SEQ ID NO 1072
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

-continued

```
<400> SEQUENCE: 1072

aaugcgucga gcucugaggu u                                          21


<210> SEQ ID NO 1073
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1073

ucuagcgacu gguggaauuu u                                          21


<210> SEQ ID NO 1074
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1074

aauuccacca gucgcuagau u                                          21
```